(12) United States Patent
Hicks et al.

(10) Patent No.: US 10,406,182 B2
(45) Date of Patent: *Sep. 10, 2019

(54) STEM CELL MICROPARTICLES AND MIRNA

(71) Applicant: RENEURON LIMITED, Guildford, Surrey (GB)

(72) Inventors: Caroline Hicks, Guildford (GB); John Sinden, Guildford (GB); Lara Stevanato, Guildford (GB); Randolph Corteling, Guildford (GB)

(73) Assignee: Reneuron Limited, Pencoed, Wales (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/027,424

(22) PCT Filed: Oct. 9, 2014

(86) PCT No.: PCT/GB2014/053044
§ 371 (c)(1),
(2) Date: Apr. 5, 2016

(87) PCT Pub. No.: WO2015/052526
PCT Pub. Date: Apr. 16, 2015

(65) Prior Publication Data
US 2016/0235788 A1 Aug. 18, 2016

(30) Foreign Application Priority Data

Oct. 9, 2013 (GB) .................................. 1317887.6
Aug. 14, 2014 (WO) ................ PCT/GB2014/052509

(51) Int. Cl.
| C12N 15/113 | (2010.01) |
| A61K 35/30 | (2015.01) |
| C12N 5/0797 | (2010.01) |
| A61K 9/00 | (2006.01) |

(52) U.S. Cl.
CPC ............ *A61K 35/30* (2013.01); *C12N 5/0623* (2013.01); *C12N 15/113* (2013.01); *A61K 9/0019* (2013.01); *C12N 2310/141* (2013.01); *C12N 2501/15* (2013.01); *C12N 2501/24* (2013.01); *C12N 2501/25* (2013.01); *C12N 2502/088* (2013.01)

(58) Field of Classification Search
None
See application file for complete search history.

(56) References Cited

U.S. PATENT DOCUMENTS

| 6,899,863 | B1 | 5/2005 | Dhellin et al. |
| 7,416,888 | B2 | 8/2008 | Sinden et al. |
| 9,783,781 | B2* | 10/2017 | Slavin .................. C12N 5/0622 |
| 2008/0268429 | A1 | 10/2008 | Pietrzkowski |
| 2010/0113290 | A1 | 5/2010 | Klass et al. |
| 2011/0003008 | A1 | 1/2011 | Lim |
| 2012/0076854 | A1 | 3/2012 | Hope et al. |
| 2012/0107413 | A1 | 5/2012 | Lim et al. |
| 2012/0183575 | A1 | 7/2012 | Gabrielsson |
| 2013/0143314 | A1 | 6/2013 | Shiels et al. |
| 2013/0150256 | A1 | 6/2013 | Synnergren et al. |
| 2013/0337066 | A1 | 12/2013 | Zhang et al. |
| 2014/0004601 | A1 | 1/2014 | Lim |
| 2014/0065240 | A1 | 3/2014 | Mitsialis et al. |
| 2014/0220053 | A1 | 8/2014 | Muraca et al. |
| 2014/0228233 | A1 | 8/2014 | Pawlowski et al. |
| 2014/0363469 | A1 | 12/2014 | Meyers et al. |
| 2015/0037299 | A1 | 2/2015 | Brodie et al. |
| 2015/0079046 | A1 | 3/2015 | Sinden et al. |
| 2015/0164955 | A1 | 6/2015 | Sinden et al. |
| 2015/0366897 | A1 | 12/2015 | Stevanato et al. |
| 2016/0002597 | A1 | 1/2016 | Sinden et al. |
| 2016/0193252 | A1 | 7/2016 | Hicks et al. |
| 2016/0235788 | A1 | 8/2016 | Hicks et al. |

FOREIGN PATENT DOCUMENTS

| EP | 2 745 840 | 6/2014 |
| KR | 20100081003 | 7/2010 |
| WO | WO-2006/087233 | 8/2006 |
| WO | WO-2007/106200 A2 | 9/2007 |
| WO | WO-2009/087361 | 7/2009 |
| WO | WO-2009/105044 | 8/2009 |

(Continued)

OTHER PUBLICATIONS

Ehtesham et al. (Cancer Research, 62:7170-7174, 2002).*
Ahmed et al. (Molecular Pharmaceutics, 8:1559-1572, 2011).*
Discher, Dennis E., et al. "Growth factors, matrices, and forces combine and control stem cells", Science, Jun. 26, 2009; 324(5935): 1673-1677.
Morin, Ryan D., et al. "Application of massively parallel sequencing to microRNA profiling and discovery in human embryonic stem cells", Genome Research, Apr. 1, 2008, vol. 18, No. 4, pp. 610-621.
Smalheiser, Neil R., "Exosomal transfer of proteins and RNAs at synapses in the nervous system", Biology Direct 2007m 2:35, 15 pgs.
Final Office Action for U.S. Appl. No. 14/390,010 dated Oct. 12, 2016.

(Continued)

*Primary Examiner* — Daniel E Kolker
*Assistant Examiner* — Aditi Dutt
(74) *Attorney, Agent, or Firm* — Kilpatrick Townsend & Stockton LLP

(57) ABSTRACT

This invention relates to stem cell microparticles and miRNA isolated from these microparticles, their use and production thereof, in particular neural stem cell microparticles and their use in therapy of cancer, typically a nestin-positive cancer. The cancer may be glioma, melanoma, breast cancer, pancreatic cancer or prostate cancer. The stem cell microparticle is typically an exosome or microvesicle and may be derived from a neural stem cell line. The neural stem cell line may be a conditionally-immortalized stem cell line such as CTX0E03 (deposited at the ECACC with Accession No. 04091601).

14 Claims, 46 Drawing Sheets
Specification includes a Sequence Listing.

(56) References Cited

FOREIGN PATENT DOCUMENTS

| WO | WO-2011/000551 A1 | 1/2011 |
|---|---|---|
| WO | WO-2011/062244 | 5/2011 |
| WO | WO-2011/069100 | 6/2011 |
| WO | WO-2011/149354 | 12/2011 |
| WO | WO-2012/004611 A1 | 1/2012 |
| WO | WO-2012/020307 | 2/2012 |
| WO | WO-2012/053976 | 4/2012 |
| WO | WO-2012/087241 | 6/2012 |
| WO | WO-2013/150303 | 10/2013 |
| WO | WO-2014/013258 | 1/2014 |
| WO | WO-2014/125276 | 8/2014 |
| WO | WO-2014/125277 | 8/2014 |
| WO | WO-2015/022545 | 2/2015 |
| WO | WO-2015/052526 | 4/2015 |
| WO | WO-2015/052527 | 4/2015 |

OTHER PUBLICATIONS

Non-Final Office Action for U.S. Appl. No. 14/767,278 dated Nov. 23, 2016.
Jeon et al., "Sphingosylphosphorylcholine induces differentiation of human mesenchymal stem cells into smooth-muscle-like cells through a TGF-β-dependent mechanism", Journal of Cell Science 119, Sep. 2006, pp. 4994-5005.
Office Action issued in U.S. Appl. No. 14/414,670, dated Oct. 7, 2016.
Office Action issued in U.S. Appl. No. 14/767,280, dated Aug. 17, 2016.
Xin, Hongqi et al., "Exosome-Mediated Transfer of miR-133b from Multipotent Mesenchymal Stromal Cells to Neural Cells Contributes to Neurite Outgrowth", Stem Cells. Jul. 2012; 30(7): 1556-1564.
Ambros, V. et al. (2003) "A uniform system for microRNA annotation," RNA 9(3):277-279.
Banerjee, S. et al. (2011) "Human stem cell therapy in ischaemic stroke: a review," Age and Ageing 40:7-13.
Bruno, Stefania et al., "Effects of Mesenchymal Stromal Cell-Derived Extracellular Vesicles on Tumor Growth", Frontiers in Immunology, vol. 5, Aug. 11, 2014 (Aug. 11, 2014), XP055161795, DOI: 10.3389/fimmu.2014.00382.
Chen, T.S. et al. (2011) "Enabling a robust scalable manufacturing process for therapeutic exosomes through oncogenic immortalization of human ESC-derived MSCs," Journal of Translational Medicine 9:47, 1-10.
Chung, Y. et al. (2008) "Human Embryonic Stem Cell Lines Generated without Embryo Destruction," Cell Stem Cell 2:113-117.
Ding, D-C. et al. (2011) "Mesenchymal Stem Cells," Cell Transplantation 20:5-14.
Einstein, O. et al. (2008) "The Changing Face of Neural Stem Cell Therapy in Neurologic Diseases," Arch Neurol. 65(4):452-456.
Fonsanto, Valentina et al., "Human Liver Stem Cell-Derived Microvesicles Inhibit Hepatoma Growth in SCID Mice by Delivering Antitumor MicroRNAS", Stem Cells, vol. 30, No. 9, Sep. 20, 2012 (Sep. 20, 2012), pp. 1985-1998, XP055161662, ISSN: 1066-5099, DOI: 10.1002/stem.1161.
Hassani, Z. et al. (2012) "Human Neural Progenitor Cell Engraftment Increases Neurogenesis and Microglial Recruitment in the Brain of Rats with Stroke," PLoS One 7(11):e50444, 1-10.
Hodges, H. et al. (2007) "Making Stem Cell Lines Suitable for Transplantation," Cell Transplantation 16(2):101-115.
Horie, N. et al. (2011) "Transplanted Stem Cell-Secreted Vascular Endothelial Growth Factor Effects Poststroke Recovery, Inflammation, and Vascular Repair," Stem Cells 29:274-285.
International Search Report and Written Opinion (ISA/EPO) for International Application No. PCT/GB2013/050879, dated Jun. 21, 2013, 13 pages.
International Search Report and Written Opinion (ISA/EPO) for International Application No. PCT/GB2013/051923, date Nov. 5, 2013, 13 pages.
International Search Report and Written Opinion (ISA/EPO) for International Application No. PCT/GB2014/050411, dated Apr. 14, 2014, 10 pages.
International Search Report and Written Opinion (ISA/EPO) for International Application No. PCT/GB2014/050412, dated Apr. 24, 2014, 15 pages.
International Search Report and Written Opinion for Intl. Appl. No. PCT/GB2014/052509 dated Feb. 25, 2015.
International Search Report and Written Opinion for Intl. Appl. No. PCT/GB2014/053044 dated Mar. 24, 2015.
International Search Report PCT/GB2014/053045 dated Feb. 20, 2015.
Kang, D. et al. (2008) "Proteomic Analysis of Exosomes from Human Neural Stem Cells by Flow Field-Flor Fractionation and Nanoflow Liquid Chromatography—Tandem Mass Spectrometry," Journal of Proteome Research 7(8):3475-3480.
Katsuda, T. et al. (2013) "Human adipose tissue-derived mesenchymal stem cells secrete functional neprilysin-bound exosomes," Scientific Reports 3:1197, 1-11.
Katsuda, T. et al. (2013) "The therapeutic potential of mesenchymal stem cell-derived extracellular vesicles," Proteomics 13:1637-1653.
Keller, S. et al. (2007) "CD24 is a marker of exosomes secreted into urine and amniotic fluid," Kidney International 72:1095-1102.
Klimanskaya, I. et al. (2006) "Human embryonic stem cell lines derived from single blastomeres," Nature 444:481-485.
Kornblum, H.I. (2007) "Introduction to Neural Stem Cells," Stroke 38(part 2):810-816.
Kosaka, N. et al., "Competitive Interactions of Cancer Cells and Normal Cells via Secretory MicroRNAs", Journal of Biological Chemistry, vol. 287, No. 2, Jan. 6, 2012 (Jan. 6, 2012), pp. 1397-1405, XP055161557, ISSN: 0021-9258, DOI: 10.1074/jbc.M111.288662.
Lai, R.C. et al. (2010) "Exosome secreted by MSC reduces myocardial ischemia/reperfusion injury," Stem Cell Research 4:214-222.
Lai, R.C. et al. (2012) "Proteolytic Potential of theMSC Exosome Proteome: Implications for an Exosome-Mediated Delivery of Therapeutic Proteasome," International Journal of Proteomics 2012 (Article ID 971907):14 pages.
Littlewood, T.D. et al. (1995) "A modified oestrogen receptor ligand-binding domain as an improved switch for the regulation of heterologous proteins," Nucleic Acids Research 23(10):1686-1690.
Marzesco, A-M. et al. (2005) "Release of extracellular membrane particles carrying the stem cell marker prominin-1 (CD133) from neural progenitors and other epithelial cells," Journal of Cell Science 118(13):2849-2858.
Miljan, E.A. et al. (2009) "Implantation of c-mycER$^{TAM}$ Immortalized Human Mesencephalic-Derived Clonal Cell Lines Ameliorates Behavior Dysfunction in a Rat Model of Parkinson's Disease," Stem Cells Dev. 18(2):307-319.
Miljan, E.A. et al. (2009) "Stem cell treatment of ischemic brain injury," Current Opinion in Molecular Therapeutics 11(4):394-403.
Mitchell, J.P. et al. (2008) "Increased exosome production from tumour cell cultures using the Integra CELLine Culture System," Journal of Immunological Methods 335:98-105.
Park, D-H. et al. (2010) "Increased Neuronal Proliferation in the Dentate Gyrus of Aged Rats Following Neural Stem Cell Implantation," Stem Cells and Development 19(2):175-180.
Pittenger, M.F. et al. (1999) "Multilineage Potential of Adult Human Mesenchymal Stem Cells," Science 284:143-147.
Pollock, K. et al. (2006) "A conditionally immortal clonal stem cell line from human corticalneuroepithelium for the treatment of ischemic stroke," Experimental Neurol. 199(1):143-155.
Ratajczak, M.Z. et al. Pivotal Role of Paracrine Effects in Stem Cell Therapies in Regenerative Medicine: Can We Translate Stem Cell-Secreted Paracrine Factors and Microvesicles Into Better Therapeutic Strategies. Leukemia, Jan. 17, 2012, vol. 26, pp. 1166-1173.
Singapore Written Opinion Application No. 11201406336Y dated Mar. 9, 2015.
Smith, E.J. et al. (2012) "Implantation Site and Lesion Topology Determine Efficacy of aHuman Neural Stem Cell Line in a Rat Model of Chronic Stroke," Stem Cells 30:785-796.

(56) References Cited

OTHER PUBLICATIONS

Stevenato, L. et al. (2009) "c-MycER$^{TAM}$ transgene silencing in a genetically modified humanneural stem cell line implanted into MCAo rodent brain," BMC Neuroscience 10:86, 1-13.
Stroemer, P. et al. (2009) "The Neural Stem Cell Line CTX0E03 Promotes Behavioral Recovery and Endogenous Neurogenesis After Experimental Stroke in a Dose-Dependent Fashion," Neurorehabilitation and Neural Repair 23(9):895-909.
Thery, C. et al. (2009) "Membrane vesicles as conveyors of immune responses," Nature Reviews Immunology 9:581-593.
Thier, M. et al. (2012) "Direct Conversion of Fibroblasts into Stably Expandable Neural Stem Cells," Cell Stem Cell 10:473-479.
Timmers, L. et al. (2008) "Reduction of myocardial infarct size by human mesenchymal stem cell conditioned medium," Stem Cell Research 1:129-137.
U.S. Non-Final Office Action for U.S. Appl. No. 14/390,010 dated Jan. 20, 2016.
Valadi et al. (2007), "Exosome-mediated transfer of mRNAs and microRNAs is a novel mechanism of genetic exchange between cells", Nature Cell Biology, vol. 9, pp. 654-659.
Van Der Pol, E. et al., "Classification, Functions, and Clinical Relevance of Extracellular Vesicles", Pharmacological Reviews, vol. 64, No. 3, Jul. 1, 2012 (Jul. 1, 2012), pp. 676-705, XP055155968, ISSN:0031-6997, DOI: 10.1124/pr.112.005983.
Vishnubhatla, Indira et al., "The Development of Stem Cell-derived Exosomes as a Cell-free Regenerative Medicine", Journal of Circulating Biomarkers, vol. 3, No. 2, Apr. 30, 2014 (Apr. 30, 2014) pp. 1-14, XP055155696, DOI: 10.5772/58597.
Yang, Chenjie et al., "Immunosuppressive Exosomes: A New Approach for Treating Arthritis", International Journal of Rheumatology, vol. 176, No. 12, Jan. 1, 2012 (Jan. 1, 2012), pp. 7385-8, XP055155835, ISSN: 1687-9260, DOI: 10.1038/labinvest. 2010.152.
Yeo, R.W.Y. et al. (2013) "Mesenchymal stem cell: An efficient mass producer of exosomes for drug delivery," Advanced Drug Delivery Reviews 65:336-341.
Yuan, S.J. et al. (2011) "Cell-Surface Marker Signatures for the Isolation of Neural Stem Cells, Glia and Neurons Derived from Human Pluripotent Stem Cells," PLoS One 6(3):e17540, 1-16.
Final Office Action for U.S. Appl. No. 14/767,280, dated Mar. 3, 2017.
Guo, Z. et al. (2010) "Critical role of L-type voltage-dependent Ca$^{2+}$ channels in neural progenitor cell proliferation induced by hypoxia," Neuroscience Letters 478:156-160.
Huang, E. et al. (2012) "Conditionally Immortalized Mouse Embryonic Fibroblasts Retain Proliferative Activity without Comprising Multipotent Differentiation Potential," PLoS One 7(2):11 pages.
Ross, H.H. et al. (2012) "In vivo intermittent hypoxia elicits enhanced expansion and neuronal differentiation in cultured neural progenitors," Experimental Neurology 235:238-245.
Sun, J. et al. (2010) "Endothelial Cells Promote Neural Stem Cell Proliferation and Differentiation Associated with VEGF Activated Notch and Pten Signaling," Developmental Dynamics 239:2345-2353.
Chen, et al., MiR-1246 promotes SiHa cervical cancer cell proliferation, invasion, and migration through suppression of its target gene thromobospondin2, 2014 Archives of Gynecology and Obsterics, vol. 290, pp. 725-732.
Guedes, et al., Early miR-155 upregulation contributes to neuroinflammation in Alzheimer's disease triple transgenic mouse model, 2014, Human Molecular Genetics, vol. 23, pp. 6286-6301.
Japanese Office Action dated May 16, 2017, from application serial No. 2015-522170.
Kim, et al., miR-126 contributes to Parkinson's disease by dysregulating the insulin-like growth factor/phosphoinositide 3-kinase signaling, 2014, Neurobiology of Aging, vol. 35, pp. 1712-1721.
Pigati, et al., Selective release of microRNA species from normal and malignant mammary epithelial cells, 2010, PLoS One, vol. 5:e13515, pp. 1-13.
U.S. Office Action dated Jul. 19, 2017, from U.S. Appl. No. 14/767,278.
U.S. Office Action dated Jul. 20, 2017, from U.S. Appl. No. 14/390,010.
U.S. Office Action dated Jun. 14, 2017, from U.S. Appl. No. 14/414,670.
Yang, et al., Expression and prognostic significance of the apoptotic genes BCL2L13, Livin, and CASP8AP2 in childhood acute lymphoblastic leukemia, 2010, Leukemia Research, vol. 34, pp. 18-23.
Zhang, et al., Clusterin inhibits apoptosis by interacting with activated Bax, 2005, Nature Cell Biology, vol. 7, pp. 909-915.
Zhang, et al., Tumour-initiating cell-specific miR-1246 and miR-1290 expression converge to promote non-small cell lung cancer progression, 2016, Nature Communication, vol. 7:11702, pp. 1-16.
U.S. Restriction Requirement for U.S. Appl. No. 14/414,670, dated Apr. 27, 2016.
U.S. Restriction Requirement for U.S. Appl. No. 14/767,278, dated Jul. 7, 2016.
Aboody et al., "Neural stem cell-mediated enzyme/prodrug therapy for glioma: preclinical studies", 2013, Science Translation Medicine, vol. 5, issue 184, pp. 1-11.
Ahmed et al., "A comparative study of neural and mesenchymal stem cell-based carriers for oncolytic adenovirus in a model of malignant glioma", 2011, Molecular Pharmaceutics, vol. 8, pp. 1559-1572.
Ames et al., "MicroRNA profiling of low-grade glial and glioneuronal tumors shows an independent role for cluster 14q32.31 member miR-487b", 2017, Modern Pathology, vol. 30, pp. 204-216.
Ehtesham et al., "Induction of glioblastoma apoptosis using neural stem cell-mediated delivery of tumor necrosis factor-related apoptosis-inducing ligand", 2002, Cancer Research, vol. 62, pp. 7170-7174.
Fan et al., "Altered microRNA expression in peripheral blood mononuclear cells from young patients with schizophrenia", 2015, Journal of Molecular Neuroscience, vol. 56, pp. 562-571.
Girgert et al., "Inactivation of GPR30 reduces growth of triple-negative breast cancer cells: possible application in targeted therapy", 2012, Breast Cancer Res Treat, 134, pp. 199-205.
Gutova et al., "Therapeutic targeting of melanoma cells using neural stem cells expressing carboxylesterase, a CPT-11 activating enzyme", 2010, Current Stem Cell Research & Therapy, vol. 5, pp. 273-276.
Li et al., "Identification of circulating microRNAs as potential biomarkers for detecting acute ischemic stroke", 2015, Cellular and Molecular Neurobiology, vol. 35, pp. 433-447.
Ouyang, et al., "A two-stage perfusion fibrous bed bioreactor system for mass production of embryonic stem cells", Expert Opin Biol Ther, Jul. 2008; 8(7):895-909.
Sakha et al., "Exosomal microRNA miR-1246 induces cell motility and invasion through the regulation of DENND2D in oral squamous cell carcinoma", 2016, Scientific Reports, vol. 6:38750, pp. 1-11.
Seol et al., "Genetically engineered human neural stem cells with rabbit carboxyl esterase can target brain metastasis from breast cancer", 2011, Cancer Letters, vol. 311, pp. 152-159.
Takeshita et al., "Serum microRNA expression profile: miR-1246 as a novel diagnostic and prognostic biomarker for oesophageal squamous cell carcinoma", 2013, British Journal of Cancer, vol. 108, pp. 644-652.
Thomas et al., "Automated, serum-free production of CTX0E03: a therapeutic clinical grade human neural stem cell line", 2009, Biotechnology Letters, vol. 31, pp. 1167-1172.
U.S. Office Action dated Dec. 13, 2017, from U.S. Appl. No. 14/767,280.
U.S. Office Action dated Feb. 16, 2018, from U.S. Appl. No. 14/767,278.
U.S. Office Action dated Jan. 22, 2018, from U.S. Appl. No. 14/912,060.
Wong et al., "Neurocognitive deficits and neurological signs in schizophrenia", 1997, Schizophrenia Research, vol. 23, pp. 139-146.
U.S. Appl. No. 14/390,010 , "Advisory Action", dated Mar. 31, 2017, 3 pages.
U.S. Appl. No. 14/390,010 , "Non-Final Office Action", dated Nov. 9, 2018, 18 pages.
U.S. Appl. No. 14/390,010 , "Restriction Requirement", dated Oct. 26, 2015, 10 pages.

(56) References Cited

OTHER PUBLICATIONS

U.S. Appl. No. 14/767,280, "Restriction Requirement", dated Mar. 16, 2016, 9 pages.
JP2015-503941, "Office Action", dated Feb. 28, 2017, 14 pages.
May et al., "Establishment of Murine Cell Lines by Constitutive and Conditional Immortalization", Journal of Biotechnology, vol. 120, 2005, pp. 99-110.
PCT/GB2013/050879, "International Preliminary Report on Patentability", dated Oct. 16, 2014, 9 pages.
PCT/GB2013/051923, "International Preliminary Report on Patentability", Jan. 29, 2015, 8 pages.
PCT/GB2014/050412, "International Preliminary Report on Patentability", dated Aug. 27, 2015, 9 pages.
PCT/GB2014/052509, "International Preliminary Report on Patentability", dated Feb. 25, 2016, 13 pages.
SG11201506284R, "Written Opinion", dated Jan. 20, 2017, 8 pages.
Volkmann et al., "A Conditionally Immortalized Dendritic Cell Line Which Differentiates in Contact With T Cells or T Cell-Derived Cytokines", Eur. J. Immunol., vol. 26, 1996, pp. 2565-2572.
Ahn, et al., "Olig2-Induced Neural Stem Cell Differentiation Involves Downregulation of Wnt Signaling and Induction of Dickkopf-1 Expression", PLos One, Dec. 2008; vol. 3, Issue 12.
CELLine Disoposable Bioreactor for Efficient Protein Expression, 38 pages, retrieved from Integra website May 14, 2018.
CELLine Operating instructions, Integra, 24 pages, retrieved from Integra website May 14, 2018.
Cho, et al., "Human neural stem cells: electrophysiological properties of voltage-gated ion channels", NeuroReport, 2002; 13: 1447-1452.
Decimo, et al., "Neural Stem Cell Niches in Health and Diseases", Current Pharmaceutical Design, 2012: 18: 1755-1783.
Jeong, et al., "Human Neural Stem Cell Transplantation Promotes Functional Recovery in Rats with Experimental Intracerebral Hemorrhage", Stroke, 2003; 34: 2258-2263.
Kim, et al., "Production and Characterization of Immortal Human Neural Stem Cell Line with Multipotent Differentiation Property", Methods in Molecular Biology, vol. 438: Neural Stem Cells, 2008, 103-121.
Lee, et al., "Braine Transplantation of Immortalized Human Neural Stem Cells Promotes Functional Recovery in Mouse Intracerebral Hemorrhage Stroke Model", Stem Cells, 2007; 25: 1204-1212.
Mitchell, et al., "Increased exosome production from tumour cell cultures using the Integra CELLine Culture System", Journal of Immunological Methods, 2008: 335: 98-105.
Non-Final Office Action dated Jun. 15, 2018, from U.S. Appl. No. 14/414,670.
Final Office Action dated Sep. 5, 2018, from U.S. Appl. No. 14/767,280.
Pradilla et al., "Local intracerebral administration of paclitaxel with the Paclimer delivery system: toxicity study in a canine model", Journal of Neuro-Oncology, 2006, 76, 131-138.
U.S. Office Action dated Apr. 2, 2018, from U.S. Appl. No. 14/390,010.

* cited by examiner

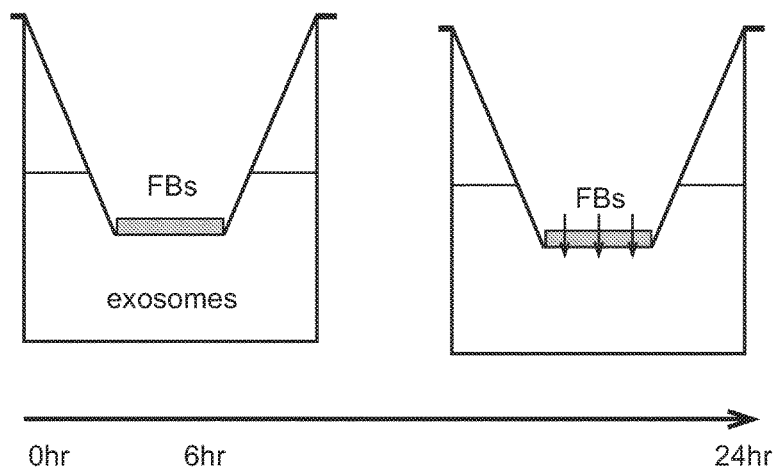
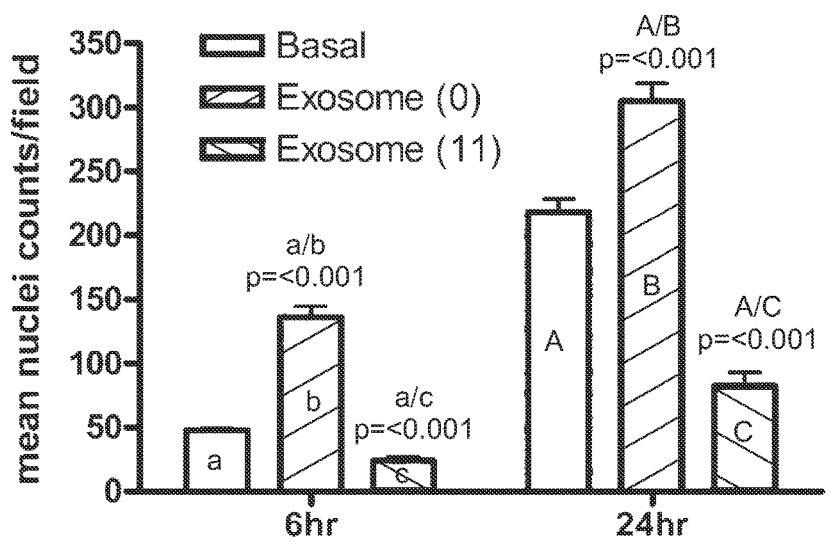
Figure 1

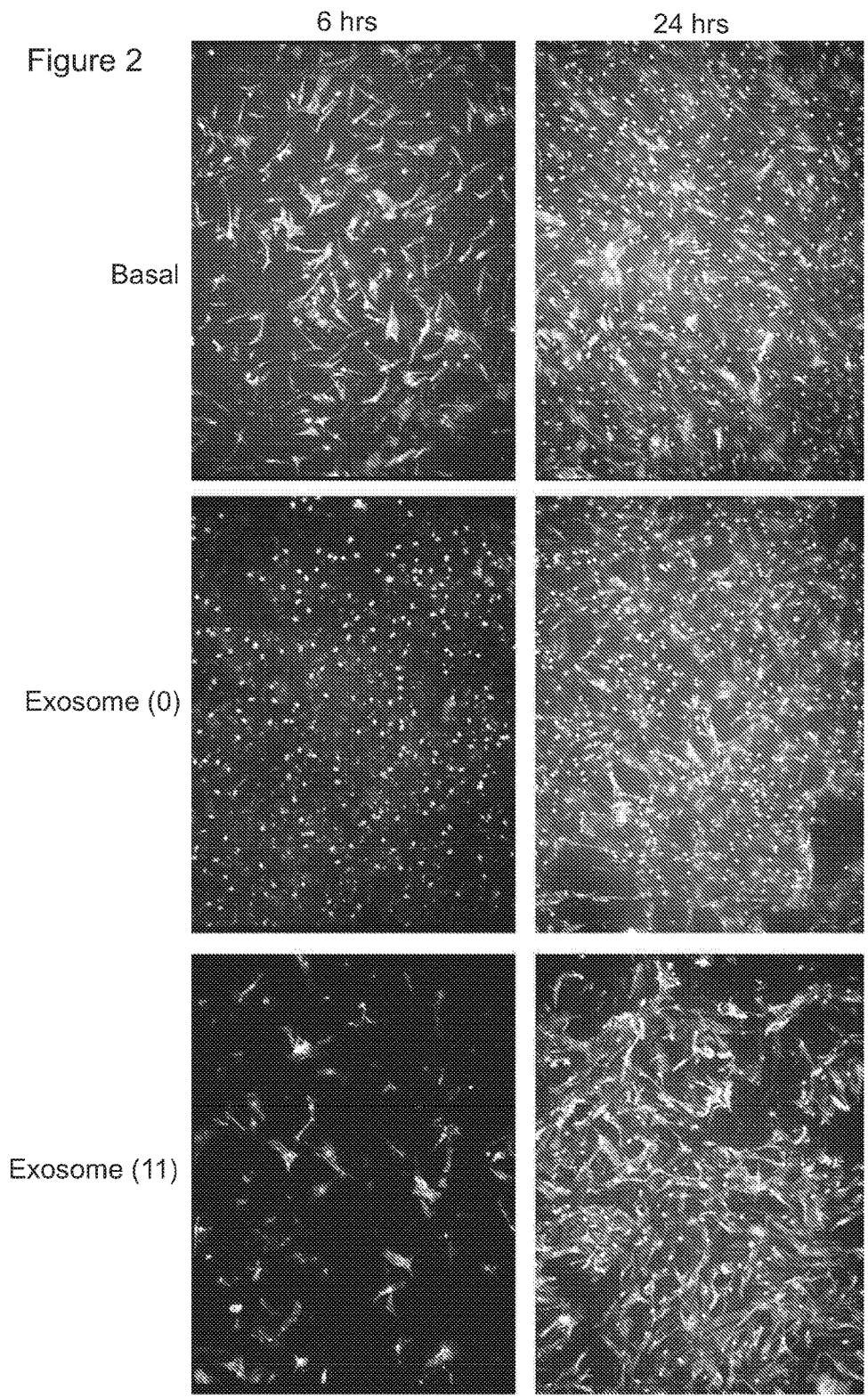

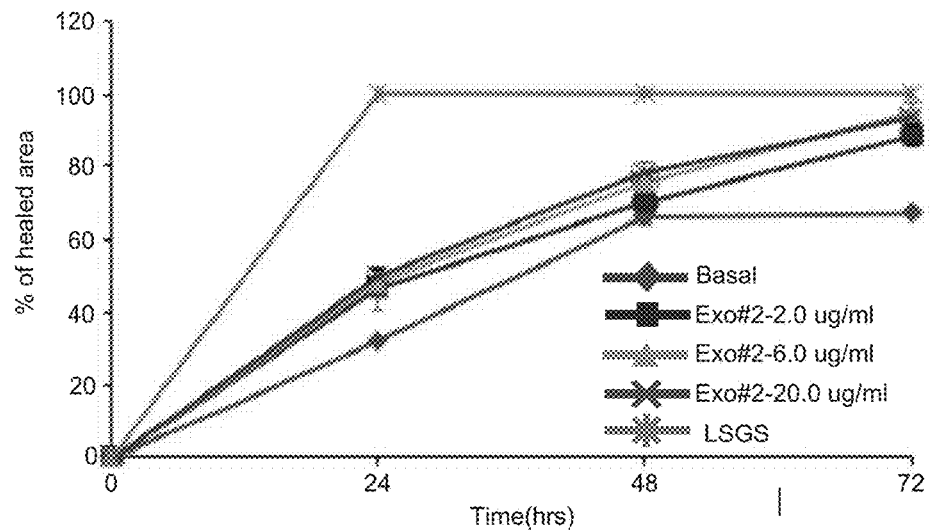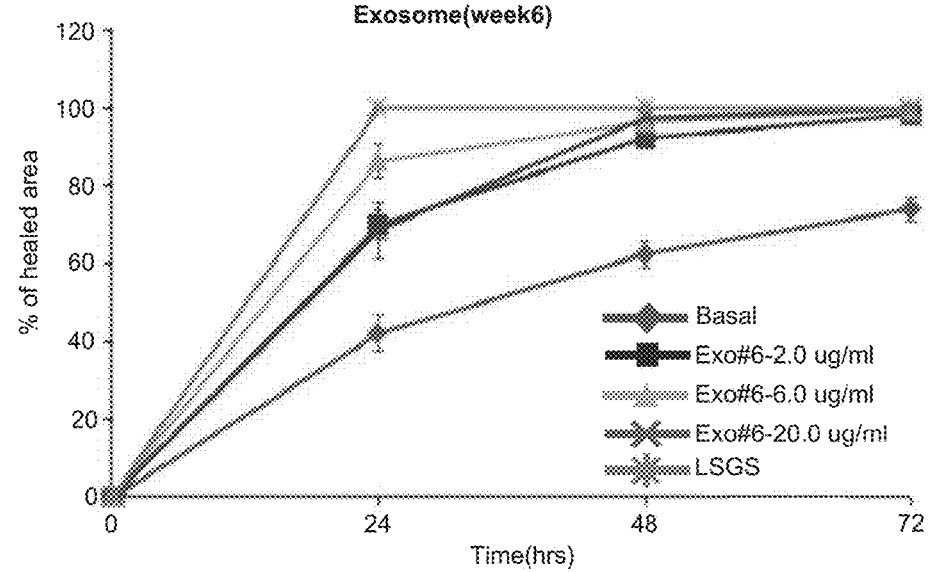
Figure 3C

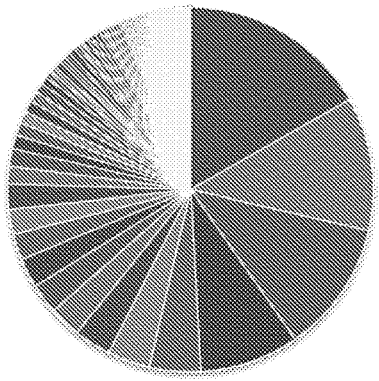
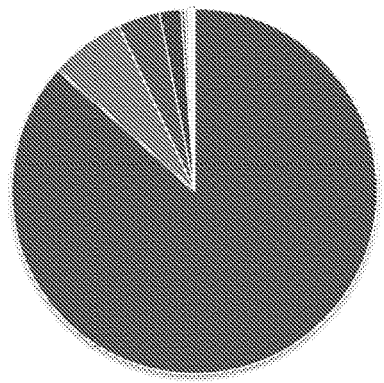
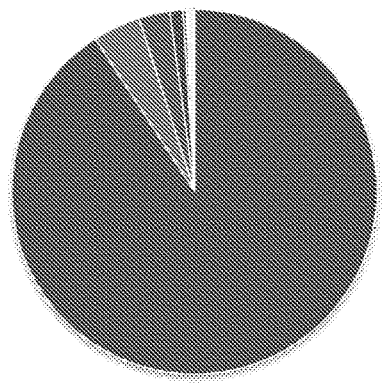
Figure 13A

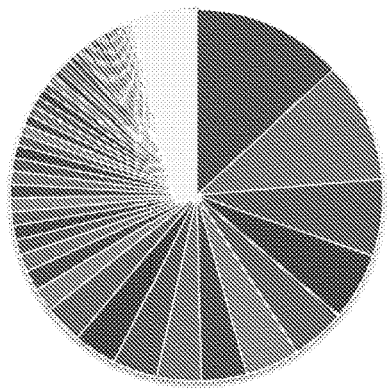
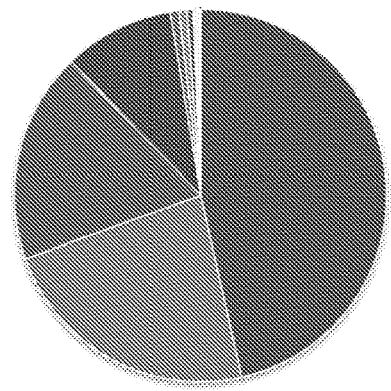
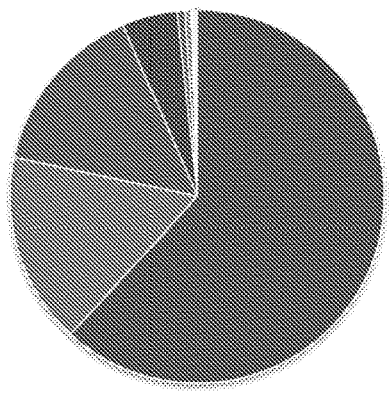
Figure 13B

Figure 13C
EXO 07EH
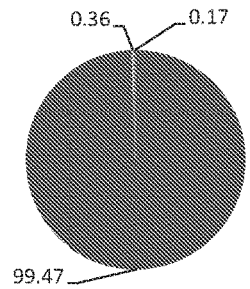
EXO 6W
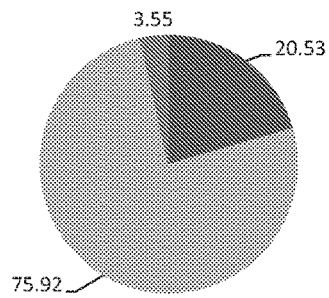
EXO1 W11       EXO2 W11       EXO3 W11
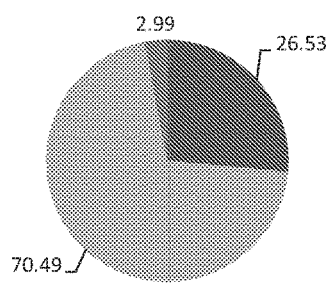 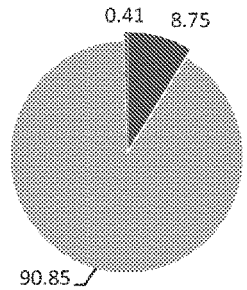 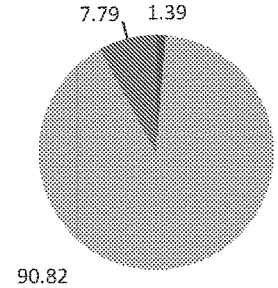

Figure 13D – Standard Culture
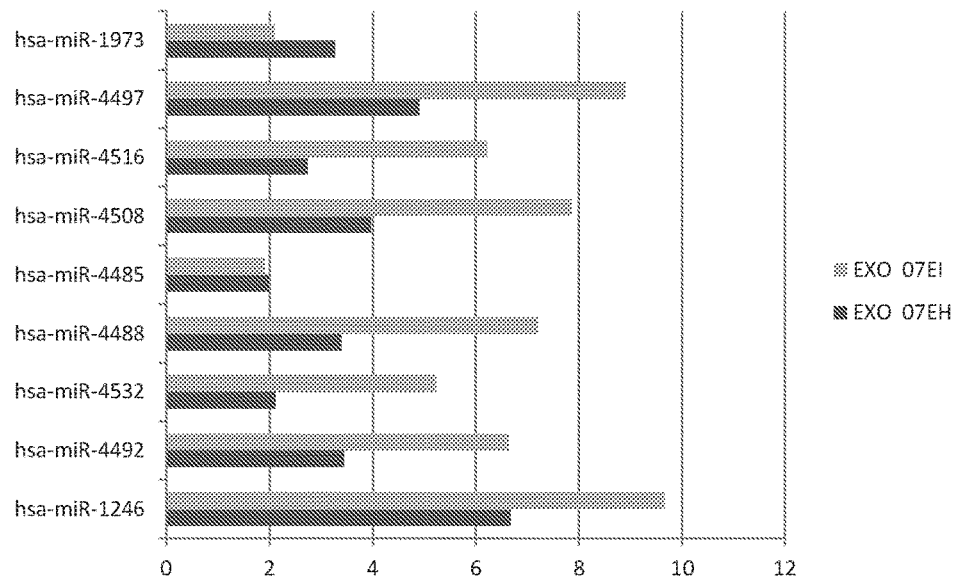
Figure 13E – Exo 6 Week
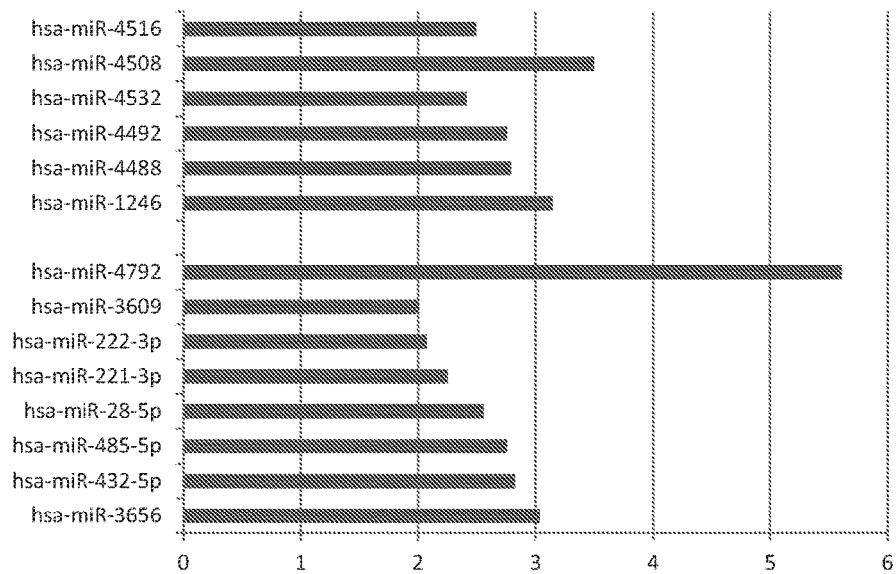

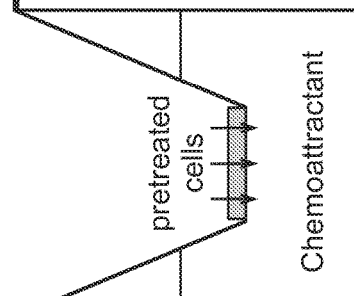
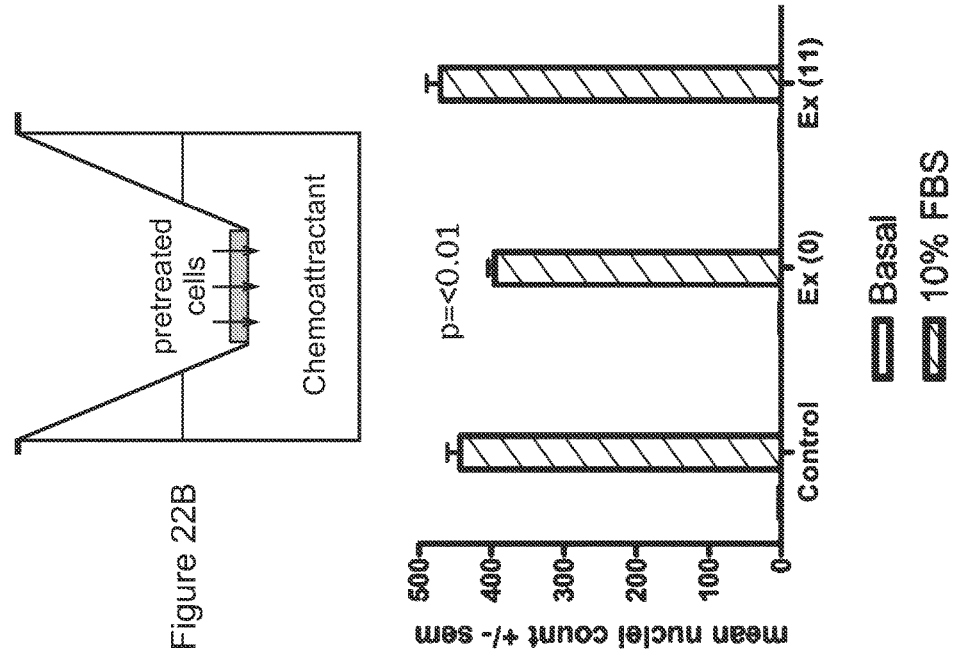
Figure 22B
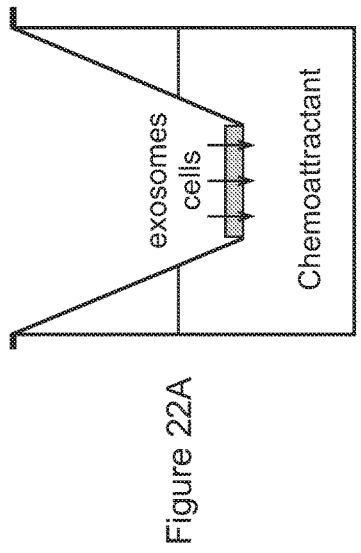
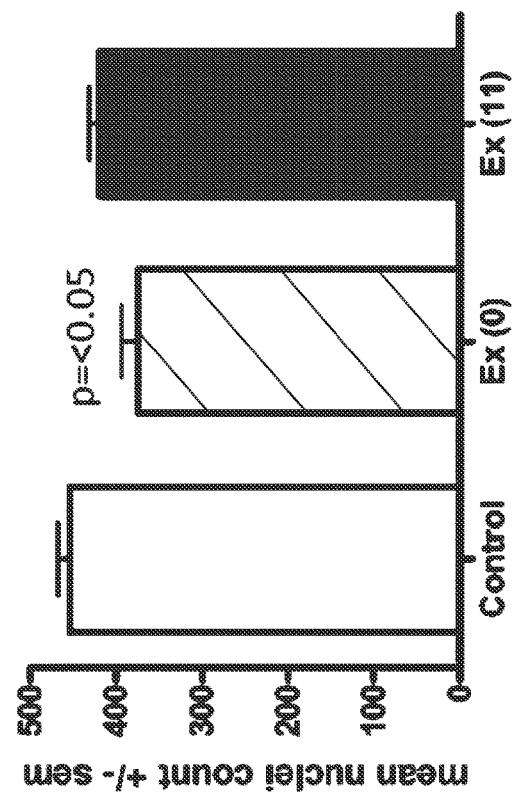
Figure 22A

Figure 22C
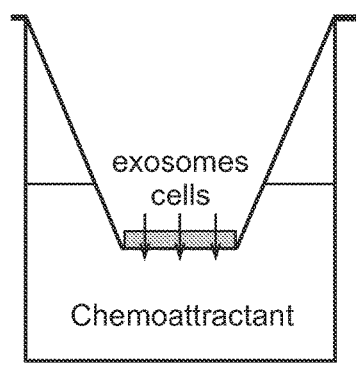
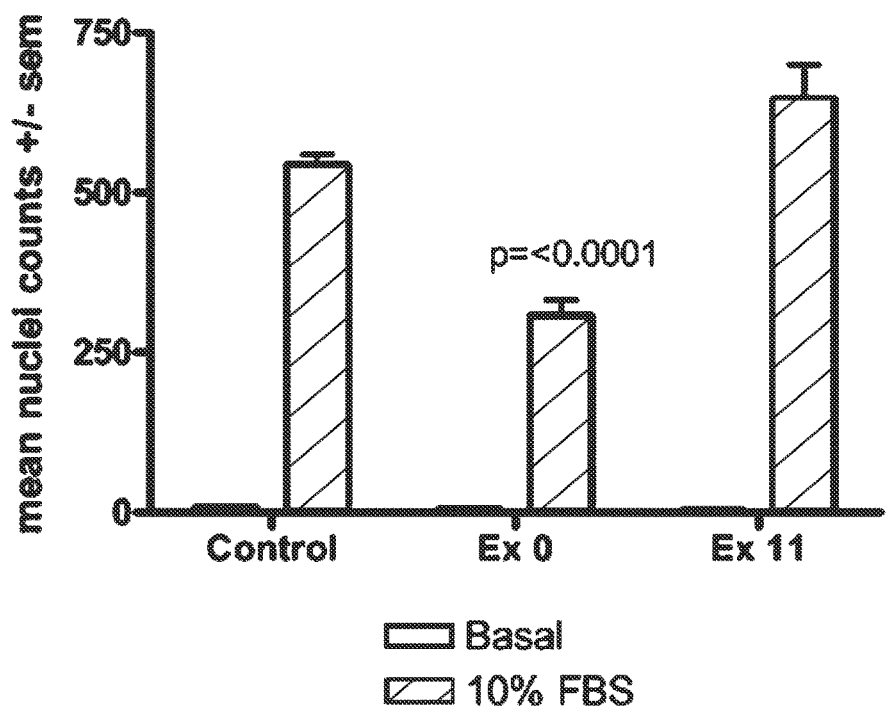

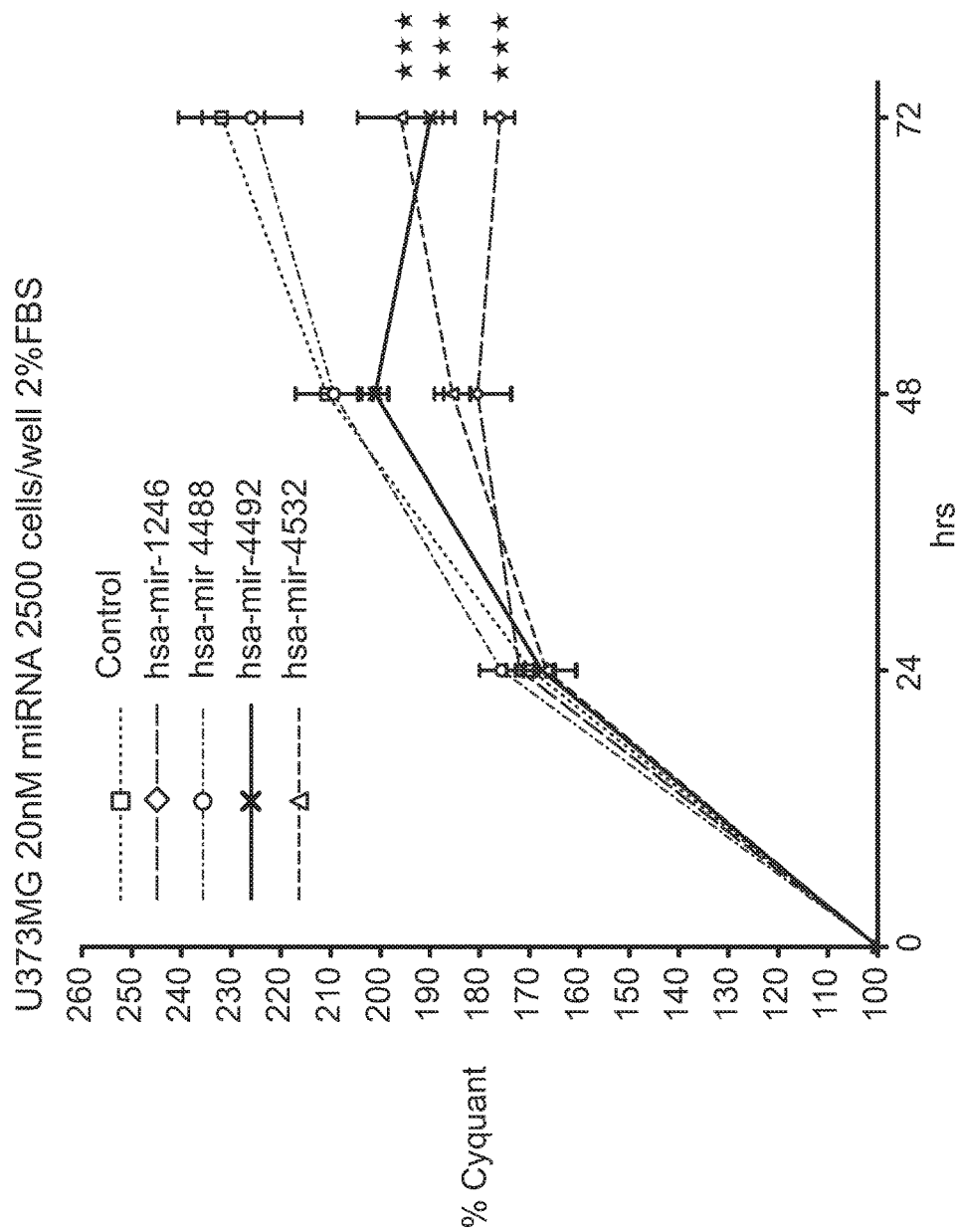

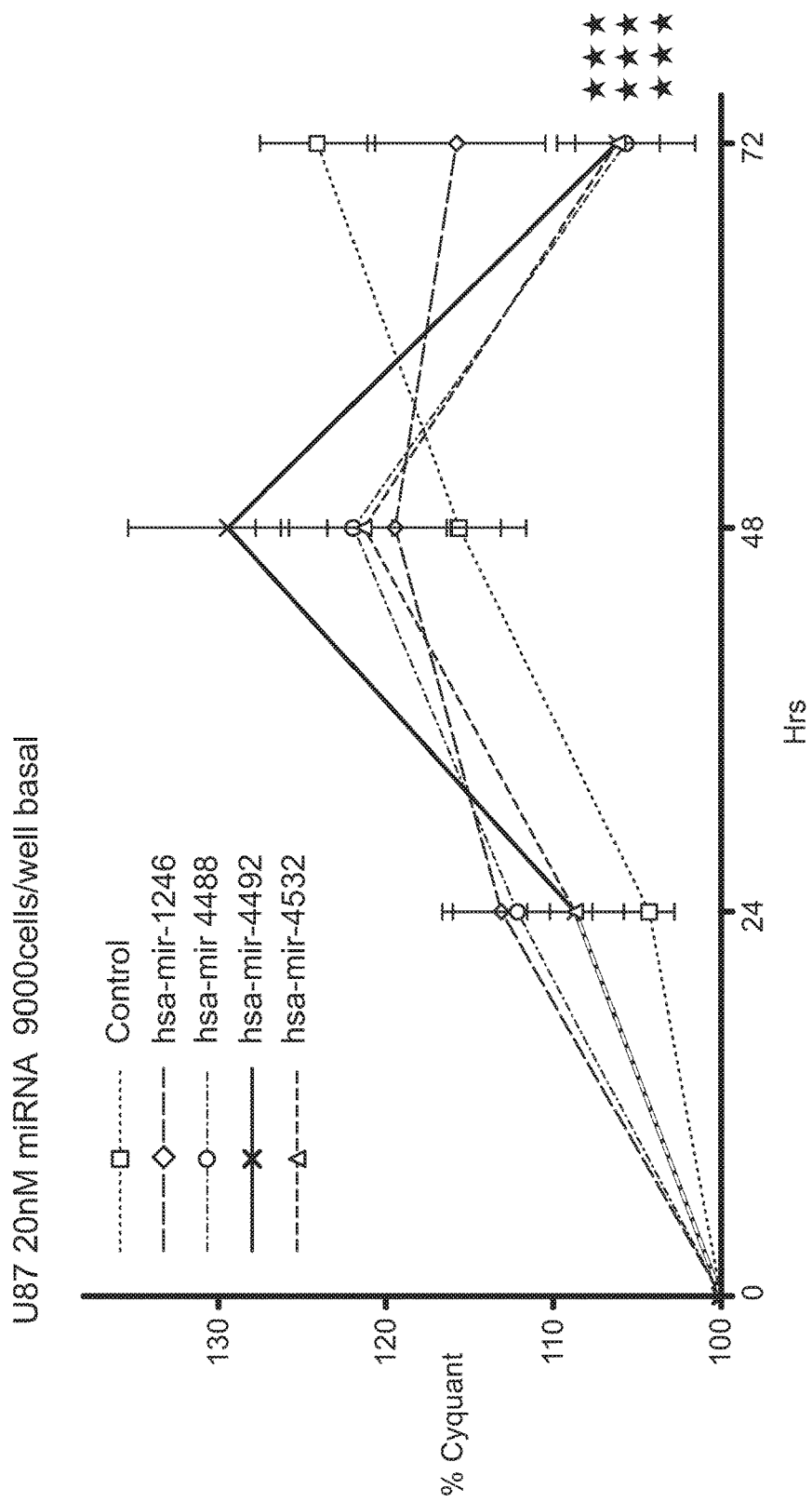

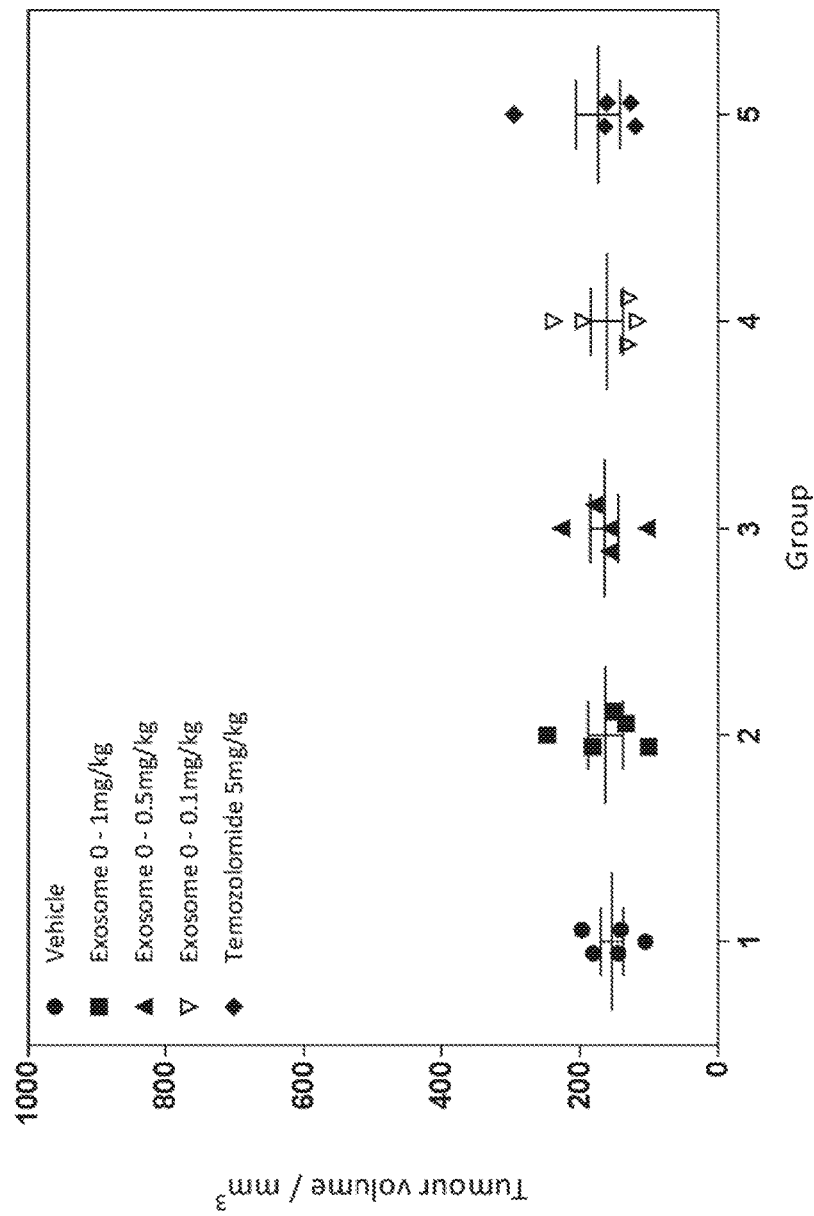

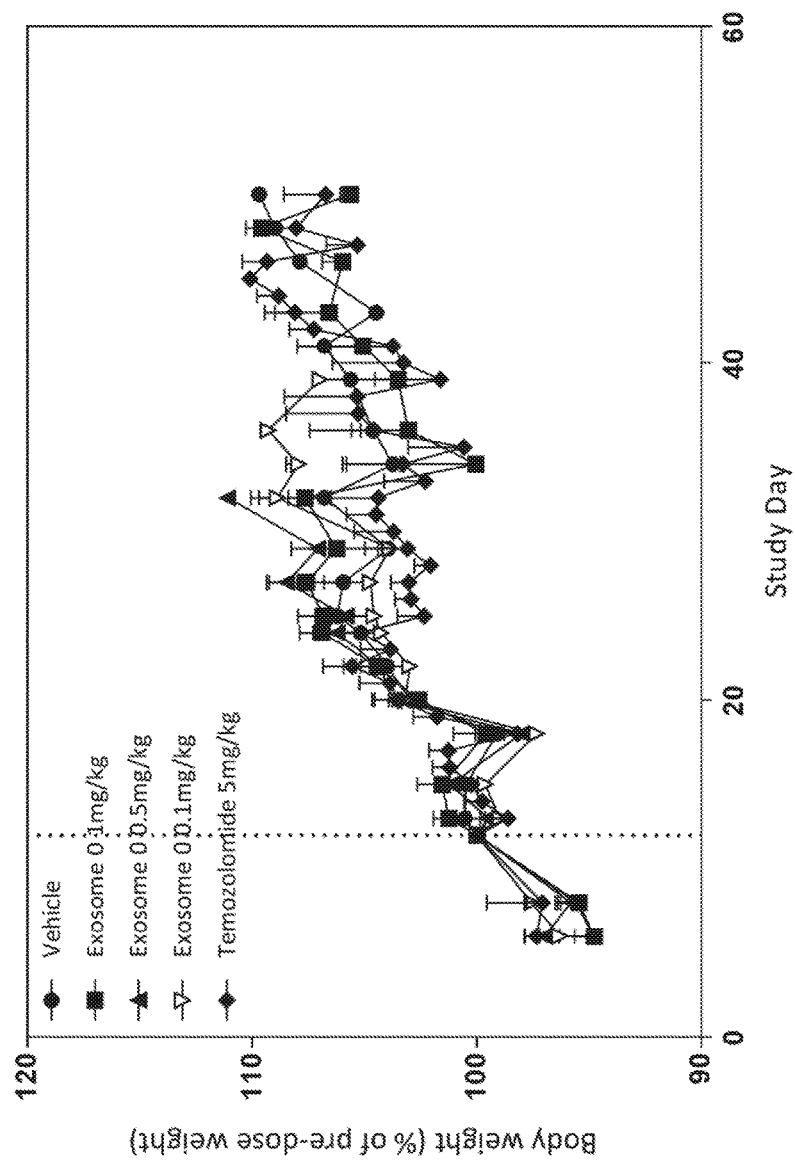

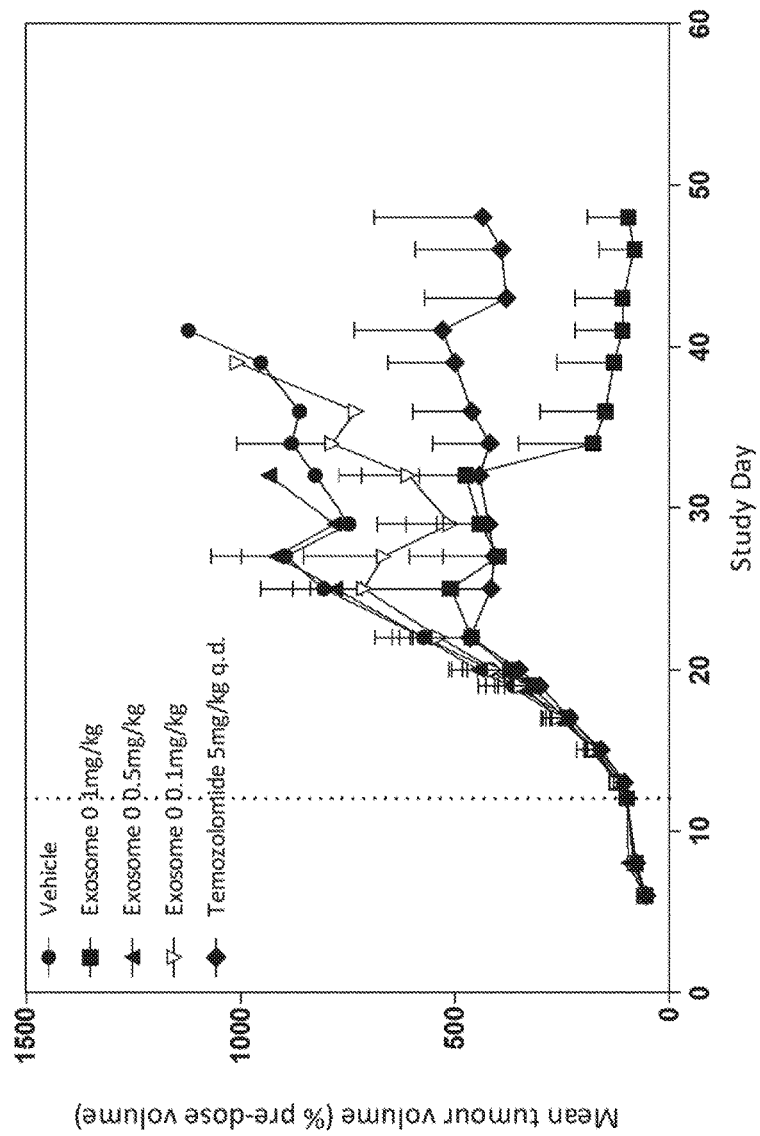

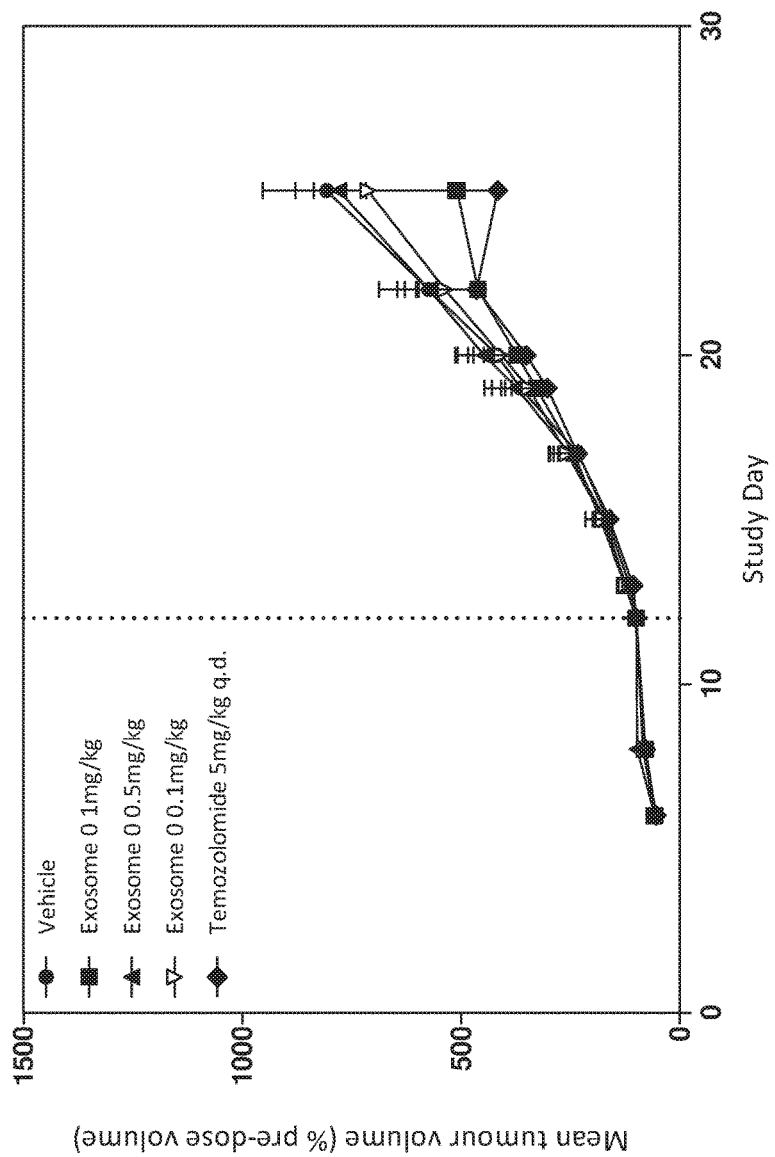
Figure 27: Mean tumour volume by study day – Day 25 truncated format

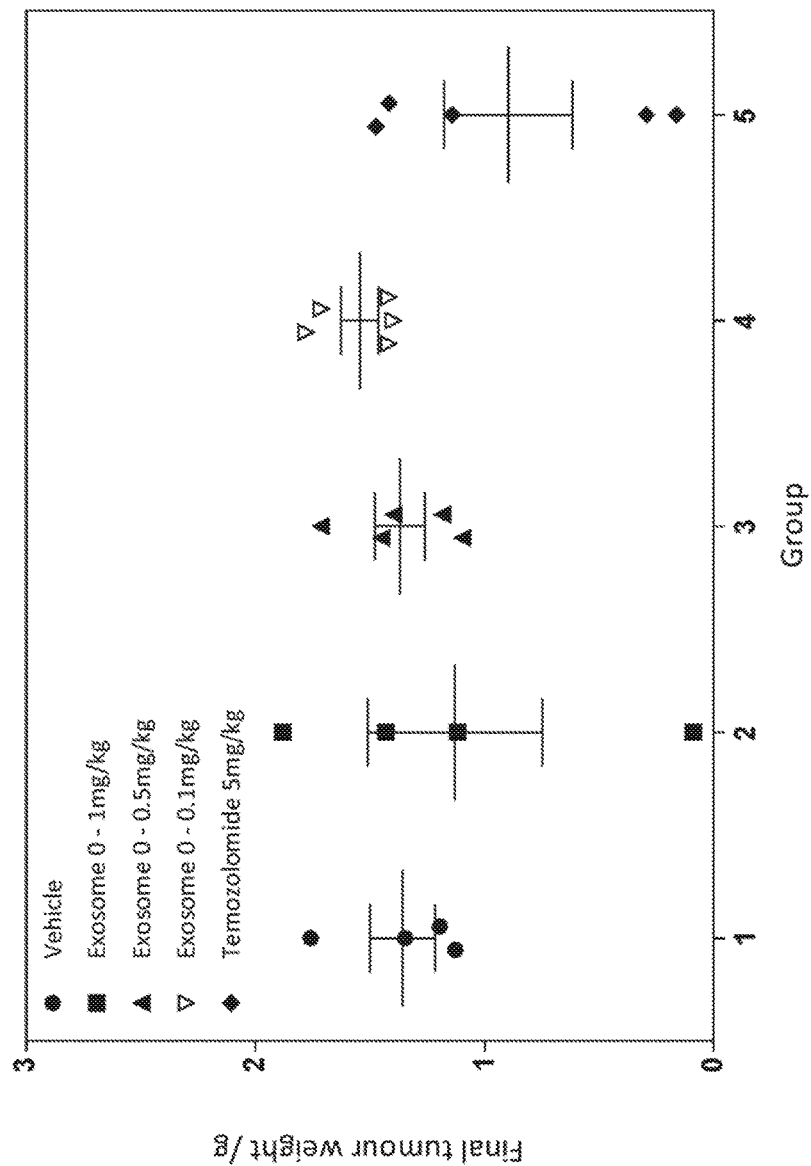
Figure 28: Final tumour weights

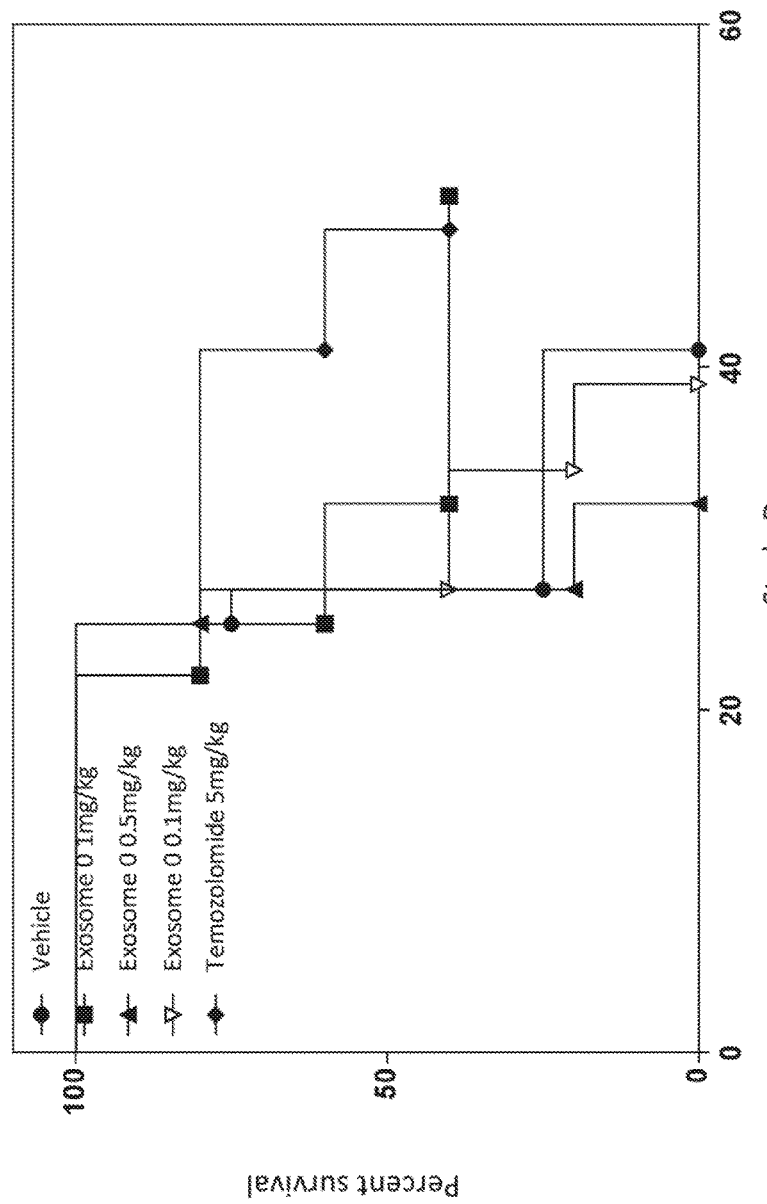
Figure 29: Survival plot for the dosing phase

Figure 30: Individual body weights – Absolute

Figure 31: Individual body weights – Relative

Figure 32: Individual tumour volume measurements

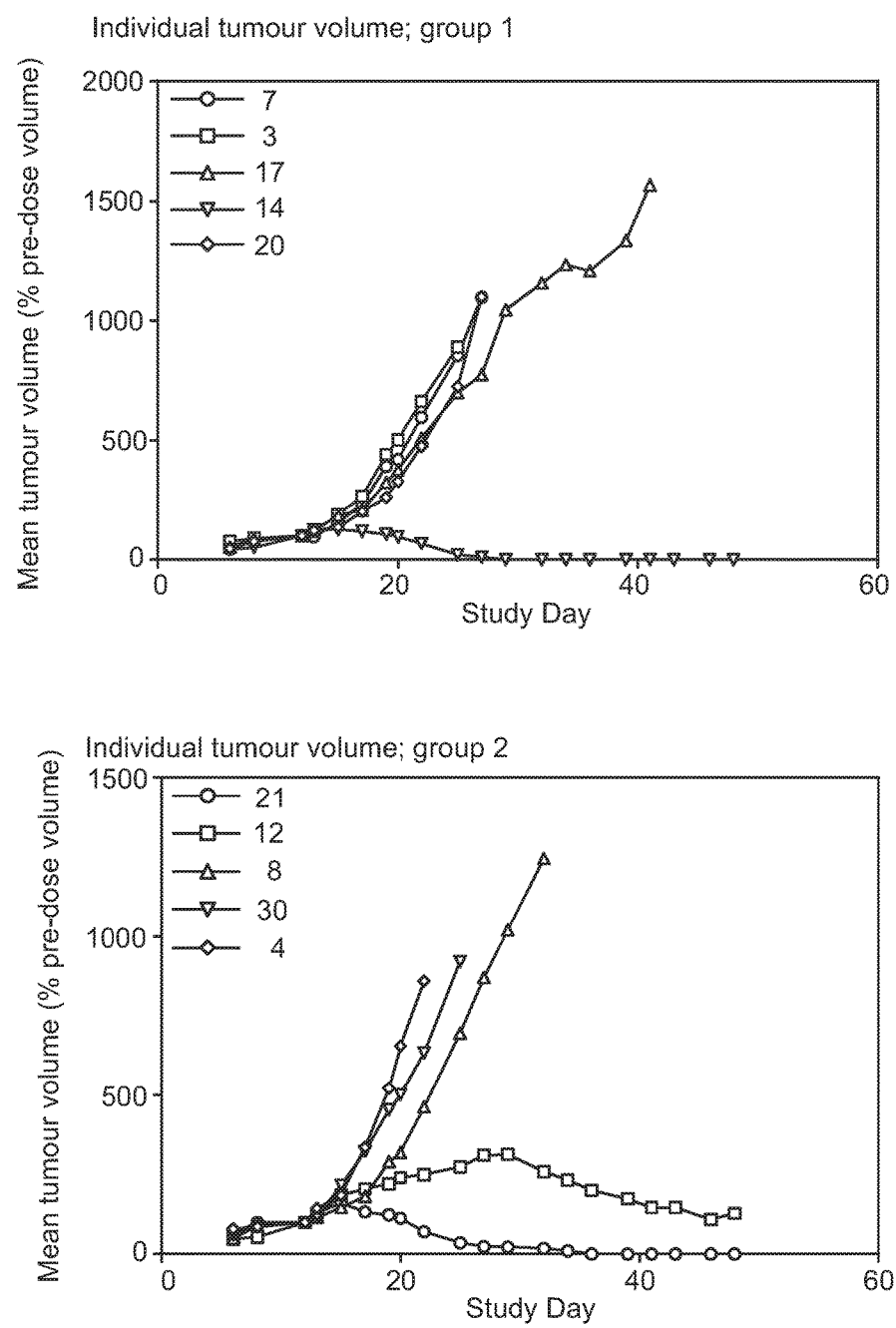
Figure 33: Individual group plots

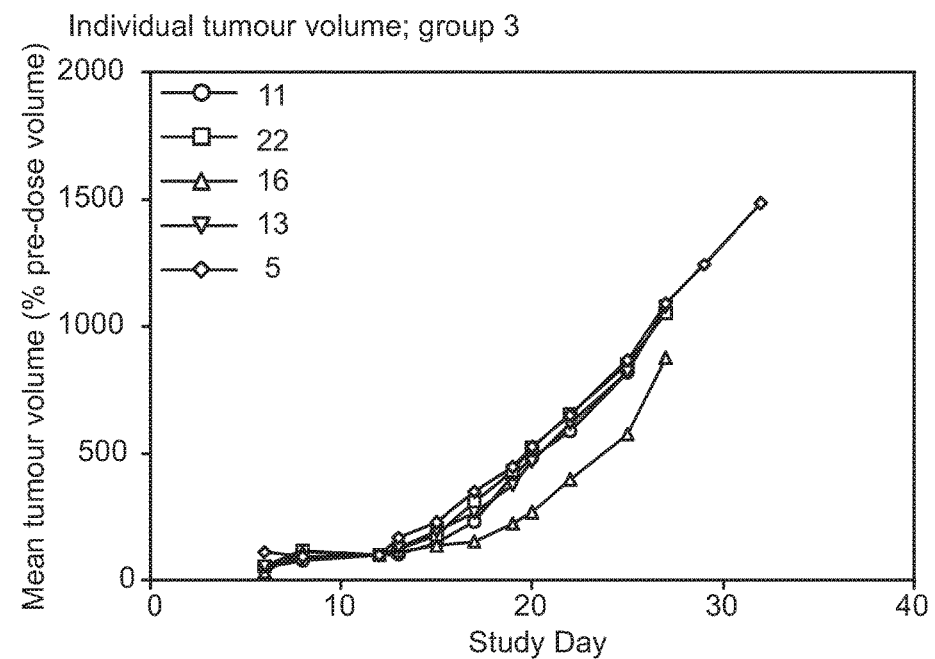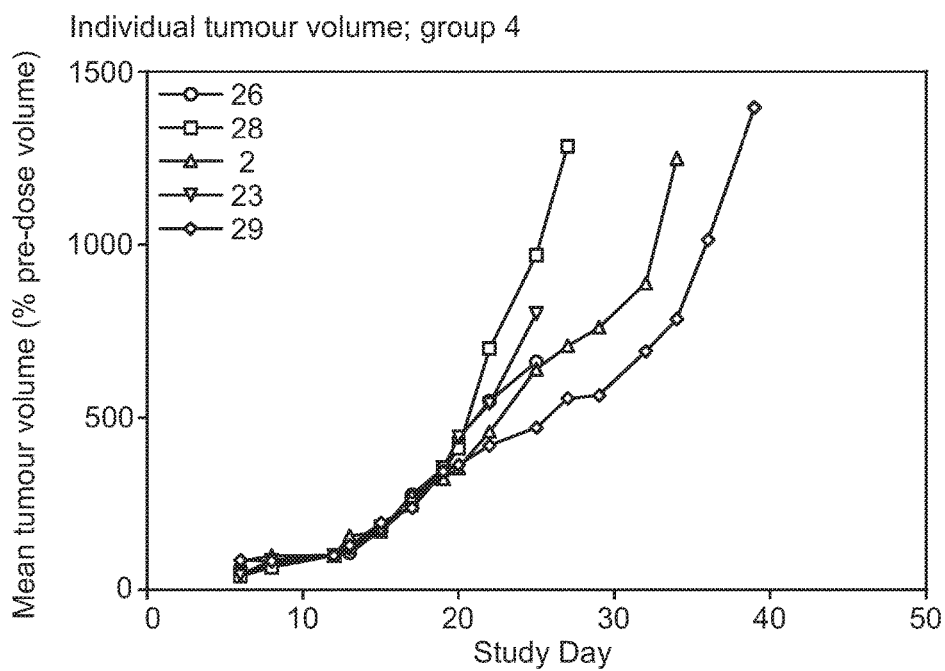
Figure 33(contd): Individual group plots

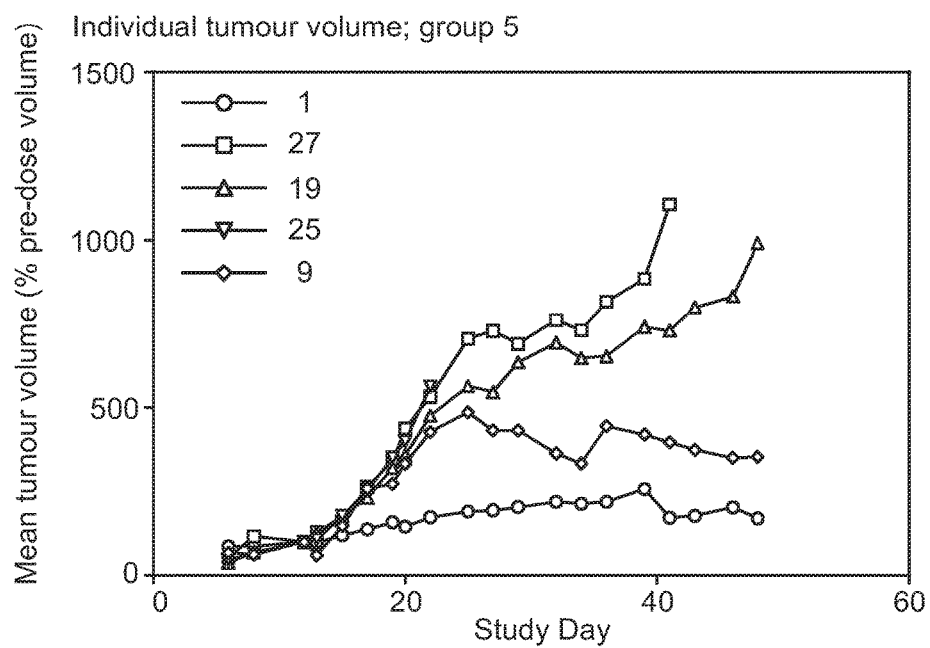
Figure 33(contd): Individual group plots

Figure 34: Tumour weight

| Group | Animal ID | Date | Day | Final Tumour Weight/ g | Endpoint |
|---|---|---|---|---|---|
| 1 | 00077E6CC9-7 | 21/05/2014 | 27 | 1.347 | Oversized tumour |
| 1 | 00077E7D9C-3 | 19/05/2014 | 25 | 1.761 | Oversized tumour |
| 1 | 00077E7ED6-17 | 04/06/2014 | 41 | 1.128 | Oversized tumour |
| 1 | 00077E7FDB-14 | 13/06/2014 | 50 | No tumour present | Study Termination |
| 1 | 00077E8B08-20 | 21/05/2014 | 27 | 1.197 | Oversized tumour |
| 2 | 00077E6AFE-21 | 13/06/2014 | 50 | No tumour present | Study Termination |
| 2 | 00077E6C4D-12 | 13/06/2014 | 50 | 0.091 | Study Termination |
| 2 | 00077E7EF9-18 | 26/05/2014 | 32 | 1.882 | Oversized tumour |
| 2 | 00077E8B5F-30 | 19/05/2014 | 25 | 1.432 | Oversized tumour |
| 2 | 00077E8C0D-4 | 16/05/2014 | 22 | 1.119 | Oversized tumour |
| 3 | 00077E6ABD-11 | 19/05/2014 | 25 | 1.717 | Oversized tumour |
| 3 | 00077E6B0F-22 | 21/05/2014 | 27 | 1.398 | Oversized tumour |
| 3 | 00077E6D43-16 | 21/05/2014 | 27 | 1.098 | Oversized tumour |
| 3 | 00077E7DF2-13 | 21/05/2014 | 27 | 1.45 | Oversized tumour |
| 3 | 00077E8C4C-5 | 26/05/2014 | 32 | 1.185 | Oversized tumour |
| 4 | 00077E6B73-26 | 19/05/2014 | 25 | 1.714 | Oversized tumour |
| 4 | 00077E6D2A-28 | 21/05/2014 | 27 | 1.399 | Oversized tumour |
| 4 | 00077E6D5A-2 | 28/05/2014 | 34 | 1.42 | Overszied tumour |
| 4 | 00077E6D6E-23 | 19/05/2014 | 25 | 1.42 | Oversized tumour |
| 4 | 00077E7DCC-29 | 02/06/2014 | 39 | 1.781 | Oversized tumour |
| 5 | 00077E6B14-1 | 13/06/2014 | 50 | 0.164 | Study Termination |
| 5 | 00077E6BD0-27 | 04/06/2014 | 41 | 1.474 | Oversized tumour |
| 5 | 00077E80AD-19 | 11/06/2014 | 48 | 1.418 | Oversized tumour |
| 5 | 00077E8A89-25 | 16/05/2014 | 22 | 1.143 | Oversized tumour |
| 5 | 00077E8CC4-9 | 13/06/2014 | 50 | 0.297 | Study Termination |

STEM CELL MICROPARTICLES AND MIRNA

CROSS-REFERENCE TO RELATED APPLICATIONS

This application is a national stage application under 35 U.S.C. § 371 of International Application No. PCT/GB2014/053044, filed Oct. 9, 2014, which in turn claims priority to United Kingdom Patent Application No. 1317887.6, filed Oct. 9, 2013, and International Application No. PCT/GB/2014/052509, filed Aug. 14, 2014, the content of each of which is hereby incorporated by reference into this application in its entirety.

FIELD OF THE INVENTION

This invention relates to stem cell microparticles and miRNA isolated from these microparticles, their use and production thereof, in particular neural stem cell microparticles and their use in therapy.

BACKGROUND OF THE INVENTION

Stem cells have the ability to self-renew and to differentiate into functionally different cell types. They have the potential to be a powerful therapeutic tool, for example in the growing field of Regenerative Medicine, in particular regenerative therapy requiring tissue replacement, regeneration or repair (Banerjee et al. 2011). Endogenous stem cells have also been implicated as targets (endogenous "cancer stem cells") of anti-cancer therapy, where it is proposed to treat the cancer by eliminating the cancer stem cells that are thought to drive cancer growth and metastasis. More recently, engineered mesenchymal stem cells have been proposed as delivery vehicles in anti-cancer therapy (Dai et al., 2011; Shah et al. 2012). However, there are drawbacks to the use of stem cells in therapy: there is a need for a consistent and substantial supply of stem cells with functional and phenotypic stability and the associated high costs and time delay caused by cell generation, storage, transport and handling; there is a requirement for immunological compatibility to avoid rejection of the stem cells by the recipient; and there are complex regulatory issues related to potential safety risks of tumour or ectopic tissue formation. Further, despite the therapeutic efficacy of stem cell transplantation, there is no convincing evidence for a direct long-term effect of the transplanted stem cells, for example through engraftment and differentiation into reparative or replacement cells.

Neural stem cells (NSCs) are self-renewing, multipotent stem cells that generate neurons, astrocytes and oligodendrocytes (Kornblum, 2007). The medical potential of neural stem cells is well-documented. Damaged central nervous system (CNS) tissue has very limited regenerative capacity so that loss of neurological function is often chronic and progressive. Neural stem cells (NSCs) have shown promising results in stem cell-based therapy of neurological injury or disease (Einstein et al. 2008). Implanting neural stem cells (NSCs) into the brains of post-stroke animals has been shown to be followed by significant recovery in motor and cognitive tests (Stroemer et al. 2009). It is not completely understood how NSCs are able to restore function in damaged tissues but it is now becoming increasingly recognised that NSCs have multimodal repairing properties, including site-appropriate cell differentiation, pro-angiogenic and neurotrophic activity and immunomodulation promoting tissue repair by the native immune system and other host cells (Miljan & Sinden, 2009, Horie et al., 2011). It is likely that many of these effects are dependent on transient signalling from implanted neural stem cells to the host milieu, for example NSCs transiently express proinflammatory markers when implanted in ischaemic muscle tissue damage which directs and amplifies the natural pro-angiogenic and regulatory immune response to promote healing and repair (Katare et al., Clinical-grade human neural stem cells promote reparative neovascularization in mouse models of hindlimb ischemia. Arteriosclerosis, Thrombosis and Vascular Biology, vol 34, no. 2, pp. 408-418). In chronic stroke brain, NSCs also have a substantial neurotrophic effect. For example, they promote the repopulation of the stoke-damaged striatal brain tissue with host brain derived doublecortin positive neuroblasts (Hassani, O'Reilly, Pearse, Stroemer et al., PLoS One. 2012; 7(11)).

Furthermore, on the basis of a large body of NSC restorative effects in animal models with chronic stroke, a clinical trial using neural stem cells is being carried out by ReNeuron Limited (Surrey, UK), to trial the treatment of disabled stroke patients using its "CTX0E03" conditionally-immortalised cortex-derived neural stem cells (Clinicaltrials.gov Identifier: NCT01151124).

Mesenchymal stem cells (MSCs) are lineage-restricted stem cells which have the potential to differentiate into mesenchymal cell types only, namely of the adipocytic, chondrocytic and osteocytic lineages (Pittenger et al. 1999; Ding et al. 2011). MSCs (also referred to as Mesenchymal Stromal Cells and Mesenchymal Progenitor Cells) are derived from a variety of sources including bone marrow, blood, adipose and other somatic tissues. The therapeutic potential of MSCs, however, is more directed towards the application of their pro-angiogenic and immune modulating properties as undifferentiated cells. Production of human MSCs is limited by the inability of these cells to expand in numbers stably beyond approximately 15-20 population doublings.

Mesenchymal stem cell-conditioned medium (MSC-CM) has a therapeutic efficacy similar to that of MSCs themselves, suggesting a paracrine mechanism of MSC-based therapy (Timmers et al. 2007). WO-A-2009/105044 discloses that particles known as exosomes, secreted by MSCs, comprise at least one biological property of the MSCs and suggests the use of these MSC particles in therapy, while Théry et al. 2011 provides a general review of exosomes and other similar secreted vesicles. Whereas some of the drawbacks of using stem cells directly as therapeutic agents are overcome by using the mesenchymal stem cell-derived exosomes (e.g. storage, transport and handling), the problem remains of providing a consistent and substantial supply of functionally and phenotypically stable stem cells to produce the exosomes. For therapeutic use, the exosomes preferably need to be produced on a large scale. In the absence of a stem cell line, replenishment of the cells through repeated derivation from a source of stem cells is required, which incurs recurring costs for testing and validation of each new batch. Furthermore, the diseases and disorders that can be treated by MSCs may be limited.

WO-A-2013/150303 and WO-A-2014/013258 disclose microparticles produced by neural stem cells, methods for making those microparticles and uses of those microparticles, in particular for use in regenerative therapy.

There remains a need for improved stem cell-based therapies.

SUMMARY OF THE INVENTION

The present invention is based on the surprising finding that neural stem cells contain microparticles that are therapeutically useful, and that neural stem cell microparticles can be used in the therapy of diseases including fibrosis, cancer, rheumatoid arthritis, atherosclerosis, or unwanted or undesirable angiogenesis.

In particular, the inventors have surprisingly identified neural stem cell microparticles that are able to: inhibit cell migration of fibroblasts; inhibit migration of cancer cells; induce differentiation of cancer cells; and/or induce or enhance an immune response against cancer cells. These properties make the neural stem cell microparticles suitable for use in therapy, in particular for treating cancer. The cancer may be a nestin-positive cancer. The cancer may be glioma, melanoma, breast cancer, pancreatic cancer or prostate cancer.

Cell migration is well-known to play an important role in the progression of diseases such as cancer (for example during angiogenesis, tumour formation, metastasis and tissue invasion), fibrosis (for example during the accumulation of fibroblasts in the fibrotic tissue), atherosclerosis and rheumatoid arthritis. Microparticles that inhibit cell migration are therefore useful in the treatment or prevention of diseases that involve unwanted cell migration, such as cancer, in particular metastatic cancer, fibrosis, atherosclerosis and rheumatoid arthritis.

Microparticles of the invention are shown, in the Examples, to inhibit fibroblast migration. Fibroblasts and the migration of fibroblasts are known to play a role in angiogenesis and so the microparticles of the invention, which inhibit fibroblast migration, are also useful for use in the therapy of unwanted or undesirable angiogenesis.

Additionally, the Examples show that glioblastoma cells, pre-treated in vitro for 24 hours with neural stem cell exosomes did not engraft into the striatum of Balb-C mice in vivo.

Histopathology demonstrated the presence of necrotic cell bodies at the site of implantation and evidence of a host cellular response. These data indicate that these microparticles are suitable for use in the treatment of cancer, particularly a cancer of the CNS such as a glioblastoma, by promoting the destruction of cancer cells by the immune system.

Neural stem cell microparticles that are able to inhibit fibroblast cell migration and induce or enhance an immune response against cancer cells have been isolated from neural stem cells cultured in a multi-compartment bioreactor for 11 weeks. Accordingly, one way to obtain these neural stem cell microparticles is to isolate them from neural stem cells that have been cultured in a multi-compartment bioreactor for at least 10 weeks, for example 71 days or more. The microparticles of the invention may also be obtained from other culture conditions and periods, in particular culture conditions that allow stem cell differentiation.

The Examples further show that tumour (glioblastoma U373) cells show significantly reduced migration when treated with neural stem cell microparticles. The microparticles of the invention may therefore be used to treat cancer, particularly a cancer of the CNS such as a glioblastoma, by inhibiting tumour cell migration.

Additionally, neural stem cell exosomes are shown in the Examples to promote differentiation of tumour (glioblastoma U373) cells in vitro. The Examples also show this differentiation in vivo, where tumour (glioblastoma U373) cells, treated with neural stem cell exosomes and implanted into mouse brains, demonstrate a reduction in the stem cell marker nestin. Cancer stem cells drive tumourigenesis, are linked with metastasis, high grade and poor prognosis. A more differentiated tumour typically correlates with improved prognosis, so exosomes that are able to effect differentiation are expected to be useful in the treatment of cancer. Therefore, the ability of microparticles isolated from neural stem cells to reduce the stemness of cancer cells indicates that these microparticles are useful in the treatment of cancer, in particular a cancer that is positive for nestin expression such as melanoma, breast cancer or glioblastoma. Typically, the cancer is a cancer of the CNS such as a glioblastoma. Nestin is reported to correlate with aggressive growth, metastasis, and poor prognosis in cancers, so agents that reduce nestin expression are greatly needed. Neural stem cell microparticles that are able to inhibit tumour cell migration and promote differentiation of tumour cells have been isolated from a neural stem cell line cultured under standard conditions. Accordingly, one way to obtain neural stem cell microparticles that are able to inhibit tumour cell migration and promote differentiation of tumour cells is to isolate them from neural stem cells that have been cultured under standard conditions. These cells may be from the CTX0E03 cell line (deposited with the ECACC as Accession No. 04091601). The standard culture conditions typically maintain the characteristics of the cell line, in particular the stemness of the cell line, typically do not permit differentiation, and typically provides proliferating cells. Typically, the cells proliferate with a doubling time of 2 to 4 days and are passaged when sub-confluent.

The Examples include a pilot in vivo study of the administration of microparticles of the invention to human glioblastoma xenografts, observing tumour sensitivity to the microparticles, a trend towards a reduction in tumour volume, and increased survival. Histopathology of the tumour cells shows, in one animal, a particularly dramatic and effective ablation of the tumour mass.

The Examples also provide Next Generation Sequence (NGS) analysis of the miRNA content of neural stem cell exosomes. One of the Examples revealed the presence of a set of miRNAs: hsa-mir-1246, hsa-mir-4488, hsa-mir-4492, and hsa-mir-4532, each of which is shown to reduce glioma cell proliferation. These data provide further evidence that microparticles containing the miRNAs may be used to treat cancer. These data also demonstrate that the various miRNAs identified in the Examples (as present in neural stem cell microparticles) have therapeutic utility themselves—alone or in combination with other identified miRNAs.

A first aspect of the invention provides a neural stem cell microparticle that: inhibits cell migration, typically fibroblast migration or cancer cell migration; and/or induces differentiation of a stem or cancer cell, typically a cancer cell that is positive for nestin expression such as a melanoma cell, breast cancer cell or glioblastoma cell. In one embodiment, the neural stem cell microparticle inhibits angiogenesis. In another embodiment, the microparticle promotes destruction of tumour cells by inducing or enhancing an immune response against the tumour cells.

The microparticle may be an exosome, microvesicle, membrane particle, membrane vesicle, exosome-like vesicle, ectosome-like vesicle, ectosome or exovesicle. Typically, the microparticle is an exosome. The microparticle may be derived from a neural stem cell that has been cultured in an environment that allows stem cell differentiation. The microparticle may or may not be isolated from partially-differentiated neural stem cells; as discussed below, the presence of GFAP (an astrocyte marker) or DCX (an early neuronal marker) on the cells indicates that the neural stem cells have begun to differentiate. In one embodiment, an environment that allows stem cell differentiation is a multi-compartment bioreactor. The microparticle may be isolated from neural stem cells that have been cultured in a multi-compartment bioreactor for at least 10 weeks. The microparticle may be isolated from cultured neural stem cells that have been confluent on the membrane of a multi-compartment bioreactor for at least one week, at least 2 weeks, typically at least 3 weeks, at least 4 weeks, at least 5 weeks or more. Conversely, microparticles can be produced from neural stem cells that have not begun to differentiate, for example by isolation from sub-confluent cultured neural stem cells, or by isolation from cells that have been confluent for less than one week on the membrane of a multi-compartment bioreactor or in a standard cell culture flask such as a T-175 flask. As used herein, the term "confluent" is given its usual meaning in the art, wherein the cells in the culture are all in contact and have no further room to grow; confluent cells cover substantially all of the membrane in the multi-compartment bioreactor.

The microparticle may be derived from a neural stem cell line. In some embodiments, the neural stem cell line may be the "CTX0E03" cell line, the "STR0CO5" cell line, the "HPC0A07" cell line or the neural stem cell line disclosed in Miljan et al Stem Cells Dev. 2009. In some embodiments, the microparticle is derived from a stem cell line that does not require serum to be maintained in culture. The microparticle may have a size of between 30 nm and 1000 nm, or between 30 and 200 nm, or between 30 and 100 nm, as determined by electron microscopy; and/or a density in sucrose of 1.1-1.2 g/ml. The microparticle may comprise RNA. The RNA may be mRNA, miRNA, and/or any other small RNA. The microparticle may comprise one, two, three or four of hsa-miR-1246, hsa-miR-4492, hsa-miR-4488 and hsa-miR-4532; alternatively, it may comprise 1, 2, 3, 4 or 5 of hsa-miR-181a-5p, hsa-miR-1246, hsa-miR-127-3p, hsa-miR-21-5p and hsa-miR-100-5p; or it may comprise 1, 2, 3, 4 or 5 of hsa-miR-181a-5p, hsa-let-7a-5p, hsa-let-7f-5p, hsa-miR-92b-3p, and hsa-miR-9-5p. The microparticle may comprise one or more lipids, typically selected from ceramide, cholesterol, sphingomyelin, phosphatidylserine, phosphatidylinositol, phosphatidylcholine. The microparticle may comprise one or more tetraspanins, typically CD63, CD81, CD9, CD53, CD82 and/or CD37. The microparticle may comprise one or more of TSG101, Alix, CD109, thy-1 and CD133. The microparticle may comprise at least 10 of the proteins present in Table 20 or Table 22. The microparticle may comprise at least one biological activity of a neural stem cell or a neural stem cell-conditioned medium. At least one biological activity may be an anti-cell migration activity, a pro-differentiation activity or an anti-angiogenic activity. The microparticle of the invention is typically isolated or purified.

A second aspect of the invention provides the neural stem cell microparticle of the first aspect, for use in therapy. The therapy may be of a disease requiring inhibition of cell migration, such as cancer, fibrosis, atherosclerosis or rheumatoid arthritis. The therapy may also be of a disease requiring inhibition of angiogenesis, such as treating a solid tumour by inhibiting angiogenesis. When the disease to be treated is a cancer, it may be a cancer of the CNS, such as a glioma, meningioma, pituitary adenoma or a nerve sheath tumour. An exemplary CNS cancer is a glioblastoma, which may be a giant cell glioblastoma or a gliosarcoma.

In one embodiment, the neural stem cell microparticle is used to treat cancer. In one embodiment, the microparticles of the invention treat the cancer by inhibiting angiogenesis. This is typically useful in treating solid tumours.

In a further embodiment, the microparticles of the invention treat the cancer by inhibiting migration of the cancer cells.

In yet a further embodiment, the microparticles of the invention treat the cancer by inducing differentiation of cancer cells. Typically, differentiation is induced in cancer cells that express nestin.

In another embodiment, the microparticles of the invention treat the cancer by inducing or enhancing an immune response against the cancer cells. When the cancer is a CNS cancer, the immune response typically comprises the activation and/or proliferation of glial cells such as microglia.

In one embodiment, the therapeutic microparticle is an exosome isolated from neural stem cells that have been cultured in a multi-compartment bioreactor for at least 10 weeks. In another embodiment, the therapeutic microparticle is a microvesicle isolated from neural stem cells that have been cultured in the multi-compartment bioreactor for at least 10 weeks.

In an alternative embodiment, the therapeutic microparticle is an exosome isolated from proliferating neural stem cells that have been cultured under conditions that typically maintain the characteristics of the cell line, in particular the stemness of the cell line. These are typically the standard culture conditions for a given cell or cell line, which do not permit differentiation of the stem cells. Typically, proliferating cells have a doubling time of 2 to 4 days. These neural stem cells are typically passaged when sub-confluent.

The therapy may also be a prophylactic therapy to induce tolerance, typically immunotolerance, in a host that is subsequently, concurrently or simultaneously to receive the stem cells from which the microparticle is derived. The administration of one or more doses of microparticles of the invention to a patient, prior to or concurrent with administration of a stem cell therapy, can be used to reduce the risk of an adverse immune response, i.e. "rejection", of the stem cell therapy.

A third aspect of the invention provides the use of the neural stem cell microparticle of the first aspect, in the manufacture of a medicament for the treatment of a disease. Typically, the disease is cancer.

It has also been found that it is possible to alter the production of microparticles by stem cells, by culturing the stem cells (optionally for at least 10 weeks) and adding components to the culture medium, by culturing the stem cells (optionally for at least 10 weeks) under hypoxic conditions, or by co-culture with other cell types (optionally for at least ten weeks), thereby providing an improved method of producing stem cell microparticles.

Accordingly, a fourth aspect of the invention provides a method of producing a stem cell microparticle that inhibits cell migration, typically a neural stem cell microparticle that inhibits cell migration. The stem cells may be cultured under conditions that allow the efficient removal of metabolic waste. The method may comprise culturing the stem cells for at least 10 weeks in an environment that allows stem cell differentiation and collecting the microparticles that are produced by the cells; microparticles produced by this method are typically able to inhibit fibroblast migration. The microparticles may be isolated from partially-differentiated neural stem cells. In one embodiment, an environment that allows stem cell differentiation is culture in a multi-compartment bioreactor, typically for a prolonged period of time, for example more than seven days and usually more than ten weeks.

The method may alternatively comprise culturing the cells under conditions that do not allow differentiation to occur, and collecting the microparticles that are produced by the cells; microparticles produced by this method are typically able to inhibit glioblastoma migration.

The method may comprise isolating a microparticle from a stem cell-conditioned medium. The stem cell-conditioned medium may comprise one or more additive components or agents which stimulate the release of microparticles by the stem cells into the medium. The one or more components may be selected from transforming growth factor-beta (TGF-β), interferon-gamma (IFN-γ) and/or tumour necrosis factor-alpha (TNF-α). The microparticles may be isolated from stem cell-conditioned medium wherein the stem cells were cultured under hypoxic conditions. The microparticles may be isolated from stem cell-conditioned medium produced by stem cells co-cultured with a different cell type, typically endothelial cells, in order to create the NSC niche environment.

A fifth aspect of the invention provides a microparticle obtainable by a method according to the fourth aspect of the invention.

A sixth aspect of the invention provides a composition comprising a neural stem cell microparticle according to the first aspect and a pharmaceutically acceptable excipient, carrier or diluent. In one embodiment, the microparticle of the invention inhibits fibroblast or glioblastoma cell migration, typically as determined in a transmembrane or wound healing (scratch) assay. In another embodiment, the microparticle of the invention induces differentiation of a tumour cell, optionally a glioblastoma cell, typically as determined by cell morphology and/or marker expression. A decrease in the stem cell marker nestin typically indicates differentiation.

An seventh aspect of the invention provides a kit for use in a method for producing a stem cell microparticle according to the first aspect, comprising: (a) a medium suitable for culturing stem cells; (b) a stem cell; (c) optionally the one or more components of the fourth aspect of the invention; (d) optionally a stem cell microparticle suitable for use as a control; (e) optionally a detection agent suitable for specific detection of the produced microparticles; and (f) instructions for producing the stem cell microparticle using the kit. The kit may optionally include means for performing a cell migration assay.

An eighth aspect of the invention provides a composition comprising one or more of the miRNAs identified in the Examples, in particular the miRNAs identified in FIG. 13. In one embodiment, the composition comprises one, two, three or all four of hsa-miR-1246, hsa-miR-4492, hsa-miR-4488 and hsa-miR-4532. In another embodiment, the composition comprises 1, 2, 3, 4 or 5 of hsa-miR-181a-5p, hsa-miR-1246, hsa-miR-127-3p, hsa-miR-21-5p and hsa-miR-100-5p. In a further embodiment, the composition comprises 1, 2, 3, 4 or 5 of hsa-miR-181a-5p, hsa-let-7a-5p, hsa-let-7f-5p, has-miR-92b-3p, and hsa-miR-9-5p. The composition is optionally a pharmaceutical composition, comprising a pharmaceutically-acceptable carrier, diluent, vehicle and/or excipient. The pharmaceutical composition is suitable for use in therapy, typically in the same therapies as the microparticles of the invention, as noted above.

BRIEF DESCRIPTION OF THE DRAWINGS

FIG. 1 shows the effect of neural stem cell exosome treatment on human dermal fibroblast migration in a transmembrane assay. The top panel depicts the assay apparatus and the bottom panel compares the number of cells that migrated through the membrane in the presence of medium alone (a, "basal"), in the presence of 20 µg/ml exosomes isolated from "0"-week CTX0E03 neural stem cells (b, "Exosome (0)") and in the presence of 20 µg/ml exosomes isolated from CTX0E03 neural stem cells cultured for 11 weeks in the Integra CELLine AD1000 culture system (c, "Exosome (11)"), determined after 6 hours and after 24 hours assay incubation.

FIG. 2 depicts the human dermal fibroblast cells that migrated through the membrane in the presence of each of the basal, 0-week and 11-week exosomes.

FIG. 3C shows the % of healed areas for basal conditions, 2 µg/ml exosomes, 6 µg/ml exosomes, 20 µg/ml exosomes and an LSGS (low serum growth supplement) positive control. The top panel of FIG. 3C shows exosomes isolated from CTX0E03 cells cultured for 2 weeks in the Integra Celline system and the bottom panel of FIG. 3C shows exosomes isolated from CTX0E03 cells cultured for 6 weeks in the Integra Celline system.

FIG. 13 depicts miRNA deep sequencing results. The miRNA profiles obtained from deep sequencing of miRNA from CTX0E03 cells ("CTX"), microvesicles ("MV") and exosomes ("EXO") cultured under standard (T175) conditions are shown in FIGS. 13A and 13B (results from two standard cultures, "EH" and "EL"). FIG. 13C shows the percentage of miRNAs that are up-shuttled, the same, or down-shuttled in the exosomes compared to producer cells, for (i) the standard culture, (ii) 6 week Integra bioreactor culture and (iii) 11 week bioreactor culture (3 samples). Up-shuttled >2, same <2>, and down-regulated<2 fold change (log 2) accordingly. FIGS. 13D to 13H show the miRNAs that are shuttled into exosomes compared with the cells producing them. Up-shuttled miRNAs are expressed as fold change calculated using the log 2 of the normalized ratio of exosomes/cell producer. The normalization is obtained by dividing reads of each miRNA by total miRNA reads. (D) summarises the most abundant miRNAs in exosomes obtained from the standard CTX0E03 cultures ("EH" and "EL"); (E) shows exosomes obtained from CTX0E03 cells cultured for 6 weeks in an Integra bioreactor, and lists up-shuttled miRNAs with more than 250 reads per exosome sample; (F) shows the miRNAs up-shuttled in exosomes when compared with the producer cells cultured for 11 weeks in an Integra bioreactor. 9 miRNA species are up-shuttled, all of which have more than 250 reads; (G) shows a second sample of the miRNAs up-shuttled in exosomes when compared with the producer cells cultured for 11 weeks in an Integra bioreactor. The diagram lists up-shuttled miRNAs with more than 250 reads per exosome sample; and (H) shows a third sample of the miRNAs up-shuttled in exosomes when compared with cell producer cultured for 11 weeks in an Integra bioreactor, showing up-shuttled miRNAs with more than 250 reads per exosome sample.

FIG. 22 shows that seeding glioblastoma cells together with 20 µg/ml CTX0E03 exosomes (FIGS. 22A and 22C) or have been pre-treating glioblastoma cells with 10 µg/ml CTX0E03 exosomes for 24 hours (FIG. 22B) reduces glioblastoma migration towards 10% FBS.

FIG. 24 shows glioblastoma xenograft individual tumour volumes of mice on the day of assignment to each treatment group.

FIG. 25 shows the mean body weights of the mice during the xenograft study. The dotted vertical line indicates the commencement of the dosing phase (on day 12).

FIG. 26 summarises the mean tumour volume for the treatment groups measured during the study.

FIG. 27 displays the tumour volume data (% pre-dose) of FIG. 26 in a truncated format up to study day 25.

FIG. 28 shows the final tumour weights, expressed as group mean+standard error of the mean (tumour weight).

FIG. 29 shows survival analysis utilising mean tumour diameter (15 mm) as the humane survival endpoint.

FIG. 30 shows the absolute individual body weights of each mouse in the study.

FIG. 31 shows the relative individual body weights of each mouse in the study.

FIG. 32 shows the raw data for individual tumour volume measurements.

FIG. 33 shows the individual tumour volume plots.

FIG. 34 details the tumour weights.

DETAILED DESCRIPTION OF THE INVENTION

Figure 3A:
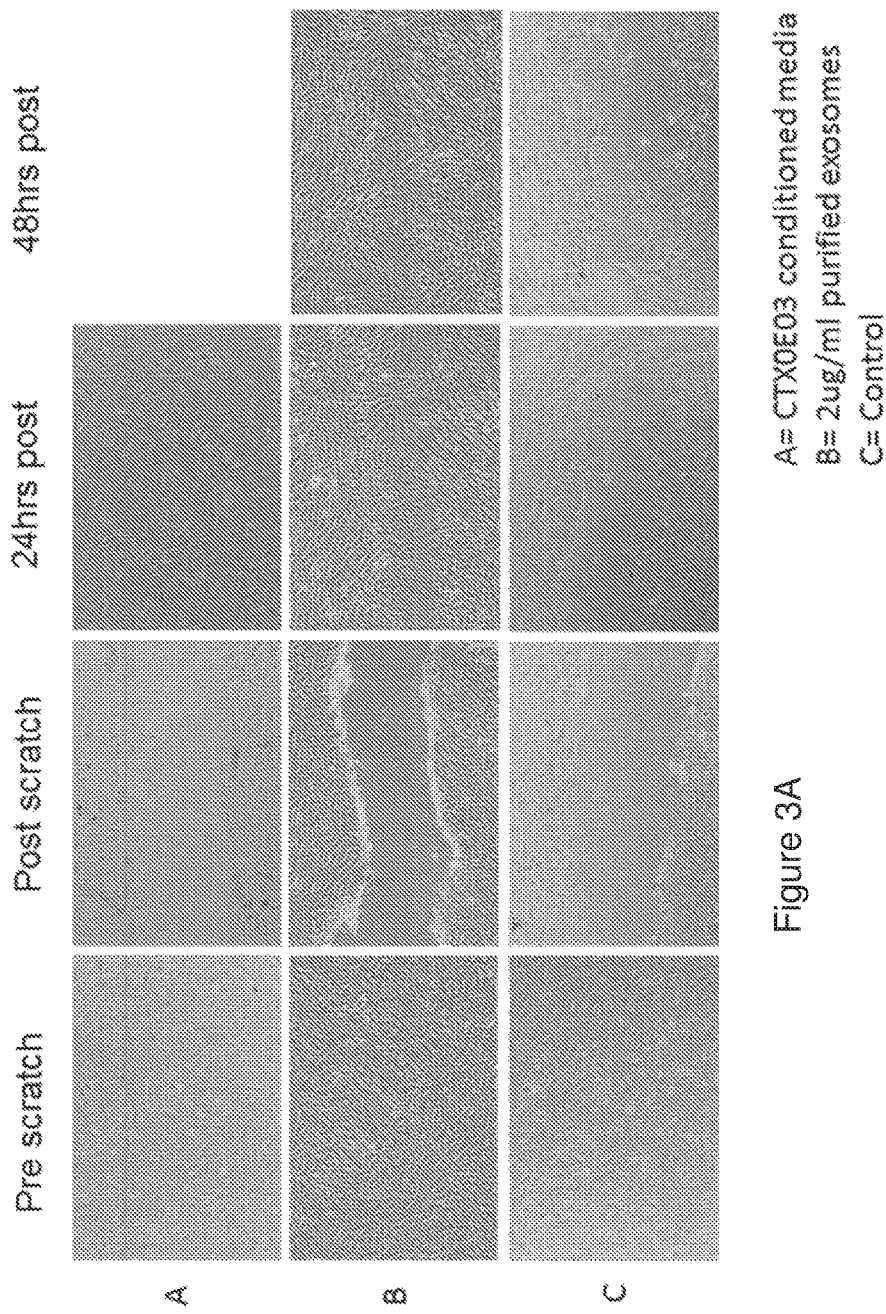
FIG. 3A shows the results of a wound closure/scratch assay representing the migration activity of normal human dermal fibroblasts (NHDF) in response to conditioned medium from CTX0E03 cells cultured for 2 weeks and exosomes purified from the conditioned medium of CTX0E03 cultured for 2 weeks in the Integra CELLine AD1000 culture system.

The present inventors have surprisingly identified that neural stem cells produce microparticles that inhibit cell migration of fibroblasts and cancer cells, induce differentiation of cancer cells, and/or induce or enhance an immune response against the cancer cells. These microparticles are shown to inhibit cell migration and are therefore useful in therapy of diseases comprising unwanted, undesired or deleterious cell migration. The microparticles inhibit fibroblast migration and are therefore also useful in therapy of diseases comprising unwanted, undesired or deleterious angiogenesis, in which fibroblasts play a key role. The microparticles also inhibit tumour cell migration, induce differentiation of tumour cells and enhance an immune response against cancer cells, and are therefore useful in the treatment of cancer. The microparticles of the invention can be characterised and identified by these properties, using the assays described herein or other assays known to the skilled person.

The microparticles are advantageous over the corresponding stem cells because they are smaller and less complex, thereby being easier to produce, maintain, store and transport, and have the potential to avoid some of the regulatory issues that surround stem cells. The microparticles can be produced continuously, by isolation from conditioned media, for example in a bioreactor such as a multi-compartment bioreactor, which allows for large scale production and the provision of an "off-the-shelf" therapy. The multi-compartment bioreactor is typically a two-compartment bioreactor. An exemplary multi-compartment bioreactor is the CeLLine AD1000 bioreactor that is commercially available from Integra Biosciences AG, Zizers, Switzerland (Item No. 90025).

The inventors have found that the properties of neural stem cell microparticles differ depending on the culture conditions of the stem cells that produce the microparticles, in particular the length of time that the neural stem cells are cultured before the microparticles are harvested. In particular, the inventors have surprisingly identified neural stem cell microparticles that inhibit cell migration and/or induce differentiation of a stem or cancer cell.

In one embodiment, microparticles that inhibit fibroblast migration can be isolated from neural stem cells that have been cultured in a multi-compartment bioreactor for at least 10 weeks, e.g. more than 10 weeks. This is particularly surprising because microparticles isolated from the same neural stem cells that have been cultured for less than 10 weeks, for example about 2-6 weeks, have been shown to enhance fibroblast cell migration as seen in wound healing assays.

In another embodiment, microparticles that are able to induce or enhance a beneficial immune response against cancer cells can also be isolated from neural stem cells that have been cultured in a multi-compartment bioreactor for at least 10 weeks, e.g. more than 10 weeks.

In a further embodiment, microparticles that are able to reduce tumour cell migration and/or induce cancer or stem cell differentiation are isolated from a proliferating neural stem cell culture. This culture may be in a standard cell culture flask (such as a T-175 flask) or may be in a multi-compartment bioreactor. When the cells producing microparticles of this embodiment are cultured in a multi-compartment bioreactor, they are typically cultured for 4 weeks or less, for example 3 weeks or less, 2 weeks or less, or 1 week or less. This is because, as described elsewhere herein, prolonged culture in a multi-compartment bioreactor allows the stem cells to begin to differentiate, i.e. to express markers for defined neural cell types. Typically, the microparticles that are able to reduce tumour cell migration and/or induce differentiation are isolated from neural stem cells that are negative for markers of differentiated neural cells (e.g. GFAP⁻ and/or DCX⁻) but are positive for one or more markers of neural stem cells (e.g. Nestin⁺).

FIG. 1 (lower panel) and FIG. 2 show that exosomes isolated from a non-proliferating CTX0E03 culture significantly abrogate migration of human dermal fibroblasts. This is in contrast to exosomes isolated from a proliferating CTX0E03 culture, which significantly promote migration of human dermal fibroblasts. Accordingly, in one embodiment, microparticles that inhibit cell (e.g. fibroblast) migration may be isolated from non-proliferating neural stem cells. Optionally, these non-proliferating stem cells may be partly differentiated, i.e. express one or more early markers of differentiation. In one embodiment, the neural stem cells from which these microparticles are isolated are positive for DCX (doublecortin), which is an early neuronal marker. In another embodiment, the neural stem cells from which the microparticles are isolated are positive for GFAP (Glial fibrillary acidic protein), which is an astrocyte marker.

FIG. 22 shows that exosomes isolated from a proliferating CTX0E03 culture inhibit the migration of glioblastoma cells towards a positive chemoattractant. Accordingly, in one embodiment, microparticles that inhibit cell (e.g. glioblastoma) migration may be isolated from proliferating neural stem cells that are typically negative for markers of differentiation. In one embodiment, the neural stem cells from which these microparticles are isolated are negative for DCX (doublecortin), which is an early neuronal marker. In another embodiment, the neural stem cells from which the microparticles are isolated are negative for GFAP (Glial fibrillary acidic protein), which is an astrocyte marker.

Cell migration is well-known to play an important role in the progression of diseases such as cancer (for example during angiogenesis, tumour formation, metastasis and tissue invasion), fibrosis (for example during the accumulation of fibroblasts in the fibrotic tissue), atherosclerosis and rheumatoid arthritis. The identification of microparticles that are able to inhibit these processes therefore provides a new therapy for these diseases.

Transmembrane and wound healing assays are physiologically relevant cell-based assays that are predictive of in vivo mechanisms of cell migration and allow the identification of compounds that are effective in promoting or inhibiting cell migration, and the recognition of potential undesirable effects. Furthermore there is a good correlation between the results obtained in scratch assays and transmembrane assays (Hulkower et al. 2011), so that these assays can be compared.

The data presented below demonstrate that microparticles that inhibit cell migration can be isolated from neural stem cells. The microparticles of the invention can be produced by any method, not limited to those disclosed or exemplified herein. Whether or not a microparticle is able to inhibit cell migration can be readily determined using the assays described herein.

It has further been found that, surprisingly, culturing stem cells (of any type, not limited to neural stem cells) in an environment that allows the stem cells to begin to differentiate, increases dramatically the yield of microparticles produced. Typically, the stem cells are NSCs, for example CTX0E03, cultured for at least 10 weeks, for example for 11 weeks, but optionally no more than 20 weeks, 30 weeks or 40 weeks.

The inventors have surprisingly observed that culturing stem cells (of any type, not limited to neural stem cells) in a multi-compartment bioreactor results in partial differentiation of the stem cells, into stem cells in a more differentiated form. This differentiation in culture does not require the addition of an agent to induce differentiation. This differentiation typically requires a culture period of at least one week, at least two weeks, at least three weeks, at least six weeks, at least eight weeks, or at least ten weeks, for example about 11 weeks, but optionally no more than 20 weeks. The changes to the stem cells that occur in culture in a multi-compartment bioreactor are reflected by the microparticles produced by the cultured stem cells. Therefore, by culturing stem cells in a multi-compartment bioreactor, it is possible to induce differentiation of the cells. Accordingly, microparticles from partially differentiated stem cells can be produced by harvesting microparticles from stem cells, for example NSCs such as CTX0E03, cultured in a multi-compartment bioreactor, typically for at least one week, at least two weeks, at least three weeks, at least four weeks, at least five weeks or at least six weeks, at least eight weeks, or at least ten weeks, for example about 11 weeks, but optionally no more than 20 weeks. Typically, the NSCs have been cultured for more than ten weeks. In one embodiment, the invention provides a method of producing microparticles by isolating the microparticles from partially-differentiated neural stem cells as described above.

The inventors have also found that it is possible to induce the secretion of microparticles from stem cells. Typically, the stem cells are NSCs, for example CTX0E03, typically cultured for at least 10 weeks, for example for 11 weeks or more, but optionally no more than 20 weeks. This finding, which also is not limited to neural stem cells and can be used for the production of microparticles from any stem cell, allows for an improved yield of microparticles to be obtained from a stem cell culture. Several agents have been identified that enhance the secretion of microparticles to different degrees, which has the further advantage of being able to control the amount of microparticles that are secreted. Culturing stem cells under hypoxic conditions also improves microparticle production. Further, it has been found that co-culturing a stem cell with a different cell type, in particular an endothelial cell type can beneficially alter the microparticles that are produced by the stem cell.

In a further embodiment, the invention provides microparticles, typically exosomes, produced by serum-free stem cells. Typically, the stem cells are NSCs, for example CTX0E03, cultured for at least 10 weeks, for example for 11 weeks, but optionally no more than 20 weeks. Serum is required for the successful culture of many cell lines, but contains many contaminants including its own exosomes. As described below, the inventors have produced microparticles from stem cells that do not require serum for successful culture.

Neural Stem Cell Microparticles

The invention provides, in one aspect, microparticles that inhibit cell migration and/or induce differentiation of a stem or cancer cell, obtainable from a neural stem cell. The microparticle is, in one embodiment, obtainable from a neural stem cell that has been cultured in a multi-compartment bioreactor, typically for at least 10 weeks, for example 11 weeks or more, or 12 weeks or more. In another embodiment, the microparticle is obtainable from a proliferating neural stem cell that has been cultured in: a standard cell culture flask such as a T-175 flask; or in a multi-compartment bioreactor for 4 weeks or less.

A neural stem cell microparticle is a microparticle that is produced by a neural stem cell. Typically, the microparticle is secreted by the neural stem cell. More typically, the microparticle is an exosome or a microvesicle. Microparticles from other cells, such as mesenchymal stem cells, are known in the art.

A "microparticle" is an extracellular vesicle of 30 to 1000 nm diameter that is released from a cell. It is limited by a lipid bilayer that encloses biological molecules. The term "microparticle" is known in the art and encompasses a number of different species of microparticle, including a membrane particle, membrane vesicle, microvesicle, exosome-like vesicle, exosome, ectosome-like vesicle, ectosome or exovesicle. The different types of microparticle are distinguished based on diameter, subcellular origin, their density in sucrose, shape, sedimentation rate, lipid composition, protein markers and mode of secretion (i.e. following a signal (inducible) or spontaneously (constitutive)). Four of the common microparticles and their typical distinguishing features are described in Table 1, below.

TABLE 1

Various Microparticles

| Microparticle | Size | Shape | Markers | Lipids | Origin |
|---|---|---|---|---|---|
| Microvesicles | 100-1000 nm | Irregular | Integrins, selectins, CD40 ligand | Phosphatidyl-serine | Plasma membrane |
| Exosome-like vesicles | 20-50 nm | Irregular | TNFRI | No lipid rafts | MVB from other organelles |
| Exosomes | 30-100 nm; (<200 nm) | Cup shaped | Tetraspanins (e.g. CD63, CD9), Alix, TSG101, ESCRT | Cholesterol, sphingomyelin, ceramide, lipid rafts, phosphatidyl-serine | Multi-vesicular endosomes |
| Membrane particles | 50-80 nm | Round | CD133, no CD63 | Unknown | Plasma membrane |

Microparticles are thought to play a role in intercellular communication by acting as vehicles between a donor and recipient cell through direct and indirect mechanisms. Direct mechanisms include the uptake of the microparticle and its donor cell-derived components (such as proteins, lipids or nucleic acids) by the recipient cell, the components having a biological activity in the recipient cell. Indirect mechanisms include microvesicle-recipient cell surface interaction, and causing modulation of intracellular signalling of the recipient cell. Hence, microparticles may mediate the acquisition of one or more donor cell-derived properties by the recipient cell. It has been observed that, despite the efficacy of stem cell therapies in animal models, the stem cells do not appear to engraft into the host. Accordingly, the mechanism by which stem cell therapies are effective is not clear. Without wishing to be bound by theory, the inventors believe that the microparticles secreted by neural stem cells play a role in the therapeutic utility of these cells and are therefore therapeutically useful themselves.

The microparticles and stem cells of the invention are isolated. The term "isolated" indicates that the microparticle, microparticle population, cell or cell population to which it refers is not within its natural environment. The microparticle, microparticle population, cell or cell population has been substantially separated from surrounding tissue. In some embodiments, the microparticle, microparticle population, cell or cell population is substantially separated from surrounding tissue if the sample contains at least about 75%, in some embodiments at least about 85%, in some embodiments at least about 90%, and in some embodiments at least about 95% microparticles and/or stem cells. In other words, the sample is substantially separated from the surrounding tissue if the sample contains less than about 25%, in some embodiments less than about 15%, and in some embodiments less than about 5% of materials other than the microparticles and/or stem cells. Such percentage values refer to percentage by weight. The term encompasses cells or microparticles which have been removed from the organism from which they originated, and exist in culture. The term also encompasses cells or microparticles which have been removed from the organism from which they originated, and subsequently re-inserted into an organism. The organism which contains the re-inserted cells may be the same organism from which the cells were removed, or it may be a different organism.

Neural stem cells naturally produce microparticles by a variety of mechanisms, including budding of the plasma membrane (to form membrane vesicles and microvesicles) and as a result of the fusion of intracellular multivesicular bodies (which contain microparticles) with the cell membrane and the release of the microparticles into the extracellular compartment (to secrete exosomes and exosome-like vesicles).

The neural stem cell that produces the microparticles of the invention can be a fetal, an embryonic, or an adult neural stem cell, such as has been described in U.S. Pat. Nos. 5,851,832, 6,777,233, 6,468,794, 5,753,506 and WO-A-2005121318. The fetal tissue may be human fetal cortex tissue. The cells can be selected as neural stem cells from the differentiation of induced pluripotent stem (iPS) cells, as has been described by Yuan et al. (2011) or a directly induced neural stem cell produced from somatic cells such as fibroblasts (for example by constitutively inducing Sox2, Klf4, and c-Myc while strictly limiting Oct4 activity to the initial phase of reprogramming as recently by Their et al, 2012). Human embryonic stem cells may be obtained by methods that preserve the viability of the donor embryo, as is known in the art (e.g. Klimanskaya et al., 2006, and Chung et al. 2008). Such non-destructive methods of obtaining human embryonic stem cell may be used to provide embryonic stem cells from which microparticles of the invention can be obtained. Alternatively, microparticles of the invention can be obtained from adult stem cells, iPS cells or directly-induced neural stem cells. Accordingly, microparticles of the invention can be produced by multiple methods that do not require the destruction of a human embryo or the use of a human embryo as a base material.

Typically, the neural stem cell population from which the microparticles are produced, is substantially pure. The term "substantially pure" as used herein, refers to a population of stem cells that is at least about 75%, in some embodiments at least about 85%, in some embodiments at least about 90%, and in some embodiments at least about 95% pure, with respect to other cells that make up a total cell population. For example, with respect to neural stem cell populations, this term means that there are at least about 75%, in some embodiments at least about 85%, in some embodiments at least about 90%, and in some embodiments at least about 95% pure, neural stem cells compared to other cells that make up a total cell population. In other words, the term "substantially pure" refers to a population of stem cells of the present invention that contain fewer than about 25%, in some embodiments fewer than about 15%, and in some embodiments fewer than about 5%, of lineage committed cells in the original unamplified and isolated population prior to subsequent culturing and amplification.

A neural stem cell microparticle comprises at least one lipid bilayer which typically encloses a milieu comprising lipids, proteins and nucleic acids. The nucleic acids may be deoxyribonucleic acid (DNA) and/or ribonucleic acid (RNA). RNA may be messenger RNA (mRNA), micro RNA (miRNA) or any miRNA precursors, such as pri-miRNA, pre-miRNA, and/or small nuclear RNA (snRNA).

A neural stem cell microparticle retains at least one biological function of the stem cell from which it is derived. Biological functions that may be retained include the ability to inhibit cell migration, for example of fibroblasts or fibroblast-like cells, or of a tumour cell such as a glioblastoma cell. In one embodiment, the at least one biological function is that of a neural stem cell that has been cultured in a multi-compartment bioreactor, for at least 10 weeks and optionally no more than 20 weeks. Alternatively the at least one biological function may be that of a neural stem cell-conditioned medium from a neural stem cell that has been cultured in a multi-compartment bioreactor, for at least 10 weeks and optionally no more than 20 weeks. In another embodiment, the at least one biological function is that of a neural stem cell that has been cultured in a T-175 flask under standard conditions.

FIGS. 1 and 2 (Example 1) demonstrate that exosomes isolated from the conditioned medium of CTX0E03 cells that have been cultured for 11 weeks have the ability to inhibit fibroblast migration in a transmembrane assay model of cell migration. Accordingly, one biological function that microparticles of the invention may retain is the ability to inhibit migration of fibroblast or fibroblast-like cells, for example of normal human dermal fibroblasts (NHDF).

In contrast, exosomes isolated from the conditioned medium of CTX0E03 cells that have been cultured for 0-6 weeks promote cell migration as determined using a scratch/wound closure assay. Examples 1 and 2, Table 2 and FIGS. 1-3 demonstrate that exosomes isolated from the conditioned medium of CTX0E03 cells that have been cultured for 0-6 weeks retain the ability to close a wound in a "scratch" model of wound healing. The results in FIG. 3A show that the migration activity of normal human dermal fibroblasts (NHDF) cultured in CTX0E03 conditioned media is almost the same as the migration activity observed on the addition of purified exosomes.

The Examples also demonstrate that exosomes isolated from the conditioned medium of CTX0E03 cells that have been cultured for 11 weeks have the ability to promote the destruction of cancer cells by the immune system. Accordingly, one biological function that microparticles of the invention may retain is the ability to promote the destruction of cancer cells by the immune system.

The Examples further demonstrate that exosomes isolated from the conditioned medium of proliferating CTX0E03 cells have the ability to inhibit tumour cell migration. Accordingly, one biological function that microparticles of the invention may retain is the ability to inhibit tumour cell migration, typically of glioblastoma cells.

Yet further, the Examples demonstrate that exosomes isolated from the conditioned medium of proliferating CTX0E03 cells have the ability to induce differentiation of tumour cells. Accordingly, one biological function that microparticles of the invention may retain is the ability to induce differentiation of tumour cells, typically glioblastoma cells. Differentiation may readily be determined by known assays, including cell morphology and the presence of stem cell markers (e.g. nestin) and/or differentiated cell markers (e.g. DCX, GFAP). In one embodiment, differentiation is determined by assaying for the stem cell marker nestin (as demonstrated in the Examples). A reduction in nestin expression indicates differentiation of the cell.

Inhibition of Cell Migration

Microparticles of the invention are able to inhibit cell migration. Typically, the migration of fibroblasts or glioblastoma cells is inhibited. Cell migration assays are known in the art. Two exemplary assays are described below, and are used in the Examples.

Transmembrane assays (sometimes referred to as "transwell" assays) are known in the art and an exemplary assay is described in Example 1. The assay uses a chamber separated into two compartments by a porous filter membrane. The cells are seeded on one side of the membrane, while medium containing the purified microparticles is placed on the opposing (lower) side. Example 1 uses fibroblasts, but other cells may be used. After an incubation period (e.g. 6-24 hours), the membrane is fixed and stained to reveal migrated cells (e.g. cell nuclei). The number of cells which have migrated through the pores of the membrane is counted microscopically.

An alternative transmembrane assay was used in Example 6, as shown in FIG. 22. Here, glioblastoma cells are seeded on one side of the porous filter membrane. These cells are either seeded together with 20 µg/ml microparticles (FIGS. 22A and C) or have been pre-treated with 10 µg/ml microparticles for 24 hours (FIG. 22B). Medium containing a chemoattractant is placed on the opposing (lower) side. In Example 6, the chemoattractant is FBS. After an incubation period (e.g. 6-24 hours), the membrane is fixed and stained to reveal migrated cells (e.g. cell nuclei). The number of cells which have migrated through the pores of the membrane is again counted microscopically.

Cell migration is calculated as the number of cells that have migrated through the pores of the membrane in relation to basal conditions (without the microparticles). Inhibition of cell migration in this assay may typically be defined as a decrease in the number of cells that have migrated through the membrane, typically the number of migrated cells is less than 90%, more typically less than 80%, more typically less than 75%, less than 60% or less than 50% of the number of cells that have migrated through the membrane under basal conditions (without the microparticles) after the same incubation period (e.g. 6 hours or 24 hours). As a guideline, inhibition of cell migration is achieved if after 24 hours incubation in the transmembrane assay, the number of human dermal fibroblasts or glioblastoma cells that have migrated through the membrane in the presence of 20 µg/ml of the microparticles is less than 80% of the number of fibroblasts that migrated under basal conditions (i.e. in the absence of the microparticles).

In one embodiment, "inhibition of cell migration" is a statistically significant reduction in cell migration of human dermal fibroblasts or glioblastoma cells in a transmembrane assay with a p value of $p<0.05$, typically $p<0.001$, in the presence of the microparticles, compared to the migration in the absence of the microparticles. Typically, this is determined after a 24 hour assay incubation period.

Cell migration may also be determined using an in vitro scratch (wound closure) assay, for example the assay of Example 2. Scratch assays were first used as models of wound healing for epithelial or mesenchymal cells. In this assay, cells are seeded into an assay plate and allowed to attach, spread, and form a confluent monolayer. Example 2 uses fibroblasts, but other cells may be used. A pin or needle is used to scratch and remove cells from a discrete area of the confluent monolayer to form a cell-free zone into which cells at the edges of the wound can migrate. Alternatively, a removable insert having a defined shape is placed on contact with the well bottom before the cells are seeded and allowed to form a confluent monolayer excluding the area covered by the insert. The insert is then removed, allowing the cells to migrate onto the newly revealed surface. Using either setup, molecules of interest as potential therapeutics (e.g. the purified microparticles of the invention) are added to the well and images of cell movement are captured at regular intervals, for example within a 24-72 hour period, for data analysis.

Cell migration/wound closure is calculated as the area covered by cells in relation to the initial wound area as determined at 0 hours. Inhibition of cell migration in this assay is typically defined as a decrease in wound closure, typically a wound closure less than 90%, more typically less than 80%, more typically less than 75%, less than 60% or less than 50% of the wound closure observed under basal conditions (without the microparticles) after 24 hours. After 48 hours, the wound closure is typically less than 90% or less than 80% of the wound closure observed using in the absence of the microparticles.

Inhibition of cell migration may also be defined as delaying a wound closure of 100%, as determined by the scratch assay, by at least 24 hours compared to the wound closure observed under basal conditions. Typically, this delay is achieved by using 2 µg/ml of the isolated microparticles, as used in Example 2.

The proteomic analysis in Example 18 indicates that neural stem cell exosomes comprise biological functions associated with the production, packaging, function and degradation of genetic material. Accordingly, in one embodiment, exosomes of the invention retain these functions, typically one or more of RNA polymerase function, RNA degradation function, ribosome function and spliceosome function.

The microparticle obtained from the neural stem cell has a diameter of 1000 nm or less. Typically, the microparticle of the invention will have a diameter of 200 nm or less, for example 100 nm or less. As noted in Table 1 above, microvesicles have a diameter of 100 nm to 1000 nm. Exosomes are typically defined as having a diameter of 30-100 nm, but more recent studies confirm that exosomes can also have a diameter between 100 nm and 200 nm, (e.g. Katsuda et al, Proteomics 2013 and Katsuda et al, Scientific Reports 2013). Accordingly, exosomes typically have a diameter between 30 nm and 150 nm. Membrane particles have a diameter of 50 nm to 80 nm and exosome-like particles have a diameter of 20 nm-50 nm. The diameter can be determined by any suitable technique, for example electron microscopy or dynamic light scattering. The term microparticle includes, but is not limited to: membrane particle, membrane vesicle, microvesicle, exosome-like vesicle, exosome, ectosome-like vesicle, ectosome or exovesicle.

Figure 4:
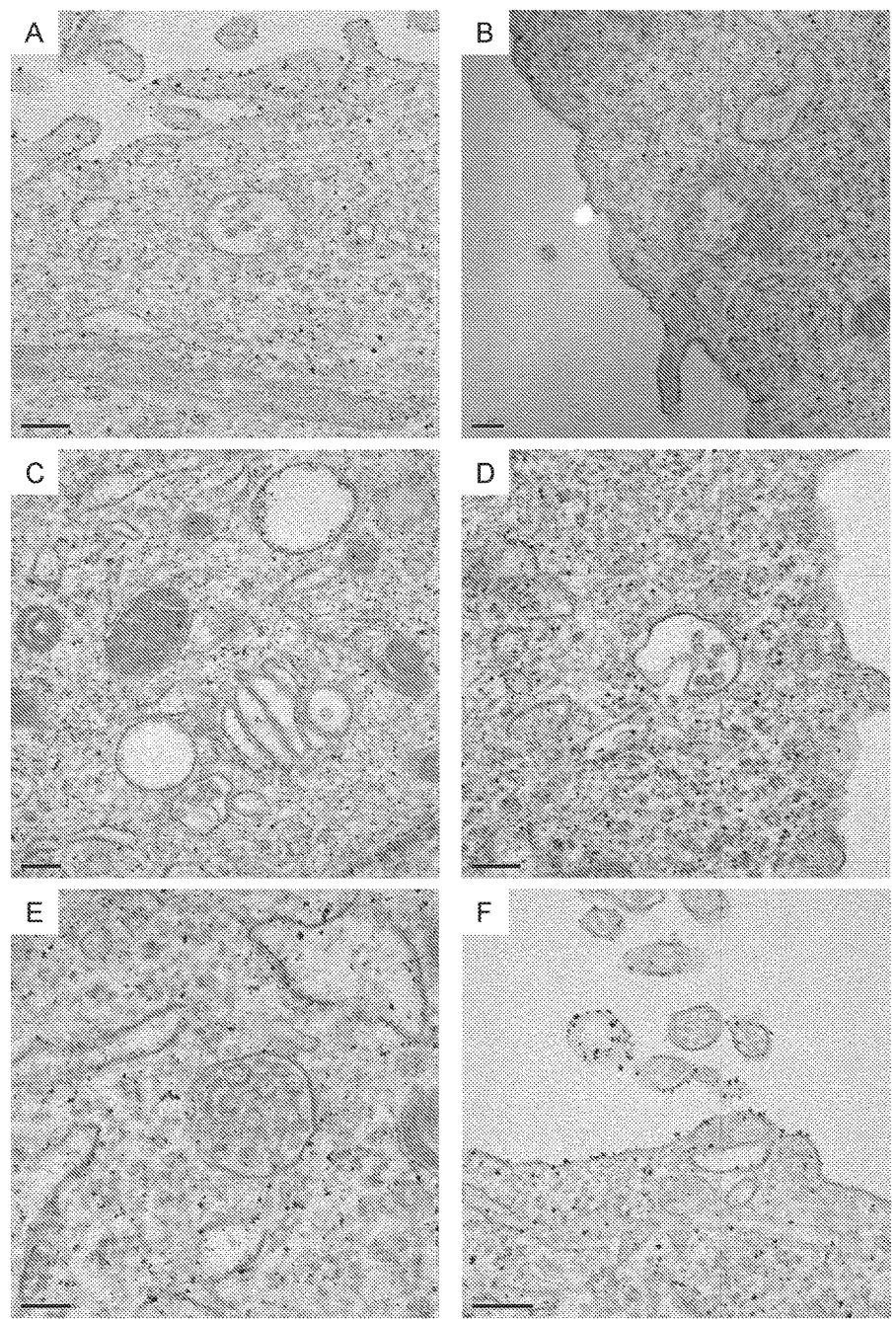
FIG. 4 depicts electron micrographs of CTX0E03 conditionally-immortalised neural stem cells producing microparticles. Panels A-E show intracellular multivesicular bodies (MVBs) containing exosomes between 30 nm and 50 nm in diameter and Panel F shows microvesicles >100 nm in diameter released from neural stem cells through a process of budding at the cell membrane.

FIG. 4 panels A-E show the presence in neural stem cells of multivesicular bodies (MVBs) containing exosomes between 30-50 nm in diameter, while panel F shows microvesicles >100 nm in diameter. Table 21 and FIG. 7 (below) show that typical neural stem cell exosomes were measured to have a diameter ranging from approximately 70 nm to approximately 150 nm, which is consistent with the size of exosomes (from mesenchymal stem cells) described in the art. Accordingly, exosomes of the invention typically have a diameter between 30 nm and 200 nm, more typically between 50 nm and 150 nm. As noted above, exosomes are typically positive for the Alix marker (UNIPROT Accession No. Q8WUM4).

FIG. 4F and Table 21 shows the observed size of typical neural stem cell microvesicles, with a mode diameter of approximately 150 nm-200 nm, or a median diameter of approximately 180 nm-350 nm. Accordingly, microvesicles of the invention typically have a diameter between 100 and 1000 nm, more typically between 150 nm and 350 nm.

Some microparticles of the invention express the CD133 surface marker. Other microparticles of the invention do not express the CD133 surface marker.

"Marker" refers to a biological molecule whose presence, concentration, activity, or phosphorylation state may be detected and used to identify the phenotype of a cell.

Exosomes are endosome-derived lipid microparticles of typically 30-100 nm diameter and sometimes between 100 nm and 200 nm diameter, that are released from the cell by exocytosis. Exosome release occurs constitutively or upon induction, in a regulated and functionally relevant manner. During their biogenesis, exosomes incorporate a wide range of cytosolic proteins (including chaperone proteins, integrins, cytoskeletal proteins and the tetraspanins) and genetic material. Consequently, exosomes are considered to be inter-cellular communication devices for the transfer of proteins, lipids and genetic material between cells, in the parent cell microenvironment and over considerable distance. Although the invention is not bound by this theory, it is possible that the exosomes are responsible for the efficacy of the neural stem cells. Therefore, exosomes from neural stem cells are themselves expected to be therapeutically efficacious.

Microparticles Designed to have Desired Functions

Microparticles retain at least some of the functions of the stem cells that produce them. Therefore, it is possible to design microparticles by manipulating the stem cell (which can be any stem cell type and is not limited to neural stem cells, although the neural stem cell microparticles of the invention are expressly included as an embodiment) to possess one or more desired functions, typically protein or miRNA. The manipulation will typically be genetic engineering, to introduce one or more exogenous coding, non-coding or regulatory nucleic acid sequences into the stem cell. For example, if an exosome containing VEGF and/or bFGF is desired, then the exosome-producing stem cell can be transformed or transfected to express (high levels of) VEGF and/or bFGF, which would then be incorporated into the microparticles produced by that stem cell. Similarly, iPS cells can be used to produce microparticles, and these cells can be designed to produce the proteins and nucleic acids (e.g. miRNA) that are required in the microparticles produced by the iPS cells. The invention therefore provides ad hoc microparticles, from any stem cell type, that contain a function that is not naturally present in the stem cell from which is produced, i.e. the microparticles (e.g. exosomes) contain one or more exogenous protein or nucleic acid sequences, are not naturally-occurring and are engineered.

In one embodiment, isolated or purified microparticles from the conditioned medium of neural stem cells that have been cultured for more than 10 weeks, for example for 11 weeks, and optionally no longer than 20 weeks, are loaded with one or more exogenous nucleic acids, lipids, proteins, drugs or prodrugs which are intended to perform a desired function in a target cell. This does not require manipulation of the stem cell and the exogenous material can optionally be directly added to the microparticles. For example, exogenous nucleic acids can be introduced into the microparticles by electroporation. The microparticles can then be used as vehicles or carriers for the exogenous material. In one embodiment, microparticles that have been isolated from the cells that produced them are loaded with exogenous siRNA, typically by electroporation, to produce microparticles that can be deployed to silence one or more pathological genes. In this way, microparticles can be used as vehicles to deliver one or more agents, typically therapeutic or diagnostic agents, to a target cell, for example to enhance or complement their endogenous inhibition of cell migration. An example of this is a neural stem cell exosome comprising exogenous siRNA capable of silencing one or more pathological genes.

Microparticle Marker

The invention provides a population of isolated neural stem cell microparticles, wherein the population essentially comprises only microparticles of the invention, i.e. the microparticle population is pure. In many aspects, the microparticle population comprises at least about 80% (in other aspects at least 85%, 90%, 91%, 92%, 93%, 94%, 95%, 96%, 97%, 98%, 99%, 99.5%, 99.9% or 100%) of the microparticles of the invention.

The isolated neural stem cell microparticle of the invention is characterised in that it has a distinctive expression profile for certain markers and is distinguished from microparticles from other cell types. When a marker is described herein, its presence or absence may be used to distinguish the microparticle. For example, the term "may comprise" or "may express" also discloses the contrary embodiment wherein that marker is not present, e.g. the phrase "the microparticle may comprise one or more tetraspanins, typically CD63, CD81, CD9, CD53, CD82 and/or CD37" also describes the contrary embodiment wherein the microparticle may not comprise one or more tetraspanins, typically CD63, CD81, CD9, CD53, CD82 and/or CD37.

The neural stem cell microparticle of the invention is typically considered to carry a marker if at least about 70% of the microparticles of the population, e.g. 70% of the membrane particles, membrane vesicles, microvesicles, exosome-like vesicles, exosomes, ectosome-like vesicles, ectosomes or exovesicles show a detectable level of the marker. In other aspects, at least about 80%, at least about 90% or at least about 95% or at least about 97% or at least about 98% or more of the population show a detectable level of the marker. In certain aspects, at least about 99% or 100% of the population show detectable level of the markers. Quantification of the marker may be detected through the use of a quantitative RT-PCR (qRT-PCR) or through fluorescence activated cell sorting (FACS). It should be appreciated that this list is provided by way of example only, and is not intended to be limiting. Typically, a neural stem cell microparticle of the invention is considered to carry a marker if at least about 90% of the microparticles of the population show a detectable level of the marker as detected by FACS.

The markers described herein are considered to be expressed by a cell of the population of the invention, if its expression level, measured by qRT-PCR has a crossing point (Cp) value below or equal to 35 (standard cut off on a qRT-PCR array). The Cp represents the point where the amplification curve crosses the detection threshold, and can also be reported as crossing threshold (ct).

In one embodiment, the invention relates to microparticles produced by a neural stem cell population characterised in that the cells of the population express one or more of the markers Nestin, Sox2, GFAP, βIII tubulin, DCX, GALC, TUBB3, GDNF and IDO. In another embodiment, the microparticle is an exosome and the population of exosomes expresses one or more of DCX (doublecortin—an early neuronal marker), GFAP (Glial fibrillary acidic protein—an astrocyte marker), GALC, TUBB3, GDNF and IDO.

The neural stem cell microparticles of the invention may express one or more protein markers at a level which is lower or higher than the level of expression of that marker in a mesenchymal stem cell microparticle of the same species. Protein markers that are expressed by the CTX0E03 cell microparticles are identified herein and below. In some embodiments, the microparticles may express a protein marker at a level relative to a tubulin or other such control protein(s). In some embodiments, the microparticles of the invention may express that protein at a level of at least +/−1.2 fold change relative to the control protein, typically at least +/−1.5 fold change relative to the control protein, at least +/−2 fold change relative to the control protein or at least +/−3 fold change relative to the control protein. In some embodiments, the microparticles may express a protein marker at a level of between $10^{-2}$ and $10^{-6}$ copies per cell relative to a tubulin or other control protein. In some embodiments, the microparticles of the invention may express that protein at a level of between $10^{-2}$ and $10^{-3}$ copies per cell relative to a tubulin or other control protein.

The neural stem cell microparticles of the invention may express one or more miRNAs (including miRNA precursors) at a level which is lower or higher than the level of expression of that miRNA (including miRNA precursors) in a mesenchymal stem cell microparticle of the same species. miRNA markers that are expressed by the CTX0E03 cell microparticles are identified below. In some embodiments, the microparticles of the invention may express the marker miRNA at a level of at least +/−1.5 fold change, typically at least +/−2 fold change or at least +/−3 fold change (calculated according to the ΔΔct method, which is well-known) relative to U6B or 15a, or any other miRNA reference gene, also referred to as an internal control gene.

The neural stem cell microparticles of the invention may express one or more mRNAs at a level which is lower or higher than the level of expression of that mRNA in a mesenchymal stem cell microparticle of the same species. In some embodiments, the microparticles of the invention may express the marker mRNA at a level of at least +/−1.5 fold change, typically at least +/−2 fold change or at least +/−3 fold change (calculated according to the ΔΔct method) relative to ATP5B or YWHAZ, or any other reference gene, also referred to as an internal control gene.

Exosomes of the invention typically express specific integrins, tetraspanins, MHC Class I and/or Class II antigens, CD antigens and cell-adhesion molecules on their surfaces, which may facilitate their uptake by specific cell types. Exosomes contain a variety of cytoskeletal proteins, GTPases, clathrin, chaperones, and metabolic enzymes (but mitochondrial, lysosomal and ER proteins are excluded, so the overall profile does not resemble the cytoplasm). They also contain mRNA splicing and translation factors. Finally, exosomes generally contain several proteins such as HSP70, HSP90, and annexins that are known to play signalling roles yet are not secreted by classical (ER-Golgi) mechanisms.

The lipid bilayer of an exosome is typically enriched with cholesterol, sphingomyelin and ceramide. Exosomes also express one or more tetraspanin marker proteins. Tetraspanins include CD81, CD63, CD9, CD53, CD82 and CD37. Exosomes can also include growth factors, cytokines and RNA, in particular miRNA. Exosomes typically express one or more of the markers TSG101, Alix, CD109, thy-1 and CD133. Alix (Uniprot accession No. Q8WUM4), TSG101 (Uniprot accession No. Q99816) and the tetraspanin proteins CD81 (Uniprot accession No. P60033) and CD9 (Uniprot accession No. P21926) are characteristic exosome markers.

Alix is an endosomal pathway marker. Exosomes are endosomal-derived and, accordingly, a microparticle positive for this marker is characterised as an exosome. Exosomes of the invention are typically positive for Alix. Microvesicles of the invention are typically negative for Alix.

Microparticle Proteome

Tables 19 and 21 list all proteins detected by mass spectrometry in exosomes and microvesicles, respectively, isolated from CTX0E03 cells cultured for two weeks in an Integra Celline multi-compartment bioreactor. Exosomes and microvesicles of the invention may contain at least a proportion of the proteins identified in Tables 19 and 21, respectively. Thus, in one embodiment, exosomes of the invention comprise at least 70%, at least 80%, at least 90%, at least 95%, at least 99% or at least 99.5% of the proteins listed in Table 19. Similarly, microvesicles of the invention typically comprise at least 70% at least 80%, at least 90%, at least 95%, at least 99% or at least 99.5% of the proteins listed in Table 21. In a further embodiment, the proteome of a microvesicle or exosome of the invention is least 70%, at least 80%, at least 90%, at least 95%, at least 99% or at least 99.5% identical to the proteome provided in Table 19 (exosome) or Table 21 (microvesicle). When determining the protein content of a microparticle or exosome, mass spectrometry is typically used, for example the LC/MS/MS method described in Example 18.

Tables 20 and 22 show the 100 most abundant proteins detected by mass spectrometry in exosomes and microvesicles, respectively, isolated from CTX0E03 cells cultured for two weeks in an Integra Celline multi-compartment bioreactor. Exosomes and microvesicles of the invention may contain at least a proportion of the proteins identified in Tables 20 and 22, respectively. Typically, an exosome of the invention comprises the first ten proteins listed in Table 20, more typically the first 20, the first 30, the first 40 or the first 50 proteins listed in Table 20. Similarly, a microparticle of the invention typically comprises the first ten proteins listed in Table 22, more typically the first 20, the first 30, the first 40 or the first 50 proteins listed in Table 22. In one embodiment, an exosome of the invention comprises all 100 proteins listed in Table 20. In one embodiment, a microvesicle of the invention comprises all 100 proteins listed in Table 22. Typically, the 100 most abundant proteins in an exosome or microvesicle of the invention contain at least 70 of the proteins identified in Table 20 (exosome) or Table 22 (microparticle). More typically, the 100 most abundant proteins in an exosome or microvesicle of the invention contain at least 80, at least 90, at least 95, 96, 97, 98 or 99, or all 100 of the proteins identified in Table 20 (exosome) or Table 22 (microparticle).

Microparticle miRNA Content

Example 17A-C (and the Related FIGS. 13A&B) Shows the Results of Deep Sequencing of miRNA present in CTX0E03 cells (standard culture) and in microvesicles and exosomes produced by these cells. This Example shows that, surprisingly, the number of different miRNA species present in the microparticles is greatly reduced compared to the number of different miRNA species present in the cells; the microparticles contain fewer than 120 different miRNAs whereas the cells contain between 450 and 700 miRNA species. The microparticles contain a majority of hsa-miR-1246.

The data in Example 17 (Tables 5-10) also show that the microparticles are characterised by four main miRNA species, namely hsa-miR-1246, hsa-miR-4492, hsa-miR-4488 and hsa-miR-4532. These four miRNAs are the only miRNAs present at a read count of greater than 1000 in the microparticles; these four miRNAs are present in massive excess compared to the other miRNAs in the microparticles. This is in contrast to the profile in the cells, which contain a much greater number of miRNAs present at high (read count greater than 1000) or very high (read count greater than 10,000) levels. Although not bound by theory, the inventors propose that hsa-miR-1246, hsa-miR-4492, hsa-miR-4488 and hsa-miR-4532 are selectively trafficked (or otherwise incorporated) into the microparticles and are thought to play a role in the function of the microparticles. A composition may comprise two, three or all four of hsa-miR-1246, hsa-miR-4492, hsa-miR-4488 and hsa-miR-4532. This composition is optionally a pharmaceutical composition, comprising a pharmaceutically-acceptable carrier, diluent, vehicle and/or excipient. The pharmaceutical composition is suitable for use in therapy, typically in the same therapies as the microparticles of the invention, as noted above.

Exosomes and microvesicles of the invention may contain at least a proportion of the miRNA species identified in Tables 7-10. In one embodiment, exosomes of the invention comprise at least 70%, at least 80%, at least 90%, at least 95%, at least 99% or at least 99.5% of the miRNAs listed in Tables 8 and 10. Similarly, microvesicles of the invention typically comprise at least 70% at least 80%, at least 90%, at least 95%, at least 99% or at least 99.5% of the miRNAs listed in Tables 7 and 9. In a further embodiment, the total miRNA profile of a microvesicle or exosome of the invention is least 70%, at least 80%, at least 90%, at least 95%, at least 99% or at least 99.5% identical to the total miRNA profile provided in Tables 8 and 10 (exosome) or Tables 7 and 9 (microvesicle). When determining the total miRNA profile of a microparticle or exosome, deep sequencing is typically used, for example the method described in Example 17.

Typically, in one embodiment microparticles, e.g. exosomes, of the invention contain one, two, three or all four of hsa-miR-1246, hsa-miR-4492, hsa-miR-4488 and hsa-miR-4532. Each of these miRNA markers is typically present at a read count (optionally determined using the deep sequence technique described in Example 17) of at least 1000 per microparticle. hsa-miR-1246 may optionally have a read count of at least 2000, 5000, 10,000, 20,000, or 25,000 per microparticle. Hsa-miR-4492 may optionally have a read count of at least 2000, 3000, 4000 or 5000 per microparticle. Hsa-miR-4532 may optionally have a read count of at least 2000 or 3000 per microparticle.

In one embodiment, each of hsa-miR-1246, hsa-miR-4492, hsa-miR-4488 and/or hsa-miR-4532 is present in the microparticle, e.g. exosome, at a higher read count than is present in the cell that produced the microparticle. In particular, miR-1246 typically has a read count in the microparticle at least twice the read count in the cell, more typically at least 4, 5, 6, 7, or 8 times the read count in the cell, and optionally 10, 15 or 20 times the read count in the cell.

In one embodiment, microparticles of the invention contain hsa-let-7a-5p, has-miR-92b-3p, hsa-miR-21-5p, hsa-miR-92a-3p, hsa-miR-10a-5p, hsa-100-5p and/or hsa-99b-5p at a lower read count than is present in the cell that produced the microparticle. Typically, each of these miRNAs has a read count of less than 1000 in the microparticles of the invention, more typically less than 100, for example less than 50. Optionally, microparticles of the invention contain hsa-let-7a-5p at a read count of less than 50 or less than 25.

In one embodiment, microparticles of the invention contain fewer than 150 types of miRNA (i.e. different miRNA species) when analysed by deep sequencing, typically fewer than 120 types of miRNA.

In one embodiment, hsa-miR-1246 is the most abundant miRNA in the microparticles of the invention (optionally determined using the deep sequence technique described in Example 17). Typically, at least 40% of the total count of miRNA in microparticles (e.g. microvesicles and exosomes) of the invention is hsa-miR-1246. Typically, at least 50% of the total count of miRNA in exosomes of the invention is hsa-miR-1246.

hsa-miR-4492 is typically the second-most abundant miRNA in the microparticles of the invention. Typically, at least 3% of the total count of miRNA in microparticles (e.g. microvesicles and exosomes) of the invention is hsa-miR-4492. More typically, at least 4% of the total count of miRNA in microparticles (e.g. microvesicles and exosomes) of the invention is hsa-miR-4492.

Typically, at least 2% of the total count of miRNA in microparticles (e.g. microvesicles and exosomes) of the invention is hsa-miR-4532.

Typically, at least 1% of the total count of miRNA in microparticles (e.g. microvesicles and exosomes) of the invention is hsa-miR-4488.

In one embodiment microparticles of the invention contain one or both of hsa-miR-4508, hsa-miR-4516 at a level at least 0.1% of the total miRNA content of the particle.

One or more of hsa-miR-3676-5p, hsa-miR-4485, hsa-miR-4497, hsa-miR-21-5p, hsa-miR-3195, hsa-miR-3648, hsa-miR-663b, hsa-miR-3656, hsa-miR-3687, hsa-miR-4466, hsa-miR-4792, hsa-miR-99b-5p and hsa-miR-1973 may be present in the microparticles of the invention.

Typically, each of hsa-let-7a-5p and hsa-100-5p is present at less than 1%, more typically less than 0.1% or less than 0.05% of the total miRNA count in microparticles of the invention.

In a typical exosome of the invention, at least 50% of the total count of miRNA is hsa-miR-1246, and less than 0.1% of the total miRNA count is hsa-let-7a-5p.

In one embodiment, at least 90% of the total count of miRNA in microparticles of the invention comprises hsa-miR-1246, hsa-miR-4492, hsa-miR-4488 and hsa-miR-4532. Typically, at least 95% or 96% of the total count of miRNA in microparticles of the invention comprises hsa-miR-1246, hsa-miR-4492, hsa-miR-4488 and hsa-miR-4532. Less than 10% of the total miRNA content of these microparticles is an miRNA that is not hsa-miR-1246, hsa-miR-4492, hsa-miR-4488 and hsa-miR-4532.

Combinations of the miRNA embodiments discussed above are provided. For example, a microparticle of the invention typically contains each of hsa-miR-1246, hsa-miR-4492, hsa-miR-4488 and hsa-miR-4532 at a read count of at least 1000 and contains each of hsa-let-7a-5p, hsa-miR-92b-3p, hsa-miR-21-5p, hsa-miR-92a-3p, hsa-miR-10a-5p, hsa-100-5p and hsa-99b-5p at a read count of less than 100. Typically, at least 90% or at least 95% of the total miRNA in these microparticles is hsa-miR-1246, hsa-miR-4492, hsa-miR-4488 and hsa-miR-4532.

A microparticle (e.g. microvesicle or exosome) of the invention typically has hsa-miR-1246 as the most abundant miRNA and hsa-miR-4492 is the second-most abundant miRNA. In this embodiment, at least 40% of the total count of miRNA in microparticles (e.g. microvesicles and exosomes) of the invention is hsa-miR-1246 and at least 3% of the total count of miRNA in the microparticle is hsa-miR-4492. At least 2% of the total count of miRNA in these microparticles is hsa-miR-4532 and at least 1% of the total count of miRNA in these microparticles is hsa-miR-4488. Each of hsa-let-7a-5p and hsa-100-5p is present at less than 0.1% of the total miRNA count in these microparticles.

Plotting the deep sequencing results in the exosomes and microvesicles as relative fold change compared to the cells confirms that hsa-miR-1246, hsa-miR-4492, hsa-miR-4488 and hsa-miR-4532 are significantly upregulated in the exosomes and microvesicles compared to the cells.

This comparison also shows that miRNA hsa-miR-3195 is the miRNA that is most upregulated, in both exosomes and microvesicles. Although the absolute reads of hsa-miR-3195 are in the range of ~40 for exosomes and microvesicles, there is no hsa-miR-3195 detected in the cells. Accordingly, hsa-miR-3195 is uniquely found in the exosomes and microvesicles and, optionally, in one embodiment, an exosome or microvesicle of the invention comprises hsa-miR-3195.

In one embodiment, microparticles of the invention comprise one or more of the following miRNA precursors:

AC079949.1
(SEQ ID NO: 738)
GGCCGCGCCCCGTTTCCCAGGACAAAGGGCACTCCGCACCGGACCCTGGT

CCCAGCG;

AP000318.1
(SEQ ID NO: 739)
CCCACTCCCTGGCGCCGCTTGTGGAGGGCCCAAGTCCTTCTGATTGAGGC

CCAACCCGTGGAAG;

AL161626.1
(SEQ ID NO: 740)
CGCCGGGACCGGGGTCCGGGGCGGAGTGCCCTTCCTCCTGGGAAACGGGG

TGCGGC;

AC004943.1
(SEQ ID NO: 741)
GCTTCACGTCCCCACCGGCGGCGGCGGCGGTGGCAGTGGCGGCGGCGGCG

GCGGTGGCGGCGGCGGCGGCGGCGGCGGCTC;
and

AL121897.1
(SEQ ID NO: 742)
GCCGCCCCGCCGCCGCCGCCGCCGCCGCCGCCGCCGCCGCCGCCCGCTT

TCGGCTCGGGCCTCAGGTGAGTCGGAGGGGCCGGGCGCC

In one embodiment, microparticles of the invention comprise one, two or three of the following mature miRNAs derived from the precursors listed above (as detailed in part D of Example 17):

(SEQ ID NO: 743)
ggcggagugcccuucuuccugg (derived from
AL161626.1-201)

(SEQ ID NO: 744)
ggagggcccaaguccuucugau (derived from
AP000318.1-201)

(SEQ ID NO: 745)
gaccaggguccggugcggagug (derived from
AC079949.1-201)

Accordingly, in one aspect, the invention provides a composition comprising one or more of the miRNA precursors AC079949.1, AP000318.1, AL161626.1, AC004943.1 and AL121897.1 in combination with a neural stem cell microparticle of the invention. In another embodiment, the invention provides a composition comprising one or more of the mature miRNAs ggcggagugcccuucuuccugg (derived from AL161626.1-201), ggagggcccaaguccuucugau (derived from AP000318.1-201) and gaccaggguccggugcggagug (derived from AC079949.1-201) in combination with a neural stem cell microparticle of the invention. Optionally, the composition is a pharmaceutical composition comprising one or more of the miRNA precursors and/or one or more of the mature miRNAs and a pharmaceutically-acceptable carrier or diluent in combination with a neural stem cell microparticle of the invention.

Example 17 shows that neural stem cell microparticles isolated from CTX0E03 cells comprise a variety of non-coding RNA species. It is expected that microparticles isolated from CTX0E03 cells cultured for at least 10 weeks, e.g. for about 11 weeks, in an Integra Celline multicompartment bioreactor will contain at least a proportion of those non-coding RNA species. Thus, in one embodiment, microparticles of the invention comprise one or more of ribosomal RNA, small nucleolar RNA, small nuclear RNA, microRNA, large intergenic non-coding RNA and miscellaneous other RNA (e.g. RMRP, vault RNA, metazoan SRP and/or RNY).

Example 12 shows miRNAs present in microparticles produced by the CTX0E03 cells and having a Cp below 35 as determined by a qRT-PCR array. Microparticles isolated from CTX0E03 cells cultured for at least 10 weeks, e.g. for about 11 weeks, in an Integra Celline multi-compartment bioreactor may, in one embodiment contain 1, 2, 3, 4, 5, 6, 7, 8, 9, 10, 15, 20, 25, 30, 35, 40, 45, 50, 60 or more, or all, of the following miRNAs (identified according by name according to Ambros et al and accessible at www.mirbase.org):

hsa-let-7a
hsa-let-7b
hsa-let-7c
hsa-let-7d
hsa-let-7e
hsa-let-7f
hsa-let-7g
hsa-let-7i
hsa-miR-100
hsa-miR-101
hsa-miR-103a
hsa-miR-106b
hsa-miR-10a
hsa-miR-10b
hsa-miR-124
hsa-miR-125a-5p
hsa-miR-125b
hsa-miR-126
hsa-miR-127-5p
hsa-miR-128
hsa-miR-129-5p
hsa-miR-130a
hsa-miR-132
hsa-miR-134
hsa-miR-137
hsa-miR-141
hsa-miR-146b-5p
hsa-miR-150
hsa-miR-155
hsa-miR-15a
hsa-miR-15b
hsa-miR-16
hsa-miR-17
hsa-miR-181a
hsa-miR-182
hsa-miR-183

-continued hsa-miR-185
hsa-miR-18a
hsa-miR-18b
hsa-miR-192
hsa-miR-194
hsa-miR-195
hsa-miR-196a
hsa-miR-205
hsa-miR-20a
hsa-miR-20b
hsa-miR-21
hsa-miR-210
hsa-miR-214
hsa-miR-218
hsa-miR-219-5p
hsa-miR-22
hsa-miR-222
hsa-miR-23b
hsa-miR-24
hsa-miR-26a
hsa-miR-301a
hsa-miR-302a
hsa-miR-302c
hsa-miR-33a
hsa-miR-345
hsa-miR-375
hsa-miR-378
hsa-miR-424
hsa-miR-7
hsa-miR-9
hsa-miR-92a
hsa-miR-93
hsa-miR-96
hsa-miR-99a In one embodiment, the CTX0E03 microparticles contain 1, 2, 3, 4, 5, 6, 7, 8, 9, 10, 15, 20, 25, 30 or more of the following miRNAs (which are selected from the list above):

hsa-let-7g
hsa-miR-101
hsa-miR-10a
hsa-miR-10b
hsa-miR-126
hsa-miR-128
hsa-miR-129-5p
hsa-miR-130a
hsa-miR-134
hsa-miR-137
hsa-miR-155
hsa-miR-15a
hsa-miR-15b
hsa-miR-16
hsa-miR-17
hsa-miR-182
hsa-miR-183
hsa-miR-185
hsa-miR-18b
hsa-miR-192
hsa-miR-194
hsa-miR-195
hsa-miR-20a
hsa-miR-20b
hsa-miR-210
hsa-miR-218
hsa-miR-301a
hsa-miR-302a
hsa-miR-302c
hsa-miR-345
hsa-miR-375
hsa-miR-378
hsa-miR-7
hsa-miR-9
hsa-miR-93
hsa-miR-96
hsa-miR-99a miRNAs Present in Exosomes from Cells Cultured in a Bioreactor for Longer Periods Examples 17D and 17E (in particular FIGS. 13D to 13H and Tables E2 to E4) demonstrate that hsa-miR-1246, hsa-miR-4492, hsa-miR-4532, and hsa-miR-4488 are still present in exosomes isolated from CTX0E03 cells that have been cultured in a bioreactor for six weeks. hsa-miR-4492, hsa-miR-4532, and hsa-miR-4488 are shown to be almost absent in exosomes isolated from CTX0E03 cells that have been cultured in a bioreactor for eleven weeks.

Exosomes and microvesicles of the invention may contain at least a proportion of the miRNA species identified in Table E3, or at least a proportion of the miRNA species identified in Table E4.

Hsa-miR-181a-5p, hsa-miR-1246, hsa-miR-127-3p, hsa-miR-21-5p, and hsa-miR-100-5p are shown to be the top 5 miRNAs present in the EXO 6W sample. Accordingly, in one embodiment, exosomes of the invention comprise 1, 2, 3, 4 or 5 of these miRNAs. In another embodiment, exosomes of the invention comprise at least 50%, at least 60%, at least 70%, at least 80%, at least 90%, or all of the miRNAs listed in Table E3. When determining the total miRNA profile of a microparticle or exosome, deep sequencing is typically used, for example the method described in Example 17.

Hsa-miR-181a-5p, hsa-let-7a-5p, hsa-let-7f-5p, hsa-miR-92b-3p, and hsa-miR-9-5p are shown to be the top 5 miRNAs present in EXO 11W samples. Accordingly, in one embodiment, exosomes of the invention comprise 1, 2, 3, 4 or 5 of these miRNAs. In another embodiment, exosomes of the invention comprise at least 50%, at least 60%, at least 70%, at least 80%, at least 90%, or all of the miRNAs listed in Table E4. When determining the total miRNA profile of a microparticle or exosome, deep sequencing is typically used, for example the method described in Example 17.

Hsa-miR-486-5p is observed to be shuttled into all three of the samples of exosomes obtained from CTX0E03 cells that have been cultured in a bioreactor for six weeks. Accordingly, in one embodiment, exosomes of the invention comprise hsa-miR-486-5p.

Figure 23A:
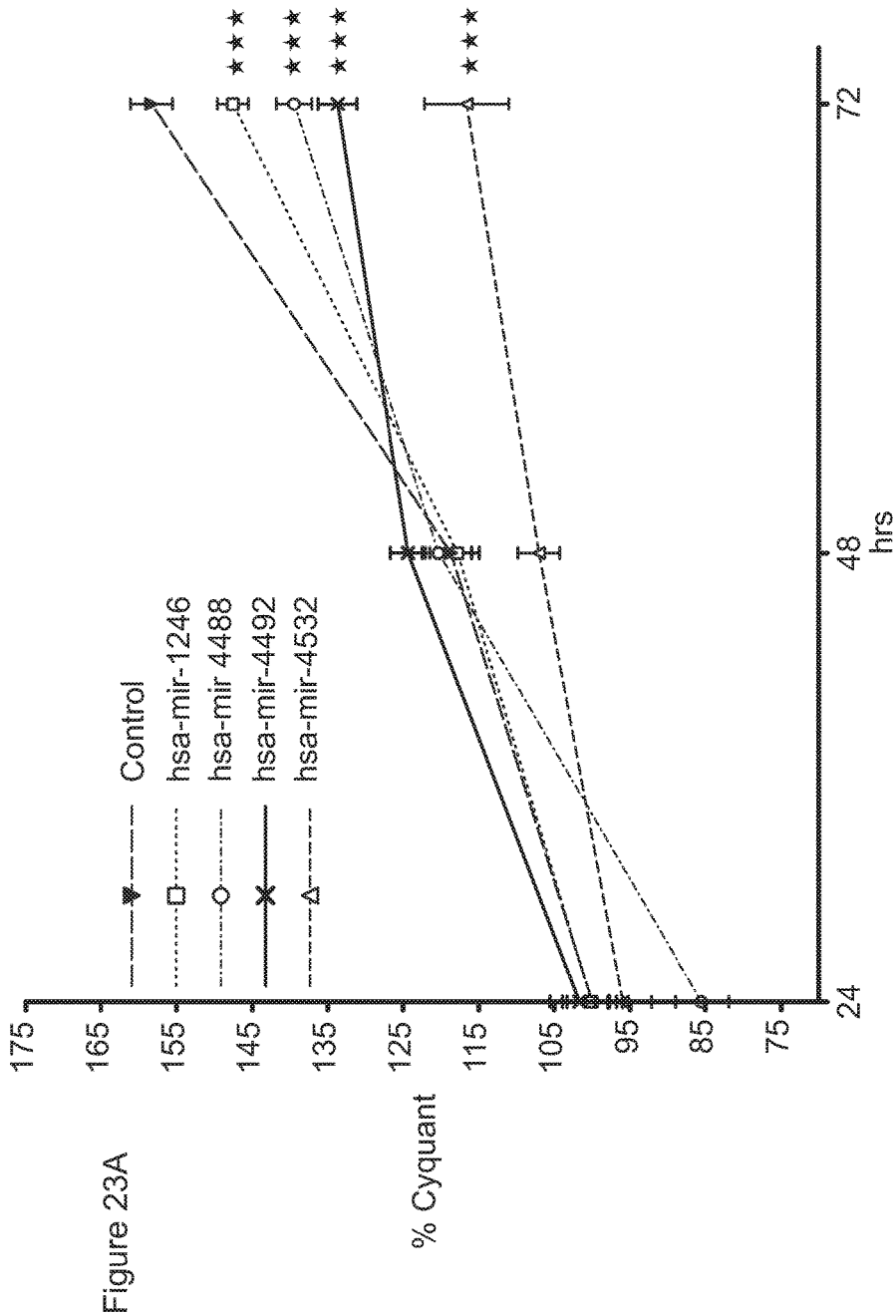
FIG. 23 shows the inhibitory effects of individual miRNAs on the proliferation of glioma cells: (A) plot of percentage of U373MG cell proliferation, compared to 24 hrs control, measured by CyQUANT assay following transfection with hsa-mir-1246, hsa-mir-4488, hsa-mir-4492, or hsa-mir-4532; (B) plot of percentage of U373MG cell proliferation, compared to 0hr control, measured by CyQUANT assay following transfection with hsa-mir-1246, hsa-mir-4488, hsa-mir-4492, or hsa-mir-4532; and (C) plot of percentage of U87 cell proliferation, compared to 0hr control, measured by CyQUANT assay following transfection with hsa-mir-1246, hsa-mir-4488, hsa-mir-4492, or hsa-mir-4532.

Individual miRNAs are Able to Reduce Cell Proliferation and have Therapeutic Utility The data in the Example 20 and FIG. 23 show that each of the four main miRNA species identified in neural stem cell microparticles, namely hsa-miR-1246, hsa-miR-4492, hsa-miR-4488 and hsa-miR-4532, significantly reduced cell proliferation in glioma proliferation assays. In addition to these data supporting the therapeutic efficacy of the microparticles that contain these miRNAs, these data also show that each of these individual miRNAs is therapeutically useful on its own. In one embodiment, the individual miRNA is useful in the treatment of cancer (optionally glioblastoma), as described below.

In one embodiment, hsa-miR-1246 is provided for use in therapy. In another embodiment, hsa-miR-4492 is provided for use in therapy. In a further embodiment, hsa-miR-4488 is provided for use in therapy. In another embodiment, has-miR-4532 is provided for use in therapy. These therapeutics can be provided in a composition that does not comprise any of the other four "main" miRNA species.

For example, in one embodiment when hsa-miR-1246 is provided for therapy, none of hsa-miR-4492, hsa-miR-4488 or hsa-miR-4532 are part of the therapy. This therapy comprises hsa-miR-1246 and does not comprise any of hsa-miR-4492, hsa-miR-4488 or hsa-miR-4532.

In one embodiment, when hsa-miR-4492 is provided for therapy, none of hsa-miR-1246, hsa-miR-4488 or hsa-miR- 4532 are part of the therapy. This therapy comprises hsa-miR-4492 and does not comprise any of hsa-miR-1246, hsa-miR-4488 or hsa-miR-4532.

In one embodiment, when hsa-miR-4488 is provided for therapy, none of hsa-miR-1246, hsa-miR-4492 or hsa-miR-4532 are part of the therapy. This therapy comprises hsa-miR-4488 and does not comprise any of hsa-miR-1246, hsa-miR-4492 or hsa-miR-4532.

In one embodiment, when hsa-miR-4532 is provided for therapy, none of hsa-miR-1246, hsa-miR-4492 or hsa-miR-4488 are part of the therapy. This therapy comprises hsa-miR-4532 and does not comprise any of hsa-miR-1246, hsa-miR-4492 or hsa-miR-4488.

The invention therefore provides, in one aspect, a composition that comprises only one of hsa-miR-1246, hsa-miR-4492, hsa-miR-4488 and hsa-miR-4532. In this aspect, the composition does not comprise two or more, e.g. two, three or four of these miRNAs.

Typically, the composition does not comprise other miRNA, i.e. the composition comprises miRNA that consists of one miRNA species selected from hsa-miR-1246, hsa-miR-4492, hsa-miR-4488 and hsa-miR-4532. The composition is typically a pharmaceutical composition and comprises a pharmaceutically acceptable carrier, diluent, vehicle or excipient, as described in detail below. The miRNAs of this aspect of the invention are typically isolated, i.e. not comprised within a microparticle. In one embodiment, the composition consists of, or consists essentially of, the single miRNA species and one or more pharmaceutically acceptable carrier, diluent, vehicle or excipient.

miRNA Compositions and Combinations

In a separate aspect of the invention, the identification of hsa-miR-1246, hsa-miR-4492, hsa-miR-4488 and hsa-miR-4532 as the four main miRNA species in neural stem cell microparticles, provides for compositions that comprise two or more, e.g. two, three or four of these miRNAs. Any combination of these miRNAs may be provided. In one embodiment, the composition may comprise hsa-miR-1246 and one or more of hsa-miR-4492, hsa-miR-4488 and hsa-miR-4532. Typically, the composition does not comprise other miRNA, i.e. the composition comprises miRNA that consists of two or more of hsa-miR-1246, hsa-miR-4492, hsa-miR-4488 and hsa-miR-4532. The composition is typically a pharmaceutical composition and comprises a pharmaceutically acceptable carrier, diluent, vehicle or excipient, as described in detail below. The miRNAs of this aspect of the invention are typically isolated, i.e. not comprised within a microparticle. In one embodiment, the composition consists of, or consists essentially of, the 2, 3 or 4 miRNA species and one or more pharmaceutically acceptable carrier, diluent, vehicle or excipient.

hsa-miR-1246, hsa-miR-4492, hsa-miR-4488 and hsa-miR-4532 are shown in the Examples to reduce cell proliferation in glioma proliferation assays. Accordingly, the miRNA composition comprising two or more of these miRNAs is useful in therapy. In one embodiment, the miRNA composition comprising two or more of these miRNAs is useful in the treatment of cancer (optionally glioblastoma), as described below.

Hsa-miR-181a-5p, hsa-miR-1246, hsa-miR-127-3p, hsa-miR-21-5p, and hsa-miR-100-5p are shown to be the top 5 miRNAs present in the EXO 6W sample. Accordingly, one embodiment provides for compositions that comprise 1, 2, 3, 4 or 5 of these miRNAs. Any one, or any combination of these miRNAs may be provided. The composition is typically a pharmaceutical composition and comprises a pharmaceutically acceptable carrier, diluent, vehicle or excipient, as described in detail below. The miRNAs of this aspect of the invention are typically isolated, i.e. not comprised within a microparticle. In one embodiment, the composition consists of, or consists essentially of, the 1, 2, 3, 4 or 5 miRNA species and one or more pharmaceutically acceptable carrier, diluent, vehicle or excipient. These miRNAs and compositions are provided, in one embodiment, for use in therapy, typically the therapy of cancer (optionally glioblastoma), as described herein.

Hsa-miR-181a-5p, hsa-let-7a-5p, hsa-let-7f-5p, hsa-miR-92b-3p, and hsa-miR-9-5p are shown to be the top 5 miRNAs present in EXO 11W samples. Accordingly, one embodiment provides for a composition that comprises 1, 2, 3, 4 or 5 of these miRNAs. Any one, or any combination of these miRNAs may be provided. The composition is typically a pharmaceutical composition and comprises a pharmaceutically acceptable carrier, diluent, vehicle or excipient, as described in detail below. The miRNAs of this aspect of the invention are typically isolated, i.e. not comprised within a microparticle. In one embodiment, the composition consists of, or consists essentially of, the 1, 2, 3, 4 or 5 miRNA species and one or more pharmaceutically acceptable carrier, diluent, vehicle or excipient. These miRNAs and compositions are provided, in one embodiment, for use in therapy, typically the therapy of cancer (optionally glioblastoma), as described herein.

Hsa-miR-486-5p is observed to be shuttled into all three of the samples of exosomes obtained from CTX0E03 cells that have been cultured in a bioreactor for 11 weeks. Accordingly, one embodiment provides for compositions that comprise hsa-miR-486-5p. The composition is typically a pharmaceutical composition and comprises a pharmaceutically acceptable carrier, diluent, vehicle or excipient, as described in detail below. The miRNA of this aspect of the invention are typically isolated, i.e. not comprised within a microparticle. This miRNA and composition are provided, in one embodiment, for use in therapy, typically the therapy of cancer (optionally glioblastoma), as described herein.

Proteins Detected by a Dot-Blot

Example 13 shows proteins present in microparticles produced by the CTX0E03 cells, as detected by a dot-blot. Microparticles of the invention may typically contain 1, 2, 3, 4, 5, 6, 7, 8, 9, 10 or all of the following proteins:

EDA-A2
Galectin-3
IGFBP-2
IGFBP-rp1/IGFBP-7
IL-1a
LECT2
MCP-1
SPARC
TIMP-1
Thrombospondin-1
VEGF Galectin-3 and Thrombospondin-1 are also identified as present in exosomes and microvesicles in Example 18. TIMP-1 is identified in Example 18 as being present in exosomes. Microparticles of the invention may contain one or more of Galectin-3, Thrombospondin and TIMP-1.

Example 13 also shows that the microparticles produced by the CTX0E03 cells may also express 1, 2, 3, 4 or 5 of the following proteins:

EGF-R/ErbB1
MDC

-continued

> Endostatin
> Follistatin
> Csk

EGF-R and Csk are also identified as present in exosomes and microvesicles in Example 18.

Neural Stem Cells in Multi-Compartment Bioreactor Culture

Figure 11:
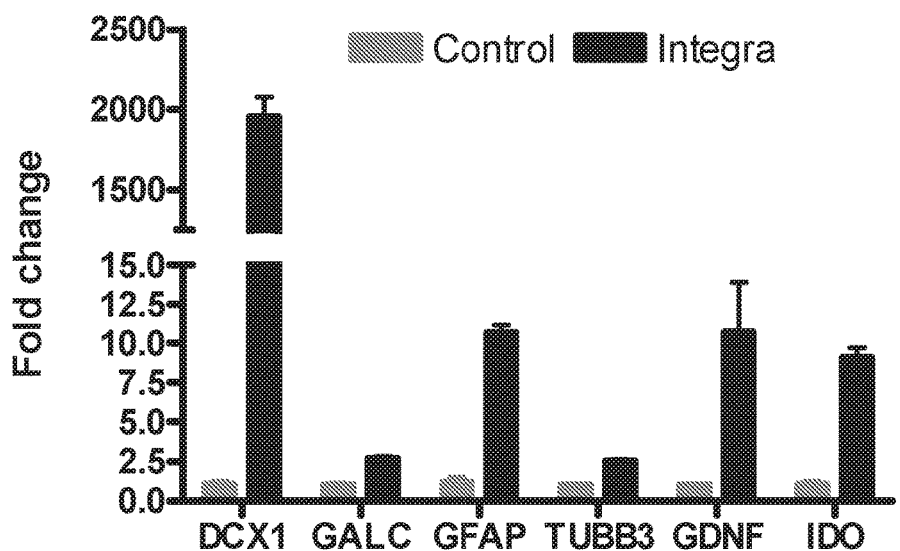
FIG. 11 shows the fold change of expression levels of various mRNA markers measured in CTX0E03 cells cultured for 3 weeks in the Integra CELLine system compared to standard ("control") CTX0E03 (T175) cultures.

As shown in Example 15 and FIG. 11 below, after multi-compartment bioreactor culture for three weeks, neural stem cells express a number of markers at significantly higher levels than neural stem cells cultured according to standard procedure in a standard single-compartment T175 flask. Neural stem cells cultured for even longer periods, e.g. at least 10 weeks, may also express a number of these markers at significantly higher levels than neural stem cells cultured according to standard procedure in a standard single-compartment T175 flask or neural stem cells cultured in a multi-compartment bioreactor culture for three weeks. In one embodiment, microparticles of the invention are isolated from NSCs that have been cultured, typically in a multi-compartment bioreactor, for at least 10 weeks, typically at least 11 weeks, at least 12 weeks, at least 13 weeks, at least 14 weeks or at least 15 weeks. Optionally, the NSCs have been cultured for no more than 20 weeks, e.g. between 10 and 20 weeks, between 11 and 20 weeks, between 12 and 20 weeks, between 13 and 20 weeks, between 14 and 20 weeks or between 15 and 20 weeks.

CTX0E03 neural stem cells cultured for three weeks in a multi-compartment bioreactor express DCX, GALC, GFAP, TUBB3, GDNF and IDO at a higher level than neural stem cells cultured in a standard single-compartment T175 cell culture. Neural stem cells cultured for even longer periods, e.g. at least 10 weeks, may also express a number of these markers at significantly higher levels than neural stem cells cultured according to standard procedure in a standard single-compartment T175 flask or, optionally, than neural stem cells cultured in a multi-compartment bioreactor culture for three weeks. Accordingly neural stem cells that produce microparticles of the invention may express one or more of DCX, GALC, GFAP, TUBB3, GDNF and IDO. Cells cultured in a two-compartment bioreactor typically show increased expression of one or more of DCX, GALC, GFAP, TUBB3, GDNF and IDO compared to the stem cells cultured under standard conditions for three weeks. The expression level of these markers in the multi-compartment bioreactor-cultured cells is typically significantly higher than in the cells cultured in a standard single-compartment T175 culture flask. Typically, a stem cell cultured in a multi-compartment bioreactor, that produces microparticles of the invention, expresses one or more of DCX1, GALC, GFAP, TUBB3, GDNF or IDO at a level least 2 fold higher than in CTX0E03 cells cultured in a T-175 flask according to standard culture procedure.

In one embodiment, microparticles, typically exosomes, are obtained from neural stem cells that show increased expression of one or more of DCX, GALC, GFAP, TUBB3, GDNF and IDO compared to the stem cells cultured under standard conditions or, optionally than in a multi-compartment bioreactor culture for three weeks. For example, microparticles can be obtained from freshly filtered conditioned medium collected from Integra CeLLine bioreactor cultured neural stem cells.

The upregulated markers include DCX (doublecortin—an early neuronal marker), GFAP (Glial fibrillary acidic protein—an astrocyte marker), GALC, TUBB3, GDNF and IDO. CTX0E03 cells are able to differentiate into 3 different cell types: neurons, astrocytes and oligodendrocytes. The high levels of DCX and GFAP after only three weeks in a multi-compartment bioreactor indicates that the cultured stem cells have partially differentiated and have entered the neuronal (DCX+ cells) and/or astrocytic (GFAP+ cells) lineage. Accordingly, in one embodiment the invention provides a microparticle that inhibits cell migration, produced by a neural stem cell population that expresses (i) one or more markers associated with a neuronal lineage, typically DCX and/or (ii) one or more markers associated with an astrocytic lineage, typically GFAP. These cells may optionally have been cultured for at least 10 weeks in a multi-compartment bioreactor. In another embodiment, the invention provides neural stem cell microparticles, typically exosomes, that express (i) one or more markers associated with a neuronal lineage, typically DCX and/or (ii) one or more markers associated with an astrocytic lineage, typically GFAP. These cells, or the microparticles (typically exosomes) derived from these cells, express DCX and/or GFAP at a higher level than the corresponding stem cells in standard (T-175) culture or, optionally, than the cells cultured in a multi-compartment bioreactor for three weeks. Typically, these cells or microparticles express DCX and/or GFAP at a level at least 2 fold more than the stem cells in standard culture, more typically at least 2.5 fold more than the corresponding stem cells in standard culture (or cultured in a multi-compartment bioreactor culture for three weeks), at least 5 fold more than the corresponding stem cells in standard culture (or cultured in a multi-compartment bioreactor culture for three weeks), at least 7.5 fold more than the corresponding stem cells in standard culture (or cultured in a multi-compartment bioreactor culture for three weeks) or at least 10 fold more than the corresponding stem cells in standard culture (or cultured in a multi-compartment bioreactor culture for three weeks). For expression of DCX, the fold change in the cells or microparticles compared to the corresponding stem cells in standard (T-175) culture (or cultured in a multi-compartment bioreactor culture for three weeks) can optionally be at least 20 fold, at least 50 fold, at least 100 fold, at least 500 fold or at least 1000 fold more than the standard stem cells (or cells cultured in a multi-compartment bioreactor culture for three weeks).

The term "bioreactor" is to be given its usual meaning in the art, i.e. an apparatus used to carry out a bioprocess. The bioreactors described herein are suitable for use in stem cell culture. Simple bioreactors for cell culture are single compartment flasks, such as the commonly-used T-175 flask (e.g. the BD Falcon™ 175 cm$^2$ Cell Culture Flask, 750 ml, tissue-culture treated polystyrene, straight neck, blue plug-seal screw cap, BD product code 353028).

Bioreactors can have multiple compartments, as is known in the art. These multi-compartment bioreactors typically contain at least two compartments separated by one or more membranes or barriers that separate the compartment containing the cells from one or more compartments containing gas and/or culture medium. Multi-compartment bioreactors are well-known in the art. An example of a multi-compartment bioreactor is the Integra CeLLine bioreactor, which contains a medium compartment and a cell compartment separated by means of a 10 kDa semi-permeable membrane; this membrane allows a continuous diffusion of nutrients into the cell compartment with a concurrent removal of any inhibitory waste product. The individual accessibility of the compartments allows to supply cells with fresh medium without mechanically interfering with the culture. A silicone membrane forms the cell compartment base and provides an optimal oxygen supply and control of carbon dioxide levels by providing a short diffusion pathway to the cell compartment. Any multi-compartment bioreactor may be used according to the invention. As shown in the Examples below, CTX0E03 cells that have been cultured in the Integra CeLLine AD1000 bioreactor for 11 weeks produce microparticles that are able to inhibit cell migration.

Figure 12:
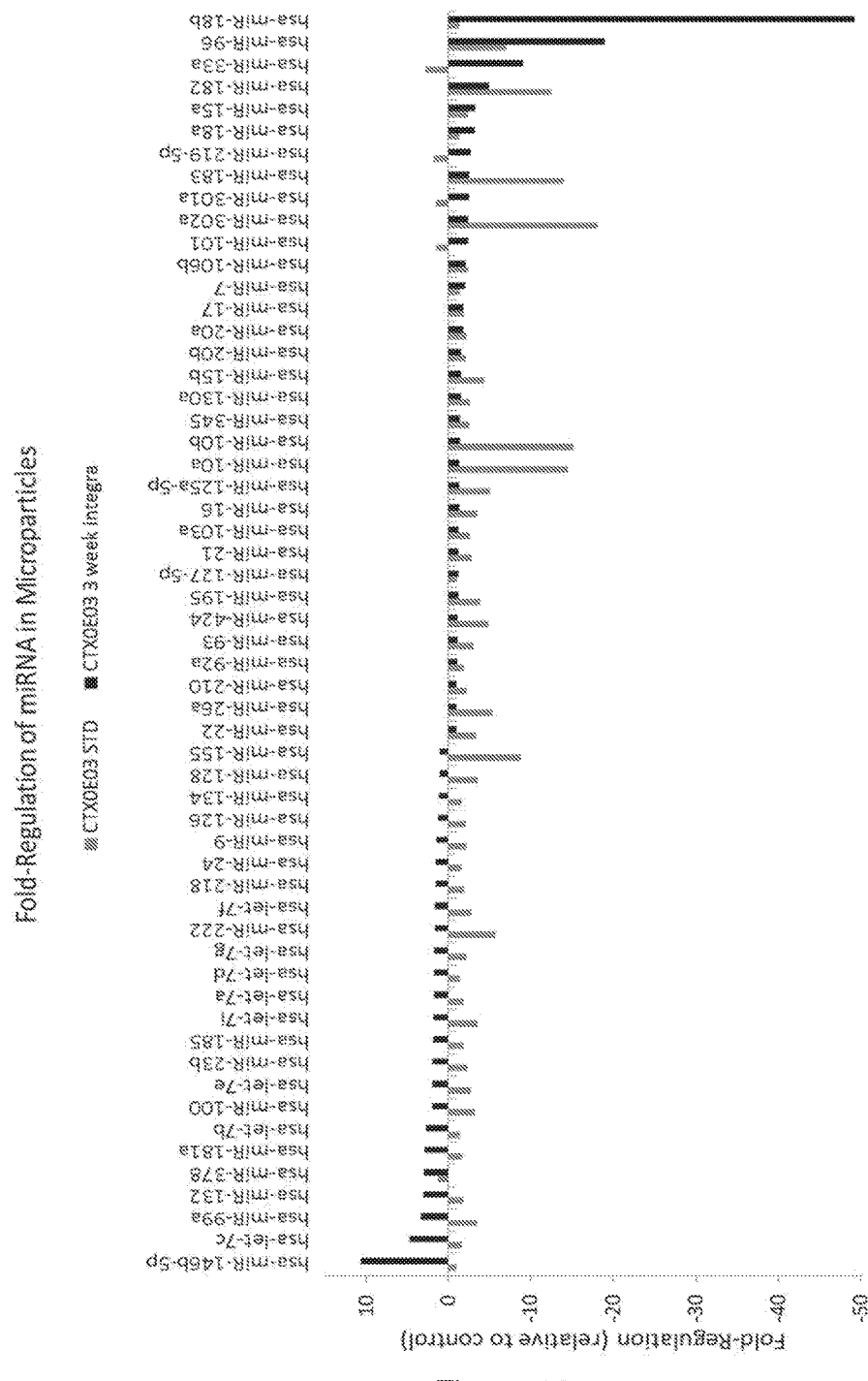
FIG. 12 shows the fold up and down regulation of various miRNAs in exosomes obtained from CTX0E03 cells cultured for 3 weeks in Integra bioreactor culture and microparticles obtained from standard CTX0E03 (T175) cultures, assessed against a baseline expression level in CTX0E03 cells in standard (T175) culture.

Example 16, Table 4 and FIG. 12 show that the miRNA content of exosomes produced by neural stem cells that have been cultured in a multi-compartment bioreactor, for three weeks, is different from the miRNA content of stem cells cultured in standard T-175 flasks and from microparticles produced by the neural stem cells cultured in a single-compartment T175 culture flask for three weeks. The miRNA content of exosomes of the invention may also differ from the miRNA content of stem cells cultured in standard T-175 or microparticles derived therefrom. In one embodiment, the invention provides a microparticle, typically an exosome, wherein at least two, three, four, five, six or seven miRNAs are up or down regulated compared to in the corresponding stem cells cultured in standard T-175 flasks, as calculated by Fold Regulation (see Example 16), and wherein the microparticle inhibits cell migration. The Fold Regulation of each miRNA is optionally at least two-fold up or down.

In one embodiment, neural stem cell exosomes of the invention express one, two, three, four, five, six or seven of the following miRNAs at a higher level than is expressed in the corresponding stem cells cultured in standard T-175 flasks, as calculated by Fold Regulation (where an asterisk indicates an miRNA where at least a two-fold regulation increase is preferred):

hsa-miR-146b-5p*
hsa-let-7c*
hsa-miR-99a*
hsa-miR-132*
hsa-miR-378*
hsa-miR-181a*
hsa-let-7b*

In one embodiment, neural stem cell exosomes of the invention express one, two, three, four, five, six, seven, eight, nine, ten or more of the following miRNAs at a lower level than is expressed in the corresponding stem cells cultured in standard T-175 flasks, as calculated by Fold Regulation (where an asterisk indicates an miRNA where at least a two-fold regulation decrease is preferred):

hsa-miR-7*
hsa-miR-106b*
hsa-miR-101*
hsa-miR-302a*
hsa-miR-301a*
hsa-miR-183*
hsa-miR-219-5p*
hsa-miR-18a*
hsa-miR-15a*
hsa-miR-182*
hsa-miR-33a*
hsa-miR-96*
hsa-miR-18b*

In a further embodiment, NSC exosomes of the invention comprise (i) an increased level of at least one, two, three, four, five, six or seven of the miRNAs indicated above as being increased in exosomes compared to the corresponding cells in standard culture and (ii) a decreased level of at least one, two, three, four, five, six, seven, eight, nine, ten or more or more of the miRNAs indicated above as being decreased in exosomes compared to the corresponding cells in standard culture. For example, a neural stem cell exosome may contain a fold-regulation increase in three or more or more of the miRNAs indicated above as being increased in exosomes compared to the corresponding cells in standard culture and a fold-regulation decrease in three or more of the miRNAs indicated above as being decreased in exosomes compared to the corresponding cells in standard culture. In another exemplary embodiment, a neural stem cell exosome may contain a fold-regulation increase in five or more of the miRNAs indicated above as being increased in exosomes compared to the corresponding cells in standard culture and a fold-regulation decrease in five or more of the miRNAs indicated above as being decreased in exosomes compared to the corresponding cells in standard culture.

The term "expressed" is used to describe the presence of a marker within a cell or microparticle. In order to be considered as being expressed, a marker must be present at a detectable level. By "detectable level" is meant that the marker can be detected using one of the standard laboratory methodologies such as qRT-PCR, or qPCR, blotting, Mass Spectrometry or FACS analysis. A gene is considered to be expressed by a cell or microparticle of the population of the invention if expression can be reasonably detected at a crossing point (cp) values below or equal 35. The terms "express" and "expression" have corresponding meanings. At an expression level below this cp value, a marker is considered not to be expressed. The comparison between the expression level of a marker in a stem cell or microparticle of the invention, and the expression level of the same marker in another cell or microparticle, such as for example an mesenchymal stem cell, may preferably be conducted by comparing the two cell/microparticle types that have been isolated from the same species. Preferably this species is a mammal, and more preferably this species is human. Such comparison may conveniently be conducted using a reverse transcriptase polymerase chain reaction (RT-PCR) experiment.

As used herein, the term "significant expression" or its equivalent terms "positive" and "+" when used in regard to a marker shall be taken to mean that, in a cell or microparticle population, more than 20%, preferably more than, 30%, 40%, 50%, 60%, 70%, 80%, 90% 95%, 98%, 99% or even all of the cells of the cells/microparticles express said marker.

As used herein, "negative" or "−" as used with respect to markers shall be taken to mean that, in a cell or microparticle population, less than 20%, 10%, preferably less than 9%, 8%, 7%, 6%, 5%, 4%, 3%, 2%, 1% or none of the cells/microparticles express said marker.

Expression of microparticle surface markers may be determined, for example, by means of flow cytometry and/or FACS for a specific cell surface marker using conventional methods and apparatus (for example a Beckman Coulter Epics XL FACS system used with commercially available antibodies and standard protocols known in the art) to determine whether the signal for a specific microparticle surface marker is greater than a background signal. The background signal is defined as the signal intensity generated by a non-specific antibody of the same isotype as the specific antibody used to detect each surface marker. For a marker to be considered positive the specific signal observed is typically more than 20%, preferably stronger than 30%, 40%, 50%, 60%, 70%, 80%, 90%, 100%, 500%, 1000%, 5000%, 10000% or above, greater relative to the background signal intensity. Alternative methods for analysing expression of microparticle surface markers of interest include visual analysis by electron microscopy using antibodies against cell-surface markers of interest.

"Fluorescence activated cell sorting (FACS)" is a method of cell purification based on the use of fluorescent labelled antibodies. The antibodies are directed to a marker on the cell surface, and therefore bind to the cells of interest. The cells are then separated based upon the fluorescent emission peak of the cells.

Microparticle markers (including surface and intracellular proteins) can also be analysed by various methods known to one skilled in the art to assay protein expression, including but not limited to gel electrophoresis followed by western blotting with suitable antibodies, immunoprecipitation followed by electrophoretic analysis, and/or electron microscopy as described above, with microparticle permeabilisation for intraparticle markers. For example, expression of one or more tetraspanins may be assayed using one or more of the above methods or any other method known to one skilled in the art. RNA levels may also be analysed to assess marker expression, for example qRT-PCR.

Microparticle Function

As noted above, a neural stem cell microparticle typically retains at least one biological function of the stem cell from which it is derived. Biological functions that may be retained include the ability to: inhibit cell migration, for example of fibroblast or fibroblast-like cells, or of tumour cells such as glioblastoma cells; inhibit wound healing, for example in a scratch assay; or treat a disease or condition that involves or is characterised by undesirable or excessive cell migration, such as cancer, fibrosis, atherosclerosis or rheumatoid arthritis.

In one embodiment, the at least one biological activity is that of a neural stem cell that has been cultured, typically in a multi-compartment bioreactor, for at least 10 weeks and optionally no more than 20 weeks. Alternatively the at least one biological activity may be that of a neural stem cell-conditioned medium from a neural stem cell that has been cultured, typically in a multi-compartment bioreactor, for at least 10 weeks and optionally no more than 20 weeks. FIGS. 1 and 2 (Example 1) demonstrate that exosomes isolated from the conditioned medium of CTX0E03 cells that have been cultured in a CeLLine bioreactor for 11 weeks have the ability to inhibit fibroblast migration in a transmembrane assay model of cell migration. Accordingly, one biological function that microparticles of the invention may retain is the ability to inhibit migration of fibroblast or fibroblast-like cells, for example of normal human dermal fibroblasts (NHDF).

Example 2, Table 2 and FIG. 3 demonstrate that CTX0E03 stem cell exosomes, obtained from cells cultured for 2 weeks and 6 weeks, retain the ability to close a wound in a "scratch" model of wound healing. The results show that the migration activity of normal human dermal fibroblasts (NHDF) cultured in CTX0E03 conditioned media is almost the same as the migration activity observed on the addition of purified exosomes. In contrast, microparticles of the invention are able to inhibit cell migration. Accordingly, one biological function that microparticles of the invention may retain is the ability to inhibit migration activity of normal human dermal fibroblasts (NHDF). NHDF migration assays are known in the art. Stimulation of NHDF migration may be determined using an in vitro scratch (wound closure) assay, for example the assay of Example 2. Wound closure is calculated as the area covered by NHDF cells in relation to the initial wound area as determined at 0 hours. Inhibition of NHDF migration in this assay is typically defined as a decrease in wound closure, as defined above.

CTX0E03 cells are known to inhibit T cell activation in a PBMC assay and, in one embodiment, the microparticles of the invention retain this ability to inhibit T cell activation in a PBMC assay. PBMC assays are well-known to the skilled person and kits for performing the assay are commercially available.

The proteomic analysis in Example 18 indicates that neural stem cell exosomes comprise biological functions associated with the production, packaging, function and degradation of genetic material. Accordingly, in one embodiment, exosomes of the invention retain these functions, typically one or more of RNA polymerase function, RNA degradation function, ribosome function and spliceosome function.

Immunogenicity

The (allogeneic) neural stem cell microparticles of the invention typically either do not trigger an immune response in vitro or in vivo or trigger an immune response which is substantially weaker than that which would be expected to be triggered upon injection of an allogeneic stem cell population into a patient. In certain aspects of the invention, the neural stem cell microparticles are considered not to trigger an immune response if at least about 70% of the microparticles do not trigger an immune response. In some embodiments, at least about 80%, at least about 90% or at least about 95%, 99% or more of the microparticles do not trigger an immune response. Preferably the microparticles of the invention do not trigger an antibody mediated immune response or do not trigger a humoral immune response. More preferably the microparticles of the invention do not trigger either an antibody mediated response or a humoral immune response in vitro. More preferably still, the microparticles of the invention do not trigger a mixed lymphocyte immune response. It will be understood by one skilled in the art that the ability of the cells of the invention to trigger an immune response can be tested in a variety of ways.

CTX0E03 cells transplanted in a rodent model of limb ischemia have been previously demonstrated a faster and transient up-regulation of host genes involved in angiogenesis, such as CCL11, CCL2, CXCL1, CXCL5, IGF1, IL1β, IL6, HGF, HIF1α, bFGF, VEGFA, and VEGFC, compared to vehicle treated controls. hNSC treatment transiently elevates host innate immune and angiogenic responses and accelerates tissue regeneration.

The CTX0E03 cell line has been previously demonstrated, using a human PBMC assay, not to be immunogenic. Accordingly, microparticles produced by CTX0E03 cells are also expected to be non-immunogenic. The lack of immunogenicity allows the microparticles to avoid clearance by the host/patient immune system and thereby exert their therapeutic effect without a deleterious immune and inflammatory response.

Neural Stem Cells

The neural stem cell that produces the microparticle may be a stem cell line, i.e. a culture of stably dividing stem cells. A stem cell line can to be grown in large quantities using a single, defined source. Immortalisation may arise from a spontaneous event or may be achieved by introducing exogenous genetic information into the stem cell which encodes immortalisation factors, resulting in unlimited cell growth of the stem cell under suitable culture conditions. Such exogenous genetic factors may include the gene "myc", which encodes the transcription factor Myc. The exogenous genetic information may be introduced into the stem cell through a variety of suitable means, such as transfection or transduction. For transduction, a genetically engineered viral vehicle may be used, such as one derived from retroviruses, for example lentivirus.

Additional advantages can be gained by using a conditionally immortalised stem cell line, in which the expression of the immortalisation factor can be regulated without adversely affecting the production of therapeutically effective microparticles. This may be achieved by introducing an immortalisation factor which is inactive unless the cell is supplied with an activating agent. Such an immortalisation factor may be a gene such as c-mycER. The c-MycER gene product is a fusion protein comprising a c-Myc variant fused to the ligand-binding domain of a mutant estrogen receptor. C-MycER only drives cell proliferation in the presence of the synthetic steroid 4-hydroxytamoxifen (4-OHT) (Littlewood et al. 1995). This approach allows for controlled expansion of neural stem cells in vitro, while avoiding undesired in vivo effects on host cell proliferation (e.g. tumour formation) due to the presence of c-Myc or the gene encoding it in microparticles derived from the neural stem cell line. A suitable c-mycER conditionally immortalized neural stem cell is described in U.S. Pat. No. 7,416,888. The use of a conditionally immortalised neural stem cell line therefore provides an improvement over existing stem cell microparticle isolation and production.

Preferred conditionally-immortalised cell lines include the CTX0E03, STR0CO5 and HPC0A07 neural stem cell lines, which have been deposited at the European Collection of Animal Cultures (ECACC), Vaccine Research and Production laboratories, Public Health Laboratory Services, Porton Down, Salisbury, Wiltshire, SP4 0JG, with Accession No. 04091601 (CTX0E03); Accession No. 04110301 (STR0C05); and Accession No. 04092302 (HPC0A07). The derivation and provenance of these cells is described in EP1645626 B1. The advantages of these cells are retained by microparticles produced by these cells.

The cells of the CTX0E03 cell line may be cultured in the following culture conditions:
 Human Serum Albumin 0.03%
 Transferrin, Human 5 µg/ml
 Putrescine Dihydrochloride 16.2 µg/ml
 Insulin Human recombinant 5 µ/ml
 Progesterone 60 ng/ml
 L-Glutamine 2 mM
 Sodium Selenite (selenium) 40 ng/ml
 Plus basic Fibroblast Growth Factor (10 ng/ml), epidermal growth factor (20 ng/ml) and 4-hydroxytamoxifen 100 nM for cell expansion. The cells can be differentiated by removal of the 4-hydroxytamoxifen. Typically, the cells can either be cultured at 5% $CO_2$/37° C. or under hypoxic conditions of 5%, 4%, 3%, 2% or 1% $O_2$. These cell lines do not require serum to be cultured successfully. Serum is required for the successful culture of many cell lines, but contains many contaminants including its own exosomes. A further advantage of the CTX0E03, STR0CO5 or HPC0A07 neural stem cell lines, or any other cell line that does not require serum, is that the contamination by serum is avoided.

The cells of the CTX0E03 cell line (and microparticles derived from these cells) are multipotent cells originally derived from 12 week human fetal cortex. The isolation, manufacture and protocols for the CTX0E03 cell line is described in detail by Sinden, et al. (U.S. Pat. No. 7,416,888 and EP1645626 B1). The CTX0E03 cells are not "embryonic stem cells", i.e. they are not pluripotent cells derived from the inner cell mass of a blastocyst; isolation of the original cells did not result in the destruction of an embryo. In growth medium CTX0E03 cells are nestin-positive with a low percentage of GFAP positive cells (i.e. the population is negative for GFAP).

CTX0E03 is a clonal cell line that contains a single copy of the c-mycER transgene that was delivered by retroviral infection and is conditionally regulated by 4-OHT (4-hydroxytamoxifen). The C-mycER transgene expresses a fusion protein that stimulates cell proliferation in the presence of 4-OHT and therefore allows controlled expansion when cultured in the presence of 4-OHT. This cell line is clonal, expands rapidly in culture (doubling time 50-60 hours) and has a normal human karyotype (46 XY). It is genetically stable and can be grown in large numbers. The cells are safe and non-tumorigenic. In the absence of growth factors and 4-OHT, the cells undergo growth arrest and differentiate into neurons and astrocytes. Once implanted into an ischemia-damaged brain, these cells migrate only to areas of tissue damage.

The development of the CTX0E03 cell line has allowed the scale-up of a consistent product for clinical use. Production of cells from banked materials allows for the generation of cells in quantities for commercial application (Hodges et al, 2007).

Pollock et al 2006 describes that transplantation of CTX0E03 in a rat model of stroke (MCAo) caused statistically significant improvements in both sensorimotor function and gross motor asymmetry at 6-12 weeks post-grafting. These data indicate that CTX0E03 has the appropriate biological and manufacturing characteristics necessary for development as a therapeutic cell line.

Stevanato et al 2009 confirms that CTX0E03 cells downregulated c-mycERTAM transgene expression both in vitro following EGF, bFGF and 4-OHT withdrawal and in vivo following implantation in MCAo rat brain. The silencing of the c-mycERTAM transgene in vivo provides an additional safety feature of CTX0E03 cells for potential clinical application.

Smith et al 2012 describe preclinical efficacy testing of CTX0E03 in a rat model of stroke (transient middle cerebral artery occlusion). The results indicate that CTX0E03 implants robustly recover behavioural dysfunction over a 3 month time frame and that this effect is specific to their site of implantation. Lesion topology is potentially an important factor in the recovery, with a stroke confined to the striatum showing a better outcome compared to a larger area of damage.

Neural retinal stem cell lines (for example as described in U.S. Pat. No. 7,514,259) may also be used according to the invention.

The term "culture medium" or "medium" is recognized in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase to which cells growing on a petri dish or other solid or semisolid support are exposed. The term "medium" also refers to material that is intended for use in a cell culture, even if it has not yet been contacted with cells. In other words, a nutrient rich liquid prepared for culture is a medium. Similarly, a powder mixture that when mixed with water or other liquid becomes suitable for cell culture may be termed a "powdered medium". "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. A "medium suitable for growth of a high density culture" is any medium that allows a cell culture to reach an OD600 of 3 or greater when other conditions (such as temperature and oxygen transfer rate) permit such growth. The term "basal medium" refers to a medium which promotes the growth of many types of microorganisms which do not require any special nutrient supplements. Most basal media generally comprise of four basic chemical groups: amino acids, carbohydrates, inorganic salts, and vitamins. A basal medium generally serves as the basis for a more complex medium, to which supplements such as serum, buffers, growth factors, lipids, and the like are added. In one aspect, the growth medium may be a complex medium with the necessary growth factors to support the growth and expansion of the cells of the invention while maintaining their self-renewal capability. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5A, Dulbecco's MEM/F-I 2, RPMI 1640, and Iscove's Modified Dulbecco's Medium (IMDM).

Culture Period

In the context of this invention, "culturing" cells for specified periods of time (e.g. at least 10 weeks) refers to a time period wherein day zero or "day 0" is the time point at which the cells are transferred to the culture vessel. The culture vessel may be a flask, for example the standard T-175 cell culture flask. Typically, the culture vessel is a multi-compartment bioreactor such as the Integra CELLine bioreactor, and day zero is the day on which the stem cells are transferred into the bioreactor. Accordingly, cells "that have been cultured for at least 10 weeks" refers to cells that have been cultured for at least 10 weeks following transfer into the culture vessel. In this 10 week period, the cells are not passaged or subcultured, i.e. they are not transferred to a new culture vessel. Optionally, cells can be removed from the culture vessel during the culture period, typically for sampling, but this does not change the cells that remain in the culture vessel, which have been in that culture vessel since day 0.

In one embodiment, as described in Example 10, on day zero approximately 15×10$^6$ CTX0E03 cells in a total of 15 ml of complete growth medium are introduced into the cell compartment of the CeLLine bioreactor, followed by the addition of a further 460 ml of complete growth medium to the cell compartment.

Pharmaceutical Compositions

The neural stem cell microparticle of the invention, and the miRNA of the invention, is useful in therapy and can therefore be formulated as a pharmaceutical composition. A pharmaceutically acceptable composition typically includes at least one pharmaceutically acceptable carrier, diluent, vehicle and/or excipient in addition to the microparticles of the invention. An example of a suitable carrier is Ringer's Lactate solution. A thorough discussion of such components is provided in Gennaro (2000) Remington: The Science and Practice of Pharmacy. 20th edition, ISBN: 0683306472.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The composition, if desired, can also contain minor amounts of pH buffering agents. The carrier may comprise storage media such as Hypothermosol®, commercially available from BioLife Solutions Inc., USA. Examples of suitable pharmaceutical carriers are described in "Remington's Pharmaceutical Sciences" by E W Martin. Such compositions will contain a prophylactically or therapeutically effective amount of a prophylactic or therapeutic microparticle preferably in purified form, together with a suitable amount of carrier so as to provide the form for proper administration to the subject. The formulation should suit the mode of administration. In a preferred embodiment, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, semi-solid, and liquid dosage forms, such as lyophilized preparations, liquid solutions or suspensions, injectable and infusible solutions. The pharmaceutical composition is preferably injectable. A particular advantage of the microparticles of the invention is their improved robustness compared to the stem cells from which they are obtained; the microparticles can therefore be subjected to formulation, such as lyophilisation, that would not be suitable for stem cells. This is also an advantage of the miRNA compositions of the invention.

It is preferred that the methods, medicaments and compositions and microparticles of the invention are used for treating cancer, fibrosis, atherosclerosis or rheumatoid arthritis, and/or for the treatment, modulation, prophylaxis, and/or amelioration of one or more symptoms associated with these disorders.

Pharmaceutical compositions will generally be in aqueous form. Compositions may include a preservative and/or an antioxidant.

To control tonicity, the pharmaceutical composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Compositions may include one or more buffers. Typical buffers include: a phosphate buffer; a Tris buffer; a borate buffer; a succinate buffer; a histidine buffer; or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

The composition is preferably sterile. The composition is preferably gluten free. The composition is preferably non-pyrogenic.

In a typical embodiment, the microparticles are suspended in a composition comprising 6-hydroxy-2,5,7,8-tetramethylchroman-2-carboxylic acid (Trolox®), Na$^+$, K$^+$, Ca$^{2+}$, Mg$^{2+}$, Cl$^-$, H$_2$PO$_4^-$, HEPES, lactobionate, sucrose, mannitol, glucose, dextron-40, adenosine and glutathione. Typically, the composition will not include a dipolar aprotic solvent, e.g. DMSO. Suitable compositions are available commercially, e.g. HypoThermasol®-FRS. Such compositions are advantageous as they allow the microparticles to be stored at 4° C. to 25° C. for extended periods (hours to days)

or preserved at cryothermic temperatures, i.e. temperatures below −20° C. The microparticles may then be administered in this composition after thawing.

The pharmaceutical composition can be administered by any appropriate route, which will be apparent to the skilled person depending on the disease or condition to be treated. Typical routes of administration include intravenous, intra-arterial, intramuscular, subcutaneous, intracranial, intranasal or intraperitoneal. For treatment of a disorder of the brain, one option is to administer the microparticles or miRNA intra-cerebrally, typically to the site of damage or disease.

The microparticles or miRNA will be administered at a therapeutically or prophylactically-effective dose, which will be apparent to the skilled person. Due to the low or non-existent immunogenicity of the microparticles, it is possible to administer repeat doses without inducing a deleterious immune response.

Therapeutic Uses

The microparticles and miRNA of the invention are useful in the treatment or prophylaxis of disease. Accordingly, the invention includes a method of treating or preventing a disease or disorder in a patient using a microparticle or miRNA of the invention. The term "patient" includes human and other mammalian subjects that receive either prophylactic or therapeutic treatment.

As noted above, the compositions comprising miRNAs of the invention are also useful in these therapies, and references to therapeutic uses of microparticles herein therefore applies equally to the compositions comprising miRNAs.

The Examples below demonstrate that neural stem cell exosomes have been identified that inhibit cell migration. Inhibition of migration has been observed in human fibroblasts. This inhibition is particularly surprising because, as also shown in the examples and as described in PCT/GB2013/050879, neural stem cell microparticles have previously been shown to stimulate fibroblast migration. Inhibition of migration has also been observed in glioblastoma cells.

Microparticles of the invention inhibit cell migration and are therefore useful in treating or preventing a disease, disorder or condition that involves or is characterised by undesired or excessive cell migration. In particular, the microparticles of the invention are particularly suitable for treating or preventing cancer, fibrosis, atherosclerosis or rheumatoid arthritis. The microparticles of the invention are also suitable in the therapy of unwanted or undesirable angiogenesis, for example treating the angiogenic component of a solid tumour. Typically, the microparticles are exosomes.

In one embodiment, the microparticles of the invention are used in the therapy of fibrosis. Fibrosis is well-known to be the formation of excess fibrous connective tissue in an organ or tissue in a reparative or reactive process. The fibrosis may be kidney fibrosis, liver fibrosis, cardiac fibrosis, lung fibrosis, skin fibrosis, age-related fibrosis, or spleen fibrosis.

In one embodiment, the microparticles of the invention are used in the therapy of cancer. The cancer may, in one embodiment, comprise a liquid tumour. In another embodiment, the cancer may comprise a solid tumour. In a further embodiment, the microparticles of the invention treat the cancer by inhibiting migration of the cancer cells. In yet a further embodiment, the microparticles of the invention treat the cancer by inducing differentiation of cancer cells, typically differentiation of a nestin-positive cancer cell. In another embodiment, the microparticles of the invention treat the cancer by inducing or enhancing an immune response against the cancer cells. When the cancer is a CNS cancer, the immune response typically comprises the activation and/or proliferation of glial cells such as microglia.

The cancer may be a solid tumour cancer, for example a sarcoma or carcinoma. The solid tumour cancer may also be a solid lymphoma. Exemplary solid tumour cancers include breast cancer, lung cancer, prostate cancer, bowel cancer, renal cancer, hepatic cancer, pancreatic cancer, cervical cancer, testicular cancer, gastric (stomach) cancer, uterine cancer, ovarian cancer, cancers of the head and neck, mouth cancer, thyroid cancer, oesophagus cancer, brain cancer including glioma (e.g. glioblastoma) and meningioma, Kaposi's sarcoma, Castleman's disease, cutaneous T-cell lymphoma (CTCL), cutaneous B-cell lymphoma, and skin cancer such as basal cell carcinoma, squamous cell carcinoma and melanoma.

In one embodiment, the solid tumour cancer is breast cancer, typically ductal carcinoma in situ, lobular carcinoma in situ, invasive ductal carcinoma, invasive lobular carcinoma, inflammatory breast cancer or Paget's disease.

In another embodiment, the solid tumour cancer is lung cancer, typically squamous cell carcinoma, adenocarcinoma or large cell carcinoma, or a small cell lung cancer.

In a further embodiment, the solid tumour cancer is prostate cancer, typically prostate adenocarcinoma.

In a further embodiment, the solid tumour cancer is skin cancer, typically a basal cell carcinoma, squamous cell carcinoma or melanoma.

The cancer may be a liquid tumour, which is typically a tumour of the blood, bone marrow, or lymph nodes. Such cancers include leukemia, lymphoma and myeloma. Exemplary liquid tumours include acute lymphoblastic leukemia, acute myelogenous leukemia (AML), multiple myeloma, Hodgkin's lymphoma and non-Hodgkins lymphoma.

The cancer may be a cancer of the CNS, typically a glioma, meningioma, pituitary adenoma or a nerve sheath tumour. An exemplary CNS cancer is a glioblastoma, which may be a giant cell glioblastoma or a gliosarcoma. The in vivo xenograft pilot data in the Examples demonstrate trends in the treatment of glioblastoma.

The Examples below demonstrate that microparticles of the invention (in the case of Example 4, exosomes isolated from proliferating CTX0E03 cell culture) reduce the expression of nestin on tumour cells. Accordingly, in one embodiment, the cancer to be treated is nestin-positive. Nestin-positive cancers include melanoma, breast cancer, CNS cancers such as glioma and typically glioblastoma, pancreatic cancer, gastrointestinal stromal tumours (GISTs), dermatofibrsarcoma protuberances, thyroid tumours and prostate cancer (see, for example, Ishiwata et al World J Gastroenterol. 2011 Jan. 28; 17(4):409-418). The nestin-positive breast cancer is typically "triple negative, nestin positive" breast cancer (ERα$^-$/PR$^-$/Her2$^-$/Nestin$^+$). Triple negative breast cancer is an aggressive disease, recurring and metastasizing more often than other kinds of breast cancer, and treatments for this are urgently needed. The effectiveness of microparticles of the invention in treating this cancer can readily be tested in vivo using a triple negative breast cancer mouse model, for example as described by Kaur et al, BMC cancer 2012m 12:120. In vivo models for other cancers exist and can be used to test the effectiveness of microparticles of the invention; for example, xenograft models of melanoma (e.g. Rofstad Br. J. Cancer (1994), 70, 804-812) and glioblastoma (e.g. Jacobs et al, ASN Neuro. 2011; 3(3); 2011).

Nestin is also reported to be expressed in endothelial cells involved in angiogenesis (Mokry et al, Stem Cells Dev.

2004; 13:658-664) and so the ability of microparticles of the invention to reduce nestin expression provides a further mechanism to inhibit angiogenesis.

Microparticles of the invention may also be used to treat or prevent metastatic cancers, for example metastasis of each of the cancers listed above.

The microparticles of the invention may also be used to treat a benign (non-cancerous, non-malignant) solid tumour, or a premalignant solid tumour.

Fibroblasts are known to play a role in angiogenesis during tumour formation. Without being bound by theory, it is thought that this is mediated in part by a paracrine mechanism wherein factors secreted by the fibroblasts, including Fibroblast Growth Factor (FGF), act on endothelial cells in the nascent or growing blood vessel. Therefore, inhibiting the migration of fibroblasts is expected to inhibit angiogenesis. Accordingly, the microparticles of the invention may be used as an anti-angiogenic therapy, i.e. in the therapy of unwanted, deleterious or undesirable angiogenesis. In one embodiment, the unwanted or undesirable angiogenesis is a component or a precursor of a solid tumour, typically a cancerous solid tumour. In this embodiment, the microparticles are used in the therapy of the tumour by preventing, inhibiting or reducing angiogenesis in the tumour. Typically, the solid tumour that is treated by targeting angiogenesis is one of the tumours described above, for example a sarcoma or carcinoma. The solid tumour cancer in this embodiment may also be a solid lymphoma. Exemplary solid tumour cancers that can be treated by targeting the angiogenic component of the tumour include breast cancer, lung cancer, prostate cancer, bowel cancer, renal cancer, hepatic cancer, pancreatic cancer, cervical cancer, testicular cancer, gastric (stomach) cancer, uterine cancer, ovarian cancer, cancers of the head and neck, mouth cancer, thyroid cancer, oesophagus cancer, brain cancer including glioma (e.g. glioblastoma) and meningioma, Kaposi's sarcoma, Castleman's disease, cutaneous T-cell lymphoma (CTCL), cutaneous B-cell lymphoma, and skin cancer such as basal cell carcinoma, squamous cell carcinoma and melanoma.

In one embodiment, the microparticles and compositions containing them are not used for immune modulation. In one embodiment, the therapy is not related to immunomodulation.

The invention also provides a method for treating or preventing a disease or condition comprising administering an effective amount of the microparticle of the invention, thereby treating or preventing the disease. Typically, the disease or condition is as identified above.

In one embodiment, the microparticles for use in therapy are isolated from NSCs (typically CTX0E03 cells) that have been cultured (typically in a multi-compartment bioreactor) for at least 10 weeks, typically at least 11 weeks, at least 12 weeks, at least 13 weeks, at least 14 weeks or at least 15 weeks. Optionally, the NSCs have been cultured for no more than 20 weeks, e.g. between 10 and 20 weeks, between 11 and 20 weeks, between 12 and 20 weeks, between 13 and 20 weeks, between 14 and 20 weeks or between 15 and 20 weeks. Typically, the microparticles are exosomes. In the examples, microparticles produced according to this embodiment are shown to inhibit fibroblast migration and induce or enhance tumour destruction by the immune system.

The observed increased efficacy of exosomes isolated from NSCs (CTX0E03 cells) that have been cultured (in a multi-compartment bioreactor) for 6 weeks correlates with the observed reduction in size of the exosomes to around 70 nm diameter, which also occurred after culturing the cells for 6 weeks. Accordingly, in one embodiment exosomes isolated from NSCs (typically CTX0E03 cells) having a diameter less than 100 nm, typically less than 80 nm, for example around 70 nm diameter, are used in therapy as described above.

In another embodiment, the microparticles for use in therapy are isolated from proliferating NSCs (typically CTX0E03 cells) that have been cultured in a standard culture vessel such as a T-175 flask, or have been cultured in a multi-compartment bioreactor for 4 weeks or less, 3 weeks or less, 2 weeks or less, or 1 week or less e.g. exosomes isolated on day 0 of the multi-compartment culture. These cells are typically passaged when sub-confluent, are positive for a stem cell marker (e.g. nestin) and negative for markers of differentiated cells (e.g. GFAP or DCX). These exosomes may have a diameter greater than 100 nm. In the examples, microparticles produced according to this embodiment are shown to inhibit cancer cell migration and induce tumour cell differentiation.

In prophylactic applications, pharmaceutical compositions or medicaments are administered to a patient susceptible to, or otherwise at risk of, a particular disease in an amount sufficient to eliminate or reduce the risk or delay the outset of the disease. In therapeutic applications, compositions or medicaments are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are typically administered in several dosages until a sufficient response has been achieved. Typically, the response is monitored and repeated dosages are given if the response starts to fade.

The microparticles of the invention may optionally be combined with a stem cell to provide a combination therapy. The stem cell is optionally the stem cell from which the microparticle is derived, e.g. if the microparticle is an exosome from a CTX0E03 cell, then the stem cell for use in combination therapy may be a CTX0E03 cell, typically but not necessarily cultured for the same period of time as the cells from which the microparticles were derived. A stem cell and microparticle can optionally be (i) administered together in a single pharmaceutical composition, (ii) administered contemporaneously or simultaneously but separately, or (iii) administered separately and sequentially, e.g. stem cell followed by microparticle, or microparticle followed by stem cell. When the stem cell and microparticle are administered separately and sequentially, the duration between the administration of the cell and microparticle may be one hour, one day, one week, two weeks or more.

In one embodiment, a prophylactic therapy induces tolerance, typically immunotolerance, in a host that is to receive the stem cells from which the microparticle is derived. In one embodiment, the administration of one or more doses of microparticles of the invention to a patient, prior to administration of a stem cell therapy, can be used to reduce the risk of an adverse immune response, i.e. "rejection", of the stem cell therapy. In another embodiment, tolerance to the stem cells can be increased by administering stem cells together with microparticles of the invention, as discussed above.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human.

The CTX0E03 cell line has been shown to be effective in treating stroke, peripheral arterial disease, brain damage such as motor, sensory and/or cognitive deficit, and psychiatric disorders. The cells are currently being tested in a clinical trial for treatment of disabled stroke patients (Clinicaltrials.gov Identifier: NCT01151124). WO-A-2012/004611 describes the use of the CTX0E03 cells in treating psychiatric disorders including unipolar and bipolar depression, schizophrenia, obsessive compulsive disorder, autism and autistic syndrome disorders.

As used herein, the terms "treat", "treatment", "treating" and "therapy" when used directly in reference to a patient or subject shall be taken to mean the amelioration of one or more symptoms associated with a disorder, or the prevention or prophylaxis of a disorder or one or more symptoms associated with a disorder. The disorders to be treated include, but are not limited to, cancer, fibrosis, rheumatoid arthritis, atherosclerosis, and other diseases involving deleterious cell migration. Amelioration or prevention of symptoms results from the administration of the microparticles of the invention, or of a pharmaceutical composition comprising these microparticles, to a subject in need of said treatment.

Tracing Administered Cells and Microparticles In Vivo

The present invention provides a distinct marker profile for microparticles produced by neural stem cells. It is therefore possible to detect the presence of these microparticles in vivo, by testing a sample obtained from a patient and determining whether the marker profile in the sample matches that of the microparticles. If the sample profile matches the profile of the microparticles described herein, then this confirms the presence of the microparticles. This can be used to detect not only the presence and/or biodistribution of the microparticles themselves, but also the presence of stem cells producing the microparticles. This is particularly useful when detecting whether a stem cell administered in vivo has engrafted into the host tissue, and/or has migrated, for example in ADME(T) studies.

Detection of the microparticles in vivo can be used to monitor the course of a treatment wherein microparticles or stem cells are administered to a patient. Determining the presence, absence or amount of microparticles or cells producing microparticles of the invention in a patient allows the dosage regime to be altered accordingly, e.g. to increase or decrease the dose as required to provide an effective amount of microparticles or stem cells in vivo.

Methods of Producing Microparticles

Microparticles are isolated from stem cell conditioned media. The "conditioned medium" (CM) may be a growth medium for stem cells, which has been used to culture a mass culture of stem cells for at least about 12 hours, at least about 24 hours, at least about 48 hours or least about 72 hours, typically up to 168 hours (7 days), removed and sterilized by any suitable means, preferably by filtration, prior to use, if required.

Microparticles that are able to inhibit fibroblast cell migration have been isolated from stem cells that have been cultured for at least 10 weeks. Accordingly, one way to produce microparticles that are able to inhibit cell migration is to culture the cells in a multi-compartment bioreactor for at least about 10 weeks before the microparticles are harvested, typically at least 11 weeks, at least 12 weeks, at least 13 weeks, at least 14 weeks, at least 15 weeks, and optionally no longer than 20 weeks. Example 10 describes a typical culture protocol using a CeLLine bioreactor.

Microparticles that are able to inhibit glioblastoma cell migration have been isolated from proliferating stem cells that have been cultured for 4 weeks or less. Accordingly, one way to produce microparticles that are able to inhibit cell migration is to culture the cells so that they are able to proliferate, for example by culturing in a T-175 flask, or in a multi-compartment bioreactor for 4 weeks or less, 3 weeks or less, 2 weeks or less, or 1 week or less e.g. exosomes isolated on day 0 of the multi-compartment culture.

Typically, microparticles may be harvested from a multi-compartment, e.g. two-compartment, bioreactor which allows the cell culture, and hence the conditioned media, to be maintained for longer periods of time, for example more than 10 weeks, at least 11 weeks, at least 12 weeks, at least 13 weeks, at least 14 weeks, at least 15 weeks, and optionally no longer than 20 weeks. The system maintains the cells and secreted microparticles within a small cell compartment (approximately 15 ml) which is separated from a larger reservoir of medium by a 10 kDa semi-permeable membrane. This allows the efficient removal of metabolic waste products while effectively maintaining an extremely high cell density to maximize microparticle production. Example 14, and FIGS. 9 and 10, demonstrate that use of a two-compartment bioreactor results in a much higher yield of microparticles than is obtained when a standard cell culture flask (T175 flask) is used.

The microparticles may be separated from other media components based on molecular weight, size, shape, hydrodynamic radius, composition, charge, substrate-ligand interaction, absorbance or scattering of electromagnetic waves, or biological activity. In one embodiment, the conditioned media is filtered using a filter of appropriate size to separate the desired microparticle, for example a 100K MWCO filter. Optionally, the stem cell-conditioned medium is concentrated prior to the isolation of the microparticles by subjecting the concentrated NSC-conditioned medium to size exclusion chromatography. The UV absorbant fractions can then be selected for isolation of the microparticles of interest.

Different microparticles can be isolated from the media by using different isolation techniques and parameters. For example, exosomes have a vesicle density of 1.13-1.19 g/mL and can be isolated by differential centrifugation and sucrose gradient ultracentrifugation at 100,000-200,000 g. Microvesicles can be isolated by filtration (100K MWCO) and differential centrifugation at 18,000-20,000 g. Membrane particles have a density of 1.04-01.07 g/ml and Exosome-like vesicles have a density of 1.1 g/ml.

A typical production method comprises: culturing stem cells to produce conditioned media; removing cell debris by centrifugation at 1500 rpm; isolating microvesicles (<1000 kDa) by ultrafiltration through a 100K MWCO filter or isolating exosomes (30-100 nm) by ultracentrifugation at 120,000 g; followed by quantification using a BCA protein assay.

Conditionally Immortalised Stem Cells as Producer Cells for Microparticles

In one aspect of the invention, conditionally immortalised stem cells are used to produce microparticles such as microvesicles and/or exosomes. These conditionally immortalised stem cells are typically neural stem cells, but may be a stem cell of any type, for example a haematopoietic stem cell or a mesenchymal stem cell. A method of producing stem cell microparticles is therefore provided, comprising the steps of culturing conditionally-immortalised stem cells and harvesting the microparticles that are produced by the cells, as described above. Conditional immortalisation of stem cells is known in the art, as described above. For the avoidance of doubt, this method is not limited to the use of neural stem cells.

When the stem cell used to produce microparticles is a neural stem cell, it may be any of the neural stem cells described herein, for example the CTX0E03 conditionally-immortalised cell line which is clonal, standardised, shows clear safety in vitro and in vivo and can be manufactured to scale thereby providing a unique resource for stable exosome production. Alternatively, the neural stem cells may be neural retinal stem cell lines, optionally as described in U.S. Pat. No. 7,514,259.

When the stem cell used to produce microparticles is a mesenchymal stem cell, it may optionally be a conditionally-immortalised adipose-derived stem cell ("ADSC") or a conditionally-immortalised version of the mesenchymal stem cells described in WO-A-2009/105044; these cells are CD29+, CD44+, CD49a+/e+, CD105+, CD166+, CD34−, CD45−.

Methods of Inducing Microparticle Secretion

The inventors have found that it is possible to increase the production of microparticles by stem cells. This finding, which is not limited to neural stem cells and can be used for the production of microparticles from any stem cell, allows for an improved yield of microparticles to be obtained from a stem cell culture.

A first technique to increase the production of microparticles by the stem cells is to treat the stem cells with one or more of TGF-β, IFN-γ or TNF-α, typically at between 1 and 25 ng/ml e.g. 10 ng/ml, for between 12 to 96 hours prior to the removal of conditioned media.

As explained in Example 8 below, the frequency of the occurrence of multivesicular bodies (MVBs) was observed to be altered by the presence of TGF-β, IFN-γ or TNF-α (10 ng/ml). The frequency was highest in the presence of TGF-β, followed by IFN-γ, followed by TNF-α. Therefore, adding one or more of TGF-β, IFN-γ or TNF-α to the stem cell culture medium will stimulate the production of microparticles by the cells. The microparticles can then be harvested, by separating the microparticles from other components as described above.

A second technique to increase the production of microparticles by the stem cells is to culture the cells under hypoxic conditions. Culturing cells under hypoxic conditions is well-known to the skilled person, and involves culturing the cells in an atmosphere that has less than atmospheric level of $O_2$, i.e. less than 21% $O_2$. This is typically achieved by placing the cells in an incubator that allows oxygen levels to be changed. Hypoxic culture typically involves culturing in an atmosphere containing less than 10% $O_2$, more typically 5% or less $O_2$, for example 4% or less, 3% or less, 2% or less, or 1% or less $O_2$.

The inventors have also realised that co-culturing a stem cell with a different cell type can alter the production of microparticles by the stem cell. The different cell type may be a non-stem cell, i.e. a terminally differentiated cell type. Typically, the different cell type is one with which the stem cell would interact in vivo. In one embodiment, neural stem cells are co-cultured with epithelial cells such as endothelial cells, typically Human Umbilical Vein Endothelial Cells (HUVEC). It has been observed that in vivo, NSCs and the vasculature interact, with proliferating NSCs being localized in close proximity or adjacent to blood vessels. Receptor tyrosine kinase activation and signal protein secretion has also been observed to be upregulated when NSCs are co-cultured with endothelial cells, again indicating that the vasculature modulates the proliferation capacity of NSCs.

Therefore, culturing a stem cell with a different cell type may improve the amount of microparticles produced and/or may refine the content of the microparticles, typically so that the microparticles produced by the stem cells are further biased towards a state of inhibition of cell migration. Accordingly, microparticles produced by stem cells that have been co-cultured with other cells, e.g. NSCs co-cultured with endothelial cells, are advantageous. These microparticles may be obtained by isolation from the co-cultured stem-cell conditioned media, as described herein.

Surprisingly, the present inventors have realised that the amount of microparticles produced by stem cells can be increased greatly simply by culturing stem cells in a multi-compartment bioreactor. This finding is not limited to neural stem cells and applies generally to the culture of all stem cells. Accordingly, one aspect of the invention provides a method of producing microparticles from stem cells that have been cultured in a multi-compartment bioreactor. The cells from which the microparticles are harvested have typically been cultured for at least one week, typically at least 8, 9, 10, 11, 12, 13 or 14 days, for example 15 days, 16 days, 17 days, 18 days, 19 days, 20 days, 21 days or more, for example at least three weeks, four weeks, five weeks, six weeks or more. To produce microparticles that inhibit cell migration, the cells from which the microparticles are harvested have typically been cultured for more than ten weeks. It can be seen from FIG. 10 that the increase in microparticle production, week on week, is not merely additive but is exponential. The prolonged culture typically has been observed in the Integra Celline system two-compartment bioreactor (commercially available from Integra Biosciences AG, Zizers, Switzerland) but the findings are not limited to this specific multi-compartment bioreactor; any multi-compartment bioreactor can be used. This culture method can be used to produce microparticles from any stem cell type, including but not limited to neural stem cells and mesenchymal stem cells.

Method of Screening for an Agent that Alters Microparticle Production

The invention provides a method of screening for an agent that alters the production of a microparticle by a stem cell. This method comprises contacting a stem cell with a candidate agent, typically under conditions suitable for microparticle production, and observing whether (i) the rate of production of microparticles by the contacted stem cell increases or decreases, or (ii) the characteristics (e.g. size, protein, mRNA or miRNA content) of the microparticles changes, compared to a control stem cell that is not contacted with the agent.

Method for screening total RNA composition of conditioned medium

Following centrifugation (5 min at 1500 rpm), microparticles are collected from conditioned medium through filtration (0.02-0.2 μm, or 100K MWCO). Total RNA is obtained using trizol based extraction followed by purification using Qiagen RNaesy mini kit. The extract in water has a 260:280 nm absorbance suggesting that it may be RNA. Total RNA is retro-transcribed with either a protocol suitable for mRNA (Superscript II RT, Invitrogen) or miRNA (mScript RT kit, Qiagen). Validation of mRNA and miRNA presence is proven by qRT-PCR using primers for ATP5B and YWHAZ for mRNA, and U6B and 15a for miRNA housekeeping genes respectively. The RNA may further be assessed by a generic gene expression analysis assay such as an array (micro array or PCR based array), and sequencing.

Kits

The invention provides a kit for use in a method for producing the microparticle of the invention. The kit comprises a neural stem cell culture medium, a neural stem cell and instructions for producing the microparticle of any of claim 1-17 or 40 using the kit. Optionally, the kit comprises one or more components of claims 36 to 38. The kit may also comprise a microparticle according to the invention, for use as a control. The control microparticle is optionally lypohilised. The kit may also contain optionally a detection agent suitable for detection of the produced microparticles, for example an antibody that binds specifically to a marker protein that can be used to identify the microparticle.

Embodiments of the Invention

The invention comprises at least the following numbered embodiments:

1. A neural stem cell microparticle that (i) inhibits cell migration; and/or (ii) induces differentiation of a cancer cell.
2. The neural stem microparticle of embodiment 1, wherein the microparticle inhibits angiogenesis.
3. The neural stem cell microparticle of embodiment 1, wherein the microparticle induces or enhances an immune response against cancer cells.
4. The microparticle of any one of embodiments 1-3, wherein the microparticle inhibits cell migration as determined using a transmembrane cell migration assay, or induces differentiation as determined by a reduction in nestin expression.
5. The neural stem cell microparticle of any one of embodiments 1-4, wherein the microparticle inhibits migration of a fibroblast or a fibroblast-like cell, or a cancer cell, typically a glioblastoma cell.
6. The neural stem cell microparticle of any preceding embodiment, wherein the microparticle is derived from a neural stem cell that:
   (a) is not proliferating;
   (b) expresses DCX or GFAP; and/or
   (c) has been cultured in a multi-compartment bioreactor for at least 10 weeks and optionally no more than 20 weeks.
7. The neural stem cell microparticle of any one of embodiments 1-5, wherein the microparticle is derived from a neural stem cell that:
   (a) is proliferating;
   (b) does not express DCX or GFAP; and/or
   (C) has been cultured in a multi-compartment bioreactor for less than 4 weeks and optionally no more than 1 week.
8. The neural stem cell microparticle of any one of embodiments 1-7, wherein the microparticle is an exosome, microvesicle, membrane particle, membrane vesicle, exosome-like vesicle, ectosome-like vesicle, ectosome or exovesicle.
9. The neural stem cell microparticle of any one of embodiments 1-8, wherein the microparticle is derived from a neural stem cell line.
10. The neural stem cell microparticle of embodiment 9, wherein the neural stem cell line is conditionally-immortalised and/or grown in serum free medium.
11. The neural stem cell microparticle of embodiment 10, wherein the neural stem cell line is CTX0E03 having ECACC Accession No. 04091601, STR0C05 having ECACC Accession No. 04110301 and HPC0A07 having ECACC Accession No. 04092302.
12. The neural stem cell microparticle of any preceding embodiment, wherein the microparticle has:
   (a) a size of between 30 nm and 1000 nm, or between 30 and 200 nm, or between 30 and 100 nm, as determined by electron microscopy; or
   (b) a density in sucrose of 1.1-1.2 g/ml.
13. The neural stem cell microparticle of any preceding embodiment, comprising RNA.
14. The neural stem cell microparticle of embodiment 13, wherein the RNA is mRNA and/or miRNA.
15. The neural stem cell microparticle of embodiment 14, wherein the microparticle comprises:
   one, two, three or four of hsa-miR-1246, hsa-miR-4492, hsa-miR-4488 and hsa-miR-4532;
   one, two, three, four or five of hsa-miR-181a-5p, hsa-miR-1246, hsa-miR-127-3p, hsa-miR-21-5p, and hsa-miR-100-5p;
   one, two, three, four or five of hsa-miR-181a-5p, hsa-let-7a-5p, hsa-let-7f-5p, hsa-miR-92b-3p, and hsa-miR-9-5p; or
   hsa-miR-486-5p.
16. The neural stem cell microparticle of any preceding embodiment, comprising one or more of:
   (a) a lipid selected from ceramide, cholesterol, sphingomyelin, phosphatidylserine, phosphatidylinositol, and/or phosphatidylcholine;
   (b) miRNA, optionally selected from hsa-let-7g, hsa-miR-101, hsa-miR-10a, hsa-miR-10b, hsa-miR-126, hsa-miR-128, hsa-miR-129-5p, hsa-miR-130a, hsa-miR-134, hsa-miR-137, hsa-miR-155, hsa-miR-15a, hsa-miR-15b, hsa-miR-16, hsa-miR-17, hsa-miR-182, hsa-miR-183, hsa-miR-185, hsa-miR-18b, hsa-miR-192, hsa-miR-194, hsa-miR-195, hsa-miR-20a, hsa-miR-20b, hsa-miR-210, hsa-miR-218, hsa-miR-301a, hsa-miR-302a, hsa-miR-302c, hsa-miR-345, hsa-miR-375, hsa-miR-378, hsa-miR-7, hsa-miR-9, hsa-miR-93, hsa-miR-96, and hsa-miR-99a;
   (c) a tetraspanin, optionally selected from CD63, CD81, CD9, CD53, CD82 and/or CD37;
   (d) TSG101, Alix, CD109 and/or thy-1; and/or
   (e) CD133.
17. The neural stem cell microparticle of any preceding embodiment, comprising at least 10 of the proteins present in Table 20 or Table 22.
18. The neural stem cell microparticle of any preceding embodiment, for use in therapy.
19. The neural stem cell microparticle of embodiment 18, wherein the therapy is of a disease or condition involving unwanted or undesirable cell migration.
20. The neural stem cell microparticle of embodiment 18 or embodiment 19, wherein the therapy is of fibrosis, cancer, rheumatoid arthritis, atherosclerosis, or unwanted or undesirable angiogenesis.
21. The neural stem cell microparticle of embodiment 20, wherein the cancer comprises a liquid tumour or a solid tumour.
22. The neural stem cell microparticle of embodiment 21, wherein the therapy of the solid tumour comprises inhibiting angiogenesis.
23. The neural stem cell microparticle of embodiment 22, wherein the angiogenesis is inhibited by inhibiting migration of fibroblasts.
24. The neural stem cell microparticle of embodiment 20 or embodiment 21, wherein the cancer is treated by inducing or enhancing or inducing an immune response against the cancer cells.

25. The neural stem cell microparticle of any of embodiments 22 to 24, wherein the microparticle is as defined in embodiment 6.
26. The neural stem cell microparticle of embodiment 20 or embodiment 21, wherein the cancer is treated by inhibiting migration of the cancer cells.
27. The neural stem cell microparticle of embodiment 20 or embodiment 21, wherein the cancer is treated by inducing differentiation of the cancer cells.
28. The neural stem cell microparticle of embodiment 26 or embodiment 27, wherein the microparticle is as defined in embodiment 7.
29. The neural stem cell microparticle of any of embodiments 20 to 28, wherein the cancer is a nestin-positive cancer.
30. The neural stem cell of embodiment 29, wherein the nestin-positive cancer is a melanoma, breast cancer, glioma, pancreatic cancer or prostate cancer.
31. The neural stem cell microparticle of any of embodiments 20 to 30, wherein the cancer is glioblastoma.
32. The neural stem cell microparticle of any of embodiments 20 to 30, wherein the cancer is triple-negative breast cancer.
33. The neural stem cell microparticle of any of embodiments 20 to 30, wherein the cancer is melanoma.
34. Use of a neural stem cell microparticle according to any of embodiments 1 to 17, in the manufacture of a medicament for the treatment of a disease, optionally cancer.
35. A method of producing a neural stem cell microparticle as defined in any one of embodiments 1-17, comprising isolating a microparticle from a neural stem cell-conditioned medium from a neural stem cell that has been cultured, typically in a multi-compartment bioreactor, typically for less than 4 weeks or at least 10 weeks and optionally no more than 20 weeks.
36. A method of producing a stem cell microparticle, comprising isolating a microparticle from a stem cell-conditioned medium wherein the neural stem cell-conditioned medium is from a neural stem cell that has been cultured, typically in a multi-compartment bioreactor, typically for less than 4 weeks or at least 10 weeks and optionally no more than 20 weeks and wherein:
  (i) the stem cell-conditioned medium comprises one or more components which induce the release of microparticles by the stem cells into the medium;
  (ii) the stem cells were cultured under hypoxic conditions;
  (iii) the stem cells were co-cultured with a different cell type;
  (iv) the stem cells were cultured in a multi-compartment bioreactor; and/or
  (v) the stem cells were partially-differentiated;
37. The method according to embodiment 36, wherein the stem cell is a neural stem cell, optionally as defined in any of embodiments 9 to 11.
38. The method according to embodiment 36(i), or embodiment 37 when dependent upon embodiment 32(i), wherein the one or more components are selected from: transforming growth factor-beta (TGF-β), interferon-gamma (INF-γ) and tumour necrosis factor-alpha (TNF-α).
39. The method according to embodiment 36(iii), embodiment 37 or 38 when dependent upon embodiment 32(iii), wherein the different cell type is an endothelial cell.
40. A microparticle obtainable by the method of any of embodiments 35-39.
41. A composition comprising:
  (i) one, two, three or four of hsa-miR-1246, hsa miR-4492, hsa-miR-4488 and hsa-miR-4532;
  (ii) one, two, three, four or five of hsa-miR-181a-5p, hsa-miR-1246, has-miR-127-3p, hsa-miR-21-5p, and hsa-miR-100-5p; or
  (iii) one, two, three, four or five of hsa-miR-181a-5p, hsa-let-7a-5p, has-let-7f-5p, hsa-miR-92b-3p, and hsa-miR-9-5p.
42. A composition according to embodiment 41, for use in therapy as defined in any of embodiments 19 to 33.
43. A composition according to embodiment 41 for use in the treatment of cancer, wherein:
  (i) the composition of embodiment 41(i) is for use in therapy as defined in embodiments 26 or 27; or
  (ii) the composition of embodiment 41(iii) is for use in therapy as defined in any of embodiments 22 to 24.
44. A composition comprising a microparticle according to any of embodiments 1-17 or 40, or miRNA according to embodiment 41, and a pharmaceutically acceptable excipient, carrier or diluent.
45. A kit for use in a method for producing the microparticle of any of embodiments 1-17 or 40 comprising: (a) a medium; (b) a neural stem cell; (c) optionally the one or more components of embodiments 36 to 38; (d) optionally the microparticle of any of embodiments 1-17 or 40 suitable for use as a control; (e) optionally a detection agent suitable for specific detection of the produced microparticles; and (f) instructions for producing the microparticle of any of embodiments 1-17 or 40 using the kit.
46. A method of screening for an agent that alters the rate of production of a microparticle by a stem cell, comprising contacting a stem cell with a candidate agent and observing whether the rate production of microparticles by the contacted stem cell increases or decreases compared to a control.

The invention is further described with reference to the following non-limiting examples.

EXAMPLES

Example 1: NSC Exosomes that Inhibit Cell Migration

A transwell assay was used to study the migratory response of human dermal fibroblasts to different populations of exosomes. Experiments were performed in triplicate. 200,000 human dermal fibroblast cells ("FBs") were placed on the upper layer of a cell permeable membrane (8 μm pore size; 24-well plate) and a solution (basal medium) containing or lacking 20 μg/ml exosomes was placed in contact with the underside of the cell permeable membrane (FIG. 1, top panel). The exosomes were collected from CTX0E03 cells cultured for 0 weeks ("0") or 11 weeks ("11") in an Integra CeLLine AD1000 multi-chamber bioreactor. Following an incubation period (6 or 24 hours; control: 0 hours), the human dermal fibroblast cells that migrated through the membrane were stained (using a fluorescent-dye conjugated anti-actin antibody and Hoechst Fluorescent Stain for nuclei) and counted (six random microscope fields per sample) as an indicator of the cells' migratory response to exosomes.

FIG. 1 (lower panel) and FIG. 2 show that exosomes isolated from a proliferating CTX0E03 culture ("0") significantly promote migration of human dermal fibroblasts compared to medium lacking exosomes ("basal"), both after a 6 hour and after a 24 hour incubation period. In contrast, exosomes isolated from a more differentiated CTX0E03 culture ("11") significantly abrogate migration of human dermal fibroblasts compared to medium lacking exosomes ("basal"), both after a 6 hour and after a 24 hour incubation period.

It can be seen that cell migration is increased in the presence of exosomes from 0-week NSCs but decreased in the presence of exosomes from 11-week NCSs, compared to control ("basal").

In summary, NSC microparticles have been identified that significantly abrogate cell migration.

These data show that neural stem cell microparticles can stimulate or inhibit cell migration. This is surprising and useful in applications where either stimulating (e.g. wound healing) or inhibiting (e.g. cancer, fibrosis, rheumatoid arthritis, atherosclerosis) cell migration is desired. The involvement of fibroblasts in angiogenesis also makes the microparticles that inhibit fibroblast migration useful in applications where inhibition of angiogenesis is desired. Angiogenesis is involved in tumour formation, survival and metastasis. These data therefore demonstrate potential for the exosomes of the invention to treat many types of cancer.

Example 2: Exosomes Isolated from the Medium of NSCs Cultured for 2 or 6 Weeks Promote Fibroblast Migration Method—Wound Closure/Scratch Assay
  Seed $0.25 \times 10^6$ NHDF (normal human dermal fibroblasts) per well of a 12 well plate and allow to become confluent (24 hours)
  Remove growth factors for 24 hrs
  Remove cells (scratch) and incubate with exosomes/conditioned media
  Image effected area over 48 hrs
  Estimate area using Image J
Results

TABLE 2

Wound closure/scratch assay representing the migration activity of normal human dermal fibroblasts (NHDF) cultured in CTX0E03 conditioned media or upon the addition of purified exosomes.

|  | Wound closure (%) | | |
| --- | --- | --- | --- |
|  | 0 h | 24 h | 48 h |
| CTX0E03 conditioned media | 0% | 100% |  |
| 2 ug/ml exosomes | 0% | 95.4% | 100% |
| Control | 0% | 48.1% | 49.7% |

Wound closure was calculated as the area covered by cells in relation to the initial wound area, as determined at 0 h. Wound closure is expressed as the percentage of the initial wound area at time 0 h. These data are also shown, photographically, in FIG. 3A. The figure shows that, in contrast to exosomes from 11-week NSCs as described in FIGS. 1 and 2, exosomes from 2-week NSCs stimulate cell migration.

Figure 3B:
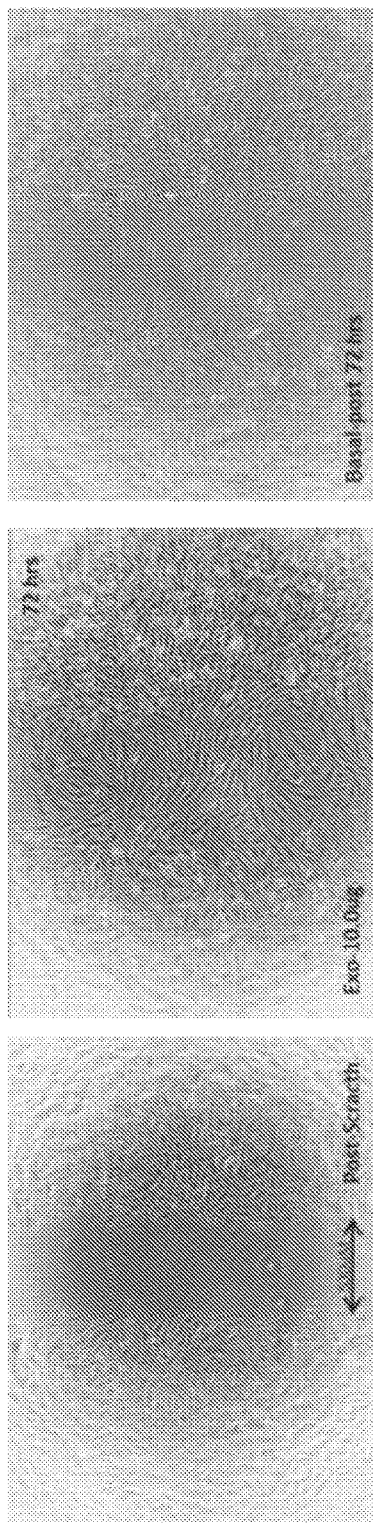
FIG. 3B shows the results of a scratch assay after 72 hours, comparing the effect of 10 µg 2-week CTX0E03 exosomes to basal conditions (without exosomes).

FIG. 3B shows that 10 μg CTX0E03 exosomes significantly increase wound closure (as determined in the HDNF scratch/migration assay) after 72 hours, compared to basal conditions (without exosomes).

Further experiments confirmed that exosomes purified (by ultracentrifugation; quantified by BCA protein assay; characterised as >99% positive for CD63 and CD81 and having a greater expression level of Alix compared to the corresponding microparticle fraction) from all time points (weeks 2-6) during continuous culture (using Integra CELLine bioreactors in the presence of growth factors and 4OHT) significantly enhanced fibroblast migration and wound healing, with a peak response between 5-10 μg/ml compared to basal conditions. FIG. 3C shows the % healed areas for basal conditions, 2 μg/ml exosomes, 6 μg/ml exosomes, 20 μg/ml exosomes and an LSGS (low serum growth supplement) positive control. The top panel of FIG. 3C shows exosomes isolated from CTX0E03 cells cultured for 2 weeks in the Integra Celline system and the bottom panel of FIG. 3C shows exosomes isolated from CTX0E03 cells cultured for 6 weeks in the Integra Celline system. These data show that all doses of all tested NSC exosomes provide increased healing compared to basal conditions, with % healing approaching the positive control (LSGS) after 72 hours.

The data in FIG. 3C also show that the exosomes isolated from NSCs cultured for 6 weeks cause faster healing (than 2 week exosomes), with the % healed approaching 100% after only 48 hours, for all doses.

Figure 3D:
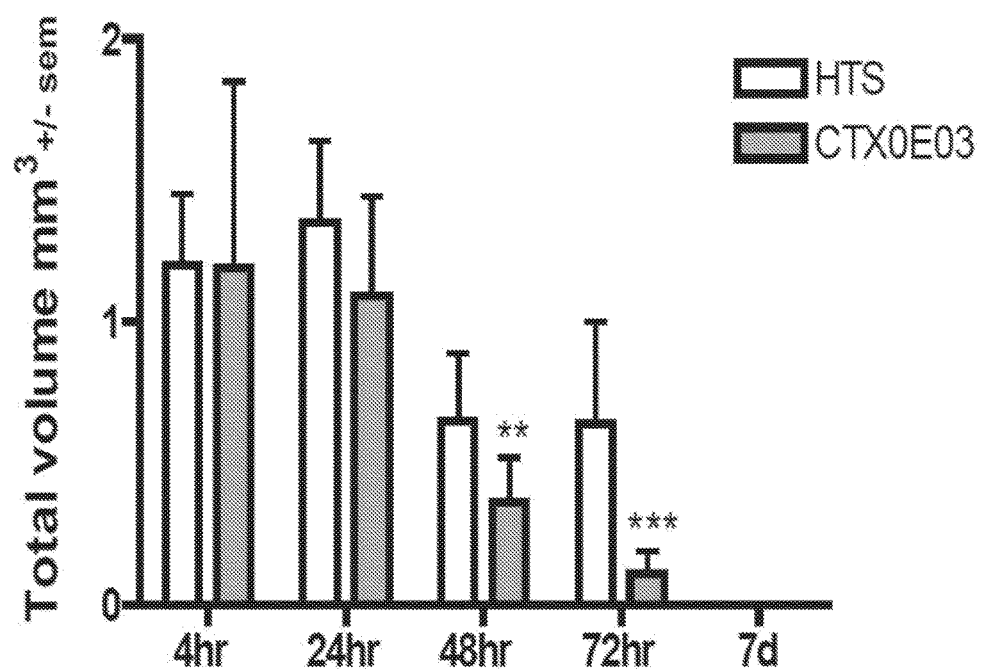
FIG. 3D compares 2-week CTX0E03 cells to a negative control (saline) in an in vivo injection wound healing assay.

FIG. 3D shows the results of an in vivo injection wound assay in a mouse, confirming that CTX0E03 cells stimulated wound healing to a statistically-significant degree in vivo. This is a simple in vivo bioassay which can be used to confirm the efficacy of microparticles in vivo.

Conclusion Exosomes released from the human neural stem cell line CTX0E03 enhance fibroblast migration in an in vitro model of wound healing, suggesting that exosomes may contribute to the mechanisms by which hNSCs promote repair. Exosomes isolated from cells cultured for 6 weeks show improved wound healing efficacy in vitro, compared to exosomes isolated from cells cultured for 2 weeks.

Example 3: Glioblastoma Engraftment Assay—Destruction of Tumour Cells

U373 glioblastoma cells were pre-treated in vitro for 24 hours with exosomes isolated from CTX0E03 cells cultured for 11 weeks in an Integra CeLLine bioreactor before implantation into the striatum of Balb-C mice brains.

Figure 19:
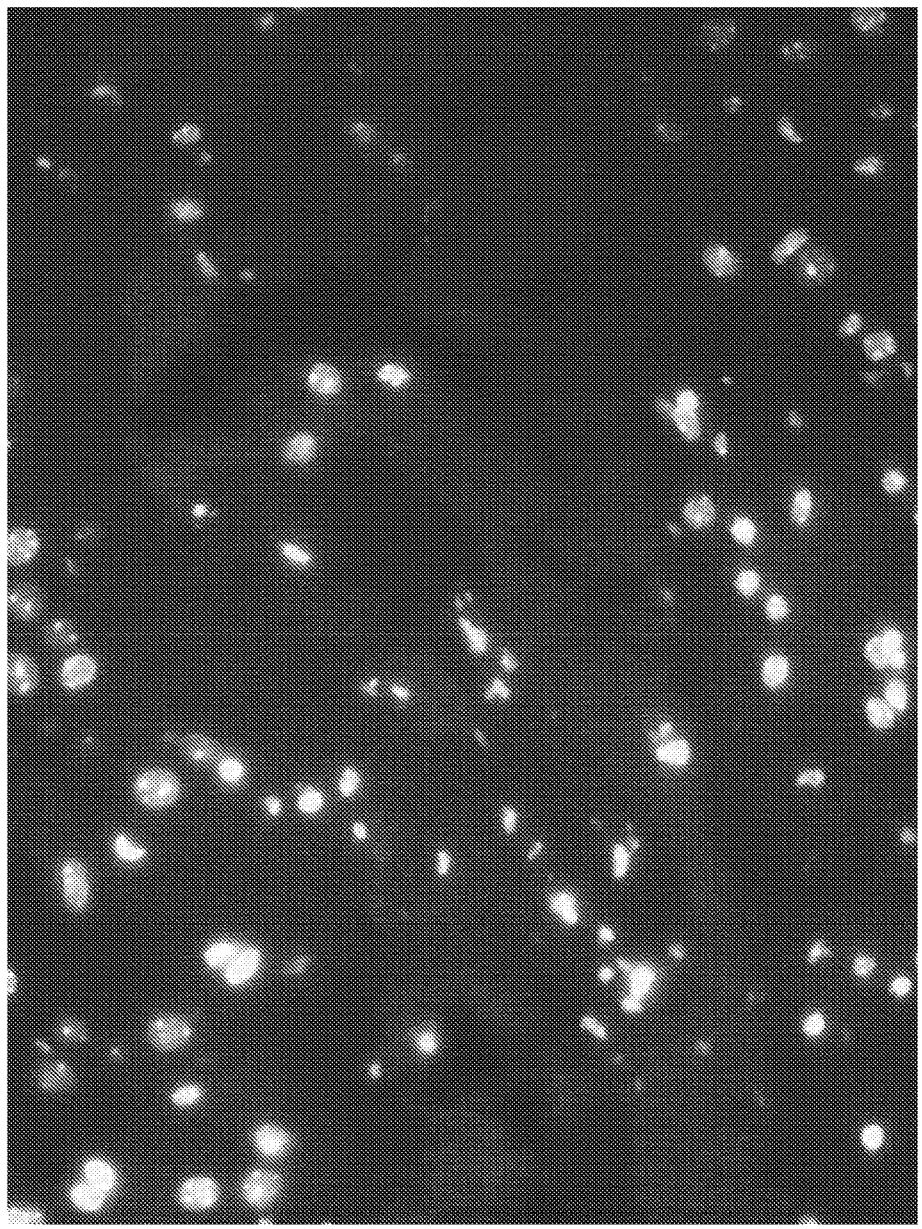
FIG. 19 shows the presence of necrotic cell bodies and evidence of a host cellular response in the striatum of Balb-C mice 24 hours after implantation of glioblastoma U373 cells that were pre-treated for 24 hours with exosomes isolated from CTX0E03 cells cultured for 11 weeks in a multi-compartment bioreactor.

As shown in FIG. 19, the exosome-treated glioblastoma cells did not engraft into the striatum. Histopathology demonstrated the presence of necrotic U373 cell bodies at the site of implantation and evidence of gliosis—a host cellular immune response.

These data suggest utility of these exosomes in the treatment of cancer, by promoting the destruction of a tumour by the immune system, particularly a tumour of the CNS such as a glioblastoma.

Example 4: Glioblastoma Engraftment Assay—Differentiation of Tumour Cells

U373 glioblastoma cells were pre-treated in vitro for 24 hours with exosomes isolated from standard CTX0E03 cell culture ("exosome 0"—proliferating cells, cultured in an Integra CeLLine bioreactor for less than 24 hours) before implantation into the striatum of Balb-C mice brains. Marker expression was then observed after 24 hours.

Figure 20:
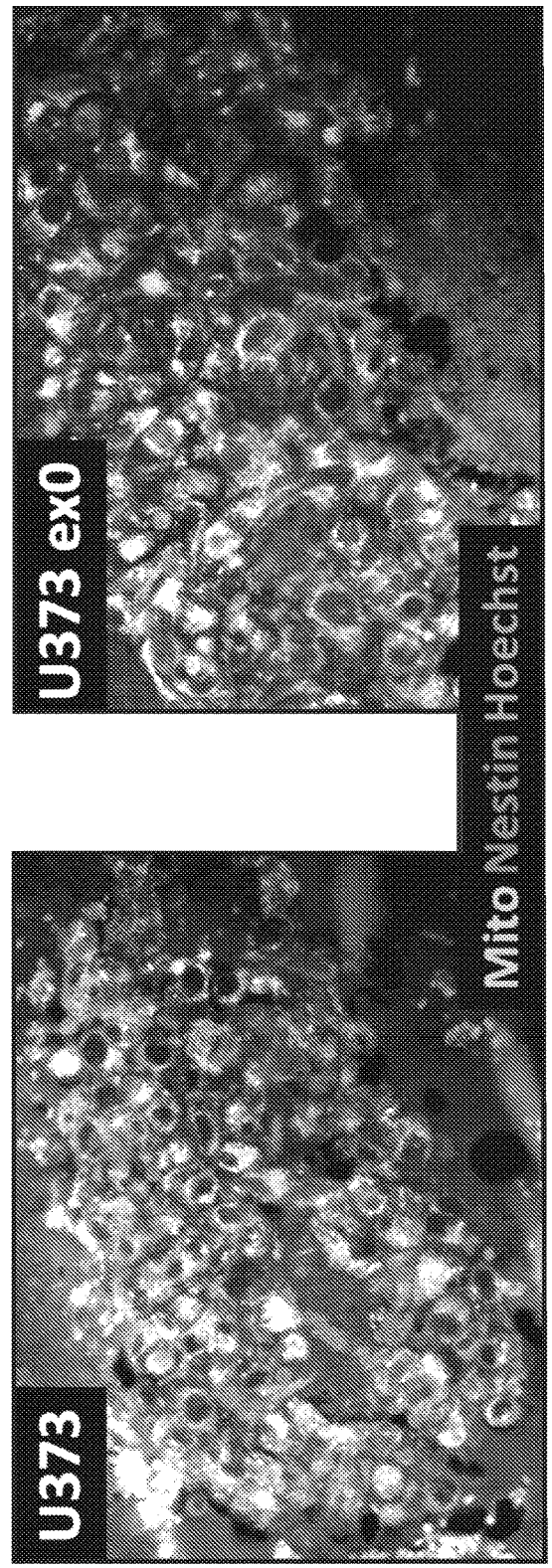
FIG. 20 shows a reduction in nestin expression in glioblastoma U373 cells that have pre-treated in vitro for 24 hours with exosomes isolated from a proliferating culture of CTX0E03 cells and implanted into the striatum of Balb-C mice.

As shown in FIG. 20, the exosome-treated glioblastoma cells demonstrated a reduction in nestin expression 24 hours post implantation into the striatum of Balb-C mice. Nestin is a stem cell marker; cancer stem cells drive tumourigenesis, are linked with metastasis, high grade and poor prognosis. The treatment of cancer by inducing cellular differentiation is particularly attractive because the therapy can be target-cell specific (i.e. will only target the undifferentiated, malignant, cells) and likely less toxic than standard chemotherapies.

These data suggest utility of these exosomes in the treatment of cancer, by inducing differentiation of the cancer cells, typically for treating a nestin-positive cancer and particularly a tumour of the CNS such as a glioblastoma.

Example 5: In Vitro Glioblastoma Differentiation Assay—Differentiation of Tumour Cells U373 glioblastoma cells were cultured for 24 hours in the presence of: (i) basal medium; (ii) +20 µg exosomes isolated from standard CTX0E03 cell culture ("exosome 0"—proliferating cells, cultured in an Integra CeLLine bioreactor for less than 24 hours); or (iii) +20 µg exosomes isolated from CTX0E03 cells cultured for 11 weeks in an Integra CeLLine bioreactor ("exosome 11"). The U373 cells were then stained for the presence of Nestin (a stem cell marker) and GFAP (an astrocyte marker of a differentiated cell).

Figure 21:
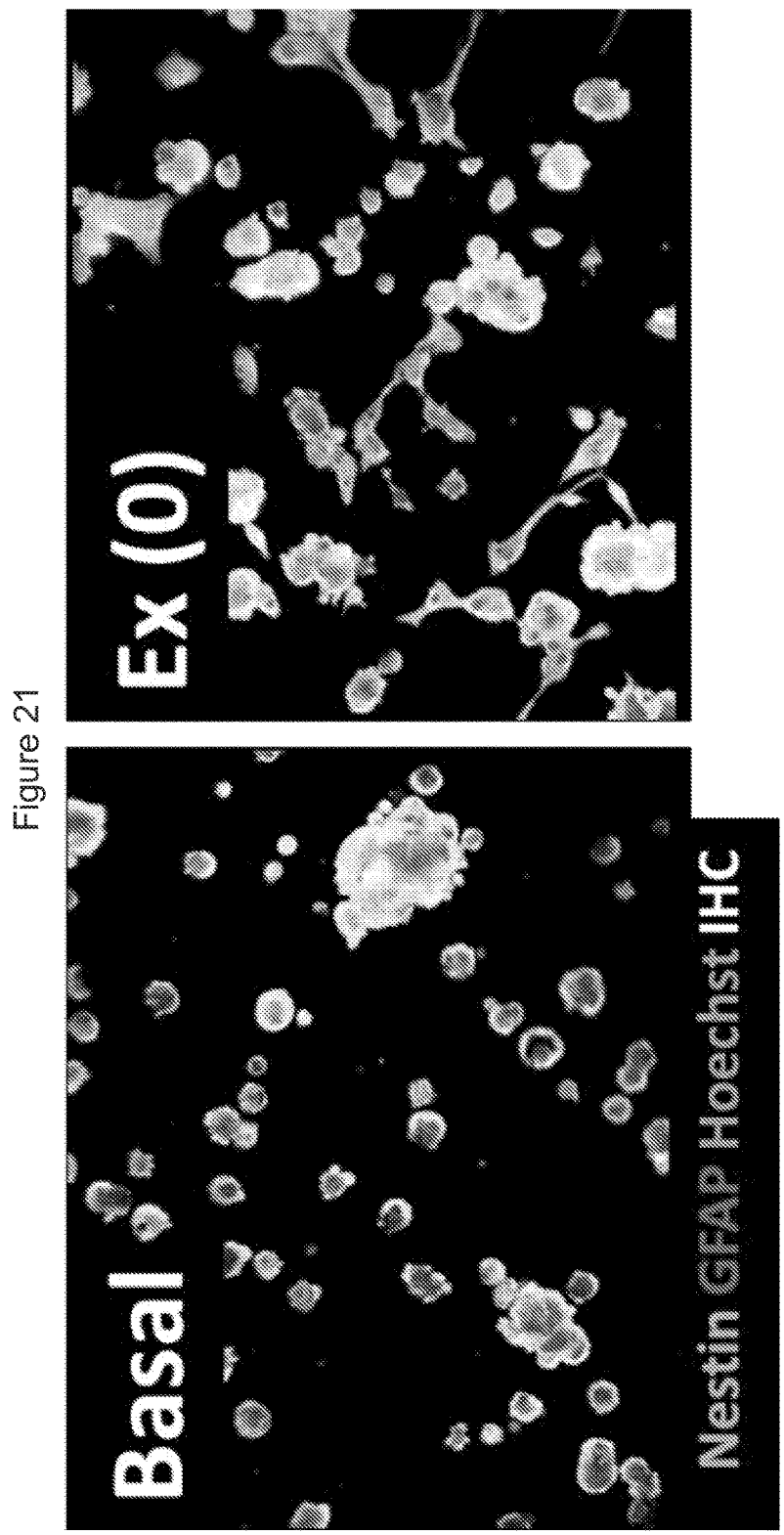
FIG. 21 shows that glioblastoma U373 cells that have been treated in vitro with exosomes isolated from a proliferating culture of CTX0E03 cells, appear morphologically differentiated and express Glial fibrillary acidic protein (GFAP).

As shown in FIG. 21, exosome 0 promoted differentiation of the glioblastoma cells in vitro. The exosome 0 treated cells appeared morphologically differentiated, with the presence of long processes. Additionally, these cells expressed Glial fibrillary acidic protein (GFAP), a marker of differentiated astroglial cells. These in vitro data agree with the in vivo data immediately above. As noted above, more differentiated (less malignant) glioblastoma tumours are linked with more favourable prognosis. These data further suggest utility of these exosomes in the treatment of cancer, by inducing differentiation of the cancer cells, particularly a tumour of the CNS such as a glioblastoma.

In contrast, the exosomes isolated from CTX0E03 cells cultured for 11 weeks ("exosome 11") promoted "stemness" in the glioblastoma cells in vitro, demonstrated by nestin expression and proliferation. However, in the in vivo assay above, these exosomes were observed to promote destruction of the tumour cells.

Example 6: Glioblastoma Migration Assays

Three separate in vitro transmembrane migration assays have demonstrated that treatment of glioblastoma (U373) cells with exosomes isolated from standard CTX0E03 cell culture ("exosome 0"—proliferating cells, cultured in an Integra CeLLine bioreactor for less than 24 hours) significantly reduces their migration towards a positive chemoattractant (Foetal Bovine Serum). These assay results are shown in FIG. 22.

Glioblastoma cells were seeded on one side of a porous filter membrane. These cells were either seeded together with 20 µg/ml CTX0E03 "exosome 0" (FIGS. 22A and 22C) or have been pre-treated with 10 µg/ml CTX0E03 "exosome 0" for 24 hours (FIG. 22B). Medium containing a 10% FBS was placed on the opposing (lower) side. After a 24 hour incubation period, the membrane was fixed and stained to reveal migrated cells (e.g. cell nuclei), which were counted microscopically.

These data show that exosomes of the invention (isolated from standard "week 0" CTX0E03 cells) are able to reduce migration of glioblastoma cells. Glioblastomas are the most common and malignant brain tumors of the central nervous system and exhibit high invasive capacity, which hinders effective therapy. Therefore, therapeutics that can inhibit glioma cell migration and invasion are highly desirable. These data demonstrate the utility of neural stem cell exosomes in the treatment of cancer, typically a glioblastoma, by reducing tumour migration/invasion.

Summary: Treatment of Cancer Using Neural Stem Cell Exosomes

The data provided above indicate therapeutic utility in the treatment of cancer using exosomes produced by neural stem cells, by one or more of: reducing tumour migration/invasion (exosome 0, glioblastoma assay); inducing tumour differentiation (exosome 0, glioblastoma assay); promoting tumour destruction (exosome 11, glioblastoma transplant); or inhibiting angiogenesis (exosome 11, fibroblast assay).

Example 7: Preparation of Neural Stem Cells and Neural Stem Cell Microparticles for Visualisation by Electron Microscopy Method
Embedding CTX0E03 Cells for Electron Microscopy
5×70% CTX0E03 cultures
Treat with +/−4OHT, IFNγ, TNFα and TGFβ (all at 10 ng for 24 hrs)
Detach cells and fix overnight in 2.5% Gluteraldehyde in 0.1M Cacodylate pH7.4
Cells spun down 300 g
Buffered osmium 2%, 1.5 hrs
Spin, wash water, overnight
Uranium acetate 2%, 2 hrs
Spin, wash water, 30 mins
Ethanol gradient 20, 35, 50, 70, 80, 90, 100%, over weekend.
100% propylene oxide (PO), 1 hr
Spin, 50% Agar LV resin in PO, 1 hr
75% LV resin/PO 5 hrs
100% resin overnight at 60° C.
Cool to RT before cutting (60-80 nm), Imaged TEM at 200 Kv.
Results
FIG. 4A-E shows the electron micrographs of the multivesicular bodies (MVBs) containing exosomes of approximately 30 nm-50 nm in diameter. FIG. 4F shows microvesicles>100 nm in diameter.

Example 8: Production of Neural Stem Cell Microparticles from a Neural Stem Cell Line Method
5 Sub-confluent flasks containing the same culture of CTX0E03 cells were individually treated with either 10 ng/ml TGF-β, 10 ng/ml IFNγ, or 10 ng/ml TNFα alongside full growth media controls with or without the addition of 4OHT. 72 hours after treatment, the cells were collected using trypzean/EDTA, washed and fixed overnight in 2.5% Gluteraldehyde in 0.1M Cacodylate pH7.4 ready for electron microscopy evaluation.
Results
The frequency of the occurrence of multivesicular bodies (MVBs) was observed to be altered by the presence of TGF-β, IFN-γ or TNF-α. The frequency was highest in the presence of TGF-β, followed by IFN-γ, followed by TNF-α.
Conclusion
The production of microparticles from neural stem cells can be stimulated by the addition of the factors TGF-β, IFN-γ or TNF-α. This has the potential for more efficient production of microparticles.

Figure 5:
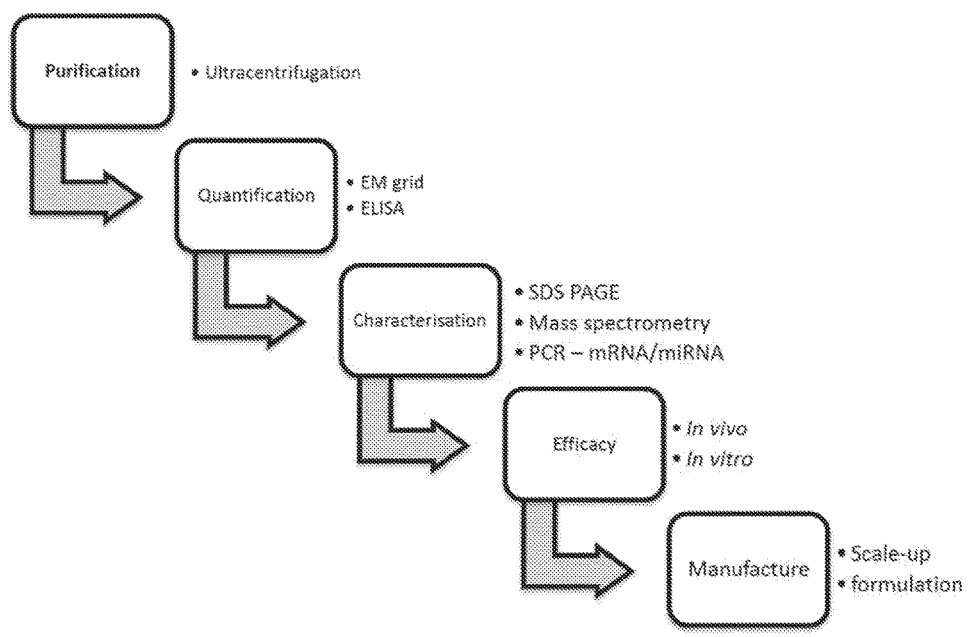
FIG. 5 is an outline protocol for the identification, characterisation and production of microparticles from stem cells.

Example 9: Purification, Quantification and Characterisation of Neural Stem Cell Microparticles Method
An outline protocol for producing large quantities of microparticles is provided in FIG. 5. The main steps are purification, quantification, characterisation, efficacy testing and manufacture.

(1) Purification

Microparticles can be purified from stem cell-conditioned medium by ultracentrifugation, e.g. at 100000×g for 1-2 hours. Alternative or additional methods for purification of may be used, such as antibody-based methods, e.g. immunoprecipitation, magnetic bead purification, resin-based purification, using specific antibodies.

(2) Quantification

Purified microparticles can be quantified by quantification of total nucleic acid or protein levels, e.g. various PCR or colorimetric protein quantification methods such as such as the BCA assay. Other quantification techniques may alternatively be used, including an electron microscopy grid or an immuneassay using antibodies or antibody fragments that specifically bind to microparticle-specific markers (e.g. ELISA, immunoblotting).

(3) Characterisation

The microparticles can be functionally or structurally characterised. RNA/mRNA/miRNA and protein profiling can be used using methods well known in the art (SDS-PAGE, mass spectrometry, PCR). Constitutively secreted microparticles can be tested and compared to microparticles that have been induced by addition of an inducing agent such as transforming growth factor-beta (TGF-β), interferon-gamma (INF-γ) and/or tumour necrosis factor-alpha (TNF-α).

(4) Therapeutic Efficacy

The efficacy of the microparticles can be tested by in vitro and in vivo assays. For in vitro evaluation, neural stem cell microparticles can be added to cultures of monocytes, PBMCs, endothelial cells and/or fibroblasts and the effect of the microparticles on these cells evaluated. Administration of neural stem cell microparticles to suitable animal models can be used to evaluate the in vivo efficacy. Clinical trials can be performed to evaluate safety and outcome of neural stem cell microparticles in human subjects.

(5) Manufacture/Scale-Up

Bioreactors, such as the Integra disposable T1000, can be used for the large-scale manufacture of neural stem cell microparticles. The purified microparticles are then formulated as a therapeutic product.

Example 10: Integra Celline—Disposable Bioreactor for the Production of Micro Particles from CTX0E03 Cells Efficient micro particle production and harvest from a cell line relies upon maintaining optimal culture conditions for the greatest density of cells. Any restriction in the oxygen or nutrients supplied to the cells or an accumulation of waste metabolic products will limit the life span of the culture, and hence the micro particle production.

The two-compartment CELLine AD 1000 is designed to accommodate adherent cells attached to a matrix inlay within a small cell compartment, separated from a larger media reservoir by means of a 10 kDa semi-permeable membrane. This membrane allows a continuous diffusion of nutrients and removal of waste products, while concentrating any micro particles produced by the cell within the smaller cell compartment. Due to the large volume capacity (1 liter) of the media compartment, the system has the potential to maintain high density cultures for longer periods of time without the need for a media change. The production of exosomes from mesothelioma tumour cell cultures is described in Mitchell et al, 2008.

Method

In order to obtain optimal performance of the CELLine AD1000, place 25 ml of complete growth medium (RMM with growth factors and 4OHT) into the medium compartment of the flask to pre-wet the semi-permeable membrane. Allow the flask to sit for 5 minutes at room temperature before coating the matrix inlay with mouse Laminin by adding 15 ml of laminin solution (20 µg/ml in DMEM/F12) to the cell compartment for a minimum of 1 hour at 37° C. Remove the laminin solution and add 15 ml of warm DMEM/F12 to the cell compartment to remove any excess laminin. Avoiding the matrix inlay drying, slowly introduce approximately $15 \times 10^6$ CTX0E03 cells in a total of 15 ml of complete growth medium. Take care to remove any air bubbles from the cell compartment. Carefully add a further 460 ml of complete growth medium to the cell compartment before incubating the flask overnight in 5% $CO_2$ at 37° C. The next day remove the medium from the cell compartment and replace with 15 ml of pre warmed growth medium.

Every 7 days harvest the microparticles/medium from the cell compartment. Centrifuge the medium at 1500 rpm for 5 minutes to remove any cell debris and store at −80° C. Carefully add another 15 ml of pre-warmed complete growth medium in to the cell compartment and 485 ml of complete growth medium to the medium compartment and incubate for another 7 days. Microparticles were isolated by 100K MWCO filtration. Repeat as necessary.

Figure 6:
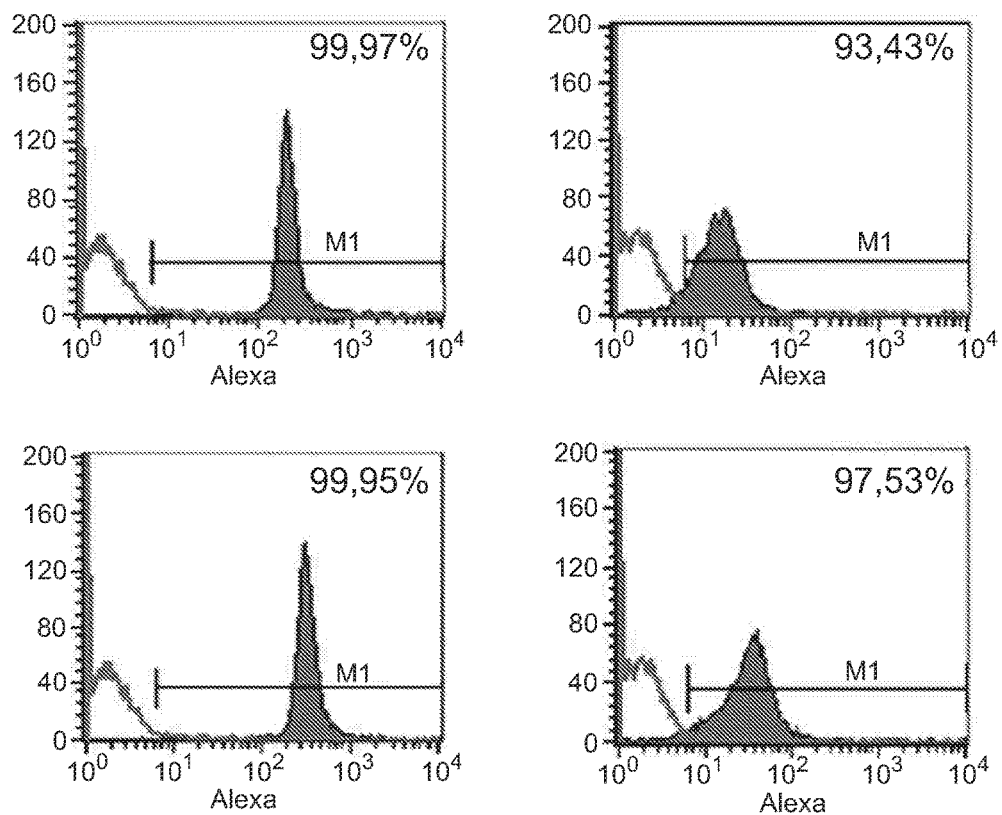
FIG. 6 shows the FACS detection (at 2 ug/ml, 1:250) of (i) CD63 in 2-week Integra cultured CTX0E03 exosomes (top left panel) and microvesicles (top right panel) and (ii) CD81 in 2-week Integra cultured CTX0E03 exosomes (bottom left panel) and microvesicles (bottom right panel).

Marker characterisations indicated that both purified populations (microvesicles and exosomes) express CD63 and CD81 (determined by FACS—FIG. 6). Only the exosomes express the endosomal marker Alix (determined by Western blot, data not shown).

Figure 8A:
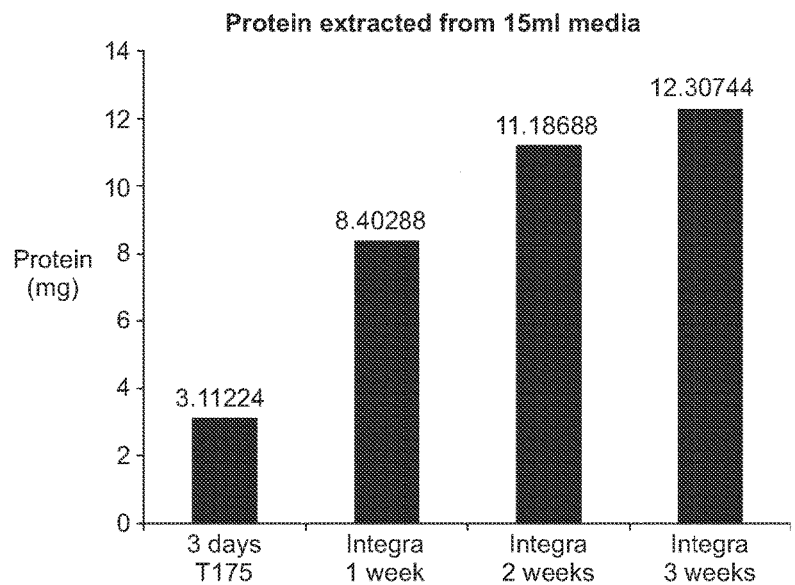
FIG. 8A shows the amount of protein (measured by BCA assay) extracted from 15 ml of media containing microparticles purified from the Integra system compared to normal culture conditions (3 days T175).
Figure 8B:
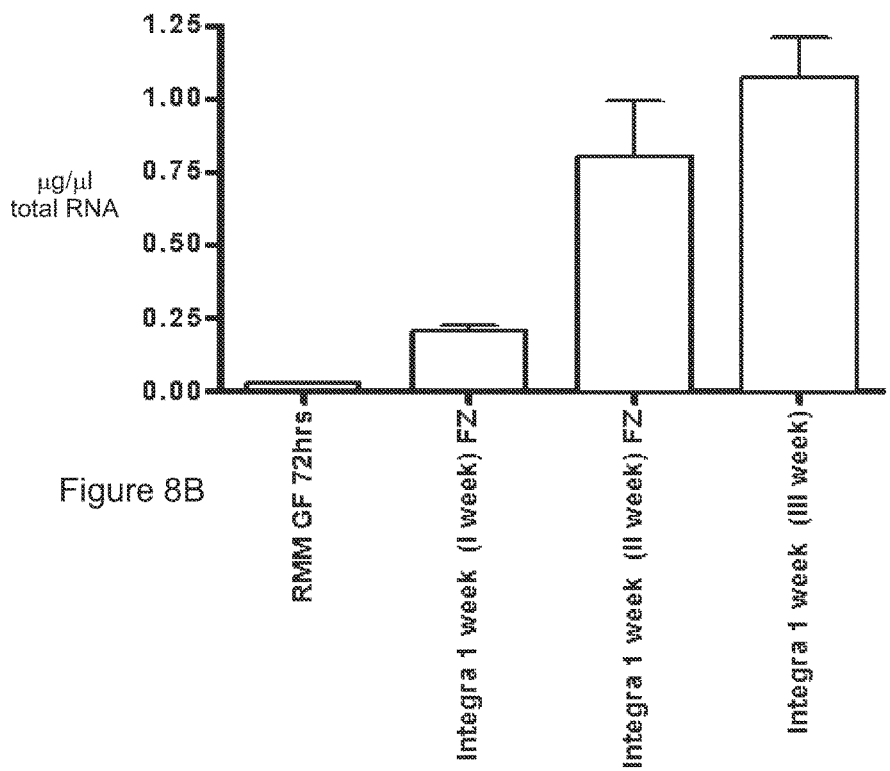
FIG. 8B shows the amount of isolated total RNA measured at 260/280 nm extracted from 15 ml of CTX0E03 conditioned media containing microparticles purified by filtration from the Integra system compared to normal culture conditions (3 days T175).

FIG. 8A shows the amount of protein extracted from 15 ml of media containing microparticles purified using the Integra system compared to normal culture conditions (3 days T175). Milligrams of protein measured by BCA assay. FIG. 8B shows the corresponding quantity of isolated total RNA measured at 260/280 nm.

Example 11: Size Distribution of Microparticles

NanoSight analysis was undertaken to determine the particle size and concentration of microvesicles ("mv1" to "mv6") and exosomes ("exo1" to "exo6") isolated from CTX0E03 cells cultured in the Integra Celline system for 1, 2, 3, 4, 5 and 6 weeks. All results are based on 5 replicate measurements.

Particle size distribution was measured using Nanoparticle Tracking Analysis (NTA). NTA detects the movement of particles in solution and relates it to particle size. Mode and median particle size was calculated for all samples. Exosome samples were analysed using the most sensitive camera settings in order to capture the smallest vesicles. Microvesicle samples were analysed using less sensitive camera settings to prevent over exposure of the larger vesicles. As a result, some smaller vesicles were not detected in the samples. Although smaller vesicles were present in the MV samples, these represent a small percentage of the sample in terms of mass.

A proportion of Exo1 was labelled with a fluorescent membrane-specific dye (CellMask™) and a combination of NTA analysis with the CellMask™ labelling confirmed that the events detected by NTA correspond to membrane vesicles (data not shown).

Figure 7A:
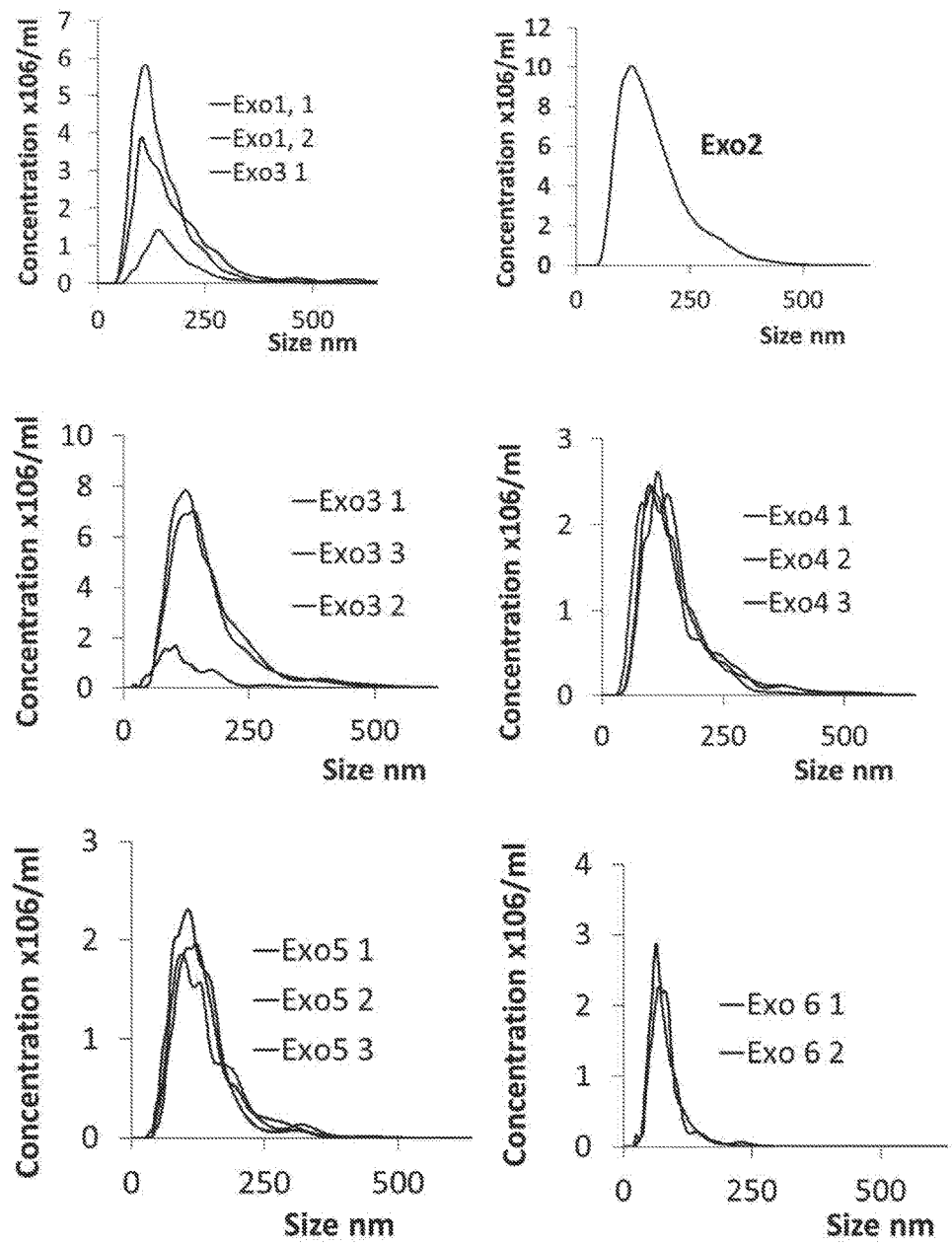
FIG. 7 shows the results of NanoSight analysis undertaken to determine the particle size and concentration of CTX0E03 exosomes (FIG. 7A) and microvesicles (FIG. 7B) cultured in the Integra Celline system for 1, 2, 3, 4, 5 and 6 weeks.
Figure 7B:
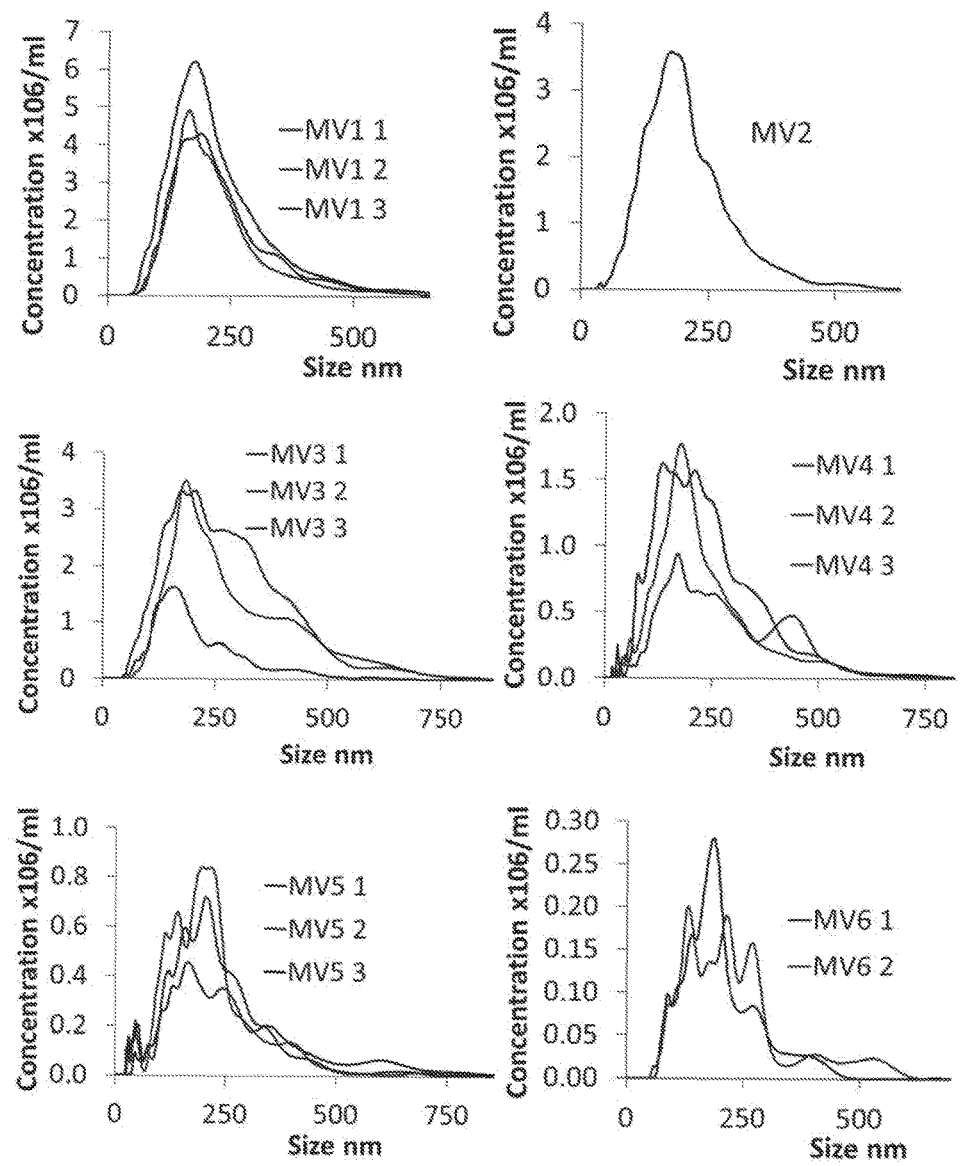

The results are shown in Table 3 below, and in FIG. 7.

The exosomes show a drop in size at week six, from a mode of approximately 110 nm to approximately 70 nm, or from a median of approximately 130 nm to approximately 75 nm. The overall size range, from 70 nm to 150 nm, is consistent with the size of exosomes from other cell types, described in the art. The observed reduction in size of the exosomes to around 70 nm diameter after culturing the cells for 6 weeks correlates with the increased efficacy of exosomes isolated from CTX0E03 cells that have been cultured in a multi-compartment bioreactor for 6 weeks correlates, as reported in Example 2 and FIG. 3.

The microvesicles are, as expected, larger, with a mode diameter of approximately 150 nm-200 nm, or a median diameter of approximately 180 nm-350 nm.

TABLE 3

Size distribution of CTX0E03 microvesicles and exosomes.

| Sample | Count | Dilution | Concentration × $10^{12}$/ml | Mode (nm) | Median (nm) |
|---|---|---|---|---|---|
| Exo1 (1) | 5.204 | 10000 | 32.26 | 107 | 151 |
| Exo1 (2) | 1.734 | 10000 | 10.75 | 135 | 164 |
| Exo1 (3) | 6.55 | 10000 | 40.61 | 108 | 128 |
| Exo2 | 14.33 | 10000 | 88.85 | 118 | 153 |
| Exo3 (1)* | 2.52 | 10000 | 15.62 | 89 | 115 |
| Exo3 (2) | 10.06 | 10000 | 62.37 | 115 | 146 |
| Exo3 (3) | 8.98 | 10000 | 55.68 | 128 | 147 |
| Exo4 (1) | 3.04 | 10000 | 18.85 | 111 | 136 |
| Exo4 (2) | 2.89 | 10000 | 17.92 | 110 | 120 |
| Exo4 (3) | 2.77 | 10000 | 17.17 | 116 | 134 |
| Exo5 (1) | 2.34 | 100 | 0.15 | 99 | 117 |
| Exo5 (2) | 2.02 | 100 | 0.13 | 102 | 124 |
| Exo5 (3) | 2.08 | 100 | 0.13 | 116 | 127 |
| Exo6 (1) | 1.45 | 100 | 0.09 | 68 | 74 |
| Exo6 (2) | 1.19 | 100 | 0.07 | 69 | 75 |
| MV1 (1) | 9.314 | 200 | 1.15 | 183 | 212 |
| MV1 (2) | 10.76 | 200 | 1.33 | 161 | 214 |
| MV1 (3) | 10.738 | 200 | 1.33 | 173 | 198 |
| MV2 | 5.89 | 1000 | 3.65 | 177 | 194 |
| MV3 (1)* | 5.68 | 2000 | 7.04 | 150 | 186 |
| MV3 (2) | 11.5 | 2000 | 14.26 | 221 | 351 |
| MV3 (3) | 9.57 | 2000 | 11.87 | 214 | 270 |
| MV4 (1) | 4.894 | 400 | 1.21 | 209 | 240 |
| MV4 (2) | 2.934 | 1000 | 1.82 | 195 | 212 |
| MV4 (3) | 2.55 | 1000 | 1.58 | 184 | 221 |
| MV5 (1) | 1.086 | 200 | 0.13 | 164 | 237 |
| MV5 (2) | 1.458 | 200 | 0.18 | 205 | 205 |
| MV5 (3) | 1.3 | 200 | 0.16 | 219 | 210 |
| MV6 (1) | 0.346 | 200 | 0.04 | 171 | 186 |
| MV6 (2) | 0.37 | 200 | 0.05 | 168 | 212 |
| Media | 0.14 | 10 | 0.00 | 100 | 149 |

*large aggregates.

Example 12: miRNA Characterization in CTX0E03 Microparticles

Methods
  3 conditions: CTX0E03 cells in standard culture; microparticles obtained from CTX0E03 cells in standard culture; and purified exosomes derived from CTX0E03 cells in Integra CELLine system (see Examples 10 to 16)
  Investigation of miRNA array using qRT-PCR panel (Qiagen) according to manufacturer's instruction. This assay provides high precision and high sensitivity, with data normalization sensitive to method/choice of reference genes. It does not provide genome wide sequencing.

Results:
A) List of miRNAs with a cp≤35 found in (i) standard CTX0E03 cells, (ii) filtered conditioned medium (0.02-0.2 μm filter) i.e. microparticles and (iii) exosomes derived from Integra CELLine system (preliminary miRNA qRT-PCR miscript array (Qiagen) results).
B) Arithmetic and geometric mean of the reference (housekeeping) genes

A

| Mature miRNA | CTX0E03 std culture | CM microparticles | CM exosome Integra |
|---|---|---|---|
| hsa-miR-21-5p | 19.52 | 20.9 | 20.72 |
| hsa-let-7a-5p | 22.64 | 23.11 | 22.36 |
| hsa-miR-125b-5p | 21.64 | 23.25 | 21.74 |
| hsa-miR-9-5p | 22.58 | 23.64 | 22.94 |
| hsa-miR-92a-3p | 23.2 | 23.94 | 24.01 |
| hsa-miR-24-3p | 23.73 | 24.24 | 23.83 |
| hsa-miR-20a-5p | 23.45 | 24.43 | 25.06 |
| hsa-miR-16-5p | 23.14 | 24.72 | 24.32 |
| hsa-miR-100-5p | 23.28 | 24.74 | 23.04 |
| hsa-let-7b-5p | 24.67 | 24.75 | 23.7 |
| hsa-let-7f-5p | 23.93 | 25.09 | 23.86 |
| hsa-miR-17-5p | 24.56 | 25.24 | 26.13 |
| hsa-miR-23b-3p | 24.3 | 25.3 | 24.13 |
| hsa-miR-106b-5p | 24.4 | 25.41 | 26.16 |
| hsa-miR-222-3p | 23.25 | 25.49 | 23.17 |
| hsa-let-7e-5p | 24.57 | 25.58 | 24.16 |
| hsa-miR-26a-5p | 23.4 | 25.63 | 24.2 |
| hsa-miR-181a-5p | 25.16 | 25.7 | 24.32 |
| hsa-miR-125a-5p | 23.56 | 25.75 | 24.88 |
| hsa-miR-103a-3p | 24.65 | 25.8 | 25.77 |
| hsa-let-7i-5p | 24.37 | 25.98 | 24.23 |
| hsa-miR-99a-5p | 24.44 | 26.05 | 23.44 |
| hsa-let-7c | 25.76 | 26.12 | 24.07 |
| hsa-let-7g | 25.2 | 26.15 | 25.17 |
| hsa-miR-195-5p | 24.72 | 26.34 | 25.67 |
| hsa-miR-93-5p | 25.15 | 26.48 | 26.06 |
| hsa-miR-22-3p | 25.03 | 26.49 | 25.66 |
| hsa-miR-20b-5p | 26.03 | 26.86 | 27.42 |
| hsa-miR-18a-5p | 26.71 | 26.87 | 29.06 |
| hsa-miR-15b-5p | 25.1 | 26.92 | 26.43 |
| hsa-let-7d-5p | 26.84 | 26.96 | 26.52 |
| hsa-miR-424-5p | 25.56 | 27.72 | 26.66 |
| hsa-miR-15a-5p | 26.88 | 27.89 | 29.3 |
| hsa-miR-130a-3p | 27.23 | 28.26 | 28.49 |
| hsa-miR-33a-5p | 30.34 | 28.54 | 34.18 |
| hsa-miR-128- | 26.94 | 28.64 | 27.66 |
| hsa-miR-218-5p | 27.79 | 28.68 | 28.03 |
| hsa-miR-301a-3p | 29.53 | 28.69 | 31.57 |
| hsa-miR-134 | 28.3 | 28.76 | 28.76 |
| hsa-miR-101-3p | 28.44 | 28.82 | 31.64 |
| hsa-miR-7-5p | 29.71 | 28.82 | 30.22 |
| hsa-miR-18b-5p | 28.83 | 28.85 | 35.47 |
| hsa-miR-185-5p | 28.34 | 28.99 | 28.13 |
| hsa-miR-378-3p | 29.76 | 29.25 | 28.97 |
| hsa-miR-132-3p | 28.65 | 29.32 | 27.72 |
| hsa-miR-345-5p | 28.49 | 29.52 | 29.66 |
| hsa-miR-219-5p | 30.58 | 29.52 | 32.7 |
| hsa-miR-127-5p | 30.05 | 29.95 | 31.11 |
| hsa-miR-146b-5p | 30.53 | 30.54 | 28.07 |
| hsa-miR-10a-5p | 27.1 | 30.69 | 28.32 |
| hsa-miR-210 | 29.85 | 30.83 | 30.65 |
| hsa-miR-129-5p | 32.51 | 30.98 | 31.69 |
| hsa-miR-137 | 31.46 | 31.13 | 30.95 |
| hsa-miR-182-5p | 28.34 | 31.64 | 31.27 |
| hsa-miR-124-3p | 33.38 | 31.71 | 33.07 |
| hsa-miR-96-5p | 29.77 | 32.27 | 34.67 |
| hsa-miR-192-5p | 31.42 | 32.42 | 32.52 |
| hsa-miR-126-3p | 31.73 | 32.44 | 32.05 |
| hsa-miR-194-5p | 31.11 | 32.49 | 31.72 |
| hsa-miR-375 | 33.77 | 32.94 | 30.94 |
| hsa-miR-205-5p | 35 | 33.01 | 32.72 |

| Mature miRNA | CTX0E03 std culture | CM microparticles | CM exosome Integra |
|---|---|---|---|
| hsa-miR-183-5p | 29.88 | 33.21 | 31.74 |
| hsa-miR-10b-5p | 29.6 | 33.22 | 30.79 |
| hsa-miR-302a-3p | 29.67 | 33.6 | 31.69 |
| hsa-miR-214-3p | 34.19 | 33.76 | 32.11 |
| hsa-miR-141-3p | 35 | 33.96 | 34.51 |
| hsa-miR-302c-3p | 31.6 | 34.29 | 33.93 |
| hsa-miR-196a-5p | 35 | 34.65 | 35.75 |
| hsa-miR-150-5p | 34.59 | 34.76 | 34.59 |
| hsa-miR-155-p | 32.04 | 35.75 | 32.76 |

B

|  | CTX0E03 std culture | CM microparticles | CM exosome Integra |
|---|---|---|---|
| Avg. of Arithmetic Mean | 23.54 | 23.82 | 24.79 |
| Avg. of Geometric Mean | 23.48 | 23.8 | 24.62 |

Example 13: CTX0E03 Conditioned Medium Analysis Using a Protein Dot Blot

Methods

Conditioned 24 hr and 72 hrs conditioned medium (RMM and ITS medium)

The collected media has been 'concentrated' by dialysis and the proteins biotinylated (typical total protein concentration appears to be 0.5 mg/ml). The media is then incubated with the Raybiotech L507 human protein arrays (total protein concentration 0.1 mg/ml). Following washing and incubation of the array with HRP-conjugated streptavidin, the presence of proteins is detected by chemiluminescence. The array provides qualitative data (i.e. the protein is present, but no indication of its level of expression compared to other proteins).

Results

| Cytokine Name | Cytokine Full Name | Function |
|---|---|---|
| EDA-A2 | ectodysplasin-A2 | May be involved in proper formation of skin appendages |
| Galectin-3* | Galectin-3 | Galactose-specific lectin which binds IgE. May mediate with the alpha-3, beta-1 integrin the stimulation by CSPG4 of endothelial cells migration. |
| IGFBP-2 | Insulin-like growth factor binding proteins 2 | IGF-binding proteins prolong the half-life of the IGFs and have been shown to either inhibit or stimulate the growth promoting effects of the IGFs on cell culture. |
| IGFBP-rp1/IGFBP-7 | Insulin-like Growth Factor Binding Protein Related Protein-1 Insulin-like Growth Factor Binding Protein-7 | soluble proteins that bind IGFs with high affinity. |
| IL-1a† | Interleukin 1 alpha | potent mediator of inflammation and immunity |
| LECT2† | Leukocyte cell-derived chemotaxin-2 | Has a neutrophil chemotactic activity. Also a positive regulator of chondrocyte proliferation. |
| MCP-1† | Monocyte chemoattractant protein 1 | plays a role in the recruitment of monocytes to sites of injury and infection. |
| SPARC* | Secreted Protein, Acidic Cysteine-rich-related modular calcium-binding protein 1 [Precursor] | matricellular protein that modulates cell adhesion and proliferation and is thought to function in tissue remodeling and angiogenesis |
| TIMP-1* | Tissue inhibitor of metalloproteinasess-2 | Complexes with metalloproteinases (such as collagenases) and irreversibly inactivates them. Also mediates erythropoiesis in vitro; but, unlike IL-3, it is species-specific, stimulating the growth and differentiation of only human and murine erythroid progenitors. |
| Thrombo-spondin-1* | Thrombospondin-1 | multimodular secreted protein that associates with the extracellular matrix and possesses a variety of biologic functions, including a potent angiogenic activity. |
| VEGF* | Vascular endothelial growth factor | Growth factor active in angiogenesis, vasculogenesis and endothelial cell growth. |

These proteins show expression in some instances-though may also be present in media.

| Cytokine Name | Cytokine Full Name | Function |
|---|---|---|
| EGF R/ErbB1 | Epidermal growth factor receptor | Receptor for EGF, but also for other members of the EGF family, as TGF-alpha, amphiregulin, betacellulin, heparin-binding EGF-like growth factor |
| MDC * | A disintegrin and metalloproteinase domain 11 Metalloproteinase-like, disintegrin-like, and cysteine-rich protein MDC | Probable ligand for integrin in the brain. This is a non catalytic metalloprotease-like protein. |
| Endostatin* | Endostatin | Angiogenesis inhibitor; inhibits endothelial cell migration but may not effect proliferation. May work in balance with VEGF to maintain level of angiogenesis. |
| Follistatin | Follistatin | Regulates stem cell renewal versus differentiation by inhibiting pro-differentiation proteins |
| Csk† | cytoplasmic tyrosine kinase | Activity is required for interleukin 6 (IL-6) induced differentiation. May play a role in the growth and differentiation of hematopoietic cells. May be involved in signal transduction in endocardial and arterial endothelial cells. |

\* = angiogenesis
† = inflammation

Example 14: Production of Exosomes Using the Integra Celline System

Figure 9:
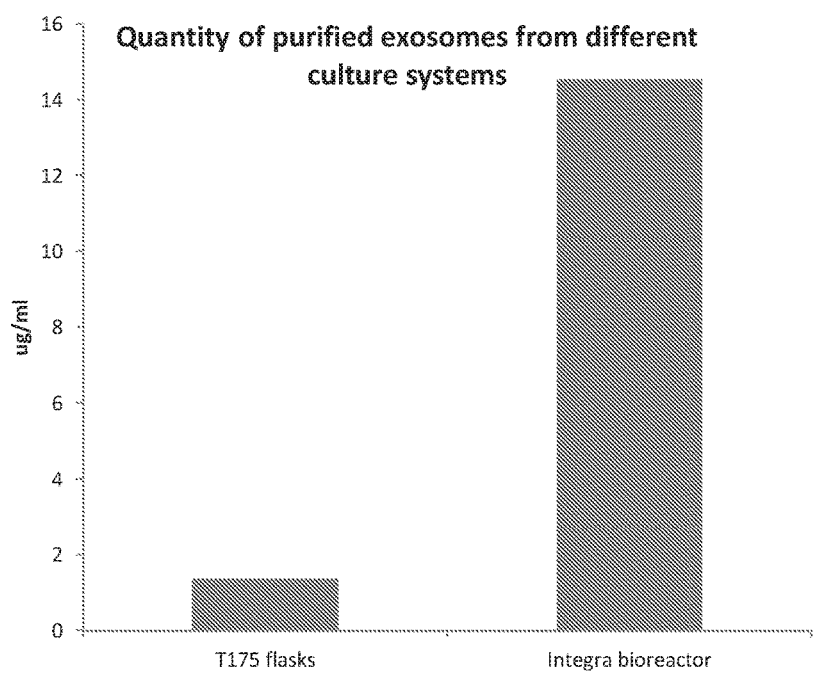
FIG. 9 shows the quantity of purified exosomes obtained per ml culture medium from standard CTX0E03 (T175) cultures vs. the Integra CELLine system at the 3 week time point.

CTX0E03 cells were cultured using the Integra CELLine system and exosomes were purified as described in Example 10. The concentration of exosomes purified from the medium using the CELLine system at the 3 week time point, and as a control a standard T175 system as routinely used in the art, was quantified (using a BCA assay to estimate protein content). FIG. 9 shows that the production of exosomes using the Integra CELLine system is increased several fold, compared to using conventional culture (T175 flasks).

Figure 10A:
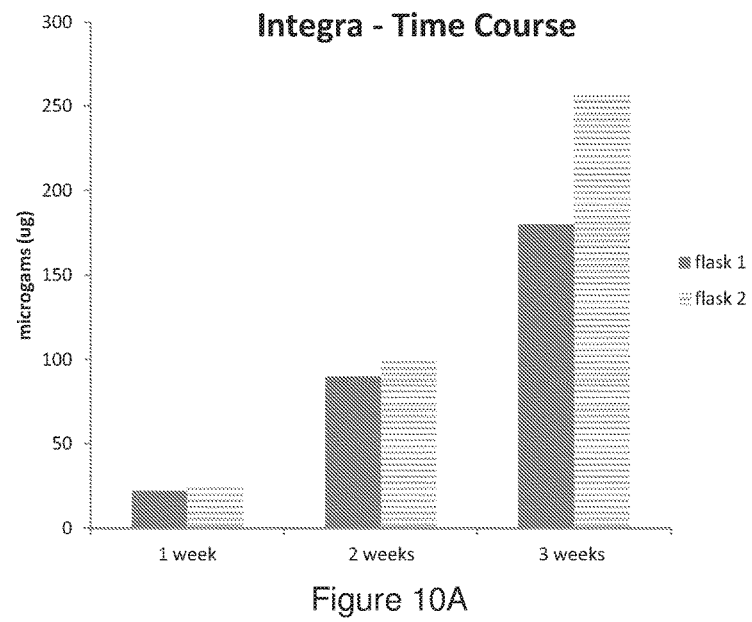
FIG. 10A shows the concentration of exosomes harvested from two different flasks after 1 week, 2 weeks and 3 weeks of CTX0E03 Integra CELLine culture system.
Figure 10B:
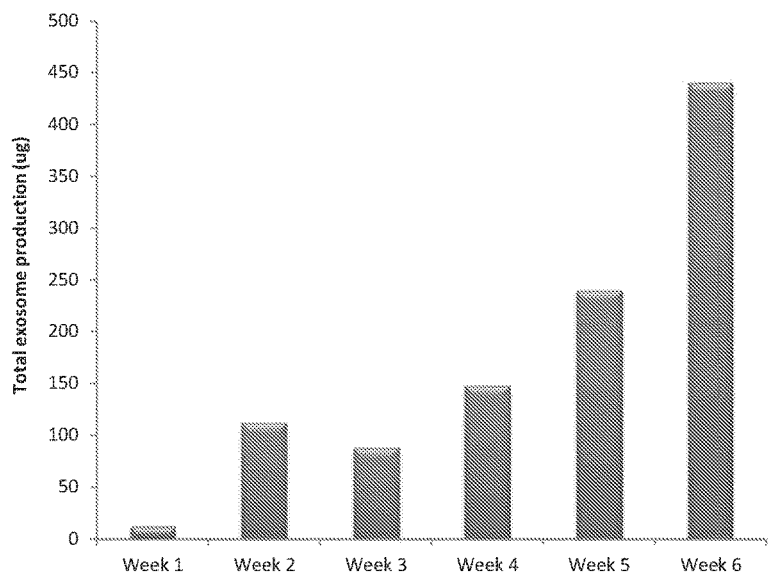
FIG. 10B shows the concentration of exosomes harvested from a single Integra CELLine flask during a 6 week continuous culture of CTX0E03 cells.

Using the Integra CELLine system, CTX0E03 cells were cultured over a 3-week period and medium was harvested at week 1, 2 and 3 for purification and quantification of exosomes, as described in Example 10. FIG. 10A shows that the production of microparticles increases exponentially over the 3-week culture period, enabling efficient and large-scale production of microparticles. The concentration of exosomes harvested from a single Integra CELLine flask was then monitored over 1-6 weeks of continuous CTX0E03 culture, with the results shown below and depicted in FIG. 10B:

| Integra time point | Total quantity of exosomes (ug) | Exosomes ug/ml |
|---|---|---|
| Week 1 | 12 | 0.80 |
| Week 2 | 112 | 7.47 |
| Week 3 | 88 | 5.87 |
| Week 4 | 148 | 9.87 |
| Week 5 | 240 | 16.00 |
| Week 6 | 440 | 29.33 |

These results show that exosome production is surprisingly enhanced when stem cells are cultured in a multi-compartment bioreactor for weeks, typically at least three weeks.

Example 15: Characterisation of Phenotype of Cells Obtained from the Integra Celline and the Standard (T175) Culture System CTX0E03 cells were cultured using the Integra CELLine bioreactor and standard culture, as described in Example 10. Expression of DCX and GFAP protein markers was confirmed using marker-specific antibodies and fluorescence microscopy.

Expression of DCX, GALC, GFAP, TUBB3, GDNF and IDO markers was detected by qRT-PCR in samples obtained from the cells. Marker expression was compared between microparticles obtained from standard (T175) culture and exosomes obtained from the 3 week cultured Integra CELLine system, assessed against a baseline of the expression level in CTX0E03 cells in standard (T175) culture.

The inventors observed a striking difference in marker expression of cells obtained from the Integra CELLine system as compared to control cells obtained from standard. Markers of partially-differentiated cells were increased several fold in cells cultured in the Integra CELLine system, compared to control cells obtained from standard cultures (FIG. 11). Particularly striking changes are increased expression of the markers DCX1 (doublecortin—a marker for entry into the neural lineage), GFAP (glial fibrillary acidic protein—a marker for entry into the astrocytic lineage), GDNF (glial cell-derived neurotrophic factor) and IDO (indoleamine 2,3-dioxygenase). This indicates that in neural stem cells cultured in a two-compartment bioreactor partially differentiate into cells of neural (DCX+) or astrocytic (GFAP+) lineage. The expression of DCX and GFAP in the Integra-cultured cells was confirmed by fluorescence microscopy, demonstrating that CTX0E03 cells cultured using the Integra CELLine bioreactor have a more differentiated neuronal phenotype than standard CTX0E03 cells.

Example 16: Characterisation of miRNA Expression Profiles of Exosomes Obtained from Integra CELLine Cultures and Microparticles Obtained from Standard (T175) Cultures CTX0E03 cells were cultured for three weeks using the Integra CELLine culture and in the standard culture in single-compartment T-175 flasks. Exosomes were purified from the Integra culture and microparticles were purified from the standard T-175 culture as described in Example 10. The relative expression levels of various miRNAs expressed in the exosomes and microparticles obtained from either the standard culture or the Integra CELLine system were determined with an miRNA array using qRT-PCR panel (Qiagen) according to manufacturer's instruction, and converted into fold up and down regulation levels as compared to a standard CTX0E03 cell line control group (see Table 4 and FIG. 12). These data show a differential miRNA expression profile between exosomes obtained from the Integra CELLine culture system for 3 weeks, microparticles, and cells obtained from the standard single-flask culture.

TABLE 4

Fold-regulation of miRNAs in microparticles obtained from standard culture or exosomes from the Integra CELLine system, relative to control (CTX0E03 cells).

| miRNA | Standard Culture (microparticles) Fold regulation relative to control (CTX0E03 cells) | Integra (exosomes) |
|---|---|---|
| hsa-miR-146b-5p | −1.0222 | 10.5805 |
| hsa-let-7c | −1.6954 | 4.7678 |
| hsa-miR-99a-5p | −3.5349 | 3.3714 |
| hsa-miR-132-3p | −1.9163 | 3.088 |
| hsa-miR-378-3p | 1.2731 | 3.0175 |
| hsa-miR-181a-5p | −1.7431 | 2.9147 |
| hsa-let-7b-5p | −1.4658 | 2.7574 |
| hsa-miR-100-5p | −3.208 | 1.977 |
| hsa-let-7e-5p | −2.7101 | 1.9274 |
| hsa-miR-23b-3p | −2.3322 | 1.8834 |
| hsa-miR-185-5p | −1.9119 | 1.8532 |
| hsa-let-7i-5p | −3.5677 | 1.8404 |
| hsa-let-7a-5p | −1.851 | 1.7736 |
| hsa-let-7d-5p | −1.5 | 1.7654 |
| hsa-let-7g-5p | −2.2527 | 1.7092 |
| hsa-miR-222-3p | −5.8092 | 1.6779 |
| hsa-let-7f-5p | −2.8712 | 1.5948 |
| hsa-miR-218-5p | −1.9611 | 1.5619 |
| hsa-miR-24-3p | −1.6721 | 1.5511 |
| hsa-miR-9-5p | −2.2475 | 1.4109 |
| hsa-miR-126-3p | −2.1263 | 1.203 |
| hsa-miR-134 | −1.6567 | 1.1783 |
| hsa-miR-128 | −3.5842 | 1.0743 |
| hsa-miR-155-5p | −8.8458 | 1.0425 |
| hsa-miR-22-3p | −3.4782 | −1.0023 |
| hsa-miR-26a-5p | −5.3579 | −1.0187 |
| hsa-miR-210 | −2.3107 | −1.0449 |
| hsa-miR-92a-3p | −1.9885 | −1.0693 |
| hsa-miR-93-5p | −3.056 | −1.1701 |
| hsa-miR-424-5p | −4.9189 | −1.2086 |
| hsa-miR-195-5p | −3.8951 | −1.2541 |
| hsa-miR-127-5p | −1.1316 | −1.2953 |
| hsa-miR-21-5p | −2.8845 | −1.3044 |
| hsa-miR-103a-3p | −2.6482 | −1.3287 |
| hsa-miR-16-5p | −3.5267 | −1.3692 |
| hsa-miR-125a-5p | −5.1159 | −1.434 |
| hsa-miR-10a-5p | −14.4701 | −1.434 |
| hsa-miR-10b-5p | −15.1194 | −1.4373 |
| hsa-miR-345-5p | −2.5521 | −1.4406 |
| hsa-miR-130a-3p | −2.6178 | −1.5728 |

TABLE 4-continued

Fold-regulation of miRNAs in microparticles obtained from standard culture or exosomes from the Integra CELLine system, relative to control (CTX0E03 cells).

| miRNA | Standard Culture (microparticles) Fold regulation relative to control (CTX0E03 cells) | Integra (exosomes) |
|---|---|---|
| hsa-miR-15b-5p | −4.4025 | −1.6058 |
| hsa-miR-20b | −2.1312 | −1.6096 |
| hsa-miR-20a-5p | −2.3107 | −1.8319 |
| hsa-miR-17-5p | −1.9296 | −1.8319 |
| hsa-miR-7-5p | −1.5105 | −2.042 |
| hsa-miR-106b-5p | −2.4708 | −2.1287 |
| hsa-miR-101-3p | 1.4794 | −2.4453 |
| hsa-miR-302a-3p | −18.0634 | −2.4623 |
| hsa-miR-301a-3p | 1.4931 | −2.5257 |
| hsa-miR-183-5p | −13.9772 | −2.5847 |
| hsa-miR-219-5p | 1.6994 | −2.7321 |
| hsa-miR-18a-5p | −1.4028 | −3.2792 |
| hsa-miR-15a-5p | −2.4766 | −3.3714 |
| hsa-miR-182-5p | −12.5099 | −4.9588 |
| hsa-miR-33a-5p | 2.7927 | −9.1472 |
| hsa-miR-96-5p | −7.0047 | −18.9396 |
| hsa-miR-18b-5p | −1.3519 | −49.18 |

Values were calculated from raw data using the following equations:

$$\Delta CT \text{ (sample/control)} = \text{Average } CT \text{ } (GOI) - \text{Average } CT \text{ } (HKG)$$

$$\text{Fold expression (sample/control)} = 2^{-(\text{Average } \Delta CT)}$$

$$\text{Fold change} = \frac{\text{Fold expression (sample)}}{\text{Fold expression (control)}}$$

If (fold change) > 1 then (fold regulation) = (fold change)

If (fold change) < 1 then (fold regulation) = $-\left(\dfrac{1}{\text{fold change}}\right)$ Wherein:
CT=cycle threshold
GOI=gene of interest (investigated miRNA)
HKG=housekeeping genes (reference miRNAs used to normalize the data)

Example 17: Total miRNA Analysis

Cells can shuttle RNA into microparticles determined for release into the extracellular space. This allows the conveyance of genetically encoded messages between cells. We here collectively refer to extracellular RNA as 'shuttle RNA'. We aimed to analyze comprehensively non coding RNA species released by CTX0E03 neural stem cells (NSCs) using Next Generation Sequencing.

Non coding RNAs are divided in two categories (small and long). Small non coding RNA biotypes include ribosomal RNA (rRNA), small nucleolar (snoRNA), small nuclear RNA (snRNA), microRNA (miRNA), miscellaneous other RNA (misc_RNA, e.g. RMRP, vault RNA, metazoa SRP, and RNY), and long non coding RNA biotypes includes long non-coding RNAs (lncRNAs) and large intergenic non-coding RNAs (lincRNAs).

Here, we characterized shuttle RNAs, including small and long non coding RNAs, released from NSC derived exosomes and microvesicles (MV) and compared with the RNA contents of the producer NSCs.

Figure 14:
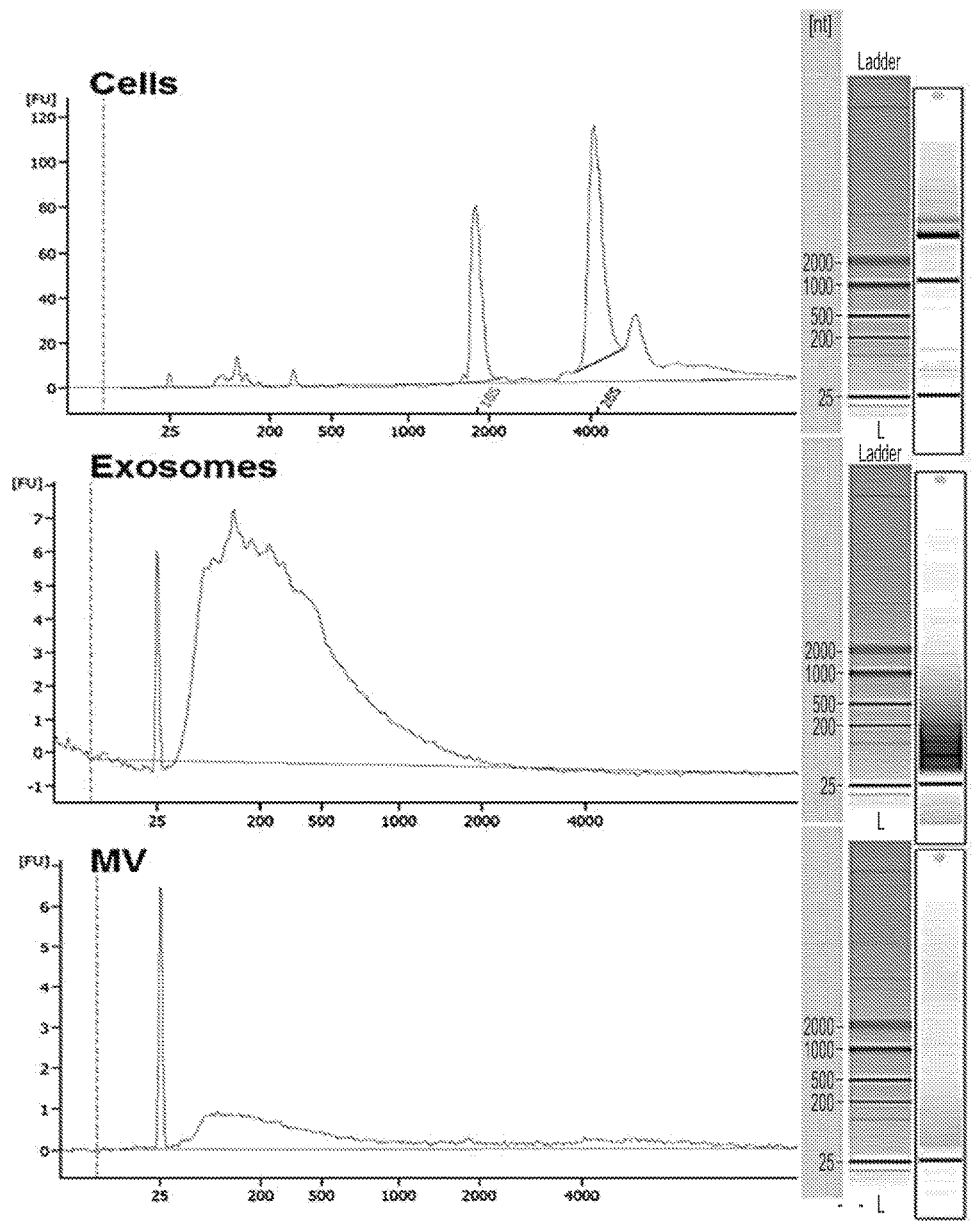
FIG. 14 is an electropherogram showing the total RNA content profile in 2-week CTX0E03 cells, exosomes and microvesicles as determined by Agilent RNA bioanalyser.

A) Total RNA Contents in Cells, Exosomes and Microvesicles Identified by Agilent RNA Bioanalyser The RNA in both exosomes and microvesicles mainly consists of small RNA species as shown in FIG. 14. The majority of the nucleotides (nt) was 200 as shown against the molecular ladder.

B) RNA Composition

Figure 15:
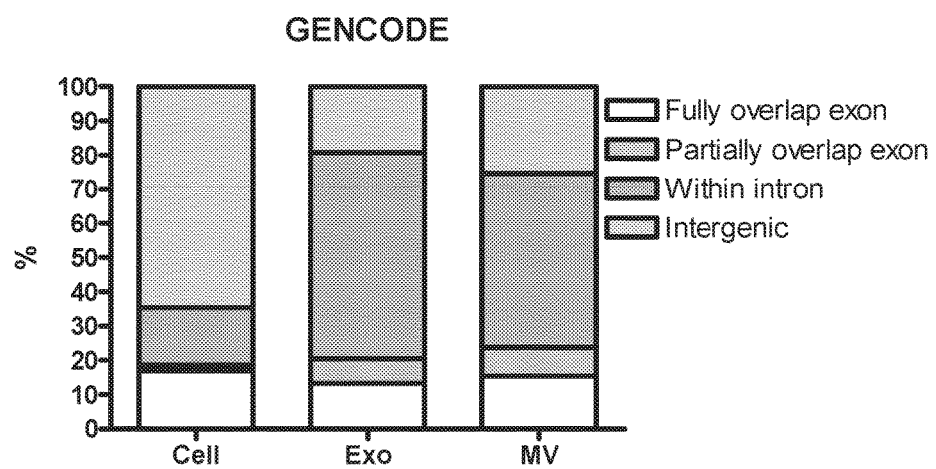
FIG. 15 is a schematic presentation of the percentage of coding genes fully overlapping exon, and non-coding transcripts located with intron or intergenic sequences (produced by running NGS BAM files against GENCODE sequence data set).

Small RNA sequencing libraries were generated to investigate the composition of shuttle and cellular RNA by deep sequencing (Next Generation Sequencing). The results are shown in FIG. 15.

C) Deep Sequencing of CTX0E03 Cell, Microvesicle and Exosome miRNA Expression from Standard (T175) Cultures.

Deep sequencing is based on the preparation of a cDNA library following by sequencing and provides information regarding the total sequence read out of different miRNAs in the microvesicles and exosomes. These deep sequence data complement the qRT-PCR array data shown above and provide a comprehensive analysis of the miRNA profile of the cells and microparticles. Unlike the qRT-PCR array analysis, deep sequencing is not restricted to identification of sequences present in the probe array and so the sequences to be identified do not need to be known in advance. Deep sequencing also provides direct read-out and the ability to sequence very short sequences. However, deep sequencing is not suitable for detection of transcripts with low expression.

Method

The presence of a variety of miRNAs in parental cells and their exosomes (30-100 μm) and microvesicles (100-1000 μm), purified by differential centrifugation, was identified by deep sequencing, following construction of 1 tagged miRNA library for each sample.

Additionally, specific primers for highly shuttled miRNAs (e.g. hsa-miR-1246) were designed and used in real-time reverse transcription PCR (qRT-PCR) to trace exosomes/microvesicles following in vivo implantation.

Deep sequencing was performed by GATC Biotech (Germany) and required the preparation of a tagged miRNA library for each samples followed by sequencing, and miRBase scanning:

Construction of tagged miRNA libraries (22 to 30 nt)
        Sequencing libraries were generated by ligation of specific RNA adapter to both 3' and 5' ends for each sample followed by reverse transcription, amplification, and purification of smallRNA libraries (size range of contained smallRNA fraction 22-30 nt).
    Sequencing on an Illumina HiSeq 2000 (single read)
        Sequencing was performed using Illumina HiSeq 2000 (single read). Analysis of one pool could include up to 45,000,000 single read, and each read length is up to 50 bases. Sequencing was quality controlled by using FastQ Files (sequences and quality scores).
    Identification of known miRNAs was performed as followed:
        RNA adapters were trimmed from resulting sequences and raw data cleaned. Raw data were clustered and for each cluster a number of reads was provided. MiRNAs were identified by miRBase scanning (Ssearch).

Results

Many microvesicle and exosome miRNAs were enriched relative to the cells, indicating that cells specially sort miRNAs for extracellular release. Furthermore, miRNA contents were similar in both exosomes and microvesicles, indicating a common apparatus of selective miRNA uptake in excreted microvesicles. Without wishing to be bound by theory, this may indicate that miRNA content in secreted microvesicles and exosomes can be used as a fingerprint to identify hNSC subtypes.

The deep sequencing analysis therefore identified a unique set of miRNAs in both hNSC exosomes and microvesicles not previously reported. MiRNA content in excreted vesicles is similar, but showed a preferential miRNA uptake compared with hNSC. These findings could support biological effects mediated by shuttle miRNA not previously described for hNSC.

The results are detailed in Tables 5 to 10, below. The data are also depicted in FIG. 13, which clearly shows the significantly different miRNA profiles present in the microvesicles and exosomes, compared to the cells. In summary, these data show a massive increase in the amount (read counts) of hsa-miR-1246, hsa-miR-4492, hsa-miR-4488 and hsa-miR-4532 in microvesicles and exosomes compared to the cells. Large increases are also seen in hsa-miR-4508, hsa-miR-4516, hsa-miR-3676-5p and hsa-miR-4485. Massive decreases are seen in the amounts (read counts) of certain miRNAs, including hsa-let-7a-5p, has-miR-92b-3p, has-miR-21-5p. hsa-miR-92a-3p, hsa-miR-10a-5p, hsa-100-5p and hsa-99b-5p.

The presence of each of hsa-miR-1246, hsa-miR-4488, hsa-miR-4492, hsa-miR-4508, hsa-miR-4516 and hsa-miR-4532 in the exosomes was validated by qRT-PCR (data not shown).

Plotting the deep sequencing results in the exosomes and microvesicles as relative fold change compared to the cells confirms that hsa-miR-1246, hsa-miR-4492, hsa-miR-4488 and hsa-miR-4532 are significantly upregulated in the exosomes and microvesicles compared to the cells. This comparison also shows that miRNA hsa-miR-3195 is the miRNA that is most upregulated, in both exosomes and microvesicles. Although the absolute reads of hsa-miR-3195 are in the range of ~40 for exosomes and microvesicles, there is no hsa-miR-3195 present in the cells.

As noted in Example 16 above, miRNA contents in exosomes, microparticles, and parental cells were also tested and validated using PCR array analysis. The following miRNAs were found present by qRT-PCR: hsa-let-7g-5p, hsa-miR-101-3p, hsa-miR-10a-5p, hsa-miR-10b-5p, hsa-miR-125b-5p, hsa-miR-128, hsa-miR-130a-3p, hsa-miR-134, hsa-miR-137, hsa-miR-146b-5p, hsa-miR-15a-5p, hsa-miR-15b-5p, hsa-miR-16-5p, hsa-miR-17-5p, hsa-miR-181a-5p, hsa-miR-182-5p, hsa-miR-185-5p, hsa-miR-18b-5p, hsa-miR-192-5p, hsa-miR-194-5p, hsa-miR-195-5p, hsa-miR-20a-5p, hsa-miR-20b-5p, hsa-miR-210, hsa-miR-21-5p, hsa-miR-218-5p, hsa-miR-219-5p, hsa-miR-222-3p, hsa-miR-22-3p, hsa-miR-23b-3p, hsa-miR-24-3p, hsa-miR-26a-5p, hsa-miR-301a-3p, hsa-miR-302a-3p, hsa-miR-302c-3p, hsa-miR-345-5p, hsa-miR-378a-3p, hsa-miR-7-5p, hsa-miR-92a-3p, hsa-miR-93-5p, hsa-miR-9-5p, hsa-miR-96-5p, and hsa-miR-99a-5p.

TABLE 5

Cells EH

| Cells: CTX0E03 07EH MIRNA | MIRNA.SEQUENCE | SEQ ID NO: | MIRNA LENGTH | READ COUNTS |
| --- | --- | --- | --- | --- |
| hsa-let-7a-5p | UGAGGUAGUAGGUUGUAUAGUU | 1 | 22 | 75110 |
| hsa-miR-10a-5p | UACCCUGUAGAUCCGAAUUUGUG | 2 | 23 | 52927 |
| hsa-miR-100-5p | AACCCGUAGAUCCGAACUUGUG | 3 | 22 | 52451 |
| hsa-miR-99b-5p | CACCCGUAGAACCGACCUUGCG | 4 | 22 | 39457 |
| hsa-miR-486-5p | UCCUGUACUGAGCUGCCCCGAG | 5 | 22 | 20310 |
| hsa-miR-27b-3p | UUCACAGUGGCUAAGUUCUGC | 6 | 21 | 16900 |
| hsa-miR-92a-3p | UAUUGCACUUGUCCCGGCCUGU | 7 | 22 | 14359 |
| hsa-miR-191-5p | CAACGGAAUCCCAAAAGCAGCUG | 8 | 23 | 12591 |
| hsa-miR-21-5p | UAGCUUAUCAGACUGAUGUUGA | 9 | 22 | 11943 |
| hsa-miR-98 | UGAGGUAGUAAGUUGUAUUGUU | 10 | 22 | 11760 |
| hsa-let-7f-5p | UGAGGUAGUAGAUUGUAUAGUU | 11 | 22 | 10349 |
| hsa-miR-26a-5p | UUCAAGUAAUCCAGGAUAGGCU | 12 | 22 | 9900 |
| hsa-miR-92b-3p | UAUUGCACUCGUCCCGGCCUCC | 13 | 22 | 9794 |
| hsa-miR-127-3p | UCGGAUCCGUCUGAGCUUGGCU | 14 | 22 | 7064 |
| hsa-miR-181a-5p | AACAUUCAACGCUGUCGGUGAGU | 15 | 23 | 6956 |
| hsa-miR-182-5p | UUUGGCAAUGGUAGAACUCACACU | 16 | 24 | 5531 |
| hsa-let-7c | UGAGGUAGUAGGUUGUAUGGUU | 17 | 22 | 5103 |
| hsa-miR-379-5p | UGGUAGACUAUGGAACGUAGG | 18 | 21 | 4746 |
| hsa-miR-146b-5p | UGAGAACUGAAUUCCAUAGGCU | 19 | 22 | 4552 |
| hsa-miR-21-3p | CAACACCAGUCGAUGGGCUGU | 20 | 21 | 4089 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-1246 | AAUGGAUUUUUGGAGCAGG | 21 | 19 | 3973 |
| hsa-let-7i-5p | UGAGGUAGUAGUUUGUGCUGUU | 22 | 22 | 3015 |
| hsa-miR-4532 | CCCCGGGGAGCCCGGCG | 23 | 17 | 2847 |
| hsa-miR-183-5p | UAUGGCACUGGUAGAAUUCACU | 24 | 22 | 2695 |
| hsa-miR-151a-3p | CUAGACUGAAGCUCCUUGAGG | 25 | 21 | 2681 |
| hsa-miR-501-3p | AAUGCACCCGGGCAAGGAUUCU | 26 | 22 | 2649 |
| hsa-let-7e-5p | UGAGGUAGGAGGUUGUAUAGUU | 27 | 22 | 2449 |
| hsa-let-7b-5p | UGAGGUAGUAGGUUGUGUGGUU | 28 | 22 | 2435 |
| hsa-miR-16-5p | UAGCAGCACGUAAAUAUUGGCG | 29 | 22 | 2173 |
| hsa-miR-30a-5p | UGUAAACAUCCUCGACUGGAAG | 30 | 22 | 2001 |
| hsa-miR-30d-5p | UGUAAACAUCCCCGACUGGAAG | 31 | 22 | 1977 |
| hsa-miR-409-5p | AGGUUACCCGAGCAACUUUGCAU | 32 | 23 | 1871 |
| hsa-miR-22-3p | AAGCUGCCAGUUGAAGAACUGU | 33 | 22 | 1826 |
| hsa-miR-4492 | GGGGCUGGGCGCGCGCC | 34 | 17 | 1754 |
| hsa-miR-125a-5p | UCCCUGAGACCCUUUAACCUGUGA | 35 | 24 | 1451 |
| hsa-miR-222-3p | AGCUACAUCUGGCUACUGGGU | 36 | 21 | 1422 |
| hsa-miR-151a-5p | UCGAGGAGCUCACAGUCUAGU | 37 | 21 | 1386 |
| hsa-miR-181b-5p | AACAUUCAUUGCUGUCGGUGGGU | 38 | 23 | 1382 |
| hsa-miR-221-5p | ACCUGGCAUACAAUGUAGAUUU | 39 | 22 | 1363 |
| hsa-miR-186-5p | CAAAGAAUUCUCCUUUUGGGCU | 40 | 22 | 1225 |
| hsa-miR-423-5p | UGAGGGGCAGAGAGCGAGACUUU | 41 | 23 | 1080 |
| hsa-miR-125b-5p | UCCCUGAGACCCUAACUUGUGA | 42 | 22 | 1002 |
| hsa-let-7g-5p | UGAGGUAGUAGUUUGUACAGUU | 43 | 22 | 959 |
| hsa-miR-500a-3p | AUGCACCUGGGCAAGGAUUCUG | 44 | 22 | 923 |
| hsa-miR-30e-5p | UGUAAACAUCCUUGACUGGAAG | 45 | 22 | 911 |
| hsa-miR-27a-3p | UUCACAGUGGCUAAGUUCCGC | 46 | 21 | 867 |
| hsa-miR-409-3p | GAAUGUUGCUCGGUGAACCCCU | 47 | 22 | 865 |
| hsa-miR-148b-3p | UCAGUGCAUCACAGAACUUUGU | 48 | 22 | 856 |
| hsa-miR-125b-1-3p | ACGGGUUAGGCUCUUGGGAGCU | 49 | 22 | 851 |
| hsa-miR-410 | AAUAUAACACAGAUGGCCUGU | 50 | 21 | 848 |
| hsa-miR-381 | UAUACAAGGGCAAGCUCUCUGU | 51 | 22 | 842 |
| hsa-miR-99a-5p | AACCCGUAGAUCCGAUCUUGUG | 52 | 22 | 773 |
| hsa-let-7d-5p | AGAGGUAGUAGGUUGCAUAGUU | 53 | 22 | 765 |
| hsa-miR-148a-3p | UCAGUGCACUACAGAACUUUGU | 54 | 22 | 702 |
| hsa-miR-23a-3p | AUCACAUUGCCAGGGAUUUCC | 55 | 21 | 654 |
| hsa-miR-28-3p | CACUAGAUUGUGAGCUCCUGGA | 56 | 22 | 593 |
| hsa-miR-423-3p | AGCUCGGUCUGAGGCCCCUCAGU | 57 | 23 | 557 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-9-5p | UCUUUGGUUAUCUAGCUGUAUGA | 58 | 23 | 518 |
| hsa-miR-23b-3p | AUCACAUUGCCAGGGAUUACC | 59 | 21 | 508 |
| hsa-miR-941 | CACCCGGCUGUGUGCACAUGUGC | 60 | 23 | 492 |
| hsa-miR-4488 | AGGGGGCGGGCUCCGGCG | 61 | 18 | 485 |
| hsa-miR-103a-3p | AGCAGCAUUGUACAGGGCUAUGA | 62 | 23 | 459 |
| hsa-miR-25-3p | CAUUGCACUUGUCUCGGUCUGA | 63 | 22 | 436 |
| hsa-miR-889 | UUAAUAUCGGACAACCAUUGU | 64 | 21 | 411 |
| hsa-miR-378a-3p | ACUGGACUUGGAGUCAGAAGG | 65 | 21 | 410 |
| hsa-miR-30c-5p | UGUAAACAUCCUACACUCUCAGC | 66 | 23 | 378 |
| hsa-miR-4485 | UAACGGCCGCGGUACCCUAA | 67 | 20 | 358 |
| hsa-miR-125b-2-3p | UCACAAGUCAGGCUCUUGGGAC | 68 | 22 | 352 |
| hsa-miR-671-3p | UCCGGUUCUCAGGGCUCCACC | 69 | 21 | 350 |
| hsa-miR-361-5p | UUAUCAGAAUCUCCAGGGGUAC | 70 | 22 | 337 |
| hsa-miR-30e-3p | CUUUCAGUCGGAUGUUUACAGC | 71 | 22 | 294 |
| hsa-miR-1271-5p | CUUGGCACCUAGCAAGCACUCA | 72 | 22 | 288 |
| hsa-miR-589-5p | UGAGAACCACGUCUGCUCUGAG | 73 | 22 | 282 |
| hsa-miR-374a-5p | UUAUAAUACAACCUGAUAAGUG | 74 | 22 | 275 |
| hsa-miR-769-5p | UGAGACCUCUGGGUUCUGAGCU | 75 | 22 | 263 |
| hsa-miR-345-5p | GCUGACUCCUAGUCCAGGGCUC | 76 | 22 | 249 |
| hsa-miR-30a-3p | CUUUCAGUCGGAUGUUUGCAGC | 77 | 22 | 236 |
| hsa-miR-15b-5p | UAGCAGCACAUCAUGGUUUACA | 78 | 22 | 229 |
| hsa-miR-221-3p | AGCUACAUUGUCUGCUGGGUUUC | 79 | 23 | 225 |
| hsa-miR-31-5p | AGGCAAGAUGCUGGCAUAGCU | 80 | 21 | 213 |
| hsa-miR-342-3p | UCUCACACAGAAAUCGCACCCGU | 81 | 23 | 205 |
| hsa-miR-136-3p | CAUCAUCGUCUCAAAUGAGUCU | 82 | 22 | 203 |
| hsa-miR-493-3p | UGAAGGUCUACUGUGUGCCAGG | 83 | 22 | 192 |
| hsa-miR-720 | UCUCGCUGGGGCCUCCA | 84 | 17 | 154 |
| hsa-miR-7-5p | UGGAAGACUAGUGAUUUUGUUGU | 85 | 23 | 154 |
| hsa-miR-130b-3p | CAGUGCAAUGAUGAAAGGGCAU | 86 | 22 | 150 |
| hsa-miR-192-5p | CUGACCUAUGAAUUGACAGCC | 87 | 21 | 138 |
| hsa-miR-493-5p | UUGUACAUGGUAGGCUUUCAUU | 88 | 22 | 115 |
| hsa-miR-204-5p | UUCCCUUUGUCAUCCUAUGCCU | 89 | 22 | 113 |
| hsa-miR-26b-5p | UUCAAGUAAUUCAGGAUAGGU | 90 | 21 | 107 |
| hsa-miR-1307-5p | UCGACCGGACCUCGACCGGCU | 91 | 21 | 105 |
| hsa-let-7d-3p | CUAUACGACCUGCUGCCUUUCU | 92 | 22 | 103 |
| hsa-miR-340-5p | UUAUAAAGCAAUGAGACUGAUU | 93 | 22 | 100 |
| hsa-miR-134 | UGUGACUGGUUGACCAGAGGGG | 94 | 22 | 99 |
| hsa-miR-432-5p | UCUUGGAGUAGGUCAUUGGGUGG | 95 | 23 | 97 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-30b-5p | UGUAAACAUCCUACACUCAGCU | 96 | 22 | 96 |
| hsa-miR-320a | AAAAGCUGGGUUGAGAGGGCGA | 97 | 22 | 95 |
| hsa-miR-100-3p | CAAGCUUGUAUCUAUAGGUAUG | 98 | 22 | 94 |
| hsa-miR-744-5p | UGCGGGGCUAGGGCUAACAGCA | 99 | 22 | 89 |
| hsa-miR-181a-3p | ACCAUCGACCGUUGAUUGUACC | 100 | 22 | 86 |
| hsa-miR-34a-5p | UGGCAGUGUCUUAGCUGGUUGU | 101 | 22 | 85 |
| hsa-miR-181a-2-3p | ACCACUGACCGUUGACUGUACC | 102 | 22 | 81 |
| hsa-miR-190a | UGAUAUGUUUGAUAUAUUAGGU | 103 | 22 | 79 |
| hsa-miR-132-3p | UAACAGUCUACAGCCAUGGUCG | 104 | 22 | 78 |
| hsa-miR-181c-5p | AACAUUCAACCUGUCGGUGAGU | 105 | 22 | 76 |
| hsa-miR-29a-3p | UAGCACCAUCUGAAAUCGGUUA | 106 | 22 | 75 |
| hsa-miR-301a-3p | CAGUGCAAUAGUAUUGUCAAAGC | 107 | 23 | 75 |
| hsa-miR-411-5p | UAGUAGACCGUAUAGCGUACG | 108 | 21 | 75 |
| hsa-miR-128 | UCACAGUGAACCGGUCUCUUU | 109 | 21 | 74 |
| hsa-miR-4516 | GGGAGAAGGGUCGGGGC | 110 | 17 | 74 |
| hsa-miR-425-5p | AAUGACACGAUCACUCCCGUUGA | 111 | 23 | 72 |
| hsa-miR-130b-5p | ACUCUUUCCCUGUUGCACUAC | 112 | 21 | 71 |
| hsa-miR-130a-3p | CAGUGCAAUGUUAAAAGGGCAU | 113 | 22 | 67 |
| hsa-miR-30d-3p | CUUUCAGUCAGAUGUUUGCUGC | 114 | 22 | 65 |
| hsa-miR-654-5p | UGGUGGGCCGCAGAACAUGUGC | 115 | 22 | 65 |
| hsa-miR-93-5p | CAAAGUGCUGUUCGUGCAGGUAG | 116 | 23 | 65 |
| hsa-miR-487b | AAUCGUACAGGGUCAUCCACUU | 117 | 22 | 63 |
| hsa-miR-484 | UCAGGCUCAGUCCCCUCCCGAU | 118 | 22 | 62 |
| hsa-miR-24-3p | UGGCUCAGUUCAGCAGGAACAG | 119 | 22 | 61 |
| hsa-miR-4677-3p | UCUGUGAGACCAAAGAACUACU | 120 | 22 | 61 |
| hsa-miR-149-5p | UCUGGCUCCGUGUCUUCACUCCC | 121 | 23 | 56 |
| hsa-miR-197-3p | UUCACCACCUUCUCCACCCAGC | 122 | 22 | 56 |
| hsa-miR-96-5p | UUUGGCACUAGCACAUUUUGCU | 123 | 23 | 56 |
| hsa-miR-1307-3p | ACUCGGCGUGGCGUCGGUCGUG | 124 | 22 | 55 |
| hsa-miR-34c-5p | AGGCAGUGUAGUUAGCUGAUUGC | 125 | 23 | 53 |
| hsa-miR-370 | GCCUGCUGGGGUGGAACCUGGU | 126 | 22 | 52 |
| hsa-miR-148b-5p | AAGUUCUGUUAUACACUCAGGC | 127 | 22 | 51 |
| hsa-miR-335-5p | UCAAGAGCAAUAACGAAAAAUGU | 128 | 23 | 51 |
| hsa-miR-4461 | GAUUGAGACUAGUAGGGCUAGGC | 129 | 23 | 50 |
| hsa-miR-27a-5p | AGGGCUUAGCUGCUUGUGAGCA | 130 | 22 | 49 |
| hsa-miR-363-3p | AAUUGCACGGUAUCCAUCUGUA | 131 | 22 | 47 |
| hsa-miR-431-5p | UGUCUUGCAGGCCGUCAUGCA | 132 | 21 | 47 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-877-5p | GUAGAGGAGAUGGCGCAGGG | 133 | 20 | 46 |
| hsa-miR-550a-5p | AGUGCCUGAGGGAGUAAGAGCCC | 134 | 23 | 45 |
| hsa-miR-4508 | GCGGGGCUGGGCGCGCG | 135 | 17 | 44 |
| hsa-miR-541-3p | UGGUGGGCACAGAAUCUGGACU | 136 | 22 | 42 |
| hsa-miR-135b-5p | UAUGGCUUUUCAUUCCUAUGUGA | 137 | 23 | 40 |
| hsa-miR-140-3p | UACCACAGGGUAGAACCACGG | 138 | 21 | 39 |
| hsa-miR-362-5p | AAUCCUUGGAACCUAGGUGUGAGU | 139 | 24 | 37 |
| hsa-miR-455-3p | GCAGUCCAUGGGCAUAUACAC | 140 | 21 | 37 |
| hsa-miR-758 | UUUGUGACCUGGUCCACUAACC | 141 | 22 | 37 |
| hsa-miR-101-3p | UACAGUACUGUGAUAACUGAA | 142 | 21 | 36 |
| hsa-miR-374b-5p | AUAUAAUACAACCUGCUAAGUG | 143 | 22 | 36 |
| hsa-miR-148a-5p | AAAGUUCUGAGACACUCCGACU | 144 | 22 | 35 |
| hsa-miR-17-5p | CAAAGUGCUUACAGUGCAGGUAG | 145 | 23 | 35 |
| hsa-miR-20a-5p | UAAAGUGCUUAUAGUGCAGGUAG | 146 | 23 | 35 |
| hsa-miR-874 | CUGCCCUGGCCCGAGGGACCGA | 147 | 22 | 35 |
| hsa-miR-193b-3p | AACUGGCCCUCAAAGUCCCGCU | 148 | 22 | 34 |
| hsa-miR-548ah-3p | CAAAAACUGCAGUUACUUUUGC | 149 | 22 | 34 |
| hsa-miR-539-3p | AUCAUACAAGGACAAUUUCUUU | 150 | 22 | 33 |
| hsa-miR-421 | AUCAACAGACAUUAAUUGGGCGC | 151 | 23 | 31 |
| hsa-miR-28-5p | AAGGAGCUCACAGUCUAUUGAG | 152 | 22 | 30 |
| hsa-miR-485-3p | GUCAUACACGGCUCUCCUCUCU | 153 | 22 | 29 |
| hsa-miR-2467-5p | UGAGGCUCUGUUAGCCUUGGCUC | 154 | 23 | 26 |
| hsa-miR-4449 | CGUCCCGGGGCUGCGCGAGGCA | 155 | 22 | 26 |
| hsa-miR-24-2-5p | UGCCUACUGAGCUGAAACACAG | 156 | 22 | 25 |
| hsa-miR-181d | AACAUUCAUUGUUGUCGGUGGGU | 157 | 23 | 24 |
| hsa-miR-323a-3p | CACAUUACACGGUCGACCUCU | 158 | 21 | 24 |
| hsa-miR-106b-3p | CCGCACUGUGGGUACUUGCUGC | 159 | 22 | 23 |
| hsa-miR-125a-3p | ACAGGUGAGGUUCUUGGGAGCC | 160 | 22 | 23 |
| hsa-miR-330-5p | UCUCUGGGCCUGUGUCUUAGGC | 161 | 22 | 23 |
| hsa-miR-1275 | GUGGGGGAGAGGCUGUC | 162 | 17 | 22 |
| hsa-miR-19b-3p | UGUGCAAAUCCAUGCAAAACUGA | 163 | 23 | 22 |
| hsa-miR-301b | CAGUGCAAUGAUAUUGUCAAAGC | 164 | 23 | 21 |
| hsa-miR-485-5p | AGAGGCUGGCCGUGAUGAAUUC | 165 | 22 | 21 |
| hsa-miR-29b-3p | UAGCACCAUUUGAAAUCAGUGUU | 166 | 23 | 20 |
| hsa-miR-3158-3p | AAGGGCUUCCUCUCUGCAGGAC | 167 | 22 | 20 |
| hsa-miR-431-3p | CAGGUCGUCUUGCAGGGCUUCU | 168 | 22 | 20 |
| hsa-miR-454-3p | UAGUGCAAUAUUGCUUAUAGGGU | 169 | 23 | 20 |
| hsa-miR-106b-5p | UAAAGUGCUGACAGUGCAGAU | 170 | 21 | 19 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-1973 | ACCGUGCAAAGGUAGCAUA | 171 | 19 | 19 |
| hsa-miR-31-3p | UGCUAUGCCAACAUAUUGCCAU | 172 | 22 | 19 |
| hsa-miR-374a-3p | CUUAUCAGAUUGUAUUGUAAUU | 173 | 22 | 19 |
| hsa-miR-433 | AUCAUGAUGGGCUCCUCGGUGU | 174 | 22 | 19 |
| hsa-miR-4417 | GGUGGGCUUCCCGGAGGG | 175 | 18 | 19 |
| hsa-miR-143-3p | UGAGAUGAAGCACUGUAGCUC | 176 | 21 | 18 |
| hsa-miR-19a-3p | UGUGCAAAUCUAUGCAAAACUGA | 177 | 23 | 18 |
| hsa-miR-532-5p | CAUGCCUUGAGUGUAGGACCGU | 178 | 22 | 18 |
| hsa-miR-561-5p | AUCAAGGAUCUUAAACUUUGCC | 179 | 22 | 18 |
| hsa-miR-663b | GGUGGCCCGGCCGUGCCUGAGG | 180 | 22 | 18 |
| hsa-miR-1301 | UUGCAGCUGCCUGGGAGUGACUUC | 181 | 24 | 17 |
| hsa-miR-299-3p | UAUGUGGGAUGGUAAACCGCUU | 182 | 22 | 17 |
| hsa-miR-9-3p | AUAAAGCUAGAUAACCGAAAGU | 183 | 22 | 17 |
| hsa-miR-17-3p | ACUGCAGUGAAGGCACUUGUAG | 184 | 22 | 15 |
| hsa-miR-376c | AACAUAGAGGAAAUUCCACGU | 185 | 21 | 15 |
| hsa-miR-424-5p | CAGCAGCAAUUCAUGUUUUGAA | 186 | 22 | 15 |
| hsa-miR-660-5p | UACCCAUUGCAUAUCGGAGUUG | 187 | 22 | 15 |
| hsa-miR-153 | UUGCAUAGUCACAAAAGUGAUC | 188 | 22 | 14 |
| hsa-miR-3605-5p | UGAGGAUGGAUAGCAAGGAAGCC | 189 | 23 | 14 |
| hsa-miR-3687 | CCCGGACAGGCGUUCGUGCGACGU | 190 | 24 | 14 |
| hsa-miR-4284 | GGGCUCACAUCACCCCAU | 191 | 18 | 14 |
| hsa-miR-455-5p | UAUGUGCCUUUGGACUACAUCG | 192 | 22 | 14 |
| hsa-miR-543 | AAACAUUCGCGGUGCACUUCUU | 193 | 22 | 14 |
| hsa-miR-1276 | UAAAGAGCCCUGUGGAGACA | 194 | 20 | 13 |
| hsa-miR-330-3p | GCAAAGCACACGGCCUGCAGAGA | 195 | 23 | 13 |
| hsa-miR-369-3p | AAUAAUACAUGGUUGAUCUUU | 196 | 21 | 13 |
| hsa-miR-4786-5p | UGAGACCAGGACUGGAUGCACC | 197 | 22 | 13 |
| hsa-miR-548k | AAAAGUACUUGCGGAUUUUGCU | 198 | 22 | 13 |
| hsa-miR-1226-3p | UCACCAGCCCUGUGUUCCCUAG | 199 | 22 | 12 |
| hsa-miR-188-3p | CUCCCACAUGCAGGGUUUGCA | 200 | 21 | 12 |
| hsa-miR-27b-5p | AGAGCUUAGCUGAUUGGUGAAC | 201 | 22 | 12 |
| hsa-miR-377-5p | AGAGGUUGCCCUUGGUGAAUUC | 202 | 22 | 12 |
| hsa-miR-487a | AAUCAUACAGGGACAUCCAGUU | 203 | 22 | 12 |
| hsa-miR-92a-1-5p | AGGUUGGGAUCGGUUGCAAUGCU | 204 | 23 | 12 |
| hsa-miR-135b-3p | AUGUAGGGCUAAAAGCCAUGGG | 205 | 22 | 11 |
| hsa-miR-218-5p | UUGUGCUUGAUCUAACCAUGU | 206 | 21 | 11 |
| hsa-miR-3943 | UAGCCCCCAGGCUUCACUUGGCG | 207 | 23 | 11 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-92b-5p | AGGGACGGGACGCGGUGCAGUG | 208 | 22 | 11 |
| hsa-miR-1185-1-3p | AUAUACAGGGGAGACUCUUAU | 209 | 22 | 10 |
| hsa-miR-1273g-3p | ACCACUGCACUCCAGCCUGAG | 210 | 21 | 10 |
| hsa-miR-2355-5p | AUCCCCAGAUACAAUGGACAA | 211 | 21 | 10 |
| hsa-miR-23a-5p | GGGGUUCCUGGGGAUGGGAUUU | 212 | 22 | 10 |
| hsa-miR-30c-1-3p | CUGGGAGAGGGUUGUUUACUCC | 213 | 22 | 10 |
| hsa-miR-329 | AACACACCUGGUUAACCUCUUU | 214 | 22 | 10 |
| hsa-miR-337-3p | CUCCUAUAUGAUGCCUUUCUUC | 215 | 22 | 10 |
| hsa-miR-3609 | CAAAGUGAUGAGUAAUACUGGCUG | 216 | 24 | 10 |
| hsa-miR-378a-5p | CUCCUGACUCCAGGUCCUGUGU | 217 | 22 | 10 |
| hsa-miR-3929 | GAGGCUGAUGUGAGUAGACCACU | 218 | 23 | 10 |
| hsa-miR-4745-5p | UGAGUGGGGCUCCCGGGACGGCG | 219 | 23 | 10 |
| hsa-miR-5096 | GUUUCACCAUGUUGGUCAGGC | 220 | 21 | 10 |
| hsa-miR-656 | AAUAUUAUACAGUCAACCUCU | 221 | 21 | 10 |
| hsa-let-7a-3p | CUAUACAAUCUACUGUCUUUC | 222 | 21 | 9 |
| hsa-miR-15a-5p | UAGCAGCACAUAAUGGUUUGUG | 223 | 22 | 9 |
| hsa-miR-185-5p | UGGAGAGAAAGGCAGUUCCUGA | 224 | 22 | 9 |
| hsa-miR-25-5p | AGGCGGAGACUUGGGCAAUUG | 225 | 21 | 9 |
| hsa-miR-3065-5p | UCAACAAAAUCACUGAUGCUGGA | 226 | 23 | 9 |
| hsa-miR-3176 | ACUGGCCUGGGACUACCGG | 227 | 19 | 9 |
| hsa-miR-339-3p | UGAGCGCCUCGACGACAGAGCCG | 228 | 23 | 9 |
| hsa-miR-374b-3p | CUUAGCAGGUUGUAUUAUCAUU | 229 | 22 | 9 |
| hsa-miR-4435 | AUGGCCAGAGCUCACACAGAGG | 230 | 22 | 9 |
| hsa-miR-4448 | GGCUCCUUGGUCUAGGGGUA | 231 | 20 | 9 |
| hsa-miR-4497 | CUCCGGGACGGCUGGGC | 232 | 17 | 9 |
| hsa-miR-4521 | GCUAAGGAAGUCCUGUGCUCAG | 233 | 22 | 9 |
| hsa-miR-539-5p | GGAGAAAUUAUCCUUGGUGUGU | 234 | 22 | 9 |
| hsa-miR-548ah-5p | AAAAGUGAUUGCAGUGUUUG | 235 | 20 | 9 |
| hsa-miR-1910 | CCAGUCCUGUGCCUGCCGCCU | 236 | 21 | 8 |
| hsa-miR-376a-3p | AUCAUAGAGGAAAAUCCACGU | 237 | 21 | 8 |
| hsa-miR-382-5p | GAAGUUGUUCGUGGUGGAUUCG | 238 | 22 | 8 |
| hsa-miR-3940-3p | CAGCCCGGAUCCCAGCCCACUU | 239 | 22 | 8 |
| hsa-miR-494 | UGAAACAUACACGGGAAACCUC | 240 | 22 | 8 |
| hsa-miR-495 | AAACAAACAUGGUGCACUUCUU | 241 | 22 | 8 |
| hsa-miR-545-3p | UCAGCAAACAUUUAUUGUGUGC | 242 | 22 | 8 |
| hsa-miR-99b-3p | CAAGCUCGUGUCUGUGGGUCCG | 243 | 22 | 8 |
| hsa-miR-1197 | UAGGACACAUGGUCUACUUCU | 244 | 21 | 7 |
| hsa-miR-181b-3p | CUCACUGAACAAUGAAUGCAA | 245 | 21 | 7 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-212-5p | ACCUUGGCUCUAGACUGCUUACU | 246 | 23 | 7 |
| hsa-miR-3200-3p | CACCUUGCGCUACUCAGGUCUG | 247 | 22 | 7 |
| hsa-miR-340-3p | UCCGUCUCAGUUACUUUAUAGC | 248 | 22 | 7 |
| hsa-miR-3607-5p | GCAUGUGAUGAAGCAAAUCAGU | 249 | 22 | 7 |
| hsa-miR-361-3p | UCCCCCAGGUGUGAUUCUGAUUU | 250 | 23 | 7 |
| hsa-miR-3656 | GGCGGGUGCGGGGUGG | 251 | 17 | 7 |
| hsa-miR-532-3p | CCUCCCACACCCAAGGCUUGCA | 252 | 22 | 7 |
| hsa-miR-574-3p | CACGCUCAUGCACACACCCACA | 253 | 22 | 7 |
| hsa-miR-107 | AGCAGCAUUGUACAGGGCUAUCA | 254 | 23 | 6 |
| hsa-miR-127-5p | CUGAAGCUCAGAGGGCUCUGAU | 255 | 22 | 6 |
| hsa-miR-18a-5p | UAAGGUGCAUCUAGUGCAGAUAG | 256 | 23 | 6 |
| hsa-miR-26a-2-3p | CCUAUUCUUGAUUACUUGUUUC | 257 | 22 | 6 |
| hsa-miR-296-5p | AGGGCCCCCCCUCAAUCCUGU | 258 | 21 | 6 |
| hsa-miR-3648 | AGCCGCGGGGAUCGCCGAGGG | 259 | 21 | 6 |
| hsa-miR-382-3p | AAUCAUUCACGGACAACACUU | 260 | 21 | 6 |
| hsa-miR-3939 | UACGCGCAGACCACAGGAUGUC | 261 | 22 | 6 |
| hsa-miR-432-3p | CUGGAUGGCUCCUCCAUGUCU | 262 | 21 | 6 |
| hsa-miR-4423-5p | AGUUGCCUUUUUGUUCCCAUGC | 263 | 22 | 6 |
| hsa-miR-4466 | GGGUGCGGGCCGGCGGGG | 264 | 18 | 6 |
| hsa-miR-454-5p | ACCCUAUCAAUAUUGUCUCUGC | 265 | 22 | 6 |
| hsa-miR-4746-5p | CCGGUCCCAGGAGAACCUGCAGA | 266 | 23 | 6 |
| hsa-miR-496 | UGAGUAUUACAUGGCCAAUCUC | 267 | 22 | 6 |
| hsa-miR-548o-3p | CCAAAACUGCAGUUACUUUUGC | 268 | 22 | 6 |
| hsa-miR-1248 | ACCUUCUUGUAUAAGCACUGUGCUAAA | 269 | 27 | 5 |
| hsa-miR-1254 | AGCCUGGAAGCUGGAGCCUGCAGU | 270 | 24 | 5 |
| hsa-miR-1296 | UUAGGGCCCUGGCUCCAUCUCC | 271 | 22 | 5 |
| hsa-miR-136-5p | ACUCCAUUUGUUUUGAUGAUGGA | 272 | 23 | 5 |
| hsa-miR-199a-5p | CCCAGUGUUCAGACUACCUGUUC | 273 | 23 | 5 |
| hsa-miR-296-3p | GAGGGUUGGGUGGAGGCUCUCC | 274 | 22 | 5 |
| hsa-miR-3177-3p | UGCACGGCACUGGGGACACGU | 275 | 21 | 5 |
| hsa-miR-324-3p | ACUGCCCCAGGUGCUGCUGG | 276 | 20 | 5 |
| hsa-miR-337-5p | GAACGGCUUCAUACAGGAGUU | 277 | 21 | 5 |
| hsa-miR-342-5p | AGGGGUGCUAUCUGUGAUUGA | 278 | 21 | 5 |
| hsa-miR-365b-3p | UAAUGCCCCUAAAAAUCCUUAU | 279 | 22 | 5 |
| hsa-miR-3676-5p | AGGAGAUCCUGGGUU | 280 | 15 | 5 |
| hsa-miR-502-3p | AAUGCACCUGGGCAAGGAUUCA | 281 | 22 | 5 |
| hsa-miR-505-3p | CGUCAACACUUGCUGGUUUCCU | 282 | 22 | 5 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-550a-3p | UGUCUUACUCCCUCAGGCACAU | 283 | 22 | 5 |
| hsa-miR-5587-3p | GCCCCGGGCAGUGUGAUCAUC | 284 | 21 | 5 |
| hsa-miR-641 | AAAGACAUAGGAUAGAGUCACCUC | 285 | 24 | 5 |
| hsa-miR-655 | AUAAUACAUGGUUAACCUCUUU | 286 | 22 | 5 |
| hsa-miR-664-3p | UAUUCAUUUAUCCCCAGCCUACA | 287 | 23 | 5 |
| hsa-miR-671-5p | AGGAAGCCCUGGAGGGGCUGGAG | 288 | 23 | 5 |
| hsa-miR-760 | CGGCUCUGGGUCUGUGGGGA | 289 | 20 | 5 |
| hsa-let-7e-3p | CUAUACGGCCUCCUAGCUUUCC | 290 | 22 | 4 |
| hsa-miR-1268a | CGGGCGUGGUGGUGGGGG | 291 | 18 | 4 |
| hsa-miR-1273f | GGAGAUGGAGGUUGCAGUG | 292 | 19 | 4 |
| hsa-miR-1286 | UGCAGGACCAAGAUGAGCCCU | 293 | 21 | 4 |
| hsa-miR-1291 | UGGCCCUGACUGAAGACCAGCAGU | 294 | 24 | 4 |
| hsa-miR-141-3p | UAACACUGUCUGGUAAAGAUGG | 295 | 22 | 4 |
| hsa-miR-1468 | CUCCGUUUGCCUGUUUCGCUG | 296 | 21 | 4 |
| hsa-miR-328 | CUGGCCCUCUCUGCCCUUCCGU | 297 | 22 | 4 |
| hsa-miR-424-3p | CAAAACGUGAGGCGCUGCUAU | 298 | 21 | 4 |
| hsa-miR-4454 | GGAUCCGAGUCACGGCACCA | 299 | 20 | 4 |
| hsa-miR-4463 | GAGACUGGGGUGGGGCC | 300 | 17 | 4 |
| hsa-miR-4671-3p | UUAGUGCAUAGUCUUUGGUCU | 301 | 21 | 4 |
| hsa-miR-4775 | UUAAUUUUUGUUUCGGUCACU | 302 | 22 | 4 |
| hsa-miR-500a-5p | UAAUCCUUGCUACCUGGGUGAGA | 303 | 23 | 4 |
| hsa-miR-548b-5p | AAAAGUAAUUGUGGUUUUGGCC | 304 | 22 | 4 |
| hsa-miR-573 | CUGAAGUGAUGUGUAACUGAUCAG | 305 | 24 | 4 |
| hsa-miR-576-5p | AUUCUAAUUUCUCCACGUCUUU | 306 | 22 | 4 |
| hsa-miR-625-3p | GACUAUAGAACUUUCCCCCUCA | 307 | 22 | 4 |
| hsa-miR-652-3p | AAUGGCGCCACUAGGGUUGUG | 308 | 21 | 4 |
| hsa-miR-665 | ACCAGGAGGCUGAGGCCCCU | 309 | 20 | 4 |
| hsa-miR-766-3p | ACUCCAGCCCCACAGCCUCAGC | 310 | 22 | 4 |
| hsa-miR-935 | CCAGUUACCGCUUCCGCUACCGC | 311 | 23 | 4 |
| hsa-miR-937 | AUCCGCGCUCUGACUCUCUGCC | 312 | 22 | 4 |
| hsa-miR-1180 | UUUCCGGCUCGCGUGGGUGUGU | 313 | 22 | 3 |
| hsa-miR-1185-2-3p | AUAUACAGGGGGAGACUCUCAU | 314 | 22 | 3 |
| hsa-miR-132-5p | ACCGUGGCUUUCGAUUGUUACU | 315 | 22 | 3 |
| hsa-miR-16-2-3p | CCAAUAUUACUGUGCUGCUUUA | 316 | 22 | 3 |
| hsa-miR-20b-5p | CAAAGUGCUCAUAGUGCAGGUAG | 317 | 23 | 3 |
| hsa-miR-2116-3p | CCUCCCAUGCCAAGAACUCCC | 318 | 21 | 3 |
| hsa-miR-299-5p | UGGUUUACCGUCCCACAUACAU | 319 | 22 | 3 |
| hsa-miR-30b-3p | CUGGGAGGUGGAUGUUUACUUC | 320 | 22 | 3 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-30c-2-3p | CUGGGAGAAGGCUGUUUACUCU | 321 | 22 | 3 |
| hsa-miR-3187-3p | UUGGCCAUGGGGCUGCGCGG | 322 | 20 | 3 |
| hsa-miR-3615 | UCUCUCGGCUCCUCGCGGCUC | 323 | 21 | 3 |
| hsa-miR-3620 | UCACCCUGCAUCCCGCACCCAG | 324 | 22 | 3 |
| hsa-miR-3654 | GACUGGACAAGCUGAGGAA | 325 | 19 | 3 |
| hsa-miR-3662 | GAAAAUGAUGAGUAGUGACUGAUG | 326 | 24 | 3 |
| hsa-miR-3681-5p | UAGUGGAUGAUGCACUCUGUGC | 327 | 22 | 3 |
| hsa-miR-4286 | ACCCCACUCCUGGUACC | 328 | 17 | 3 |
| hsa-miR-4640-3p | CACCCCCUGUUUCCUGGCCCAC | 329 | 22 | 3 |
| hsa-miR-4717-3p | ACACAUGGGUGGCUGUGGCCU | 330 | 21 | 3 |
| hsa-miR-542-3p | UGUGACAGAUUGAUAACUGAAA | 331 | 22 | 3 |
| hsa-miR-5584-5p | CAGGGAAAUGGGAAGAACUAGA | 332 | 22 | 3 |
| hsa-miR-570-3p | CGAAAACAGCAAUUACCUUUGC | 333 | 22 | 3 |
| hsa-miR-574-5p | UGAGUGUGUGUGUGUGAGUGUGU | 334 | 23 | 3 |
| hsa-miR-628-3p | UCUAGUAAGAGUGGCAGUCGA | 335 | 21 | 3 |
| hsa-miR-654-3p | UAUGUCUGCUGACCAUCACCUU | 336 | 22 | 3 |
| hsa-miR-769-3p | CUGGGAUCUCCGGGGUCUUGGUU | 337 | 23 | 3 |
| hsa-miR-943 | CUGACUGUUGCCGUCCUCCAG | 338 | 21 | 3 |
| hsa-let-7b-3p | CUAUACAACCUACUGCCUUCCC | 339 | 22 | 2 |
| hsa-miR-1244 | AAGUAGUUGGUUUGUAUGAGAUGGUU | 340 | 26 | 2 |
| hsa-miR-1255a | AGGAUGAGCAAAGAAAGUAGAUU | 341 | 23 | 2 |
| hsa-miR-1273e | UUGCUUGAACCCAGGAAGUGGA | 342 | 22 | 2 |
| hsa-miR-1289 | UGGAGUCCAGGAAUCUGCAUUUU | 343 | 23 | 2 |
| hsa-miR-152 | UCAGUGCAUGACAGAACUUGG | 344 | 21 | 2 |
| hsa-miR-194-5p | UGUAACAGCAACUCCAUGUGGA | 345 | 22 | 2 |
| hsa-miR-195-5p | UAGCAGCACAGAAAUAUUGGC | 346 | 21 | 2 |
| hsa-miR-200c-3p | UAAUACUGCCGGGUAAUGAUGGA | 347 | 23 | 2 |
| hsa-miR-212-3p | UAACAGUCUCCAGUCACGGCC | 348 | 21 | 2 |
| hsa-miR-222-5p | CUCAGUAGCCAGUGUAGAUCCU | 349 | 22 | 2 |
| hsa-miR-3065-3p | UCAGCACCAGGAUAUUGUUGGAG | 350 | 23 | 2 |
| hsa-miR-3115 | AUAUGGGUUUACUAGUUGGU | 351 | 20 | 2 |
| hsa-miR-3126-5p | UGAGGGACAGAUGCCAGAAGCA | 352 | 22 | 2 |
| hsa-miR-3174 | UAGUGAGUUAGAGAUGCAGAGCC | 353 | 23 | 2 |
| hsa-miR-324-5p | CGCAUCCCCUAGGGCAUUGGUGU | 354 | 23 | 2 |
| hsa-miR-33a-5p | GUGCAUUGUAGUUGCAUUGCA | 355 | 21 | 2 |
| hsa-miR-3677-3p | CUCGUGGGCUCUGGCCACGGCC | 356 | 22 | 2 |
| hsa-miR-369-5p | AGAUCGACCGUGUUAUAUUCGC | 357 | 22 | 2 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-425-3p | AUCGGGAAUGUCGUGUCCGCCC | 358 | 22 | 2 |
| hsa-miR-4426 | GAAGAUGGACGUACUUU | 359 | 17 | 2 |
| hsa-miR-4467 | UGGCGGCGGUAGUUAUGGGCUU | 360 | 22 | 2 |
| hsa-miR-4482-3p | UUUCUAUUUCUCAGUGGGGCUC | 361 | 22 | 2 |
| hsa-miR-4515 | AGGACUGGACUCCCGGCAGCCC | 362 | 22 | 2 |
| hsa-miR-4792 | CGGUGAGCGCUCGCUGGC | 363 | 18 | 2 |
| hsa-miR-659-5p | AGGACCUUCCCUGAACCAAGGA | 364 | 22 | 2 |
| hsa-miR-663a | AGGCGGGGCGCCGCGGGACCGC | 365 | 22 | 2 |
| hsa-miR-940 | AAGGCAGGGCCCCCGCUCCCC | 366 | 21 | 2 |
| hsa-miR-99a-3p | CAAGCUCGCUUCUAUGGGUCUG | 367 | 22 | 2 |
| hsa-miR-1185-5p | AGAGGAUACCCUUUGUAUGUU | 368 | 21 | 1 |
| hsa-miR-1225-3p | UGAGCCCCUGUGCCGCCCCAG | 369 | 22 | 1 |
| hsa-miR-1237 | UCCUUCUGCUCCGUCCCCAG | 370 | 21 | 1 |
| hsa-miR-1252 | AGAAGGAAAUUGAAUUCAUUUA | 371 | 22 | 1 |
| hsa-miR-1257 | AGUGAAUGAUGGGUUCUGACC | 372 | 21 | 1 |
| hsa-miR-1260b | AUCCCACCACUGCCACCAU | 373 | 19 | 1 |
| hsa-miR-1273d | GAACCCAUGAGGUUGAGGCUGCAGU | 374 | 25 | 1 |
| hsa-miR-1290 | UGGAUUUUUGGAUCAGGGA | 375 | 19 | 1 |
| hsa-miR-1306-3p | ACGUUGGCUCUGGUGGUG | 376 | 18 | 1 |
| hsa-miR-1321 | CAGGGAGGUGAAUGUGAU | 377 | 18 | 1 |
| hsa-miR-1343 | CUCCUGGGGCCCGCACUCUCGC | 378 | 22 | 1 |
| hsa-miR-138-5p | AGCUGGUGUUGUGAAUCAGGCCG | 379 | 23 | 1 |
| hsa-miR-140-5p | CAGUGGUUUUACCCUAUGGUAG | 380 | 22 | 1 |
| hsa-miR-146b-3p | UGCCCUGUGGACUCAGUUCUGG | 381 | 22 | 1 |
| hsa-miR-186-3p | GCCCAAAGGUGAAUUUUUUGGG | 382 | 22 | 1 |
| hsa-miR-1908 | CGGCGGGGACGGCGAUUGGUC | 383 | 21 | 1 |
| hsa-miR-1915-3p | CCCCAGGGCGACGCGGCGGG | 384 | 20 | 1 |
| hsa-miR-1915-5p | ACCUUGCCUUGCUGCCCGGGCC | 385 | 22 | 1 |
| hsa-miR-193a-3p | AACUGGCCUACAAAGUCCCAGU | 386 | 22 | 1 |
| hsa-miR-19b-1-5p | AGUUUUGCAGGUUUGCAUCCAGC | 387 | 23 | 1 |
| hsa-miR-208b | AUAAGACGAACAAAAGGUUUGU | 388 | 22 | 1 |
| hsa-miR-2110 | UUGGGGAAACGGCCGCUGAGUG | 389 | 22 | 1 |
| hsa-miR-219-1-3p | AGAGUUGAGUCUGGACGUCCCG | 390 | 22 | 1 |
| hsa-miR-26b-3p | CCUGUUCUCCAUUACUUGGCUC | 391 | 22 | 1 |
| hsa-miR-2964a-3p | AGAAUUGCGUUUGGACAAUCAGU | 392 | 23 | 1 |
| hsa-miR-29a-5p | ACUGAUUUCUUUUGGUGUUCAG | 393 | 22 | 1 |
| hsa-miR-3126-3p | CAUCUGGCAUCCGUCACACAGA | 394 | 22 | 1 |
| hsa-miR-3130-3p | GCUGCACCGGAGACUGGGUAA | 395 | 21 | 1 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-3130-5p | UACCCAGUCUCCGGUGCAGCC | 396 | 21 | 1 |
| hsa-miR-3140-5p | ACCUGAAUUACCAAAAGCUUU | 397 | 21 | 1 |
| hsa-miR-3155a | CCAGGCUCUGCAGUGGGAACU | 398 | 21 | 1 |
| hsa-miR-3157-3p | CUGCCCUAGUCUAGCUGAAGCU | 399 | 22 | 1 |
| hsa-miR-3180-3p | UGGGGCGGAGCUUCCGGAGGCC | 400 | 22 | 1 |
| hsa-miR-323b-5p | AGGUUGUCCGUGGUGAGUUCGCA | 401 | 23 | 1 |
| hsa-miR-339-5p | UCCCUGUCCUCCAGGAGCUCACG | 402 | 23 | 1 |
| hsa-miR-34a-3p | CAAUCAGCAAGUAUACUGCCCU | 403 | 22 | 1 |
| hsa-miR-34b-3p | CAAUCACUAACUCCACUGCCAU | 404 | 22 | 1 |
| hsa-miR-34c-3p | AAUCACUAACCACACGGCCAGG | 405 | 22 | 1 |
| hsa-miR-3658 | UUUAAGAAAACACCAUGGAGAU | 406 | 22 | 1 |
| hsa-miR-365a-5p | AGGGACUUUUGGGGGCAGAUGUG | 407 | 23 | 1 |
| hsa-miR-3676-3p | CCGUGUUUCCCCCACGCUUU | 408 | 20 | 1 |
| hsa-miR-3691-5p | AGUGGAUGAUGGAGACUCGGUAC | 409 | 23 | 1 |
| hsa-miR-376a-5p | GUAGAUUCUCCUUCUAUGAGUA | 410 | 22 | 1 |
| hsa-miR-378g | ACUGGGCUUGGAGUCAGAAG | 411 | 20 | 1 |
| hsa-miR-3909 | UGUCCUCUAGGGCCUGCAGUCU | 412 | 22 | 1 |
| hsa-miR-3928 | GGAGGAACCUUGGAGCUUCGGC | 413 | 22 | 1 |
| hsa-miR-3942-3p | UUUCAGAUAACAGUAUUACAU | 414 | 21 | 1 |
| hsa-miR-3944-5p | UGUGCAGCAGGCCAACCGAGA | 415 | 21 | 1 |
| hsa-miR-3960 | GGCGGCGGCGGAGGCGGGGG | 416 | 20 | 1 |
| hsa-miR-4326 | UGUUCCUCUGUCUCCCAGAC | 417 | 20 | 1 |
| hsa-miR-4444 | CUCGAGUUGGAAGAGGCG | 418 | 18 | 1 |
| hsa-miR-4450 | UGGGGAUUUGGAGAAGUGGUGA | 419 | 22 | 1 |
| hsa-miR-4642 | AUGGCAUCGUCCCCUGGUGGCU | 420 | 22 | 1 |
| hsa-miR-4668-5p | AGGGAAAAAAAAAAGGAUUUGUC | 421 | 23 | 1 |
| hsa-miR-4673 | UCCAGGCAGGAGCCGGACUGGA | 422 | 22 | 1 |
| hsa-miR-4688 | UAGGGGCAGCAGAGGACCUGGG | 423 | 22 | 1 |
| hsa-miR-4700-3p | CACAGGACUGACUCCUCACCCCAGUG | 424 | 26 | 1 |
| hsa-miR-4731-3p | CACACAAGUGGCCCCCAACACU | 425 | 22 | 1 |
| hsa-miR-4749-3p | CGCCCCUCCUGCCCCCACAG | 426 | 20 | 1 |
| hsa-miR-4769-5p | GGUGGGAUGGAGAGAAGGUAUGAG | 427 | 24 | 1 |
| hsa-miR-4800-5p | AGUGGACCGAGGAAGGAAGGA | 428 | 21 | 1 |
| hsa-miR-491-5p | AGUGGGGAACCCUUCCAUGAGG | 429 | 22 | 1 |
| hsa-miR-501-5p | AAUCCUUUGUCCCUGGGUGAGA | 430 | 22 | 1 |
| hsa-miR-5092 | AAUCCACGCUGAGCUUGGCAUC | 431 | 22 | 1 |
| hsa-miR-541-5p | AAAGGAUUCUGCUGUCGGUCCCACU | 432 | 25 | 1 |

TABLE 5-continued

Cells EH

| Cells: CTX0E03 07EH MIRNA | MIRNA.SEQUENCE | SEQ ID NO: | MIRNA LENGTH | READ COUNTS |
|---|---|---|---|---|
| hsa-miR-542-5p | UCGGGGAUCAUCAUGUCACGAGA | 433 | 23 | 1 |
| hsa-miR-551b-3p | GCGACCCAUACUUGGUUUCAG | 434 | 21 | 1 |
| hsa-miR-5690 | UCAGCUACUACCUCUAUUAGG | 435 | 21 | 1 |
| hsa-miR-577 | UAGAUAAAAUAUUGGUACCUG | 436 | 21 | 1 |
| hsa-miR-584-3p | UCAGUUCCAGGCCAACCAGGCU | 437 | 22 | 1 |
| hsa-miR-589-3p | UCAGAACAAAUGCCGGUUCCCAGA | 438 | 24 | 1 |
| hsa-miR-616-5p | ACUCAAAACCCUUCAGUGACUU | 439 | 22 | 1 |
| hsa-miR-628-5p | AUGCUGACAUAUUUACUAGAGG | 440 | 22 | 1 |
| hsa-miR-629-5p | UGGGUUUACGUUGGGAGAACU | 441 | 21 | 1 |
| hsa-miR-644b-3p | UUCAUUUGCCUCCCAGCCUACA | 442 | 22 | 1 |
| hsa-miR-664-5p | ACUGGCUAGGGAAAAUGAUUGGAU | 443 | 24 | 1 |
| hsa-miR-922 | GCAGCAGAGAAUAGGACUACGUC | 444 | 23 | 1 |

TABLE 6

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-let-7a-5p | UGAGGUAGUAGGUUGUAUAGUU | 1 | 22 | 305060 |
| hsa-miR-92b-3p | UAUUGCACUCGUCCCGGCCUCC | 13 | 22 | 242715 |
| hsa-miR-21-5p | UAGCUUAUCAGACUGAUGUUGA | 9 | 22 | 154626 |
| hsa-miR-92a-3p | UAUUGCACUUGUCCCGGCCUGU | 7 | 22 | 137412 |
| hsa-miR-127-3p | UCGGAUCCGUCUGAGCUUGGCU | 14 | 22 | 110806 |
| hsa-miR-100-5p | AACCCGUAGAUCCGAACUUGUG | 3 | 22 | 109290 |
| hsa-miR-27b-3p | UUCACAGUGGCUAAGUUCUGC | 6 | 21 | 91902 |
| hsa-miR-191-5p | CAACGGAAUCCCAAAAGCAGCUG | 8 | 23 | 89150 |
| hsa-miR-26a-5p | UUCAAGUAAUCCAGGAUAGGCU | 12 | 22 | 88724 |
| hsa-miR-99b-5p | CACCCGUAGAACCGACCUUGCG | 4 | 22 | 87399 |
| hsa-let-7f-5p | UGAGGUAGUAGAUUGUAUAGUU | 11 | 22 | 78395 |
| hsa-miR-181a-5p | AACAUUCAACGCUGUCGGUGAGU | 15 | 23 | 47686 |
| hsa-miR-486-5p | UCCUGUACUGAGCUGCCCCGAG | 5 | 22 | 41639 |
| hsa-miR-30a-5p | UGUAAACAUCCUCGACUGGAAG | 30 | 22 | 35465 |
| hsa-miR-98 | UGAGGUAGUAAGUUGUAUUGUU | 10 | 22 | 30440 |
| hsa-miR-151a-3p | CUAGACUGAAGCUCCUUGAGG | 25 | 21 | 29047 |
| hsa-miR-21-3p | CAACACCAGUCGAUGGGCUGU | 20 | 21 | 27733 |
| hsa-miR-30d-5p | UGUAAACAUCCCCGACUGGAAG | 31 | 22 | 27307 |
| hsa-let-7c | UGAGGUAGUAGGUUGUAUGGUU | 17 | 22 | 27224 |
| hsa-miR-10a-5p | UACCCUGUAGAUCCGAAUUUGUG | 2 | 23 | 26908 |
| hsa-miR-22-3p | AAGCUGCCAGUUGAAGAACUGU | 33 | 22 | 26456 |

TABLE 6-continued

| Cells EI | | | | |
|---|---|---|---|---|
| CELLS - CTX0E03 07EI MIRNA | MIRNA.SEQUENCE | SEQ ID NO: | MIRNA LENGTH | READ COUNTS |
| hsa-miR-182-5p | UUUGGCAAUGGUAGAACUCACACU | 16 | 24 | 25885 |
| hsa-miR-222-3p | AGCUACAUCUGGCUACUGGGU | 36 | 21 | 22187 |
| hsa-miR-125a-5p | UCCCUGAGACCCUUUAACCUGUGA | 35 | 24 | 20960 |
| hsa-miR-16-5p | UAGCAGCACGUAAAUAUUGGCG | 29 | 22 | 19856 |
| hsa-let-7b-5p | UGAGGUAGUAGGUUGUGUGGUU | 28 | 22 | 19774 |
| hsa-miR-151a-5p | UCGAGGAGCUCACAGUCUAGU | 37 | 21 | 19773 |
| hsa-let-7e-5p | UGAGGUAGGAGGUUGUAUAGUU | 27 | 22 | 19035 |
| hsa-miR-125b-5p | UCCCUGAGACCCUAACUUGUGA | 42 | 22 | 17965 |
| hsa-let-7i-5p | UGAGGUAGUAGUUUGUGCUGUU | 22 | 22 | 17802 |
| hsa-let-7g-5p | UGAGGUAGUAGUUUGUACAGUU | 43 | 22 | 15467 |
| hsa-miR-409-3p | GAAUGUUGCUCGGUGAACCCCU | 47 | 22 | 14133 |
| hsa-miR-30e-5p | UGUAAACAUCCUUGACUGGAAG | 45 | 22 | 13889 |
| hsa-miR-181b-5p | AACAUUCAUUGCUGUCGGUGGGU | 38 | 23 | 12606 |
| hsa-miR-186-5p | CAAAGAAUUCUCCUUUUGGGCU | 40 | 22 | 12441 |
| hsa-miR-381 | UAUACAAGGGCAAGCUCUCUGU | 51 | 22 | 9851 |
| hsa-miR-423-5p | UGAGGGGCAGAGAGCGAGACUUU | 41 | 23 | 8893 |
| hsa-miR-30c-5p | UGUAAACAUCCUACACUCUCAGC | 66 | 23 | 8737 |
| hsa-miR-410 | AAUAUAACACAGAUGGCCUGU | 50 | 21 | 8509 |
| hsa-miR-146b-5p | UGAGAACUGAAUUCCAUAGGCU | 19 | 22 | 8434 |
| hsa-miR-654-3p | UAUGUCUGCUGACCAUCACCUU | 336 | 22 | 8392 |
| hsa-miR-9-5p | UCUUUGGUUAUCUAGCUGUAUGA | 58 | 23 | 7957 |
| hsa-miR-28-3p | CACUAGAUUGUGAGCUCCUGGA | 56 | 22 | 7767 |
| hsa-miR-148a-3p | UCAGUGCACUACAGAACUUUGU | 54 | 22 | 6599 |
| hsa-miR-379-5p | UGGUAGACUAUGGAACGUAGG | 18 | 21 | 6135 |
| hsa-let-7d-5p | AGAGGUAGUAGGUUGCAUAGUU | 53 | 22 | 5972 |
| hsa-miR-183-5p | UAUGGCACUGGUAGAAUUCACU | 24 | 22 | 5477 |
| hsa-miR-25-3p | CAUUGCACUUGUCUCGGUCUGA | 63 | 22 | 5303 |
| hsa-miR-423-3p | AGCUCGGUCUGAGGCCCCUCAGU | 57 | 23 | 5225 |
| hsa-miR-889 | UUAAUAUCGGACAACCAUUGU | 64 | 21 | 4597 |
| hsa-miR-221-5p | ACCUGGCAUACAAUGUAGAUUU | 39 | 22 | 4379 |
| hsa-miR-125b-1-3p | ACGGGUUAGGCUCUUGGGAGCU | 49 | 22 | 4192 |
| hsa-miR-409-5p | AGGUUACCCGAGCAACUUUGCAU | 32 | 23 | 3970 |
| hsa-miR-4492 | GGGGCUGGGCGCGCGCC | 34 | 17 | 3864 |
| hsa-miR-148b-3p | UCAGUGCAUCACAGAACUUUGU | 48 | 22 | 3593 |
| hsa-miR-103a-3p | AGCAGCAUUGUACAGGGCUAUGA | 62 | 23 | 3518 |
| hsa-miR-1271-5p | CUUGGCACCUAGCAAGCACUCA | 72 | 22 | 3477 |
| hsa-miR-136-3p | CAUCAUCGUCUCAAAUGAGUCU | 82 | 22 | 3373 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-769-5p | UGAGACCUCUGGGUUCUGAGCU | 75 | 22 | 2957 |
| hsa-miR-4532 | CCCCGGGGAGCCCGGCG | 23 | 17 | 2915 |
| hsa-miR-378a-3p | ACUGGACUUGGAGUCAGAAGG | 65 | 21 | 2895 |
| hsa-miR-99a-5p | AACCCGUAGAUCCGAUCUUGUG | 52 | 22 | 2767 |
| hsa-miR-221-3p | AGCUACAUUGUCUGCUGGGUUUC | 79 | 23 | 2764 |
| hsa-miR-30e-3p | CUUUCAGUCGGAUGUUUACAGC | 71 | 22 | 2441 |
| hsa-miR-26b-5p | UUCAAGUAAUUCAGGAUAGGU | 90 | 21 | 2432 |
| hsa-miR-4488 | AGGGGGCGGGCUCCGGCG | 61 | 18 | 2391 |
| hsa-miR-27a-3p | UUCACAGUGGCUAAGUUCCGC | 46 | 21 | 2385 |
| hsa-miR-23b-3p | AUCACAUUGCCAGGGAUUACC | 59 | 21 | 2316 |
| hsa-miR-500a-3p | AUGCACCUGGGCAAGGAUUCUG | 44 | 22 | 2144 |
| hsa-miR-941 | CACCCGGCUGUGUGCACAUGUGC | 60 | 23 | 2114 |
| hsa-miR-23a-3p | AUCACAUUGCCAGGGAUUUCC | 55 | 21 | 2086 |
| hsa-miR-30a-3p | CUUUCAGUCGGAUGUUUGCAGC | 77 | 22 | 2045 |
| hsa-miR-30b-5p | UGUAAACAUCCUACACUCAGCU | 96 | 22 | 1936 |
| hsa-miR-501-3p | AAUGCACCCGGGCAAGGAUUCU | 26 | 22 | 1895 |
| hsa-miR-130b-3p | CAGUGCAAUGAUGAAAGGGCAU | 86 | 22 | 1862 |
| hsa-miR-1246 | AAUGGAUUUUUGGAGCAGG | 21 | 19 | 1783 |
| hsa-miR-140-3p | UACCACAGGGUAGAACCACGG | 138 | 21 | 1735 |
| hsa-miR-31-5p | AGGCAAGAUGCUGGCAUAGCU | 80 | 21 | 1705 |
| hsa-miR-493-3p | UGAAGGUCUACUGUGUGCCAGG | 83 | 22 | 1698 |
| hsa-miR-181c-5p | AACAUUCAACCUGUCGGUGAGU | 105 | 22 | 1554 |
| hsa-miR-93-5p | CAAAGUGCUGUUCGUGCAGGUAG | 116 | 23 | 1492 |
| hsa-miR-181a-2-3p | ACCACUGACCGUUGACUGUACC | 102 | 22 | 1491 |
| hsa-miR-15b-5p | UAGCAGCACAUCAUGGUUUACA | 78 | 22 | 1465 |
| hsa-miR-7-5p | UGGAAGACUAGUGAUUUUGUUGU | 85 | 23 | 1460 |
| hsa-miR-192-5p | CUGACCUAUGAAUUGACAGCC | 87 | 21 | 1453 |
| hsa-miR-425-5p | AAUGACACGAUCACUCCCGUUGA | 111 | 23 | 1432 |
| hsa-miR-204-5p | UUCCCUUUGUCAUCCUAUGCCU | 89 | 22 | 1378 |
| hsa-miR-340-5p | UUAUAAAGCAAUGAGACUGAUU | 93 | 22 | 1360 |
| hsa-miR-190a | UGAUAUGUUUGAUAUAUUAGGU | 103 | 22 | 1305 |
| hsa-miR-34a-5p | UGGCAGUGUCUUAGCUGGUUGU | 101 | 22 | 1283 |
| hsa-miR-20a-5p | UAAAGUGCUUAUAGUGCAGGUAG | 146 | 23 | 1257 |
| hsa-miR-29a-3p | UAGCACCAUCUGAAAUCGGUUA | 106 | 22 | 1206 |
| hsa-miR-361-5p | UUAUCAGAAUCUCCAGGGGUAC | 70 | 22 | 1173 |
| hsa-miR-671-3p | UCCGGUUCUCAGGGCUCCACC | 69 | 21 | 1166 |
| hsa-miR-411-5p | UAGUAGACCGUAUAGCGUACG | 108 | 21 | 1130 |
| hsa-miR-589-5p | UGAGAACCACGUCUGCUCUGAG | 73 | 22 | 1067 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-130a-3p | CAGUGCAAUGUUAAAAGGGCAU | 113 | 22 | 1020 |
| hsa-miR-320a | AAAAGCUGGGUUGAGAGGGCGA | 97 | 22 | 994 |
| hsa-miR-149-5p | UCUGGCUCCGUGUCUUCACUCCC | 121 | 23 | 948 |
| hsa-miR-335-5p | UCAAGAGCAAUAACGAAAAAUGU | 128 | 23 | 945 |
| hsa-miR-134 | UGUGACUGGUUGACCAGAGGGG | 94 | 22 | 941 |
| hsa-miR-17-5p | CAAAGUGCUUACAGUGCAGGUAG | 145 | 23 | 939 |
| hsa-miR-493-5p | UUGUACAUGGUAGGCUUUCAUU | 88 | 22 | 876 |
| hsa-miR-34c-5p | AGGCAGUGUAGUUAGCUGAUUGC | 125 | 23 | 846 |
| hsa-miR-484 | UCAGGCUCAGUCCCCUCCCGAU | 118 | 22 | 835 |
| hsa-miR-181a-3p | ACCAUCGACCGUUGAUUGUACC | 100 | 22 | 803 |
| hsa-miR-24-3p | UGGCUCAGUUCAGCAGGAACAG | 119 | 22 | 740 |
| hsa-miR-128 | UCACAGUGAACCGGUCUCUUU | 109 | 21 | 707 |
| hsa-miR-342-3p | UCUCACACAGAAAUCGCACCCGU | 81 | 23 | 698 |
| hsa-miR-454-3p | UAGUGCAAUAUUGCUUAUAGGGU | 169 | 23 | 690 |
| hsa-miR-1307-5p | UCGACCGGACCUCGACCGGCU | 91 | 21 | 616 |
| hsa-miR-487b | AAUCGUACAGGGUCAUCCACUU | 117 | 22 | 590 |
| hsa-miR-130b-5p | ACUCUUUCCCUGUUGCACUAC | 112 | 21 | 568 |
| hsa-miR-197-3p | UUCACCACCUUCUCCACCCAGC | 122 | 22 | 544 |
| hsa-miR-432-5p | UCUUGGAGUAGGUCAUUGGGUGG | 95 | 23 | 542 |
| hsa-miR-374a-5p | UUAUAAUACAACCUGAUAAGUG | 74 | 22 | 537 |
| hsa-miR-345-5p | GCUGACUCCUAGUCCAGGGCUC | 76 | 22 | 527 |
| hsa-miR-744-5p | UGCGGGGCUAGGGCUAACAGCA | 99 | 22 | 515 |
| hsa-miR-376c | AACAUAGAGGAAAUUCCACGU | 185 | 21 | 506 |
| hsa-miR-181d | AACAUUCAUUGUUGUCGGUGGGU | 157 | 23 | 497 |
| hsa-miR-363-3p | AAUUGCACGGUAUCCAUCUGUA | 131 | 22 | 493 |
| hsa-miR-539-3p | AUCAUACAAGGACAAUUUCUUU | 150 | 22 | 493 |
| hsa-miR-758 | UUUGUGACCUGGUCCACUAACC | 141 | 22 | 477 |
| hsa-miR-323a-3p | CACAUUACACGGUCGACCUCU | 158 | 21 | 443 |
| hsa-miR-107 | AGCAGCAUUGUACAGGGCUAUCA | 254 | 23 | 431 |
| hsa-miR-720 | UCUCGCUGGGGCCUCCA | 84 | 17 | 427 |
| hsa-miR-654-5p | UGGUGGGCCGCAGAACAUGUGC | 115 | 22 | 409 |
| hsa-miR-370 | GCCUGCUGGGGUGGAACCUGGU | 126 | 22 | 406 |
| hsa-miR-421 | AUCAACAGACAUUAAUUGGGCGC | 151 | 23 | 399 |
| hsa-miR-30d-3p | CUUUCAGUCAGAUGUUUGCUGC | 114 | 22 | 358 |
| hsa-miR-148b-5p | AAGUUCUGUUAUACACUCAGGC | 127 | 22 | 354 |
| hsa-miR-1301 | UUGCAGCUGCCUGGGAGUGACUUC | 181 | 24 | 346 |
| hsa-miR-374b-5p | AUAUAAUACAACCUGCUAAGUG | 143 | 22 | 339 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-125b-2-3p | UCACAAGUCAGGCUCUUGGGAC | 68 | 22 | 333 |
| hsa-miR-28-5p | AAGGAGCUCACAGUCUAUUGAG | 152 | 22 | 332 |
| hsa-miR-495 | AAACAAACAUGGUGCACUUCUU | 241 | 22 | 321 |
| hsa-miR-15a-5p | UAGCAGCACAUAAUGGUUUGUG | 223 | 22 | 320 |
| hsa-miR-100-3p | CAAGCUUGUAUCUAUAGGUAUG | 98 | 22 | 314 |
| hsa-miR-193b-3p | AACUGGCCCUCAAAGUCCCGCU | 148 | 22 | 305 |
| hsa-miR-330-5p | UCUCUGGGCCUGUGUCUUAGGC | 161 | 22 | 303 |
| hsa-miR-376a-3p | AUCAUAGAGGAAAAUCCACGU | 237 | 21 | 298 |
| hsa-miR-135b-5p | UAUGGCUUUUCAUUCCUAUGUGA | 137 | 23 | 289 |
| hsa-miR-301a-3p | CAGUGCAAUAGUAUUGUCAAAGC | 107 | 23 | 280 |
| hsa-miR-218-5p | UUGUGCUUGAUCUAACCAUGU | 206 | 21 | 276 |
| hsa-miR-143-3p | UGAGAUGAAGCACUGUAGCUC | 176 | 21 | 256 |
| hsa-miR-27b-5p | AGAGCUUAGCUGAUUGGUGAAC | 201 | 22 | 255 |
| hsa-miR-369-3p | AAUAAUACAUGGUUGAUCUUU | 196 | 21 | 255 |
| hsa-miR-877-5p | GUAGAGGAGAUGGCGCAGGG | 133 | 20 | 249 |
| hsa-miR-19b-3p | UGUGCAAAUCCAUGCAAAACUGA | 163 | 23 | 246 |
| hsa-miR-424-5p | CAGCAGCAAUUCAUGUUUUGAA | 186 | 22 | 245 |
| hsa-miR-660-5p | UACCCAUUGCAUAUCGGAGUUG | 187 | 22 | 244 |
| hsa-miR-532-5p | CAUGCCUUGAGUGUAGGACCGU | 178 | 22 | 238 |
| hsa-miR-299-3p | UAUGUGGGAUGGUAAACCGCUU | 182 | 22 | 235 |
| hsa-miR-431-3p | CAGGUCGUCUUGCAGGGCUUCU | 168 | 22 | 231 |
| hsa-miR-374a-3p | CUUAUCAGAUUGUAUUGUAAUU | 173 | 22 | 220 |
| hsa-miR-148a-5p | AAAGUUCUGAGACACUCCGACU | 144 | 22 | 214 |
| hsa-miR-4516 | GGGAGAAGGGUCGGGGC | 110 | 17 | 207 |
| hsa-miR-92b-5p | AGGGACGGGACGCGGUGCAGUG | 208 | 22 | 206 |
| hsa-miR-16-2-3p | CCAAUAUUACUGUGCUGCUUUA | 316 | 22 | 202 |
| hsa-miR-101-3p | UACAGUACUGUGAUAACUGAA | 142 | 21 | 201 |
| hsa-let-7a-3p | CUAUACAAUCUACUGUCUUUC | 222 | 21 | 199 |
| hsa-miR-4485 | UAACGGCCGCGGUACCCUAA | 67 | 20 | 195 |
| hsa-miR-455-3p | GCAGUCCAUGGGCAUAUACAC | 140 | 21 | 192 |
| hsa-miR-185-5p | UGGAGAGAAAGGCAGUUCCUGA | 224 | 22 | 188 |
| hsa-miR-1185-1-3p | AUAUACAGGGGGAGACUCUUAU | 209 | 22 | 187 |
| hsa-miR-1197 | UAGGACACAUGGUCUACUUCU | 244 | 21 | 185 |
| hsa-miR-106b-3p | CCGCACUGUGGGUACUUGCUGC | 159 | 22 | 178 |
| hsa-miR-24-2-5p | UGCCUACUGAGCUGAAACACAG | 156 | 22 | 178 |
| hsa-miR-4677-3p | UCUGUGAGACCAAAGAACUACU | 120 | 22 | 177 |
| hsa-miR-380-3p | UAUGUAAUAUGGUCCACAUCUU | 445 | 22 | 174 |
| hsa-miR-548k | AAAAGUACUUGCGGAUUUUGCU | 198 | 22 | 171 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-1307-3p | ACUCGGCGUGGCGUCGGUCGUG | 124 | 22 | 169 |
| hsa-miR-485-3p | GUCAUACACGGCUCUCCUCUCU | 153 | 22 | 168 |
| hsa-miR-494 | UGAAACAUACACGGGAAACCUC | 240 | 22 | 165 |
| hsa-miR-17-3p | ACUGCAGUGAAGGCACUUGUAG | 184 | 22 | 163 |
| hsa-miR-561-5p | AUCAAGGAUCUUAAACUUUGCC | 179 | 22 | 160 |
| hsa-miR-27a-5p | AGGGCUUAGCUGCUUGUGAGCA | 130 | 22 | 158 |
| hsa-miR-874 | CUGCCCUGGCCCGAGGGACCGA | 147 | 22 | 151 |
| hsa-miR-9-3p | AUAAAGCUAGAUAACCGAAAGU | 183 | 22 | 151 |
| hsa-miR-96-5p | UUUGGCACUAGCACAUUUUGCU | 123 | 23 | 151 |
| hsa-miR-656 | AAUAUUAUACAGUCAACCUCU | 221 | 21 | 147 |
| hsa-miR-379-3p | UAUGUAACAUGGUCCACUAACU | 446 | 22 | 145 |
| hsa-miR-382-5p | GAAGUUGUUCGUGGUGGAUUCG | 238 | 22 | 144 |
| hsa-miR-541-3p | UGGUGGGCACAGAAUCUGGACU | 136 | 22 | 141 |
| hsa-miR-337-3p | CUCCUAUAUGAUGCCUUUCUUC | 215 | 22 | 139 |
| hsa-miR-15b-3p | CGAAUCAUUAUUUGCUGCUCUA | 447 | 22 | 137 |
| hsa-miR-20b-5p | CAAAGUGCUCAUAGUGCAGGUAG | 317 | 23 | 136 |
| hsa-miR-329 | AACACACCUGGUUAACCUCUUU | 214 | 22 | 136 |
| hsa-miR-3676-5p | AGGAGAUCCUGGGUU | 280 | 15 | 134 |
| hsa-miR-543 | AAACAUUCGCGGUGCACUUCUU | 193 | 22 | 134 |
| hsa-miR-365b-3p | UAAUGCCCCUAAAAAUCCUUAU | 279 | 22 | 133 |
| hsa-miR-125a-3p | ACAGGUGAGGUUCUUGGGAGCC | 160 | 22 | 131 |
| hsa-miR-3065-5p | UCAACAAAAUCACUGAUGCUGGA | 226 | 23 | 130 |
| hsa-miR-1296 | UUAGGGCCCUGGCUCCAUCUCC | 271 | 22 | 126 |
| hsa-miR-935 | CCAGUUACCGCUUCCGCUACCGC | 311 | 23 | 118 |
| hsa-miR-132-3p | UAACAGUCUACAGCCAUGGUCG | 104 | 22 | 116 |
| hsa-miR-4284 | GGGCUCACAUCACCCCAU | 191 | 18 | 116 |
| hsa-miR-487a | AAUCAUACAGGGACAUCCAGUU | 203 | 22 | 113 |
| hsa-miR-574-5p | UGAGUGUGUGUGUGAGUGUGU | 334 | 23 | 113 |
| hsa-miR-301b | CAGUGCAAUGAUAUUGUCAAAGC | 164 | 23 | 111 |
| hsa-miR-548o-3p | CCAAAACUGCAGUUACUUUUGC | 268 | 22 | 105 |
| hsa-miR-18a-5p | UAAGGUGCAUCUAGUGCAGAUAG | 256 | 23 | 104 |
| hsa-miR-485-5p | AGAGGCUGGCCGUGAUGAAUUC | 165 | 22 | 104 |
| hsa-miR-548ah-5p | AAAAGUGAUUGCAGUGUUUG | 235 | 20 | 103 |
| hsa-miR-361-3p | UCCCCCAGGUGUGAUUCUGAUUU | 250 | 23 | 101 |
| hsa-miR-433 | AUCAUGAUGGGCUCCUCGGUGU | 174 | 22 | 101 |
| hsa-miR-337-5p | GAACGGCUUCAUACAGGAGUU | 277 | 21 | 100 |
| hsa-miR-1276 | UAAAGAGCCCUGUGGAGACA | 194 | 20 | 99 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-30c-1-3p | CUGGGAGAGGGUUGUUUACUCC | 213 | 22 | 99 |
| hsa-miR-31-3p | UGCUAUGCCAACAUAUUGCCAU | 172 | 22 | 96 |
| hsa-miR-424-3p | CAAAACGUGAGGCGCUGCUAU | 298 | 21 | 96 |
| hsa-miR-550a-5p | AGUGCCUGAGGGAGUAAGAGCCC | 134 | 23 | 95 |
| hsa-miR-4454 | GGAUCCGAGUCACGGCACCA | 299 | 20 | 94 |
| hsa-miR-541-5p | AAAGGAUUCUGCUGUCGGUCCCACU | 432 | 25 | 92 |
| hsa-miR-106b-5p | UAAAGUGCUGACAGUGCAGAU | 170 | 21 | 89 |
| hsa-miR-153 | UUGCAUAGUCACAAAGUGAUC | 188 | 22 | 88 |
| hsa-miR-135b-3p | AUGUAGGGCUAAAAGCCAUGGG | 205 | 22 | 87 |
| hsa-miR-574-3p | CACGCUCAUGCACACACCCACA | 253 | 22 | 87 |
| hsa-miR-1226-3p | UCACCAGCCCUGUGUUCCCUAG | 199 | 22 | 85 |
| hsa-miR-576-5p | AUUCUAAUUUCUCCACGUCUUU | 306 | 22 | 84 |
| hsa-miR-127-5p | CUGAAGCUCAGAGGGCUCUGAU | 255 | 22 | 83 |
| hsa-miR-155-5p | UUAAUGCUAAUCGUGAUAGGGGU | 448 | 23 | 83 |
| hsa-miR-3176 | ACUGGCCUGGGACUACCGG | 227 | 19 | 83 |
| hsa-miR-382-3p | AAUCAUUCACGGACAACACUU | 260 | 21 | 83 |
| hsa-miR-1275 | GUGGGGGAGAGGCUGUC | 162 | 17 | 82 |
| hsa-miR-671-5p | AGGAAGCCCUGGAGGGGCUGGAG | 288 | 23 | 82 |
| hsa-miR-23a-5p | GGGGUUCCUGGGGAUGGGAUUU | 212 | 22 | 81 |
| hsa-miR-25-5p | AGGCGGAGACUUGGGCAAUUG | 225 | 21 | 80 |
| hsa-miR-641 | AAAGACAUAGGAUAGAGUCACCUC | 285 | 24 | 80 |
| hsa-miR-19a-3p | UGUGCAAAUCUAUGCAAAACUGA | 177 | 23 | 79 |
| hsa-miR-377-3p | AUCACACAAAGGCAACUUUUGU | 449 | 22 | 78 |
| hsa-miR-454-5p | ACCCUAUCAAUAUUGUCUCUGC | 265 | 22 | 78 |
| hsa-miR-496 | UGAGUAUUACAUGGCCAAUCUC | 267 | 22 | 78 |
| hsa-miR-29b-3p | UAGCACCAUUUGAAAUCAGUGUU | 166 | 23 | 77 |
| hsa-miR-26a-2-3p | CCUAUUCUUGAUUACUUGUUUC | 257 | 22 | 76 |
| hsa-miR-1260b | AUCCCACCACUGCCACCAU | 373 | 19 | 74 |
| hsa-miR-2467-5p | UGAGGCUCUGUUAGCCUUGGCUC | 154 | 23 | 74 |
| hsa-miR-377-5p | AGAGGUUGCCCUUGGUGAAUUC | 202 | 22 | 74 |
| hsa-miR-330-3p | GCAAAGCACACGGCCUGCAGAGA | 195 | 23 | 73 |
| hsa-miR-1180 | UUUCCGGCUCGCGUGGGUGUGU | 313 | 22 | 71 |
| hsa-miR-99b-3p | CAAGCUCGUGUCUGUGGGUCCG | 243 | 22 | 71 |
| hsa-miR-299-5p | UGGUUUACCGUCCCACAUACAU | 319 | 22 | 69 |
| hsa-miR-374b-3p | CUUAGCAGGUUGUAUUAUCAUU | 229 | 22 | 69 |
| hsa-miR-4746-5p | CCGGUCCAGGAGAACCUGCAGA | 266 | 23 | 69 |
| hsa-miR-331-3p | GCCCCUGGGCCUAUCCUAGAA | 450 | 21 | 68 |
| hsa-miR-340-3p | UCCGUCUCAGUUACUUUAUAGC | 248 | 22 | 68 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-92a-1-5p | AGGUUGGGAUCGGUUGCAAUGCU | 204 | 23 | 68 |
| hsa-miR-542-3p | UGUGACAGAUUGAUAACUGAAA | 331 | 22 | 66 |
| hsa-miR-431-5p | UGUCUUGCAGGCCGUCAUGCA | 132 | 21 | 65 |
| hsa-miR-1254 | AGCCUGGAAGCUGGAGCCUGCAGU | 270 | 24 | 61 |
| hsa-miR-3158-3p | AAGGGCUUCCUCUCUGCAGGAC | 167 | 22 | 61 |
| hsa-miR-362-5p | AAUCCUUGGAACCUAGGUGUGAGU | 139 | 24 | 61 |
| hsa-miR-30c-2-3p | CUGGGAGAAGGCUGUUUACUCU | 321 | 22 | 59 |
| hsa-miR-4461 | GAUUGAGACUAGUAGGGCUAGGC | 129 | 23 | 59 |
| hsa-miR-3200-3p | CACCUUGCGCUACUCAGGUCUG | 247 | 22 | 57 |
| hsa-miR-215 | AUGACCUAUGAAUUGACAGAC | 451 | 21 | 56 |
| hsa-miR-1185-5p | AGAGGAUACCCUUUGUAUGUU | 368 | 21 | 55 |
| hsa-miR-328 | CUGGCCCUCUCUGCCCUUCCGU | 297 | 22 | 55 |
| hsa-miR-655 | AUAAUACAUGGUUAACCUCUUU | 286 | 22 | 55 |
| hsa-miR-181b-3p | CUCACUGAACAAUGAAUGCAA | 245 | 21 | 54 |
| hsa-miR-376b | AUCAUAGAGGAAAAUCCAUGUU | 452 | 22 | 54 |
| hsa-miR-486-3p | CGGGGCAGCUCAGUACAGGAU | 453 | 21 | 54 |
| hsa-miR-760 | CGGCUCUGGGUCUGUGGGGA | 289 | 20 | 54 |
| hsa-miR-3909 | UGUCCUCUAGGGCCUGCAGUCU | 412 | 22 | 53 |
| hsa-miR-4508 | GCGGGGCUGGGCGCGCG | 135 | 17 | 53 |
| hsa-miR-4521 | GCUAAGGAAGUCCUGUGCUCAG | 233 | 22 | 53 |
| hsa-let-7e-3p | CUAUACGGCCUCCUAGCUUUCC | 290 | 22 | 52 |
| hsa-miR-455-5p | UAUGUGCCUUUGGACUACAUCG | 192 | 22 | 52 |
| hsa-miR-93-3p | ACUGCUGAGCUAGCACUUCCCG | 454 | 22 | 51 |
| hsa-miR-151b | UCGAGGAGCUCACAGUCU | 455 | 18 | 49 |
| hsa-miR-887 | GUGAACGGGCGCCAUCCCGAGG | 456 | 22 | 49 |
| hsa-miR-152 | UCAGUGCAUGACAGAACUUGG | 344 | 21 | 48 |
| hsa-miR-324-3p | ACUGCCCCAGGUGCUGCUGG | 276 | 20 | 48 |
| hsa-miR-1266 | CCUCAGGGCUGUAGAACAGGGCU | 457 | 23 | 47 |
| hsa-miR-302b-3p | UAAGUGCUUCCAUGUUUUAGUAG | 458 | 23 | 47 |
| hsa-miR-548e | AAAAACUGAGACUACUUUUGCA | 459 | 22 | 47 |
| hsa-miR-502-3p | AAUGCACCUGGGCAAGGAUUCA | 281 | 22 | 46 |
| hsa-miR-302d-3p | UAAGUGCUUCCAUGUUUGAGUGU | 460 | 23 | 45 |
| hsa-miR-3943 | UAGCCCCAGGCUUCACUUGGCG | 207 | 23 | 45 |
| hsa-miR-1286 | UGCAGGACCAAGAUGAGCCCU | 293 | 21 | 44 |
| hsa-miR-3605-5p | UGAGGAUGGAUAGCAAGGAAGCC | 189 | 23 | 44 |
| hsa-miR-505-3p | CGUCAACACUUGCUGGUUUCCU | 282 | 22 | 44 |
| hsa-miR-3615 | UCUCUCGGCUCCUCGCGGCUC | 323 | 21 | 43 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-4435 | AUGGCCAGAGCUCACACAGAGG | 230 | 22 | 43 |
| hsa-miR-598 | UACGUCAUCGUUGUCAUCGUCA | 461 | 22 | 43 |
| hsa-miR-126-5p | CAUUAUUACUUUUGGUACGCG | 462 | 21 | 42 |
| hsa-miR-4671-3p | UUAGUGCAUAGUCUUUGGUCU | 301 | 21 | 41 |
| hsa-miR-652-3p | AAUGGCGCCACUAGGGUUGUG | 442 | 21 | 41 |
| hsa-miR-3687 | CCCGGACAGGCGUUCGUGCGACGU | 190 | 24 | 40 |
| hsa-miR-4286 | ACCCCACUCCUGGUACC | 328 | 17 | 40 |
| hsa-miR-590-3p | UAAUUUUAUGUAUAAGCUAGU | 463 | 21 | 40 |
| hsa-miR-1285-3p | UCUGGGCAACAAAGUGAGACCU | 464 | 22 | 39 |
| hsa-miR-2355-5p | AUCCCCAGAUACAAUGGACAA | 593 | 21 | 38 |
| hsa-miR-550a-3p | UGUCUUACUCCCUCAGGCACAU | 283 | 22 | 38 |
| hsa-let-7d-3p | CUAUACGACCUGCUGCCUUUCU | 92 | 22 | 37 |
| hsa-miR-136-5p | ACUCCAUUUGUUUUGAUGAUGGA | 272 | 23 | 37 |
| hsa-miR-1468 | CUCCGUUUGCCUGUUUCGCUG | 296 | 21 | 37 |
| hsa-miR-3609 | CAAAGUGAUGAGUAAUACUGGCUG | 216 | 24 | 37 |
| hsa-miR-548b-5p | AAAAGUAAUUGUGGUUUUGGCC | 304 | 22 | 37 |
| hsa-miR-664-3p | UAUUCAUUUAUCCCCAGCCUACA | 287 | 23 | 37 |
| hsa-miR-99a-3p | CAAGCUCGCUUCUAUGGGUCUG | 367 | 22 | 37 |
| hsa-miR-532-3p | CCUCCCACACCCAAGGCUUGCA | 252 | 22 | 36 |
| hsa-miR-10b-5p | UACCCUGUAGAACCGAAUUUGUG | 465 | 23 | 33 |
| hsa-miR-369-5p | AGAUCGACCGUGUUAUAUUCGC | 357 | 22 | 33 |
| hsa-miR-3161 | CUGAUAAGAACAGAGGCCCAGAU | 466 | 23 | 32 |
| hsa-miR-3940-3p | CAGCCCGGAUCCCAGCCCACUU | 239 | 22 | 32 |
| hsa-miR-663b | GGUGGCCCGGCCGUGCCUGAGG | 180 | 22 | 32 |
| hsa-miR-219-2-3p | AGAAUUGUGGCUGGACAUCUGU | 467 | 22 | 31 |
| hsa-miR-2277-5p | AGCGCGGGCUGAGCGCUGCCAGUC | 735 | 24 | 31 |
| hsa-miR-4448 | GGCUCCUUGGUCUAGGGGUA | 231 | 20 | 31 |
| hsa-miR-339-5p | UCCCUGUCCUCCAGGAGCUCACG | 402 | 23 | 30 |
| hsa-miR-3613-5p | UGUUGUACUUUUUUUUUGUUC | 469 | 22 | 30 |
| hsa-miR-4775 | UUAAUUUUUUGUUUCGGUCACU | 302 | 22 | 30 |
| hsa-miR-212-5p | ACCUUGGCUCUAGACUGCUUACU | 246 | 23 | 29 |
| hsa-miR-324-5p | CGCAUCCCCUAGGGCAUUGGUGU | 354 | 23 | 27 |
| hsa-miR-4326 | UGUUCCUCUGUCUCCCAGAC | 417 | 20 | 27 |
| hsa-miR-582-3p | UAACUGGUUGAACAACUGAACC | 470 | 22 | 27 |
| hsa-miR-34a-3p | CAAUCAGCAAGUAUACUGCCCU | 403 | 22 | 26 |
| hsa-miR-106a-5p | AAAAGUGCUUACAGUGCAGGUAG | 471 | 23 | 25 |
| hsa-miR-4745-5p | UGAGUGGGGCUCCCGGGACGGCG | 219 | 23 | 25 |
| hsa-miR-769-3p | CUGGGAUCUCCGGGGUCUUGGUU | 337 | 23 | 25 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-1268a | CGGGCGUGGUGGUGGGGG | 291 | 18 | 24 |
| hsa-miR-154-3p | AAUCAUACACGGUUGACCUAUU | 472 | 22 | 24 |
| hsa-miR-188-3p | CUCCCACAUGCAGGGUUUGCA | 200 | 21 | 24 |
| hsa-miR-29c-3p | UAGCACCAUUUGAAAUCGGUUA | 473 | 22 | 24 |
| hsa-miR-539-5p | GGAGAAAUUAUCCUUGGUGUGU | 234 | 22 | 24 |
| hsa-miR-766-3p | ACUCCAGCCCCACAGCCUCAGC | 310 | 22 | 24 |
| hsa-miR-30b-3p | CUGGGAGGUGGAUGUUUACUUC | 320 | 22 | 23 |
| hsa-miR-3177-3p | UGCACGGCACUGGGGACACGU | 275 | 21 | 23 |
| hsa-miR-191-3p | GCUGCGCUUGGAUUUCGUCCCC | 474 | 22 | 22 |
| hsa-miR-296-3p | GAGGGUUGGGUGGAGGCUCUCC | 274 | 22 | 22 |
| hsa-miR-296-5p | AGGGCCCCCCUCAAUCCUGU | 258 | 21 | 22 |
| hsa-miR-339-3p | UGAGCGCCUCGACGACAGAGCCG | 228 | 23 | 22 |
| hsa-miR-501-5p | AAUCCUUUGUCCCUGGGUGAGA | 430 | 22 | 22 |
| hsa-miR-200b-3p | UAAUACUGCCUGGUAAUGAUGA | 475 | 22 | 21 |
| hsa-miR-212-3p | UAACAGUCUCCAGUCACGGCC | 348 | 21 | 21 |
| hsa-miR-26b-3p | CCUGUUCUCCAUUACUUGGCUC | 391 | 22 | 21 |
| hsa-miR-665 | ACCAGGAGGCUGAGGCCCCU | 309 | 20 | 21 |
| hsa-miR-668 | UGUCACUCGGCUCGGCCCACUAC | 476 | 23 | 21 |
| hsa-miR-146a-5p | UGAGAACUGAAUUCCAUGGGUU | 477 | 22 | 20 |
| hsa-miR-1973 | ACCGUGCAAAGGUAGCAUA | 171 | 19 | 20 |
| hsa-miR-210 | CUGUGCGUGUGACAGCGGCUGA | 478 | 22 | 20 |
| hsa-miR-3607-5p | GCAUGUGAUGAAGCAAAUCAGU | 249 | 22 | 20 |
| hsa-miR-378a-5p | CUCCUGACUCCAGGUCCUGUGU | 217 | 22 | 20 |
| hsa-miR-4449 | CGUCCCGGGGCUGCGCGAGGCA | 155 | 22 | 20 |
| hsa-miR-138-5p | AGCUGGUGUUGUGAAUCAGGCCG | 379 | 23 | 19 |
| hsa-miR-146b-3p | UGCCCUGUGGACUCAGUUCUGG | 381 | 22 | 18 |
| hsa-miR-3065-3p | UCAGCACCAGGAUAUUGUUGGAG | 350 | 23 | 18 |
| hsa-miR-4417 | GGUGGGCUUCCCGGAGGG | 175 | 18 | 18 |
| hsa-miR-497-5p | CAGCAGCACACUGUGGUUUGU | 479 | 21 | 18 |
| hsa-miR-500a-5p | UAAUCCUUGCUACCUGGGUGAGA | 303 | 23 | 18 |
| hsa-miR-625-3p | GACUAUAGAACUUUCCCCCUCA | 307 | 22 | 18 |
| hsa-miR-628-3p | UCUAGUAAGAGUGGCAGUCGA | 335 | 21 | 18 |
| hsa-miR-1343 | CUCCUGGGGCCCGCACUCUCGC | 378 | 22 | 17 |
| hsa-miR-3648 | AGCCGCGGGAUCGCCGAGGG | 259 | 21 | 17 |
| hsa-miR-432-3p | CUGGAUGGCUCCUCCAUGUCU | 262 | 21 | 17 |
| hsa-miR-4482-3p | UUUCUAUUUCUCAGUGGGGCUC | 361 | 22 | 17 |
| hsa-miR-542-5p | UCGGGGAUCAUCAUGUCACGAGA | 433 | 23 | 17 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-551b-3p | GCGACCCAUACUUGGUUUCAG | 434 | 21 | 17 |
| hsa-miR-7-1-3p | CAACAAAUCACAGUCUGCCAUA | 480 | 22 | 17 |
| hsa-miR-219-1-3p | AGAGUUGAGUCUGGACGUCCCG | 390 | 22 | 16 |
| hsa-miR-3656 | GGCGGGUGCGGGGGUGG | 251 | 17 | 16 |
| hsa-miR-3661 | UGACCUGGGACUCGGACAGCUG | 481 | 22 | 16 |
| hsa-miR-411-3p | UAUGUAACACGGUCCACUAACC | 482 | 22 | 16 |
| hsa-miR-5096 | GUUUCACCAUGUUGGUCAGGC | 220 | 21 | 16 |
| hsa-miR-577 | UAGAUAAAAUAUUGGUACCUG | 436 | 21 | 16 |
| hsa-let-7i-3p | CUGCGCAAGCUACUGCCUUGCU | 483 | 22 | 15 |
| hsa-miR-132-5p | ACCGUGGCUUUCGAUUGUUACU | 315 | 22 | 15 |
| hsa-miR-140-5p | CAGUGGUUUUACCCUAUGGUAG | 380 | 22 | 15 |
| hsa-miR-195-5p | UAGCAGCACAGAAAUAUUGGC | 346 | 21 | 15 |
| hsa-miR-3187-3p | UUGGCCAUGGGGCUGCGCGG | 322 | 20 | 15 |
| hsa-miR-342-5p | AGGGGUGCUAUCUGUGAUUGA | 278 | 21 | 15 |
| hsa-miR-34b-3p | CAAUCACUAACUCCACUGCCAU | 404 | 22 | 15 |
| hsa-miR-4661-5p | AACUAGCUCUGUGGAUCCUGAC | 484 | 22 | 15 |
| hsa-miR-584-5p | UUAUGGUUUGCCUGGGACUGAG | 485 | 22 | 15 |
| hsa-miR-744-3p | CUGUUGCCACUAACCUCAACCU | 486 | 22 | 15 |
| hsa-miR-770-5p | UCCAGUACCACGUGUCAGGGCCA | 487 | 23 | 15 |
| hsa-miR-3677-3p | CUCGUGGGCUCUGGCCACGCC | 356 | 22 | 14 |
| hsa-miR-425-3p | AUCGGGAAUGUCGUGUCCGCCC | 358 | 22 | 14 |
| hsa-miR-548ah-3p | CAAAAACUGCAGUUACUUUUGC | 149 | 22 | 14 |
| hsa-miR-5699 | UCCUGUCUUUCCUUGUUGGAGC | 488 | 22 | 14 |
| hsa-miR-582-5p | UUACAGUUGUUCAACCAGUUACU | 489 | 23 | 14 |
| hsa-miR-1185-2-3p | AUAUACAGGGGGAGACUCUCAU | 314 | 22 | 13 |
| hsa-miR-1249 | ACGCCCUUCCCCCCUUCUUCA | 490 | 22 | 13 |
| hsa-miR-1255a | AGGAUGAGCAAAGAAAGUAGAUU | 341 | 23 | 13 |
| hsa-miR-1910 | CCAGUCCUGUGCCUGCCGCCU | 236 | 21 | 13 |
| hsa-miR-301a-5p | GCUCUGACUUUAUUGCACUACU | 491 | 22 | 13 |
| hsa-miR-5001-3p | UUCUGCCUCUGUCCAGGUCCUU | 492 | 22 | 13 |
| hsa-miR-5094 | AAUCAGUGAAUGCCUUGAACCU | 493 | 22 | 13 |
| hsa-miR-628-5p | AUGCUGACAUAUUUACUAGAGG | 440 | 22 | 13 |
| hsa-miR-629-5p | UGGGUUUACGUUGGGAGAACU | 441 | 21 | 13 |
| hsa-miR-937 | AUCCGCGCUCUGACUCUCUGCC | 312 | 22 | 13 |
| hsa-miR-940 | AAGGCAGGGCCCCCGCUCCCC | 366 | 21 | 13 |
| hsa-miR-1248 | ACCUUCUUGUAUAAGCACUGUGCUAAA | 269 | 27 | 12 |
| hsa-miR-194-5p | UGUAACAGCAACUCCAUGUGGA | 345 | 22 | 12 |
| hsa-miR-199b-3p | ACAGUAGUCUGCACAUUGGUUA | 494 | 22 | 12 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-22-5p | AGUUCUUCAGUGGCAAGCUUUA | 495 | 22 | 12 |
| hsa-miR-3605-3p | CCUCCGUGUUACCUGUCCUCUAG | 496 | 23 | 12 |
| hsa-miR-3654 | GACUGGACAAGCUGAGGAA | 325 | 19 | 12 |
| hsa-miR-504 | AGACCCUGGUCUGCACUCUAUC | 497 | 22 | 12 |
| hsa-miR-1291 | UGGCCCUGACUGAAGACCAGCAGU | 294 | 24 | 11 |
| hsa-miR-1299 | UUCUGGAAUUCUGUGUGAGGGA | 498 | 22 | 11 |
| hsa-miR-188-5p | CAUCCCUUGCAUGGUGGAGGG | 499 | 21 | 11 |
| hsa-miR-222-5p | CUCAGUAGCCAGUGUAGAUCCU | 349 | 22 | 11 |
| hsa-miR-331-5p | CUAGGUAUGGUCCCAGGGAUCC | 500 | 22 | 11 |
| hsa-miR-3939 | UACGCGCAGACCACAGGAUGUC | 261 | 22 | 11 |
| hsa-miR-154-5p | UAGGUUAUCCGUGUUGCCUUCG | 501 | 22 | 10 |
| hsa-miR-18a-3p | ACUGCCCUAAGUGCUCCUUCUGG | 502 | 23 | 10 |
| hsa-miR-1908 | CGGCGGGGACGGCGAUUGGUC | 383 | 21 | 10 |
| hsa-miR-200c-3p | UAAUACUGCCGGGUAAUGAUGGA | 347 | 23 | 10 |
| hsa-miR-2116-3p | CCUCCCAUGCCAAGAACUCCC | 318 | 21 | 10 |
| hsa-miR-302a-3p | UAAGUGCUUCCAUGUUUUGGUGA | 503 | 23 | 10 |
| hsa-miR-3174 | UAGUGAGUUAGAGAUGCAGAGCC | 353 | 23 | 10 |
| hsa-miR-326 | CCUCUGGGCCCUUCCUCCAG | 504 | 20 | 10 |
| hsa-let-7g-3p | CUGUACAGGCCACUGCCUUGC | 505 | 21 | 9 |
| hsa-miR-141-3p | UAACACUGUCUGGUAAAGAUGG | 295 | 22 | 9 |
| hsa-miR-24-1-5p | UGCCUACUGAGCUGAUAUCAGU | 506 | 22 | 9 |
| hsa-miR-3115 | AUAUGGGUUUACUAGUUGGU | 351 | 20 | 9 |
| hsa-miR-3180-3p | UGGGGCGGAGCUUCCGGAGGCC | 400 | 22 | 9 |
| hsa-miR-33a-5p | GUGCAUUGUAGUUGCAUUGCA | 355 | 21 | 9 |
| hsa-miR-34c-3p | AAUCACUAACCACACGGCCAGG | 405 | 22 | 9 |
| hsa-miR-3929 | GAGGCUGAUGUGAGUAGACCACU | 218 | 23 | 9 |
| hsa-miR-4517 | AAAUAUGAUGAAACUCACAGCUGAG | 507 | 25 | 9 |
| hsa-miR-576-3p | AAGAUGUGGAAAAAUUGGAAUC | 508 | 22 | 9 |
| hsa-miR-1229 | CUCUCACCACUGCCCUCCCACAG | 509 | 23 | 8 |
| hsa-miR-1289 | UGGAGUCCAGGAAUCUGCAUUUU | 343 | 23 | 8 |
| hsa-miR-1915-5p | ACCUUGCCUUGCUGCCCGGGCC | 385 | 22 | 8 |
| hsa-miR-23b-5p | UGGGUUCCUGGCAUGCUGAUUU | 510 | 22 | 8 |
| hsa-miR-302a-5p | ACUUAAACGUGGAUGUACUUGCU | 511 | 23 | 8 |
| hsa-miR-3938 | AAUUCCCUUGUAGAUAACCCGG | 512 | 22 | 8 |
| hsa-miR-4466 | GGGUGCGGGCCGGCGGGG | 264 | 18 | 8 |
| hsa-miR-4786-5p | UGAGACCAGGACUGGAUGCACC | 197 | 22 | 8 |
| hsa-miR-589-3p | UCAGAACAAAUGCCGGUUCCCAGA | 438 | 24 | 8 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-616-5p | ACUCAAAACCCUUCAGUGACUU | 439 | 22 | 8 |
| hsa-miR-943 | CUGACUGUUGCCGUCCUCCAG | 338 | 21 | 8 |
| hsa-miR-1237 | UCCUUCUGCUCCGUCCCCCAG | 370 | 21 | 7 |
| hsa-miR-1915-3p | CCCCAGGGCGACGCGGCGGG | 384 | 20 | 7 |
| hsa-miR-3620 | UCACCCUGCAUCCCGCACCCAG | 324 | 22 | 7 |
| hsa-miR-3691-5p | AGUGGAUGAUGGAGACUCGGUAC | 409 | 23 | 7 |
| hsa-miR-4426 | GAAGAUGGACGUACUUU | 359 | 17 | 7 |
| hsa-let-7a-2-3p | CUGUACAGCCUCCUAGCUUUCC | 513 | 22 | 6 |
| hsa-miR-10a-3p | CAAAUUCGUAUCUAGGGGAAUA | 514 | 22 | 6 |
| hsa-miR-1287 | UGCUGGAUCAGUGGUUCGAGUC | 515 | 22 | 6 |
| hsa-miR-145-5p | GUCCAGUUUUCCCAGGAAUCCCU | 516 | 23 | 6 |
| hsa-miR-29b-1-5p | GCUGGUUUCAUAUGGUGGUUUAGA | 517 | 24 | 6 |
| hsa-miR-3128 | UCUGGCAAGUAAAAAACUCUCAU | 518 | 23 | 6 |
| hsa-miR-33b-5p | GUGCAUUGCUGUUGCAUUGC | 519 | 20 | 6 |
| hsa-miR-3681-5p | UAGUGGAUGAUGCACUCUGUGC | 327 | 22 | 6 |
| hsa-miR-3685 | UUUCCUACCCUACCUGAAGACU | 520 | 22 | 6 |
| hsa-miR-3918 | ACAGGGCCGCAGAUGGAGACU | 521 | 21 | 6 |
| hsa-miR-551b-5p | GAAAUCAAGCGUGGGUGAGACC | 522 | 22 | 6 |
| hsa-miR-1273f | GGAGAUGGAGGUUGCAGUG | 292 | 19 | 5 |
| hsa-miR-1273g-3p | ACCACUGCACUCCAGCCUGAG | 210 | 21 | 5 |
| hsa-miR-1304-5p | UUUGAGGCUACAGUGAGAUGUG | 523 | 22 | 5 |
| hsa-miR-1538 | CGGCCCGGGCUGCUGCUGUUCCU | 524 | 23 | 5 |
| hsa-miR-181c-3p | AACCAUCGACCGUUGAGUGGAC | 525 | 22 | 5 |
| hsa-miR-193a-5p | UGGGUCUUUGCGGGCGAGAUGA | 526 | 22 | 5 |
| hsa-miR-208b | AUAAGACGAACAAAAGGUUUGU | 388 | 22 | 5 |
| hsa-miR-219-5p | UGAUUGUCCAAACGCAAUUCU | 527 | 21 | 5 |
| hsa-miR-3159 | UAGGAUUACAAGUGUCGGCCAC | 528 | 22 | 5 |
| hsa-miR-3173-5p | UGCCCUGCCUGUUUUCUCCUUU | 529 | 22 | 5 |
| hsa-miR-3175 | CGGGGAGAGAACGCAGUGACGU | 530 | 22 | 5 |
| hsa-miR-3200-5p | AAUCUGAGAAGGCGCACAAGGU | 531 | 22 | 5 |
| hsa-miR-3662 | GAAAAUGAUGAGUAGUGACUGAUG | 326 | 24 | 5 |
| hsa-miR-3928 | GGAGGAACCUUGGAGCUUCGGC | 413 | 22 | 5 |
| hsa-miR-4709-3p | UUGAAGAGGAGGUGCUCUGUAGC | 532 | 23 | 5 |
| hsa-miR-4787-3p | GAUGCGCCGCCCACUGCCCCGCGC | 533 | 24 | 5 |
| hsa-miR-499a-5p | UUAAGACUUGCAGUGAUGUUU | 534 | 21 | 5 |
| hsa-miR-545-3p | UCAGCAAACAUUUAUUGUGUGC | 242 | 22 | 5 |
| hsa-miR-548u | CAAAGACUGCAAUUACUUUUGCG | 535 | 23 | 5 |
| hsa-miR-659-5p | AGGACCUUCCCUGAACCAAGGA | 364 | 22 | 5 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-1257 | AGUGAAUGAUGGGUUCUGACC | 372 | 21 | 4 |
| hsa-miR-1292 | UGGGAACGGGUUCCGGCAGACGCUG | 536 | 25 | 4 |
| hsa-miR-1914-5p | CCCUGUGCCCGGCCCACUUCUG | 537 | 22 | 4 |
| hsa-miR-195-3p | CCAAUAUUGGCUGUGCUGCUCC | 538 | 22 | 4 |
| hsa-miR-2110 | UUGGGGAAACGGCCGCUGAGUG | 389 | 22 | 4 |
| hsa-miR-302c-5p | UUUAACAUGGGGGUACCUGCUG | 539 | 22 | 4 |
| hsa-miR-3126-3p | CAUCUGGCAUCCGUCACACAGA | 394 | 22 | 4 |
| hsa-miR-3126-5p | UGAGGGACAGAUGCCAGAAGCA | 352 | 22 | 4 |
| hsa-miR-3150a-5p | CAACCUCGACGAUCUCCUCAGC | 540 | 22 | 4 |
| hsa-miR-3157-3p | CUGCCCUAGUCUAGCUGAAGCU | 399 | 22 | 4 |
| hsa-miR-323b-3p | CCCAAUACACGGUCGACCUCUU | 541 | 22 | 4 |
| hsa-miR-335-3p | UUUUUCAUUAUUGCUCCUGACC | 542 | 22 | 4 |
| hsa-miR-3607-3p | ACUGUAAACGCUUUCUGAUG | 543 | 20 | 4 |
| hsa-miR-3653 | CUAAGAAGUUGACUGAAG | 544 | 18 | 4 |
| hsa-miR-3663-3p | UGAGCACCACACAGGCCGGGCGC | 545 | 23 | 4 |
| hsa-miR-376a-5p | GUAGAUUCUCCUUCUAUGAGUA | 410 | 22 | 4 |
| hsa-miR-4423-3p | AUAGGCACCAAAAAGCAACAA | 662 | 21 | 4 |
| hsa-miR-4423-5p | AGUUGCCUUUUUGUUCCCAUGC | 263 | 22 | 4 |
| hsa-miR-4463 | GAGACUGGGGUGGGGCC | 300 | 17 | 4 |
| hsa-miR-449a | UGGCAGUGUAUUGUUAGCUGGU | 547 | 22 | 4 |
| hsa-miR-4511 | GAAGAACUGUUGCAUUUGCCCU | 548 | 22 | 4 |
| hsa-miR-4640-3p | CACCCCCUGUUUCCUGGCCCAC | 329 | 22 | 4 |
| hsa-miR-4800-3p | CAUCCGUCCGUCUGUCCAC | 549 | 19 | 4 |
| hsa-miR-505-5p | GGGAGCCAGGAAGUAUUGAUGU | 550 | 22 | 4 |
| hsa-miR-548a-3p | CAAAACUGGCAAUUACUUUUGC | 551 | 22 | 4 |
| hsa-miR-570-3p | CGAAAACAGCAAUUACCUUUGC | 333 | 22 | 4 |
| hsa-miR-663a | AGGCGGGGCGCCGCGGGACCGC | 365 | 22 | 4 |
| hsa-miR-877-3p | UCCUCUUCUCCCUCCUCCCAG | 552 | 21 | 4 |
| hsa-miR-103a-2-5p | AGCUUCUUUACAGUGCUGCCUUG | 553 | 23 | 3 |
| hsa-miR-1268b | CGGGCGUGGUGGUGGGGGUG | 554 | 20 | 3 |
| hsa-miR-1270 | CUGGAGAUAUGGAAGAGCUGUGU | 555 | 23 | 3 |
| hsa-miR-1293 | UGGGUGGUCGGAGAUUUGUGC | 556 | 22 | 3 |
| hsa-miR-1322 | GAUGAUGCUGCUGAUGCUG | 557 | 19 | 3 |
| hsa-miR-150-5p | UCUCCCAACCCUUGUACCAGUG | 558 | 22 | 3 |
| hsa-miR-190b | UGAUAUGUUUGAUAUUGGGUU | 559 | 21 | 3 |
| hsa-miR-193a-3p | AACUGGCCUACAAAGUCCCAGU | 386 | 22 | 3 |
| hsa-miR-193b-5p | CGGGGUUUUGAGGGCGAGAUGA | 560 | 22 | 3 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-199a-5p | CCCAGUGUUCAGACUACCUGUUC | 273 | 23 | 3 |
| hsa-miR-20a-3p | ACUGCAUUAUGAGCACUUAAAG | 561 | 22 | 3 |
| hsa-miR-216a | UAAUCUCAGCUGGCAACUGUGA | 562 | 22 | 3 |
| hsa-miR-2682-5p | CAGGCAGUGACUGUUCAGACGUC | 563 | 23 | 3 |
| hsa-miR-2964a-5p | AGAUGUCCAGCCACAAUUCUCG | 564 | 22 | 3 |
| hsa-miR-3177-5p | UGUGUACACACGUGCCAGGCGCU | 565 | 23 | 3 |
| hsa-miR-320c | AAAAGCUGGGUUGAGAGGGU | 566 | 20 | 3 |
| hsa-miR-323a-5p | AGGUGGUCCGUGGCGCGUUCGC | 567 | 22 | 3 |
| hsa-miR-3622a-5p | CAGGCACGGGAGCUCAGGUGAG | 568 | 22 | 3 |
| hsa-miR-3912 | UAACGCAUAAUAUGGACAUGU | 569 | 21 | 3 |
| hsa-miR-3934 | UCAGGUGUGGAAACUGAGGCAG | 570 | 22 | 3 |
| hsa-miR-3942-3p | UUUCAGAUAACAGUAUUACAU | 414 | 21 | 3 |
| hsa-miR-3942-5p | AAGCAAUACUGUUACCUGAAAU | 571 | 22 | 3 |
| hsa-miR-4523 | GACCGAGAGGGCCUCGGCUGU | 572 | 21 | 3 |
| hsa-miR-4640-5p | UGGGCCAGGGAGCAGCUGGUGGG | 573 | 23 | 3 |
| hsa-miR-4671-5p | ACCGAAGACUGUGCGCUAAUCU | 574 | 22 | 3 |
| hsa-miR-4709-5p | ACAACAGUGACUUGCUCUCCAA | 575 | 22 | 3 |
| hsa-miR-4731-3p | CACACAAGUGGCCCCCAACACU | 425 | 22 | 3 |
| hsa-miR-4731-5p | UGCUGGGGGCCACAUGAGUGUG | 576 | 22 | 3 |
| hsa-miR-4762-5p | CCAAAUCUUGAUCAGAAGCCU | 577 | 21 | 3 |
| hsa-miR-5010-5p | AGGGGGAUGGCAGAGCAAAAUU | 578 | 22 | 3 |
| hsa-miR-502-5p | AUCCUUGCUAUCUGGGUGCUA | 579 | 21 | 3 |
| hsa-miR-548d-5p | AAAAGUAAUUGUGGUUUUUGCC | 580 | 22 | 3 |
| hsa-miR-548i | AAAAGUAAUUGCGGAUUUUGCC | 581 | 22 | 3 |
| hsa-miR-548j | AAAAGUAAUUGCGGUCUUUGGU | 582 | 22 | 3 |
| hsa-miR-5587-3p | GCCCCGGGCAGUGUGAUCAUC | 284 | 21 | 3 |
| hsa-miR-1225-3p | UGAGCCCCUGUGCCGCCCCCAG | 369 | 22 | 2 |
| hsa-miR-1227 | CGUGCCACCCUUUUCCCCAG | 583 | 20 | 2 |
| hsa-miR-1252 | AGAAGGAAAUUGAAUUCAUUUA | 371 | 22 | 2 |
| hsa-miR-1280 | UCCCACCGCUGCCACCC | 584 | 17 | 2 |
| hsa-miR-1288 | UGGACUGCCCUGAUCUGGAGA | 585 | 21 | 2 |
| hsa-miR-1303 | UUUAGAGACGGGGUCUUGCUCU | 586 | 22 | 2 |
| hsa-miR-1306-3p | ACGUUGGCUCUGGUGGUG | 376 | 18 | 2 |
| hsa-miR-139-5p | UCUACAGUGCACGUGUCUCCAG | 587 | 22 | 2 |
| hsa-miR-149-3p | AGGGAGGGACGGGGGCUGUGC | 588 | 21 | 2 |
| hsa-miR-16-1-3p | CCAGUAUUAACUGUGCUGCUGA | 589 | 22 | 2 |
| hsa-miR-1909-5p | UGAGUGCCGGUGCCUGCCCUG | 590 | 21 | 2 |
| hsa-miR-224-5p | CAAGUCACUAGUGGUUCCGUU | 591 | 21 | 2 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-2276 | UCUGCAAGUGUCAGAGGCGAGG | 592 | 22 | 2 |
| hsa-miR-2355-3p | AUUGUCCUUGCUGUUUGGAGAU | 468 | 22 | 2 |
| hsa-miR-2964a-3p | AGAAUUGCGUUUGGACAAUCAGU | 392 | 23 | 2 |
| hsa-miR-29c-5p | UGACCGAUUUCUCCUGGUGUUC | 594 | 22 | 2 |
| hsa-miR-3074-3p | GAUAUCAGCUCAGUAGGCACCG | 595 | 22 | 2 |
| hsa-miR-3120-3p | CACAGCAAGUGUAGACAGGCA | 596 | 21 | 2 |
| hsa-miR-3130-5p | UACCCAGUCUCCGGUGCAGCC | 396 | 21 | 2 |
| hsa-miR-3140-3p | AGCUUUUGGGAAUUCAGGUAGU | 597 | 22 | 2 |
| hsa-miR-3155a | CCAGGCUCUGCAGUGGGAACU | 398 | 21 | 2 |
| hsa-miR-3163 | UAUAAAAUGAGGGCAGUAAGAC | 598 | 22 | 2 |
| hsa-miR-3167 | AGGAUUUCAGAAAUACUGGUGU | 599 | 22 | 2 |
| hsa-miR-363-5p | CGGGUGGAUCACGAUGCAAUUU | 600 | 22 | 2 |
| hsa-miR-3676-3p | CCGUGUUUCCCCCACGCUUU | 408 | 20 | 2 |
| hsa-miR-378g | ACUGGGCUUGGAGUCAGAAG | 411 | 20 | 2 |
| hsa-miR-4467 | UGGCGGCGGUAGUUAUGGGCUU | 360 | 22 | 2 |
| hsa-miR-4498 | UGGGCUGGCAGGGCAAGUGCUG | 601 | 22 | 2 |
| hsa-miR-4654 | UGUGGGAUCUGGAGGCAUCUGG | 420 | 22 | 2 |
| hsa-miR-4659a-3p | UUUCUUCUUAGACAUGGCAACG | 603 | 22 | 2 |
| hsa-miR-4662a-5p | UUAGCCAAUUGUCCAUCUUUAG | 604 | 22 | 2 |
| hsa-miR-4683 | UGGAGAUCCAGUGCUCGCCCGAU | 605 | 23 | 2 |
| hsa-miR-4738-3p | UGAAACUGGAGCGCCUGGAGGA | 606 | 22 | 2 |
| hsa-miR-4746-3p | AGCGGUGCUCCUGCGGGCCGA | 607 | 21 | 2 |
| hsa-miR-4748 | GAGGUUUGGGGAGGAUUUGCU | 608 | 21 | 2 |
| hsa-miR-4792 | CGGUGAGCGCUCGCUGGC | 363 | 18 | 2 |
| hsa-miR-491-5p | AGUGGGGAACCCUUCCAUGAGG | 429 | 22 | 2 |
| hsa-miR-5000-3p | UCAGGACACUUCUGAACUUGGA | 609 | 22 | 2 |
| hsa-miR-503 | UAGCAGCGGGAACAGUUCUGCAG | 610 | 23 | 2 |
| hsa-miR-5189 | UCUGGGCACAGGCGGAUGGACAGG | 611 | 24 | 2 |
| hsa-miR-548aq-3p | CAAAAACUGCAAUUACUUUUGC | 612 | 22 | 2 |
| hsa-miR-548av-3p | AAAACUGCAGUUACUUUUGC | 613 | 20 | 2 |
| hsa-miR-5584-5p | CAGGGAAAUGGGAAGAACUAGA | 332 | 22 | 2 |
| hsa-miR-5690 | UCAGCUACUACCUCUAUUAGG | 435 | 21 | 2 |
| hsa-miR-573 | CUGAAGUGAUGUGUAACUGAUCAG | 305 | 24 | 2 |
| hsa-miR-597 | UGUGUCACUCGAUGACCACUGU | 614 | 22 | 2 |
| hsa-miR-622 | ACAGUCUGCUGAGGUUGGAGC | 615 | 21 | 2 |
| hsa-miR-636 | UGUGCUUGCUCGUCCCGCCCGCA | 616 | 23 | 2 |
| hsa-miR-1193 | GGGAUGGUAGACCGGUGACGUGC | 617 | 23 | 1 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-1224-3p | CCCCACCUCCUCUCUCCUCAG | 618 | 21 | 1 |
| hsa-miR-122-5p | UGGAGUGUGACAAUGGUGUUUG | 720 | 22 | 1 |
| hsa-miR-1228-5p | GUGGGCGGGGGCAGGUGUGUG | 620 | 21 | 1 |
| hsa-miR-1244 | AAGUAGUUGGUUUGUAUGAGAUGGUU | 340 | 26 | 1 |
| hsa-miR-1247-5p | ACCCGUCCCGUUCGUCCCCGGA | 621 | 22 | 1 |
| hsa-miR-1255b-5p | CGGAUGAGCAAAGAAAGUGGUU | 622 | 22 | 1 |
| hsa-miR-1269b | CUGGACUGAGCCAUGCUACUGG | 623 | 22 | 1 |
| hsa-miR-1272 | GAUGAUGAUGGCAGCAAAUUCUGAAA | 624 | 26 | 1 |
| hsa-miR-1273c | GGCGACAAAACGAGACCCUGUC | 625 | 22 | 1 |
| hsa-miR-1273e | UUGCUUGAACCCAGGAAGUGGA | 342 | 22 | 1 |
| hsa-miR-1282 | UCGUUUGCCUUUUCUGCUU | 626 | 20 | 1 |
| hsa-miR-1290 | UGGAUUUUUGGAUCAGGGA | 375 | 19 | 1 |
| hsa-miR-1294 | UGUGAGGUUGGCAUUGUUGUCU | 627 | 22 | 1 |
| hsa-miR-1306-5p | CCACCUCCCCUGCAAACGUCCA | 628 | 22 | 1 |
| hsa-miR-1321 | CAGGGAGGUGAAUGUGAU | 377 | 18 | 1 |
| hsa-miR-135a-5p | UAUGGCUUUUUAUUCCUAUGUGA | 629 | 23 | 1 |
| hsa-miR-137 | UUAUUGCUUAAGAAUACGCGUAG | 630 | 23 | 1 |
| hsa-miR-142-5p | CAUAAAGUAGAAAGCACUACU | 631 | 21 | 1 |
| hsa-miR-143-5p | GGUGCAGUGCUGCAUCUCUGGU | 632 | 22 | 1 |
| hsa-miR-15a-3p | CAGGCCAUAUUGUGCUGCCUCA | 633 | 22 | 1 |
| hsa-miR-186-3p | GCCCAAAGGUGAAUUUUUUGGG | 382 | 22 | 1 |
| hsa-miR-192-3p | CUGCCAAUUCCAUAGGUCACAG | 634 | 22 | 1 |
| hsa-miR-19b-1-5p | AGUUUUGCAGGUUUGCAUCCAGC | 387 | 23 | 1 |
| hsa-miR-200a-3p | UAACACUGUCUGGUAACGAUGU | 635 | 22 | 1 |
| hsa-miR-204-3p | GCUGGGAAGGCAAAGGGACGU | 636 | 21 | 1 |
| hsa-miR-214-3p | ACAGCAGGCACAGACAGGCAGU | 637 | 22 | 1 |
| hsa-miR-29a-5p | ACUGAUUUCUUUUGGUGUUCAG | 393 | 22 | 1 |
| hsa-miR-3064-5p | UCUGGCUGUUGUGGUGUGCAA | 638 | 21 | 1 |
| hsa-miR-3116 | UGCCUGGAACAUAGUAGGGACU | 639 | 22 | 1 |
| hsa-miR-3125 | UAGAGGAAGCUGUGGAGAGA | 640 | 20 | 1 |
| hsa-miR-3127-3p | UCCCCUUCUGCAGGCCUGCUGG | 641 | 22 | 1 |
| hsa-miR-3130-3p | GCUGCACCGGAGACUGGGUAA | 395 | 21 | 1 |
| hsa-miR-3140-5p | ACCUGAAUUACCAAAAGCUUU | 397 | 21 | 1 |
| hsa-miR-3157-5p | UUCAGCCAGGCUAGUGCAGUCU | 642 | 22 | 1 |
| hsa-miR-3179 | AGAAGGGGUGAAAUUUAAACGU | 643 | 22 | 1 |
| hsa-miR-3181 | AUCGGGCCCUCGGCGCCGG | 644 | 19 | 1 |
| hsa-miR-3187-5p | CCUGGGCAGCGUGUGGCUGAAGG | 645 | 23 | 1 |
| hsa-miR-3190-5p | UCUGGCCAGCUACGUCCCCA | 646 | 20 | 1 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-3198 | GUGGAGUCCUGGGGAAUGGAGA | 647 | 22 | 1 |
| hsa-miR-320b | AAAAGCUGGGUUGAGAGGGCAA | 648 | 22 | 1 |
| hsa-miR-323b-5p | AGGUUGUCCGUGGUGAGUUCGCA | 401 | 23 | 1 |
| hsa-miR-3591-5p | UUUAGUGUGAUAAUGGCGUUUGA | 649 | 23 | 1 |
| hsa-miR-3619-5p | UCAGCAGGCAGGCUGGUGCAGC | 650 | 22 | 1 |
| hsa-miR-3659 | UGAGUGUUGUCUACGAGGGCA | 651 | 21 | 1 |
| hsa-miR-3674 | AUUGUAGAACCUAAGAUUGGCC | 652 | 22 | 1 |
| hsa-miR-3679-3p | CUUCCCCCCAGUAAUCUUCAUC | 653 | 22 | 1 |
| hsa-miR-375 | UUUGUUCGUUCGGCUCGCGUGA | 654 | 22 | 1 |
| hsa-miR-378b | ACUGGACUUGGAGGCAGAA | 655 | 19 | 1 |
| hsa-miR-3908 | GAGCAAUGUAGGUAGACUGUUU | 656 | 22 | 1 |
| hsa-miR-3911 | UGUGUGGAUCCUGGAGGAGGCA | 657 | 22 | 1 |
| hsa-miR-3913-5p | UUUGGGACUGAUCUUGAUGUCU | 658 | 22 | 1 |
| hsa-miR-3917 | GCUCGGACUGAGCAGGUGGG | 659 | 20 | 1 |
| hsa-miR-3944-3p | UUCGGGCUGGCCUGCUGCUCCGG | 660 | 23 | 1 |
| hsa-miR-429 | UAAUACUGUCUGGUAAAACCGU | 661 | 22 | 1 |
| hsa-miR-4421 | ACCUGUCUGUGGAAAGGAGCUA | 718 | 22 | 1 |
| hsa-miR-4443 | UUGGAGGCGUGGGUUUU | 663 | 17 | 1 |
| hsa-miR-4459 | CCAGGAGGCGGAGGAGGUGGAG | 664 | 22 | 1 |
| hsa-miR-4473 | CUAGUGCUCUCCGUUACAAGUA | 665 | 22 | 1 |
| hsa-miR-4479 | CGCGCGGCCGUGCUCGGAGCAG | 666 | 22 | 1 |
| hsa-miR-4497 | CUCCGGGACGGCUGGGC | 232 | 17 | 1 |
| hsa-miR-4504 | UGUGACAAUAGAGAUGAACAUG | 667 | 22 | 1 |
| hsa-miR-4520b-3p | UUUGGACAGAAAACACGCAGGU | 668 | 22 | 1 |
| hsa-miR-452-5p | AACUGUUUGCAGAGGAAACUGA | 669 | 22 | 1 |
| hsa-miR-4636 | AACUCGUGUUCAAAGCCUUUAG | 670 | 22 | 1 |
| hsa-miR-4659b-3p | UUUCUUCUUAGACAUGGCAGCU | 671 | 22 | 1 |
| hsa-miR-4664-3p | CUUCCGGUCUGUGAGCCCCGUC | 672 | 22 | 1 |
| hsa-miR-4665-5p | CUGGGGGACGCGUGAGCGCGAGC | 673 | 23 | 1 |
| hsa-miR-4666a-5p | AUACAUGUCAGAUUGUAUGCC | 674 | 21 | 1 |
| hsa-miR-4673 | UCCAGGCAGGAGCCGGACUGGA | 422 | 22 | 1 |
| hsa-miR-4681 | AACGGGAAUGCAGGCUGUAUCU | 675 | 22 | 1 |
| hsa-miR-4682 | UCUGAGUUCCUGGAGCCUGGUCU | 676 | 23 | 1 |
| hsa-miR-4690-5p | GAGCAGGCGAGGCUGGGCUGAA | 677 | 22 | 1 |
| hsa-miR-4699-5p | AGAAGAUUGCAGAGUAAGUUCC | 678 | 22 | 1 |
| hsa-miR-4700-3p | CACAGGACUGACUCCUCACCCCAGUG | 424 | 26 | 1 |
| hsa-miR-4706 | AGCGGGGAGGAAGUGGGCGCUGCUU | 679 | 25 | 1 |

TABLE 6-continued

Cells EI

| CELLS - CTX0E03 07EI MIRNA | MIRNA.SEQUENCE | SEQ ID NO: | MIRNA LENGTH | READ COUNTS |
|---|---|---|---|---|
| hsa-miR-4721 | UGAGGGCUCCAGGUGACGGUGG | 680 | 22 | 1 |
| hsa-miR-4728-3p | CAUGCUGACCUCCCUCCUGCCCCAG | 681 | 25 | 1 |
| hsa-miR-4742-5p | UCAGGCAAAGGGAUAUUUACAGA | 682 | 23 | 1 |
| hsa-miR-4747-3p | AAGGCCCGGGCUUUCCUCCCAG | 683 | 22 | 1 |
| hsa-miR-4749-5p | UGCGGGGACAGGCCAGGGCAUC | 684 | 22 | 1 |
| hsa-miR-4755-3p | AGCCAGGCUCUGAAGGGAAAGU | 685 | 22 | 1 |
| hsa-miR-4763-5p | CGCCUGCCCAGCCCUCCUGCU | 686 | 21 | 1 |
| hsa-miR-4766-3p | AUAGCAAUUGCUCUUUUGGAA | 687 | 21 | 1 |
| hsa-miR-4781-3p | AAUGUUGGAAUCCUCGCUAGAG | 688 | 22 | 1 |
| hsa-miR-4793-3p | UCUGCACUGUGAGUUGGCUGGCU | 689 | 23 | 1 |
| hsa-miR-488-3p | UUGAAAGGCUAUUUCUUGGUC | 690 | 21 | 1 |
| hsa-miR-4999-5p | UGCUGUAUUGUCAGGUAGUGA | 691 | 21 | 1 |
| hsa-miR-5001-5p | AGGGCUGGACUCAGCGGCGGAGCU | 692 | 24 | 1 |
| hsa-miR-5002-5p | AAUUUGGUUUCUGAGGCACUUAGU | 693 | 24 | 1 |
| hsa-miR-5004-5p | UGAGGACAGGGCAAAUUCACGA | 694 | 22 | 1 |
| hsa-miR-5006-3p | UUUCCCUUUCCAUCCUGGCAG | 695 | 21 | 1 |
| hsa-miR-5088 | CAGGGCUCAGGGAUUGGAUGGAG | 696 | 23 | 1 |
| hsa-miR-544a | AUUCUGCAUUUUUAGCAAGUUC | 697 | 22 | 1 |
| hsa-miR-548al | AACGGCAAUGACUUUUGUACCA | 698 | 22 | 1 |
| hsa-miR-548aq-5p | GAAAGUAAUUGCUGUUUUUGCC | 699 | 22 | 1 |
| hsa-miR-548at-5p | AAAAGUUAUUGCGGUUUUGGCU | 700 | 22 | 1 |
| hsa-miR-548au-5p | AAAAGUAAUUGCGGUUUUUGC | 701 | 21 | 1 |
| hsa-miR-548b-3p | CAAGAACCUCAGUUGCUUUUGU | 702 | 22 | 1 |
| hsa-miR-556-3p | AUAUUACCAUUAGCUCAUCUUU | 703 | 22 | 1 |
| hsa-miR-5582-3p | UAAAACUUUAAGUGUGCCUAGG | 704 | 22 | 1 |
| hsa-miR-5586-3p | CAGAGUGACAAGCUGGUUAAAG | 705 | 22 | 1 |
| hsa-miR-5588-5p | ACUGGCAUUAGUGGGACUUUU | 706 | 21 | 1 |
| hsa-miR-5683 | UACAGAUGCAGAUUCUCUGACUUC | 707 | 24 | 1 |
| hsa-miR-5696 | CUCAUUUAAGUAGUCUGAUGCC | 708 | 22 | 1 |
| hsa-miR-5701 | UUAUUGUCACGUUCUGAUU | 709 | 19 | 1 |
| hsa-miR-5706 | UUCUGGAUAACAUGCUGAAGCU | 710 | 22 | 1 |
| hsa-miR-592 | UUGUGUCAAUAUGCGAUGAUGU | 711 | 22 | 1 |
| hsa-miR-603 | CACACACUGCAAUUACUUUUGC | 712 | 22 | 1 |
| hsa-miR-624-3p | CACAAGGUAUUGGUAUUACCU | 713 | 21 | 1 |
| hsa-miR-885-5p | UCCAUUACACUACCCUGCCUCU | 714 | 22 | 1 |
| hsa-miR-933 | UGUGCGCAGGGAGACCUCUCCC | 715 | 22 | 1 |

TABLE 7

Microvesicles EI

| MICROVESICLES CTX0E0307EI MIRNA | MIRNA.SEQUENCE | SEQ ID NO: | MIRNA LENGTH | READ COUNTS |
|---|---|---|---|---|
| hsa-miR-1246 | AAUGGAUUUUUGGAGCAGG | 21 | 19 | 32723 |
| hsa-miR-4492 | GGGGCUGGGCGCGCGCC | 34 | 17 | 16225 |
| hsa-miR-4488 | AGGGGGCGGGCUCCGGCG | 61 | 18 | 12878 |
| hsa-miR-4532 | CCCCGGGGAGCCCGGCG | 23 | 17 | 6746 |
| hsa-miR-4508 | GCGGGGCUGGGCGCGCG | 135 | 17 | 531 |
| hsa-miR-4516 | GGGAGAAGGGUCGGGGC | 110 | 17 | 500 |
| hsa-miR-3676-5p | AGGAGAUCCUGGGUU | 280 | 15 | 357 |
| hsa-miR-4485 | UAACGGCCGCGGUACCCUAA | 67 | 20 | 44 |
| hsa-miR-4497 | CUCCGGGACGGCUGGGC | 232 | 17 | 43 |
| hsa-miR-21-5p | UAGCUUAUCAGACUGAUGUUGA | 9 | 22 | 33 |
| hsa-miR-3195 | CGCGCCGGGCCCGGGUU | 716 | 17 | 28 |
| hsa-miR-3648 | AGCCGCGGGGAUCGCCGAGGG | 259 | 21 | 26 |
| hsa-miR-663b | GGUGGCCCGGCCGUGCCUGAGG | 180 | 22 | 24 |
| hsa-miR-3656 | GGCGGGUGCGGGGGUGG | 251 | 17 | 19 |
| hsa-miR-3687 | CCCGGACAGGCGUUCGUGCGACGU | 190 | 24 | 19 |
| hsa0miR-4466 | GGGUGCGGGCCGGCGGGG | 264 | 18 | 19 |
| hsa-miR-4792 | CGGUGAGCGCUCGCUGGC | 363 | 18 | 19 |
| hsa-miR-99b-5p | CACCCGUAGAACCGACCUUGCG | 4 | 22 | 18 |
| hsa-let-7a-5p | UGAGGUAGUAGGUUGUAUAGUU | 1 | 22 | 15 |
| hsa-miR-1290 | UGGAUUUUUGGAUCAGGGA | 375 | 19 | 7 |
| hsa-miR-1291 | UGGCCCUGACUGAAGACCAGCAGU | 294 | 24 | 7 |
| hsa-miR-182-5p | UUUGGCAAUGGUAGAACUCACACU | 16 | 24 | 7 |
| hsa-miR-5096 | GUUUCACCAUGUUGGUCAGGC | 220 | 21 | 7 |
| hsa-miR-1273f | GGAGAUGGAGGUUGCAGUG | 292 | 19 | 5 |
| hsa-miR-26a-5p | UUCAAGUAAUCCAGGAUAGGCU | 12 | 22 | 5 |
| hsa-miR-4284 | GGGCUCACAUCACCCCAU | 191 | 18 | 5 |
| hsa-miR-92b-3p | UAUUGCACUCGUCCCGGCCUCC | 13 | 22 | 5 |
| hsa-let-7b-5p | UGAGGUAGUAGGUUGUGUGGUU | 28 | 22 | 4 |
| hsa-let-7c | UGAGGUAGUAGGUUGUAUGGUU | 17 | 22 | 4 |
| hsa-let-7f-5p | UGAGGUAGUAGAUUGUAUAGUU | 11 | 22 | 4 |
| hsa-miR-100-5p | AACCCGUAGAUCCGAACUUGUG | 3 | 22 | 4 |
| hsa-miR-1248 | ACCUUCUUGUAUAAGCACUGUGCUAAA | 269 | 27 | 4 |
| hsa-miR-1973 | ACCGUGCAAAGGUAGCAUA | 171 | 19 | 4 |
| hsa-miR-21-3p | CAACACCAGUCGAUGGGCUGU | 20 | 21 | 4 |
| hsa-miR-3654 | GACUGGACAAGCUGAGGAA | 325 | 19 | 4 |
| hsa-miR-92a-3p | UAUUGCACUUGUCCCGGCCUGU | 7 | 22 | 4 |
| hsa-miR-1273g-3p | ACCACUGCACUCCAGCCUGAG | 210 | 21 | 3 |

TABLE 7-continued

| Microvesicles EI | | | | |
|---|---|---|---|---|
| MICROVESICLES CTX0E0307EI MIRNA | MIRNA.SEQUENCE | SEQ ID NO: | MIRNA LENGTH | READ COUNTS |
| hsa-miR-23b-3p | AUCACAUUGCCAGGGAUUACC | 59 | 21 | 3 |
| hsa-miR-3609 | CAAAGUGAUGAGUAAUACUGGCUG | 216 | 24 | 3 |
| hsa-miR-3615 | UCUCUCGGCUCCUCGCGGCUC | 323 | 21 | 3 |
| hsa-miR-3653 | CUAAGAAGUUGACUGAAG | 544 | 18 | 3 |
| hsa-miR-3960 | GGCGGCGGCGGAGGCGGGGG | 416 | 20 | 3 |
| hsa-miR-4448 | GGCUCCUUGGUCUAGGGGUA | 231 | 20 | 3 |
| hsa-let-7d-5p | AGAGGUAGUAGGUUGCAUAGUU | 92 | 22 | 2 |
| hsa-miR-16-5p | UAGCAGCACGUAAAUAUUGGCG | 29 | 22 | 2 |
| hsa-miR-181a-5p | AACAUUCAACGCUGUCGGUGAGU | 15 | 23 | 2 |
| hsa-miR-181b-5p | AACAUUCAUUGCUGUCGGUGGGU | 38 | 23 | 2 |
| hsa-miR-222-3p | AGCUACAUCUGGCUACUGGGU | 36 | 21 | 2 |
| hsa-miR-24-3p | UGGCUCAGUUCAGCAGGAACAG | 119 | 22 | 2 |
| hsa-miR-3196 | CGGGGCGGCAGGGGCCUC | 717 | 18 | 2 |
| hsa-miR-4419b | GAGGCUGAAGGAAGAUGG | 718 | 18 | 2 |
| hsa-miR-4461 | GAUUGAGACUAGUAGGGCUAGGC | 129 | 23 | 2 |
| hsa-miR-4486 | GCUGGGCGAGGCUGGCA | 719 | 17 | 2 |
| hsa-miR-663a | AGGCGGGGCGCCGCGGGACCGC | 365 | 22 | 2 |
| hsa-miR-9-5p | UCUUUGGUUAUCUAGCUGUAUGA | 58 | 23 | 2 |
| hsa-let-7i-3p | CUGCGCAAGCUACUGCCUUGCU | 483 | 22 | 1 |
| hsa-let-7i-5p | UGAGGUAGUAGUUUGUGCUGUU | 22 | 22 | 1 |
| hsa-miR-1225-5p | GUGGGUACGGCCCAGUGGGGGG | 720 | 22 | 1 |
| hsa-miR-1244 | AAGUAGUUGGUUUGUAUGAGAUGGUU | 340 | 26 | 1 |
| hsa-miR-125b-5p | UCCCUGAGACCCUAACUUGUGA | 42 | 22 | 1 |
| hsa-miR-1275 | GUGGGGGAGAGGCUGUC | 162 | 17 | 1 |
| hsa-miR-1280 | UCCCACCGCUGCCACCC | 584 | 17 | 1 |
| hsa-miR-134 | UGUGACUGGUUGACCAGAGGGG | 94 | 22 | 1 |
| hsa-miR-149-5p | UCUGGCUCCGUGUCUUCACUCCC | 121 | 23 | 1 |
| hsa-miR-191-5p | CAACGGAAUCCCAAAAGCAGCUG | 8 | 23 | 1 |
| hsa-miR-221-3p | AGCUACAUUGUCUGCUGGGUUUC | 79 | 23 | 1 |
| hsa-miR-22-3p | AAGCUGCCAGUUGAAGAACUGU | 33 | 22 | 1 |
| hsa-miR-26b-5p | UUCAAGUAAUUCAGGAUAGGU | 90 | 21 | 1 |
| hsa-miR-30c-5p | UGUAAACAUCCUACACUCUCAGC | 66 | 23 | 1 |
| hsa-miR-30d-5p | UGUAAACAUCCCCGACUGGAAG | 31 | 22 | 1 |
| hsa-miR-3182 | GCUUCUGUAGUGUAGUC | 721 | 17 | 1 |
| hsa-miR-320a | AAAAGCUGGGUUGAGAGGGCGA | 97 | 22 | 1 |
| hsa-miR-34a-5p | UGGCAGUGUCUUAGCUGGUUGU | 101 | 22 | 1 |
| hsa-miR-3607-3p | ACUGUAAACGCUUUCUGAUG | 543 | 20 | 1 |

TABLE 7-continued

Microvesicles EI

| MICROVESICLES CTX0E0307EI MIRNA | MIRNA.SEQUENCE | SEQ ID NO: | MIRNA LENGTH | READ COUNTS |
|---|---|---|---|---|
| hsa-miR-361-5p | UUAUCAGAAUCUCCAGGGGUAC | 70 | 22 | 1 |
| hsa-miR-3652 | CGGCUGGAGGUGUGAGGA | 722 | 18 | 1 |
| hsa-miR-409-3p | GAAUGUUGCUCGGUGAACCCCU | 47 | 22 | 1 |
| hsa-miR-423-3p | AGCUCGGUCUGAGGCCCCUCAGU | 57 | 23 | 1 |
| hsa-miR-423-5p | UGAGGGGCAGAGAGCGAGACUUU | 41 | 23 | 1 |
| hsa-miR-432-5p | UCUUGGAGUAGGUCAUUGGGUGG | 95 | 23 | 1 |
| hsa-miR-4417 | GGUGGGCUUCCCGGAGGG | 175 | 18 | 1 |
| hsa-miR-4426 | GAAGAUGGACGUACUUU | 359 | 17 | 1 |
| hsa-miR-4449 | CGUCCCGGGGCUGCGCGAGGCA | 155 | 22 | 1 |
| hsa-miR-4800-3p | CAUCCGUCCGUCUGUCCAC | 549 | 19 | 1 |
| hsa-miR-484 | UCAGGCUCAGUCCCCUCCCGAU | 118 | 22 | 1 |
| hsa-miR-486-5p | UCCUGUACUGAGCUGCCCCGAG | 5 | 22 | 1 |
| hsa-miR-493-3p | UGAAGGUCUACUGUGUGCCAGG | 83 | 22 | 1 |
| hsa-miR-5095 | UUACAGGCGUGAACCACCGCG | 723 | 21 | 1 |
| hsa-miR-556-3p | AUAUUACCAUUAGCUCAUCUUU | 703 | 22 | 1 |
| hsa-miR-644b-5p | UGGGCUAAGGGAGAUGAUUGGGUA | 724 | 24 | 1 |
| hsa-miR-664-5p | ACUGGCUAGGGAAAAUGAUUGGAU | 443 | 24 | 1 |
| hsa-miR-760 | CGGCUCUGGGUCUGUGGGGA | 289 | 20 | 1 |
| hsa-miR-941 | CACCCGGCUGUGUGCACAUGUGC | 60 | 23 | 1 |
| hsa-miR-98 | UGAGGUAGUAAGUUGUAUUGUU | 10 | 22 | 1 |
| hsa-miR-99a-5p | AACCCGUAGAUCCGAUCUUGUG | 52 | 22 | 1 |

TABLE 8

Exosomes EI

| EXOSOMES CTX0E0307EI MIRNA | MIRNA.SEQUENCE | SEQ ID NO: | MIRNA LENGTH | READ COUNTS |
|---|---|---|---|---|
| hsa-miR-1246 | AAUGGAUUUUUGGAGCAGG | 21 | 19 | 83958 |
| hsa-miR-4492 | GGGGCUGGGCGCGCGCC | 34 | 17 | 22482 |
| hsa-miR-4488 | AGGGGGCGGGCUCCGGCG | 61 | 18 | 20618 |
| hsa-miR-4532 | CCCCGGGGAGCCCGGCG | 23 | 17 | 6419 |
| hsa-miR-4516 | GGGAGAAGGGUCGGGGC | 110 | 17 | 904 |
| hsa-miR-4508 | GCGGGGCUGGGCGCGCG | 135 | 17 | 723 |
| hsa-miR-3676-5p | AGGAGAUCCUGGGUU | 280 | 15 | 174 |
| hsa-miR-4485 | UAACGGCCGCGGUACCCUAA | 67 | 20 | 43 |
| hsa-miR-21-5p | UAGCUUAUCAGACUGAUGUUGA | 9 | 22 | 41 |
| hsa-miR-4497 | CUCCGGGACGGCUGGGC | 232 | 17 | 28 |
| hsa-miR-663b | GGUGGCCCGGCCGUGCCUGAGG | 180 | 22 | 26 |

TABLE 8-continued

Exosomes EI

| EXOSOMES CTX0E0307EI MIRNA | MIRNA.SEQUENCE | SEQ ID NO: | MIRNA LENGTH | READ COUNTS |
|---|---|---|---|---|
| hsa-miR-4792 | CGGUGAGCGCUCGCUGGC | 363 | 18 | 24 |
| hsa-miR-4454 | GGAUCCGAGUCACGGCACCA | 299 | 20 | 22 |
| hsa-miR-1291 | UGGCCCUGACUGAAGACCAGCAGU | 294 | 24 | 17 |
| hsa-miR-26a-5p | UUCAAGUAAUCCAGGAUAGGCU | 12 | 22 | 17 |
| hsa-miR-3195 | CGCGCCGGGCCCGGGUU | 716 | 17 | 17 |
| hsa-let-7a-5p | UGAGGUAGUAGGUUGUAUAGUU | 1 | 22 | 15 |
| hsa-miR-182-5p | UUUGGCAAUGGUAGAACUCACACU | 16 | 24 | 15 |
| hsa-miR-99b-5p | CACCCGUAGAACCGACCUUGCG | 4 | 22 | 15 |
| hsa-miR-5096 | GUUUCACCAUGUUGGUCAGGC | 220 | 21 | 14 |
| hsa-miR-3648 | AGCCGCGGGGAUCGCCGAGGG | 259 | 21 | 13 |
| hsa-miR-3654 | GACUGGACAAGCUGAGGAA | 325 | 19 | 13 |
| hsa-miR-4466 | GGGUGCGGGCCGGCGGGG | 264 | 18 | 12 |
| hsa-miR-3687 | CCCGGACAGGCGUUCGUGCGACGU | 190 | 24 | 11 |
| hsa-miR-4284 | GGGCUCACAUCACCCCAU | 191 | 18 | 11 |
| hsa-miR-3656 | GGCGGGUGCGGGGGUGG | 251 | 17 | 10 |
| hsa-miR-3609 | CAAAGUGAUGAGUAAUACUGGCUG | 216 | 24 | 8 |
| hsa-miR-644b-5p | UGGGCUAAGGGAGAUGAUUGGGUA | 724 | 24 | 8 |
| hsa-miR-664-5p | ACUGGCUAGGGAAAAUGAUUGGAU | 443 | 24 | 8 |
| hsa-miR-92a-3p | UAUUGCACUUGUCCCGGCCUGU | 7 | 22 | 7 |
| hsa-miR-92b-3p | UAUUGCACUCGUCCCGGCCUCC | 13 | 22 | 7 |
| hsa-let-7b-5p | UGAGGUAGUAGGUUGUGUGGUU | 28 | 22 | 6 |
| hsa-let-7f-5p | UGAGGUAGUAGAUUGUAUAGUU | 11 | 22 | 6 |
| hsa-miR-127-3p | UCGGAUCCGUCUGAGCUUGGCU | 14 | 22 | 6 |
| hsa-miR-1290 | UGGAUUUUUGGAUCAGGGA | 375 | 19 | 6 |
| hsa-miR-4449 | CGUCCCGGGGCUGCGCGAGGCA | 155 | 22 | 6 |
| hsa-miR-4461 | GAUUGAGACUAGUAGGGCUAGGC | 129 | 23 | 6 |
| hsa-miR-100-5p | AACCCGUAGAUCCGAACUUGUG | 3 | 22 | 5 |
| hsa-miR-1248 | ACCUUCUUGUAUAAGCACUGUGCUAAA | 269 | 27 | 5 |
| hsa-miR-1973 | ACCGUGCAAAGGUAGCAUA | 171 | 19 | 5 |
| hsa-miR-3653 | CUAAGAAGUUGACUGAAG | 544 | 18 | 5 |
| hsa-miR-4417 | GGUGGGCUUCCCGGAGGG | 175 | 18 | 5 |
| hsa-miR-125b-5p | UCCCUGAGACCCUAACUUGUGA | 42 | 22 | 4 |
| hsa-miR-151a-3p | CUAGACUGAAGCUCCUUGAGG | 25 | 21 | 4 |
| hsa-miR-16-5p | UAGCAGCACGUAAAUAUUGGCG | 29 | 22 | 4 |
| hsa-miR-21-3p | CAACACCAGUCGAUGGGCUGU | 20 | 21 | 4 |
| hsa-miR-23a-3p | AUCACAUUGCCAGGGAUUUCC | 55 | 21 | 4 |
| hsa-miR-4419b | GAGGCUGAAGGAAGAUGG | 718 | 18 | 4 |

TABLE 8-continued

Exosomes EI

| EXOSOMES CTX0E0307EI MIRNA | MIRNA.SEQUENCE | SEQ ID NO: | MIRNA LENGTH | READ COUNTS |
|---|---|---|---|---|
| hsa-miR-1273f | GGAGAUGGAGGUUGCAGUG | 292 | 19 | 3 |
| hsa-miR-1273g-3p | ACCACUGCACUCCAGCCUGAG | 210 | 21 | 3 |
| hsa-miR-181b-5p | AACAUUCAUUGCUGUCGGUGGGU | 38 | 23 | 3 |
| hsa-miR-221-3p | AGCUACAUUGUCUGCUGGGUUUC | 79 | 23 | 3 |
| hsa-miR-3615 | UCUCUCGGCUCCUCGCGGCUC | 323 | 21 | 3 |
| hsa-miR-9-5p | UCUUUGGUUAUCUAGCUGUAUGA | 58 | 23 | 3 |
| hsa-let-7c | UGAGGUAGUAGGUUGUAUGGUU | 17 | 22 | 2 |
| hsa-let-7e-5p | UGAGGUAGGAGGUUGUAUAGUU | 27 | 22 | 2 |
| hsa-let-7i-5p | UGAGGUAGUAGUUUGUGCUGUU | 22 | 22 | 2 |
| hsa-miR-103a-3p | AGCAGCAUUGUACAGGGCUAUGA | 62 | 23 | 2 |
| hsa-miR-106b-5p | UAAAGUGCUGACAGUGCAGAU | 170 | 21 | 2 |
| hsa-miR-1273e | UUGCUUGAACCCAGGAAGUGGA | 342 | 22 | 2 |
| hsa-miR-221-5p | ACCUGGCAUACAAUGUAGAUUU | 39 | 22 | 2 |
| hsa-miR-222-3p | AGCUACAUCUGGCUACUGGGU | 36 | 21 | 2 |
| hsa-miR-30d-5p | UGUAAACAUCCCCGACUGGAAG | 31 | 22 | 2 |
| hsa-miR-3960 | GGCGGCGGCGGAGGCGGGGG | 416 | 20 | 2 |
| hsa-let-7d-3p | CUAUACGACCUGCUGCCUUUCU | 92 | 22 | 1 |
| hsa-let-7d-5p | AGAGGUAGUAGGUUGCAUAGUU | 53 | 22 | 1 |
| hsa-let-7g-5p | UGAGGUAGUAGUUUGUACAGUU | 43 | 22 | 1 |
| hsa-let-7i-3p | CUGCGCAAGCUACUGCCUUGCU | 483 | 22 | 1 |
| hsa-miR-10a-5p | UACCCUGUAGAUCCGAAUUUGUG | 2 | 23 | 1 |
| hsa-miR-1181 | CCGUCGCCGCCACCCGAGCCG | 725 | 21 | 1 |
| hsa-miR-1225-3p | UGAGCCCCUGUGCCGCCCCCAG | 369 | 22 | 1 |
| hsa-miR-1244 | AAGUAGUUGGUUUGUAUGAGAUGGUU | 340 | 26 | 1 |
| hsa-miR-125a-5p | UCCCUGAGACCCUUUAACCUGUGA | 35 | 24 | 1 |
| hsa-miR-1296 | UUAGGGCCCUGGCUCCAUCUCC | 271 | 22 | 1 |
| hsa-miR-1307-5p | UCGACCGGACCUCGACCGGCU | 91 | 21 | 1 |
| hsa-miR-146b-5p | UGAGAACUGAAUUCCAUAGGCU | 19 | 22 | 1 |
| hsa-miR-149-5p | UCUGGCUCCGUGUCUUCACUCCC | 121 | 23 | 1 |
| hsa-miR-151a-5p | UCGAGGAGCUCACAGUCUAGU | 37 | 21 | 1 |
| hsa-miR-15b-5p | UAGCAGCACAUCAUGGUUUACA | 78 | 22 | 1 |
| hsa-miR-181a-2-3p | ACCACUGACCGUUGACUGUACC | 102 | 22 | 1 |
| hsa-miR-181a-5p | AACAUUCAACGCUGUCGGUGAGU | 15 | 23 | 1 |
| hsa-miR-191-5p | CAACGGAAUCCCAAAAGCAGCUG | 8 | 23 | 1 |
| hsa-miR-198 | GGUCCAGAGGGGAGAUAGGUUC | 726 | 22 | 1 |
| hsa-miR-204-5p | UUCCCUUUGUCAUCCUAUGCCU | 89 | 22 | 1 |
| hsa-miR-20a-5p | UAAAGUGCUUAUAGUGCAGGUAG | 146 | 23 | 1 |

TABLE 8-continued

| Exosomes EI | | | | |
|---|---|---|---|---|
| EXOSOMES CTX0E0307EI MIRNA | MIRNA.SEQUENCE | SEQ ID NO: | MIRNA LENGTH | READ COUNTS |
| hsa-miR-219-5p | UGAUUGUCCAAACGCAAUUCU | 527 | 21 | 1 |
| hsa-miR-22-3p | AAGCUGCCAGUUGAAGAACUGU | 33 | 22 | 1 |
| hsa-miR-23b-3p | AUCACAUUGCCAGGGAUUACC | 59 | 21 | 1 |
| hsa-miR-26b-3p | CCUGUUCUCCAUUACUUGGCUC | 391 | 22 | 1 |
| hsa-miR-299-5p | UGGUUUACCGUCCCACAUACAU | 319 | 22 | 1 |
| hsa-miR-29a-3p | UAGCACCAUCUGAAAUCGGUUA | 106 | 22 | 1 |
| hsa-miR-30e-3p | CUUUCAGUCGGAUGUUUACAGC | 71 | 22 | 1 |
| hsa-miR-31-3p | UGCUAUGCCAACAUAUUGCCAU | 172 | 22 | 1 |
| hsa-miR-3198 | GUGGAGUCCUGGGGAAUGGAGA | 647 | 22 | 1 |
| hsa-miR-323a-3p | CACAUUACACGGUCGACCUCU | 158 | 21 | 1 |
| hsa-miR-342-3p | UCUCACACAGAAAUCGCACCCGU | 81 | 23 | 1 |
| hsa-miR-3607-3p | ACUGUAAACGCUUUCUGAUG | 543 | 20 | 1 |
| hsa-miR-3651 | CAUAGCCCGGUCGCUGGUACAUGA | 727 | 24 | 1 |
| hsa-miR-378a-3p | ACUGGACUUGGAGUCAGAAGG | 65 | 21 | 1 |
| hsa-miR-379-5p | UGGUAGACUAUGGAACGUAGG | 18 | 21 | 1 |
| hsa-miR-423-3p | AGCUCGGUCUGAGGCCCCUCAGU | 57 | 23 | 1 |
| hsa-miR-423-5p | UGAGGGGCAGAGAGCGAGACUUU | 41 | 23 | 1 |
| hsa-miR-425-5p | AAUGACACGAUCACUCCCGUUGA | 111 | 23 | 1 |
| hsa-miR-4258 | CCCCGCCACCGCCUUGG | 728 | 17 | 1 |
| hsa-miR-4426 | GAAGAUGGACGUACUUU | 359 | 17 | 1 |
| hsa-miR-4443 | UUGGAGGCGUGGGUUUU | 663 | 17 | 1 |
| hsa-miR-4448 | GGCUCCUUGGUCUAGGGGUA | 231 | 20 | 1 |
| hsa-miR-4697-3p | UGUCAGUGACUCCUGCCCCUUGGU | 729 | 24 | 1 |
| hsa-miR-4700-3p | CACAGGACUGACUCCUCACCCCAGUG | 424 | 26 | 1 |
| hsa-miR-4700-5p | UCUGGGGAUGAGGACAGUGUGU | 730 | 22 | 1 |
| hsa-miR-4797-3p | UCUCAGUAAGUGGCACUCUGU | 731 | 21 | 1 |
| hsa-miR-484 | UCAGGCUCAGUCCCCUCCCGAU | 118 | 22 | 1 |
| hsa-miR-486-5p | UCCUGUACUGAGCUGCCCCGAG | 5 | 22 | 1 |
| hsa-miR-494 | UGAAACAUACACGGGAAACCUC | 240 | 22 | 1 |
| hsa-miR-500a-5p | UAAUCCUUGCUACCUGGGUGAGA | 303 | 23 | 1 |
| hsa-miR-644b-3p | UUCAUUUGCCUCCCAGCCUACA | 442 | 22 | 1 |
| hsa-miR-663a | AGGCGGGGCGCCGCGGGACCGC | 365 | 22 | 1 |

TABLE 9

| Microvesicles EH | | | | |
|---|---|---|---|---|
| MICROVESICLES CTX0E03 07EH MIRNA | MIRNA.SEQUENCE | SEQ ID NO: | MIRNA LENGTH | READ COUNTS |
| hsa-miR-1246 | AAUGGAUUUUUGGAGCAGG | 21 | 19 | 78791 |
| hsa-miR-4492 | GGGGCUGGGCGCGCGCC | 34 | 17 | 6012 |
| hsa-miR-4532 | CCCCGGGGAGCCCGGCG | 23 | 17 | 3410 |
| hsa-miR-4488 | AGGGGGCGGGCUCCGGCG | 61 | 18 | 1737 |
| hsa-miR-4485 | UAACGGCCGCGGUACCCUAA | 67 | 20 | 319 |
| hsa-miR-4508 | GCGGGGCUGGGCGCGCG | 135 | 17 | 221 |
| hsa-miR-4516 | GGGAGAAGGGUCGGGGC | 110 | 17 | 114 |
| hsa-miR-4466 | GGGUGCGGGCCGGCGGGG | 264 | 18 | 61 |
| hsa-miR-4497 | CUCCGGGACGGCUGGGC | 232 | 17 | 51 |
| hsa-miR-3195 | CGCGCCGGGCCCGGGUU | 716 | 17 | 41 |
| hsa-miR-1973 | ACCGUGCAAAGGUAGCAUA | 171 | 19 | 30 |
| hsa-miR-21-5p | UAGCUUAUCAGACUGAUGUUGA | 9 | 22 | 22 |
| hsa-miR-4284 | GGGCUCACAUCACCCCAU | 191 | 18 | 20 |
| hsa-miR-4792 | CGGUGAGCGCUCGCUGGC | 363 | 18 | 12 |
| hsa-miR-92a-3p | UAUUGCACUUGUCCCGGCCUGU | 7 | 22 | 12 |
| hsa-miR-1291 | UGGCCCUGACUGAAGACCAGCAGU | 294 | 24 | 11 |
| hsa-miR-3676-5p | AGGAGAUCCUGGGUU | 280 | 15 | 10 |
| hsa-miR-100-5p | AACCCGUAGAUCCGAACUUGUG | 3 | 22 | 8 |
| hsa-miR-3656 | GGCGGGUGCGGGGGUGG | 251 | 17 | 8 |
| hsa-miR-663b | GGUGGCCCGGCCGUGCCUGAGG | 180 | 22 | 8 |
| hsa-let-7a-5p | UGAGGUAGUAGGUUGUAUAGUU | 1 | 22 | 7 |
| hsa-miR-1290 | UGGAUUUUUGGAUCAGGGA | 375 | 19 | 7 |
| hsa-miR-3687 | CCCGGACAGGCGUUCGUGCGACGU | 190 | 24 | 7 |
| hsa-miR-4461 | GAUUGAGACUAGUAGGGCUAGGC | 52 | 23 | 6 |
| hsa-miR-664-5p | ACUGGCUAGGGAAAAUGAUUGGAU | 91 | 24 | 6 |
| hsa-miR-92b-3p | UAUUGCACUCGUCCCGGCCUCC | 13 | 22 | 6 |
| hsa-miR-125b-5p | UCCCUGAGACCCUAACUUGUGA | 42 | 22 | 5 |
| hsa-miR-3653 | CUAAGAAGUUGACUGAAG | 544 | 18 | 5 |
| hsa-let-7f-5p | UGAGGUAGUAGAUUGUAUAGUU | 11 | 22 | 4 |
| hsa-miR-16-5p | UAGCAGCACGUAAAUAUUGGCG | 29 | 22 | 4 |
| hsa-miR-181a-5p | AACAUUCAACGCUGUCGGUGAGU | 15 | 23 | 4 |
| hsa-miR-3609 | CAAAGUGAUGAGUAAUACUGGCUG | 216 | 24 | 4 |
| hsa-miR-9-5p | UCUUUGGUUAUCUAGCUGUAUGA | 58 | 23 | 4 |
| hsa-let-7c | UGAGGUAGUAGGUUGUAUGGUU | 17 | 22 | 3 |
| hsa-miR-1244 | AAGUAGUUGGUUUGUAUGAGAUGGUU | 59 | 26 | 3 |
| hsa-miR-127-3p | UCGGAUCCGUCUGAGCUUGGCU | 14 | 22 | 3 |
| hsa-miR-181b-5p | AACAUUCAUUGCUGUCGGUGGGU | 38 | 23 | 3 |

TABLE 9-continued

Microvesicles EH

| MICROVESICLES CTX0E03 07EH MIRNA | MIRNA.SEQUENCE | SEQ ID NO: | MIRNA LENGTH | READ COUNTS |
|---|---|---|---|---|
| hsa-miR-21-3p | CAACACCAGUCGAUGGGCUGU | 20 | 21 | 3 |
| hsa-miR-26a-5p | UUCAAGUAAUCCAGGAUAGGCU | 12 | 22 | 3 |
| hsa-miR-30c-5p | UGUAAACAUCCUACACUCUCAGC | 66 | 23 | 3 |
| hsa-miR-3960 | GGCGGCGGCGGAGGCGGGGG | 416 | 20 | 3 |
| hsa-miR-485-3p | GUCAUACACGGCUCUCCUCUCU | 153 | 22 | 3 |
| hsa-let-7b-5p | UGAGGUAGUAGGUUGUGUGGUU | 28 | 22 | 2 |
| hsa-let-7g-5p | UGAGGUAGUAGUUUGUACAGUU | 43 | 22 | 2 |
| hsa-miR-1273f | GGAGAUGGAGGUUGCAGUG | 292 | 19 | 2 |
| hsa-miR-151a-3p | CUAGACUGAAGCUCCUUGAGG | 25 | 21 | 2 |
| hsa-miR-182-5p | UUUGGCAAUGGUAGAACUCACACU | 16 | 24 | 2 |
| hsa-miR-191-5p | CAACGGAAUCCCAAAAGCAGCUG | 8 | 23 | 2 |
| hsa-miR-197-3p | UUCACCACCUUCUCCACCCAGC | 122 | 22 | 2 |
| hsa-miR-423-5p | UGAGGGGCAGAGAGCGAGACUUU | 41 | 23 | 2 |
| hsa-miR-4468 | AGAGCAGAAGGAUGAGAU | 732 | 18 | 2 |
| hsa-miR-644b-5p | UGGGCUAAGGGAGAUGAUUGGGUA | 724 | 24 | 2 |
| hsa-miR-93-5p | CAAAGUGCUGUUCGUGCAGGUAG | 116 | 23 | 2 |
| hsa-let-7d-5p | AGAGGUAGUAGGUUGCAUAGUU | 92 | 22 | 1 |
| hsa-miR-1225-3p | UGAGCCCCUGUGCCGCCCCCAG | 369 | 22 | 1 |
| hsa-miR-1254 | AGCCUGGAAGCUGGAGCCUGCAGU | 270 | 24 | 1 |
| hsa-miR-1273g-3p | ACCACUGCACUCCAGCCUGAG | 210 | 21 | 1 |
| hsa-miR-1275 | GUGGGGGAGAGGCUGUC | 162 | 17 | 1 |
| hsa-miR-1296 | UUAGGGCCCUGGCUCCAUCUCC | 271 | 22 | 1 |
| hsa-miR-1307-5p | UCGACCGGACCUCGACCGGCU | 91 | 21 | 1 |
| hsa-miR-134 | UGUGACUGGUUGACCAGAGGGG | 94 | 22 | 1 |
| hsa-miR-15b-5p | UAGCAGCACAUCAUGGUUUACA | 78 | 22 | 1 |
| hsa-miR-17-5p | CAAAGUGCUUACAGUGCAGGUAG | 145 | 23 | 1 |
| hsa-miR-1972 | UCAGGCCAGGCACAGUGGCUCA | 733 | 22 | 1 |
| hsa-miR-22-3p | AAGCUGCCAGUUGAAGAACUGU | 33 | 22 | 1 |
| hsa-miR-25-3p | CAUUGCACUUGUCUCGGUCUGA | 63 | 22 | 1 |
| hsa-miR-27b-3p | UUCACAGUGGCUAAGUUCUGC | 6 | 21 | 1 |
| hsa-miR-3065-5p | UCAACAAAAUCACUGAUGCUGGA | 226 | 23 | 1 |
| hsa-miR-30d-5p | UGUAAACAUCCCCGACUGGAAG | 31 | 22 | 1 |
| hsa-miR-320a | AAAAGCUGGGUUGAGAGGGCGA | 97 | 22 | 1 |
| hsa-miR-342-3p | UCUCACACAGAAAUCGCACCCGU | 81 | 23 | 1 |
| hsa-miR-3648 | AGCCGCGGGGAUCGCCGAGGG | 259 | 21 | 1 |
| hsa-miR-3652 | CGGCUGGAGGUGUGAGGA | 722 | 18 | 1 |
| hsa-miR-376c | AACAUAGAGGAAAUUCCACGU | 185 | 21 | 1 |

TABLE 9-continued

Microvesicles EH

| MICROVESICLES CTX0E03 07EH MIRNA | MIRNA.SEQUENCE | SEQ ID NO: | MIRNA LENGTH | READ COUNTS |
|---|---|---|---|---|
| hsa-miR-378a-3p | ACUGGACUUGGAGUCAGAAGG | 65 | 21 | 1 |
| hsa-miR-409-3p | GAAUGUUGCUCGGUGAACCCCU | 47 | 22 | 1 |
| hsa-miR-433 | AUCAUGAUGGGCUCCUCGGUGU | 174 | 22 | 1 |
| hsa-miR-4417 | GGUGGGCUUCCCGGAGGG | 175 | 18 | 1 |
| hsa-miR-4448 | GGCUCCUUGGUCUAGGGGUA | 231 | 20 | 1 |
| hsa-miR-4454 | GGAUCCGAGUCACGGCACCA | 299 | 20 | 1 |
| hsa-miR-454-3p | UAGUGCAAUAUUGCUUAUAGGGU | 169 | 23 | 1 |
| hsa-miR-4800-3p | CAUCCGUCCGUCUGUCCAC | 549 | 19 | 1 |
| hsa-miR-493-3p | UGAAGGUCUACUGUGUGCCAGG | 83 | 22 | 1 |
| hsa-miR-5095 | UUACAGGCGUGAACCACCGCG | 723 | 21 | 1 |
| hsa-miR-574-3p | CACGCUCAUGCACACACCCACA | 253 | 22 | 1 |
| hsa-miR-665 | ACCAGGAGGCUGAGGCCCCU | 309 | 20 | 1 |
| hsa-miR-720 | UCUCGCUGGGGCCUCCA | 84 | 17 | 1 |
| hsa-miR-99a-5p | AACCCGUAGAUCCGAUCUUGUG | 52 | 22 | 1 |
| hsa-miR-99b-5p | CACCCGUAGAACCGACCUUGCG | 4 | 22 | 1 |

TABLE 10

Exosomes EH

| EXOSOMES CTX0E03 07EH MIRNA | MIRNA.SEQUENCE | SEQ ID NO: | MIRNA LENGTH | READ COUNTS |
|---|---|---|---|---|
| hsa-miR-1246 | AAUGGAUUUUUGGAGCAGG | 21 | 19 | 111092 |
| hsa-miR-4492 | GGGGCUGGGCGCGCGCC | 34 | 17 | 5188 |
| hsa-miR-4532 | CCCCGGGGAGCCCGGCG | 23 | 17 | 3368 |
| hsa-miR-4488 | AGGGGGCGGGCUCCGGCG | 61 | 18 | 1389 |
| hsa-miR-4485 | UAACGGCCGCGGUACCCUAA | 67 | 20 | 386 |
| hsa-miR-4508 | GCGGGGCUGGGCGCGCG | 135 | 17 | 188 |
| hsa-miR-4516 | GGGAGAAGGGUCGGGGC | 110 | 17 | 135 |
| hsa-miR-4497 | CUCCGGGACGGCUGGGC | 232 | 17 | 73 |
| hsa-miR-1973 | ACCGUGCAAAGGUAGCAUA | 171 | 19 | 50 |
| hsa-miR-3195 | CGCGCCGGGCCCGGGUU | 716 | 17 | 48 |
| hsa-miR-4466 | GGGUGCGGGCCGGCGGGG | 264 | 18 | 43 |
| hsa-let-7a-5p | UGAGGUAGUAGGUUGUAUAGUU | 1 | 22 | 20 |
| hsa-miR-99b-5p | CACCCGUAGAACCGACCUUGCG | 4 | 22 | 19 |
| hsa-miR-21-5p | UAGCUUAUCAGACUGAUGUUGA | 9 | 22 | 18 |
| hsa-miR-92a-3p | UAUUGCACUUGUCCCGGCCUGU | 7 | 22 | 18 |
| hsa-miR-3676-5p | AGGAGAUCCUGGGUU | 280 | 15 | 17 |
| hsa-miR-4792 | CGGUGAGCGCUCGCUGGC | 363 | 18 | 15 |

TABLE 10-continued

| Exosomes EH | | | | |
|---|---|---|---|---|
| EXOSOMES CTX0E03 07EH MIRNA | MIRNA.SEQUENCE | SEQ ID NO: | MIRNA LENGTH | READ COUNTS |
| hsa-miR-664-5p | ACUGGCUAGGGAAAAUGAUUGGAU | 443 | 24 | 13 |
| hsa-miR-100-5p | AACCCGUAGAUCCGAACUUGUG | 3 | 22 | 11 |
| hsa-miR-1291 | UGGCCCUGACUGAAGACCAGCAGU | 294 | 24 | 10 |
| hsa-miR-16-5p | UAGCAGCACGUAAAUAUUGGCG | 29 | 22 | 10 |
| hsa-miR-4284 | GGGCUCACAUCACCCCAU | 191 | 18 | 10 |
| hsa-miR-663b | GGUGGCCCGGCCGUGCCUGAGG | 180 | 22 | 9 |
| hsa-miR-25-3p | CAUUGCACUUGUCUCGGUCUGA | 63 | 22 | 8 |
| hsa-miR-3656 | GGCGGGUGCGGGGGUGG | 251 | 17 | 8 |
| hsa-miR-181a-5p | AACAUUCAACGCUGUCGGUGAGU | 15 | 23 | 7 |
| hsa-miR-26a-5p | UUCAAGUAAUCCAGGAUAGGCU | 12 | 22 | 6 |
| hsa-miR-3654 | GACUGGACAAGCUGAGGAA | 325 | 19 | 6 |
| hsa-miR-644b-5p | UGGGCUAAGGGAGAUGAUUGGGUA | 724 | 24 | 6 |
| hsa-let-7b-5p | UGAGGUAGUAGGUUGUGUGGUU | 28 | 22 | 5 |
| hsa-let-7f-5p | UGAGGUAGUAGAUUGUAUAGUU | 11 | 22 | 5 |
| hsa-miR-1290 | UGGAUUUUUGGAUCAGGGA | 375 | 19 | 5 |
| hsa-miR-4426 | GAAGAUGGACGUACUUU | 359 | 17 | 5 |
| hsa-miR-5096 | GUUUCACCAUGUUGGUCAGGC | 220 | 21 | 5 |
| hsa-miR-125b-5p | UCCCUGAGACCCUAACUUGUGA | 42 | 22 | 4 |
| hsa-miR-1273f | GGAGAUGGAGGUUGCAGUG | 292 | 19 | 4 |
| hsa-miR-191-5p | CAACGGAAUCCCAAAAGCAGCUG | 8 | 23 | 4 |
| hsa-miR-22-3p | AAGCUGCCAGUUGAAGAACUGU | 33 | 22 | 4 |
| hsa-miR-3609 | CAAAGUGAUGAGUAAUACUGGCUG | 216 | 24 | 4 |
| hsa-miR-3687 | CCCGGACAGGCGUUCGUGCGACGU | 190 | 24 | 4 |
| hsa-miR-93-5p | CAAAGUGCUGUUCGUGCAGGUAG | 116 | 23 | 4 |
| hsa-miR-1248 | ACCUUCUUGUAUAAGCACUGUGCUAAA | 269 | 27 | 3 |
| hsa-miR-1273g-3p | ACCACUGCACUCCAGCCUGAG | 210 | 21 | 3 |
| hsa-miR-151a-3p | CUAGACUGAAGCUCCUUGAGG | 25 | 21 | 3 |
| hsa-miR-182-5p | UUUGGCAAUGGUAGAACUCACACU | 16 | 24 | 3 |
| hsa-miR-221-3p | AGCUACAUUGUCUGCUGGGUUUC | 79 | 23 | 3 |
| hsa-miR-222-3p | AGCUACAUCUGGCUACUGGGU | 36 | 21 | 3 |
| hsa-miR-29a-3p | UAGCACCAUCUGAAAUCGGUUA | 106 | 22 | 3 |
| hsa-miR-4461 | GAUUGAGACUAGUAGGGCUAGGC | 129 | 23 | 3 |
| hsa-miR-486-5p | UCCUGUACUGAGCUGCCCCGAG | 5 | 22 | 3 |
| hsa-miR-92b-3p | UAUUGCACUCGUCCCGGCCUCC | 13 | 22 | 3 |
| hsa-miR-9-5p | UCUUUGGUUAUCUAGCUGUAUGA | 58 | 23 | 3 |
| hsa-miR-98 | UGAGGUAGUAAGUUGUAUUGUU | 10 | 22 | 3 |
| hsa-let-7d-5p | AGAGGUAGUAGGUUGCAUAGUU | 53 | 22 | 2 |

TABLE 10-continued

| Exosomes EH | | | | |
|---|---|---|---|---|
| EXOSOMES CTX0E03 07EH MIRNA | MIRNA.SEQUENCE | SEQ ID NO: | MIRNA LENGTH | READ COUNTS |
| hsa-miR-134 | UGUGACUGGUUGACCAGAGGGG | 94 | 22 | 2 |
| hsa-miR-151a-5p | UCGAGGAGCUCACAGUCUAGU | 37 | 21 | 2 |
| hsa-miR-15b-5p | UAGCAGCACAUCAUGGUUUACA | 78 | 22 | 2 |
| hsa-miR-30a-5p | UGUAAACAUCCUCGACUGGAAG | 30 | 22 | 2 |
| hsa-miR-3124-3p | ACUUUCCUCACUCCCGUGAAGU | 734 | 22 | 2 |
| hsa-miR-3653 | CUAAGAAGUUGACUGAAG | 544 | 18 | 2 |
| hsa-let-7c | UGAGGUAGUAGGUUGUAUGGUU | 17 | 22 | 1 |
| hsa-let-7d-3p | CUAUACGACCUGCUGCCUUUCU | 92 | 22 | 1 |
| hsa-let-7g-5p | UGAGGUAGUAGUUUGUACAGUU | 43 | 22 | 1 |
| hsa-let-7i-5p | UGAGGUAGUAGUUUGUGCUGUU | 22 | 22 | 1 |
| hsa-miR-103a-3p | AGCAGCAUUGUACAGGGCUAUGA | 62 | 23 | 1 |
| hsa-miR-106b-5p | UAAAGUGCUGACAGUGCAGAU | 170 | 21 | 1 |
| hsa-miR-1244 | AAGUAGUUGGUUUGUAUGAGAUGGUU | 340 | 26 | 1 |
| hsa-miR-128 | UCACAGUGAACCGGUCUCUUU | 109 | 21 | 1 |
| hsa-miR-1285-3p | UCUGGGCAACAAAGUGAGACCU | 464 | 22 | 1 |
| hsa-miR-1307-3p | ACUCGGCGUGGCGUCGGUCGUG | 124 | 22 | 1 |
| hsa-miR-140-3p | UACCACAGGGUAGAACCACGG | 138 | 21 | 1 |
| hsa-miR-148b-3p | UCAGUGCAUCACAGAACUUUGU | 48 | 22 | 1 |
| hsa-miR-181b-5p | AACAUUCAUUGCUGUCGGUGGGU | 38 | 23 | 1 |
| hsa-miR-193a-3p | AACUGGCCUACAAAGUCCCAGU | 386 | 22 | 1 |
| hsa-miR-1972 | UCAGGCCAGGCACAGUGGCUCA | 733 | 22 | 1 |
| hsa-miR-21-3p | CAACACCAGUCGAUGGGCUGU | 20 | 21 | 1 |
| hsa-miR-2277-3p | UGACAGCGCCCUGCCUGGCUC | 735 | 21 | 1 |
| hsa-miR-23a-3p | AUCACAUUGCCAGGGAUUUCC | 55 | 21 | 1 |
| hsa-miR-23b-3p | AUCACAUUGCCAGGGAUUACC | 59 | 21 | 1 |
| hsa-miR-24-3p | UGGCUCAGUUCAGCAGGAACAG | 119 | 22 | 1 |
| hsa-miR-27a-3p | UUCACAGUGGCUAAGUUCCGC | 46 | 21 | 1 |
| hsa-miR-27b-3p | UUCACAGUGGCUAAGUUCUGC | 6 | 21 | 1 |
| hsa-miR-299-3p | UAUGUGGGAUGGUAAACCGCUU | 182 | 22 | 1 |
| hsa-miR-30b-5p | UGUAAACAUCCUACACUCAGCU | 96 | 22 | 1 |
| hsa-miR-30c-5p | UGUAAACAUCCUACACUCUCAGC | 66 | 23 | 1 |
| hsa-miR-31-3p | UGCUAUGCCAACAUAUUGCCAU | 172 | 22 | 1 |
| hsa-miR-3196 | CGGGGCGGCAGGGGCCUC | 717 | 18 | 1 |
| hsa-miR-3198 | GUGGAGUCCUGGGGAAUGGAGA | 647 | 22 | 1 |
| hsa-miR-320a | AAAAGCUGGGUUGAGAGGGCGA | 97 | 22 | 1 |
| hsa-miR-329 | AACACACCUGGUUAACCUCUUU | 214 | 22 | 1 |
| hsa-miR-339-5p | UCCCUGUCCUCCAGGAGCUCACG | 402 | 23 | 1 |

TABLE 10-continued

Exosomes EH

| EXOSOMES CTX0E03 07EH MIRNA | MIRNA.SEQUENCE | SEQ ID NO: | MIRNA LENGTH | READ COUNTS |
|---|---|---|---|---|
| hsa-miR-34a-5p | UGGCAGUGUCUUAGCUGGUUGU | 101 | 22 | 1 |
| hsa-miR-3607-5p | GCAUGUGAUGAAGCAAAUCAGU | 249 | 22 | 1 |
| hsa-miR-3648 | AGCCGCGGGGAUCGCCGAGGG | 259 | 21 | 1 |
| hsa-miR-376c | AACAUAGAGGAAAUUCCACGU | 185 | 21 | 1 |
| hsa-miR-3960 | GGCGGCGGCGGAGGCGGGGG | 416 | 20 | 1 |
| hsa-miR-411-3p | UAUGUAACACGGUCCACUAACC | 482 | 22 | 1 |
| hsa-miR-423-3p | AGCUCGGUCUGAGGCCCCUCAGU | 57 | 23 | 1 |
| hsa-miR-423-5p | UGAGGGGCAGAGAGCGAGACUUU | 41 | 23 | 1 |
| hsa-miR-4417 | GGUGGGCUUCCCGGAGGG | 175 | 18 | 1 |
| hsa-miR-4444 | CUCGAGUUGGAAGAGGCG | 418 | 18 | 1 |
| hsa-miR-4499 | AAGACUGAGAGGAGGGA | 736 | 17 | 1 |
| hsa-miR-4521 | GCUAAGGAAGUCCUGUGCUCAG | 233 | 22 | 1 |
| hsa-miR-4680-5p | AGAACUCUUGCAGUCUUAGAUGU | 737 | 23 | 1 |
| hsa-miR-4709-5p | ACAACAGUGACUUGCUCUCCAA | 575 | 22 | 1 |
| hsa-miR-501-3p | AAUGCACCCGGGCAAGGAUUCU | 26 | 22 | 1 |
| hsa-miR-644b-3p | UUCAUUUGCCUCCCAGCCUACA | 442 | 22 | 1 |
| hsa-miR-654-3p | UAUGUCUGCUGACCAUCACCUU | 336 | 22 | 1 |
| hsa-miR-9-3p | AUAAAGCUAGAUAACCGAAAGU | 183 | 22 | 1 |
| hsa-miR-940 | AAGGCAGGGCCCCCGCUCCCC | 366 | 21 | 1 |
| hsa-miR-99a-5p | AACCCGUAGAUCCGAUCUUGUG | 52 | 22 | 1 |

Identification of Top Ranking Coding and Non-Coding RNAs by GENCODE Analysis Performed in Exosomes, MV and Producer Cells

TABLE 11

Total number of sequence reads identified by using GENCODE in each tested samples

| CTX0E03 07EH cells | CTX0E03 07EH EXO | CTX0E03 07EH MV | CTX0E03 07EI cells | CTX0E03 07EIE XO | CTX0E03 07EI MV |
|---|---|---|---|---|---|
| 18741941 | 12678688 | 10876797 | 22116110 | 16311289 | 835970 |

Figure 16:
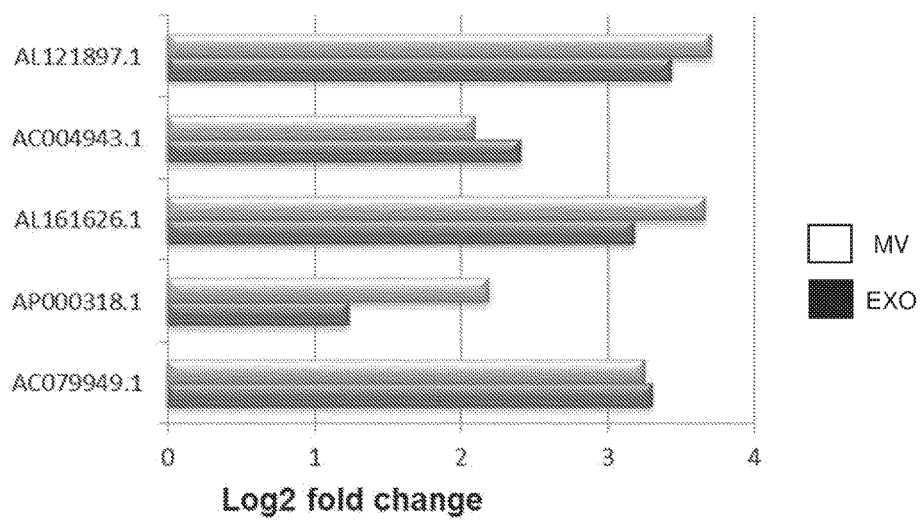
FIG. 16 depicts the top ranking preferentially shuttled novel miRNAs in exosomes and MV compared to CTX0E03 producer cells.

Using GENCODE database analysis of the sequence results, seven putative novel miRNA sequences were identified in exosomes (EXO), microvesicles (MV) and producer cells, as shown in Table 12. (nb CTX0E03 07EI MV reads are misrepresented due to the lower amount of starting material—see Table 11). These data are shown graphically in FIG. 16, which shows that these sequences are preferentially shuttled into exosomes and microvesicles compared to the cells.

TABLE 12

Identification of putative novel miRNA sequences using GENCODE in exosomes (EXO), microvesicles (MV) and producer cells. CTX0E03 07EI MV reads are misrepresented due to the lower amount of starting material (table 11). The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| AC079949.1 | AC079949.1-201 | 57 | Novel miRNA | 2629 | 27006 |
| AP000318.1 | AP000318.1-201 | 64 | Novel miRNA | 1353 | 9379 |
| AL161626.1 | AL161626.1-201 | 57 | Novel miRNA | 471 | 4450 |

TABLE 12-continued

Identification of putative novel miRNA sequences using GENCODE in exosomes (EXO), microvesicles (MV) and producer cells. CTX0E03 07EI MV reads are misrepresented due to the lower amount of starting material (table 11). The transcript IDs are taken from Ensembl database (www.ensembl.org).

| | | | | | |
|---|---|---|---|---|---|
| AC004943.1 | AC004943.1-201 | 81 | Novel miRNA | 24 | 81 |
| AL121897.1 | AL121897.1-201 | 89 | Novel miRNA | 6 | 22 |

| Gene Symbol | Transcript ID | CTX0E03 07EH MV | CTX0E03 07EI cells | CTX0E03 07EI EXO | CTX0E03 07EI MV |
|---|---|---|---|---|---|
| AC079949.1 | AC079949.1-201 | 14873 | 2425 | 11433 | 848 |
| AP000318.1 | AP000318.1-201 | 11002 | 7469 | 2963 | 419 |
| AL161626.1 | AL161626.1-201 | 3712 | 291 | 1263 | 129 |
| AC004943.1 | AC004943.1-201 | 43 | 23 | 94 | 5 |
| AL121897.1 | AL121897.1-201 | 14 | 2 | 30 | 3 |

Validation and of Novel miRNAs

```
AC079949.1-201
                                         (SEQ ID NO: 738)
Gene: AC079949.1 ENSG00000239776
>12 dna:chromosome
chromosome:GRCh37:12:127650616:127650672:1
GGCCGCGCCCCGTTTCCCAGGACAAAGGGCACTCCGCACCGGACCCTGGT

CCCAGCG
```

For AC079949.1-201 putative mature miRNA, gaccagg-guccggugcggagug (SEQ ID NO:745) was identified as the possible 5' stem mature miRNA using MatureBayes, a tool for finding mature miRNA within a miRNA precursor sequence using a Naive Bays classifier. Its presence validation was performed using AGGGTCCGGTGCGGAGT (SEQ ID NO:746) primer sequence. This sequence was entered in mirbase (mirbase.org) and the following miRNA was found with similar sequence: *Bos taurus* miR-2887-1 (Accession No. MIMAT0013845).

```
    bta-miR-2887:  9-20
                                         (SEQ ID NO: 747)
    AC079949 (5)      2 ggguccggugcg 13
                        ||||||||||||
    bta-miR-2887      9 ggguccggugcg 20
```

The presence of this novel miRNA was tested by qRT-PCR on purified exosomes retro transcribed miRNA.

The same analysis was performed using the 3' stem of AC079949, sequence TGCGGAGTGCCCTTTGTCCT (SEQ ID NO:748), but in this case no similar miRNA was identified in mirbase.

```
AP000318.1-201
                                         (SEQ ID NO: 739)
Gene: AP000318.1 ENSG00000266007
>21 dna:chromosome
chromosome:GRCh37:21:35677430:35677493:1
CCCACTCCCTGGCGCCGCTTGTGGAGGGCCCAAGTCCTTCTGATTGAGGC

CCAACCCGTGGAAG
```

For AP000318.1-201 putative mature miRNA, ggagggc-ccaaguccuucugau (SEQ ID NO:744) was identified as the possible 5' stem mature miRNA. Its presence validation was performed using GGAGGGCCCAAGTCCTTCTGAT (SEQ ID NO:749) primer sequence. *Caenorhabditis remanei* miR-55 stem-loop was identified as similar miRNA. Primer validation was again carried out by qRT-PCR.

```
    crm-miR-55-5p: 4-17
                                         (SEQ ID NO: 750)
    AP000318.1        20 cccaaguccuucug  7
                         |||||| ||||||
    crm-miR-55-5p      4 cccaagugcuucug 17

AL161626.1-201
                                         (SEQ ID NO: 740)
Gene: AL161626.1 ENSG00000241781
>9 dna:chromosome
chromosome:GRCh37:9:79186731:79186787:1
CGCCGGGACCGGGGTCCGGGGCGGAGTGCCCTTCCTCCTGGGAAACGGGG

TGCGGC
```

For AL161626.1-201 putative mature miRNA, ggcg-gagugcccuucuuccugg (SEQ ID NO:743) was identified as the possible 5' stem mature miRNA. Its presence validation was performed using CGGAGTGCCCTTCTTCCT (SEQ ID NO:751) primer sequence. *Zea mays* miR164c stem-loop and *Achypodium distachyon* miR164f stem-loop were identified as similar miRNA. Primer validation was again carried out by qRT-PCR.

```
    zma-miR164c-3p: 4-15
                                         (SEQ ID NO: 752)
    AL161626.1        5 gugcccuucuuc 16
                        ||||||||||||
    zma-miR164c-3p    4 gugcccuucuuc 15

AC004943.1
                                         (SEQ ID NO: 741)
Gene: AC004943.1 ENSG00000265573
>16 dna:chromosome
chromosome:GRCh37:16:72821592:72821672:-1
GCTTCACGTCCCCACCGGCGGCGGCGGCGGTGGCAGTGGCGGCGGCGGCG

GCGGTGGCGGCGGCGGCGGCGGCGGCGGCTC

AL121897.1
                                         (SEQ ID NO: 742)
Gene: AL121897.1 ENSG00000264308
>20 dna: chromosome chromosome: GRCh37: 20:
30865503: 30865591: 1
GCCGCCCCGCCGCCGCCGCCGCCGCCGCCGCCGCCGCCGCCGCCCGCTT

TCGGCTCGGGCCTCAGGTGAGTCGGAGGGGCCGGGCGCC
```

Miscellaneous RNA (Misc_RNA), Including Novel Putative

Misc_RNA is short for miscellaneous RNA, a general term for a series of miscellaneous small RNA. Miscellaneous transcript feature are not defined by other RNA keys.

List of top ranking previously known and novel misc_RNAs identified using GENCODE sequence data set:

TABLE 13

Identification of misc_RNA, including putative novel misc_RNA, sequences using GENCODE in exosomes (EXO), microvesicles (MV) and producer cells. CTX0E03 07EI MV reads are misrepresented due to the lower amount of starting material - Table 11). The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| RPPH1 | RPPH1-201 | 333 | misc RNA | 76 | 2229 |
| RMRP | RMRP-201 | 264 | misc RNA | 139 | 1803 |
| RPPH1 | RPPH1-001 | 638 | misc RNA | 182 | 931 |
| VTRNA1-1 | VTRNA1-1-201 | 99 | misc RNA | 43 | 720 |
| Y_RNA | Y_RNA.321-201 | 93 | Novel misc RNA | 159 | 196 |
| Y_RNA | Y_RNA.725-201 | 95 | Novel misc RNA | 1092 | 18 |
| Y_RNA | Y_RNA.125-201 | 96 | Novel misc RNA | 1079 | 15 |
| Y_RNA | Y_RNA.118-201 | 99 | Novel misc RNA | 134 | 12 |
| Y_RNA | Y_RNA.394-201 | 109 | Novel misc RNA | 9 | 9 |
| Y_RNA | Y_RNA.687-201 | 111 | Novel misc RNA | 36 | 6 |
| Y_RNA | Y_RNA.144-201 | 102 | Novel misc RNA | 129 | 5 |
| Y_RNA | Y_RNA.337-201 | 105 | Novel misc RNA | 7 | 4 |
| Y_RNA | Y_RNA.413-201 | 97 | Novel misc RNA | 136 | 4 |
| Y_RNA | Y_RNA.30-201 | 103 | Novel misc RNA | 74 | 3 |

| Gene Symbol | Transcript ID | CTX0E03 07EH MV | CTX0E03 07EI cells | CTX0E03 07EI EXO | CTX0E03 07EI MV |
|---|---|---|---|---|---|
| RPPH1 | RPPH1-201 | 1785 | 0 | 1077 | 197 |
| RMRP | RMRP-201 | 1443 | 191 | 659 | 87 |
| RPPH1 | RPPH1-001 | 1372 | 795 | 2017 | 157 |
| VTRNA1-1 | VTRNA1-1-201 | 52 | 247 | 210 | 9 |
| Y_RNA | Y_RNA.321-201 | 661 | 960 | 903 | 217 |
| Y_RNA | Y_RNA.725-201 | 74 | 1005 | 39 | 11 |
| Y_RNA | Y_RNA.125-201 | 58 | 906 | 27 | 12 |
| Y_RNA | Y_RNA.118-201 | 9 | 156 | 45 | 7 |
| Y_RNA | Y_RNA.394-201 | 7 | 33 | 13 | 1 |
| Y_RNA | Y_RNA.687-201 | 15 | 103 | 41 | 10 |
| Y_RNA | Y_RNA.144-201 | 21 | 187 | 84 | 5 |
| Y_RNA | Y_RNA.337-201 | 0 | 15 | 4 | 0 |
| Y_RNA | Y_RNA.413-201 | 8 | 125 | 46 | 3 |
| Y_RNA | Y_RNA.30-201 | 3 | 62 | 21 | 2 |

Among the misc_RNA the following sequences were found preferentially down or up shuttled in exosomes and MV: RPHI, RMRP, and VTRNA1-1 up shuttled and Y_RNA.725-201, and Y_RNA.125-201 down respectively. RPHI is a ribonuclease P RNA component H1. RMRP gene encodes the RNA component of mitochondrial RNA processing endoribonuclease, which cleaves mitochondrial RNA at a priming site of mitochondrial DNA replication. This RNA also interacts with the telomerase reverse transcriptase catalytic subunit to form a distinct ribonucleoprotein complex that has RNA-dependent RNA polymerase activity and produces double-stranded RNAs that can be processed into small interfering RNA. VTRNA1-1 is vault RNA component 1. Vaults are large cytoplasmic ribonucleoproteins and they are composed of a major vault protein, MVP, 2 minor vault proteins, TEP1 and PARP4, and a non-translated RNA component, VTRNA1-1. Y_RNA.725-201, and Y_RNA.125-201 are novel misc_RNAs and their function is not defined.

Metazoa Miscellaneous RNA

The signal recognition particle RNA, also known as 7SL, 6S, ffs, or 4.5S RNA, is the RNA component of the signal recognition particle (SRP) ribonucleoprotein complex. SRP is a universally conserved ribonucleoprotein that directs the traffic of proteins within the cell and allows them to be secreted. The SRP RNA, together with one or more SRP proteins contributes to the binding and release of the signal peptide. The RNA and protein components of this complex are highly conserved but do vary between the different kingdoms of life.

List of top ranking Metazoa misc_RNAs identified using GENCODE sequence data set:

TABLE 14

Identification signal recognition particle RNA (misc_RNA) sequences using GENCODE in exosomes (EXO), microvesicles (MV) and producer cells. The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| Metazoa_SRP | Metazoa_SRP.791-201 | 288 | Metazoan signal recognition particle RNA | 679 | 2324 |
| Metazoa_SRP | Metazoa_SRP.561-201 | 294 | Metazoan signal recognition particle RNA | 634 | 2006 |
| Metazoa_SRP | Metazoa_SRP.864-201 | 297 | Metazoan signal recognition particle RNA | 252 | 1884 |
| Metazoa_SRP | Metazoa_SRP.824-201 | 297 | Metazoan signal recognition particle RNA | 438 | 881 |

TABLE 14-continued

Identification signal recognition particle RNA (misc_RNA) sequences using GENCODE in exosomes (EXO), microvesicles (MV) and producer cells. The transcript IDs are taken from Ensembl database (www.ensembl.org).

| | | | | | |
|---|---|---|---|---|---|
| Metazoa_SRP | Metazoa_SRP.72-201 | 278 | Metazoan signal recognition particle RNA | 441 | 630 |
| Metazoa_SRP | Metazoa_SRP.151-201 | 307 | Metazoan signal recognition particle RNA | 377 | 464 |
| Metazoa_SRP | Metazoa_SRP.208-201 | 277 | Metazoan signal recognition particle RNA | 382 | 410 |
| Metazoa_SRP | Metazoa_SRP.501-201 | 280 | Metazoan signal recognition particle RNA | 265 | 272 |
| Metazoa_SRP | Metazoa_SRP.682-201 | 298 | Metazoan signal recognition particle RNA | 12 | 52 |

| Gene Symbol | Transcript ID | CTX0E03 07EH MV | CTX0E03 07EI cells | CTX0E0307EI EXO | CTX0E03 07EI MV |
|---|---|---|---|---|---|
| Metazoa_SRP | Metazoa_SRP.791-201 | 2058 | 771 | 2698 | 465 |
| Metazoa_SRP | Metazoa_SRP.561-201 | 1683 | 744 | 2147 | 432 |
| Metazoa_SRP | Metazoa_SRP.864-201 | 1544 | 78 | 170 | 148 |
| Metazoa_SRP | Metazoa_SRP.824-201 | 958 | 505 | 1860 | 342 |
| Metazoa_SRP | Metazoa_SRP.72-201 | 631 | 494 | 2184 | 349 |
| Metazoa_SRP | Metazoa_SRP.151-201 | 470 | 432 | 1431 | 265 |
| Metazoa_SRP | Metazoa_SRP.208-201 | 431 | 422 | 1104 | 242 |
| Metazoa_SRP | Metazoa_SRP.501-201 | 266 | 236 | 434 | 44 |
| Metazoa_SRP | Metazoa_SRP.682-201 | 21 | 10 | 13 | 2 |

RRNA (Ribosomal RNA)

Ribosomal RNA (rRNA) forms part of the protein-synthesizing organelle known as a ribosome and that is exported to the cytoplasm to help translate the information in messenger RNA (mRNA) into protein. Eukaryotic ribosome (80S) rRNA components are: large unit (rRNA 5S, 5.8S, and 28S) small unit (rRNA 18S). Both rRNA 28S and 5.8S are selectively up-shuttled in exosomes and MV.

List of top ranking rRNA identified using GENCODE sequence data set:

Small Nucleolar RNA: snoRNA

Small nucleolar RNAs (snoRNAs) are a class of small RNA molecules that primarily guides chemical modifications of other RNAs, mainly ribosomal RNAs, transfer RNAs and small nuclear RNAs. There are two main classes of snoRNA, the C/D box snoRNAs which are associated with methylation, and the H/ACA box snoRNAs which are associated with pseudouridylation.

List of top ranking snoRNA identified using GENCODE sequence data set:

TABLE 15

Identification rRNA sequences using GENCODE in exosomes (EXO), microvesicles (MV) and producer cells. The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| RNA5-8SP6 | RNA5-8SP6-201 | 152 | rRNA | 205008 | 1148190 |
| RNA28S5 | RNA28S5-001 | 432 | rRNA | 86111 | 458585 |
| RNA18S5 | RNA18S5-001 | 599 | rRNA | 74634 | 52055 |
| RNA5-8SP2 | RNA5-8SP2-201 | 152 | rRNA | 6488 | 1719 |
| RNA5-8SP5 | RNA5-8SP5-201 | 152 | rRNA | 2794 | 7393 |

| Gene Symbol | Transcript ID | CTX0E03 07EH MV | CTX0E03 07EI cells | CTX0E03 07EI EXO | CTX0E03 07EI MV |
|---|---|---|---|---|---|
| RNA5-8SP6 | RNA5-8SP6-201 | 706558 | 213187 | 135909 | 14732 |
| RNA28S5 | RNA28S5-001 | 516754 | 62829 | 390237 | 47483 |
| RNA18S5 | RNA18S5-001 | 61639 | 116874 | 138484 | 14616 |
| RNA5-8SP2 | RNA5-8SP2-201 | 1540 | 9231 | 3112 | 149 |
| RNA5-8SP5 | RNA5-8SP5-201 | 3924 | 7314 | 3579 | 232 |

TABLE 16

Identification of snoRNA sequences using GENCODE in exosomes (EXO), microvesicles (MV) and producer cells. The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| SNORD3A | SNORD3A-201 | 216 | snoRNA | 1433 | 2085 |
| SNORD3C | SNORD3C-201 | 216 | snoRNA | 1169 | 1702 |
| SNORD29 | SNORD29-201 | 65 | snoRNA | 28130 | 1633 |
| SNORD83B | SNORD83B-201 | 93 | snoRNA | 1835 | 675 |
| SNORD30 | SNORD30-201 | 70 | snoRNA | 29743 | 254 |

| Gene Symbol | Transcript ID | CTX0E03 07EH MV | CTX0E03 07EI cells | CTX0E03 07EI EXO | CTX0E03 07EI MV |
|---|---|---|---|---|---|
| SNORD3A | SNORD3A-201 | 1621 | 906 | 1732 | 120 |
| SNORD3C | SNORD3C-201 | 1220 | 639 | 1176 | 86 |
| SNORD29 | SNORD29-201 | 1070 | 36677 | 1752 | 45 |
| SNORD83B | SNORD83B-201 | 487 | 638 | 575 | 29 |
| SNORD30 | SNORD30-201 | 244 | 29071 | 283 | 24 |

Small Nuclear RNA (snRNA)

Small nuclear ribonucleic acid (snRNA), also commonly referred to as U-RNA, is a class of small RNA molecules that make up the major spliceosome are named U1, U2, U4, U5, and U6, and participate in several RNA-RNA and RNA-protein interactions. Their primary function is in the processing of pre-mRNA (hnRNA) in the nucleus. They have also been shown to aide in the regulation of transcription factors (7SK RNA) or RNA polymerase II (B2 RNA), and maintaining the telomeres.

List of top ranking snRNA identified using GENCODE sequence data set:

LincRNA and Novel lincRNA

Large intergenic non-coding RNAs (lincRNAs) are emerging as key regulators of diverse cellular processes. Determining the function of individual lincRNAs remains a challenge. Long non-coding RNAs (long ncRNAs, lncRNA) are non-protein coding transcripts longer than 200 nucleotides.

List of top ranking previously known and novel lincRNAs identified using GENCODE sequence data set:

TABLE 17A

Identification of snRNA sequences using GENCODE in exosomes (EXO), microvesicles (MV) and producer cells. The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| U2 | U2.38-201 | 191 | snRNA | 1354 | 71596 |
| U2 | U2.6-201 | 192 | snRNA | 834 | 15561 |
| U1 | U1.81-201 | 164 | snRNA | 584 | 10901 |
| U1 | U1.90-201 | 167 | snRNA | 533 | 9927 |
| U2 | U2.7-201 | 191 | snRNA | 201 | 9267 |

| Gene Symbol | Transcript ID | CTX0E03 07EH MV | CTX0E03 07EI cells | CTX0E03 07EI EXO | CTX0E03 07EI MV |
|---|---|---|---|---|---|
| U2 | U2.38-201 | 49223 | 751 | 35290 | 1919 |
| U2 | U2.6-201 | 13594 | 303 | 8146 | 272 |
| U1 | U1.81-201 | 7307 | 91 | 3197 | 121 |
| U1 | U1.90-201 | 6689 | 48 | 2187 | 84 |
| U2 | U2.7-201 | 3109 | 288 | 6736 | 262 |

TABLE 17B

Identification of lincRNA and putative novel lincRNA sequences using GENCODE in exosomes (EXO), microvesicles (MV) and producer cells. The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| RP11-108M9.3 | RP11-108M9.3-0 | 1761 | Novel lincRNA | 244 | 159 |
| RP11-329L6.1 | RP11-329L6.1-001 | 507 | Novel lincRNA | 19 | 70 |
| RP11-160E2.6 | RP11-160E2.6-00 | 637 | Novel lincRNA | 228 | 67 |
| AC004528.3 | AC004528.3-001 | 107 | Novel lincRNA | 16 | 58 |
| MALAT1 | MALAT1-201 | 4585 | lincRNA | 150 | 308 |
| GAS5 | GAS5-007 | 2743 | lincRNA | 12024 | 215 |

| Gene Symbol | Transcript ID | CTX0E03 07 EH MV | CTX0E03 07EI cells | CTX0E03 07EI EXO | CTX0E03 07EI MV |
|---|---|---|---|---|---|
| RP11-108M9.3 | RP11-108M9.3-0 | 240 | 539 | 324 | 45 |
| RP11-329L6.1 | RP11-329L6.1-001 | 41 | 29 | 84 | 2 |
| RP11-160E2.6 | RP11-160E2.6-00 | 115 | 489 | 74 | 6 |
| AC004528.3 | AC004528.3-001 | 46 | 14 | 55 | 4 |
| MALAT1 | MALAT1-201 | 234 | 26 | 182 | 12 |
| GAS5 | GAS5-007 | 120 | 46501 | 875 | 13 |

GAS5 lincRNA is highly expressed in cell producer compared to in exosomes and microvesicles (down shuttled in both exosomes and MV).

mRNA

Coding sequencing mRNA were also identified.

TABLE 18

Identification of mRNA sequences using GENCODE in exosomes (EXO), microvesicles (MV) and producer cells. The transcript IDs are taken from Ensembl database (www.ensembl.org).

| Gene Symbol | Transcript ID | Length | Type of RNA | CTX0E03 07EH cells | CTX0E03 07EH EXO |
|---|---|---|---|---|---|
| EEF2 | EEF2-201 | 9407 | mRNA | 710 | 578 |
| MTRNR2L8 | MTRNR2L8-201 | 1290 | mRNA | 1383 | 548 |
| NES | NES-001 | 8635 | mRNA | 668 | 406 |
| VIM | VIM-001 | 8316 | mRNA | 563 | 911 |

| Gene Symbol | Transcript ID | CTX0E03 07 EH MV | CTX0E03 07 EI cells | CTX0E03 07 EI EXO | CTX0E03 07EI MV |
|---|---|---|---|---|---|
| EEF2 | EEF2-201 | 449 | 1155 | 471 | 33 |
| MTRNR2L8 | MTRNR2L8-201 | 642 | 1323 | 258 | 15 |
| NES | NES-001 | 234 | 1448 | 267 | 20 |
| VIM | VIM-001 | 501 | 1500 | 618 | 36 |

Example 17A-C: Conclusion

The main scope of the deep sequence analysis was to identify their miRNA components in neural stem cell-derived vesicles (exosomes and microvesicles). This analysis identified a new set of known and novel miRNAs that are preferentially shuttled into both exosomes and MV. Among the identified miRNAs already included in mirbase database were hsa-miR-1246, hsa-miR-4488, hsa-miR-4492, hsa-miR-4508, hsa-miR-4516, hsa-miR-4532, and among the novel miRNAs were AC079949.1, AP000318.1, AL161626.1, AC004943.1, AL121897.1. Top ranking shuttled miRNAs, including novel ones were validated by qRT-PCR in exosomes.

The size distribution of shuttle RNA, as shown here, is mostly in the range of 20 to 200 nt and other RNA species are released by cells into the extracellular space. By deep sequencing and GENCODE sequence set analysis we found a greater complexity and diversity of non-coding RNA transcripts. We extended this analysis with detailed evaluation and this led to the discovery of preferentially up (defined as log 2 fold change 2) and down (defined as log 2 fold change≤−2) shuttle of other non-coding RNAs in both exosomes and microvesicles. Differentially shuttled non coding RNA were found in almost all the non-coding RNA subtypes, ribosomal RNA (rRNA), small nucleolar (snoRNA), small nuclear RNA (snRNA), microRNA (miRNA), miscellaneous other RNA (misc_RNA, e.g. RMRP, vault RNA, metazoa SRP, and RNY), and large intergenic non-coding RNAs (lincRNAs).

The unequal distribution of the detected RNA species over cellular and shuttle RNA, combined with increasing evidence for their role in gene regulation strongly suggest that cells specifically release these RNAs to modify the function of target cells.

D) Deep Sequencing of CTX0E03 Cell and Exosome miRNA Expression from 6 Week Bioreactor Culture Next generation deep sequencing was also carried out on CTX0E03 cells and their derived exosomes, following culture for six weeks in an Integra bioreactor. The results showed that hsa-miR-1246, hsa-miR-4492, hsa-miR-4532, and hsa-miR-4488 are also up-shuttled in exosomes derived from 6 week Integra culture (6W). In EXO 6W a total of 61 miRNA types are up-shuttled. Up-shuttled miRNAs with more than 250 reads per exosome sample are listed in FIG. 13E.

Conclusions

Hsa-miR-1246, hsa-miR-4492, hsa-miR-4532, and hsa-miR-4488 are still up-shuttled in EXO 6W as observed on proliferative EXO (07E1 & EH; FIGS. 13 A&B). New up-shuttled miRNAs are also identified, including hsa-miR-4792.

20.53% of the identified miRNA are up-shuttled in the exosomes derived from 6 week Integra CTX cultures (shown in FIG. 13C, middle panel). This compares to 99% of the identified miRNAs that are up-shuttled in the exosomes derived from proliferative CTX0E03 cultures (FIG. 13C, top panel).

E) Deep Sequencing of CTX0E03 Cell and Exosome miRNA Expression from 11 Week Bioreactor Culture Next generation deep sequencing was also carried out on CTX0E03 cells and their derived exosomes, following culture for 11 weeks in an Integra bioreactor. Three samples were tested.

Figure 13F:
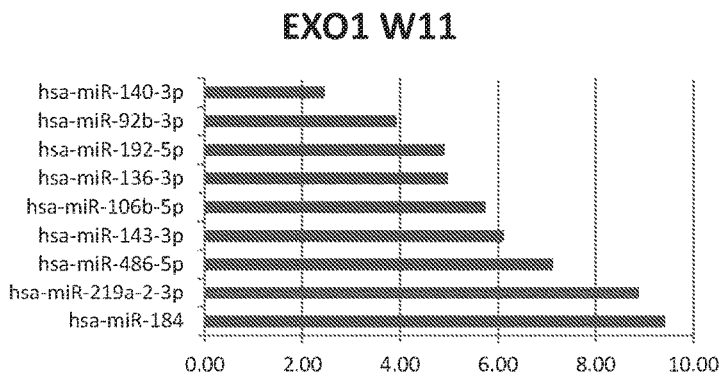

In sample 1, 9 miRNA species are up-shuttled, all of which have more than 250 reads, as shown in FIG. 13F.

Figure 13G:
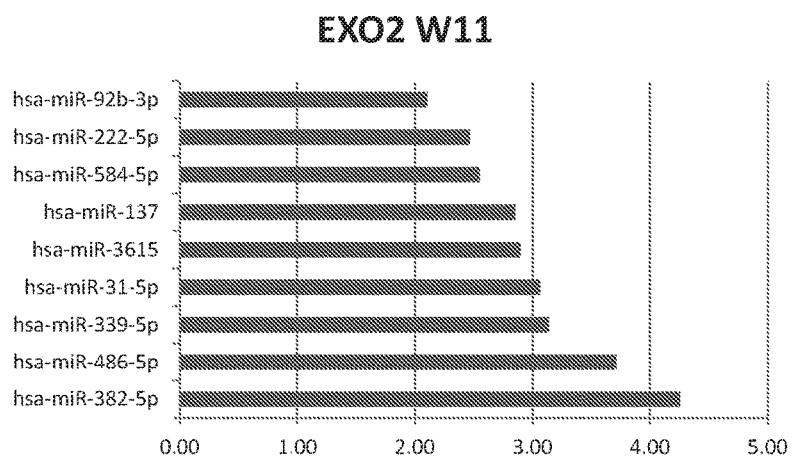

In sample 2, 68 miRNA species are up-shuttled into the exosomes. The miRNAs with more than 250 reads per exosome sample are shown in FIG. 13G.

Figure 13H:
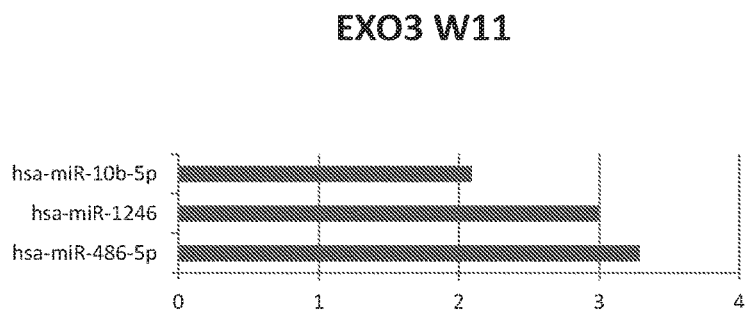

In sample 3, 47 miRNA species are up-shuttled. FIG. 13H shows the three miRNA species with a read count>250: hsa-miR-10b-5p, hsa-miR-1246 and hsa-miR-486-5p.

Conclusions

TABLE E1

W11 summary table of reads and log2 values of miRNA types previously reported as up-shuttled in proliferative CTX0E03 exosomes.

| MiRNA | Reads | | | | | | Log2 | | |
|---|---|---|---|---|---|---|---|---|---|
| | Cell1 | Cell2 | Cell3 | EXO1 | EXO2 | EXO3 | EXO1 | EXO2 | EXO3 |
| hsa-miR-4488 | 0 | 0 | 1 | 0 | 0 | 0 | N/A | N/A | N/A |
| hsa-miR-4492 | 0 | 1 | 0 | 1 | 0 | 0 | N/A | N/A | N/A |
| hsa-miR-4532 | 0 | 0 | 0 | 0 | 0 | 0 | N/A | N/A | N/A |
| hsa-miR-1246 | 483 | 1122 | 3470 | 18 | 2726 | 24152 | −4.20 | 1.26 | 2.99 |

Hsa-miR-1246 is present in 11W exosomes, but was only observed to be up-shuttled in EXO3.

Hsa-miR-4488, hsa-miR-4492, and hsa-miR-4532, identified in proliferative CTX0E03 cells and their exosomes, are almost absent in 11 week samples (both cells and exosomes).

Hsa-miR-486-5p was the only miRNA up-shuttled in all three EXO W11 samples.

An average 12.22% of the identified miRNAs are up-shuttled in the exosomes derived from 11 week Integra CTX0E03 cultures (FIG. 13C, lower panel).

Comparative Summary Tables

Comparative Analysis of miRNA Expression in EXO Samples Sorted by Largest Reads in EXO Derived from Proliferative CTX0E03/07EH

TABLE E2

Summary table listing miRNA reads and log2. Log2 is calculated using the normalized ratio of either EXO 6W or EXO 11W samples/averaged reads in EXO derived from proliferative cells. Up-shuttled miRNAs (log2 > 2), in EXO derived from CTX0E03 cultured for 6 and 11 weeks in Integra flasks, are italicized and down-shuttled (log2 < 2) in bold respectively. The table presents only the top 30 more abundant miRNAs.

| MiRNA | Reads | | | | | | LOG2 | | | |
|---|---|---|---|---|---|---|---|---|---|---|
| | EXO 07EH | EXO 07EI | EXO WK6 | EXO1 WK11 | EXO2 WK11 | EXO3 WK11 | EXO WK6 | EXO1 WK11 | EXO2 WK11 | EXO3 WK11 |
| hsa-miR-1246 | 111092 | 83958 | 77678 | 18 | 2726 | 24152 | −1.40 | −13.43 | −9.32 | −5.96 |
| hsa-miR-4492 | 5188 | 22482 | 9528 | 1 | | | −2.65 | −15.82 | | |
| hsa-miR-4532 | 3368 | 6419 | 3463 | | | | −2.39 | | | |
| hsa-miR-4488 | 1389 | 20618 | 11048 | | | | −2.12 | | | |
| hsa-miR-4485 | 386 | 43 | 13 | | 11 | 69 | −5.46 | | −8.80 | −5.93 |
| hsa-miR-4508 | 188 | 723 | 1245 | | | 20 | −0.68 | | | −9.51 |
| hsa-miR-4516 | 135 | 904 | 1153 | | | | −0.96 | | | |

TABLE E2-continued

Summary table listing miRNA reads and log2. Log2 is calculated using the normalized ratio of either EXO 6W or EXO 11W samples/averaged reads in EXO derived from proliferative cells. Up-shuttled miRNAs (log2 > 2), in EXO derived from CTX0E03 cultured for 6 and 11 weeks in Integra flasks, are italicized and down-shuttled (log2 < 2) in bold respectively. The table presents only the top 30 more abundant miRNAs.

| | Reads | | | | | | LOG2 | | | |
|---|---|---|---|---|---|---|---|---|---|---|
| MiRNA | EXO 07EH | EXO 07EI | EXO WK6 | EXO1 WK11 | EXO2 WK11 | EXO3 WK11 | EXO WK6 | EXO1 WK11 | EXO2 WK11 | EXO3 WK11 |
| hsa-miR-4497 | 73 | 28 | 61 | | | | −1.64 | | | |
| hsa-miR-1973 | 50 | 5 | 1 | | | | −7.05 | | | |
| hsa-miR-3195 | 48 | 17 | 14 | | | | −3.40 | | | |
| hsa-miR-4466 | 43 | 12 | 15 | | | 9 | −2.38 | | | −5.99 |
| hsa-let-7a-5p | 20 | 15 | 18306 | 69521 | 496463 | 509272 | *7.80* | *9.77* | *9.47* | *9.72* |
| hsa-miR-99b-5p | 19 | 15 | 25938 | 6984 | 56360 | 50611 | *8.35* | *6.50* | *6.37* | *6.44* |
| hsa-miR-21-5p | 18 | 41 | 35754 | 12191 | 134432 | 150516 | *8.01* | *6.50* | *6.82* | *7.21* |
| hsa-miR-92a-3p | 18 | 7 | 15054 | 5504 | 89826 | 73306 | *8.00* | *6.59* | *7.48* | *7.41* |
| hsa-miR-3676-5p | 17 | 174 | 59 | | | | −2.88 | | | |
| hsa-miR-4792 | 15 | 24 | 254 | | | | 1.54 | | | |
| hsa-miR-664-5p | 13 | 8 | 1 | | | | −5.53 | | | |
| hsa-miR-100-5p | 11 | 5 | 30124 | 22 | 56751 | 43080 | *9.68* | −0.69 | *7.50* | *7.32* |
| hsa-miR-1291 | 10 | 17 | 18 | | | 34 | −1.83 | | | −3.79 |
| hsa-miR-16-5p | 10 | 4 | 5502 | 15 | 6580 | 9510 | *7.32* | −1.15 | *4.48* | *5.24* |
| hsa-miR-4284 | 10 | 11 | 5 | | | | −3.26 | | | |
| hsa-miR-663b | 9 | 26 | 39 | | | | −1.03 | | | |
| hsa-miR-25-3p | 8 | | 1383 | 5825 | 42402 | 29320 | *6.09* | *8.21* | *7.94* | *7.63* |
| hsa-miR-3656 | 8 | 10 | 743 | 2023 | 1 | | *4.20* | *5.69* | −8.43 | |
| hsa-miR-181a-5p | 7 | 1 | 81465 | 56064 | 1289686 | 1023049 | *12.19* | *11.69* | *13.08* | *12.96* |
| hsa-miR-3654 | 6 | 13 | 3 | | | 9 | −3.90 | | | −5.19 |
| hsa-miR-26a-5p | 6 | 17 | 18836 | 3542 | 49957 | 54929 | *8.45* | *6.08* | *6.76* | *7.12* |

Comparative Analysis of miRNA Expression in EXO Samples Sorted by Largest Reads in EXO Derived from 6W Integra CTX0E03 Culture

TABLE E3

Summary table listing miRNA reads and log2. Log2 is calculated using the normalized ratio of either EXO 6W or EXO 11W samples/averaged reads in EXO derived from proliferative cells. Up-shuttled miRNAs (log2 > 2), in EXO derived from CTX0E03 cultured for 6 and 11 weeks in Integra flasks, are italicized and down-shuttled (log2 < 2) in bold respectively. The table presents only the top 30 more abundant miRNAs.

| | Reads | | | | | | LOG2 | | | |
|---|---|---|---|---|---|---|---|---|---|---|
| MiRNA | EXO 07EH | EXO 07EI | EXO WK6 | EXO1 WK11 | EXO2 WK11 | EXO3 WK11 | EXO WK6 | EXO1 WK11 | EXO2 WK11 | EXO3 WK11 |
| hsa-miR-181a-5p | 7 | 1 | 81465 | 56064 | 1289686 | 1023049 | *12.19* | *11.69* | *13.08* | *12.96* |
| hsa-miR-1246 | 111092 | 83958 | 77678 | 18 | 2726 | 24152 | −1.40 | −13.43 | −9.32 | −5.96 |
| hsa-miR-127-3p | | 6 | 36828 | 29 | 22175 | 48371 | *11.39* | 1.13 | *7.57* | *8.92* |

TABLE E3-continued

Summary table listing miRNA reads and log2. Log2 is calculated using the normalized ratio of either EXO 6W or EXO 11W samples/averaged reads in EXO derived from proliferative cells. Up-shuttled miRNAs (log2 > 2), in EXO derived from CTX0E03 cultured for 6 and 11 weeks in Integra flasks, are italicized and down-shuttled (log2 < 2) in bold respectively. The table presents only the top 30 more abundant miRNAs.

| | Reads | | | | | | LOG2 | | | |
| --- | --- | --- | --- | --- | --- | --- | --- | --- | --- | --- |
| MiRNA | EXO 07EH | EXO 07EI | EXO WK6 | EXO1 WK11 | EXO2 WK11 | EXO3 WK11 | EXO WK6 | EXO1 WK11 | EXO2 WK11 | EXO3 WK11 |
| hsa-miR-21-5p | 18 | 41 | 35754 | 12191 | 134432 | 150516 | *8.01* | *6.50* | *6.82* | *7.21* |
| hsa-miR-100-5p | 11 | 5 | 30124 | 22 | 56751 | 43080 | *9.68* | −0.69 | *7.50* | *7.32* |
| hsa-miR-99b-5p | 19 | 15 | 25938 | 6984 | 56360 | 50611 | *8.25* | *6.50* | *6.37* | *6.44* |
| hsa-miR-26a-5p | 6 | 17 | 18836 | 3542 | 49957 | 54929 | *8.45* | *6.08* | *6.76* | *7.12* |
| hsa-let-7a-5p | 20 | 15 | 18306 | 69521 | 496463 | 509272 | *7.80* | *9.77* | *9.47* | *9.72* |
| hsa-miR-191-5p | 4 | 1 | 17845 | 10674 | 130737 | 104349 | *10.49* | *9.79* | *10.27* | *10.17* |
| hsa-miR-27b-3p | 1 | | 15232 | 7344 | 33638 | 47061 | *12.55* | *11.55* | *10.60* | *11.31* |
| hsa-miR-92a-3p | 18 | 7 | 15054 | 5504 | 89826 | 73306 | *8.00* | *6.59* | *7.48* | *7.41* |
| hsa-miR-146b-5p | | 1 | 12960 | 12 | 29712 | 13822 | *12.47* | 2.44 | *10.58* | *9.69* |
| hsa-let-7i-5p | 1 | 2 | 12914 | 6928 | 157331 | 149116 | *10.83* | *9.98* | *11.34* | *11.49* |
| hsa-miR-222-3p | 3 | 2 | 12671 | 46 | 89141 | 64302 | *10.03* | 1.97 | *9.75* | *9.50* |
| hsa-let-7c | 1 | 2 | 12414 | | | | *10.77* | | | |
| hsa-miR-4488 | 1389 | 20618 | 11048 | | | | −2.12 | | | |
| hsa-miR-4492 | 5188 | 22482 | 9528 | 1 | | | −2.65 | −15.82 | | |
| hsa-let-7b-5p | 5 | 6 | 8914 | 34 | 86886 | 33259 | *8.40* | 0.41 | *8.59* | *7.43* |
| hsa-let-7f-5p | 5 | 6 | 8766 | 13898 | 293116 | 427140 | *8.38* | *9.09* | *10.35* | *11.11* |
| hsa-miR-92b-3p | 3 | 7 | 8141 | 73468 | 420313 | 291688 | *8.43* | *11.65* | *11.03* | *10.72* |
| hsa-miR-181b-5p | 1 | 3 | 7919 | 6713 | 226010 | 167200 | *9.72* | *9.53* | *11.46* | *11.25* |
| hsa-miR-221-3p | 3 | 3 | 6391 | 4927 | 17702 | 12768 | *8.76* | *8.46* | *7.17* | *6.92* |
| hsa-miR-125b-5p | 4 | 4 | 6107 | 2181 | 54267 | 37113 | *8.31* | *6.87* | *8.37* | *8.04* |
| hsa-miR-151a-3p | 3 | 4 | 6014 | 2776 | 26457 | 29135 | *8.49* | *7.42* | *7.53* | *7.89* |
| 30a-5p | 2 | | 5613 | 15559 | 136508 | 96950 | *10.11* | *11.63* | *11.62* | *11.35* |
| hsa-miR-16-5p | 10 | 4 | 5502 | 15 | 6580 | 9510 | *7.32* | −1.15 | 4.48 | 5.24 |
| hsa-miR-22-3p | 4 | 1 | 5489 | 2914 | 8193 | 10780 | *8.79* | *7.92* | *6.27* | *6.89* |
| hsa-miR-99a-5p | 1 | | 5116 | 14 | 27513 | 17532 | *10.98* | 2.51 | *10.31* | *9.88* |

Comparative Analysis of miRNA Expression in EXO Samples Sorted by Largest Reads in EXO3 Derived from 11W Integra CTX0E03 Culture

TABLE E4

Summary table listing miRNA reads and log2. Log2 is calculated using the normalized ratio of either EXO 6W or EXO 11W samples/averaged reads in EXO derived from proliferative cells. Up-shuttled miRNAs (log2 > 2), in EXO derived from CTX0E03 cultured for 6 and 11 weeks in Integra flasks, are italicized and down-shuttled (log2 < 2) in bold respectively. The table presents only the top 30 more abundant miRNAs.

| MiRNA | Reads | | | | | | LOG2 | | | |
| --- | --- | --- | --- | --- | --- | --- | --- | --- | --- | --- |
| | EXO 07EH | EXO 07EI | EXO WK6 | EXO1 WK11 | EXO2 WK11 | EXO3 WK11 | EXO WK6 | EXO1 WK11 | EXO2 WK11 | EXO3 WK11 |
| hsa-miR-181a-5p | 7 | 1 | 81465 | 56064 | 1289686 | 1023049 | *12.19* | *11.69* | *13.08* | *12.96* |
| hsa-let-7a-5p | 20 | 15 | 18306 | 69521 | 496463 | 509272 | 7.80 | *9.77* | *9.47* | *9.72* |
| hsa-let-7f-5p | 5 | 6 | 8766 | 13898 | 293116 | 427140 | 8.38 | *9.09* | *10.35* | *11.11* |
| hsa-miR-92b-5p | 3 | 7 | 8141 | 73468 | 420313 | 291688 | 8.43 | *11.65* | *11.03* | *10.72* |
| hsa-miR-9-5p | 3 | 3 | 2196 | 155707 | 481660 | 263043 | 7.25 | *13.44* | *11.93* | *11.28* |
| hsa-miR-181b-5p | 1 | 3 | 7919 | 6713 | 226010 | 167200 | *9.72* | *9.53* | *11.46* | *11.25* |
| hsa-miR-21-5p | 18 | 41 | 35754 | 12191 | 134432 | 150516 | 8.01 | 6.50 | 6.82 | 7.21 |
| hsa-let-7i-5p | 1 | 2 | 12914 | 6928 | 157331 | 149116 | *10.83* | *9.98* | *11.34* | *11.49* |
| hsa-miR-191-5p | 4 | 1 | 17845 | 10674 | 130737 | 104349 | *10.49* | *9.79* | *10.27* | *10.17* |
| hsa-miR-30a-5p | 2 | | 5613 | 15559 | 136508 | 96950 | *10.11* | *11.63* | *11.62* | *11.35* |
| hsa-miR-92a-3p | 18 | 7 | 15054 | 5504 | 89826 | 73306 | 8.00 | 6.59 | 7.48 | 7.41 |
| hsa-miR-10a-5p | | 1 | 3754 | 5840 | 132775 | 66316 | *10.69* | *11.37* | *12.74* | *11.96* |
| hsa-miR-222-3p | 3 | 2 | 12671 | 46 | 89141 | 64302 | *10.03* | 1.97 | *9.75* | *9.50* |
| hsa-let-7c-5p | | | | 13106 | 68120 | 59498 | | | | |
| hsa-miR-26a-5p | 6 | 17 | 18836 | 3542 | 49957 | 54929 | 8.45 | 6.08 | 6.76 | 7.12 |
| hsa-miR-423-5p | 1 | 1 | 538 | 2606 | 45587 | 52945 | 6.81 | *9.13* | *10.12* | *10.55* |
| hsa-miR-99b-5p | 19 | 15 | 25938 | 6984 | 56360 | 50611 | 8.35 | 6.50 | 6.37 | 6.44 |
| hsa-miR-127-3p | | 6 | 36828 | 29 | 22175 | 48371 | *11.39* | 1.13 | 7.57 | 8.92 |
| hsa-miR-27b-3p | 1 | | 15232 | 7344 | 33638 | 47061 | *12.55* | *11.55* | *10.60* | *11.31* |
| hsa-miR-100-5p | 11 | 5 | 30124 | 22 | 56751 | 43080 | *9.68* | −0.69 | 7.50 | 7.32 |
| hsa-let-7e-5p | | 2 | 1932 | 5398 | 27921 | 41799 | 8.73 | *10.26* | *9.49* | *10.29* |
| hsa-miR-486-5p | 3 | 1 | 3503 | 44199 | 20054 | 37232 | 8.47 | *12.17* | 7.89 | *9.01* |
| hsa-miR-125b-5p | 4 | 4 | 6107 | 2181 | 54267 | 37113 | 8.31 | 6.87 | 8.37 | 8.04 |
| hsa-let-7b-5p | 5 | 6 | 8914 | 34 | 86886 | 33259 | 8.40 | 0.41 | 8.59 | 7.43 |
| hsa-miR-182-5p | 3 | 15 | 833 | 22 | 33064 | 32491 | 4.32 | −0.88 | 6.53 | 6.73 |
| hsa-miR-30d-5p | | 2 | 3946 | 22 | 26066 | 32148 | *9.76* | 2.32 | *9.39* | *9.91* |
| hsa-miR-25-3p | 8 | | 1383 | 5825 | 42402 | 29320 | 6.09 | 8.21 | 7.94 | 7.63 |
| hsa-miR-151a-3p | 3 | 4 | 6014 | 2776 | 26457 | 29135 | 8.49 | 7.42 | 7.53 | 7.89 |

Conclusions for Comparative Summary of miRNA Reads Present in Exosome Samples

Hsa-miR-1246, hsa-miR-4492, hsa-miR-4532, and hsa-miR-4488 are the most up-shuttled miRNA types in exosomes derived from proliferative CTX0E03 cells.

Hsa-miR-1246, hsa-miR-4492, hsa-miR-4532, and hsa-miR-4488 are still present in EXO 6W sample, but hsa-miR-4492, hsa-miR-4532, and hsa-miR-4488 are almost absent in EXO 11W samples.

Hsa-miR-181a-5p, hsa-miR-1246, hsa-miR-127-3p, hsa-miR-21-5p, and hsa-miR-100-5p are the top 5 miRNAs present in EXO 6W sample.

Hsa-miR-181a-5p, hsa-let-7a-5p, hsa-let-7f-5p, hsa-miR-92b-3p, and hsa-miR-9-5p are the top 5 miRNAs present in EXO 11W samples.

Comparative Analysis of miRNA Expression in Cell Samples Sorted by Largest Reads in Proliferative Cell 07EH

TABLE E5

Summary table listing miRNA reads and log2. Log2 is calculated using the normalized ratio of either cell 6W or cell 11W samples/averaged reads in proliferative cells. Up-expressed miRNAs (log2 > 2), in CTX0E03 cultured for 6 and 11 weeks in Integra flasks, are italicized and down-expressed (log2 < 2) in bold respectively. The table presents only the top 30 more abundant miRNAs.

| | Reads | | | | | | LOG2 | | | |
|---|---|---|---|---|---|---|---|---|---|---|
| miRNA | Cell (07EH) | Cells (07EI) | Cell 6WK | Cell1 WK11 | Cell2 WK11 | Cell3 WK11 | Cell 6WK | Cell1 WK11 | Cell2 WK11 | Cell3 WK11 |
| hsa-let-7a-5p | 75110 | 305060 | 357507 | 82000 | 572638 | 945050 | 0.08 | −0.68 | −0.44 | −0.58 |
| hsa-miR-92b-3p | 9794 | 242715 | 51788 | 7070 | 95904 | 269851 | −1.46 | −2.97 | −1.78 | −1.15 |
| hsa-miR-21-5p | 11943 | 154626 | 109713 | 36935 | 165335 | 350731 | 0.06 | −0.15 | −0.55 | −0.33 |
| hsa-miR-92a-3p | 14359 | 137412 | 136842 | 15296 | 99662 | 238214 | 0.41 | −1.39 | −1.25 | −0.86 |
| hsa-miR-127-3p | 7064 | 110806 | 54214 | 4015 | 20215 | 70609 | −0.40 | −2.79 | −3.03 | −2.09 |
| hsa-miR-100-5p | 52451 | 109290 | 121101 | 8268 | 35093 | 40100 | −0.61 | −3.12 | −3.60 | −4.28 |
| hsa-miR-27b-3p | 16900 | 91902 | 55177 | 15130 | 73464 | 113623 | −0.66 | −1.16 | −1.45 | −1.69 |
| hsa-miR-191-5p | 12591 | 89150 | 58145 | 16786 | 74782 | 151339 | −0.37 | −0.80 | −1.21 | −1.06 |
| hsa-miR-26a-5p | 9900 | 88724 | 164401 | 24518 | 127010 | 271289 | 1.27 | −0.11 | −0.30 | −0.08 |
| hsa-miR-99b-5p | 39457 | 87399 | 46207 | 3177 | 14278 | 22554 | −1.62 | −4.12 | −4.52 | −4.72 |
| hsa-let-7f-5p | 10349 | 78395 | 61473 | 115717 | 457274 | 982774 | −0.06 | *2.21* | *1.63* | 1.87 |
| hsa-miR-181a-5p | 6956 | 47686 | 180839 | 150467 | 1304081 | 1909336 | *2.15* | *3.25* | *3.80* | *3.48* |
| hsa-miR-486-5p | 20310 | 41639 | 4938 | 465 | 1500 | 4379 | −3.85 | −5.90 | −6.78 | −6.10 |
| hsa-miR-30a-5p | 2001 | 35465 | 16099 | 23958 | 94346 | 201534 | −0.47 | 1.47 | 0.88 | 1.11 |
| hsa-miR-98 | 11760 | 30440 | 14559 | | | | −1.61 | | | |
| hsa-miR-151a-3p | 2681 | 29047 | 15661 | 5186 | 22917 | 58870 | −0.42 | −0.65 | −1.07 | −0.57 |
| hsa-miR-21-3p | 4089 | 27733 | 10626 | 2682 | 10247 | 30683 | −1.16 | −1.78 | −2.42 | −1.70 |
| hsa-miR-30d-5p | 1977 | 27307 | 17522 | 4802 | 35022 | 65318 | −0.06 | −0.56 | −0.26 | −0.23 |
| hsa-let-7c | 5103 | 27224 | 70342 | | | | 1.43 | | | |
| hsa-miR-10a-5p | 52927 | 26908 | 28817 | 11983 | 49442 | 69645 | −2.35 | −2.25 | −2.77 | −3.14 |
| hsa-miR-22-3p | 1826 | 26456 | 10088 | 5318 | 33593 | 54769 | −0.79 | −0.35 | −0.26 | −0.42 |
| hsa-miR-182-5p | 5531 | 25885 | 12376 | 2528 | 18519 | 49416 | −1.10 | −2.03 | −1.75 | −1.17 |
| hsa-miR-222-3p | 1422 | 22187 | 10960 | 13094 | 53385 | 90511 | −0.39 | 1.23 | 0.69 | 0.59 |
| hsa-miR-125a-5p | 1451 | 20960 | 9101 | 1406 | 12194 | 16095 | −0.61 | −1.94 | −1.39 | −1.85 |
| hsa-miR-16-5p | 2173 | 19856 | 69449 | 8542 | 42494 | 81960 | *2.20* | 0.54 | 0.29 | 0.37 |
| hsa-let-7b-5p | 2435 | 19774 | 61291 | 13225 | 75017 | 99021 | 1.96 | 1.11 | 1.05 | 0.58 |
| hsa-miR-151a-5p | 1386 | 19773 | 10790 | 1621 | 9192 | 17997 | −0.28 | −1.65 | −1.72 | −1.61 |
| hsa-let-7e-5p | 2449 | 19035 | 14175 | 7948 | 40674 | 84912 | −0.12 | 0.41 | 0.20 | 0.39 |

Comparative Analysis of miRNA Expression in Cell Samples Sorted by Largest Reads in Cells Cultured for 6 Week in Integra Flasks (Cell 6W)

TABLE E6

Summary table listing miRNA reads and log2. Log2 is calculated using the normalized ratio of either cell 6W or cell 11W samples/averaged reads in proliferative cells. Up-expressed miRNAs (log2 > 2), in CTX0E03 cultured for 6 and 11 weeks in Integra flasks, are italicized and down-expressed (log2 < 2) in bold respectively. The table presents only the top 30 more abundant miRNAs.

| | Reads | | | | | | LOG2 | | | |
|---|---|---|---|---|---|---|---|---|---|---|
| miRNA | Cell (07EH) | Cells (07EI) | Cell 6WK | Cell1 WK11 | Cell2 WK11 | Cell3 WK11 | Cell 6WK | Cell1 WK11 | Cell2 WK11 | Cell3 WK11 |
| hsa-let-7a-5p | 75110 | 305060 | 357507 | 82000 | 572638 | 945050 | 0.08 | −0.68 | −0.44 | −0.58 |
| hsa-miR-181a-5p | 6956 | 47686 | 180839 | 150467 | 1304081 | 1909336 | *2.15* | *3.25* | *3.80* | *3.48* |
| hsa-miR-26a-5p | 9900 | 88724 | 164401 | 24518 | 127010 | 271289 | 1.27 | −0.11 | −0.30 | −0.08 |
| hsa-miR-92a-3p | 14359 | 137412 | 136842 | 15296 | 99662 | 238214 | 0.41 | −1.39 | −1.25 | −0.86 |
| hsa-miR-100-5p | 52451 | 109290 | 121101 | 8268 | 35093 | 40100 | −0.61 | −3.12 | −3.60 | −4.28 |
| hsa-miR-21-5p | 11943 | 154626 | 109713 | 36935 | 165335 | 350731 | 0.06 | −0.15 | −0.55 | −0.33 |
| hsa-let-7c | 5103 | 27224 | 70342 | | | | 1.43 | | | |
| hsa-miR-16-5p | 2173 | 19856 | 69449 | 8542 | 42494 | 81960 | *2.20* | 0.54 | 0.29 | 0.37 |
| hsa-let-7f-5p | 10349 | 78395 | 61473 | 115717 | 457274 | 982774 | −0.06 | *2.21* | 1.63 | 1.87 |
| hsa-let-7b-5p | 2435 | 19774 | 61291 | 13225 | 75017 | 99021 | 1.96 | 1.11 | 1.05 | 0.58 |
| hsa-miR-191-5p | 12591 | 89150 | 58145 | 16783 | 74782 | 151339 | −0.37 | −0.80 | −1.21 | −1.06 |
| hsa-miR-27b-3p | 16900 | 91902 | 55177 | 15130 | 73464 | 113623 | −0.66 | −1.16 | −1.45 | −1.69 |
| hsa-miR-127-3p | 7064 | 110806 | 54214 | 4015 | 20215 | 70609 | −0.40 | −2.79 | −3.03 | −2.09 |
| hsa-miR-92b-3p | 9794 | 242715 | 51788 | 7070 | 95904 | 269851 | −1.46 | −2.97 | −1.78 | −1.15 |
| hsa-miR-9-5p | 518 | 7957 | 49128 | 113170 | 696970 | 1266994 | *3.25* | *5.82* | *5.87* | *5.87* |
| hsa-miR-99b-5p | 39457 | 87399 | 46207 | 3177 | 14278 | 22554 | −1.62 | −4.12 | −4.52 | −4.72 |
| hsa-miR-146b-5p | 4552 | 8434 | 38088 | 7472 | 43047 | 20961 | 1.29 | 0.30 | 0.26 | −1.64 |
| hsa-miR-125b-5p | 1002 | 17965 | 34339 | 2841 | 21418 | 24635 | 1.61 | −0.62 | −0.28 | −0.94 |
| hsa-miR-1246 | 3973 | 1783 | 32042 | 483 | 1122 | 3470 | 1.56 | −3.13 | −4.48 | −3.72 |
| hsa-miR-10a-5p | 52927 | 26908 | 28817 | 11983 | 49442 | 69645 | −2.35 | −2.25 | −2.77 | −3.14 |
| hsa-let-7i-5p | 3015 | 17802 | 21469 | 33910 | 167628 | 432785 | 0.40 | *2.43* | *2.16* | *2.67* |
| hsa-miR-99a-5p | 773 | 2767 | 19124 | 1826 | 11313 | 14604 | *2.54* | 0.51 | 0.58 | 0.08 |
| hsa-miR-30d-5p | 1977 | 27307 | 17522 | 4802 | 35022 | 65318 | −0.06 | −0.56 | −0.26 | −0.23 |
| hsa-let-7g-5p | 959 | 15467 | 16691 | 4240 | 19981 | 36131 | 0.75 | 0.14 | −0.20 | −0.21 |
| hsa-miR-30a-5p | 2001 | 35465 | 16099 | 23958 | 94346 | 201534 | −0.47 | 1.47 | 0.88 | 1.11 |
| hsa-miR-151a-3p | 2681 | 29047 | 15661 | 5186 | 22917 | 58870 | −0.42 | −0.65 | −1.07 | −0.57 |
| hsa-miR-98 | 11760 | 30440 | 14559 | | | | −1.61 | | | |
| hsa-miR-204-5p | 113 | 1378 | 14322 | 1554 | 8147 | 18192 | *3.91* | *2.07* | 1.89 | *2.18* |

Comparative Analysis of miRNA Expression in Cell Samples Sorted by Largest Reads in Cells Cultured 11 Week in Integra Flasks (Cell1 W11)

TABLE E7

Summary table listing miRNA reads and log2. Log2 is calculated using the normalized ratio of either cell 6W or cell 11W samples/averaged reads in proliferative cells. Up-expressed miRNAs (log2 > 2), in CTX0E03 cultured for 6 and 11 weeks in Integra flasks, are italicized and down-expressed (log2 < 2) in bold respectively. The table presents only the top 30 more abundant miRNAs.

| | Reads | | | | | | LOG2 | | | |
|---|---|---|---|---|---|---|---|---|---|---|
| miRNA | Cell (07EH) | Cells (07EI) | Cell 6WK | Cell1 WK11 | Cell2 WK11 | Cell3 WK11 | Cell 6WK | Cell1 WK11 | Cell2 WK11 | Cell3 WK11 |
| hsa-miR-181a-5p | 6956 | 47686 | 180839 | 150467 | 1304081 | 1909336 | *2.15* | *3.25* | *3.80* | *3.48* |
| hsa-miR-9-5p | 518 | 7957 | 49128 | 113170 | 696970 | 1266994 | *3.25* | *5.82* | *5.87* | *5.87* |
| hsa-let-7f-5p | 10349 | 78395 | 61473 | 115717 | 457274 | 982774 | −0.06 | *2.21* | 1.63 | 1.87 |
| hsa-let-7a-5p | 75110 | 305060 | 357507 | 82000 | 572638 | 945050 | 0.08 | −0.68 | −0.44 | −0.58 |
| hsa-let-7i-5p | 3015 | 17802 | 21469 | 33910 | 167628 | 432785 | 0.40 | *2.43* | *2.16* | *2.67* |
| hsa-miR-21-5p | 11943 | 154626 | 109713 | 36935 | 165335 | 350731 | 0.06 | −0.15 | −0.55 | −0.33 |
| hsa-miR-181b-5p | 1382 | 12606 | 11845 | 17620 | 135852 | 275865 | 0.30 | *2.24* | *2.62* | *2.77* |
| hsa-miR-26a-5p | 9900 | 88724 | 164401 | 24518 | 127010 | 271289 | 1.27 | −0.11 | −0.30 | −0.08 |
| hsa-miR-92b-3p | 9794 | 242715 | 51788 | 7070 | 95904 | 269851 | −1.46 | −2.97 | −1.78 | −1.15 |
| hsa-miR-92a-3p | 14359 | 137412 | 136842 | 15296 | 99662 | 238214 | 0.41 | −1.39 | −1.25 | −0.86 |
| hsa-miR-30a-5p | 2001 | 35465 | 16099 | 23958 | 94346 | 201534 | −0.47 | 1.47 | 0.88 | 1.11 |
| hsa-miR-191-5p | 12591 | 89150 | 58145 | 16783 | 74782 | 151339 | −0.37 | −0.80 | −1.21 | −1.06 |
| hsa-let-7c-5p | | | | 18010 | 106589 | 130919 | | | | |
| hsa-miR-27b-3p | 16900 | 91902 | 55177 | 15130 | 73464 | 113623 | −0.66 | −1.16 | −1.45 | −1.69 |
| hsa-let-7b-5p | 2435 | 19774 | 61291 | 13225 | 75017 | 99021 | 1.96 | 1.11 | 1.05 | 0.58 |
| hsa-miR-423-5p | 1080 | 8893 | 3219 | 9325 | 40672 | 93044 | −1.13 | 1.77 | 1.33 | 1.65 |
| hsa-miR-222-3p | 1422 | 22187 | 10960 | 13094 | 53385 | 90511 | −0.39 | 1.23 | 0.69 | 0.59 |
| hsa-let-7e-5p | 2449 | 19035 | 14175 | 7948 | 40674 | 84912 | −0.12 | 0.41 | 0.20 | 0.39 |
| hsa-miR-16-5p | 2173 | 19856 | 69449 | 8542 | 42494 | 81960 | *2.20* | 0.54 | 0.29 | 0.37 |
| hsa-miR-25-3p | 436 | 5303 | 8387 | 5633 | 31971 | 77502 | 1.19 | 1.98 | 1.92 | *2.33* |
| hsa-miR-127-3p | 7064 | 110806 | 54214 | 4015 | 20215 | 70609 | −0.40 | −2.79 | −3.03 | −2.09 |
| hsa-miR-10a-5p | 52927 | 26908 | 28817 | 11983 | 49442 | 69645 | −2.35 | −2.25 | −2.77 | −3.14 |
| hsa-miR-30d-5p | 1977 | 27307 | 17522 | 4802 | 35022 | 65318 | −0.06 | −0.56 | −0.26 | −0.23 |
| hsa-miR-151a-3p | 2681 | 29047 | 15661 | 5186 | 22917 | 58870 | −0.42 | −0.65 | −1.07 | −0.57 |
| hsa-miR-22-3p | 1826 | 26456 | 10088 | 5318 | 33593 | 54768 | −0.79 | −0.35 | −0.26 | −0.42 |
| hsa-miR-182-5p | 5531 | 25885 | 12376 | 2528 | 18519 | 49416 | −1.10 | −2.03 | −1.72 | −1.17 |
| hsa-miR-181a-3p | 86 | 803 | 1186 | 2490 | 24343 | 44745 | 0.97 | *3.40* | *3.93* | *4.13* |
| hsa-miR-100-5p | 52451 | 109290 | 121101 | 8268 | 35093 | 40400 | −0.61 | −3.12 | −3.60 | −4.28 |

Conclusions for Comparative Summary of miRNA Reads Present in Cell Samples

Hsa-let-7a-5p, hsa-miR-92b-3p, hsa-miR-21-5p, hsa-miR-92a-3p, and hsa-miR-127-3p are the top 5 most expressed miRNA types in proliferative CTX0E03 cells.

Hsa-let-7a-5p, hsa-miR-181a-5p, hsa-miR-26a-5p, hsa-miR-92a-3p, hsa-miR-100-5p are the top 5 most expressed miRNA types in CTX0E03 Integra 6W culture.

Hsa-miR-181a-5p, hsa-miR-9-5p, hsa-let-7f-5p, hsa-let-7a-5p, and hsa-let-7i-5p are the top 5 most expressed miRNA types in CTX0E03 Integra 11W cultures.

Hsa-miR-181a-5p and hsa-miR-9-5p are up-expressed in all cell samples cultured in Integra flasks (6 and 11 weeks).

Hsa-let-7i-5p, hsa-let-7c-5p, hsa-miR-181a-3p and hsa-miR-181b-5p were solely up-expressed in W11 cells.

Hsa-miR-181 family seems to play an important role in CTX0E03 long term culture and possible differentiation.

Example 18: Proteomic Analysis

Methods

Exosomes and microvesicle fractions were prepared from a CTX0E03 cell Integra culture (week 2), using differential ultracentrifugation. Exosomes and microvesicles were disrupted in modified RIPA buffer (50 mM Tris HCl, pH 8.0, 150 mM NaCl, 1% SDS, 0.1% Triton X100, 10 mM DTT, 1× Complete protease inhibitor (Roche) and 1×PhosStop phosphatase inhibitor (Roche)) and subjected to manual shearing using a 1 mL tuberculin syringe and 25 gauge needle. Samples were re-quantitated post disruption using the Qubit fluorometer (Invitrogen). 20 μg of each sample was loaded onto a 4-12% SDS-PAGE gel (Novex, Invitrogen). The gel was excised into forty segments per lane and gel slices were processed using a robot (ProGest, DigiLab) with the following protocol:
a) wash with 25 mM ammonium bicarbonate followed by acetonitrile;
b) reduce with 10 mM dithiothreitol at 60° C. followed by alkylation with 50 mM iodoacetamide at room temperature;
c) digest with trypsin (Promega) at 37° C. for 4 h;
d) quench with formic acid;
e) the supernatant was analysed by mass spectrometry directly without further processing.

Mass Spectrometry

Each gel digest was analysed by nano LC/MS/MS with a Waters NanoAcquity HPLC system interfaced to a Thermo-Fisher Q Exactive. Peptides were loaded on a trapping column and eluted over a 75 μm analytical column at 350 nL/min; both columns were packed with Jupiter Proteo resin (Phenomenex). The mass spectrometer was operated in data-dependent mode, with MS and MS/MS performed in the Orbitrap at 70,000 FWHM and 17,500 FWHM resolution, respectively.

Exosomes 2572 proteins were identified by Mass spectrometry in exosomes purified by ultracentrifugation. The exosomes were isolated from the initial stages of an Integra culture (week 2). The gene names and corresponding SWISSPROT accession numbers (in brackets) of all 2572 proteins are listed in Table 19 (in alphabetical order of gene name) and the 100 most abundant proteins are listed in Table 20, in order of decreasing abundance. The characteristic exosome markers CD9, CD81 and Alix (also known as PDCD6IP) are present in the most abundant 100 proteins.

TABLE 19

Gene names and SWISSPROT accession numbers of all 2572 proteins identified in CTX0E03 exosomes (listed in alphabetical order of gene name).

A1BG (P04217), A2M (P01023), AACS (Q86V21), AAMP (Q13685), AARS (P49588), AARSD1 (Q9BTE6), AASDHPPT (Q9NRN7), ABCA3 (Q99758), ABCE1 (P61221), ABCF1 (Q8NE71), ABCF3 (Q9NUQ8), ABHD10 (Q9NUJ1), ABHD14B (Q96IU4), ABI1 (Q8IZP0), ABR (Q12979), ACAA2 (P42765), ACACA (Q13085), ACADVL (P49748), ACAP2 (Q15057), ACAT1 (P24752), ACAT2 (Q9BWD1), ACBD7 (Q8N6N7), ACLY (P53396), ACO1 (P21399), ACO2 (Q99798), ACOT1 (Q86TX2), ACOT13 (Q9NPJ3), ACOT7 (O00154), ACP1 (P24666), ACSL1 (P33121), ACSL3 (O95573), ACSL4 (O60488), ACSS2 (Q9NR19), ACTC1 (P68032), ACTG1 (P63261), ACTL6A (O96019), ACTN1 (P12814), ACTN4 (O43707), ACTR10 (Q9NZ32), ACTR1A (P61163), ACTR1B (P42025), ACTR2 (P61160), ACTR3 (P61158), ADAM10 (O14672), ADAM12 (O43184), ADAMTS15 (Q8TE58), ADAMTS16 (Q8TE57), ADAR (P55265), ADAT2 (Q7Z6V5), ADH5 (P11766), ADI1 (Q9BV57), ADK (P55263), ADRBK1 (P25098), ADRM1 (Q16186), ADSL (P30566), ADSS (P30520), AEBP1 (Q8IUX7), AFM (P43652), AGL (P35573), AGRN (O00468), AGT (P01019), AHCY (P23526), AHCYL1 (O43865), AHNAK (Q09666), AHSA1 (O95433), AHSG (P02765), AIDA (Q96BJ3), AIFM1 (O95831), AIMP1 (Q12904), AIMP2 (Q13155), AIP (O00170), AK1 (P00568), AK3 (Q9UIJ7), AK4 (P27144), AKAP12 (Q02952), AKAP9 (Q99996), AKR1A1 (P14550), AKR1B1 (P15121), AKR1C1 (Q04828), AKR7A2 (O43488), AKR7A3 (O95154), AKT1 (P31749), ALCAM (Q13740), ALDH16A1 (Q8IZ83), ALDH3A1 (P30838), ALDH7A1 (P49419), ALDH9A1 (P49189), ALDOA (P04075), ALDOC (P09972), ALKBH2 (Q6NS38), ALKBH4 (Q9NXW9), AMBP (P02760), AMDHD2 (Q9Y303), AMPD2 (Q01433), AMZ2 (Q86W34), ANAPC1 (Q9H1A4), ANAPC4 (Q9UJX5), ANAPC5 (Q9UJX4), ANAPC7 (Q9UJX3), ANKFY1 (Q9P2R3), ANKRD28 (O15084), ANP32A (P39687), ANP32B (Q92688), ANP32E (Q9BTT0), ANXA1 (P04083), ANXA2 (P07355), ANXA4 (P09525), ANXA5 (P08758), ANXA6 (P08133), ANXA7 (P20073), AP1B1 (Q10567), AP1G1 (O43747), AP1M1 (Q9BXS5), AP1S1 (P61966), AP1S2 (P56377), AP2A1 (O95782), AP2A2 (O94973), AP2B1 (P63010), AP2M1 (Q96CW1), AP2S1 (P53680), AP3B1 (O00203), AP3D1 (O14617), AP3M1 (Q9Y2T2), AP3S1 (Q92572), AP3S2 (P59780), AP4S1 (Q9Y587), APEH (P13798), APEX1 (P27695), API5 (Q9BZZ5), APIP (Q96GX9), APOA1 (P02647), APOA1BP (Q8NCW5), APOA2 (P02652), APOBEC3C (Q9NRW3), APOC2 (P02655), APOD (P05090), APOH (P02749), APOM (O95445), APPL1 (Q9UKG1), APRT (P07741), AQR (O60306), ARCN1 (P48444), ARF1 (P84077), ARF4 (P18085), ARF5 (P84085), ARF6 (P62330), ARFIP1 (P53367), ARFIP2 (P53365), ARHGAP1 (Q07960), ARHGAP12 (Q8IWW6), ARHGDIA (P52565), ARHGEF1 (Q92888), ARHGEF10 (O15013), ARHGEF7 (Q14155), ARIH1 (Q9Y4X5), ARIH2 (O95376), ARL1 (P40616), ARL2 (P36404), ARL3 (P36405), ARL6IP1 (Q15041), ARL8B (Q9NVJ2), ARMC10 (Q8N2F6), ARMC6 (Q6NXE6), ARMC8 (Q8IUR7), ARMC9 (Q7Z3E5), ARMCX3 (Q9UH62), ARPC1A (Q92747), ARPC1B (O15143), ARPC2 (O15144),

TABLE 19-continued

Gene names and SWISSPROT accession numbers of all 2572 proteins identified in CTX0E03 exosomes (listed in alphabetical order of gene name).

ARPC3 (O15145), ARPC4 (P59998), ARPC5 (O15511), ARPC5L (Q9BPX5), ARRDC1 (Q8N5I2), ASB6 (Q9NWX5), ASCC1 (Q8N9N2), ASCC2 (Q9H1I8), ASCC3 (Q8N3C0), ASF1A (Q9Y294), ASH2L (Q9UBL3), ASMTL (O95671), ASNA1 (O43681), ASNS (P08243), ASS1 (P00966), ATG16L1 (Q676U5), ATG3 (Q9NT62), ATG4B (Q9Y4P1), ATG7 (O95352), ATIC (P31939), ATL3 (Q6DD88), ATM (Q13315), ATOX1 (O00244), ATP1A1 (P05023), ATP1B1 (P05026), ATP1B3 (P54709), ATP2B1 (P20020), ATP2B4 (P23634), ATP5B (P06576), ATP5E (P56381), ATP5I (P56385), ATP6AP2 (O75787), ATP6V0D1 (P61421), ATP6V1A (P38606), ATP6V1B2 (P21281), ATP6V1C1 (P21283), ATP6V1D (Q9Y5K8), ATP6V1E1 (P36543), ATP6V1G1 (O75348), ATP6V1H (Q9UI12), ATR (Q13535), ATRN (O75882), ATXN10 (Q9UBB4), B2M (P61769), B3GAT3 (O94766), B3GNT1 (O43505), B4GALT7 (Q9UBV7), BAG2 (O95816), BAIAP2 (Q9UQB8), BANF1 (O75531), BAT1 (Q13838), BAT3 (P46379), BBOX1 (O75936), BCAS2 (O75934), BCAT1 (P54687), BCCIP (Q9P287), BCL2L13 (Q9BXK5), BCLAF1 (Q9NYF8), BDH2 (Q9BUT1), BICD2 (Q8TD16), BLOC1S1 (P78537), BLVRA (P53004), BLVRB (P30043), BMP1 (P13497), BOLA2 (Q9H3K6), BPGM (P07738), BPHL (Q86WA6), BPNT1 (O95861), BRCC3 (P46736), BRE (Q9NXR7), BROX (Q5VW32), BRP16L (P0CB43), BSG (P35613), BST1 (Q10588), BTAF1 (O14981), BUB3 (O43684), BUD31 (P41223), BYSL (Q13895), BZW1 (Q7L1Q6), BZW2 (Q9Y6E2), C10orf119 (Q9BTE3), C10orf58 (Q9BRX8), C10orf76 (Q5T2E6), C11orf54 (Q9H0W9), C11orf68 (Q9H3H3), C12orf10 (Q9HB07), C14orf149 (Q96EM0), C14orf166 (Q9Y224), C15orf58 (Q6ZNW5), C16orf13 (Q96S19), C16orf80 (Q9Y6A4), C1D (Q13901), C1orf123 (Q9NWV4), C1orf50 (Q9BV19), C1orf57 (Q9BSD7), C1RL (Q9NZP8), C20orf11 (Q9NWU2), C20orf27 (Q9GZN8), C20orf4 (Q9Y312), C21orf59 (P57076), C22orf25 (Q6ICL3), C22orf28 (Q9Y3I0), C2orf29 (Q9UKZ1), C2orf79 (Q6GMV3), C3orf10 (Q8WUW1), C3orf26 (Q9BQ75), C3orf75 (Q0PNE2), C4orf27 (Q9NWY4), C4orf41 (Q7Z392), C5orf32 (Q9H1C7), C6orf130 (Q9Y530), C6orf211 (Q9H993), C7orf25 (Q9BPX7), C7orf28B (P86790), C7orf41 (Q8N3F0), C7orf59 (Q0VGL1), C9orf142 (Q9BUH6), C9orf23 (Q8N5L8), C9orf41 (Q8N4J0), C9orf64 (Q5T6V5), CA11 (O75493), CAB39 (Q9Y376), CACNA2D1 (P54289), CACYBP (Q9HB71), CAD (P27708), CADM1 (Q9BY67), CADM4 (Q8NFZ8), CALB1 (P05937), CALD1 (Q05682), CALM1 (P62158), CAMK2D (Q13557), CAND1 (Q86VP6), CAP1 (Q01518), CAPN1 (P07384), CAPN2 (P17655), CAPN5 (O15484), CAPNS1 (P04632), CAPS (Q13938), CAPZA1 (P52907), CAPZA2 (P47755), CAPZB (P47756), CARHSP1 (Q9Y2V2), CARKD (Q8IW45), CARM1 (Q86X55), CARS (P49589), CASK (O14936), CASP3 (P42574), CASP6 (P55212), CAT (P04040), CBFB (Q13951), CBR1 (P16152), CBR3 (O75828), CBS (P35520), CBWD2 (Q8IUF1), CBX1 (P83916), CBX3 (Q13185), CBX5 (P45973), CC2D1A (Q6P1N0), CC2D1B (Q5T0F9), CCAR1 (Q8IX12), CCBL1 (Q16773), CCBL2 (Q6YP21), CCDC22 (O60826), CCDC25 (Q86WR0), CCDC53 (Q9Y3C0), CCDC56 (Q9Y2R0), CCDC93 (Q567U6), CCNC (P24863), CCND2 (P30279), CCNH (P51946), CCT2 (P78371), CCT3 (P49368), CCT4 (P50991), CCT5 (P48643), CCT6A (P40227), CCT7 (Q99832), CCT8 (P50990), CD109 (Q6YHK3), CD151 (P48509), CD276 (Q5ZPR3), CD44 (P16070), CD47 (Q08722), CD59 (P13987), CD63 (P08962), CD81 (P60033), CD9 (P21926), CD99 (P14209), CDC16 (Q13042), CDC23 (Q9UJX2), CDC27 (P30260), CDC34 (P49427), CDC37 (Q16543), CDC40 (O60508), CDC42 (P60953), CDC5L (Q99459), CDCP1 (Q9H5V8), CDH2 (P19022), CDK1 (P06493), CDK2 (P24941), CDK2AP2 (O75956), CDK4 (P11802), CDK5 (Q00535), CDK5RAP3 (Q96JB5), CDK7 (P50613), CDKN2A (P42771), CDKN2AIP (Q9NXV6), CELSR1 (Q9NYQ6), CELSR2 (Q9HCU4), CEP57 (Q86XR8), CFL1 (P23528), CFL2 (Q9Y281), CHAC2 (Q8WUX2), CHAF1B (Q13112), CHD4 (Q14839), CHEK2 (O96017), CHERP (Q8IWX8), CHID1 (Q9BWS9), CHML (P26374), CHMP1B (Q7LBR1), CHMP2A (O43633), CHMP4A (Q9BY43), CHMP4B (Q9H444), CHMP6 (Q96FZ7), CHORDC1 (Q9UHD1), CHP (Q99653), CHRAC1 (Q9NRG0), CHST14 (Q8NCH0), CHST3 (Q7LGC8), CHURC1 (Q8WUH1), CIAO1 (O76071), CIAPIN1 (Q6FI81), CIRH1A (Q969X6), CKAP5 (Q14008), CKB (P12277), CLASP1 (Q7Z460), CLDN3 (O15551), CLEC18B (Q6UXF7), CLIC1 (O00299), CLIC4 (Q9Y696), CLLD6 (Q5W111), CLNS1A (P54105), CLP1 (Q92989), CLPB (Q9H078), CLTA (P09496), CLTC (Q00610), CLU (P10909), CMAS (Q8NFW8), CMBL (Q96DG6), CMPK1 (P30085), CNBP (P62633), CNDP2 (Q96KP4), CNN2 (Q99439), CNN3 (Q15417), CNOT1 (A5YKK6), CNOT10 (Q9H9A5), CNOT6L (Q96LI5), CNOT7 (Q9UIV1), CNP (P09543), COASY (Q13057), COBRA1 (Q8WX92), COG1 (Q8WTW3), COG2 (Q14746), COG3 (Q96JB2), COG4 (Q9H9E3), COG5 (Q9UP83), COG6 (Q9Y2V7), COG7 (P83436), COG8 (Q96MW5), COL11A1 (P12107), COL14A1 (Q05707), COL6A1 (P12109), COMMD1 (Q8N668), COMMD10 (Q9Y6G5), COMMD2 (Q86X83), COMMD3 (Q9UBI1), COMMD4 (Q9H0A8), COMMD5 (Q9GZQ3), COMMD6 (Q7Z4G1), COMMD7 (Q86VX2), COMMD8 (Q9NX08), COMMD9 (Q9P000), COMT (P21964), COPA (P53621), COPB1 (P53618), COPB2 (P35606), COPE (O14579), COPG (Q9Y678), COPG2 (Q9UBF2), COPS2 (P61201), COPS3 (Q9UNS2), COPS4 (Q9BT78), COPS5 (Q92905), COPS6 (Q7L5N1), COPS7A (Q9UBW8), COPS7B (Q9H9Q2), COPS8 (Q99627), COPZ1 (P61923), CORO1A (P31146), CORO1B (Q9BR76), CORO1C (Q9ULV4), CORO2B (Q9UQ03), CORO7 (P57737), COTL1 (Q14019), COX5A (P20674), COX5B (P10606), COX6C (P09669), COX7A2 (P14406), CP (P00450), CPD (O75976), CPN2 (P22792), CPNE1 (Q99829), CPNE3 (O75131), CPNE7 (Q9UBL6), CPSF1 (Q10570), CPSF2 (Q9P2I0), CPSF3 (Q9UKF6), CPSF7 (Q8N684), CPXM1 (Q96SM3), CRIP2 (P52943), CRK (P46108), CRLF3 (Q8IUI8), CRTAP (O75718), CRYAB (P02511), CRYM (Q14894), CRYZ (Q08257), CRYZL1 (O95825), CS (O75390), CSDE1 (O75534), CSE1L (P55060), CSK (P41240), CSNK1A1 (P48729), CSNK2A1 (P68400), CSNK2B (P67870), CSRP1 (P21291), CSRP2 (Q16527), CSTB (P04080), CSTF1 (Q05048), CSTF2T (Q9H0L4), CSTF3 (Q12996), CTBP1 (Q13363), CTBP2 (P56545), CTNNA1 (P35221), CTNNB1 (P35222), CTNNBL1 (Q8WYA6), CTNND1 (O60716), CTPS (P17812), CTPS2 (Q9NRF8), CTR9 (Q6PD62), CTSC (P53634), CTSD (P07339), CTSF (Q9UBX1), CTSL2 (O60911), CTU1 (Q7Z7A3), CTU2 (Q2VPK5), CUL1 (Q13616), CUL2 (Q13617), CUL3 (Q13618), CUL4A (Q13619), CUL4B (Q13620), CUL5 (Q93034), CWF19L1 (Q69YN2), CXADR (P78310), CXorf26 (Q9BVG4), CYB5A (P00167), CYCS (P99999), CYFIP1 (Q7L576), CYFIP2 (Q96F07), CYR61 (O00622), TABLE 19-continued Gene names and SWISSPROT accession numbers of all 2572 proteins identified
in CTX0E03 exosomes (listed in alphabetical order of gene name).

DAG1 (Q14118), DAK (Q3LXA3), DARS (P14868), DAZAP1 (Q96EP5), DBI (P07108), DBN1
(Q16643), DBNL (Q9UJU6), DBR1 (Q9UK59), DCAF7 (P61962), DCAF8 (Q5TAQ9), DCD
(P81605), DCK (P27707), DCLK1 (O15075), DCPS (Q96C86), DCTD (P32321), DCTN1
(Q14203), DCTN2 (Q13561), DCTN3 (O75935), DCTN4 (Q9UJW0), DCTN5 (Q9BTE1), DCTN6
(O00399), DCUN1D1 (Q96GG9), DCUN1D5 (Q9BTE7), DCXR (Q7Z4W1), DDA1 (Q9BW61),
DDAH2 (O95865), DDB1 (Q16531), DDB2 (Q92466), DDI2 (Q5TDH0), DDR1 (Q08345), DDT
(P30046), DDX1 (Q92499), DDX17 (Q92841), DDX19A (Q9NUU7), DDX21 (Q9NR30), DDX23
(Q9BUQ8), DDX39 (O00148), DDX3X (O00571), DDX5 (P17844), DDX51 (Q8N8A6), DDX6
(P26196), DECR1 (Q16698), DEF (Q68CQ4), DEFA1 (P59665), DENR (O43583), DERA
(Q9Y315), DFFA (O00273), DHFR (P00374), DHPS (P49366), DHRS1 (Q96LJ7), DHRS11
(Q6UWP2), DHRS4 (Q9BTZ2), DHX15 (O43143), DHX16 (O60231), DHX29 (Q7Z478), DHX36
(Q9H2U1), DHX9 (Q08211), DIAPH1 (O60610), DIAPH2 (O60879), DIMT1L (Q9UNQ2), DIP2B
(Q9P265), DIP2C (Q9Y2E4), DIS3 (Q9Y2L1), DIS3L2 (Q8IYB7), DKC1 (O60832), DLG1
(Q12959), DNAH17 (Q9UFH2), DNAJA1 (P31689), DNAJA2 (O60884), DNAJB1 (P25685),
DNAJB4 (Q9UDY4), DNAJC13 (O75165), DNAJC3 (Q13217), DNAJC7 (Q99615), DNASE1L1
(P49184), DNM1 (Q05193), DNM1L (O00429), DNM2 (P50570), DNPEP (Q9ULA0), DOCK1
(Q14185), DOCK4 (Q8N1I0), DOCK5 (Q9H7D0), DOCK7 (Q96N67), DOHH (Q9BU89), DOM3Z
(O77932), DPCD (Q9BVM2), DPH1 (Q9BZG8), DPH2 (Q9BQC3), DPH5 (Q9H2P9), DPM1
(O60762), DPP3 (Q9NY33), DPP9 (Q86TI2), DPY30 (Q9C005), DPYSL2 (Q16555), DPYSL3
(Q14195), DPYSL4 (O14531), DPYSL5 (Q9BPU6), DRG1 (Q9Y295), DRG2 (P55039), DSG1
(Q02413), DSP (P15924), DST (Q03001), DSTN (P60981), DTD1 (Q8TEA8), DTYMK
(P23919), DUS2L (Q9NX74), DUSP12 (Q9UNI6), DUSP23 (Q9BVJ7), DUSP3 (P51452), DYM
(Q7RTS9), DYNC1H1 (Q14204), DYNC1I2 (Q13409), DYNC1LI1 (Q9Y6G9), DYNC1LI2
(O43237), DYNC2H1 (Q8NCM8), DYNLL1 (P63167), DYNLL2 (Q96FJ2), DYNLRB1 (Q9NP97),
DYNLT1 (P63172), ECHDC1 (Q9NTX5), ECHDC3 (Q96DC8), ECHS1 (P30084), ECM29
(Q5VYK3), EDC4 (Q6P2E9), EEA1 (Q15075), EEF1A1 (P68104), EEF1B2 (P24534), EEF1D
(P29692), EEF1E1 (O43324), EEF1G (P26641), EEF2 (P13639), EEFSEC (P57772), EFEMP2
(O95967), EFHD2 (Q96C19), EFNB2 (P52799), EFTUD1 (Q7Z2Z2), EFTUD2 (Q15029), EGFR
(P00533), EHD1 (Q9H4M9), EHD2 (Q9NZN4), EHD4 (Q9H223), EIF1 (P41567), EIF1AX
(P47813), EIF2A (Q9BY44), EIF2AK2 (P19525), EIF2B1 (Q14232), EIF2B2 (P49770), EIF2B3
(Q9NR50), EIF2B4 (Q9UI10), EIF2B5 (Q13144), EIF2C2 (Q9UKV8), EIF2S1 (P05198), EIF2S2
(P20042), EIF2S3 (P41091), EIF3A (Q14152), EIF3B (P55884), EIF3C (Q99613), EIF3D
(O15371), EIF3E (P60228), EIF3F (O00303), EIF3G (O75821), EIF3H (O15372), EIF3I
(Q13347), EIF3J (O75822), EIF3K (Q9UBQ5), EIF3L (Q9Y262), EIF3M (Q7L2H7), EIF4A1
(P60842), EIF4A2 (Q14240), EIF4A3 (P38919), EIF4E (P06730), EIF4E2 (O60573), EIF4G1
(Q04637), EIF4G2 (P78344), EIF4G3 (O43432), EIF4H (Q15056), EIF5 (P55010), EIF5A
(P63241), EIF5B (O60841), EIF6 (P56537), ELAC2 (Q9BQ52), ELAVL1 (Q15717), ELMO2
(Q96JJ3), ELP2 (Q6IA86), ELP3 (Q9H9T3), EMG1 (Q92979), EMILIN1 (Q9Y6C2), EML1
(O00423), EML2 (Q95834), EML3 (Q32P44), EML4 (Q9HC35), ENAH (Q8N8S7), ENO1
(P06733), ENO2 (P09104), ENOPH1 (Q9UHY7), ENY2 (Q9NPA8), EPB41L2 (O43491),
EPB41L3 (Q9Y2J2), EPHA2 (P29317), EPHB3 (P54753), EPHX1 (P07099), EPM2AIP1
(Q7L775), EPRS (P07814), ERH (P84090), ERI1 (Q8IV48), ERI3 (O43414), ERP44 (Q9BS26),
ESD (P10768), ESYT1 (Q9BSJ8), ETF1 (P62495), ETFA (P13804), ETFB (P38117), EXOC1
(Q9NV70), EXOC2 (Q96KP1), EXOC3 (O60645), EXOC4 (Q96A65), EXOC5 (O00471),
EXOC6 (Q8TAG9), EXOC7 (Q9UPT5), EXOC8 (Q8IYI6), EXOSC1 (Q9Y3B2), EXOSC2
(Q13868), EXOSC3 (Q9NQT5), EXOSC4 (Q9NPD3), EXOSC5 (Q9NQT4), EXOSC6
(Q5RKV6), EXOSC7 (Q15024), EXOSC8 (Q96B26), EXOSC9 (Q06265), EXTL3 (O43909),
EYA3 (Q99504), EZR (P15311), F3 (P13726), F8 (P00451), F8A1 (P23610), FABP5 (Q01469),
FABP7 (O15540), FADD (Q13158), FAF1 (Q9UNN5), FAH (P16930), FAHD2A (Q96GK7),
FAM114A2 (Q9NRY5), FAM115A (Q9Y4C2), FAM120A (Q9NZB2), FAM125A (Q96EY5),
FAM127A (A6ZKI3), FAM129B (Q96TA1), FAM136A (Q96C01), FAM168A (Q92567),
FAM175B (Q15018), FAM188A (Q9H8M7), FAM3A (P98173), FAM3C (Q92520), FAM45B
(Q6NSW5), FAM49B (Q9NUQ9), FAM82B (Q96DB5), FAM84B (Q96KN1), FAM98A (Q8NCA5),
FAM98B (Q52LJ0), FARP1 (Q9Y4F1), FARP2 (O94887), FARSA (Q9Y285), FARSB
(Q9NSD9), FASN (P49327), FAT1 (Q14517), FBL (P22087), FBLN2 (P98095), FBN1 (P35555),
FBN2 (P35556), FBXL18 (Q96ME1), FBXO21 (O94952), FBXO22 (Q8NEZ5), FDFT1 (P37268),
FDPS (P14324), FEN1 (P39748), FERMT1 (Q9BQL6), FERMT2 (Q96AC1), FGF1 (P05230),
FGFRL1 (Q8N441), FGGY (Q96C11), FH (P07954), FHL1 (Q13642), FHL2 (Q14192), FHL3
(Q13643), FIS1 (Q9Y3D6), FKBP1A (P62942), FKBP3 (Q00688), FKBP4 (Q02790), FKBP5
(Q13451), FLII (Q13045), FLNA (P21333), FLNB (O75369), FLNC (Q14315), FLOT1 (O75955),
FMNL2 (Q96PY5), FN3K (Q9H479), FN3KRP (Q9HA64), FNTA (P49354), FNTB (P49356),
FOLR1 (P15328), FREM2 (Q5SZK8), FRMD8 (Q9BZ67), FSCN1 (Q16658), FSD1 (Q9BTV5),
FTH1 (P02794), FTL (P02792), FTO (Q9C0B1), FTSJD2 (Q8N1G2), FUBP1 (Q96AE4), FUCA2
(Q9BTY2), FUK (Q8N0W3), FXR1 (P51114), G3BP1 (Q13283), G3BP2 (Q9UN86), G6PD
(P11413), GAA (P10253), GALK1 (P51570), GALK2 (Q01415), GALNT1 (Q10472), GALNT2
(Q10471), GANAB (Q14697), GAP43 (P17677), GAPDH (P04406), GAPVD1 (Q14C86), GAR1
(Q9NY12), GARS (P41250), GART (P22102), GATSL2 (A6NHX0), GBA (P04062), GBE1
(Q04446), GCLM (P48507), GCN1L1 (Q92616), GDI1 (P31150), GDI2 (P50395), GEMIN5
(Q8TEQ6), GEMIN6 (Q8WXD5), GET4 (Q7L5D6), GFAP (P14136), GFPT1 (Q06210), GFPT2
(O94808), GGCT (O75223), GGPS1 (O95749), GINS1 (Q14691), GINS4 (Q9BRT9), GIPC1
(O14908), GIT1 (Q9Y2X7), GLA (P06280), GLB1 (P16278), GLB1L2 (Q8IW92), GLG1
(Q92896), GLIPR2 (Q9H4G4), GLMN (Q92990), GLO1 (Q04760), GLOD4 (Q9HC38), GLRX
(P35754), GLRX3 (O76003), GLT25D1 (Q8NBJ5), GLTP (Q9NZD2), GLTPD1 (Q5TA50),
GLUD1 (P00367), GLUL (P15104), GMDS (O60547), GMFB (P60983), GMPPA (Q96IJ6),
GMPPB (Q9Y5P6), GMPR (P36959), GMPR2 (Q9P2T1), GMPS (P49915), GNA11 (P29992),
GNA13 (Q14344), GNAI2 (P04899), GNAI3 (P08754), GNAQ (P50148), GNAS (Q5JWF2),
GNB1 (P62873), GNB2 (P62879), GNB2L1 (P63244), GNB4 (Q9HAV0), GNE (Q9Y223),

TABLE 19-continued

Gene names and SWISSPROT accession numbers of all 2572 proteins identified
in CTX0E03 exosomes (listed in alphabetical order of gene name).

GNG12 (Q9UBI6), GNG4 (P50150), GNG5 (P63218), GNPDA1 (P46926), GNPNAT1
(Q96EK6), GOLGA7 (Q7Z5G4), GOLGB1 (Q14789), GOLIM4 (O00461), GOLM1 (Q8NBJ4),
GOLPH3 (Q9H4A6), GORASP2 (Q9H8Y8), GPC1 (P35052), GPC4 (O75487), GPC6
(Q9Y625), GPD1L (Q8N335), GPI (P06744), GPLD1 (P80108), GPM6A (P51674), GPM6B
(Q13491), GPN1 (Q9HCN4), GPR56 (Q9Y653), GPS1 (Q13098), GPX1 (P07203), GPX4
(P36969), GRB2 (P62993), GRHPR (Q9UBQ7), GRP (Q3ZCW2), GRPEL1 (Q9HAV7), GRWD1
(Q9BQ67), GSK3A (P49840), GSK3B (P49841), GSN (P06396), GSPT1 (P15170), GSS
(P48637), GSTK1 (Q9Y2Q3), GSTM2 (P28161), GSTM3 (P21266), GSTM4 (Q03013), GSTO1
(P78417), GSTP1 (P09211), GSTT2 (POCG29), GSTZ1 (O43708), GTF2F2 (P13984), GTF2H2
(Q13888), GTF2I (P78347), GTF3C1 (Q12789), GTF3C2 (Q8WUA4), GTF3C4 (Q9UKN8),
GTPBP1 (O00178), GUK1 (Q16774), GYG1 (P46976), GYS1 (P13807), H2AFY (O75367),
H2AFZ (P0C0S5), HADH (Q16836), HAGH (Q16775), HARS (P12081), HAT1 (O14929),
HAUS3 (Q68CZ6), HAUS4 (Q9H6D7), HBA1 (P69905), HBB (P68871), HCFC1 (P51610),
HDAC1 (Q13547), HDAC2 (Q92769), HDAC3 (O15379), HDHD2 (Q9H0R4), HDLBP (Q00341),
HEATR1 (Q9H583), HEATR2 (Q86Y56), HEBP1 (Q9NRV9), HECTD3 (Q5T447), HEG1
(Q9ULI3), HELZ (P42694), HERC4 (Q5GLZ8), HEXB (P07686), HGS (O14964), HHIP
(Q96QV1), HIBCH (Q6NVY1), HIF1AN (Q9NWT6), HINT1 (P49773), HIP1R (O75146),
HIST1H1B (P16401), HIST1H1C (P16403), HIST1H2BM (Q99879), HIST1H2BO (P23527),
HIST1H4A (P62805), HIST2H2AA3 (Q6FI13), HIST2H3A (Q71DI3), HK1 (P19367), HK2
(P52789), HLA-A (P30443), HLA-A (P01892), HLCS (P50747), HMGA1 (P17096), HMGB1
(P09429), HMGCL (P35914), HMGCS1 (Q01581), HMGN2 (P05204), HNRNPA1 (P09651),
HNRNPA2B1 (P22626), HNRNPA3 (P51991), HNRNPAB (Q99729), HNRNPC (P07910),
HNRNPD (Q14103), HNRNPF (P52597), HNRNPH1 (P31943), HNRNPH2 (P55795),
HNRNPH3 (P31942), HNRNPK (P61978), HNRNPL (P14866), HNRNPM (P52272), HNRNPR
(O43390), HNRNPU (Q00839), HNRNPUL2 (Q1KMD3), HNRPDL (O14979), HNRPLL
(Q8WVV9), HOOK3 (Q86VS8), HP (P00738), HP1BP3 (Q5SSJ5), HPCAL1 (P37235), HPRT1
(P00492), HPX (P02790), HRAS (P01112), HS6ST2 (Q96MM7), HSD17B10 (Q99714),
HSD17B4 (P51659), HSP90AA1 (P07900), HSP90AB1 (P08238), HSP90B1 (P14625),
HSPA12A (O43301), HSPA14 (Q0VDF9), HSPA1A (P08107), HSPA2 (P54652), HSPA4
(P34932), HSPA4L (O95757), HSPA5 (P11021), HSPA8 (P11142), HSPA9 (P38646), HSPB1
(P04792), HSPB11 (Q9Y547), HSPBP1 (Q9NZL4), HSPD1 (P10809), HSPE1 (P61604),
HSPG2 (P98160), HSPH1 (Q92598), HTATIP2 (Q9BUP3), HTRA1 (Q92743), HTT (P42858),
HUWE1 (Q7Z6Z7), HYOU1 (Q9Y4L1), IARS (P41252), ICAM1 (P05362), IDE (P14735), IDH1
(O75874), IDH2 (P48735), IDI1 (Q13907), IDUA (P35475), IFI16 (Q16666), IFI35 (P80217),
IFIT5 (Q13325), IFITM3 (Q01628), IGF1R (P08069), IGF2BP2 (Q9Y6M1), IGF2BP3 (O00425),
IGF2R (P11717), IGFBP3 (P17936), IGSF3 (O75054), IGSF8 (Q969P0), IKBKAP (O95163),
IL1RAP (Q9NPH3), ILF2 (Q12905), ILF3 (Q12906), ILK (Q13418), ILKAP (Q9H0C8), IMP4
(Q96G21), IMPA1 (P29218), IMPA2 (O14732), IMPAD1 (Q9NX62), IMPDH2 (P12268), INF2
(Q27J81), INPP1 (P49441), INPPL1 (O15357), INTS1 (Q8N201), INTS10 (Q9NVR2), INTS3
(Q68E01), INTS5 (Q6P9B9), IPO11 (Q9UI26), IPO13 (O94829), IPO4 (Q8TEX9), IPO5
(O00410), IPO7 (O95373), IPO8 (O15397), IPO9 (Q96P70), IQGAP1 (P46940), IRF2BP2
(Q7Z5L9), IRF3 (Q14653), IRGQ (Q8WZA9), ISG15 (P05161), ISOC1 (Q96CN7), ISPD
(A4D126), ISYNA1 (Q9NPH2), ITFG3 (Q9H0X4), ITGA2 (P17301), ITGA3 (P26006), ITGA4
(P13612), ITGA5 (P08648), ITGA6 (P23229), ITGA7 (Q13683), ITGAV (P06756), ITGB1
(P05556), ITGB4 (P16144), ITGB8 (P26012), ITPA (Q9BY32), JAM3 (Q9BX67), JUP (P14923),
KARS (Q15046), KBTBD4 (Q9NVX7), KBTBD6 (Q86V97), KCTD12 (Q96CX2), KDM1A
(O60341), KEAP1 (Q14145), KHDRBS1 (Q07666), KHSRP (Q92945), KIAA0174 (P53990),
KIAA0196 (Q12768), KIAA0319L (Q8IZA0), KIAA0664 (O75153), KIAA0776 (O94874),
KIAA1033 (Q2M389), KIAA1279 (Q96EK5), KIAA1468 (Q9P260), KIAA1598 (A0MZ66),
KIAA1797 (Q5VW36), KIAA1967 (Q8N163), KIF1A (Q12756), KIF3A (Q9Y496), KIF5B
(P33176), KIF5C (O60282), KLC1 (Q07866), KLC2 (Q9H0B6), KLC4 (Q9NSK0), KLHDC3
(Q9BQ90), KLHL13 (Q9P2N7), KNG1 (P01042), KNTC1 (P50748), KPNA1 (P52294), KPNA2
(P52292), KPNA3 (O00505), KPNA4 (O00629), KPNA6 (O60684), KPNB1 (Q14974), KPRP
(Q5T749), KRAS (P01116), KRIT1 (O00522), KRT13 (P13646), KRT14 (P02533), KRT71
(Q3SY84), KTN1 (Q86UP2), L1CAM (P32004), LAGE3 (Q14657), LAMA4 (Q16363), LAMA5
(O15230), LAMB1 (P07942), LAMC1 (P11047), LAMP1 (P11279), LAMP2 (P13473), LANCL1
(O43813), LANCL2 (Q9NS86), LAP3 (P28838), LARP1 (Q6PKG0), LARS (Q9P2J5), LASP1
(Q14847), LCAT (P04180), LCMT1 (Q9UIC8), LDHA (P00338), LDHB (P07195), LDLR
(P01130), LEFTY2 (O00292), LEPRE1 (Q32P28), LFNG (Q8NES3), LGALS1 (P09382),
LGALS3 (P17931), LGALS3BP (Q08380), LHFP (Q9Y693), LIMA1 (Q9UHB6), LIMS1
(P48059), LIN7C (Q9NUP9), LIPG (Q9Y5X9), LLGL1 (Q15334), LMCD1 (Q9NZU5), LMNA
(P02545), LMNB1 (P20700), LOXL4 (Q96JB6), LPL (P06858), LRBA (P50851), LRCH3
(Q96II8), LRG1 (P02750), LRP1 (Q07954), LRRC20 (Q8TCA0), LRRC40 (Q9H9A6), LRRC47
(Q8N1G4), LRRC57 (Q8N9N7), LRSAM1 (Q6UWE0), LRWD1 (Q9UFC0), LSM1 (O15116),
LSM12 (Q3MHD2), LSM2 (Q9Y333), LSM3 (P62310), LSM4 (Q9Y4Z0), LSM6 (P62312), LSM7
(Q9UK45), LSS (P48449), LTA4H (P09960), LTBP2 (Q14767), LTBP3 (Q9NS15), LUM
(P51884), LYPLA1 (O75608), LYPLA2 (O95372), LYPLAL1 (Q5VWZ2), M6PR (P20645),
MACF1 (Q9UPN3), MAD1L1 (Q9Y6D9), MAD2L1 (Q13257), MAEA (Q7L5Y9), MAGEE1
(Q9HCI5), MAGOHB (Q96A72), MALT1 (Q9UDY8), MAN1B1 (Q9UKM7), MAN2A1 (Q16706),
MANBA (O00462), MAP1B (P46821), MAP1S (Q66K74), MAP2K1 (Q02750), MAP2K2
(P36507), MAP2K3 (P46734), MAP3K4 (Q9Y6R4), MAP4 (P27816), MAP4K4 (O95819),
MAPK1 (P28482), MAPK12 (P53778), MAPK3 (P27361), MAPK9 (P45984), MAPKAPK2
(P49137), MAPKSP1 (Q9UHA4), MAPRE1 (Q15691), MAPRE3 (Q9UPY8), MARCKS
(P29966), MARCKSL1 (P49006), MARK2 (Q7KZI7), MARS (P56192), MAT2A (P31153),
MAT2B (Q9NZL9), MATR3 (P43243), MBD3 (O95983), MBNL1 (Q9NR56), MCAM (P43121),
MCAT (Q8IVS2), MCM2 (P49736), MCM3 (P25205), MCM4 (P33991), MCM5 (P33992), MCM6
(Q14566), MCM7 (P33993), MCTS1 (Q9ULC4), MDH1 (P40925), MDH2 (P40926), MDK

TABLE 19-continued

Gene names and SWISSPROT accession numbers of all 2572 proteins identified in CTX0E03 exosomes (listed in alphabetical order of gene name).

(P21741), MDN1 (Q9NU22), ME1 (P48163), ME2 (P23368), MED1 (Q15648), MED16 (Q9Y2X0), MED17 (Q9NVC6), MED18 (Q9BUE0), MED20 (Q9H944), MED22 (Q15528), MED23 (Q9ULK4), MED27 (Q6P2C8), MED30 (Q96HR3), MED31 (Q9Y3C7), MEMO1 (Q9Y316), MERIT40 (Q9NWV8), METAP1 (P53582), METAP2 (P50579), METT10D (Q86W50), METTL1 (Q9UBP6), METTL11A (Q9BV86), METTL13 (Q8N6R0), METTL2B (Q6P1Q9), METTL5 (Q9NRN9), MFAP2 (P55001), MFAP4 (P55083), MFGE8 (Q08431), MFI2 (P08582), MGAT4B (Q9UQ53), MGAT5 (Q09328), MGEA5 (O60502), MICAL1 (Q8TDZ2), MIF (P14174), MIF4GD (A9UHW6), MINA (Q8IUF8), MINK1 (Q8N4C8), MIOS (Q9NXC5), MIS12 (Q9H081), MKLN1 (Q9UL63), MLTK (Q9NYL2), MMP14 (P50281), MMS19 (Q96T76), MOB2 (Q70IA6), MOBKL1B (Q9H8S9), MOBKL2A (Q96BX8), MOBKL3 (Q9Y3A3), MOCS2 (O96033), MON2 (Q7Z3U7), MORC2 (Q9Y6X9), MOV10 (Q9HCE1), MOXD1 (Q6UVY6), MPI (P34949), MPP6 (Q9NZW5), MPRIP (Q6WCQ1), MPST (P25325), MPZL1 (O95297), MRC2 (Q9UBG0), MRI1 (Q9BV20), MRTO4 (Q9UKD2), MSH2 (P43246), MSN (P26038), MSTO1 (Q9BUK6), MTA1 (Q13330), MTA2 (O94776), MTAP (Q13126), MTHFD1 (P11586), MTHFS (P49914), MTM1 (Q13496), MTMR1 (Q13613), MTMR6 (Q9Y217), MTMR9 (Q96QG7), MTOR (P42345), MTPN (P58546), MTR (Q99707), MVD (P53602), MVK (Q03426), MVP (Q14764), MYADM (Q96S97), MYBBP1A (Q9BQG0), MYCBP (Q99417), MYD88 (Q99836), MYH10 (P35580), MYH9 (P35579), MYL12B (O14950), MYL6 (P60660), MYO18A (Q92614), MYO1B (O43795), MYO1C (O00159), MYO1E (Q12965), MYO6 (Q9UM54), MYOF (Q9NZM1), MZT1 (Q08AG7), NAA10 (P41227), NAA15 (Q9BXJ9), NAA16 (Q6N069), NAA20 (P61599), NAA30 (Q147X3), NAA38 (O95777), NAA50 (Q9GZZ1), NACA (Q13765), NADSYN1 (Q6IA69), NAE1 (Q13564), NAGK (Q9UJ70), NAGLU (P54802), NAMPT (P43490), NANS (Q9NR45), NAP1L1 (P55209), NAP1L4 (Q99733), NAPA (P54920), NAPG (Q99747), NAPRT1 (Q6XQN6), NARS (O43776), NASP (P49321), NCAM1 (P13591), NCAPD2 (Q15021), NCAPG (Q9BPX3), NCBP1 (Q09161), NCBP2 (P52298), NCDN (Q9UBB6), NCKAP1 (Q9Y2A7), NCKIPSD (Q9NZQ3), NCL (P19338), NCS1 (P62166), NCSTN (Q92542), NDRG3 (Q9UGV2), NDRG4 (Q9ULP0), NDUFA2 (O43678), NDUFA3 (O95167), NDUFA5 (Q16718), NDUFAB1 (O14561), NDUFS6 (O75380), NEDD4L (Q96PU5), NEFL (P07196), NEK9 (Q8TD19), NES (P48681), NF1 (P21359), NFIC (P08651), NFIX (Q14938), NFKB2 (Q00653), NHLRC2 (Q8NBF2), NHP2L1 (P55769), NID1 (P14543), NIP7 (Q9Y221), NIT1 (Q86X76), NIT2 (Q9NQR4), NLE1 (Q9NVX2), NLGN4X (Q8N0W4), NLN (Q9BYT8), NMD3 (Q96D46), NME1 (P15531), NME2 (P22392), NME3 (Q13232), NME7 (Q9Y5B8), NMT1 (P30419), NNMT (P40261), NOB1 (Q9ULX3), NOL11 (Q9H8H0), NOL6 (Q9H6R4), NOMO2 (Q5JPE7), NONO (Q15233), NOP10 (Q9NPE3), NOP2 (P46087), NOTCH1 (P46531), NOTCH3 (Q9UM47), NOVA2 (Q9UNW9), NPEPPS (P55786), NPLOC4 (Q8TAT6), NPM1 (P06748), NPM3 (O75607), NPTN (Q9Y639), NPW (Q8N729), NQO1 (P15559), NQO2 (P16083), NR2C2AP (Q86WQ0), NRAS (P01111), NRBP1 (Q9UHY1), NRBP2 (Q9NSY0), NRD1 (O43847), NRP2 (O60462), NSF (P46459), NSMAF (Q92636), NSMCE1 (Q8WV22), NSUN2 (Q08J23), NT5C (Q8TCD5), NT5DC1 (Q5TFE4), NTN1 (O95631), NUBP1 (P53384), NUBP2 (Q9Y5Y2), NUCB1 (Q02818), NUDC (Q9Y266), NUDCD1 (Q96RS6), NUDCD2 (Q8WVJ2), NUDT1 (P36639), NUDT10 (Q8NFP7), NUDT12 (Q9BQG2), NUDT16 (Q96DE0), NUDT16L1 (Q9BRJ7), NUDT2 (P50583), NUDT21 (O43809), NUDT4 (Q9NZJ9), NUDT5 (Q9UKK9), NUMA1 (Q14980), NUP188 (Q5SRE5), NUP37 (Q8NFH4), NUP43 (Q8NFH3), NUP54 (Q7Z3B4), NUP88 (Q99567), NUP93 (Q8N1F7), NUTF2 (P61970), NXN (Q6DKJ4), OBFC2B (Q9BQ15), OCRL (Q01968), ODZ2 (Q9NT68), ODZ3 (Q9P273), OGFOD1 (Q8N543), OGT (O15294), OLA1 (Q9NTK5), OLFML3 (Q9NRN5), OPA1 (O60313), OPLAH (O14841), OSBP (P22059), OSBPL1A (Q9BXW6), OSGEP (Q9NPF4), OTUB1 (Q96FW1), OVCA2 (Q8WZ82), OXCT1 (P55809), OXSR1 (O95747), P4HB (P07237), PA2G4 (Q9UQ80), PAAF1 (Q9BRP4), PABPC1 (P11940), PABPC4 (Q13310), PABPN1 (Q86U42), PACSIN2 (Q9UNF0), PACSIN3 (Q9UKS6), PAF1 (Q8N7H5), PAFAH1B1 (P43034), PAFAH1B2 (P68402), PAFAH1B3 (Q15102), PAICS (P22234), PAIP1 (Q9H074), PAK2 (Q13177), PALD (Q9ULE6), PALLD (Q8WX93), PANK4 (Q9NVE7), PAPOLA (P51003), PAPSS1 (O43252), PARF (Q3YEC7), PARK7 (Q99497), PARN (O95453), PARP1 (P09874), PARP4 (Q9UKK3), PARVA (Q9NVD7), PBK (Q96KB5), PBLD (P30039), PCBP1 (Q15365), PCBP2 (Q15366), PCDHB2 (Q9Y5E7), PCDHGB4 (Q9UN71), PCDHGC3 (Q9UN70), PCID2 (Q5JVF3), PCMT1 (P22061), PCNA (P12004), PCOLCE2 (Q9UKZ9), PCYT2 (Q99447), PDCD10 (Q9BUL8), PDCD2L (Q9BRP1), PDCD4 (Q53EL6), PDCD5 (O14737), PDCD6 (O75340), PDCD6IP (Q8WUM4), PDCL3 (Q9H2J4), PDDC1 (Q8NB37), PDE12 (Q6L8Q7), PDE6D (O43924), PDGFC (Q9NRA1), PDIA3 (P30101), PDIA6 (Q15084), PDLIM1 (O00151), PDLIM4 (P50479), PDLIM5 (Q96HC4), PDLIM7 (Q9NR12), PDRG1 (Q9NUG6), PDRO (Q6IAA8), PDS5A (Q29RF7), PDXK (O00764), PDXP (Q96GD0), PEA15 (Q15121), PEBP1 (P30086), PEF1 (Q9UBV8), PELO (Q9BRX2), PELP1 (Q8IZL8), PEPD (P12955), PFAS (O15067), PFDN2 (Q9UHV9), PFDN5 (Q99471), PFDN6 (O15212), PFKL (P17858), PFKM (P08237), PFKP (Q01813), PFN1 (P07737), PFN2 (P35080), PGAM1 (P18669), PGAM5 (Q96HS1), PGD (P52209), PGGT1B (P53609), PGK1 (P00558), PGLS (O95336), PGLYRP2 (Q96PD5), PGM1 (P36871), PGM2L1 (Q6PCE3), PGM3 (O95394), PGP (A6NDG6), PGRMC1 (O00264), PGRMC2 (O15173), PHF5A (Q7RTV0), PHGDH (O43175), PHKB (Q93100), PHLDA3 (Q9Y5J5), PHPT1 (Q9NRX4), PIK3CB (P42338), PIK3R4 (Q99570), PIN1 (Q13526), PIP4K2A (P48426), PIPOX (Q9P0Z9), PITPNB (P48739), PKM2 (P14618), PKP1 (Q13835), PLAA (Q9Y263), PLCD3 (Q8N3E9), PLCG1 (P19174), PLD3 (Q8IV08), PLEC (Q15149), PLEKHB2 (Q96CS7), PLIN3 (O60664), PLOD1 (Q02809), PLOD2 (O00469), PLOD3 (O60568), PLRG1 (O43660), PLS1 (Q14651), PLS3 (P13797), PLSCR3 (Q9NRY6), PLTP (P55058), PLXNA1 (Q9UIW2), PLXNB2 (O15031), PLXND1 (Q9Y4D7), PM20D2 (Q8IYS1), PML (P29590), PMM2 (O15305), PMPCA (Q10713), PMPCB (O75439), PMVK (Q15126), PNMA2 (Q9UL42), PNO1 (Q9NRX1), PNP (P00491), PODXL (O00592), POLA1 (P09884), POLD1 (P28340), POLD2 (P49005), POLE3 (Q9NRF9), POLR1A (O95602), POLR1B (Q9H9Y6), POLR1C (O15160), POLR1D (Q9Y2S0), POLR1E (Q9GZS1), POLR2A (P24928), POLR2B (P30876), POLR2C (P19387), POLR2E (P19388), POLR2G (P62487), POLR2H (P52434), POLR2J (P52435),

TABLE 19-continued

Gene names and SWISSPROT accession numbers of all 2572 proteins identified
in CTX0E03 exosomes (listed in alphabetical order of gene name).

POLR2L (P62875), POLR3A (O14802), POLR3B (Q9NW08), POLR3C (Q9BUI4), POLR3F
(Q9H1D9), POP1 (Q99575), POP4 (O95707), POP5 (Q969H6), POP7 (O75817), PPA1
(Q15181), PPA2 (Q9H2U2), PPAT (Q06203), PPCS (Q9HAB8), PPIA (P62937), PPIB
(P23284), PPID (Q08752), PPIF (P30405), PPIH (O43447), PPIL1 (Q9Y3C6), PPM1A
(P35813), PPM1F (P49593), PPM1G (O15355), PPME1 (Q9Y570), PPP1CA (P62136),
PPP1CB (P62140), PPP1CC (P36873), PPP1R7 (Q15435), PPP1R8 (Q12972), PPP2CA
(P67775), PPP2CB (P62714), PPP2R1A (P30153), PPP2R2A (P63151), PPP2R4 (Q15257),
PPP2R5C (Q13362), PPP2R5D (Q14738), PPP2R5E (Q16537), PPP3CA (Q08209), PPP4C
(P60510), PPP4R1 (Q8TF05), PPP5C (P53041), PPP6C (O00743), PPP6R3 (Q5H9R7),
PPPDE2 (Q6ICB0), PPT1 (P50897), PPWD1 (Q96BP3), PRCP (P42785), PRDX1 (Q06830),
PRDX2 (P32119), PRDX3 (P30048), PRDX5 (P30044), PRDX6 (P30041), PREP (P48147),
PREPL (Q4J6C6), PRIM1 (P49642), PRIM2 (P49643), PRKACA (P17612), PRKACB (P22694),
PRKAG1 (P54619), PRKAR1A (P10644), PRKAR2A (P13861), PRKAR2B (P31323), PRKDC
(P78527), PRMT1 (Q99873), PRMT3 (O60678), PRMT5 (O14744), PROM1 (O43490), PROSC
(O94903), PRPF19 (Q9UMS4), PRPF31 (Q8WWY3), PRPF4 (O43172), PRPF4B (Q13523),
PRPF8 (Q6P2Q9), PRPS1 (P60891), PRPS2 (P11908), PRPSAP1 (Q14558), PRPSAP2
(O60256), PRSS23 (O95084), PRTFDC1 (Q9NRG1), PSAT1 (Q9Y617), PSMA1 (P25786),
PSMA2 (P25787), PSMA3 (P25788), PSMA4 (P25789), PSMA5 (P28066), PSMA6 (P60900),
PSMA7 (O14818), PSMB1 (P20618), PSMB2 (P49721), PSMB3 (P49720), PSMB4 (P28070),
PSMB5 (P28074), PSMB6 (P28072), PSMB7 (Q99436), PSMB8 (P28062), PSMC1 (P62191),
PSMC2 (P35998), PSMC3 (P17980), PSMC4 (P43686), PSMC5 (P62195), PSMC6 (P62333),
PSMD1 (Q99460), PSMD10 (O75832), PSMD11 (O00231), PSMD12 (O00232), PSMD13
(Q9UNM6), PSMD14 (O00487), PSMD2 (Q13200), PSMD3 (O43242), PSMD4 (P55036),
PSMD5 (Q16401), PSMD6 (Q15008), PSMD7 (P51665), PSMD8 (P48556), PSMD9 (O00233),
PSME1 (Q06323), PSME2 (Q9UL46), PSME3 (P61289), PSME4 (Q14997), PSMF1 (Q92530),
PSMG1 (O95456), PSMG2 (Q969U7), PSMG3 (Q9BT73), PSPC1 (Q8WXF1), PSPH (P78330),
PTBP1 (P26599), PTGES3 (Q15185), PTGFRN (Q9P2B2), PTGR1 (Q14914), PTGR2
(Q8N8N7), PTK2 (Q05397), PTK7 (Q13308), PTN (P21246), PTP4A1 (Q93096), PTPN1
(P18031), PTPN11 (Q06124), PTPN23 (Q9H3S7), PTPRA (P18433), PTPRG (P23470),
PTPRZ1 (P23471), PUF60 (Q9UHX1), PUM1 (Q14671), PURB (Q96QR8), PUS7 (Q96PZ0),
PVR (P15151), PWP1 (Q13610), PXDN (Q92626), PXK (Q7Z7A4), PYCR1 (P32322), PYCRL
(Q53H96), PYGB (P11216), PYGL (P06737), QARS (P47897), QDPR (P09417), QKI
(Q96PU8), QRICH1 (Q2TAL8), QSOX2 (Q6ZRP7), QTRT1 (Q9BXR0), RAB10 (P61026),
RAB11A (P62491), RAB11FIP1 (Q6WKZ4), RAB12 (Q6IQ22), RAB13 (P51153), RAB14
(P61106), RAB18 (Q9NP72), RAB1A (P62820), RAB1B (Q9H0U4), RAB21 (Q9UL25), RAB22A
(Q9UL26), RAB23 (Q9ULC3), RAB27A (P51159), RAB2A (P61019), RAB34 (Q9BZG1), RAB35
(Q15286), RAB3A (P20336), RAB3GAP1 (Q15042), RAB3GAP2 (Q9H2M9), RAB4A (P20338),
RAB5A (P20339), RAB5B (P61020), RAB5C (P51148), RAB6A (P20340), RAB6B (Q9NRW1),
RAB7A (P51149), RAB8A (P61006), RAB8B (Q92930), RABAC1 (Q9UI14), RABGAP1
(Q9Y3P9), RABGGTA (Q92696), RABGGTB (P53611), RABIF (P47224), RAC1 (P63000),
RAD1 (O60671), RAD50 (Q92878), RAE1 (P78406), RAI14 (Q9P0K7), RALA (P11233), RALB
(P11234), RALY (Q9UKM9), RAN (P62826), RANBP1 (P43487), RANBP2 (P49792), RANBP6
(O60518), RANBP9 (Q96S59), RANGAP1 (P46060), RAP1A (P62834), RAP1B (P61224),
RAP1GDS1 (P52306), RAP2B (P61225), RARS (P54136), RASA1 (P20936), RBBP4 (Q09028),
RBBP5 (Q15291), RBBP7 (Q16576), RBBP9 (O75884), RBM12 (Q9NTZ6), RBM15 (Q96T37),
RBM17 (Q96I25), RBM22 (Q9NW64), RBM4 (Q9BWF3), RBMX (P38159), RBP1 (P09455),
RBPJ (Q06330), RBX1 (P62877), RCC1 (P18754), RCC2 (Q9P258), RCL (O43598), RDX
(P35241), RECQL (P46063), REEP5 (Q00765), REEP6 (Q96HR9), REPS1 (Q96D71), RFC4
(P35249), RFC5 (P40937), RFTN1 (Q14699), RHEB (Q15382), RHOA (P61586), RHOB
(P62745), RHOC (P08134), RHOF (Q9HBH0), RHOG (P84095), RIC8A (Q9NPQ8), RMND5A
(Q9H871), RNASEH2A (O75792), RNASEH2C (Q8TDP1), RNF123 (Q5XPI4), RNF20
(Q5VTR2), RNF213 (Q63HN8), RNF7 (Q9UBF6), RNGTT (O60942), RNH1 (P13489), RNMT
(O43148), RNPEP (Q9H4A4), ROBLD3 (Q9Y2Q5), ROCK1 (Q13464), ROCK2 (O75116),
ROR1 (Q01973), RP2 (O75695), RPA1 (P27694), RPA2 (P15927), RPA3 (P35244), RPE
(Q96AT9), RPF2 (Q9H7B2), RPL10 (P27635), RPL10A (P62906), RPL11 (P62913), RPL12
(P30050), RPL13 (P26373), RPL13A (P40429), RPL14 (P50914), RPL15 (P61313), RPL17
(P18621), RPL18 (Q07020), RPL18A (Q02543), RPL19 (P84098), RPL21 (P46778), RPL22
(P35268), RPL22L1 (Q6P5R6), RPL23 (P62829), RPL23A (P62750), RPL24 (P83731), RPL26
(P61254), RPL27 (P61353), RPL27A (P46776), RPL28 (P46779), RPL3 (P39023), RPL30
(P62888), RPL31 (P62899), RPL32 (P62910), RPL34 (P49207), RPL35 (P42766), RPL35A
(P18077), RPL36 (Q9Y3U8), RPL36A (P83881), RPL36AL (Q969Q0), RPL37A (P61513),
RPL38 (P63173), RPL4 (P36578), RPL5 (P46777), RPL6 (Q02878), RPL7 (P18124), RPL7A
(P62424), RPL8 (P62917), RPL9 (P32969), RPLP0 (P05388), RPLP1 (P05386), RPLP2
(P05387), RPP30 (P78346), RPP40 (O75818), RPRD1A (Q96P16), RPS10 (P46783), RPS11
(P62280), RPS12 (P25398), RPS13 (P62277), RPS14 (P62263), RPS15 (P62841), RPS15A
(P62244), RPS16 (P62249), RPS17 (P08708), RPS18 (P62269), RPS19 (P39019), RPS2
(P15880), RPS20 (P60866), RPS21 (P63220), RPS23 (P62266), RPS24 (P62847), RPS25
(P62851), RPS26 (P62854), RPS27 (P42677), RPS27A (P62979), RPS27L (Q71UM5), RPS28
(P62857), RPS29 (P62273), RPS3 (P23396), RPS3A (P61247), RPS4X (P62701), RPS4Y1
(P22090), RPS5 (P46782), RPS6 (P62753), RPS6KA3 (P51812), RPS7 (P62081), RPS8
(P62241), RPS9 (P46781), RPSA (P08865), RQCD1 (Q92600), RRAGA (Q7L523), RRAS
(P10301), RRAS2 (P62070), RRBP1 (Q9P2E9), RRM1 (P23921), RRM2 (P31350), RRM2B
(Q7LG56), RRP12 (Q5JTH9), RRP9 (O43818), RSL1D1 (O76021), RSU1 (Q15404), RTCD1
(O00442), RTN3 (O95197), RTN4 (Q9NQC3), RUVBL1 (Q9Y265), RUVBL2 (Q9Y230),
RWDD2B (P57060), S100A10 (P60903), S100A11 (P31949), S100A13 (Q99584), S100A16
(Q96FQ6), S100A4 (P26447), S100A6 (P06703), S100A8 (P05109), SAAL1 (Q96ER3), SACS
(Q9NZJ4), SAE1 (Q9UBE0), SAFB2 (Q14151), SAMHD1 (Q9Y3Z3), SAP18 (O00422), SAR1A

TABLE 19-continued

Gene names and SWISSPROT accession numbers of all 2572 proteins identified in CTX0E03 exosomes (listed in alphabetical order of gene name).

(Q9NR31), SARM1 (Q6SZW1), SARS (P49591), SART3 (Q15020), SBDS (Q9Y3A5), SBF1 (O95248), SCARB1 (Q8WTV0), SCARB2 (Q14108), SCFD1 (Q8WVM8), SCLY (Q96I15), SCP2 (P22307), SCPEP1 (Q9HB40), SCRG1 (O75711), SCRIB (Q14160), SCRN1 (Q12765), SCRN2 (Q96FV2), SCYL1 (Q96KG9), SCYL2 (Q6P3W7), SDC1 (P18827), SDC2 (P34741), SDCBP (O00560), SDF4 (Q9BRK5), SDHA (P31040), SDK1 (Q7Z5N4), SDSL (Q96GA7), SEC11A (P67812), SEC13 (P55735), SEC22B (O75396), SEC23A (Q15436), SEC23B (Q15437), SEC23IP (Q9Y6Y8), SEC24A (O95486), SEC24B (O95487), SEC24C (P53992), SEC24D (O94855), SEC31A (O94979), SEH1L (Q96EE3), SELH (Q8IZQ5), SEMA3A (Q14563), SEPSECS (Q9HD40), 40787 (Q9NVA2), 37500 (Q15019), 38596 (Q99719), 39326 (Q16181), 39692 (Q92599), 40057 (Q9UHD8), SERBP1 (Q8NC51), SERPINA1 (P01009), SERPINA3 (P01011), SERPINA7 (P05543), SERPINB6 (P35237), SERPINB8 (P50452), SERPINE1 (P05121), SERPINE2 (P07093), SERPING1 (P05155), SERPINH1 (P50454), SETD3 (Q86TU7), SETD7 (Q8WTS6), SF3A1 (Q15459), SF3A2 (Q15428), SF3A3 (Q12874), SF3B1 (O75533), SF3B14 (Q9Y3B4), SF3B2 (Q13435), SF3B3 (Q15393), SF3B4 (Q15427), SF3B5 (Q9BWJ5), SFPQ (P23246), SFRP4 (Q6FHJ7), SGTA (O43765), SH3BP4 (Q9P0V3), SH3GL1 (Q99961), SH3GLB1 (Q9Y371), SHBG (P04278), SHC1 (P29353), SHMT1 (P34896), SHMT2 (P34897), SHOC2 (Q9UQ13), SHPK (Q9UHJ6), SKIV2L (Q15477), SKIV2L2 (P42285), SKP1 (P63208), SLC16A1 (P53985), SLC1A3 (P43003), SLC1A5 (Q15758), SLC29A1 (Q99808), SLC2A1 (P11166), SLC31A1 (O15431), SLC3A2 (P08195), SLC44A2 (Q8IWA5), SLC5A3 (P53794), SLC7A5 (Q01650), SLC9A3R1 (O14745), SLC9A3R2 (Q15599), SLIRP (Q9GZT3), SMAD4 (Q13485), SMARCA4 (P51532), SMARCA5 (O60264), SMARCC1 (Q92922), SMARCC2 (Q8TAQ2), SMARCD1 (Q96GM5), SMARCD2 (Q92925), SMARCE1 (Q969G3), SMC1A (Q14683), SMC2 (O95347), SMC3 (Q9UQE7), SMC4 (Q9NTJ3), SMC5 (Q8IY18), SMC6 (Q96SB8), SMCHD1 (A6NHR9), SMEK1 (Q6IN85), SMS (P52788), SMU1 (Q2TAY7), SMYD5 (Q6GMV2), SNAP23 (O00161), SNAPIN (O95295), SND1 (Q7KZF4), SNF8 (Q96H20), SNRNP200 (O75643), SNRNP40 (Q96DI7), SNRPA1 (P09661), SNRPB (P14678), SNRPD1 (P62314), SNRPD2 (P62316), SNRPD3 (P62318), SNRPE (P62304), SNRPF (P62306), SNRPG (P62308), SNTB1 (Q13884), SNUPN (O95149), SNX1 (Q13596), SNX12 (Q9UMY4), SNX17 (Q15036), SNX18 (Q96RF0), SNX2 (O60749), SNX27 (Q96L92), SNX3 (O60493), SNX5 (Q9Y5X3), SNX6 (Q9UNH7), SNX8 (Q9Y5X2), SNX9 (Q9Y5X1), SOD1 (P00441), SORD (Q00796), SORT1 (Q99523), SPAG9 (O60271), SPC24 (Q8NBT2), SPC25 (Q9HBM1), SPG21 (Q9NZD8), SPR (P35270), SPRYD4 (Q8WW59), SPTAN1 (Q13813), SPTBN1 (Q01082), SPTBN2 (O15020), SRGAP2 (O75044), SRI (P30626), SRM (P19623), SRP14 (P37108), SRP19 (P09132), SRP54 (P61011), SRP68 (Q9UHB9), SRP72 (O76094), SRP9 (P49458), SRPX (P78539), SRPX2 (O60687), SRR (Q9GZT4), SRRT (Q9BXP5), SRSF1 (Q07955), SRSF11 (Q05519), SRSF2 (Q01130), SRSF3 (P84103), SRSF6 (Q13247), SRSF7 (Q16629), SRSF9 (Q13242), SRXN1 (Q9BYN0), SSB (P05455), SSBP1 (Q04837), SSRP1 (Q08945), SSSCA1 (O60232), ST13 (P50502), STAG2 (Q8N3U4), STAM (Q92783), STAMBP (O95630), STAT1 (P42224), STAT3 (P40763), STIP1 (P31948), STK24 (Q9Y6E0), STK25 (O00506), STK38L (Q9Y2H1), STOM (P27105), STON2 (Q8WXE9), STRAP (Q9Y3F4), STUB1 (Q9UNE7), STX12 (Q86Y82), STX4 (Q12846), STX5 (Q13190), STX7 (O15400), STXBP1 (P61764), STXBP3 (O00186), STYX (Q8WUJ0), SUB1 (P53999), SUDS3 (Q9H7L9), SUGT1 (Q9Y2Z0), SUMO1 (P63165), SUPT16H (Q9Y5B9), SUPT4H1 (P63272), SUPT5H (O00267), SUPT6H (Q7KZ85), SVEP1 (Q4LDE5), SWAP70 (Q9UH65), SYMPK (Q92797), SYNCRIP (O60506), SYNE1 (Q8NF91), SYNE2 (Q8WXH0), SYNGR2 (O43760), SYNJ2BP (P57105), TAB1 (Q15750), TAF9 (Q9Y3D8), TAF9 (Q16594), TAGLN (Q01995), TAGLN2 (P37802), TALDO1 (P37837), TARDBP (Q13148), TARS (P26639), TATDN1 (Q6P1N9), TAX1BP3 (O14907), TBC1D13 (Q9NVG8), TBC1D15 (Q8TC07), TBC1D23 (Q9NUY8), TBC1D24 (Q9ULP9), TBC1D4 (O60343), TBC1D9B (Q66K14), TBCA (O75347), TBCB (Q99426), TBCD (Q9BTW9), TBCE (Q15813), TBL1XR1 (Q9BZK7), TCEA1 (P23193), TCEB1 (Q15369), TCEB2 (Q15370), TCERG1 (O14776), TCP1 (P17987), TDP2 (O95551), TEP1 (Q99973), TEX10 (Q9NXF1), TF (P02787), TFCP2 (Q12800), TFG (Q92734), TFRC (P02786), TGFB1 (P01137), TGFB2 (P61812), TGFBI (Q15582), TGM1 (P22735), TH1L (Q8IXH7), THBS1 (P07996), THBS3 (P49746), THG1L (Q9NWX6), THOC2 (Q8NI27), THOC3 (Q96J01), THOC5 (Q13769), THOC6 (Q86W42), THOC7 (Q6I9Y2), THOP1 (P52888), THUMPD1 (Q9NXG2), THY1 (P04216), THYN1 (Q9P016), TIA1 (P31483), TIGAR (Q9NQ88), TIMM13 (Q9Y5L4), TIMM50 (Q3ZCQ8), TIMM8B (Q9Y5J9), TIMM9 (Q9Y5J7), TIMP1 (P01033), TIPRL (O75663), TKT (P29401), TLN1 (Q9Y490), TLN2 (Q9Y4G6), TM9SF2 (Q99805), TM9SF3 (Q9HD45), TMED10 (P49755), TMED2 (Q15363), TMED7 (Q9Y3B3), TMED9 (Q9BVK6), TMEM167A (Q8TBQ9), TMEM2 (Q9UHN6), TMEM50B (P56557), TMEM87A (Q8NBN3), TMOD3 (Q9NYL9), TNC (P24821), TNPO1 (Q92973), TNPO2 (O14787), TNPO3 (Q9Y5L0), TOLLIP (Q9H0E2), TOMM20 (Q15388), TOMM22 (Q9NS69), TOMM34 (Q15785), TOMM5 (Q8N4H5), TOMM70A (O94826), TOP1 (P11387), TOP2B (Q02880), TOR1B (O14657), TP53BP1 (Q12888), TP53RK (Q96S44), TPI1 (P60174), TPM3 (P06753), TPM3L (A6NL28), TPM4 (P67936), TPMT (P51580), TPP1 (O14773), TPP2 (P29144), TPR (P12270), TPRG1L (Q5T0D9), TPRKB (Q9Y3C4), TPT1 (P13693), TRAF2 (Q12933), TRAP1 (Q12931), TRAPPC1 (Q9Y5R8), TRAPPC2L (Q9UL33), TRAPPC3 (O43617), TRAPPC4 (Q9Y296), TRAPPC5 (Q8IUR0), TRAPPC6A (O75865), TRAPPC6B (Q86SZ2), TRIM22 (Q8IYM9), TRIM25 (Q14258), TRIM28 (Q13263), TRIP12 (Q14669), TRIP13 (Q15645), TRIP6 (Q15654), TRMT1 (Q9NXH9), TRMT112 (Q9UI30), TRMT5 (Q32P41), TRMT6 (Q9UJA5), TRMT61A (Q96FX7), TRNT1 (Q96Q11), TROVE2 (P10155), TRRAP (Q9Y4A5), TSG101 (Q99816), TSKU (Q8WUA8), TSPAN14 (Q8NG11), TSPAN4 (O14817), TSPAN5 (P62079), TSPAN6 (O43657), TSPAN9 (O75954), TSSC1 (Q53HC9), TSTA3 (Q13630), TTC1 (Q99614), TTC37 (Q6PGP7), TTC38 (Q5R3I4), TTC5 (Q8N0Z6), TTC9C (Q8N5M4), TTL (Q8NG68), TTLL12 (Q14166), TTN (Q8WZ42), TTR (P02766), TTYH1 (Q9H313), TTYH2 (Q9BSA4), TTYH3 (Q9C0H2), TUBA1B (P68363), TUBA1C (Q9BQE3), TUBB (P07437), TUBB2A (Q13885), TUBB2B (Q9BVA1), TUBB2C (P68371), TUBB3 (Q13509), TUBB4 (P04350), TUBB6 (Q9BUF5), TUBG1 (P23258),

TABLE 19-continued

Gene names and SWISSPROT accession numbers of all 2572 proteins identified in CTX0E03 exosomes (listed in alphabetical order of gene name).

TUBGCP2 (Q9BSJ2), TUBGCP3 (Q96CW5), TWF1 (Q12792), TWF2 (Q6IBS0), TXN (P10599), TXNDC17 (Q9BRA2), TXNDC9 (O14530), TXNL1 (O43396), TXNL4B (Q9NX01), TXNRD1 (Q16881), TYMS (P04818), U2AF1 (Q01081), U2AF2 (P26368), UAP1 (Q16222), UBA1 (P22314), UBA2 (Q9UBT2), UBA3 (Q8TBC4), UBA5 (Q9GZZ9), UBA6 (A0AVT1), UBE2D1 (P51668), UBE2D3 (P61077), UBE2E1 (P51965), UBE2G2 (P60604), UBE2I (P63279), UBE2J2 (Q8N2K1), UBE2K (P61086), UBE2L3 (P68036), UBE2M (P61081), UBE2N (P61088), UBE2O (Q9C0C9), UBE2V1 (Q13404), UBE2V2 (Q15819), UBE2Z (Q9H832), UBE3A (Q05086), UBE4A (Q14139), UBE4B (O95155), UBL3 (O95164), UBL4A (P11441), UBL5 (Q9BZL1), UBR1 (Q8IWV7), UBR4 (Q5T4S7), UBTD1 (Q9HAC8), UBXN1 (Q04323), UCHL1 (P09936), UCHL3 (P15374), UCHL5 (Q9Y5K5), UCK2 (Q9BZX2), UFC1 (Q9Y3C8), UFD1L (Q92890), UFSP2 (Q9NUQ7), UGDH (O60701), UGP2 (Q16851), UMPS (P11172), UNC119B (A6NIH7), UNC45A (Q9H3U1), UPF1 (Q92900), UPP1 (Q16831), UROD (P06132), UROS (P10746), USO1 (O60763), USP10 (Q14694), USP11 (P51784), USP14 (P54578), USP15 (Q9Y4E8), USP24 (Q9UPU5), USP39 (Q53GS9), USP5 (P45974), USP7 (Q93009), USP9X (Q93008), UTP15 (Q8TED0), UXS1 (Q8NBZ7), UXT (Q9UBK9), VAC14 (Q08AM6), VAMP3 (Q15836), VAMP5 (O95183), VAPA (Q9P0L0), VAPB (O95292), VARS (P26640), VASN (Q6EMK4), VASP (P50552), VAT1 (Q99536), VAV2 (P52735), VBP1 (P61758), VCAN (P13611), VCL (P18206), VCP (P55072), VIM (P08670), VPRBP (Q9Y4B6), VPS11 (Q9H270), VPS13C (Q709C8), VPS16 (Q9H269), VPS18 (Q9P253), VPS24 (Q9Y3E7), VPS25 (Q9BRG1), VPS26A (O75436), VPS26B (Q4G0F5), VPS28 (Q9UK41), VPS29 (Q9UBQ0), VPS33A (Q96AX1), VPS33B (Q9H267), VPS35 (Q96QK1), VPS36 (Q86VN1), VPS37B (Q9H9H4), VPS39 (Q96JC1), VPS45 (Q9NRW7), VPS4A (Q9UN37), VPS4B (O75351), VPS53 (Q5VIR6), VRK1 (Q99986), VTA1 (Q9NP79), VWA1 (Q6PCB0), VWA5A (O00534), WARS (P23381), WASF1 (Q92558), WASL (O00401), WDFY1 (Q8IWB7), WDR1 (O75083), WDR11 (Q9BZH6), WDR12 (Q9GZL7), WDR18 (Q9BV38), WDR26 (Q9H7D7), WDR33 (Q9C0J8), WDR4 (P57081), WDR43 (Q15061), WDR45L (Q5MNZ6), WDR48 (Q8TAF3), WDR5 (P61964), WDR54 (Q9H977), WDR55 (Q9H6Y2), WDR59 (Q6PJI9), WDR6 (Q9NNW5), WDR61 (Q9GZS3), WDR73 (Q6P4I2), WDR77 (Q9BQA1), WDR82 (Q6UXN9), WDR91 (A4D1P6), WDR92 (Q96MX6), WNK1 (Q9H4A3), XPNPEP1 (Q9NQW7), XPO1 (O14980), XPO4 (Q9C0E2), XPO5 (Q9HAV4), XPO6 (Q96QU8), XPO7 (Q9UIA9), XPOT (O43592), XRCC1 (P18887), XRCC5 (P13010), XRCC6 (P12956), XRN2 (Q9H0D6), YARS (P54577), YBX1 (P67809), YEATS4 (O95619), YES1 (P07947), YIPF4 (Q9BSR8), YKT6 (O15498), YPEL5 (P62699), YRDC (Q86U90), YTHDF2 (Q9Y5A9), YWHAB (P31946), YWHAE (P62258), YWHAG (P61981), YWHAH (Q04917), YWHAQ (P27348), YWHAZ (P63104), ZC3HAV1L (Q96H79), ZCCHC3 (Q9NUD5), ZER1 (Q7Z7L7), ZFPL1 (O95159), ZFR (Q96KR1), ZMAT2 (Q96NC0), ZNF259 (O75312), ZW10 (O43264), ZWILCH (Q9H900), ZYG11B (Q9C0D3), ZYX (Q15942), ZZEF1 (O43149).

TABLE 20

100 most abundant proteins (name and SwissProt accession number) observed in CTX0E03 exosomes

| Identified proteins | Accession number |
|---|---|
| Actin, cytoplasmic 2 | P63261 |
| Glyceraldehyde-3-phosphate dehydrogenase | P04406 |
| Histone H4 | P62805 |
| Pyruvate kinase isozymes M1/M2 | P14618 |
| Alpha-enolase | P06733 |
| Heat shock protein HSP 90-beta | P08238 |
| Ubiquitin-40S ribosomal protein S27a | P62979 |
| Heat shock cognate 71 kDa protein | P11142 |
| Haptoglobin | P00738 |
| Heat shock protein HSP 90-alpha | P07900 |
| Phosphoglycerate kinase 1 | P00558 |
| Actin, alpha cardiac muscle 1 | P68032 |
| 40S ribosomal protein S3 | P23396 |
| Elongation factor 1-alpha 1 | P68104 |
| GTP-binding nuclear protein Ran | P62826 |
| Histone H2B type 1-M | Q99879 |
| Peptidyl-prolyl cis-trans isomerase A | P62937 |
| Profilin-1 | P07737 |
| Elongation factor 2 | P13639 |
| Fatty acid synthase | P49327 |
| Tubulin beta-2C chain | P68371 |
| Tubulin alpha-1B chain | P68363 |
| Tubulin beta chain | P07437 |
| 40S ribosomal protein S11 | P62280 |
| Eukaryotic initiation factor 4A-1 | P60842 |
| T-complex protein 1 subunit theta | P50990 |
| 14-3-3 protein theta | P27348 |
| 40S ribosomal protein S18 | P62269 |
| Tubulin beta-3 chain | Q13509 |
| T-complex protein 1 subunit beta | P78371 |
| 40S ribosomal protein S16 | P62249 |
| Heat shock 70 kDa protein 1A/1B | P08107 |
| Histone H3.2 | Q71DI3 |
| Transketolase | P29401 |
| 40S ribosomal protein SA | P08865 |
| Clusterin | P10909 |
| Fatty acid-binding protein, brain | O15540 |
| Hemopexin | P02790 |
| T-complex protein 1 subunit gamma | P49368 |
| Tubulin beta-2B chain | Q9BVA1 |
| Adenosylhomocysteinase | P23526 |
| T-complex protein 1 subunit eta | Q99832 |
| 40S ribosomal protein S15a | P62244 |
| T-complex protein 1 subunit delta | P50991 |
| Vimentin | P08670 |
| Guanine nucleotide-binding protein subunit beta-2-like 1 | P63244 |
| Dihydropyrimidinase-related protein 3 | Q14195 |
| Elongation factor 1-gamma | P26641 |
| Fascin | Q16658 |
| Creatine kinase B-type | P12277 |
| X-ray repair cross-complementing protein 5 | P13010 |
| 40S ribosomal protein S2 | P15880 |
| Histone H2A type 2-A | Q6FI13 |
| 40S ribosomal protein S4, X isoform | P62701 |
| 14-3-3 protein zeta/delta | P63104 |
| Heterogeneous nuclear ribonucleoprotein A1 | P09651 |
| CD81 antigen | P60033 |

TABLE 20-continued 100 most abundant proteins (name and SwissProt accession number) observed in CTX0E03 exosomes

| Identified proteins | Accession number |
|---|---|
| Keratin, type I cytoskeletal 14 | P02533 |
| ATP-citrate synthase | P53396 |
| 40S ribosomal protein S9 | P46781 |
| Transgelin-2 | P37802 |
| Fructose-bisphosphate aldolase A | P04075 |
| Ubiquitin-like modifier-activating enzyme 1 | P22314 |
| Peroxiredoxin-1 | Q06830 |
| 40S ribosomal protein S5 | P46782 |
| T-complex protein 1 subunit epsilon | P48643 |
| 60S ribosomal protein L30 | P62888 |
| T-complex protein 1 subunit alpha | P17987 |
| 60S ribosomal protein L12 | P30050 |
| Cofilin-1 | P23528 |
| Heterogeneous nuclear ribonucleoproteins A2/B1 | P22626 |
| Eukaryotic translation initiation factor 5A-1 | P63241 |
| Phosphoglycerate mutase 1 | P18669 |
| Clathrin heavy chain 1 | Q00610 |
| Dihydropyrimidinase-related protein 2 | Q16555 |
| 60S ribosomal protein L35a | P18077 |
| T-complex protein 1 subunit zeta | P40227 |
| Carbonyl reductase [NADPH] 1 | P16152 |
| 40S ribosomal protein S3a | P61247 |
| Ferritin heavy chain | P02794 |
| Annexin A2 | P07355 |
| Myosin light polypeptide 6 | P60660 |
| Major vault protein | Q14764 |
| Heterogeneous nuclear ribonucleoprotein D0 | Q14103 |
| 60S acidic ribosomal protein P0 | P05388 |
| X-ray repair cross-complementing protein 6 | P12956 |
| 40S ribosomal protein S20 | P60866 |
| Protein arginine N-methyltransferase 1 | Q99873 |
| 40S ribosomal protein S10 | P46783 |
| Transaldolase | P37837 |
| Histone H2B type 1- | P23527 |
| Triosephosphate isomerase | P60174 |
| Protein S100-A6 | P06703 |
| 40S ribosomal protein S17 | P08708 |
| CD9 antigen | P21926 |
| Filamin-A | P21333 |
| Peptidyl-prolyl cis-trans isomerase FKBP4 | Q02790 |
| Programmed cell death 6-interacting protein | Q8WUM4 |
| Glutathione S-transferase P | P09211 |
| 14-3-3 protein epsilon | P62258 |

Microvesicles 2940 proteins were identified by Mass spectrometry in Microvesicles isolated from the initial stages of an Integra culture (week 2) and purified by centrifugation at 10,000×g. The gene names and corresponding SWISSPROT accession numbers (in brackets) of all 2940 proteins are listed in Table 21 (in alphabetical order of gene name) and the 100 most abundant proteins are listed in Table 22, in order of decreasing abundance.

TABLE 21

Gene names and SWISSPROT accession numbers of all 2940 proteins identified in CTX0E03 microvesicles (listed in alphabetical order of gene name).

A1BG (P04217), AACS (Q86V21), AAMP (Q13685), AARS (P49588), AARSD1 (Q9BTE6), AASDHPPT (Q9NRN7), ABCA3 (Q99758), ABCC1 (P33527), ABCC4 (O15439), ABCE1 (P61221), ABCF1 (Q8NE71), ABCF2 (Q9UG63), ABCF3 (Q9NUQ8), ABHD14B (Q96IU4), ABI1 (Q8IZP0), ABR (Q12979), ACAA1 (P09110), ACAA2 (P42765), ACACA (Q13085), ACADM (P11310), ACADVL (P49748), ACAT1 (P24752), ACAT2 (Q9BWD1), ACBD6 (Q9BR61), ACBD7 (Q8N6N7), ACLY (P53396), ACO1 (P21399), ACO2 (Q99798), ACOT1 (Q86TX2), ACOT13 (Q9NPJ3), ACOT7 (O00154), ACOX1 (Q15067), ACOX3 (O15254), ACP1 (P24666), ACSL1 (P33121), ACSL3 (O95573), ACSL4 (O60488), ACSS2 (Q9NR19), ACTC1 (P68032), ACTG1 (P63261), ACTL6A (O96019), ACTN1 (P12814), ACTN4 (O43707), ACTR10 (Q9NZ32), ACTR1A (P61163), ACTR1B (P42025), ACTR2 (P61160), ACTR3 (P61158), ACY1 (Q03154), ADAM10 (O14672), ADAM9 (Q13443), ADAMTS15 (Q8TE58), ADAMTS16 (Q8TE57), ADAR (P55265), ADD1 (P35611), ADD3 (Q9UEY8), ADH5 (P11766), ADK (P55263), ADO (Q96SZ5), ADPRH (P54922), ADRBK1 (P25098), ADRM1 (Q16186), ADSL (P30566), ADSS (P30520), AEBP1 (Q8IUX7), AFM (P43652), AGL (P35573), AGPS (O00116), AGRN (O00468), AHCY (P23526), AHCYL1 (O43865), AHNAK (Q09666), AHNAK2 (Q8IVF2), AHSA1 (O95433), AHSG (P02765), AIDA (Q96BJ3), AIFM1 (O95831), AIMP1 (Q12904), AIMP2 (Q13155), AIP (O00170), AK1 (P00568), AK2 (P54819), AK3 (Q9UIJ7), AK4 (P27144), AKAP12 (Q02952), AKAP9 (Q99996), AKR1A1 (P14550), AKR1B1 (P15121), AKR1C1 (Q04828), AKR7A2 (O43488), AKR7A3 (O95154), AKT1 (P31749), ALCAM (Q13740), ALDH16A1 (Q8IZ83), ALDH18A1 (P54886), ALDH2 (P05091), ALDH3A1 (P30838), ALDH7A1 (P49419), ALDH9A1 (P49189), ALDOA (P04075), ALDOC (P09972), ALKBH2 (Q6NS38), ALOX12B (O75342), AMDHD2 (Q9Y303), AMPD2 (Q01433), ANAPC1 (Q9H1A4), ANAPC4 (Q9UJX5), ANAPC5 (Q9UJX4), ANAPC7 (Q9UJX3), ANKFY1 (Q9P2R3), ANKRD17 (O75179), ANKRD28 (O15084), ANKRD52 (Q8NB46), ANP32A (P39687), ANP32B (Q92688), ANP32E (Q9BTT0), ANXA1 (P04083), ANXA11 (P50995), ANXA2 (P07355), ANXA3 (P12429), ANXA4 (P09525), ANXA5 (P08758), ANXA6 (P08133), ANXA7 (P20073), AP1B1 (Q10567), AP1G1 (O43747), AP1M1 (Q9BXS5), AP1S2 (P56377), AP2A1 (O95782), AP2A2 (O94973), AP2B1 (P63010), AP2M1 (Q96CW1), AP2S1 (P53680), AP3B1 (O00203), AP3D1 (O14617), AP3M1 (Q9Y2T2), AP3S1 (Q92572), AP4S1 (Q9Y587), APEH (P13798), APEX1 (P27695), API5 (Q9BZZ5), APIP (Q96GX9), APMAP (Q9HDC9), APOA2 (P02652), APOBEC3C (Q9NRW3), APOH (P02749), APOL2 (Q9BQE5), APPL1 (Q9UKG1), APRT (P07741), AQR (O60306), ARAF (P10398), ARCN1 (P48444), ARF1 (P84077), ARF4 (P18085), ARF6 (P62330), ARFGAP2 (Q8N6H7), ARFIP1 (P53367), ARFIP2 (P53365), ARG1 (P05089), ARHGAP1 (Q07960), ARHGAP5 (Q13017), ARHGDIA (P52565), ARHGEF1 (Q92888), ARHGEF10 (O15013), ARHGEF6 (Q15052), ARHGEF7 (Q14155), ARIH1 (Q9Y4X5), ARIH2 (O95376), ARL1 (P40616), ARL2 (P36404), ARL3 (P36405), ARL6IP1 (Q15041), ARL8A (Q96BM9), ARL8B (Q9NVJ2), ARMC10 (Q8N2F6), ARMC6 (Q6NXE6), ARMC8 (Q8IUR7), ARMC9 (Q7Z3E5), ARPC1A (Q92747), ARPC1B (O15143), ARPC2 (O15144), ARPC3 (O15145), ARPC4 (P59998), ARPC5 (O15511), ARPC5L (Q9BPX5), ASAH1 (Q13510), ASCC1 (Q8N9N2), ASCC3 (Q8N3C0), ASMTL (O95671), ASNA1 (O43681), ASNS (P08243), ASPSCR1 (Q9BZE9), ASS1 (P00966), ATAD3A

TABLE 21-continued

Gene names and SWISSPROT accession numbers of all 2940 proteins identified in CTX0E03 microvesicles (listed in alphabetical order of gene name).

(Q9NVI7), ATE1 (O95260), ATG101 (Q9BSB4), ATG16L1 (Q676U5), ATG3 (Q9NT62), ATG4B (Q9Y4P1), ATG7 (O95352), ATIC (P31939), ATL3 (Q6DD88), ATM (Q13315), ATOX1 (O00244), ATP1A1 (P05023), ATP1B1 (P05026), ATP1B3 (P54709), ATP2A2 (P16615), ATP2B1 (P20020), ATP2B4 (P23634), ATP5A1 (P25705), ATP5B (P06576), ATP5C1 (P36542), ATP5E (P56381), ATP5F1 (P24539), ATP5H (O75947), ATP5I (P56385), ATP5L (O75964), ATP5O (P48047), ATP6AP1 (Q15904), ATP6AP2 (O75787), ATP6V0A1 (Q93050), ATP6V0D1 (P61421), ATP6V1A (P38606), ATP6V1B2 (P21281), ATP6V1C1 (P21283), ATP6V1D (Q9Y5K8), ATP6V1E1 (P36543), ATP6V1G1 (O75348), ATP6V1H (Q9UI12), ATR (Q13535), ATRN (O75882), ATXN10 (Q9UBB4), B2M (P61769), B3GAT3 (O94766), B3GNT1 (O43505), BAG2 (O95816), BAG5 (Q9UL15), BAIAP2 (Q9UQB8), BANF1 (O75531), BAT1 (Q13838), BAT3 (P46379), BCAM (P50895), BCAS2 (O75934), BCAT1 (P54687), BCCIP (Q9P287), BCL2L12 (Q9HB09), BDH2 (Q9BUT1), BICD2 (Q8TD16), BLMH (Q13867), BLVRA (P53004), BLVRB (P30043), BMP1 (P13497), BOLA2 (Q9H3K6), BOP1 (Q14137), BPGM (P07738), BPNT1 (O95861), BRCC3 (P46736), BRE (Q9NXR7), BRIX1 (Q8TDN6), BROX (Q5VW32), BRP16L (P0CB43), BSG (P35613), BST1 (Q10588), BTAF1 (O14981), BUB3 (O43684), BUD31 (P41223), BYSL (Q13895), BZW1 (Q7L1Q6), BZW2 (Q9Y6E2), C10orf119 (Q9BTE3), C10orf58 (Q9BRX8), C10orf76 (Q5T2E6), C11orf54 (Q9H0W9), C11orf68 (Q9H3H3), C12orf10 (Q9HB07), C12orf57 (Q99622), C14orf149 (Q96EM0), C14orf166 (Q9Y224), C14orf21 (Q86U38), C15orf58 (Q6ZNW5), C16orf13 (Q96S19), C16orf61 (Q9NRP2), C16orf80 (Q9Y6A4), C18orf21 (Q32NC0), C18orf8 (Q96DM3), C1orf123 (Q9NWV4), C1orf128 (Q9GZP4), C1orf57 (Q9BSD7), C20orf11 (Q9NWU2), C20orf4 (Q9Y312), C21orf33 (P30042), C21orf59 (P57076), C22orf28 (Q9Y3I0), C3orf10 (Q8WUW1), C3orf26 (Q9BQ75), C3orf75 (Q0PNE2), C4orf27 (Q9NWY4), C4orf41 (Q7Z392), C4orf43 (Q96EY4), C5orf33 (Q4G0N4), C6orf211 (Q9H993), C7orf28B (P86790), C7orf50 (Q9BRJ6), C7orf59 (Q0VGL1), C8orf33 (Q9H7E9), C9orf142 (Q9BUH6), C9orf23 (Q8N5L8), C9orf41 (Q8N4J0), C9orf64 (Q5T6V5), CA11 (O75493), CA12 (O43570), CA2 (P00918), CAB39 (Q9Y376), CACNA2D1 (P54289), CACYBP (Q9HB71), CAD (P27708), CADM1 (Q9BY67), CADM4 (Q8NFZ8), CALB1 (P05937), CALD1 (Q05682), CALM1 (P62158), CALR (P27797), CALU (O43852), CAMK1 (Q14012), CAMK2D (Q13557), CAMKV (Q8NCB2), CAND1 (Q86VP6), CANX (P27824), CAP1 (Q01518), CAPN1 (P07384), CAPN2 (P17655), CAPN5 (O15484), CAPN7 (Q9Y6W3), CAPNS1 (P04632), CAPRIN1 (Q14444), CAPS (Q13938), CAPZA1 (P52907), CAPZA2 (P47755), CAPZB (P47756), CARHSP1 (Q9Y2V2), CARKD (Q8IW45), CARM1 (Q86X55), CARS (P49589), CASK (O14936), CASP14 (P31944), CASP3 (P42574), CASP7 (P55210), CAT (P04040), CBFB (Q13951), CBR1 (P16152), CBR3 (O75828), CBS (P35520), CBX1 (P83916), CBX3 (Q13185), CBX5 (P45973), CC2D1A (Q6P1N0), CCAR1 (Q8IX12), CCBL2 (Q6YP21), CCDC102B (Q68D86), CCDC22 (O60826), CCDC25 (Q86WR0), CCDC93 (Q567U6), CCND2 (P30279), CCNY (Q8ND76), CCT2 (P78371), CCT3 (P49368), CCT4 (P50991), CCT5 (P48643), CCT6A (P40227), CCT7 (Q99832), CCT8 (P50990), CD109 (Q6YHK3), CD151 (P48509), CD276 (Q5ZPR3), CD44 (P16070), CD46 (P15529), CD47 (Q08722), CD58 (P19256), CD59 (P13987), CD63 (P08962), CD81 (P60033), CD9 (P21926), CD97 (P48960), CD99 (P14209), CDC123 (O75794), CDC16 (Q13042), CDC23 (Q9UJX2), CDC34 (P49427), CDC37 (Q16543), CDC40 (O60508), CDC42 (P60953), CDC42BPB (Q9Y5S2), CDC5L (Q99459), CDCP1 (Q9H5V8), CDH2 (P19022), CDK1 (P06493), CDK2 (P24941), CDK4 (P11802), CDK5 (Q00535), CDK5RAP3 (Q96JB5), CDK7 (P50613), CDKN2A (P42771), CDKN2AIP (Q9NXV6), CECR5 (Q9BXW7), CELF1 (Q92879), CELSR1 (Q9NYQ6), CELSR2 (Q9HCU4), CFL1 (P23528), CFL2 (Q9Y281), CHCHD3 (Q9NX63), CHD4 (Q14839), CHEK2 (O96017), CHERP (Q8IWX8), CHID1 (Q9BWS9), CHMP1A (Q9HD42), CHMP1B (Q7LBR1), CHMP2A (O43633), CHMP4A (Q9BY43), CHMP4B (Q9H444), CHMP5 (Q9NZZ3), CHMP6 (Q96FZ7), CHN1 (P15882), CHORDC1 (Q9UHD1), CHP (Q99653), CHRAC1 (Q9NRG0), CHST3 (Q7LGC8), CIAO1 (O76071), CIAPIN1 (Q6FI81), CIRBP (Q14011), CIRH1A (Q969X6), CISD2 (Q8N5K1), CKAP4 (Q07065), CKAP5 (Q14008), CKB (P12277), CLASP1 (Q7Z460), CLIC1 (O00299), CLIC4 (Q9Y696), CLLD6 (Q5W111), CLNS1A (P54105), CLPB (Q9H078), CLTA (P09496), CLTC (Q00610), CLTCL1 (P53675), CLU (P10909), CMBL (Q96DG6), CMC1 (Q7Z7K0), CMPK1 (P30085), CMTM6 (Q9NX76), CNBP (P62633), CNDP2 (Q96KP4), CNN2 (Q99439), CNN3 (Q15417), CNNM3 (Q8NE01), CNOT1 (A5YKK6), CNOT10 (Q9H9A5), CNOT6L (Q96LI5), CNP (P09543), COASY (Q13057), COBRA1 (Q8WX92), COG1 (Q8WTW3), COG3 (Q96JB2), COG4 (Q9H9E3), COG5 (Q9UP83), COG6 (Q9Y2V7), COL11A1 (P12107), COL14A1 (Q05707), COL18A1 (P39060), COL6A1 (P12109), COMMD10 (Q9Y6G5), COMMD2 (Q86X83), COMMD3 (Q9UBI1), COMMD5 (Q9GZQ3), COMMD8 (Q9NX08), COMMD9 (Q9P000), COMT (P21964), COPA (P53621), COPB1 (P53618), COPB2 (P35606), COPE (O14579), COPG (Q9Y678), COPG2 (Q9UBF2), COPS2 (P61201), COPS3 (Q9UNS2), COPS4 (Q9BT78), COPS5 (Q92905), COPS6 (Q7L5N1), COPS7A (Q9UBW8), COPS7B (Q9H9Q2), COPS8 (Q99627), CORO1B (Q9BR76), CORO1C (Q9ULV4), CORO2B (Q9UQ03), CORO7 (P57737), COTL1 (Q14019), COX4NB (O43402), COX5A (P20674), COX5B (P10606), COX6C (P09669), CP (P00450), CPD (O75976), CPNE1 (Q99829), CPNE2 (Q96FN4), CPNE3 (O75131), CPNE4 (Q96A23), CPNE7 (Q9UBL6), CPOX (P36551), CPSF1 (Q10570), CPSF2 (Q9P2I0), CPSF3 (Q9UKF6), CPSF3L (Q5TA45), CPSF6 (Q16630), CPSF7 (Q8N684), CPXM1 (Q96SM3), CRABP2 (P29373), CRIP2 (P52943), CRK (P46108), CRLF3 (Q8IUI8), CRNKL1 (Q9BZJ0), CRTAP (O75718), CRYAB (P02511), CRYM (Q14894), CRYZ (Q08257), CRYZL1 (O95825), CS (O75390), CSDE1 (O75534), CSE1L (P55060), CSK (P41240), CSNK1A1 (P48729), CSNK2A1 (P68400), CSNK2A2 (P19784), CSNK2B (P67870), CSRP1 (P21291), CSRP2 (Q16527), CSTB (P04080), CSTF1 (Q05048), CSTF2T (Q9H0L4), CSTF3 (Q12996), CTBP1 (Q13363), CTBP2 (P56545), CTNNA1 (P35221), CTNNAL1 (Q9UBT7), CTNNB1 (P35222), CTNNBL1 (Q8WYA6), CTNND1 (O60716), CTPS (P17812), CTPS2 (Q9NRF8), CTR9 (Q6PD62), CTSC (P53634), CTSD (P07339), CTSF (Q9UBX1), CTSL2 (O60911), CTTN (Q14247), CTU1 (Q7Z7A3), CUL1 (Q13616), CUL2 (Q13617), CUL3 (Q13618), CUL4A (Q13619), CUL4B (Q13620), CUL5 (Q93034), CUL7 (Q14999), CXADR (P78310), CXCL14

TABLE 21-continued

Gene names and SWISSPROT accession numbers of all 2940 proteins identified
in CTX0E03 microvesicles (listed in alphabetical order of gene name).

(O95715), CXorf26 (Q9BVG4), CXorf38 (Q8TB03), CYB5R3 (P00387), CYC1 (P08574), CYCS
(P99999), CYFIP1 (Q7L576), CYFIP2 (Q96F07), CYR61 (O00622), DAB1 (O75553), DAD1
(P61803), DAG1 (Q14118), DAK (Q3LXA3), DAPK3 (O43293), DARS (P14868), DAZAP1
(Q96EP5), DBI (P07108), DBN1 (Q16643), DBNL (Q9UJU6), DCAF7 (P61962), DCAF8
(Q5TAQ9), DCBLD2 (Q96PD2), DCK (P27707), DCLK1 (O15075), DCPS (Q96C86), DCTD
(P32321), DCTN1 (Q14203), DCTN2 (Q13561), DCTN3 (O75935), DCTN4 (Q9UJW0), DCTN5
(Q9BTE1), DCTN6 (O00399), DCUN1D1 (Q96GG9), DCUN1D3 (Q8IWE4), DCUN1D5
(Q9BTE7), DCXR (Q7Z4W1), DDA1 (Q9BW61), DDAH1 (O94760), DDAH2 (O95865), DDB1
(Q16531), DDB2 (Q92466), DDI2 (Q5TDH0), DDOST (P39656), DDR1 (Q08345), DDT
(P30046), DDX1 (Q92499), DDX17 (Q92841), DDX18 (Q9NVP1), DDX19A (Q9NUU7), DDX20
(Q9UHI6), DDX21 (Q9NR30), DDX23 (Q9BUQ8), DDX24 (Q9GZR7), DDX27 (Q96GQ7),
DDX39 (O00148), DDX3X (O00571), DDX46 (Q7L014), DDX47 (Q9H0S4), DDX49 (Q9Y6V7),
DDX5 (P17844), DDX50 (Q9BQ39), DDX51 (Q8N8A6), DDX52 (Q9Y2R4), DDX54 (Q8TDD1),
DDX55 (Q8NHQ9), DDX56 (Q9NY93), DDX6 (P26196), DECR1 (Q16698), DECR2 (Q9NUI1),
DEF (Q68CQ4), DEK (P35659), DENR (O43583), DERA (Q9Y315), DFFA (O00273), DFFB
(O76075), DHCR24 (Q15392), DHCR7 (Q9UBM7), DHFR (P00374), DHPS (P49366), DHRS11
(Q6UWP2), DHRS4 (Q9BTZ2), DHX15 (O43143), DHX16 (O60231), DHX29 (Q7Z478), DHX30
(Q7L2E3), DHX32 (Q7L7V1), DHX36 (Q9H2U1), DHX37 (Q8IY37), DHX38 (Q92620), DHX9
(Q08211), DIAPH1 (O60610), DIAPH2 (O60879), DIMT1L (Q9UNQ2), DIP2A (Q14689), DIP2B
(Q9P265), DIP2C (Q9Y2E4), DIS3 (Q9Y2L1), DIS3L2 (Q8IYB7), DKC1 (O60832), DLAT
(P10515), DLD (P09622), DLG1 (Q12959), DLGAP4 (Q9Y2H0), DLST (P36957), DMD
(P11532), DNAJA1 (P31689), DNAJA2 (O60884), DNAJB1 (P25685), DNAJB11 (Q9UBS4),
DNAJB4 (Q9UDY4), DNAJB6 (O75190), DNAJC13 (O75165), DNAJC2 (Q99543), DNAJC3
(Q13217), DNAJC7 (Q99615), DNASE1L1 (P49184), DNM1 (Q05193), DNM1L (O00429),
DNM2 (P50570), DNMT1 (P26358), DNPEP (Q9ULA0), DOCK1 (Q14185), DOCK4 (Q8N1I0),
DOCK5 (Q9H7D0), DOCK7 (Q96N67), DOCK9 (Q9BZ29), DOHH (Q9BU89), DPCD
(Q9BVM2), DPH2 (Q9BQC3), DPH5 (Q9H2P9), DPM1 (O60762), DPM3 (Q9P2X0), DPP3
(Q9NY33), DPP9 (Q86TI2), DPY30 (Q9C005), DPYSL2 (Q16555), DPYSL3 (Q14195), DPYSL4
(O14531), DPYSL5 (Q9BPU6), DRG1 (Q9Y295), DRG2 (P55039), DSC1 (Q08554), DSG1
(Q02413), DSP (P15924), DST (Q03001), DSTN (P60981), DTD1 (Q8TEA8), DTNA (Q9Y4J8),
DTYMK (P23919), DUS2L (Q9NX74), DUS3L (Q96G46), DUSP12 (Q9UNI6), DUSP3 (P51452),
DYM (Q7RTS9), DYNC1H1 (Q14204), DYNC1I2 (Q13409), DYNC1LI1 (Q9Y6G9), DYNC1LI2
(O43237), DYNC2H1 (Q8NCM8), DYNLL1 (P63167), DYNLL2 (Q96FJ2), DYNLRB1 (Q9NP97),
DYNLT1 (P63172), EBNA1BP2 (Q99848), ECE1 (P42892), ECHDC1 (Q9NTX5), ECHS1
(P30084), ECM29 (Q5VYK3), EDC3 (Q96F86), EDC4 (Q6P2E9), EEA1 (Q15075), EEF1A1
(P68104), EEF1B2 (P24534), EEF1D (P29692), EEF1E1 (O43324), EEF1G (P26641), EEF2
(P13639), EEF2K (O00418), EEFSEC (P57772), EFEMP2 (O95967), EFHD2 (Q96C19),
EFTUD1 (Q7Z2Z2), EFTUD2 (Q15029), EGFR (P00533), EHD1 (Q9H4M9), EHD2 (Q9NZN4),
EHD3 (Q9NZN3), EHD4 (Q9H223), EIF1AX (P47813), EIF2A (Q9BY44), EIF2AK2 (P19525),
EIF2AK4 (Q9P2K8), EIF2B1 (Q14232), EIF2B2 (P49770), EIF2B3 (Q9NR50), EIF2B4
(Q9UI10), EIF2B5 (Q13144), EIF2C1 (Q9UL18), EIF2C2 (Q9UKV8), EIF2S1 (P05198), EIF2S2
(P20042), EIF2S3 (P41091), EIF3A (Q14152), EIF3B (P55884), EIF3C (Q99613), EIF3D
(O15371), EIF3E (P60228), EIF3F (O00303), EIF3G (O75821), EIF3H (O15372), EIF3I
(Q13347), EIF3J (O75822), EIF3K (Q9UBQ5), EIF3L (Q9Y262), EIF3M (Q7L2H7), EIF4A1
(P60842), EIF4A2 (Q14240), EIF4A3 (P38919), EIF4E (P06730), EIF4G1 (Q04637), EIF4G2
(P78344), EIF4H (Q15056), EIF5 (P55010), EIF5A (P63241), EIF5B (O60841), EIF6 (P56537),
ELAC2 (Q9BQ52), ELAVL1 (Q15717), ELMO2 (Q96JJ3), ELP2 (Q6IA86), ELP3 (Q9H9T3),
EMD (P50402), EMG1 (Q92979), EML1 (O00423), EML2 (O95834), EML3 (Q32P44), EML4
(Q9HC35), ENAH (Q8N8S7), ENC1 (O14682), ENO1 (P06733), ENO2 (P09104), ENOPH1
(Q9UHY7), ENY2 (Q9NPA8), EPB41L2 (O43491), EPB41L3 (Q9Y2J2), EPDR1 (Q9UM22),
EPHA2 (P29317), EPHB2 (P29323), EPHB3 (P54753), EPHB4 (P54760), EPHX1 (P07099),
EPM2AIP1 (Q7L775), EPN1 (Q9Y6I3), EPRS (P07814), ERBB2IP (Q96RT1), ERGIC1
(Q969X5), ERH (P84090), ERI1 (Q8IV48), ERI3 (O43414), ERLIN2 (O94905), ERO1L
(Q96HE7), ERP29 (P30040), ERP44 (Q9BS26), ESD (P10768), ESYT1 (Q9BSJ8), ETF1
(P62495), ETFA (P13804), ETFB (P38117), EXOC1 (Q9NV70), EXOC2 (Q96KP1), EXOC3
(O60645), EXOC4 (Q96A65), EXOC5 (O00471), EXOC6 (Q8TAG9), EXOC6B (Q9Y2D4),
EXOC7 (Q9UPT5), EXOC8 (Q8IYI6), EXOSC1 (Q9Y3B2), EXOSC10 (Q01780), EXOSC2
(Q13868), EXOSC3 (Q9NQT5), EXOSC4 (Q9NPD3), EXOSC5 (Q9NQT4), EXOSC6
(Q5RKV6), EXOSC7 (Q15024), EXOSC8 (Q96B26), EXOSC9 (Q06265), EZR (P15311), F11R
(Q9Y624), F8 (P00451), F8A1 (P23610), FABP5 (Q01469), FABP7 (O15540), FADD (Q13158),
FAH (P16930), FAHD1 (Q6P587), FAHD2A (Q96GK7), FAM115A (Q9Y4C2), FAM120A
(Q9NZB2), FAM125A (Q96EY5), FAM127A (A6ZKI3), FAM129A (Q9BZQ8), FAM129B
(Q96TA1), FAM136A (Q96C01), FAM175B (Q15018), FAM3C (Q92520), FAM45B (Q6NSW5),
FAM49B (Q9NUQ9), FAM82B (Q96DB5), FAM84B (Q96KN1), FAM96B (Q9Y3D0), FAM98A
(Q8NCA5), FAM98B (Q52LJ0), FANCI (Q9NVI1), FAR1 (Q8WVX9), FARP1 (Q9Y4F1), FARP2
(O94887), FARSA (Q9Y285), FARSB (Q9NSD9), FAS (P25445), FASN (P49327), FAT1
(Q14517), FAU (P62861), FBL (P22087), FBLN2 (P98095), FBN1 (P35555), FBN2 (P35556),
FBXL18 (Q96ME1), FBXO21 (O94952), FBXO22 (Q8NEZ5), FBXW11 (Q9UKB1), FCF1
(Q9Y324), FDFT1 (P37268), FDPS (P14324), FDXR (P22570), FEN1 (P39748), FERMT1
(Q9BQL6), FERMT2 (Q96AC1), FFR (Q9UID3), FGFBP3 (Q8TAT2), FH (P07954), FHL1
(Q13642), FHL2 (Q14192), FHL3 (Q13643), FIBP (O43427), FKBP10 (Q96AY3), FKBP1A
(P62942), FKBP2 (P26885), FKBP3 (Q00688), FKBP4 (Q02790), FKBP5 (Q13451), FLG
(P20930), FLG2 (Q5D862), FLII (Q13045), FLNA (P21333), FLNB (O75369), FLNC (Q14315),
FLOT1 (O75955), FLOT2 (Q14254), FMNL2 (Q96PY5), FN3K (Q9H479), FN3KRP (Q9HA64),
FNTA (P49354), FNTB (P49356), FOLR1 (P15328), FREM2 (Q5SZK8), FRG1 (Q14331),
FRMD5 (Q7Z6J6), FRMD8 (Q9BZ67), FRYL (O94915), FSCN1 (Q16658), FSD1 (Q8BTV5),
FTH1 (P02794), FTL (P02792), FTO (Q9C0B1), FTSJD2 (Q8N1G2), FUBP1 (Q96AE4), FUBP3

TABLE 21-continued

Gene names and SWISSPROT accession numbers of all 2940 proteins identified in CTX0E03 microvesicles (listed in alphabetical order of gene name).

(Q96I24), FUCA2 (Q9BTY2), FUK (Q8N0W3), FUS (P35637), FXR1 (P51114), FXR2 (P51116), FYCO1 (Q9BQS8), FYN (P06241), G3BP1 (Q13283), G3BP2 (Q9UN86), G6PD (P11413), GAA (P10253), GALK1 (P51570), GALK2 (Q01415), GALNT1 (Q10472), GALNT2 (Q10471), GALNT7 (Q86SF2), GAN (Q9H2C0), GANAB (Q14697), GAP43 (P17677), GAPDH (P04406), GAPVD1 (Q14C86), GAR1 (Q9NY12), GARS (P41250), GART (P22102), GATSL2 (A6NHX0), GBA (P04062), GBE1 (Q04446), GBF1 (Q92538), GCDH (Q92947), GCLC (P48506), GCLM (P48507), GCN1L1 (Q92616), GDI1 (P31150), GDI2 (P50395), GEMIN4 (P57678), GEMIN5 (Q8TEQ6), GEMIN6 (Q8WXD5), GET4 (Q7L5D6), GFAP (P14136), GFM1 (Q96RP9), GFPT1 (Q06210), GFPT2 (O94808), GGCT (O75223), GGPS1 (O95749), GINS1 (Q14691), GINS2 (Q9Y248), GINS4 (Q9BRT9), GIPC1 (O14908), GIT1 (Q9Y2X7), GLA (P06280), GLB1L2 (Q8IW92), GLE1 (Q53GS7), GLG1 (Q92896), GLIPR2 (Q9H4G4), GLMN (Q92990), GLO1 (Q04760), GLOD4 (Q9HC38), GLRX (P35754), GLRX3 (O76003), GLT25D1 (Q8NBJ5), GLT25D2 (Q8IYK4), GLTP (Q9NZD2), GLUD1 (P00367), GLUL (P15104), GMDS (O60547), GMFB (P60983), GMPPA (Q96IJ6), GMPPB (Q9Y5P6), GMPR (P36959), GMPR2 (Q9P2T1), GMPS (P49915), GNA11 (P29992), GNA12 (Q03113), GNA13 (Q14344), GNAI1 (P63096), GNAI2 (P04899), GNAI3 (P08754), GNAQ (P50148), GNAS (Q5JWF2), GNB1 (P62873), GNB1L (Q9BYB4), GNB2 (P62879), GNB2L1 (P63244), GNB4 (Q9HAV0), GNE (Q9Y223), GNG10 (P50151), GNG12 (Q9UBI6), GNG4 (P50150), GNG5 (P63218), GNL3 (Q9BVP2), GNPDA1 (P46926), GNPNAT1 (Q96EK6), GOLGA7 (Q7Z5G4), GOLM1 (Q8NBJ4), GOLPH3 (Q9H4A6), GORASP2 (Q9H8Y8), GOT1 (P17174), GOT2 (P00505), GPC1 (P35052), GPC4 (O75487), GPC6 (Q9Y625), GPD1L (Q8N335), GPHN (Q9NQX3), GPI (P06744), GPM6A (P51674), GPN1 (Q9HCN4), GPR50 (Q13585), GPR56 (Q9Y653), GPS1 (Q13098), GPSM1 (Q86YR5), GPX1 (P07203), GPX4 (P36969), GRB2 (P62993), GRHPR (Q9UBQ7), GRP (Q3ZCW2), GRWD1 (Q9BQ67), GSDMA (Q96QA5), GSK3A (P49840), GSK3B (P49841), GSN (P06396), GSPT1 (P15170), GSR (P00390), GSS (P48637), GSTK1 (Q9Y2Q3), GSTM2 (P28161), GSTM3 (P21266), GSTM4 (Q03013), GSTO1 (P78417), GSTP1 (P09211), GSTT2 (P0CG29), GSTZ1 (O43708), GTF2E2 (P29084), GTF2F2 (P13984), GTF2H3 (Q13889), GTF2I (P78347), GTF3C2 (Q8WUA4), GTF3C3 (Q9Y5Q9), GTF3C4 (Q9UKN8), GTPBP1 (O00178), GTPBP4 (Q9BZE4), GUK1 (Q16774), GYG1 (P46976), GYS1 (P13807), H1F0 (P07305), H1FX (Q92522), H2AFX (P16104), H2AFY (O75367), H2AFZ (P0C0S5), HADH (Q16836), HADHA (P40939), HARS (P12081), HAT1 (O14929), HAUS3 (Q68CZ6), HAUS4 (Q9H6D7), HBA1 (P69905), HBB (P68871), HBS1L (Q9Y450), HBXIP (O43504), HCFC1 (P51610), HDAC1 (Q13547), HDAC2 (Q92769), HDDC2 (Q7Z4H3), HDGF (P51858), HDGFRP2 (Q7Z4V5), HDHD2 (Q9H0R4), HDLBP (Q00341), HEATR1 (Q9H583), HEATR2 (Q86Y56), HEBP1 (Q9NRV9), HECTD3 (Q5T447), HERC4 (Q5GLZ8), HEXB (P07686), HGS (O14964), HHIP (Q96QV1), HINT1 (P49773), HINT2 (Q9BX68), HINT3 (Q9NQE9), HIP1R (O75146), HIST1H1B (P16401), HIST1H1C (P16403), HIST1H1D (P16402), HIST1H1E (P10412), HIST1H2AD (P20671), HIST1H2BJ (P06899), HIST1H2BM (Q99879), HIST1H2BO (P23527), HIST1H4A (P62805), HIST2H2AA3 (Q6FI13), HIST2H2AB (Q8IUE6), HIST2H2BE (Q16778), HIST2H3A (Q71DI3), HIST3H2BB (Q8N257), HK1 (P19367), HK2 (P52789), HLA-A (P30443), HLA-A (P01892), HLA-B (P03989), HMGA1 (P17096), HMGB1 (P09429), HMGB2 (P26583), HMGCL (P35914), HMGCS1 (Q01581), HMGN1 (P05114), HMGN2 (P05204), HMGN4 (O00479), HNRNPA0 (Q13151), HNRNPA1 (P09651), HNRNPA2B1 (P22626), HNRNPA3 (P51991), HNRNPAB (Q99729), HNRNPC (P07910), HNRNPD (Q14103), HNRNPF (P52597), HNRNPH1 (P31943), HNRNPH2 (P55795), HNRNPH3 (P31942), HNRNPK (P61978), HNRNPL (P14866), HNRNPM (P52272), HNRNPR (O43390), HNRNPU (Q00839), HNRNPUL1 (Q9BUJ2), HNRNPUL2 (Q1KMD3), HNRPDL (O14979), HNRPLL (Q8WVV9), HOOK3 (Q86VS8), HP (P00738), HP1BP3 (Q5SSJ5), HPCAL1 (P37235), HPRT1 (P00492), HPX (P02790), HRAS (P01112), HRNR (Q86YZ3), HSD17B10 (Q99714), HSD17B12 (Q53GQ0), HSD17B4 (P51659), HSDL2 (Q6YN16), HSP90AA1 (P07900), HSP90AB1 (P08238), HSP90B1 (P14625), HSPA12A (O43301), HSPA14 (Q0VDF9), HSPA1A (P08107), HSPA4 (P34932), HSPA4L (O95757), HSPA5 (P11021), HSPA8 (P11142), HSPA9 (P38646), HSPB1 (P04792), HSPBP1 (Q9NZL4), HSPD1 (P10809), HSPE1 (P61604), HSPG2 (P98160), HSPH1 (Q92598), HTRA1 (Q92743), HTT (P42858), HUWE1 (Q7Z6Z7), HYOU1 (Q9Y4L1), IARS (P41252), ICAM1 (P05362), IDE (P14735), IDH1 (O75874), IDH2 (P48735), IDH3A (P50213), IDI1 (Q13907), IFI16 (Q16666), IFIT5 (Q13325), IFITM3 (Q01628), IFRD2 (Q12894), IFT172 (Q9UG01), IGF1R (P08069), IGF2BP2 (Q9Y6M1), IGF2BP3 (O00425), IGF2R (P11717), IGFBP3 (P17936), IGFBP5 (P24593), IGHG1 (P01857), IGHG2 (P01859), IGSF3 (O75054), IGSF8 (Q969P0), IKBKAP (O95163), IKBKB (O14920), IL1RAP (Q9NPH3), ILF2 (Q12905), ILF3 (Q12906), ILK (Q13418), ILKAP (Q9H0C8), IMMT (Q16891), IMP3 (Q9NV31), IMPA1 (P29218), IMPA2 (O14732), IMPAD1 (Q9NX62), IMPDH1 (P20839), IMPDH2 (P12268), INA (Q16352), INF2 (Q27J81), INPP1 (P49441), INPPL1 (O15357), INTS10 (Q9NVR2), INTS3 (Q68E01), INTS7 (Q9NVH2), INTS8 (Q75QN2), IPO11 (Q9UI26), IPO4 (Q8TEX9), IPO5 (O00410), IPO7 (O95373), IPO8 (O15397), IPO9 (Q96P70), IQGAP1 (P46940), IRF2BP2 (Q7Z5L9), IRF3 (Q14653), IRGQ (Q8WZA9), ISOC1 (Q96CN7), ISYNA1 (Q9NPH2), ITFG3 (Q9H0X4), ITGA2 (P17301), ITGA3 (P26006), ITGA4 (P13612), ITGA5 (P08648), ITGA6 (P23229), ITGA7 (Q13683), ITGAV (P06756), ITGB1 (P05556), ITGB1BP1 (O14713), ITGB3 (P05106), ITGB4 (P16144), ITGB5 (P18084), ITGB8 (P26012), ITPA (Q9BY32), JAM3 (Q9BX67), JUP (P14923), KARS (Q15046), KATNB1 (Q9BVA0), KBTBD6 (Q86V97), KCTD21 (Q4G0X4), KDM1A (O60341), KEAP1 (Q14145), KHDRBS1 (Q07666), KHSRP (Q92945), KIAA0020 (Q15397), KIAA0090 (Q8N766), KIAA0174 (P53990), KIAA0196 (Q12768), KIAA0664 (O75153), KIAA0776 (O94874), KIAA1033 (Q2M389), KIAA1279 (Q96EK5), KIAA1598 (A0MZ66), KIAA1797 (Q5VW36), KIAA1949 (Q6NYC8), KIAA1967 (Q8N163), KIDINS220 (Q9ULH0), KIF1A (Q12756), KIF2A (O00139), KIF5B (P33176), KIF5C (O60282), KLC1 (Q07866), KLHDC4 (Q8TBB5), KLHL13 (Q9P2N7), KLHL22 (Q53GT1), KLHL26 (Q53HC5), KNTC1 (P50748), KPNA1 (P52294), KPNA2 (P52292), KPNA3 (O00505), KPNA4 (O00629), KPNA6 (O60684), KPNB1 (Q14974), KPRP (Q5T749), KRAS (P01116), KRIT1 (O00522), KRT13 (P13646), KRT14 (P02533),

TABLE 21-continued

Gene names and SWISSPROT accession numbers of all 2940 proteins identified in CTX0E03 microvesicles (listed in alphabetical order of gene name).

KRT71 (Q3SY84), KTN1 (Q86UP2), L1CAM (P32004), LACTB2 (Q53H82), LAMA1 (P25391), LAMA4 (Q16363), LAMA5 (O15230), LAMB1 (P07942), LAMB2 (P55268), LAMC1 (P11047), LAMP1 (P11279), LAMP2 (P13473), LANCL1 (O43813), LANCL2 (Q9NS86), LAP3 (P28838), LARP1 (Q6PKG0), LARS (Q9P2J5), LAS1L (Q9Y4W2), LASP1 (Q14847), LBR (Q14739), LCMT1 (Q9UIC8), LDHA (P00338), LDHB (P07195), LDLR (P01130), LEFTY2 (O00292), LEPRE1 (Q32P28), LGALS1 (P09382), LGALS3 (P17931), LGALS3BP (Q08380), LGALS7 (P47929), LIMA1 (Q9UHB6), LIMS1 (P48059), LIN7C (Q9NUP9), LIPG (Q9Y5X9), LLGL1 (Q15334), LMAN1 (P49257), LMAN2 (Q12907), LMCD1 (Q9NZU5), LMNA (P02545), LMNB1 (P20700), LMNB2 (Q03252), LNPEP (Q9UIQ6), LOH12CR1 (Q969J3), LONP1 (P36776), LOR (Q23490), LOXL4 (Q96JB6), LPHN2 (O95490), LPL (P06858), LRBA (P50851), LRG1 (P02750), LRP1 (Q07954), LRPPRC (P42704), LRRC1 (Q9BTT6), LRRC40 (Q9H9A6), LRRC47 (Q8N1G4), LRRC57 (Q8N9N7), LRRC59 (Q96AG4), LRRC8A (Q8IWT6), LRSAM1 (Q6UWE0), LSM1 (O15116), LSM12 (Q3MHD2), LSM2 (Q9Y333), LSM4 (Q9Y4Z0), LSM6 (P62312), LSM7 (Q9UK45), LSS (P48449), LTA4H (P09960), LTBP2 (Q14767), LTBP3 (Q9NS15), LTN1 (O94822), LUC7L (Q9NQ29), LUC7L2 (Q9Y383), LUC7L3 (O95232), LYAR (Q9NX58), LYPLA1 (O75608), LYPLA2 (O95372), LYPLAL1 (Q5VWZ2), LZTR1 (Q8N653), M6PR (P20645), MACF1 (Q9UPN3), MACF1 (Q96PK2), MACROD1 (Q9BQ69), MAD1L1 (Q9Y6D9), MAD2L1 (Q13257), MAGEE1 (Q9HCI5), MAK16 (Q9BXY0), MALT1 (Q9UDY8), MAN1A2 (O60476), MAN1B1 (Q9UKM7), MAN2C1 (Q9NTJ4), MAP1B (P46821), MAP1LC3A (Q9H492), MAP1LC3B2 (A6NCE7), MAP2K1 (Q02750), MAP2K2 (P36507), MAP2K3 (P46734), MAP2K4 (P45985), MAP2K7 (O14733), MAP4 (P27816), MAP4K4 (O95819), MAPK1 (P28482), MAPK14 (Q16539), MAPK3 (P27361), MAPKSP1 (Q9UHA4), MAPRE1 (Q15691), MAPRE3 (Q9UPY8), MARCKS (P29966), MARCKSL1 (P49006), MARK2 (Q7KZI7), MARS (P56192), MAT2A (P31153), MAT2B (Q9NZL9), MATR3 (P43243), MBD3 (O95983), MBLAC2 (Q68D91), MBNL1 (Q9NR56), MBNL2 (Q5VZF2), MCAM (P43121), MCM2 (P49736), MCM3 (P25205), MCM4 (P33991), MCM5 (P33992), MCM6 (Q14566), MCM7 (P33993), MCTS1 (Q9ULC4), MDH1 (P40925), MDH2 (P40926), MDK (P21741), MDN1 (Q9NU22), ME1 (P48163), ME2 (P23368), MED1 (Q15648), MED10 (Q9BTT4), MED11 (Q9P086), MED17 (Q9NVC6), MED18 (Q9BUE0), MED20 (Q9H944), MED23 (Q9ULK4), MED24 (O75448), MED28 (Q9H204), MED31 (Q9Y3C7), MEMO1 (Q9Y316), MEN1 (O00255), MERIT40 (Q9NWV8), METAP1 (P53582), METAP2 (P50579), METT10D (Q86W50), METTL1 (Q9UBP6), METTL11A (Q9BV86), METTL13 (Q8N6R0), METTL2B (Q6P1Q9), METTL5 (Q9NRN9), METTL9 (Q9H1A3), MFAP2 (P55001), MFAP4 (P55083), MFGE8 (Q08431), MFI2 (P08582), MGEA5 (O60502), MICA (Q29983), MICAL1 (Q8TDZ2), MIF (P14174), MINA (Q8IUF8), MIOS (Q9NXC5), MKI67IP (Q9BYG3), MLEC (Q14165), MLLT4 (P55196), MLST8 (Q9BVC4), MLTK (Q9NYL2), MMP14 (P50281), MMP2 (P08253), MMS19 (Q96T76), MOB2 (Q70IA6), MOBKL1B (Q9H8S9), MOBKL2A (Q96BX8), MOBKL3 (Q9Y3A3), MOCS2 (O96033), MOGS (Q13724), MON2 (Q7Z3U7), MORC2 (Q9Y6X9), MOV10 (Q9HCE1), MOXD1 (Q6UVY6), MPG (P29372), MPI (P34949), MPP6 (Q9NZW5), MPRIP (Q6WCQ1), MPST (P25325), MPZL1 (O95297), MRC2 (Q9UBG0), MRE11A (P49959), MRI1 (Q9BV20), MRPS27 (Q92552), MRPS28 (Q9Y2Q9), MRPS33 (Q9Y291), MRPS34 (P82930), MRPS6 (P82932), MRTO4 (Q9UKD2), MSH2 (P43246), MSH3 (P20585), MSH6 (P52701), MSN (P26038), MSTO1 (Q9BUK6), MTA1 (Q13330), MTA2 (O94776), MTAP (Q13126), MTHFD1 (P11586), MTHFS (P49914), MTM1 (Q13496), MTMR1 (Q13613), MTMR2 (Q13614), MTMR6 (Q9Y217), MTMR9 (Q96QG7), MTOR (P42345), MTPN (P58546), MTR (Q99707), MTRR (Q9UBK8), MVD (P53602), MVK (Q03426), MVP (Q14764), MX1 (P20591), MYADM (Q96S97), MYBBP1A (Q9BQG0), MYCBP (Q99417), MYD88 (Q99836), MYH10 (P35580), MYH14 (Q7Z406), MYH9 (P35579), MYL12B (O14950), MYL6 (P60660), MYO18A (Q92614), MYO1B (O43795), MYO1C (O00159), MYO1E (Q12965), MYO5A (Q9Y4I1), MYO6 (Q9UM54), MYOF (Q9NZM1), NAA10 (P41227), NAA15 (Q9BXJ9), NAA16 (Q6N069), NAA25 (Q14CX7), NAA38 (O95777), NAA50 (Q9GZZ1), NACA (Q13765), NAE1 (Q13564), NAGK (Q9UJ70), NAGLU (P54802), NAMPT (P43490), NANS (Q9NR45), NAP1L1 (P55209), NAP1L4 (Q99733), NAPA (P54920), NAPG (Q99747), NAPRT1 (Q6XQN6), NARFL (Q9H6Q4), NARS (O43776), NASP (P49321), NAT10 (Q9H0A0), NAT9 (Q9BTE0), NCAM1 (P13591), NCAN (O14594), NCAPD2 (Q15021), NCAPG (Q9BPX3), NCBP1 (Q09161), NCCRP1 (Q6ZVX7), NCDN (Q9UBB6), NCKAP1 (Q9Y2A7), NCKIPSD (Q9NZQ3), NCL (P19338), NCLN (Q969V3), NCS1 (P62166), NCSTN (Q92542), NDOR1 (Q9UHB4), NDRG3 (Q9UGV2), NDRG4 (Q9ULP0), NDUFA2 (O43678), NDUFA7 (O95182), NDUFAB1 (O14561), NDUFB4 (O95168), NDUFC2 (O95298), NDUFS5 (O43920), NDUFS6 (O75380), NEDD8 (Q15843), NEFL (P07196), NEFM (P07197), NEK6 (Q9HC98), NEK9 (Q8TD19), NES (P48681), NF1 (P21359), NF2 (P35240), NFIX (Q14938), NHLRC2 (Q8NBF2), NHP2L1 (P55769), NID1 (P14543), NIP7 (Q9Y221), NIPSNAP1 (Q9BPW8), NIT1 (Q86X76), NIT2 (Q9NQR4), NKRF (O15226), NLE1 (Q9NVX2), NLGN4X (Q8N0W4), NLN (Q9BYT8), NMD3 (Q96D46), NME2 (P22392), NME3 (Q13232), NME7 (Q9Y5B8), NMT1 (P30419), NNMT (P40261), NOB1 (Q9ULX3), NOC2L (Q9Y3T9), NOC3L (Q8WTT2), NOC4L (Q9BVI4), NOG (Q13253), NOL11 (Q9H8H0), NOL6 (Q9H6R4), NOL9 (Q5SY16), NOMO2 (Q5JPE7), NONO (Q15233), NOP10 (Q9NPE3), NOP16 (Q9Y3C1), NOP2 (P46087), NOP56 (O00567), NOP58 (Q9Y2X3), NOS1AP (O75052), NOSIP (Q9Y314), NOTCH2 (Q04721), NOVA2 (Q9UNW9), NPC1 (O15118), NPC2 (P61916), NPEPPS (P55786), NPLOC4 (Q8TAT6), NPM1 (P06748), NPTN (Q9Y639), NPW (Q8N729), NQO1 (P15559), NQO2 (P16083), NRAS (P01111), NRBP1 (Q9UHY1), NRD1 (O43847), NRP1 (O14786), NRP2 (O60462), NSDHL (Q15738), NSF (P46459), NSUN2 (Q08J23), NSUN5 (Q96P11), NSUN6 (Q8TEA1), NT5C (Q8TCD5), NT5C2 (P49902), NT5C3L (Q969T7), NT5E (P21589), NTN1 (O95631), NUBP1 (P53384), NUBP2 (Q9Y5Y2), NUCB1 (Q02818), NUCKS1 (Q9H1E3), NUDC (Q9Y266), NUDCD1 (Q96RS6), NUDCD2 (Q8WVJ2), NUDT1 (P36639), NUDT10 (Q8NFP7), NUDT16 (Q96DE0), NUDT16L1 (Q9BRJ7), NUDT21 (O43809), NUDT4 (Q9NZJ9), NUDT5 (Q9UKK9), NUMA1 (Q14980), NUP188 (Q5SRE5), NUP210 (Q8TEM1), NUP37 (Q8NFH4), NUP43 (Q8NFH3), NUP54 (Q7Z3B4), NUP62 (P37198), NUP85 (Q9BW27), NUP88 (Q99567), NUP93 (Q8N1F7), NUTF2

TABLE 21-continued

Gene names and SWISSPROT accession numbers of all 2940 proteins identified
in CTX0E03 microvesicles (listed in alphabetical order of gene name).

(P61970), NXF1 (Q9UBU9), NXN (Q6DKJ4), NXT1 (Q9UKK6), OAT (P04181), OBSL1
(O75147), OCRL (Q01968), ODR4 (Q5SWX8), ODZ2 (Q9NT68), ODZ3 (Q9P273), OGFOD1
(Q8N543), OGT (O15294), OLA1 (Q9NTK5), OLFML3 (Q9NRN5), OPA1 (O60313), ORC3
(Q9UBD5), OSBP (P22059), OSBPL6 (Q9BZF3), OSGEP (Q9NPF4), OTUB1 (Q96FW1),
OVCA2 (Q8WZ82), OXCT1 (P55809), OXSR1 (O95747), P4HA1 (P13674), P4HB (P07237),
PA2G4 (Q9UQ80), PAAF1 (Q9BRP4), PABPC1 (P11940), PABPC4 (Q13310), PABPN1
(Q86U42), PACSIN2 (Q9UNF0), PACSIN3 (Q9UKS6), PAF1 (Q8N7H5), PAFAH1B1 (P43034),
PAFAH1B2 (P68402), PAFAH1B3 (Q15102), PAICS (P22234), PAIP1 (Q9H074), PAK1IP1
(Q9NWT1), PAK2 (Q13177), PALD (Q9ULE6), PALLD (Q8WX93), PANK4 (Q9NVE7), PAPOLA
(P51003), PAPSS1 (O43252), PARK7 (Q99497), PARN (O95453), PARP1 (P09874), PARP4
(Q9UKK3), PARVA (Q9NVD7), PBLD (P30039), PCBD1 (P61457), PCBP1 (Q15365), PCBP2
(Q15366), PCDHB2 (Q9Y5E7), PCDHGC3 (Q9UN70), PCID2 (Q5JVF3), PCMT1 (P22061),
PCNA (P12004), PCOLCE2 (Q9UKZ9), PCYOX1 (Q9UHG3), PCYOX1L (Q8NBM8), PCYT2
(Q99447), PDCD10 (Q9BUL8), PDCD11 (Q14690), PDCD4 (Q53EL6), PDCD5 (O14737),
PDCD6 (O75340), PDCD6IP (Q8WUM4), PDCL3 (Q9H2J4), PDDC1 (Q8NB37), PDE12
(Q6L8Q7), PDGFRA (P16234), PDIA3 (P30101), PDIA4 (P13667), PDIA5 (Q14554), PDIA6
(Q15084), PDLIM1 (O00151), PDLIM4 (P50479), PDLIM5 (Q96HC4), PDLIM7 (Q9NR12),
PDRO (Q6IAA8), PDS5A (Q29RF7), PDS5B (Q9NTI5), PDXK (O00764), PDXP (Q96GD0),
PEA15 (Q15121), PEBP1 (P30086), PECI (O75521), PEF1 (Q9UBV8), PELO (Q9BRX2),
PELP1 (Q8IZL8), PEPD (P12955), PES1 (O00541), PFAS (O15067), PFDN1 (O60925), PFDN2
(Q9UHV9), PFDN4 (Q9NQP4), PFDN5 (Q99471), PFDN6 (O15212), PFKL (P17858), PFKM
(P08237), PFKP (Q01813), PFN1 (P07737), PFN2 (P35080), PGAM1 (P18669), PGAM5
(Q96HS1), PGD (P52209), PGGT1B (P53609), PGK1 (P00558), PGLS (O95336), PGLYRP2
(Q96PD5), PGM1 (P36871), PGM2L1 (Q6PCE3), PGM3 (O95394), PGP (A6NDG6), PGRMC1
(O00264), PGRMC2 (O15173), PHB (P35232), PHB2 (Q99623), PHF5A (Q7RTV0), PHF6
(Q8IWS0), PHGDH (O43175), PHKB (Q93100), PHLDA1 (Q8WV24), PHLDA3 (Q9Y5J5),
PHLDB1 (Q86UU1), PHPT1 (Q9NRX4), PI15 (O43692), PI4KA (P42356), PICALM (Q13492),
PIGT (Q969N2), PIK3CA (P42336), PIK3R4 (Q99570), PIN1 (Q13526), PIP4K2A (P48426),
PIP4K2B (P78356), PIP4K2C (Q8TBX8), PIPOX (Q9P0Z9), PIPSL (A2A3N6), PITPNB
(P48739), PKM2 (P14618), PKP1 (Q13835), PLAA (Q9Y263), PLCB3 (Q01970), PLCD1
(P51178), PLCD3 (Q8N3E9), PLCG1 (P19174), PLCG2 (P16885), PLD3 (Q8IV08), PLEC
(Q15149), PLIN2 (Q99541), PLIN3 (O60664), PLK1 (P53350), PLOD1 (Q02809), PLOD2
(O00469), PLOD3 (O60568), PLRG1 (O43660), PLS1 (Q14651), PLS3 (P13797), PLSCR3
(Q9NRY6), PLTP (P55058), PLXNA1 (Q9UIW2), PLXNB2 (O15031), PLXND1 (Q9Y4D7),
PMM2 (O15305), PMPCA (Q10713), PMPCB (O75439), PMVK (Q15126), PNMA2 (Q9UL42),
PNN (Q9H307), PNO1 (Q9NRX1), PNP (P00491), PNPLA2 (Q96AD5), PODXL (O00592),
POLD1 (P28340), POLD2 (P49005), POLE3 (Q9NRF9), POLR1A (O95602), POLR1B
(Q9H9Y6), POLR1C (O15160), POLR1D (Q9Y2S0), POLR2A (P24928), POLR2B (P30876),
POLR2C (P19387), POLR2E (P19388), POLR2G (P62487), POLR2H (P52434), POLR2J
(P52435), POLR2K (P53803), POLR3A (O14802), POLR3B (Q9NW08), POLR3C (Q9BUI4),
POP1 (Q99575), POP4 (O95707), POP7 (O75817), POR (P16435), PPA1 (Q15181), PPA2
(Q9H2U2), PPAN (Q9NQ55), PPAP2A (O14494), PPAT (Q06203), PPCS (Q9HAB8), PPFIBP1
(Q86W92), PPIA (P62937), PPIB (P23284), PPIC (P45877), PPID (Q08752), PPIF (P30405),
PPIH (O43447), PPIL1 (Q9Y3C6), PPM1F (P49593), PPM1G (O15355), PPME1 (Q9Y570),
PPP1CA (P62136), PPP1CB (P62140), PPP1CC (P36873), PPP1R14B (Q96C90), PPP1R7
(Q15435), PPP1R8 (Q12972), PPP2CA (P67775), PPP2CB (P62714), PPP2R1A (P30153),
PPP2R2A (P63151), PPP2R2D (Q66LE6), PPP2R4 (Q15257), PPP2R5D (Q14738), PPP2R5E
(Q16537), PPP3CA (Q08209), PPP4C (P60510), PPP4R1 (Q8TF05), PPP5C (P53041), PPP6C
(O00743), PPP6R3 (Q5H9R7), PPPDE2 (Q6ICB0), PPT1 (P50897), PPWD1 (Q96BP3), PRCP
(P42785), PRDX1 (Q06830), PRDX2 (P32119), PRDX3 (P30048), PRDX4 (Q13162), PRDX6
(P30041), PREP (P48147), PREPL (Q4J6C6), PRIM1 (P49642), PRIM2 (P49643), PRKAA1
(Q13131), PRKACA (P17612), PRKACB (P22694), PRKAG1 (P54619), PRKAR1A (P10644),
PRKAR2A (P13861), PRKCA (P17252), PRKCI (P41743), PRKCSH (P14314), PRKDC
(P78527), PRKRA (O75569), PRMT1 (Q99873), PRMT10 (Q6P2P2), PRMT3 (O60678),
PRMT5 (O14744), PRMT7 (Q9NVM4), PROSC (O94903), PRPF19 (Q9UMS4), PRPF3
(O43395), PRPF31 (Q8WWY3), PRPF4 (O43172), PRPF40A (O75400), PRPF4B (Q13523),
PRPF6 (O94906), PRPF8 (Q6P2Q9), PRPS1 (P60891), PRPS2 (P11908), PRPSAP2
(O60256), PRRC1 (Q96M27), PRSS23 (O95084), PRTFDC1 (Q9NRG1), PSAP (P07602),
PSAT1 (Q9Y617), PSD3 (Q9NYI0), PSENEN (Q9NZ42), PSIP1 (O75475), PSMA1 (P25786),
PSMA2 (P25787), PSMA3 (P25788), PSMA4 (P25789), PSMA5 (P28066), PSMA6 (P60900),
PSMA7 (O14818), PSMB1 (P20618), PSMB2 (P49721), PSMB3 (P49720), PSMB4 (P28070),
PSMB5 (P28074), PSMB6 (P28072), PSMB7 (Q99436), PSMC1 (P62191), PSMC2 (P35998),
PSMC3 (P17980), PSMC4 (P43686), PSMC5 (P62195), PSMC6 (P62333), PSMD1 (Q99460),
PSMD10 (O75832), PSMD11 (O00231), PSMD12 (O00232), PSMD13 (Q9UNM6), PSMD14
(O00487), PSMD2 (Q13200), PSMD3 (O43242), PSMD4 (P55036), PSMD5 (Q16401), PSMD6
(Q15008), PSMD7 (P51665), PSMD8 (P48556), PSMD9 (O00233), PSME1 (Q06323), PSME2
(Q9UL46), PSME3 (P61289), PSME4 (Q14997), PSMG1 (O95456), PSMG2 (Q969U7), PSPC1
(Q8WXF1), PSPH (P78330), PTBP1 (P26599), PTGES2 (Q9H7Z7), PTGES3 (Q15185),
PTGFRN (Q9P2B2), PTGR1 (Q14914), PTHLH (P12272), PTK2 (Q05397), PTK7 (Q13308),
PTMA (P06454), PTN (P21246), PTP4A1 (Q93096), PTPN1 (P18031), PTPN11 (Q06124),
PTPN23 (Q9H3S7), PTPRA (P18433), PTPRE (P23469), PTPRG (P23470), PTPRJ (Q12913),
PTPRZ1 (P23471), PUF60 (Q9UHX1), PURA (Q00577), PURB (Q96QR8), PUS1 (Q9Y606),
PUS7 (Q96PZ0), PVR (P15151), PVRL2 (Q92692), PWP1 (Q13610), PWP2 (Q15269), PXDN
(Q92626), PXK (Q7Z7A4), PXN (P49023), PYCR1 (P32322), PYCRL (Q53H96), PYGB
(P11216), PYGL (P06737), QARS (P47897), QDPR (P09417), QKI (Q96PU8), QTRT1
(Q9BXR0), RAB10 (P61026), RAB11A (P62491), RAB11FIP1 (Q6WKZ4), RAB12 (Q6IQ22),
RAB13 (P51153), RAB14 (P61106), RAB18 (Q9NP72), RAB1A (P62820), RAB1B (Q9H0U4),

TABLE 21-continued

Gene names and SWISSPROT accession numbers of all 2940 proteins identified in CTX0E03 microvesicles (listed in alphabetical order of gene name).

RAB21 (Q9UL25), RAB22A (Q9UL26), RAB23 (Q9ULC3), RAB27A (P51159), RAB2A (P61019), RAB2B (Q8WUD1), RAB32 (Q13637), RAB34 (Q9BZG1), RAB35 (Q15286), RAB3A (P20336), RAB3GAP1 (Q15042), RAB3GAP2 (Q9H2M9), RAB4A (P20338), RAB5A (P20339), RAB5B (P61020), RAB5C (P51148), RAB6A (P20340), RAB7A (P51149), RAB8A (P61006), RAB8B (Q92930), RABAC1 (Q9UI14), RABGAP1 (Q9Y3P9), RABGGTA (Q92696), RABGGTB (P53611), RABL2A (Q9UBK7), RABL3 (Q5HYI8), RAC1 (P63000), RAC3 (P60763), RAD23B (P54727), RAD50 (Q92878), RAE1 (P78406), RAF1 (P04049), RALA (P11233), RALB (P11234), RALY (Q9UKM9), RAN (P62826), RANBP1 (P43487), RANBP2 (P49792), RANGAP1 (P46060), RAP1A (P62834), RAP1B (P61224), RAP1GDS1 (P52306), RAP2B (P61225), RAPH1 (Q70E73), RARS (P54136), RASA1 (P20936), RASA3 (Q14644), RBBP4 (Q09028), RBBP5 (Q15291), RBBP7 (Q16576), RBM12 (Q9NTZ6), RBM14 (Q96PK6), RBM15 (Q96T37), RBM22 (Q9NW64), RBM25 (P49756), RBM26 (Q5T8P6), RBM28 (Q9NW13), RBM39 (Q14498), RBM4 (Q9BWF3), RBM8A (Q9Y5S9), RBMX (P38159), RBP1 (P09455), RBPJ (Q06330), RBX1 (P62877), RCC1 (P18754), RCC2 (Q9P258), RCL (O43598), RCL1 (Q9Y2P8), RCN1 (Q15293), RDH11 (Q8TC12), RDH13 (Q8NBN7), RDX (P35241), RECQL (P46063), RELA (Q04206), REPS1 (Q96D71), RETSAT (Q6NUM9), RFC2 (P35250), RFC3 (P40938), RFC4 (P35249), RFC5 (P40937), RFFL (Q8WZ73), RFTN1 (Q14699), RHEB (Q15382), RHOA (P61586), RHOB (P62745), RHOC (P08134), RHOF (Q9HBH0), RHOG (P84095), RHOT2 (Q8IXI1), RIC8A (Q9NPQ8), RNASEH2C (Q8TDP1), RNF114 (Q9Y508), RNF20 (Q5VTR2), RNF213 (Q63HN8), RNF7 (Q9UBF6), RNGTT (O60942), RNH1 (P13489), RNMT (O43148), RNPEP (Q9H4A4), ROBLD3 (Q9Y2Q5), ROCK1 (Q13464), ROCK2 (O75116), RP2 (O75695), RPA1 (P27694), RPA2 (P15927), RPA3 (P35244), RPE (Q96AT9), RPF2 (Q9H7B2), RPIA (P49247), RPL10 (P27635), RPL10A (P62906), RPL11 (P62913), RPL12 (P30050), RPL13 (P26373), RPL13A (P40429), RPL14 (P50914), RPL15 (P61313), RPL17 (P18621), RPL18 (Q07020), RPL18A (Q02543), RPL19 (P84098), RPL21 (P46778), RPL22 (P35268), RPL22L1 (Q6P5R6), RPL23 (P62829), RPL23A (P62750), RPL24 (P83731), RPL26 (P61254), RPL26L1 (Q9UNX3), RPL27 (P61353), RPL27A (P46776), RPL28 (P46779), RPL29 (P47914), RPL3 (P39023), RPL30 (P62888), RPL31 (P62899), RPL32 (P62910), RPL34 (P49207), RPL35 (P42766), RPL35A (P18077), RPL36 (Q9Y3U8), RPL36A (P83881), RPL36AL (Q969Q0), RPL37 (P61927), RPL37A (P61513), RPL38 (P63173), RPL4 (P36578), RPL5 (P46777), RPL6 (Q02878), RPL7 (P18124), RPL7A (P62424), RPL7L1 (Q6DKI1), RPL8 (P62917), RPL9 (P32969), RPLP0 (P05388), RPLP1 (P05386), RPLP2 (P05387), RPN1 (P04843), RPN2 (P04844), RPP30 (P78346), RPP38 (P78345), RPRD1A (Q96P16), RPRD1B (Q9NQG5), RPS10 (P46783), RPS11 (P62280), RPS12 (P25398), RPS13 (P62277), RPS14 (P62263), RPS15 (P62841), RPS15A (P62244), RPS16 (P62249), RPS17 (P08708), RPS18 (P62269), RPS19 (P39019), RPS2 (P15880), RPS20 (P60866), RPS21 (P63220), RPS23 (P62266), RPS24 (P62847), RPS25 (P62851), RPS26 (P62854), RPS27 (P42677), RPS27A (P62979), RPS27L (Q71UM5), RPS28 (P62857), RPS29 (P62273), RPS3 (P23396), RPS3A (P61247), RPS4X (P62701), RPS4Y1 (P22090), RPS5 (P46782), RPS6 (P62753), RPS6KA1 (Q15418), RPS6KA3 (P51812), RPS7 (P62081), RPS8 (P62241), RPS9 (P46781), RPSA (P08865), RQCD1 (Q92600), RRAGC (Q9HB90), RRAS2 (P62070), RRBP1 (Q9P2E9), RRM1 (P23921), RRM2 (P31350), RRM2B (Q7LG56), RRP1 (P56182), RRP12 (Q5JTH9), RRP1B (Q14684), RRP7A (Q9Y3A4), RRP9 (O43818), RRS1 (Q15050), RSL1D1 (O76021), RSL24D1 (Q9UHA3), RSPRY1 (Q96DX4), RSU1 (Q15404), RTCD1 (O00442), RTKN (Q9BST9), RTN3 (O95197), RTN4 (Q9NQC3), RUVBL1 (Q9Y265), RUVBL2 (Q9Y230), RWDD2B (P57060), S100A10 (P60903), S100A11 (P31949), S100A13 (Q99584), S100A16 (Q96FQ6), S100A2 (P29034), S100A4 (P26447), S100A6 (P06703), S100A7 (P31151), S100A8 (P05109), S100A9 (P06702), SAAL1 (Q96ER3), SACS (Q9NZJ4), SAE1 (Q9UBE0), SAMHD1 (Q9Y3Z3), SAP18 (O00422), SAR1A (Q9NR31), SARM1 (Q6SZW1), SARNP (P82979), SARS (P49591), SARS2 (Q9NP81), SART3 (Q15020), SBDS (Q9Y3A5), SBF1 (O95248), SCARB1 (Q8WTV0), SCARB2 (Q14108), SCCPDH (Q8NBX0), SCFD1 (Q8WVM8), SCFD2 (Q8WU76), SCP2 (P22307), SCPEP1 (Q9HB40), SCRG1 (O75711), SCRIB (Q14160), SCRN1 (Q12765), SCRN2 (Q96FV2), SCYL1 (Q96KG9), SDC2 (P34741), SDC4 (P31431), SDCBP (O00560), SDCCAG1 (O60524), SDCCAG3 (Q96C92), SDHA (P31040), SDHB (P21912), SDK1 (Q7Z5N4), SDSL (Q96GA7), SEC13 (P55735), SEC14L2 (O76054), SEC22B (O75396), SEC23A (Q15436), SEC23B (Q15437), SEC23IP (Q9Y6Y8), SEC24A (O95486), SEC24B (O95487), SEC24C (P53992), SEC24D (O94855), SEC31A (O94979), SEC61B (P60468), SEC61G (P60059), SEH1L (Q96EE3), SELH (Q8IZQ5), SELO (Q9BVL4), SEMA3A (Q14563), SENP3 (Q9H4L4), SEPSECS (Q9HD40), 40422 (Q9P0V9), 40787 (Q9NVA2), 37500 (Q15019), 38596 (Q99719), 39326 (Q16181), 40057 (Q9UHD8), SERBP1 (Q8NC51), SERPINB12 (Q96P63), SERPINB3 (P29508), SERPINB6 (P35237), SERPINH1 (P50454), SESN2 (P58004), SET (Q01105), SETD3 (Q86TU7), SF3A1 (Q15459), SF3A2 (Q15428), SF3A3 (Q12874), SF3B1 (O75533), SF3B14 (Q9Y3B4), SF3B2 (Q13435), SF3B3 (Q15393), SF3B4 (Q15427), SF3B5 (Q9BWJ5), SFN (P31947), SFPQ (P23246), SFRP4 (Q6FHJ7), SFXN3 (Q9BWM7), SGTA (Q43765), SH3BGRL3 (Q9H299), SH3BP4 (Q9P0V3), SH3GL1 (Q99961), SH3GLB1 (Q9Y371), SHC1 (P29353), SHMT1 (P34896), SHMT2 (P34897), SHOC2 (Q9UQ13), SHPK (Q9UHJ6), SIRT5 (Q9NXA8), SKIV2L (Q15477), SKIV2L2 (P42285), SKP1 (P63208), SLC12A2 (P55011), SLC12A4 (Q9UP95), SLC16A1 (P53985), SLC1A3 (P43003), SLC1A5 (Q15758), SLC25A10 (Q9UBX3), SLC25A11 (Q02978), SLC25A13 (Q9UJS0), SLC25A22 (Q9H936), SLC25A3 (Q00325), SLC25A5 (P05141), SLC25A6 (P12236), SLC26A2 (P50443), SLC29A1 (Q99808), SLC29A2 (Q14542), SLC2A1 (P11166), SLC30A1 (Q9Y6M5), SLC38A1 (Q9H2H9), SLC3A2 (P08195), SLC44A2 (Q8IWA5), SLC4A2 (P04920), SLC4A7 (Q9Y6M7), SLC5A3 (P53794), SLC5A6 (Q9Y289), SLC6A8 (P48029), SLC7A1 (P30825), SLC7A5 (Q01650), SLC9A3R1 (O14745), SLC9A3R2 (Q15599), SLIRP (Q9GZT3), SLK (Q9H2G2), SMAD1 (Q15797), SMAD2 (Q15796), SMARCA4 (P51532), SMARCA5 (O60264), SMARCB1 (Q12824), SMARCC1 (Q92922), SMARCC2 (Q8TAQ2), SMARCD2 (Q92925), SMC1A (Q14683), SMC2 (O95347), SMC3 (Q9UQE7), SMC4 (Q9NTJ3), SMC5 (Q8IY18), SMCHD1 (A6NHR9), SMEK1 (Q6IN85),

TABLE 21-continued

Gene names and SWISSPROT accession numbers of all 2940 proteins identified
in CTX0E03 microvesicles (listed in alphabetical order of gene name).

SMG1 (Q96Q15), SMN1 (Q16637), SMS (P52788), SMU1 (Q2TAY7), SMYD3 (Q9H7B4),
SMYD5 (Q6GMV2), SNAP23 (O00161), SND1 (Q7KZF4), SNF8 (Q96H20), SNRNP200
(O75643), SNRNP40 (Q96DI7), SNRNP70 (P08621), SNRPA1 (P09661), SNRPB (P14678),
SNRPB2 (P08579), SNRPD1 (P62314), SNRPD2 (P62316), SNRPD3 (P62318), SNRPE
(P62304), SNRPF (P62306), SNRPG (P62308), SNTB1 (Q13884), SNTB2 (Q13425), SNX1
(Q13596), SNX12 (Q9UMY4), SNX17 (Q15036), SNX18 (Q96RF0), SNX2 (O60749), SNX27
(Q96L92), SNX3 (O60493), SNX5 (Q9Y5X3), SNX6 (Q9UNH7), SNX9 (Q9Y5X1), SOD1
(P00441), SOD2 (P04179), SORD (Q00796), SORT1 (Q99523), SPATS2L (Q9NUQ6), SPC24
(Q8NBT2), SPCS2 (Q15005), SPCS3 (P61009), SPG21 (Q9NZD8), SPIN1 (Q9Y657), SPR
(P35270), SPRR1B (P22528), SPRR2E (P22531), SPTAN1 (Q13813), SPTBN1 (Q01082),
SPTBN2 (O15020), SR140 (O15042), SRBD1 (Q8N5C6), SRCRL (A1L4H1), SRGAP2
(O75044), SRI (P30626), SRM (P19623), SRP14 (P37108), SRP19 (P09132), SRP54
(P61011), SRP68 (Q9UHB9), SRP72 (O76094), SRP9 (P49458), SRPK1 (Q96SB4), SRPR
(P08240), SRPRB (Q9Y5M8), SRPX (P78539), SRPX2 (O60687), SRR (Q9GZT4), SRRM1
(Q8IYB3), SRRM2 (Q9UQ35), SRRT (Q9BXP5), SRSF1 (Q07955), SRSF10 (O75494),
SRSF11 (Q05519), SRSF2 (Q01130), SRSF3 (P84103), SRSF5 (Q13243), SRSF6 (Q13247),
SRSF7 (Q16629), SRSF9 (Q13242), SRXN1 (Q9BYN0), SSB (P05455), SSBP1 (Q04837),
SSR1 (P43307), SSR3 (Q9UNL2), SSRP1 (Q08945), SSSCA1 (O60232), SSU72 (Q9NP77),
ST13 (P50502), STAG1 (Q8WVM7), STAM (Q92783), STAMBP (O95630), STAT1 (P42224),
STAT2 (P52630), STAT3 (P40763), STAU1 (O95793), STIP1 (P31948), STK10 (O94804),
STK24 (Q9Y6E0), STK25 (O00506), STK38 (Q15208), STK38L (Q9Y2H1), STOM (P27105),
STOML2 (Q9UJZ1), STON2 (Q8WXE9), STRAP (Q9Y3F4), STT3A (P46977), STUB1
(Q9UNE7), STX12 (Q86Y82), STX4 (Q12846), STX5 (Q13190), STXBP1 (P61764), STXBP3
(O00186), STYX (Q8WUJ0), SUB1 (P53999), SUCLA2 (Q9P2R7), SUCLG2 (Q96I99), SUGT1
(Q9Y2Z0), SULF2 (Q8IWU5), SUMO1 (P63165), SUPT16H (Q9Y5B9), SUPT4H1 (P63272),
SUPT5H (O00267), SUPT6H (Q7KZ85), SUSD5 (O60279), SVEP1 (Q4LDE5), SVIL (O95425),
SWAP70 (Q9UH65), SYMPK (Q92797), SYNCRIP (O60506), SYNGR2 (O43760), SYNJ2BP
(P57105), SYNM (O15061), SYPL1 (Q16563), TAB1 (Q15750), TAF9 (Q9Y3D8), TAGLN
(Q01995), TAGLN2 (P37802), TALDO1 (P37837), TAOK1 (Q7L7X3), TARDBP (Q13148),
TARS (P26639), TATDN1 (Q6P1N9), TAX1BP3 (O14907), TBC1D13 (Q9NVG8), TBC1D15
(Q8TC07), TBC1D23 (Q9NUY8), TBC1D24 (Q9ULP9), TBC1D4 (O60343), TBC1D9B
(Q66K14), TBCA (O75347), TBCB (Q99426), TBCC (Q15814), TBCD (Q9BTW9), TBCE
(Q15813), TBK1 (Q9UHD2), TBL1XR1 (Q9BZK7), TBL2 (Q9Y4P3), TBL3 (Q12788), TBPL1
(P62380), TCEA1 (P23193), TCEB1 (Q15369), TCEB2 (Q15370), TCERG1 (O14776), TCF25
(Q9BQ70), TCP1 (P17987), TELO2 (Q9Y4R8), TEX10 (Q9NXF1), TEX15 (Q9BXT5), TF
(P02787), TFCP2 (Q12800), TFG (Q92734), TFRC (P02786), TGFB1 (P01137), TGFB2
(P61812), TGFBI (Q15582), TGFBRAP1 (Q8WUH2), TGM1 (P22735), TGM3 (Q08188), TH1L
(Q8IXH7), THBS1 (P07996), THBS3 (P49746), THG1L (Q9NWX6), THOC2 (Q8NI27), THOC3
(Q96J01), THOC5 (Q13769), THOC6 (Q86W42), THOC7 (Q6I9Y2), THOP1 (P52888), THTPA
(Q9BU02), THUMPD1 (Q9NXG2), THUMPD3 (Q9BV44), THY1 (P04216), THYN1 (Q9P016),
TIA1 (P31483), TIAL1 (Q01085), TIGAR (Q9NQ88), TIMM13 (Q9Y5L4), TIMM44 (O43615),
TIMM50 (Q3ZCQ8), TIMM8A (O60220), TIMM8B (Q9Y5J9), TIMM9 (Q9Y5J7), TIMP2
(P16035), TIPRL (O75663), TJP1 (Q07157), TKT (P29401), TLN1 (Q9Y490), TLN2 (Q9Y4G6),
TM9SF3 (Q9HD45), TMED10 (P49755), TMED2 (Q15363), TMED5 (Q9Y3A6), TMED7
(Q9Y3B3), TMED9 (Q9BVK6), TMEFF2 (Q9UIK5), TMEM132A (Q24JP5), TMEM2 (Q9UHN6),
TMEM30A (Q9NV96), TMEM33 (P57088), TMOD3 (Q9NYL9), TMPO (P42166), TMX1
(Q9H3N1), TNC (P24821), TNKS1BP1 (Q9C0C2), TNPO1 (Q92973), TNPO2 (O14787),
TNPO3 (Q9Y5L0), TOM1L2 (Q6ZVM7), TOMM20 (Q15388), TOMM34 (Q15785), TOMM5
(Q8N4H5), TOMM70A (O94826), TOP1 (P11387), TOP2A (P11388), TOP2B (Q02880), TP53I3
(Q53FA7), TP53RK (Q96S44), TPBG (Q13641), TPD52 (P55327), TPI1 (P60174), TPM1
(P09493), TPM2 (P07951), TPM3 (P06753), TPM3L (A6NL28), TPM4 (P67936), TPP2
(P29144), TPT1 (P13693), TRA2A (Q13595), TRA2B (P62995), TRAF2 (Q12933), TRAP1
(Q12931), TRAPPC1 (Q9Y5R8), TRAPPC2L (Q9UL33), TRAPPC3 (O43617), TRAPPC4
(Q9Y296), TRAPPC5 (Q8IUR0), TRIM16 (O95361), TRIM22 (Q8IYM9), TRIM25 (Q14258),
TRIM26 (Q12899), TRIM28 (Q13263), TRIM47 (Q96LD4), TRIM5 (Q9C035), TRIO (O75962),
TRIP13 (Q15645), TRIP6 (Q15654), TRMT1 (Q9NXH9), TRMT112 (Q9UI30), TRMT5
(Q32P41), TRMT6 (Q9UJA5), TRMT61A (Q96FX7), TRNT1 (Q96Q11), TROVE2 (P10155),
TRRAP (Q9Y4A5), TSG101 (Q99816), TSKU (Q8WUA8), TSN (Q15631), TSPAN14 (Q8NG11),
TSPAN6 (O43657), TSR1 (Q2NL82), TSSC1 (Q53HC9), TSTA3 (Q13630), TTC1 (Q99614),
TTC15 (Q8VWT3), TTC27 (Q6P3X3), TTC37 (Q6PGP7), TTC38 (Q5R3I4), TTC7B (Q86TV6),
TTC9C (Q8N5M4), TTL (Q8NG68), TTLL12 (Q14166), TTN (Q8WZ42), TTYH1 (Q9H313),
TTYH3 (Q9C0H2), TUBA1B (P68363), TUBA4A (P68366), TUBB (P07437), TUBB2B
(Q9BVA1), TUBB2C (P68371), TUBB3 (Q13509), TUBB6 (Q9BUF5), TUBG1 (P23258),
TUBGCP2 (Q9BSJ2), TUBGCP3 (Q96CW5), TUFM (P49411), TWF1 (Q12792), TWF2
(Q6IBS0), TXN (P10599), TXNDC17 (Q9BRA2), TXNDC5 (Q8NBS9), TXNDC9 (O14530),
TXNL1 (O43396), TXNRD1 (Q16881), TYK2 (P29597), TYMS (P04818), U2AF1 (Q01081),
U2AF2 (P26368), UAP1 (Q16222), UBA1 (P22314), UBA2 (Q9UBT2), UBA3 (Q8TBC4), UBA52
(P62987), UBA6 (A0AVT1), UBE2D1 (P51668), UBE2D3 (P61077), UBE2E1 (P51965),
UBE2G2 (P60604), UBE2I (P63279), UBE2J2 (Q8N2K1), UBE2K (P61086), UBE2L3 (P68036),
UBE2M (P61081), UBE2N (P61088), UBE2O (Q9C0C9), UBE2S (Q16763), UBE2V1 (Q13404),
UBE2V2 (Q15819), UBE3A (Q05086), UBE3C (Q15386), UBE4A (Q14139), UBE4B (O95155),
UBFD1 (O14562), UBL3 (O95164), UBL4A (P11441), UBL5 (Q9BZL1), UBLCP1 (Q8WVY7),
UBP1 (Q9NZI7), UBQLN2 (Q9UHD9), UBR1 (Q8IWV7), UBR4 (Q5T4S7), UBTD1 (Q9HAC8),
UBXN1 (Q04323), UBXN6 (Q9BZV1), UCHL1 (P09936), UCHL3 (P15374), UCHL5 (Q9Y5K5),
UCK2 (Q9BZX2), UFC1 (Q9Y3C8), UFD1L (Q92890), UGDH (O60701), UGGT1 (Q9NYU2),
UGP2 (Q16851), ULK3 (Q6PHR2), UMPS (P11172), UNC119B (A6NIH7), UNC45A (Q9H3U1),
UPF1 (Q92900), UPP1 (Q16831), UQCRC1 (P31930), UQCRC2 (P22695), UQCRFS1

TABLE 21-continued

Gene names and SWISSPROT accession numbers of all 2940 proteins identified
in CTX0E03 microvesicles (listed in alphabetical order of gene name).

(P47985), URB1 (O60287), URB2 (Q14146), UROD (P06132), UROS (P10746), USO1
(O60763), USP10 (Q14694), USP11 (P51784), USP13 (Q92995), USP14 (P54578), USP15
(Q9Y4E8), USP24 (Q9UPU5), USP39 (Q53GS9), USP5 (P45974), USP7 (Q93009), USP9X
(Q93008), UTP15 (Q8TED0), UTP18 (Q9Y5J1), UTP20 (O75691), UTP6 (Q9NYH9), UTRN
(P46939), UXS1 (Q8NBZ7), UXT (Q9UBK9), VAC14 (Q08AM6), VAMP3 (Q15836), VAMP5
(O95183), VAPA (Q9P0L0), VAPB (O95292), VARS (P26640), VASP (P50552), VAT1
(Q99536), VAV2 (P52735), VBP1 (P61758), VCAN (P13611), VCL (P18206), VCP (P55072),
VDAC1 (P21796), VDAC2 (P45880), VDAC3 (Q9Y277), VIM (P08670), VPRBP (Q9Y4B6),
VPS11 (Q9H270), VPS13A (Q96RL7), VPS13C (Q709C8), VPS16 (Q9H269), VPS18
(Q9P253), VPS24 (Q9Y3E7), VPS25 (Q9BRG1), VPS26A (O75436), VPS26B (Q4G0F5),
VPS28 (Q9UK41), VPS29 (Q9UBQ0), VPS33A (Q96AX1), VPS33B (Q9H267), VPS35
(Q96QK1), VPS36 (Q86VN1), VPS37B (Q9H9H4), VPS39 (Q96JC1), VPS41 (P49754), VPS45
(Q9NRW7), VPS4A (Q9UN37), VPS4B (O75351), VPS53 (Q5VIR6), VPS8 (Q8N3P4), VRK1
(Q99986), VTA1 (Q9NP79), VWA1 (Q6PCB0), VWA5A (O00534), WARS (P23381), WASF2
(Q9Y6W5), WASL (O00401), WBSCR22 (O43709), WDFY1 (Q8IWB7), WDR1 (O75083),
WDR11 (Q9BZH6), WDR12 (Q9GZL7), WDR18 (Q9BV38), WDR26 (Q9H7D7), WDR3
(Q9UNX4), WDR36 (Q8NI36), WDR4 (P57081), WDR43 (Q15061), WDR45L (Q5MNZ6),
WDR48 (Q8TAF3), WDR5 (P61964), WDR54 (Q9H977), WDR6 (Q9NNW5), WDR61
(Q9GZS3), WDR73 (Q6P4I2), WDR74 (Q6RFH5), WDR75 (Q8IWA0), WDR77 (Q9BQA1),
WDR82 (Q6UXN9), WDR92 (Q96MX6), WHSC2 (Q9H3P2), WRNIP1 (Q96S55), XP32
(Q5T750), XPC (Q01831), XPNPEP1 (Q9NQW7), XPO1 (O14980), XPO4 (Q9C0E2), XPO5
(Q9HAV4), XPO6 (Q96QU8), XPO7 (Q9UIA9), XPOT (O43592), XRCC1 (P18887), XRCC5
(P13010), XRCC6 (P12956), XRN2 (Q9H0D6), YARS (P54577), YBX1 (P67809), YES1
(P07947), YKT6 (O15498), YRDC (Q86U90), YTHDC1 (Q96MU7), YTHDF2 (Q9Y5A9),
YWHAB (P31946), YWHAE (P62258), YWHAG (P61981), YWHAH (Q04917), YWHAQ
(P27348), YWHAZ (P63104), ZC3H15 (Q8WU90), ZC3HAV1 (Q7Z2W4), ZC3HAV1L
(Q96H79), ZCCHC3 (Q9NUD5), ZFAND1 (Q8TCF1), ZFR (Q96KR1), ZMAT2 (Q96NC0),
ZNF259 (O75312), ZNF326 (Q5BKZ1), ZNF330 (Q9Y3S2), ZNF622 (Q969S3), ZNF765
(Q7L2R6), ZNFX1 (Q9P2E3), ZW10 (O43264), ZWILCH (Q9H900), ZYG11B (Q9C0D3), ZYX
(Q15942).

TABLE 22

100 most abundant proteins (name and SwissProt accession number) in CTX0E03 microvesicles

| Identified proteins | Accession number |
| --- | --- |
| Actin, cytoplasmic 2 | P63261 |
| Histone H4 | P62805 |
| Histone H2B | Q99879 |
| Histone H3.2 | Q71DI3 |
| Histone H2B type 1 | P23527 |
| Glyceraldehyde-3-phosphate dehydrogenase | P04406 |
| Histone H2A type 2-A | Q6FI13 |
| Ubiquitin-40S ribosomal protein S27a | P62979 |
| Annexin A2 | P07355 |
| Alpha-enolase | P06733 |
| Pyruvate kinase isozymes M1/M2 | P14618 |
| 60S ribosomal protein L6 | Q02878 |
| Histone H2B type 2-E | Q16778 |
| Heat shock cognate 71 kDa protein | P11142 |
| Actin, alpha cardiac muscle 1 | P68032 |
| Heat shock protein HSP 90-beta | P08238 |
| Histone H2B type 1-J | P06899 |
| Elongation factor 1-alpha 1 | P68104 |
| Tubulin beta-2C chain | P68371 |
| 60S ribosomal protein L18 | Q07020 |
| Tubulin beta chain | P07437 |
| 40S ribosomal protein S2 | P15880 |
| 40S ribosomal protein S11 | P62280 |
| Histone H2B type 3-B | Q8N257 |
| Tubulin alpha-1B chain | P68363 |
| 40S ribosomal protein S3 | P23396 |
| 40S ribosomal protein S3a | P61247 |
| Histone H2A type 1-D | P20671 |
| Elongation factor 2 | P13639 |
| Heat shock protein HSP 90-alpha | P07900 |
| GTP-binding nuclear protein Ran | P62826 |
| 60S ribosomal protein L4 | P36578 |
| 40S ribosomal protein S9 | P46781 |
| Profilin-1 | P07737 |
| 60S ribosomal protein L13a | P40429 |
| Phosphoglycerate kinase 1 | P00558 |
| Fatty acid synthase | P49327 |
| Annexin A1 | P04083 |
| Histone H2A.Z | P0C0S5 |
| Vimentin | P08670 |
| 40S ribosomal protein S6 | P62753 |
| Moesin | P26038 |
| Peptidyl-prolyl cis-trans isomerase A | P62937 |
| 60S ribosomal protein L26 | P61254 |
| 60S ribosomal protein L3 | P39023 |
| 40S ribosomal protein S8 | P62241 |
| 60S ribosomal protein L28 | P46779 |
| Ezrin | P15311 |
| 40S ribosomal protein S4, X isoform | P62701 |
| 60S ribosomal protein L7a | P62424 |
| 60S ribosomal protein L13 | P26373 |
| 60S ribosomal protein L7 | P18124 |
| 40S ribosomal protein S23 | P62266 |
| 60S ribosomal protein L5 | P46777 |
| Eukaryotic initiation factor 4A-I | P60842 |
| 40S ribosomal protein S24 | P62847 |
| Tubulin beta-2B chain | Q9BVA1 |
| 60S ribosomal protein L8 | P62917 |
| 60S ribosomal protein L15 | P61313 |
| 60S ribosomal protein L10 | P27635 |
| Peroxiredoxin-1 | Q06830 |
| Keratin, type I cytoskeletal 14 | P02533 |
| 14-3-3 protein theta | P27348 |
| 40S ribosomal protein S18 | P62269 |
| Transketolase | P29401 |
| 60S ribosomal protein L24 | P83731 |
| Histone H1.5 | P16401 |
| Cofilin-1 | P23528 |
| Dihydropyrimidinase-related protein 3 | Q14195 |
| 60S ribosomal protein L21 | P46778 |
| 60S ribosomal protein L36 | Q9Y3U8 |

TABLE 22-continued 100 most abundant proteins (name and SwissProt accession number) in CTX0E03 microvesicles

| Identified proteins | Accession number |
|---|---|
| Sodium/potassium-transporting ATPase subunit alpha-1 | P05023 |
| 40S ribosomal protein S16 | P62249 |
| T-complex protein 1 subunit gamma | P49368 |
| Heterogeneous nuclear ribonucleoprotein A1 | P09651 |
| 60S ribosomal protein L14 | P50914 |
| Heat shock 70 kDa protein 1A/1B | P08107 |
| T-complex protein 1 subunit theta | P50990 |
| 60S ribosomal protein L30 | P62888 |
| Protein S100-A6 | P06703 |
| 40S ribosomal protein SA | P08865 |
| CD44 antigen | P16070 |
| 60S ribosomal protein L35a | P18077 |
| Tubulin beta-3 chain | Q13509 |
| T-complex protein 1 subunit delta | P50991 |
| 4F2 cell-surface antigen heavy chain | P08195 |
| T-complex protein 1 subunit beta | P78371 |
| Myosin-9 | P35579 |
| Adenosylhomocysteinase | P23526 |
| Filamin-A | P21333 |
| Fatty acid-binding protein, brain | O15540 |
| Myristoylated alanine-rich C-kinase substrate | P29966 |
| T-complex protein 1 subunit eta | Q99832 |
| Fascin | Q16658 |
| Fructose-bisphosphate aldolase A | P04075 |
| 60S ribosomal protein L27 | P61353 |
| 60S ribosomal protein L17 | P18621 |
| Heterogeneous nuclear ribonucleoproteins A2/B1 | P22626 |
| 60S ribosomal protein L10a | P62906 |
| 60S ribosomal protein L35 | P42766 |

Discussion of Proteomic Data

CD63 (also known as MLA1 and TSPAN30), TSG101 (also known as ESCRT-I complex subunit TSG101), CD109 (also known as 150 kDa TGF-beta-1-binding protein) and thy-1 (also known as CD90) were detected in both exosomes and microvesicles.

Other tetraspanins were also detected: Tetraspanin-4, -5, -6, -9 and 14 were detected in the exosome fraction; tetraspanins-6 and -14 were detected in the microvesicles.

CD133 (also known as AC133, Prominin-1, PROM1, PROML1 and MSTP061) was detected in the exosomes but not the microvesicles.

CD53 (also known as MOX44 and TSPAN25), CD82 (also known as KAI1, SAR2, ST6 and TSPAN27), CD37 (also known as TSPAN26) and CD40 ligand (also known as CD40LG, CD40L and TNFSF5) were not detected in the exosomes or the microvesicles.

Nestin, GFAP and tubulin beta-3 chain (also known as TUBB3) were detected in both the exosome and microvesicle fractions, with tubulin beta-3 chain being particularly prominent within the top 100 proteins in both fractions. Sox2, DCX, GALC, GDNF and IDO were not detected.

Selectins and TNFRI (also known as TNF receptor 1, TNFRSF1A, TNFAR and TNFR1) were not detected.

Integrin alpha-2, -3, -4, -5, -6, -7, -V and integrin beta-1, -4 and -8 were detected in both exosome and microvesicle fractions. Integrin beta-3 and -5 were detected in the microvesicles only.

MHC Class I antigens (e.g. HLA_A1, HLA-A2 and HLA-B27) were detected in both the exosomes and microvesicles.

Cell-adhesion molecules (e.g. CADM1, CADM4, ICAM1, JAM3, L1CAM, NCAM) were detected in both the exosomes and microvesicles.

Cytoskeletal proteins (e.g. actin, vimentin, keratins, catenins, dystroglucan, neurofilament polypeptide, microtubule-associated protein, tubulin, desmoplaktin, plectin, plakophilin, septin, spectrin, talin, vinculin and zyxin) were detected in both the exosome and microvesicle fractions.

GTPases, clathrin, chaperones, heat-shock proteins (e.g. Hsp90, Hsp70), splicing factors, translation factors, annexins and growth factors (e.g. TGF-beta) were detected in both the exosomes and microvesicles.

Galectin-3, TIMP-1, thrombosponding-1, EGF receptor and CSK were detected in both the exosomes and microvesicles.

FIG. 17 compares the proteomic data from the exosomes and microvesicles. FIG. 17A illustrates the number of unique proteins within each micro particle population, isolated from week 2 Integra culture system. FIG. 17B compares the biological processes associated with the identified proteins within each micro particle population, isolated from week 2 Integra system. The proteins identified within exosomes and microvesicles are associated with very similar biological processes.

Proteins associated with biotin metabolism were only found in exosomes and proteins involved in tryptophan biosynthesis and taurine/alpha-linolenic acid metabolism were only identified in microvesicles.

Figure 17A:
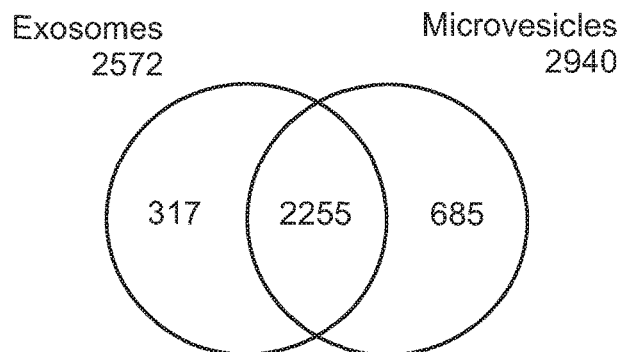
FIG. 17A illustrates the number of unique proteins within CTX0E03 exosomes and microvesicles, isolated from week 2 Integra culture system.
Figure 17B:
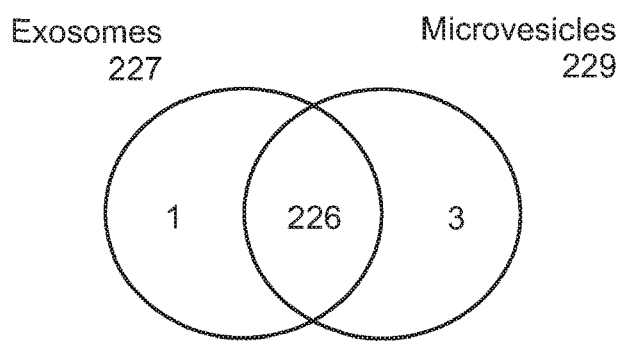
FIG. 17B compares the biological processes associated with the identified proteins within the CTX0E03 exosomes and microvesicles.
Figure 17C:
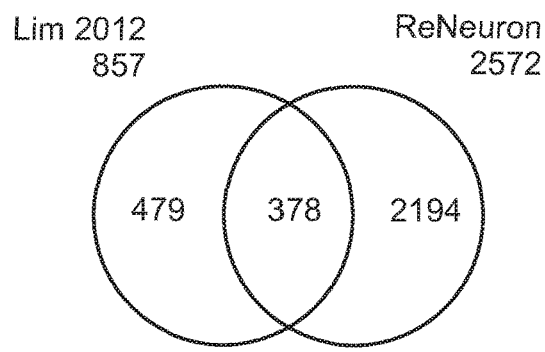
FIG. 17C compares the CTX0E03 neural stem cell exosome proteome to a Mesenchymal Stem Cell exosome, and FIG. 17D compares biological processes associated with the identified proteins in the MSC derived exosomes with the neural stem cell derived exosomes.

FIG. 17C compares the CTX0E03 proteome to the Mesenchymal Stem Cell exosome proteome disclosed in Lai et al 2012, in which a total of 857 proteins were identified in exosomes released from mesenchymal stem cells.

Figure 17D:
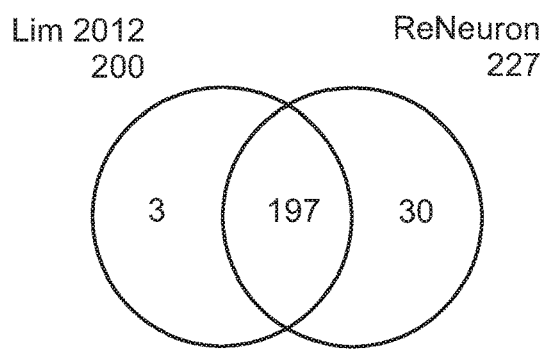
FIG. 17 shows Venn diagrams comparing the proteomic data from CTX0E03 exosomes and microvesicles (17A and 17B), and comparing neural stem cell exosomes with mesenchymal stem cell exosomes (17C and 17D).
Figure 18:
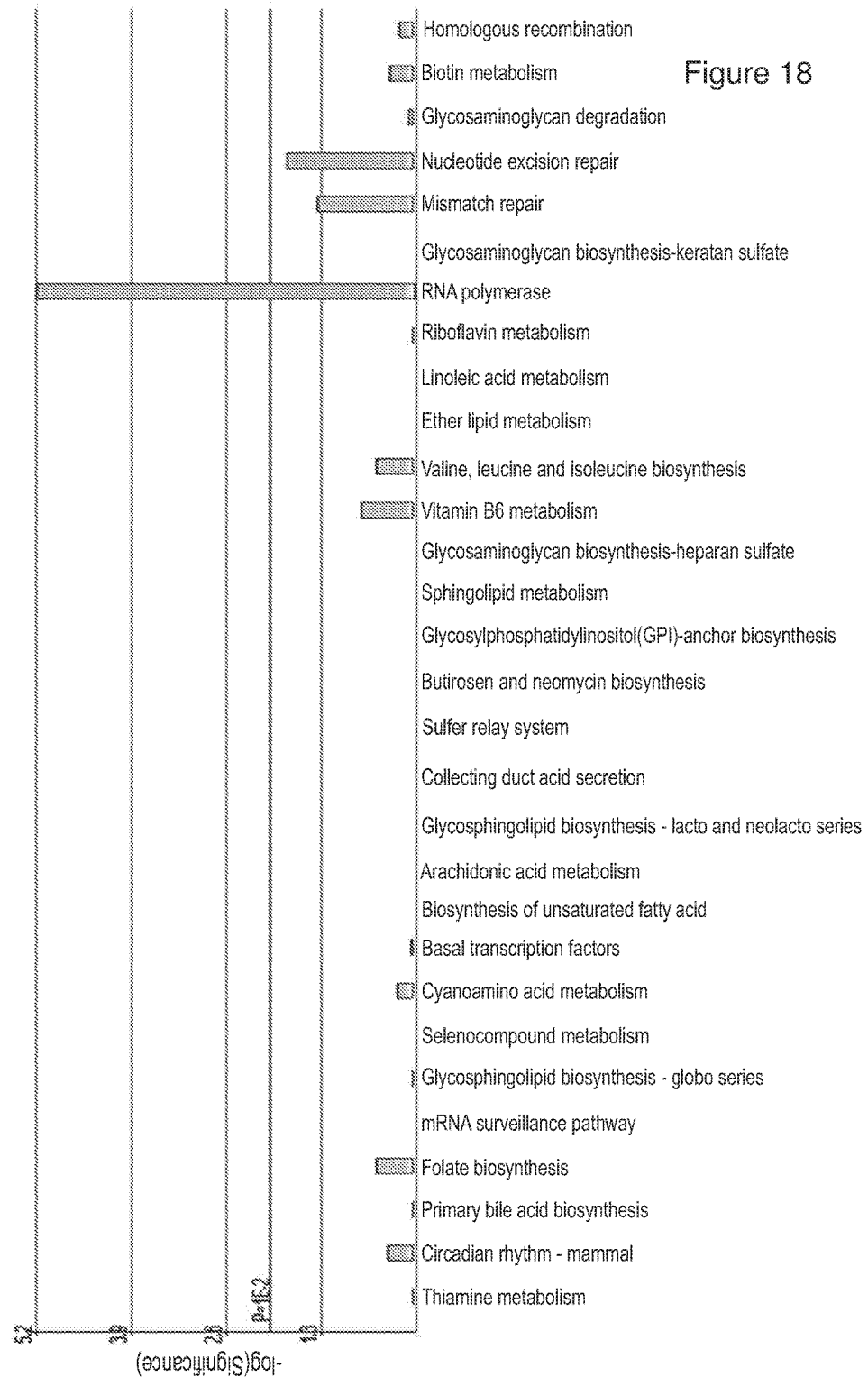
FIG. 18 shows the 30 biological processes found to be associated with NSC derived exosomes and not mesenchymal stem cell exosomes.

FIG. 17D compares the biological processes associated with the identified proteins within the MSC derived exosomes (Lim 2012) with the neural stem cell derived exosomes of the invention. The three biological processes found to be associated with the MSC derived exosomes only are (in decreasing order of significance): Asthma; phenylalanine, tyrosine and tryptophan biosynthesis; and primary immunodeficiency. The thirty biological processes found to be associated only with the neural stem cell derived exosomes are shown in FIG. 18; the most significant biological function identified relates to RNA polymerase.

A further comparison of the 197 biological processes shared by both MSC derived exosomes and NSC derived exosomes shows that NSC exosomes contain notably more processes involved in RNA degradation, the Ribosome and spliceosomes, when compared to MSC exosomes.

The above comparison indicates a number of significant differences between NSC derived exosomes and MSC derived exosomes (as characterised by Lim et al 2012). The 4 most significant biological differences identified as present in NSC exosomes compared to being very low/absent in those identified by the Lim's group, all involve proteins associated with the production, packaging, function and degradation of genetic material, i.e RNA polymerase, RNA degradation, Ribosome and spliceosomes.

Example 20: Functional Analysis of Individual miRNAs

Methods

MiRNA Mimic Transfection and Evaluation of Cell Proliferation by Cyquant

Twenty four hours prior to transfection, glioma cells, U373 or U87, were seeded into a 96-well plate. MiRNA transfection optimization was performed using AllStars Negative Control siRNA AF 488 (Qiagen). MiRNA transfection efficiency was 100% when the following conditions were used. 20 nM of each miRNA mimics (Qiagen), hsamiR-1246 (SEQ ID No. 21), hsa-miR-4492 (SEQ ID no. 34), hsa-miR-4532 (SEQ ID No. 23), and hsa-miR-4488 (SEQ ID No. 61) were combined with Lipofectamine® 2000 (Invitrogen) and transfection performed according to manufacturer's instructions.

Experiment 1 (U373MG; 2500 Cells/Well; 10% FBS)

2500 U373MG cells were seeded per 96-well and cultured in DMEM glutamax/10% FBS for 24 hrs, 48 hrs and 72 hrs post-transfection. Cell proliferation was measured by CyQUANT® Cell Proliferation Assay Kit (Invitrogen). Briefly, following removal of the culture medium, 200 µl of the CyQUANT® GR dye/cell-lysis buffer was added into each well of the 96-well plate and incubated for 15 min. Fluorescence intensity of each well was obtained using a GloMax™ 96 microplate (Promega) plate counter at excitation and emission wavelengths of 480 and 520 nm, respectively.

Experiment 2 (U373MG; 2500 Cell/Well; 2% FBS)

2500 U373MG cells were seeded per 96-well and cultured in DMEM glutamax/2% FBS for 24 hrs, 48 hrs and 72 hrs post-transfection. Cell proliferation was measured by CyQUANT® Cell Proliferation Assay Kit (Invitrogen). Briefly, following removal of the culture medium, 200 µl of the CyQUANT® GR dye/cell-lysis buffer was added into each well of the 96-well plate and incubated for 15 min. Fluorescence intensity of each well was obtained using a GloMax™96 microplate (Promega) plate counter at excitation and emission wavelengths of 480 and 520 nm, respectively.

Experiment 3 (U87; 9000 Cells/Well; Basal)

9000 U87 cells were seeded per 96 well and cultured in EMEM+2 nM glutamine for 0 hrs, 24 hrs, 48 hrs and 72 hrs post-transfection. Cell proliferation was measured by CyQUANT® Cell Proliferation Assay Kit (Invitrogen). Briefly, following removal of the culture medium, 200 µl of the CyQUANT® GR dye/cell-lysis buffer was added into each well of the 96-well plate and incubated for 15 min. Fluorescence intensity of each well was obtained using a GloMax™ 96 Microplate (Promega) plate counter at excitation and emission wavelengths of 480 and 520 nm, respectively.

Results

Next generation sequence (NGS) analysis of miRNA contents in CTX0E03-derived exosomes revealed the presence of a set of top-ranked miRNAs, hsa-mir-1246, hsa-mir-4488, hsa-mir-4492, and hsa-mir-4532. To assess the functionality of these individual miRNAs in reducing glioma cell proliferation, each (mimic) miRNA was transfected into two cell line models of glioma: U373MG and U87.

The incidence of reduction of cell proliferation was dependent on the glioma model and cell culturing conditions, but each of the four miRNAs tested significantly reduced tumour cell proliferation in at least one of the models. hsa-mir-4492 and hsa-mir-4532 significantly reduced cell proliferation in each of the models tested. The results of Experiments 1 to 3 are shown in FIGS. 23 A, B and C, respectively.

Example 21: Tolerability and Pilot Efficacy of Exosomes in U-87Mg Human Glioblastoma Subcutaneous Xenografts Objective To assess the tolerability and pilot efficacy of exosomes in U-87MG subcutaneous xenografts Methods Animals

| | |
|---|---|
| Number | 30 |
| No. of Groups & No per Group | 5 groups, 5 mice/group |
| Species | *Mus musculus* |
| Strain | Athymic nude (Hsd: AthymicNude-Fxn1$^{nu}$) |
| Age | 5-7 weeks |
| Gender | Female |
| Body Weight | N/A |
| Animal ID | Transponder chip according to PRECOS Standard Operating Methods (SOMs) |
| Acclimatisation | ≥1 week |
| Implantation site | Left flank |
| Anaesthesia | In accordance with PRECOS SOMs |
| Housing | According to PPL 70/7317 and PRECOS Standard Operating Procedures (SOPs) |
| Animal | Harlan UK |

Cell Lines, In Vitro Expansion

| | |
|---|---|
| Cell Line Name | U-87MG |
| Supplier and catalogue number | ECACC, 89081402 |
| Culture Medium | EMEM culture medium (Sigma, UK) containing 10% (v/v) heat inactivated foetal bovine serum (Hyclone, Thermo Scientific, UK) |
| Number of mice to be implanted | 30 |
| Number of cells per mouse | $8 \times 10^6$ per mouse |
| Matrigel/Cultrex/PBS/other | PBS supplemented with 0.1% glucose |
| Volume of diluent per mouse | 0.1 mL |
| Number of batches | 1 |

Cells will be harvested, washed in the culture medium described above and cells with viability of ≥90% will be re-suspended for in vivo administration. Cells will be stored on ice for a minimum period of time (e.g. no longer than 30 minutes) prior to implantation.

Implantation

Transponder Implantation:

Implanted at initiation (tumour implantation).

Tumour Implantation:

$8 \times 10^6$ viable cells in 100 µl PBS+0.1% glucose will be injected subcutaneously into the left flank of each mouse. A total of 30 mice will be implanted.

Data Capture

Body weight, dosing and any comments relating to clinical condition will be captured in real-time using the study management software, StudyDirector (StudyLog Systems Inc.). Data will be exported into Microsoft Excel and/or GraphPad Prism for subsequent data analysis and transformation.

Study specific data capture schedules will be created in Excel and completed by the study team. These data capture schedules will include study specific clinical observations; the recording of these observations and will be included in the final report and uploaded to the study folder at the end of the study.

Body Weight:

Mice will be weighed×3 weekly during the dosing phase, weekly thereafter; clinical condition monitored daily for the duration of the study by an experienced technician.

Tumour Monitoring (Inc. BLI):

Tumour will be measured 3 times a week and tumour volumes will be estimated using the formula $0.5(L \times W^2)$ by measuring the tumour in two dimensions using electronic callipers for the duration of the study.

Treatment Initiation and Duration:

The mice will be randomly allocated to the treatment groups (e.g. using a stratified randomisation software tool) such that there is a similar distribution of tumour size within and between treatment groups. Dosing will be initiated when the mean tumour volume of groups approximates 100-150 mm³. The study will terminate 3 weeks following initiation.

Test & Reference Substance Id Storage & Formulation

Test & Reference Substance ID and Storage

| Compound ID | Compound Source | Compound Storage | Vehicle Name | Vehicle Source | Vehicle Storage | Post-formulation storage |
|---|---|---|---|---|---|---|
| Exosome 0 | Reneuron Ltd | −80° C. | 0.9% saline | ReNeuron Ltd. | 2-8° C. | 2-8° C. Kept on ice during administration |
| Temozolomide | PRECOS Ltd | RT powder | 10% DMSO | PRECOS | n/a | +4° C. |

Prepare dosing solutions freshly made before dosing.

Dosing

Mice will be dosed according to the following dosing schedule:

| Group (No per group) | Compound ID | Dose mg/kg | Dose Volume (mg/ml) | Dose conc. (mg/ml) | Route | Dosing Frequency (bid/qd/tid) including wording e.g. twice daily etc. |
|---|---|---|---|---|---|---|
| 1(5) | Vehicle | n/a | 50 μl[1] | 0 | Intratumoural | Once only |
| 2(5) | Exosome 0 | 1 | 50 μl[1] | TBD[2] | Intratumoural | Once only |
| 3(5) | Exosome 0 | 0.5 | 50 μl[1] | TBD[2] | Intratumoural | Once only |
| 4(5) | Exosome 0 | 0.1 | 50 μl[1] | TBD[2] | Intratumoural | Once only |
| 5(5) | Temozolomide | 5 | 10.0 | 5 | p.o. | Daily (q.d.) |

[1]Dose calculated on mean body weight and delivered in a fixed volume of 50 μl.
[2]Concentration to be determined, dependent upon mean group body weight.

Study Endpoints/Body Weight Loss (BWL) During the Study

Terminate any mouse with sudden body weight loss approaching 20%

Any mouse with continuous BWL approaching 20% over several daily measurements will be removed and terminated.

After one measurement of body weight loss (BWL)>10%, a dose holiday will be given to the individual mouse. All dose holidays must be recorded on a Protocol Deviation.

Whether to give dose holidays to all the mice or the individual mouse in the group should be done so in consultation with the client, but is ultimately at the Named Persons (or appointed deputies) discretion based on the severity/incidence of the BWL.

Termination

Each mouse will remain in the study until terminated (day 21), or until circumstances necessitate removal of an animal from the study e.g. loss of clinical condition and/or body weight.

Animals may also be terminated at any time during the study if any adverse effects are noted according to Home Office Project Licence PPL 70/7317.

Termination will be performed in accordance with United Kingdom Home Office Animals, (Scientific Procedures) Act 1986 and PRECOS SOPs.

Terminal Samples

At termination the tumour will be excised and weighed. Tumours will be fixed in 10% Neutral Buffered Formalin and processing to FFPE blocks.

Animal Welfare and Regulation Guidelines

Housing and Environment

Mice will be housed and cared for in accordance with the UK Animals (Scientific Procedures) Act 1986 (ASPA) and in line with the Directive 2010/63/EU of the European Parliament and of the Council of 22 Sep. 2010 "on the protection of animals used for scientific purposes" and according to the and PRECOS Policies, SOPs and SOMs.

Animal Welfare Monitoring

This study will be conducted in line with the FELASSA Guidelines on Pain & Suffering in Experimental Animals and the NCRI Guidelines for the welfare and use of animals in Cancer Research (Workman et al., British Journal of Cancer (2010) 102, 1555-1577).

An experienced technician will check the condition of the mice at least daily. Unexpected adverse effects will be recorded and reported to the Named Animal Care & Welfare Officer (NACWO) and Named Veterinary Surgeon (NVS).

Animals may be terminated at any time during the study if any unexpected adverse effects are noted according to Home Office Project Licence PPL 70/7317 and the permitted severity band.

Statistics and Reporting

Statistical Methods

Statistical analysis if required will be performed in appropriate using the Minitab or PRISM statistical programmes for the PC.

Results

Tumours were implanted on day 0 and measured from day 6; tumours were measured three times weekly by callipers and the tumour volume calculated. When tumours reached a mean tumour volume of ~165 mm³ they were assigned to treatment groups based on mean tumour volume per cage in order to achieve a minimum amount of variation between and within groups.

Figure 32:
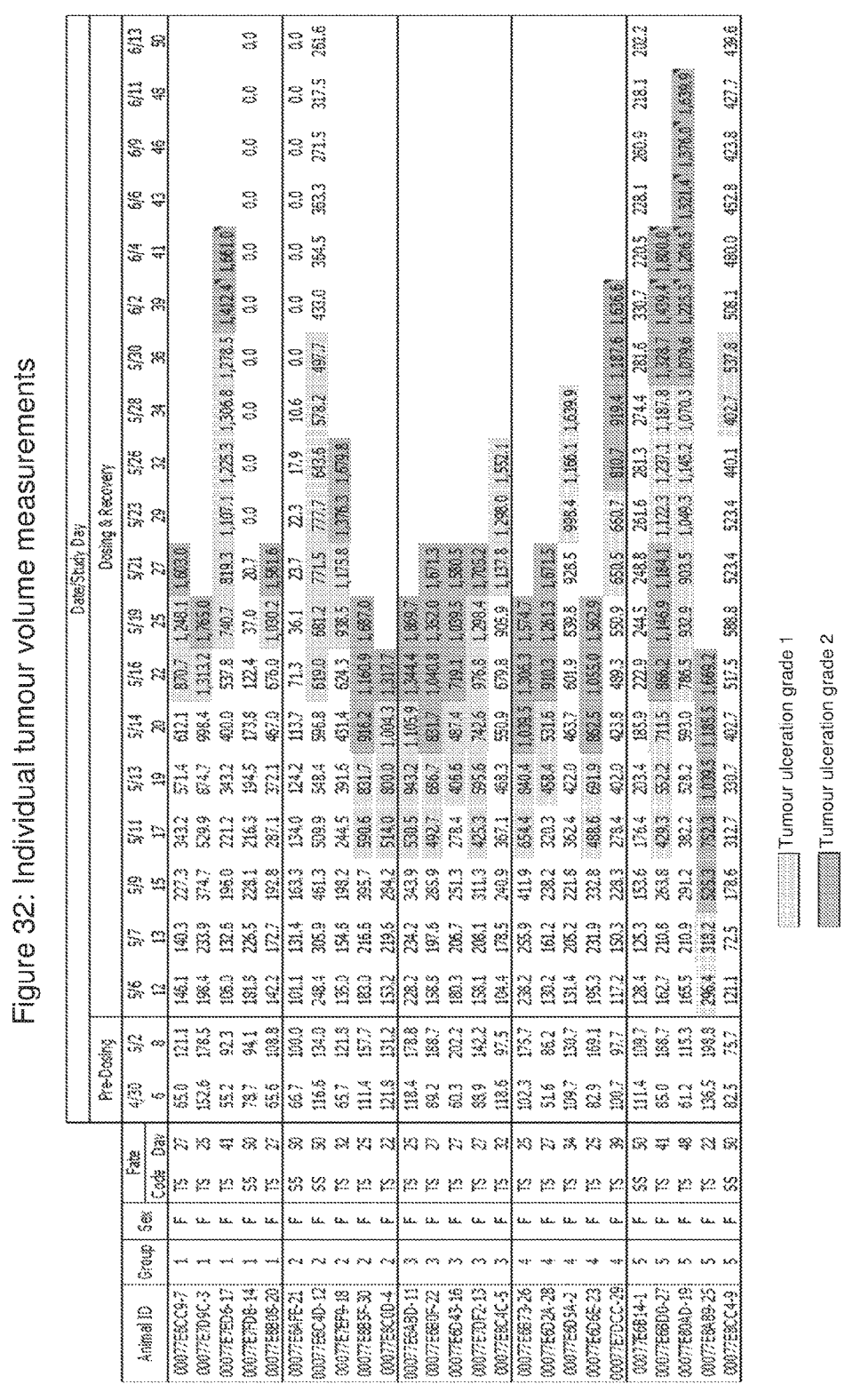

The individual tumour volumes of each group on the day of assignment are presented in FIG. 24; the mice were dosed on study day 12. The raw data for individual tumour volumes can be found in FIG. 32.

Figure 30:
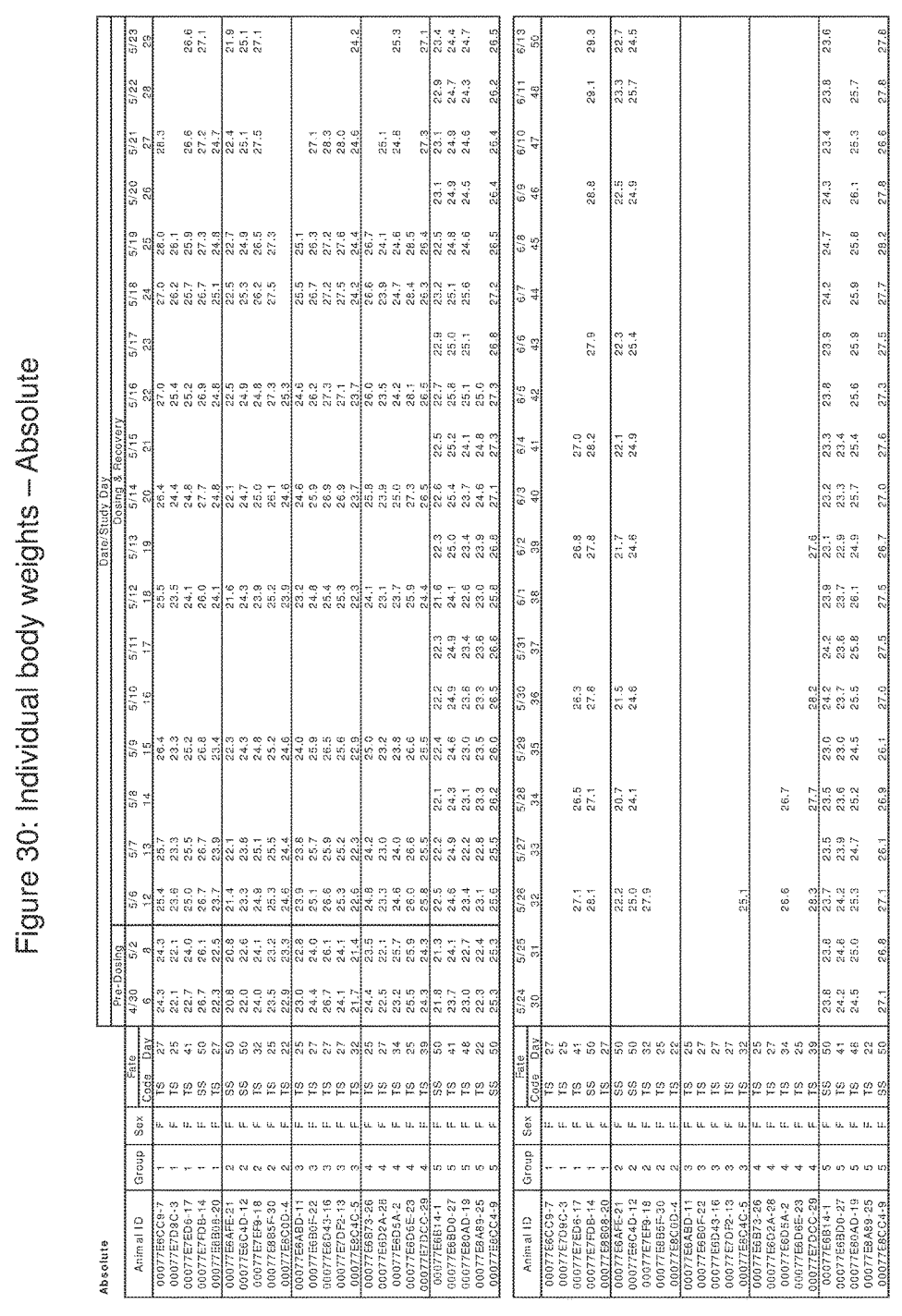
Figure 31:
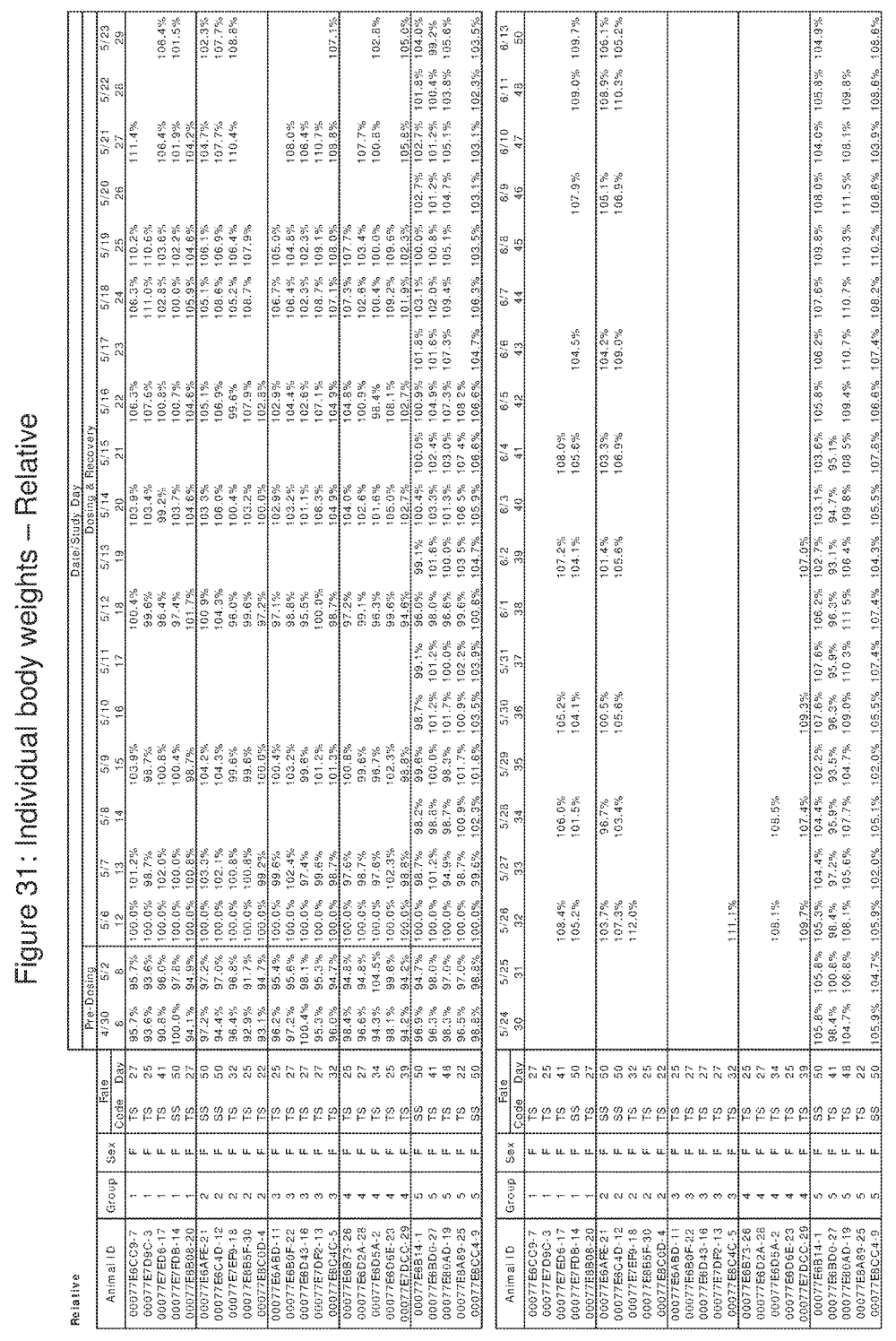

Mouse body weights were monitored for the duration of the study. The data, expressed as the mean+standard error of the mean (% of the pre-dose weight), is presented graphically in FIG. 25 (the dotted vertical line indicates the commencement of the dosing phase); the raw data for individual body weights can be found in FIGS. 30 and 31, absolute and relative measurements respectively. Body weight was stable over the duration of the study for each of the test agents and no adverse effects relating to the dosing protocols were documented in any of the treatment groups.

Mouse IDs recruited in dosing groups 1-4 received a single dose of increasing dose levels of Exosome 0 on study day 12. The Temozolomide dosing phase continued until study day 46 (35 oral doses). However, a number of mice were terminated prior to this point due to a number of listed adverse effects (see FIG. 34; tumours reached the maximum permitted size as defined by UKCCCR guidelines (mean diameter 15 mm)).

FIG. 26 summarises the mean tumour volume for the treatment groups measured during the study, expressed as the group mean+standard error of the mean (% of the pre-dose volume).

One tumour from vehicle group 1 (ID4; 00077E7FDB-14) failed to demonstrate progressive growth following assignment and regressed to zero volume by day 29, as this is an untreated group the mouse has been classified as an outlier and removed from all analysis.

Loss of mice due to early terminations results in a reduction of the mean tumour volume from day 27 onwards. FIG. 27 displays the tumour volume data (group mean+standard error of the mean; % pre-dose volume) of FIG. 26 but in a truncated format i.e. all the line plots are graphed up to study day 25 before termination as a result of adverse effects occurred. The raw data for individual tumour volumes and individual tumour plots are detailed in appendices 3 and 4 respectively.

Mean tumour volumes were analysed statistically using a two-way ANOVA test (FIG. 27 data set; GraphPad Prism; GraphPad Software, Inc.) for day 25. (The tumour volume data of G1 mouse ID14 was excluded from the statistical analysis; individual TV plots detailed in Appendix 4.) Although there was a trend showing reduction in tumour volume for both 1 mg/kg Exosome 0 (group 2) and Temozolomide (group 5), no statistically significant reduction in tumour volume was observed when compared to the vehicle group over the course of the study (GraphPad Prism; two-way ANOVA). The Bonferroni multiple comparison post-test did indicate a statistically significant reduction in tumour volume on day 25 for group 5 versus group 1 ($p > 0.01$).

Terminal tumour weights were analysed statistically using a one-way ANOVA test (GraphPad Prism; GraphPad Software, Inc.); individual group comparisons were carried out on the total group tumour weights. No statistically significant differences among the mean tumour weight for each treatment group were observed using one-way ANOVA ($p = 0.2703$).

From the final tumour weight assessment (FIG. 28; expressed as group mean+standard error of the mean (tumour weight)), what is noticeable in the Exosome 0 1 mg/kg dosing group (group 1) is that some of the tumours showed sensitivity to the treatment (IDs 12 and 21). Additionally, Temozolomide appears to increase the latency of the tumour instead of a significant decrease in tumour volume.

In survival analysis (FIG. 29) utilising mean tumour diameter (15 mm) as the humane survival endpoint, a trend in increased survival was observed for 1 mg/kg Exosome 0 and Temozolomide. However, no significant increase in survival for any of the treatment groups was observed when compared with the vehicle group ($p = 0.3651$; Log-Rank (Mantel-Cox) test; GraphPad Prism; GraphPad Software, Inc.). Temozolomide did result in an increase in survival compared with the two lower doses of Exosome 0 (groups 3 and 4; $p \geq 0.05$).

Discussion

The primary objective of this pilot study was to assess the effect of several doses of Exosome 0 on the growth of U87MG subcutaneous glioblastoma xenografts and a dose of Temozolomide; an oral alkylating agent commonly used for the treatment of glioblastoma multiforme.

The agents under test in this study were well tolerated with no loss of body weight or adverse effects relating to treatment noted; however, tumour size and ulceration resulted in a decrease in mice per group from day 27. As the group sizes in this pilot study were already small the statistical significance that could be achieved with the test agents was therefore limited. The three dosing levels of the Exosome 0 were inefficacious in significantly reducing tumour volume (or tumour weight) when compared to the vehicle group, however, 40% of the tumours treated with the highest dose of Exosome 0 (1 mg/kg; Group 1) showed sensitivity to the treatment.

Similarly the reduction in tumour size with Temozolomide was not significant, which also suggest the group sizes were too small to achieve statistical significance.

A trend in increased survival was also observed for 1 mg/kg Exosome 0 and Temozolomide however significance was not achieved versus the vehicle group.

In conclusion, the dose levels of the Exosome 0 used in this study were well tolerated, but efficacy was emerging but not significant which was confounded by group size. Samples collected from this study could be analysed further for effect on proliferation, angiogenesis, necrosis and apoptosis. Further investigation using larger group sizes and higher dose of Exosome, if tolerated and soluble, could yield significant results.

Example 22: Histological Evaluation of Slides for U-87Mg Human Glioblastoma Subcutaneous Xenografts Summary Tissues for histopathological examination (from Example 21) were stained with haematoxylin and eosin before being subjected to histopathological evaluation. This examination was to determine any differences in the appearance of U87 human glioblastoma tumours in animals given Exosome 0 or Temozolomide when compared to those given a vehicle alone.

In one animal given 1 mg/kg Exosome 0 there was a particularly dramatic and effective ablation of the tumour mass.

Study Aims

The study was designed to investigate the properties of Exosome 0 in an in vivo model of tumourogenesis. This study was an investigation of the activity of this product in vivo, to assess tolerability and compare with an existing agent (temozolomide).

Temozolomide is an oral chemotherapy drug. It is an alkylating agent used for the treatment of glioblastoma. Temozolomide is also indicated for relapsed Grade III anaplastic astrocytoma, replacing the less well tolerated PCV (Procarbazine-Lomustine-Vincristine) regimen.
Methods
Histological Examination to determine any differences in the appearance of U87 human glioblastoma tumours in animals given Exosome 0 or Temozolomide when compared to those given a vehicle alone.

Results

1. Microscopic Findings

The tumours examined were large ovoid masses of apparently comparable sizes in the majority of cases, although the masses in animals 12 (Exosome 1.0 mg/kg), 1 and 9 (Temozolomide) were noticeably smaller. The majority of the tumours had necrotic centres and other necrotic foci with in the mass. The extent of the necrosis was quite variable and did affect the appearance of the tumours, but there was no clear difference in the extent of necrosis between the groups. The tumour cells themselves were clonal with a little dysplasia and occasional apoptotic cells. The mitotic rate was relatively low and appeared to be consistent between treatment groups. The response of the host seemed variable, with several showing no evidence of a host response at all while other showed a slight to moderate inflammatory response with some fibroplasia in occasional animals forming a rudimentary capsule.
a) Vehicle Controls The tumours in the vehicle control group all had the appearance as described above. The extent of central necrosis was minimal in animal 20, but in the rest of the animals was fairly extensive. The inflammatory response in 17 was greater than in the other members of this group.
b) Exosome 0 (1 mg/kg)

The majority of tumours had an appearance that was indistinguishable from the tumours that were seen in the vehicle control animals. There was however one animal (12) where there was a dramatic response. In this animal the tumour appeared to have completely infarcted and there were no viable tumour cells visible in the section presented, only dense fibrous tissue and a slight infiltration of inflammatory cells, a large proportion of which appeared to be macrophages.
c) Exosome 0 (0.5 mg/kg)

The tumours in this group had an appearance that was indistinguishable from the tumours that were seen in the vehicle control animals.
d) Exosome 0 (0.1 mg/kg)

The tumours in this group had an appearance that was indistinguishable from the tumours that were seen in the vehicle control animals.
e) Temozolomide (5 mg/kg)

Three of the tumours in this group had an appearance that was indistinguishable from the tumours that were seen in the vehicle control animals, but there were two animals (1 and 9) where there seemed to be a response to treatment. In both animals the tumour had shrunk to quite a small size but there still appeared to be a substantial number of tumour cells in the section. These cells displayed rather more atypia than was seen in the other tumours, perhaps indicating an selective killing of the majority of cells, but potentially a selection of a more malignant phenotype by the test item. In two of the remaining animals (19 and 25) in this group tumours appeared similar in size to those seen in the vehicle control, there was however a clearly reduce cellularity compared to the vehicle control groups, but the increased atypia seen in animals 1 and 9 was again apparent. In the remaining animal the appearance was similar to the vehicle control.

2. Discussion and Conclusion

The consistent appearance of the tumour indicates a robust test system, which is suitable for assessment of efficacy. In one animal given 1 mg/kg Exosome 0 there was a particularly dramatic and effective ablation of the tumour mass. In the animals that had received Temozolomide effects were seen in more animals, but the long term efficacy is perhaps more questionable as the effect appeared to be the selection of more atypical tumour cells, potentially with resistance to Temozolomide.

Given the consistency of the tumour appearance, it would suggest that the genotype of the tumours is well preserved and that, without being bound by theory—the large difference seen in animal 12 may be a result of a specific Exozome/host interaction, rather than a direct effect of Exosome 0 on the tumour.

REFERENCES

Ambros et al RNA 2003. 9: 277-279
Banerjee, S., Williamson, D., Habib, N., Gordon, M., Chataway, J. (2011) Age and Ageing 40:7-13
Chung et al., Cell Stem Cell, 2, 113-117, 2008
Dai, L. J., Moniri, M. R., Zeng, Z. R. et al. (2011) Cancer Lett 305(1):8-20.
Ding, D. C., Shyu, W. C., Lin S. Z. (2011) Cell Transplant 20: 5-14
Einstein, O., Ben-Hur, T. (2008) Arch Neurol 65:452-456
Gennaro (2000) Remington: The Science and Practice of Pharmacy. 20th edition, ISBN: 0683306472
Hassani Z, O'Reilly J, Pearse Y, Stroemer P, Tang E, Sinden J, Price J, Thuret S. "Human neural progenitor cell engraftment increases neurogenesis and microglial recruitment in the brain of rats with stroke." PLoS One. 2012; 7(11):e50444. doi: 10.1371/journal.pone.0050444. Epub 2012 Nov. 21.
Hodges et al. Cell Transplant. 2007; 16(2):101-15
Horie, N., Pereira, N. P., Niizuma, K. Sun, G. et al. (2011) Stem Cells 29:274-285.
Hulkower, K. I., Herber, R. L., (2011) Pharmaceutics 3:107-124
Katare et al., Clinical-grade human neural stem cells promote reparative neovascularization in mouse models of hindlimb ischemia. Arteriosclerosis, Thrombosis and Vascular Biology, vol 34, no. 2, pp. 408-418
Katsuda, Kosaka, Takeshita, Ochiya. Proteomics 2013, 00, 1-17
Katsuda, Tsuchiya, Kosaka, Yoshioka, Takagaki, Oki, Takeshita, Sakai, Kuroda, Ochiya. Scientific Reports 2013, 3:1197, p 1-11.
Klimanskaya et al., 2006, Nature 444:481-485
Kornblum, Stroke 2007, 38:810-816
Lai et al "Proteolytic Potential of the MSC Exosome Proteome: Implications for an Exosome-Mediated Delivery of Therapeutic Proteasome". International Journal of Proteomics (2012) Article ID 971907, 14 pages.
Littlewood, T. D., Hancock, D. C., Danielian, P. S. et al. (1995) Nucleic Acid Research 23:1686-1690.
Miljan, E. A. & Sinden, J. D. (2009) Current Opinion in Molecular Therapeutics 4:394-403
Miljan E A, Hines S J, Pande P, Corteling R L, Hicks C, Zbarsky V, Umachandran, M, Sowinski P, Richardson S, Tang E, Wieruszew M, Patel S, Stroemer P, Sinden J D.

Implantation of c-mycER TAM immortalized human mesencephalic-derived clonal cell lines ameliorates behavior dysfunction in a rat model of Parkinson's disease. Stem Cells Dev. 2009 March; 18(2):307-19

Mitchell et al Journal of Immunological Methods 335 (2008) 98-105

Pollock et al, Exp Neurol. 2006 May; 199(1):143-55.

Mark F Pittenger; Alastair M Mackay; Stephen C Beck; Rama K Jaiswal; et al Science; Apr. 2, 1999; 284, 5411

Shah, K., (2012) Adv Drug Deliv Rev 64(8):739-748.

Smith, E. J., Stroemer, R. P., Gorenkova, N., Nakajima, M. et al. (2012) Stem Cells 30:785-796.

Stevenato, L., Corteling, R., Stroemer, P., Hope, A. et al. (2009) BMC Neuroscience 10:86

Stroemer, P., Patel, S., Hope, A., Oliveira, C., Pollock, K., Sinden, J. (2009) Neurorehabil Neural Repair 23: 895-909.

Théry, C., Ostrowski, M., Segura, E. et al. (2009) Nature Reviews Immunology 9: 581-593

Their et al, "Direct Conversion of Fibroblasts into Stably Expandable Neural Stem Cells". Cell Stem Cell. 2012 Mar. 20.

Timmers, L., Lim, S. K., Arslan, F., Armstrong, J. S. et al. (2007) Stem Cell Res 1: 129-137

Yuan, S. J., Martin, J, Elia, J., Flippin, J. et al. (2011) PLoS ONE 6:e17540

The invention claimed is:

1. A method for treating a nestin-positive glioma, comprising administering to a subject in need thereof an exosome isolated from a neural stem cell.

2. The method according to claim 1, wherein the treatment comprises inhibiting migration of the glioma cells.

3. The method of claim 2, wherein the exosome is isolated from a neural stem cell that:
   (a) is proliferating;
   (b) does not express doublecortin or glial fibrillary acidic protein; and/or
   (c) has been cultured in a multi-compartment bioreactor for less than 4 weeks and optionally no more than 1 week.

4. The method according to claim 1, wherein the treatment comprises inducing differentiation of the glioma cells.

5. The method of claim 4, wherein the exosome is isolated from a neural stem cell that:
   (a) is proliferating;
   (b) does not express doublecortin or glial fibrillary acidic protein; and/or
   (c) has been cultured in a multi-compartment bioreactor for less than 4 weeks and optionally no more than 1 week.

6. The method of claim 1, wherein the exosome is isolated from a neural stem cell that:
   (a) is proliferating;
   (b) does not express doublecortin or glial fibrillary acidic protein; and/or
   (c) has been cultured in a multi-compartment bioreactor for less than 4 weeks and optionally no more than 1 week.

7. The method of claim 1, wherein the exosome is isolated from a neural stem cell line.

8. The method of claim 7, wherein the neural stem cell line is conditionally-immortalised and/or grown in serum free medium.

9. The method of claim 7, wherein the neural stem cell line is a stem cell line selected from the group of: CTX0E03 having ECACC Accession No. 04091601, STR0C05 having ECACC Accession No. 04110301, or HPC0A07 having ECACC Accession No. 04092302.

10. The method of claim 1, wherein the exosome has:
    (a) a size of between 30 nm and 1000 nm, or between 30 and 200 nm, or between 30 and 100 nm, as determined by electron microscopy; or
    (b) a density in sucrose of 1.1-1.2 g/ml.

11. The method of claim 1, wherein the exosome comprises mRNA and/or miRNA.

12. The method of claim 11, wherein the exosome comprises:
    one, two, three or four of hsa-miR-1246, hsa-miR-4492, hsa-miR-4488 and hsa-miR-4532;
    one, two, three, four or five of hsa-miR-181a-5p, hsa-miR-1246, hsa-miR-127-3p, hsa-miR-21-5p, and hsa-miR-100-5p;
    one, two, three, four or five of hsa-miR-181a-5p, hsa-let-7a-5p, hsa-let-7f-5p, hsa-miR-92b-3p, and hsa-miR-9-5p; or
    hsa-miR-486-5p.

13. The method of claim 1, wherein the exosome comprises one or more of:
    (a) a lipid selected from ceramide, cholesterol, sphingomyelin, phosphatidylserine, phosphatidylinositol, and/or phosphatidylcholine;
    (b) miRNA, optionally selected from hsa-let-7g, hsa-miR-101, hsa-miR-10a, hsa-miR-10b, hsa-miR-126, hsa-miR-128, hsa-miR-129-5p, hsa-miR-130a, hsa-miR-134, hsa-miR-137, hsa-miR-155, hsa-miR-15a, hsa-miR-15b, hsa-miR-16, hsa-miR-17, hsa-miR-182, hsa-miR-183, hsa-miR-185, hsa-miR-18b, hsa-miR-192, hsa-miR-194, hsa-miR-195, hsa-miR-20a, hsa-miR-20b, hsa-miR-210, hsa-miR-218, hsa-miR-301a, hsa-miR-302a, hsa-miR-302c, hsa-miR-345, hsa-miR-375, hsa-miR-378, hsa-miR-7, hsa-miR-9, hsa-miR-93, hsa-miR-96, and hsa-miR-99a;
    (c) a tetraspanin, optionally selected from CD63, CD81, CD9, CD53, CD82 and/or CD37;
    (d) TSG101, Alix, CD109 and/or thy-1; and/or
    (e) CD133.

14. The method of claim 1, wherein the exosome comprises at least 10 of the proteins present in Table 20 or Table 22.

* * * * *

SEQUENCE LISTING

```
<160> NUMBER OF SEQ ID NOS: 752

<210> SEQ ID NO 1
<211> LENGTH: 22
<212> TYPE: RNA
<213> ORGANISM: Homo sapiens

<400> SEQUENCE: 1
ugagguagua gguuguauag uu                                              22

<210> SEQ ID NO 2
<211> LENGTH: 23
<212> TYPE: RNA
<213> ORGANISM: Homo sapiens

<400> SEQUENCE: 2
uacccuguag auccgaauuu gug                                             23

<210> SEQ ID NO 3
<211> LENGTH: 22
<212> TYPE: RNA
<213> ORGANISM: Homo sapiens

<400> SEQUENCE: 3
aacccguaga uccgaacuug ug                                              22

<210> SEQ ID NO 4
<211> LENGTH: 22
<212> TYPE: RNA
<213> ORGANISM: Homo sapiens

<400> SEQUENCE: 4
cacccguaga accgaccuug cg                                              22

<210> SEQ ID NO 5
<211> LENGTH: 22
<212> TYPE: RNA
<213> ORGANISM: Homo sapiens

<400> SEQUENCE: 5
uccuguacug agcugccccg ag                                              22

<210> SEQ ID NO 6
<211> LENGTH: 21
<212> TYPE: RNA
<213> ORGANISM: Homo sapiens

<400> SEQUENCE: 6
uucacagugg cuaaguucug c                                               21
```

```
<210> SEQ ID NO 7
<211> LENGTH: 22
<212> TYPE: RNA
<213> ORGANISM: Homo sapiens

<400> SEQUENCE: 7
uauugcacuu gucccggccu gu                                           22

<210> SEQ ID NO 8
<211> LENGTH: 23
<212> TYPE: RNA
<213> ORGANISM: Homo sapiens

<400> SEQUENCE: 8
caacggaauc ccaaaagcag cug                                          23

<210> SEQ ID NO 9
<211> LENGTH: 22
<212> TYPE: RNA
<213> ORGANISM: Homo sapiens

<400> SEQUENCE: 9
uagcuuauca gacugauguu ga                                           22

<210> SEQ ID NO 10
<211> LENGTH: 22
<212> TYPE: RNA
<213> ORGANISM: Homo sapiens

<400> SEQUENCE: 10
ugagguagua aguuguauug uu                                           22

<210> SEQ ID NO 11
<211> LENGTH: 22
<212> TYPE: RNA
<213> ORGANISM: Homo sapiens

<400> SEQUENCE: 11
ugagguagua gauuguauag uu                                           22

<210> SEQ ID NO 12
<211> LENGTH: 22
<212> TYPE: RNA
<213> ORGANISM: Homo sapiens

<400> SEQUENCE: 12
uucaaguaau ccaggauagg cu                                           22

<210> SEQ ID NO 13
<211> LENGTH: 22
<212> TYPE: RNA
<213> ORGANISM: Homo sapiens

<400> SEQUENCE: 13
uauugcacuc gucccggccu cc                                           22

<210> SEQ ID NO 14
<211> LENGTH: 22
<212> TYPE: RNA
<213> ORGANISM: Homo sapiens

<400> SEQUENCE: 14
```
ucggauccgu cugagcuugg cu                                              22

<210> SEQ ID NO 15
<211> LENGTH: 23
<212> TYPE: RNA
<213> ORGANISM: Homo sapiens

<400> SEQUENCE: 15
aacauucaac gcugucggug agu                                             23

<210> SEQ ID NO 16
<211> LENGTH: 24
<212> TYPE: RNA
<213> ORGANISM: Homo sapiens

<400> SEQUENCE: 16
uuuggcaaug guagaacuca cacu                                            24

<210> SEQ ID NO 17
<211> LENGTH: 22
<212> TYPE: RNA
<213> ORGANISM: Homo sapiens

<400> SEQUENCE: 17
ugagguagua gguuguaugg uu                                              22

<210> SEQ ID NO 18
<211> LENGTH: 21
<212> TYPE: RNA
<213> ORGANISM: Homo sapiens

<400> SEQUENCE: 18
ugguagacua uggaacguag g                                               21

<210> SEQ ID NO 19
<211> LENGTH: 22
<212> TYPE: RNA
<213> ORGANISM: Homo sapiens

<400> SEQUENCE: 19
ugagaacuga auuccauagg cu                                              22

<210> SEQ ID NO 20
<211> LENGTH: 21
<212> TYPE: RNA
<213> ORGANISM: Homo sapiens

<400> SEQUENCE: 20
caacaccagu cgaugggcug u                                               21

<210> SEQ ID NO 21
<211> LENGTH: 19
<212> TYPE: RNA
<213> ORGANISM: Homo sapiens

<400> SEQUENCE: 21
aauggauuuu uggagcagg                                                  19

<210> SEQ ID NO 22
<211> LENGTH: 22
<212> TYPE: RNA
<213> ORGANISM: Homo sapiens

<400> SEQUENCE: 22
ugagguagua guuugugcug uu                                          22

<210> SEQ ID NO 23
<211> LENGTH: 17
<212> TYPE: RNA
<213> ORGANISM: Homo sapiens

<400> SEQUENCE: 23
ccccggggag cccggcg                                                17

<210> SEQ ID NO 24
<211> LENGTH: 22
<212> TYPE: RNA
<213> ORGANISM: Homo sapiens

<400> SEQUENCE: 24
uauggcacug guagaauuca cu                                          22

<210> SEQ ID NO 25
<211> LENGTH: 21
<212> TYPE: RNA
<213> ORGANISM: Homo sapiens

<400> SEQUENCE: 25
cuagacugaa gcuccuugag g                                           21

<210> SEQ ID NO 26
<211> LENGTH: 22
<212> TYPE: RNA
<213> ORGANISM: Homo sapiens

<400> SEQUENCE: 26
aaugcacccg ggcaaggauu cu                                          22

<210> SEQ ID NO 27
<211> LENGTH: 22
<212> TYPE: RNA
<213> ORGANISM: Homo sapiens

<400> SEQUENCE: 27
ugagguagga gguuguauag uu                                          22

<210> SEQ ID NO 28
<211> LENGTH: 22
<212> TYPE: RNA
<213> ORGANISM: Homo sapiens

<400> SEQUENCE: 28
ugagguagua gguugugugg uu                                          22

<210> SEQ ID NO 29
<211> LENGTH: 22
<212> TYPE: RNA
<213> ORGANISM: Homo sapiens

<400> SEQUENCE: 29
uagcagcacg uaaauauugg cg                                          22

<210> SEQ ID NO 30
<211> LENGTH: 22
<212> TYPE: RNA
<213> ORGANISM: Homo sapiens

```
<400> SEQUENCE: 30
uguaaacauc cucgacugga ag                                             22

<210> SEQ ID NO 31
<211> LENGTH: 22
<212> TYPE: RNA
<213> ORGANISM: Homo sapiens

<400> SEQUENCE: 31
uguaaacauc cccgacugga ag                                             22

<210> SEQ ID NO 32
<211> LENGTH: 23
<212> TYPE: RNA
<213> ORGANISM: Homo sapiens

<400> SEQUENCE: 32
agguuacccg agcaacuuug cau                                            23

<210> SEQ ID NO 33
<211> LENGTH: 22
<212> TYPE: RNA
<213> ORGANISM: Homo sapiens

<400> SEQUENCE: 33
aagcugccag uugaagaacu gu                                             22

<210> SEQ ID NO 34
<211> LENGTH: 17
<212> TYPE: RNA
<213> ORGANISM: Homo sapiens

<400> SEQUENCE: 34
ggggcugggc gcgcgcc                                                   17

<210> SEQ ID NO 35
<211> LENGTH: 24
<212> TYPE: RNA
<213> ORGANISM: Homo sapiens

<400> SEQUENCE: 35
ucccugagac ccuuuaaccu guga                                           24

<210> SEQ ID NO 36
<211> LENGTH: 21
<212> TYPE: RNA
<213> ORGANISM: Homo sapiens

<400> SEQUENCE: 36
agcuacaucu ggcuacuggg u                                              21

<210> SEQ ID NO 37
<211> LENGTH: 21
<212> TYPE: RNA
<213> ORGANISM: Homo sapiens

<400> SEQUENCE: 37
ucgaggagcu cacagucuag u                                              21

<210> SEQ ID NO 38
<211> LENGTH: 23
<212> TYPE: RNA
<213> ORGANISM: Homo sapiens
```

```
<400> SEQUENCE: 38
aacauucauu gcugucggug ggu                                              23

<210> SEQ ID NO 39
<211> LENGTH: 22
<212> TYPE: RNA
<213> ORGANISM: Homo sapiens

<400> SEQUENCE: 39
accuggcaua caauguagau uu                                               22

<210> SEQ ID NO 40
<211> LENGTH: 22
<212> TYPE: RNA
<213> ORGANISM: Homo sapiens

<400> SEQUENCE: 40
caaagaauuc uccuuuuggg cu                                               22

<210> SEQ ID NO 41
<211> LENGTH: 23
<212> TYPE: RNA
<213> ORGANISM: Homo sapiens

<400> SEQUENCE: 41
ugaggggcag agagcgagac uuu                                              23

<210> SEQ ID NO 42
<211> LENGTH: 22
<212> TYPE: RNA
<213> ORGANISM: Homo sapiens

<400> SEQUENCE: 42
ucccugagac ccuaacuugu ga                                               22

<210> SEQ ID NO 43
<211> LENGTH: 22
<212> TYPE: RNA
<213> ORGANISM: Homo sapiens

<400> SEQUENCE: 43
ugagguagua guuuguacag uu                                               22

<210> SEQ ID NO 44
<211> LENGTH: 22
<212> TYPE: RNA
<213> ORGANISM: Homo sapiens

<400> SEQUENCE: 44
augcaccugg gcaaggauuc ug                                               22

<210> SEQ ID NO 45
<211> LENGTH: 22
<212> TYPE: RNA
<213> ORGANISM: Homo sapiens

<400> SEQUENCE: 45
uguaaacauc cuugacugga ag                                               22

<210> SEQ ID NO 46
<211> LENGTH: 21
<212> TYPE: RNA
```

-continued

```
<213> ORGANISM: Homo sapiens

<400> SEQUENCE: 46
uucacagugg cuaaguuccg c                                              21

<210> SEQ ID NO 47
<211> LENGTH: 22
<212> TYPE: RNA
<213> ORGANISM: Homo sapiens

<400> SEQUENCE: 47
gaauguugcu cggugaaccc cu                                             22

<210> SEQ ID NO 48
<211> LENGTH: 22
<212> TYPE: RNA
<213> ORGANISM: Homo sapiens

<400> SEQUENCE: 48
ucagugcauc acagaacuuu gu                                             22

<210> SEQ ID NO 49
<211> LENGTH: 22
<212> TYPE: RNA
<213> ORGANISM: Homo sapiens

<400> SEQUENCE: 49
acggguuagg cucuugggag cu                                             22

<210> SEQ ID NO 50
<211> LENGTH: 21
<212> TYPE: RNA
<213> ORGANISM: Homo sapiens

<400> SEQUENCE: 50
aauauaacac agauggccug u                                              21

<210> SEQ ID NO 51
<211> LENGTH: 22
<212> TYPE: RNA
<213> ORGANISM: Homo sapiens

<400> SEQUENCE: 51
uauacaaggg caagcucucu gu                                             22

<210> SEQ ID NO 52
<211> LENGTH: 22
<212> TYPE: RNA
<213> ORGANISM: Homo sapiens

<400> SEQUENCE: 52
aacccguaga uccgaucuug ug                                             22

<210> SEQ ID NO 53
<211> LENGTH: 22
<212> TYPE: RNA
<213> ORGANISM: Homo sapiens

<400> SEQUENCE: 53
agagguagua gguugcauag uu                                             22

<210> SEQ ID NO 54
<211> LENGTH: 22
```

```
<212> TYPE: RNA
<213> ORGANISM: Homo sapiens

<400> SEQUENCE: 54
ucagugcacu acagaacuuu gu                                              22

<210> SEQ ID NO 55
<211> LENGTH: 21
<212> TYPE: RNA
<213> ORGANISM: Homo sapiens

<400> SEQUENCE: 55
aucacauugc cagggauuuc c                                               21

<210> SEQ ID NO 56
<211> LENGTH: 22
<212> TYPE: RNA
<213> ORGANISM: Homo sapiens

<400> SEQUENCE: 56
cacuagauug ugagcuccug ga                                              22

<210> SEQ ID NO 57
<211> LENGTH: 23
<212> TYPE: RNA
<213> ORGANISM: Homo sapiens

<400> SEQUENCE: 57
agcucggucu gaggccccuc agu                                             23

<210> SEQ ID NO 58
<211> LENGTH: 23
<212> TYPE: RNA
<213> ORGANISM: Homo sapiens

<400> SEQUENCE: 58
ucuuugguua ucuagcugua uga                                             23

<210> SEQ ID NO 59
<211> LENGTH: 21
<212> TYPE: RNA
<213> ORGANISM: Homo sapiens

<400> SEQUENCE: 59
aucacauugc cagggauuac c                                               21

<210> SEQ ID NO 60
<211> LENGTH: 23
<212> TYPE: RNA
<213> ORGANISM: Homo sapiens

<400> SEQUENCE: 60
cacccggcug ugugcacaug ugc                                             23

<210> SEQ ID NO 61
<211> LENGTH: 18
<212> TYPE: RNA
<213> ORGANISM: Homo sapiens

<400> SEQUENCE: 61 aggggggcggg cuccggcg                                                  18

<210> SEQ ID NO 62
```

```
<211> LENGTH: 23
<212> TYPE: RNA
<213> ORGANISM: Homo sapiens

<400> SEQUENCE: 62
agcagcauug uacagggcua uga                                              23

<210> SEQ ID NO 63
<211> LENGTH: 22
<212> TYPE: RNA
<213> ORGANISM: Homo sapiens

<400> SEQUENCE: 63
cauugcacuu gucucggucu ga                                               22

<210> SEQ ID NO 64
<211> LENGTH: 21
<212> TYPE: RNA
<213> ORGANISM: Homo sapiens

<400> SEQUENCE: 64
uuaauaucgg acaaccauug u                                                21

<210> SEQ ID NO 65
<211> LENGTH: 21
<212> TYPE: RNA
<213> ORGANISM: Homo sapiens

<400> SEQUENCE: 65
acuggacuug gagucagaag g                                                21

<210> SEQ ID NO 66
<211> LENGTH: 23
<212> TYPE: RNA
<213> ORGANISM: Homo sapiens

<400> SEQUENCE: 66
uguaaacauc cuacacucuc agc                                              23

<210> SEQ ID NO 67
<211> LENGTH: 20
<212> TYPE: RNA
<213> ORGANISM: Homo sapiens

<400> SEQUENCE: 67
uaacggccgc gguacccuaa                                                  20

<210> SEQ ID NO 68
<211> LENGTH: 22
<212> TYPE: RNA
<213> ORGANISM: Homo sapiens

<400> SEQUENCE: 68
ucacaaguca ggcucuuggg ac                                               22

<210> SEQ ID NO 69
<211> LENGTH: 21
<212> TYPE: RNA
<213> ORGANISM: Homo sapiens

<400> SEQUENCE: 69
uccgguucuc agggcuccac c                                                21
```

```
<210> SEQ ID NO 70
<211> LENGTH: 22
<212> TYPE: RNA
<213> ORGANISM: Homo sapiens

<400> SEQUENCE: 70
uuaucagaau cuccaggggu ac                                              22

<210> SEQ ID NO 71
<211> LENGTH: 22
<212> TYPE: RNA
<213> ORGANISM: Homo sapiens

<400> SEQUENCE: 71
cuuucagucg gauguuuaca gc                                              22

<210> SEQ ID NO 72
<211> LENGTH: 22
<212> TYPE: RNA
<213> ORGANISM: Homo sapiens

<400> SEQUENCE: 72
cuuggcaccu agcaagcacu ca                                              22

<210> SEQ ID NO 73
<211> LENGTH: 22
<212> TYPE: RNA
<213> ORGANISM: Homo sapiens

<400> SEQUENCE: 73
ugagaaccac gucugcucug ag                                              22

<210> SEQ ID NO 74
<211> LENGTH: 22
<212> TYPE: RNA
<213> ORGANISM: Homo sapiens

<400> SEQUENCE: 74
uuauaauaca accugauaag ug                                              22

<210> SEQ ID NO 75
<211> LENGTH: 22
<212> TYPE: RNA
<213> ORGANISM: Homo sapiens

<400> SEQUENCE: 75
ugagaccucu ggguucugag cu                                              22

<210> SEQ ID NO 76
<211> LENGTH: 22
<212> TYPE: RNA
<213> ORGANISM: Homo sapiens

<400> SEQUENCE: 76
gcugacuccu aguccagggc uc                                              22

<210> SEQ ID NO 77
<211> LENGTH: 22
<212> TYPE: RNA
<213> ORGANISM: Homo sapiens

<400> SEQUENCE: 77
cuuucagucg gauguuugca gc                                              22
```

```
<210> SEQ ID NO 78
<211> LENGTH: 22
<212> TYPE: RNA
<213> ORGANISM: Homo sapiens

<400> SEQUENCE: 78
uagcagcaca ucaugguuua ca                                        22

<210> SEQ ID NO 79
<211> LENGTH: 23
<212> TYPE: RNA
<213> ORGANISM: Homo sapiens

<400> SEQUENCE: 79
agcuacauug ucugcugggu uuc                                       23

<210> SEQ ID NO 80
<211> LENGTH: 21
<212> TYPE: RNA
<213> ORGANISM: Homo sapiens

<400> SEQUENCE: 80
aggcaagaug cuggcauagc u                                         21

<210> SEQ ID NO 81
<211> LENGTH: 23
<212> TYPE: RNA
<213> ORGANISM: Homo sapiens

<400> SEQUENCE: 81
ucucacacag aaaucgcacc cgu                                       23

<210> SEQ ID NO 82
<211> LENGTH: 22
<212> TYPE: RNA
<213> ORGANISM: Homo sapiens

<400> SEQUENCE: 82
caucaucguc ucaaaugagu cu                                        22

<210> SEQ ID NO 83
<211> LENGTH: 22
<212> TYPE: RNA
<213> ORGANISM: Homo sapiens

<400> SEQUENCE: 83
ugaaggucua cugugugcca gg                                        22

<210> SEQ ID NO 84
<211> LENGTH: 17
<212> TYPE: RNA
<213> ORGANISM: Homo sapiens

<400> SEQUENCE: 84
ucucgcuggg gccucca                                              17

<210> SEQ ID NO 85
<211> LENGTH: 23
<212> TYPE: RNA
<213> ORGANISM: Homo sapiens

<400> SEQUENCE: 85
uggaagacua gugauuuugu ugu                                       23
```

```
<210> SEQ ID NO 86
<211> LENGTH: 22
<212> TYPE: RNA
<213> ORGANISM: Homo sapiens

<400> SEQUENCE: 86
cagugcaaug augaaagggc au                                              22

<210> SEQ ID NO 87
<211> LENGTH: 21
<212> TYPE: RNA
<213> ORGANISM: Homo sapiens

<400> SEQUENCE: 87
cugaccuaug aauugacagc c                                               21

<210> SEQ ID NO 88
<211> LENGTH: 22
<212> TYPE: RNA
<213> ORGANISM: Homo sapiens

<400> SEQUENCE: 88
uuguacaugg uaggcuuuca uu                                              22

<210> SEQ ID NO 89
<211> LENGTH: 22
<212> TYPE: RNA
<213> ORGANISM: Homo sapiens

<400> SEQUENCE: 89
uucccuuugu cauccuaugc cu                                              22

<210> SEQ ID NO 90
<211> LENGTH: 21
<212> TYPE: RNA
<213> ORGANISM: Homo sapiens

<400> SEQUENCE: 90
uucaaguaau ucaggauagg u                                               21

<210> SEQ ID NO 91
<211> LENGTH: 21
<212> TYPE: RNA
<213> ORGANISM: Homo sapiens

<400> SEQUENCE: 91
ucgaccggac cucgaccggc u                                               21

<210> SEQ ID NO 92
<211> LENGTH: 22
<212> TYPE: RNA
<213> ORGANISM: Homo sapiens

<400> SEQUENCE: 92
cuauacgacc ugcugccuuu cu                                              22

<210> SEQ ID NO 93
<211> LENGTH: 22
<212> TYPE: RNA
<213> ORGANISM: Homo sapiens

<400> SEQUENCE: 93
```
uuauaaagca augagacuga uu 22

<210> SEQ ID NO 94
<211> LENGTH: 22
<212> TYPE: RNA
<213> ORGANISM: Homo sapiens

<400> SEQUENCE: 94
ugugacuggu ugaccagagg gg 22

<210> SEQ ID NO 95
<211> LENGTH: 23
<212> TYPE: RNA
<213> ORGANISM: Homo sapiens

<400> SEQUENCE: 95
ucuuggagua ggucauuggg ugg 23

<210> SEQ ID NO 96
<211> LENGTH: 22
<212> TYPE: RNA
<213> ORGANISM: Homo sapiens

<400> SEQUENCE: 96
uguaaacauc cuacacucag cu 22

<210> SEQ ID NO 97
<211> LENGTH: 22
<212> TYPE: RNA
<213> ORGANISM: Homo sapiens

<400> SEQUENCE: 97
aaaagcuggg uugagagggc ga 22

<210> SEQ ID NO 98
<211> LENGTH: 22
<212> TYPE: RNA
<213> ORGANISM: Homo sapiens

<400> SEQUENCE: 98
caagcuugua ucuauaggua ug 22

<210> SEQ ID NO 99
<211> LENGTH: 22
<212> TYPE: RNA
<213> ORGANISM: Homo sapiens

<400> SEQUENCE: 99
ugcggggcua gggcuaacag ca 22

<210> SEQ ID NO 100
<211> LENGTH: 22
<212> TYPE: RNA
<213> ORGANISM: Homo sapiens

<400> SEQUENCE: 100
accaucgacc guugauugua cc 22

<210> SEQ ID NO 101
<211> LENGTH: 22
<212> TYPE: RNA
<213> ORGANISM: Homo sapiens

<400> SEQUENCE: 101
uggcaguguc uuagcugguu gu                                                22

<210> SEQ ID NO 102
<211> LENGTH: 22
<212> TYPE: RNA
<213> ORGANISM: Homo sapiens

<400> SEQUENCE: 102
accacugacc guugacugua cc                                                22

<210> SEQ ID NO 103
<211> LENGTH: 22
<212> TYPE: RNA
<213> ORGANISM: Homo sapiens

<400> SEQUENCE: 103
ugauauguuu gauauauuag gu                                                22

<210> SEQ ID NO 104
<211> LENGTH: 22
<212> TYPE: RNA
<213> ORGANISM: Homo sapiens

<400> SEQUENCE: 104
uaacagucua cagccauggu cg                                                22

<210> SEQ ID NO 105
<211> LENGTH: 22
<212> TYPE: RNA
<213> ORGANISM: Homo sapiens

<400> SEQUENCE: 105
aacauucaac cugucgguga gu                                                22

<210> SEQ ID NO 106
<211> LENGTH: 22
<212> TYPE: RNA
<213> ORGANISM: Homo sapiens

<400> SEQUENCE: 106
uagcaccauc ugaaaucggu ua                                                22

<210> SEQ ID NO 107
<211> LENGTH: 23
<212> TYPE: RNA
<213> ORGANISM: Homo sapiens

<400> SEQUENCE: 107
cagugcaaua guauugucaa agc                                               23

<210> SEQ ID NO 108
<211> LENGTH: 21
<212> TYPE: RNA
<213> ORGANISM: Homo sapiens

<400> SEQUENCE: 108
uaguagaccg uauagcguac g                                                 21

<210> SEQ ID NO 109
<211> LENGTH: 21
<212> TYPE: RNA
<213> ORGANISM: Homo sapiens

```
<400> SEQUENCE: 109
ucacagugaa ccggucucuu u                                          21

<210> SEQ ID NO 110
<211> LENGTH: 17
<212> TYPE: RNA
<213> ORGANISM: Homo sapiens

<400> SEQUENCE: 110
gggagaaggg ucggggc                                               17

<210> SEQ ID NO 111
<211> LENGTH: 23
<212> TYPE: RNA
<213> ORGANISM: Homo sapiens

<400> SEQUENCE: 111
aaugacacga ucacucccgu uga                                        23

<210> SEQ ID NO 112
<211> LENGTH: 21
<212> TYPE: RNA
<213> ORGANISM: Homo sapiens

<400> SEQUENCE: 112
acucuuuccc uguugcacua c                                          21

<210> SEQ ID NO 113
<211> LENGTH: 22
<212> TYPE: RNA
<213> ORGANISM: Homo sapiens

<400> SEQUENCE: 113
cagugcaaug uuaaaagggc au                                         22

<210> SEQ ID NO 114
<211> LENGTH: 22
<212> TYPE: RNA
<213> ORGANISM: Homo sapiens

<400> SEQUENCE: 114
cuuucaguca gauguuugcu gc                                         22

<210> SEQ ID NO 115
<211> LENGTH: 22
<212> TYPE: RNA
<213> ORGANISM: Homo sapiens

<400> SEQUENCE: 115
uggugggccg cagaacaugu gc                                         22

<210> SEQ ID NO 116
<211> LENGTH: 23
<212> TYPE: RNA
<213> ORGANISM: Homo sapiens

<400> SEQUENCE: 116
caaagugcug uucgugcagg uag                                        23

<210> SEQ ID NO 117
<211> LENGTH: 22
<212> TYPE: RNA
<213> ORGANISM: Homo sapiens
```

-continued

```
<400> SEQUENCE: 117
aaucguacag ggucauccac uu                                              22

<210> SEQ ID NO 118
<211> LENGTH: 22
<212> TYPE: RNA
<213> ORGANISM: Homo sapiens

<400> SEQUENCE: 118
ucaggcucag uccccucccg au                                              22

<210> SEQ ID NO 119
<211> LENGTH: 22
<212> TYPE: RNA
<213> ORGANISM: Homo sapiens

<400> SEQUENCE: 119
uggcucaguu cagcaggaac ag                                              22

<210> SEQ ID NO 120
<211> LENGTH: 22
<212> TYPE: RNA
<213> ORGANISM: Homo sapiens

<400> SEQUENCE: 120
ucugugagac caaagaacua cu                                              22

<210> SEQ ID NO 121
<211> LENGTH: 23
<212> TYPE: RNA
<213> ORGANISM: Homo sapiens

<400> SEQUENCE: 121
ucuggcuccg ugucuucacu ccc                                             23

<210> SEQ ID NO 122
<211> LENGTH: 22
<212> TYPE: RNA
<213> ORGANISM: Homo sapiens

<400> SEQUENCE: 122
uucaccaccu ucuccaccca gc                                              22

<210> SEQ ID NO 123
<211> LENGTH: 23
<212> TYPE: RNA
<213> ORGANISM: Homo sapiens

<400> SEQUENCE: 123
uuuggcacua gcacauuuuu gcu                                             23

<210> SEQ ID NO 124
<211> LENGTH: 22
<212> TYPE: RNA
<213> ORGANISM: Homo sapiens

<400> SEQUENCE: 124
acucggcgug gcgucggucg ug                                              22

<210> SEQ ID NO 125
<211> LENGTH: 23
<212> TYPE: RNA
```

<213> ORGANISM: Homo sapiens

<400> SEQUENCE: 125
aggcagugua guuagcugau ugc                           23

<210> SEQ ID NO 126
<211> LENGTH: 22
<212> TYPE: RNA
<213> ORGANISM: Homo sapiens

<400> SEQUENCE: 126
gccugcuggg guggaaccug gu                            22

<210> SEQ ID NO 127
<211> LENGTH: 22
<212> TYPE: RNA
<213> ORGANISM: Homo sapiens

<400> SEQUENCE: 127
aaguucuguu auacacucag gc                            22

<210> SEQ ID NO 128
<211> LENGTH: 23
<212> TYPE: RNA
<213> ORGANISM: Homo sapiens

<400> SEQUENCE: 128
ucaagagcaa uaacgaaaaa ugu                           23

<210> SEQ ID NO 129
<211> LENGTH: 23
<212> TYPE: RNA
<213> ORGANISM: Homo sapiens

<400> SEQUENCE: 129
gauugagacu aguagggcua ggc                           23

<210> SEQ ID NO 130
<211> LENGTH: 22
<212> TYPE: RNA
<213> ORGANISM: Homo sapiens

<400> SEQUENCE: 130
agggcuuagc ugcuugugag ca                            22

<210> SEQ ID NO 131
<211> LENGTH: 22
<212> TYPE: RNA
<213> ORGANISM: Homo sapiens

<400> SEQUENCE: 131
aauugcacgg uauccaucug ua                            22

<210> SEQ ID NO 132
<211> LENGTH: 21
<212> TYPE: RNA
<213> ORGANISM: Homo sapiens

<400> SEQUENCE: 132
ugucuugcag gccgucaugc a                             21

<210> SEQ ID NO 133
<211> LENGTH: 20

```
<212> TYPE: RNA
<213> ORGANISM: Homo sapiens

<400> SEQUENCE: 133
guagaggaga uggcgcaggg                                              20

<210> SEQ ID NO 134
<211> LENGTH: 23
<212> TYPE: RNA
<213> ORGANISM: Homo sapiens

<400> SEQUENCE: 134
agugccugag ggaguaagag ccc                                          23

<210> SEQ ID NO 135
<211> LENGTH: 17
<212> TYPE: RNA
<213> ORGANISM: Homo sapiens

<400> SEQUENCE: 135
gcggggcugg gcgcgcg                                                 17

<210> SEQ ID NO 136
<211> LENGTH: 22
<212> TYPE: RNA
<213> ORGANISM: Homo sapiens

<400> SEQUENCE: 136
uggugggcac agaaucugga cu                                           22

<210> SEQ ID NO 137
<211> LENGTH: 23
<212> TYPE: RNA
<213> ORGANISM: Homo sapiens

<400> SEQUENCE: 137
uauggcuuuu cauuccuaug uga                                          23

<210> SEQ ID NO 138
<211> LENGTH: 21
<212> TYPE: RNA
<213> ORGANISM: Homo sapiens

<400> SEQUENCE: 138
uaccacaggg uagaaccacg g                                            21

<210> SEQ ID NO 139
<211> LENGTH: 24
<212> TYPE: RNA
<213> ORGANISM: Homo sapiens

<400> SEQUENCE: 139
aauccuugga accaggugu gagu                                          24

<210> SEQ ID NO 140
<211> LENGTH: 21
<212> TYPE: RNA
<213> ORGANISM: Homo sapiens

<400> SEQUENCE: 140
gcaguccaug ggcauauaca c                                            21

<210> SEQ ID NO 141
```

```
<211> LENGTH: 22
<212> TYPE: RNA
<213> ORGANISM: Homo sapiens

<400> SEQUENCE: 141
uuugugaccu gguccacuaa cc                                              22

<210> SEQ ID NO 142
<211> LENGTH: 21
<212> TYPE: RNA
<213> ORGANISM: Homo sapiens

<400> SEQUENCE: 142
uacaguacug ugauaacuga a                                               21

<210> SEQ ID NO 143
<211> LENGTH: 22
<212> TYPE: RNA
<213> ORGANISM: Homo sapiens

<400> SEQUENCE: 143
auauaauaca accugcuaag ug                                              22

<210> SEQ ID NO 144
<211> LENGTH: 22
<212> TYPE: RNA
<213> ORGANISM: Homo sapiens

<400> SEQUENCE: 144
aaaguucuga gacacuccga cu                                              22

<210> SEQ ID NO 145
<211> LENGTH: 23
<212> TYPE: RNA
<213> ORGANISM: Homo sapiens

<400> SEQUENCE: 145
caaagugcuu acagugcagg uag                                             23

<210> SEQ ID NO 146
<211> LENGTH: 23
<212> TYPE: RNA
<213> ORGANISM: Homo sapiens

<400> SEQUENCE: 146
uaaagugcuu auagugcagg uag                                             23

<210> SEQ ID NO 147
<211> LENGTH: 22
<212> TYPE: RNA
<213> ORGANISM: Homo sapiens

<400> SEQUENCE: 147
cugcccuggc ccgagggacc ga                                              22

<210> SEQ ID NO 148
<211> LENGTH: 22
<212> TYPE: RNA
<213> ORGANISM: Homo sapiens

<400> SEQUENCE: 148
aacuggcccu caaagucccg cu                                              22
```

```
<210> SEQ ID NO 149
<211> LENGTH: 22
<212> TYPE: RNA
<213> ORGANISM: Homo sapiens

<400> SEQUENCE: 149
caaaaacugc aguuacuuuu gc                                                  22

<210> SEQ ID NO 150
<211> LENGTH: 22
<212> TYPE: RNA
<213> ORGANISM: Homo sapiens

<400> SEQUENCE: 150
aucauacaag gacaauuucu uu                                                  22

<210> SEQ ID NO 151
<211> LENGTH: 23
<212> TYPE: RNA
<213> ORGANISM: Homo sapiens

<400> SEQUENCE: 151
aucaacagac auuaauuggg cgc                                                 23

<210> SEQ ID NO 152
<211> LENGTH: 22
<212> TYPE: RNA
<213> ORGANISM: Homo sapiens

<400> SEQUENCE: 152
aaggagcuca cagucuauug ag                                                  22

<210> SEQ ID NO 153
<211> LENGTH: 22
<212> TYPE: RNA
<213> ORGANISM: Homo sapiens

<400> SEQUENCE: 153
gucauacacg gcucuccucu cu                                                  22

<210> SEQ ID NO 154
<211> LENGTH: 23
<212> TYPE: RNA
<213> ORGANISM: Homo sapiens

<400> SEQUENCE: 154
ugaggcucug uuagccuugg cuc                                                 23

<210> SEQ ID NO 155
<211> LENGTH: 22
<212> TYPE: RNA
<213> ORGANISM: Homo sapiens

<400> SEQUENCE: 155
cgucccgggg cugcgcgagg ca                                                  22

<210> SEQ ID NO 156
<211> LENGTH: 22
<212> TYPE: RNA
<213> ORGANISM: Homo sapiens

<400> SEQUENCE: 156
ugccuacuga gcugaaacac ag                                                  22
```

```
<210> SEQ ID NO 157
<211> LENGTH: 23
<212> TYPE: RNA
<213> ORGANISM: Homo sapiens

<400> SEQUENCE: 157
aacauucauu guugucggug ggu                                              23

<210> SEQ ID NO 158
<211> LENGTH: 21
<212> TYPE: RNA
<213> ORGANISM: Homo sapiens

<400> SEQUENCE: 158
cacauuacac ggucgaccuc u                                                21

<210> SEQ ID NO 159
<211> LENGTH: 22
<212> TYPE: RNA
<213> ORGANISM: Homo sapiens

<400> SEQUENCE: 159
ccgcacugug gguacuugcu gc                                               22

<210> SEQ ID NO 160
<211> LENGTH: 22
<212> TYPE: RNA
<213> ORGANISM: Homo sapiens

<400> SEQUENCE: 160
acaggugagg uucuugggag cc                                               22

<210> SEQ ID NO 161
<211> LENGTH: 22
<212> TYPE: RNA
<213> ORGANISM: Homo sapiens

<400> SEQUENCE: 161
ucucugggcc ugugucuuag gc                                               22

<210> SEQ ID NO 162
<211> LENGTH: 17
<212> TYPE: RNA
<213> ORGANISM: Homo sapiens

<400> SEQUENCE: 162 guggggaga ggcuguc                                                      17

<210> SEQ ID NO 163
<211> LENGTH: 23
<212> TYPE: RNA
<213> ORGANISM: Homo sapiens

<400> SEQUENCE: 163
ugugcaaauc caugcaaaac uga                                              23

<210> SEQ ID NO 164
<211> LENGTH: 23
<212> TYPE: RNA
<213> ORGANISM: Homo sapiens

<400> SEQUENCE: 164
cagugcaaug auauugucaa agc                                              23
```

```
<210> SEQ ID NO 165
<211> LENGTH: 22
<212> TYPE: RNA
<213> ORGANISM: Homo sapiens

<400> SEQUENCE: 165
agaggcuggc cgugaugaau uc                                              22

<210> SEQ ID NO 166
<211> LENGTH: 23
<212> TYPE: RNA
<213> ORGANISM: Homo sapiens

<400> SEQUENCE: 166
uagcaccauu ugaaaucagu guu                                             23

<210> SEQ ID NO 167
<211> LENGTH: 22
<212> TYPE: RNA
<213> ORGANISM: Homo sapiens

<400> SEQUENCE: 167
aagggcuucc ucucugcagg ac                                              22

<210> SEQ ID NO 168
<211> LENGTH: 22
<212> TYPE: RNA
<213> ORGANISM: Homo sapiens

<400> SEQUENCE: 168
caggucgucu ugcagggcuu cu                                              22

<210> SEQ ID NO 169
<211> LENGTH: 23
<212> TYPE: RNA
<213> ORGANISM: Homo sapiens

<400> SEQUENCE: 169
uagugcaaua uugcuuauag ggu                                             23

<210> SEQ ID NO 170
<211> LENGTH: 21
<212> TYPE: RNA
<213> ORGANISM: Homo sapiens

<400> SEQUENCE: 170
uaaagugcug acagugcaga u                                               21

<210> SEQ ID NO 171
<211> LENGTH: 19
<212> TYPE: RNA
<213> ORGANISM: Homo sapiens

<400> SEQUENCE: 171
accgugcaaa gguagcaua                                                  19

<210> SEQ ID NO 172
<211> LENGTH: 22
<212> TYPE: RNA
<213> ORGANISM: Homo sapiens

<400> SEQUENCE: 172
```
ugcuaugcca acauauugcc au                                          22

<210> SEQ ID NO 173
<211> LENGTH: 22
<212> TYPE: RNA
<213> ORGANISM: Homo sapiens

<400> SEQUENCE: 173
cuuaucagau uguauuguaa uu                                          22

<210> SEQ ID NO 174
<211> LENGTH: 22
<212> TYPE: RNA
<213> ORGANISM: Homo sapiens

<400> SEQUENCE: 174
aucaugaugg gcuccucggu gu                                          22

<210> SEQ ID NO 175
<211> LENGTH: 18
<212> TYPE: RNA
<213> ORGANISM: Homo sapiens

<400> SEQUENCE: 175
ggugggcuuc ccggaggg                                               18

<210> SEQ ID NO 176
<211> LENGTH: 21
<212> TYPE: RNA
<213> ORGANISM: Homo sapiens

<400> SEQUENCE: 176
ugagaugaag cacuguagcu c                                           21

<210> SEQ ID NO 177
<211> LENGTH: 23
<212> TYPE: RNA
<213> ORGANISM: Homo sapiens

<400> SEQUENCE: 177
ugugcaaauc uaugcaaaac uga                                         23

<210> SEQ ID NO 178
<211> LENGTH: 22
<212> TYPE: RNA
<213> ORGANISM: Homo sapiens

<400> SEQUENCE: 178
caugccuuga guguaggacc gu                                          22

<210> SEQ ID NO 179
<211> LENGTH: 22
<212> TYPE: RNA
<213> ORGANISM: Homo sapiens

<400> SEQUENCE: 179
aucaaggauc uuaaacuuug cc                                          22

<210> SEQ ID NO 180
<211> LENGTH: 22
<212> TYPE: RNA
<213> ORGANISM: Homo sapiens

<400> SEQUENCE: 180
gguggcccgg ccgugccuga gg                                                    22

<210> SEQ ID NO 181
<211> LENGTH: 24
<212> TYPE: RNA
<213> ORGANISM: Homo sapiens

<400> SEQUENCE: 181
uugcagcugc cugggaguga cuuc                                                  24

<210> SEQ ID NO 182
<211> LENGTH: 22
<212> TYPE: RNA
<213> ORGANISM: Homo sapiens

<400> SEQUENCE: 182 uauguggau gguaaaccgc uu                                                     22

<210> SEQ ID NO 183
<211> LENGTH: 22
<212> TYPE: RNA
<213> ORGANISM: Homo sapiens

<400> SEQUENCE: 183
auaaagcuag auaaccgaaa gu                                                    22

<210> SEQ ID NO 184
<211> LENGTH: 22
<212> TYPE: RNA
<213> ORGANISM: Homo sapiens

<400> SEQUENCE: 184
acugcaguga aggcacuugu ag                                                    22

<210> SEQ ID NO 185
<211> LENGTH: 21
<212> TYPE: RNA
<213> ORGANISM: Homo sapiens

<400> SEQUENCE: 185
aacauagagg aaauuccacg u                                                     21

<210> SEQ ID NO 186
<211> LENGTH: 22
<212> TYPE: RNA
<213> ORGANISM: Homo sapiens

<400> SEQUENCE: 186
cagcagcaau ucauguuuug aa                                                    22

<210> SEQ ID NO 187
<211> LENGTH: 22
<212> TYPE: RNA
<213> ORGANISM: Homo sapiens

<400> SEQUENCE: 187
uacccauugc auaucggagu ug                                                    22

<210> SEQ ID NO 188
<211> LENGTH: 22
<212> TYPE: RNA
<213> ORGANISM: Homo sapiens

```
<400> SEQUENCE: 188
uugcauaguc acaaaaguga uc                                      22

<210> SEQ ID NO 189
<211> LENGTH: 23
<212> TYPE: RNA
<213> ORGANISM: Homo sapiens

<400> SEQUENCE: 189
ugaggaugga uagcaaggaa gcc                                     23

<210> SEQ ID NO 190
<211> LENGTH: 24
<212> TYPE: RNA
<213> ORGANISM: Homo sapiens

<400> SEQUENCE: 190
cccggacagg cguucgugcg acgu                                    24

<210> SEQ ID NO 191
<211> LENGTH: 18
<212> TYPE: RNA
<213> ORGANISM: Homo sapiens

<400> SEQUENCE: 191
gggcucacau caccccau                                           18

<210> SEQ ID NO 192
<211> LENGTH: 22
<212> TYPE: RNA
<213> ORGANISM: Homo sapiens

<400> SEQUENCE: 192
uaugugccuu uggacuacau cg                                      22

<210> SEQ ID NO 193
<211> LENGTH: 22
<212> TYPE: RNA
<213> ORGANISM: Homo sapiens

<400> SEQUENCE: 193
aaacauucgc ggugcacuuc uu                                      22

<210> SEQ ID NO 194
<211> LENGTH: 20
<212> TYPE: RNA
<213> ORGANISM: Homo sapiens

<400> SEQUENCE: 194
uaaagagccc uguggagaca                                         20

<210> SEQ ID NO 195
<211> LENGTH: 23
<212> TYPE: RNA
<213> ORGANISM: Homo sapiens

<400> SEQUENCE: 195
gcaaagcaca cggccugcag aga                                     23

<210> SEQ ID NO 196
<211> LENGTH: 21
<212> TYPE: RNA
<213> ORGANISM: Homo sapiens
```

```
<400> SEQUENCE: 196
aauaauacau gguugaucuu u                                          21

<210> SEQ ID NO 197
<211> LENGTH: 22
<212> TYPE: RNA
<213> ORGANISM: Homo sapiens

<400> SEQUENCE: 197
ugagaccagg acuggaugca cc                                         22

<210> SEQ ID NO 198
<211> LENGTH: 22
<212> TYPE: RNA
<213> ORGANISM: Homo sapiens

<400> SEQUENCE: 198
aaaaguacuu gcggauuuug cu                                         22

<210> SEQ ID NO 199
<211> LENGTH: 22
<212> TYPE: RNA
<213> ORGANISM: Homo sapiens

<400> SEQUENCE: 199
ucaccagccc uguguucccu ag                                         22

<210> SEQ ID NO 200
<211> LENGTH: 21
<212> TYPE: RNA
<213> ORGANISM: Homo sapiens

<400> SEQUENCE: 200
cucccacaug caggguuugc a                                          21

<210> SEQ ID NO 201
<211> LENGTH: 22
<212> TYPE: RNA
<213> ORGANISM: Homo sapiens

<400> SEQUENCE: 201
agagcuuagc ugauugguga ac                                         22

<210> SEQ ID NO 202
<211> LENGTH: 22
<212> TYPE: RNA
<213> ORGANISM: Homo sapiens

<400> SEQUENCE: 202
agagguugcc cuuggugaau uc                                         22

<210> SEQ ID NO 203
<211> LENGTH: 22
<212> TYPE: RNA
<213> ORGANISM: Homo sapiens

<400> SEQUENCE: 203
aaucauacag ggacauccag uu                                         22

<210> SEQ ID NO 204
<211> LENGTH: 23
<212> TYPE: RNA
```

```
<213> ORGANISM: Homo sapiens

<400> SEQUENCE: 204
agguugggau cgguugcaau gcu                                    23

<210> SEQ ID NO 205
<211> LENGTH: 22
<212> TYPE: RNA
<213> ORGANISM: Homo sapiens

<400> SEQUENCE: 205
auguagggcu aaaagccaug gg                                     22

<210> SEQ ID NO 206
<211> LENGTH: 21
<212> TYPE: RNA
<213> ORGANISM: Homo sapiens

<400> SEQUENCE: 206
uugugcuuga ucuaaccaug u                                      21

<210> SEQ ID NO 207
<211> LENGTH: 23
<212> TYPE: RNA
<213> ORGANISM: Homo sapiens

<400> SEQUENCE: 207
uagcccccag gcuucacuug gcg                                    23

<210> SEQ ID NO 208
<211> LENGTH: 22
<212> TYPE: RNA
<213> ORGANISM: Homo sapiens

<400> SEQUENCE: 208
agggacggga cgcggugcag ug                                     22

<210> SEQ ID NO 209
<211> LENGTH: 22
<212> TYPE: RNA
<213> ORGANISM: Homo sapiens

<400> SEQUENCE: 209
auauacaggg ggagacucuu au                                     22

<210> SEQ ID NO 210
<211> LENGTH: 21
<212> TYPE: RNA
<213> ORGANISM: Homo sapiens

<400> SEQUENCE: 210
accacugcac uccagccuga g                                      21

<210> SEQ ID NO 211
<211> LENGTH: 21
<212> TYPE: RNA
<213> ORGANISM: Homo sapiens

<400> SEQUENCE: 211
auccccagau acaauggaca a                                      21

<210> SEQ ID NO 212
<211> LENGTH: 22
```

<212> TYPE: RNA
<213> ORGANISM: Homo sapiens

<400> SEQUENCE: 212
gggguuccug gggaugggau uu                                          22

<210> SEQ ID NO 213
<211> LENGTH: 22
<212> TYPE: RNA
<213> ORGANISM: Homo sapiens

<400> SEQUENCE: 213
cugggagagg guuguuuacu cc                                          22

<210> SEQ ID NO 214
<211> LENGTH: 22
<212> TYPE: RNA
<213> ORGANISM: Homo sapiens

<400> SEQUENCE: 214
aacacaccug guuaaccucu uu                                          22

<210> SEQ ID NO 215
<211> LENGTH: 22
<212> TYPE: RNA
<213> ORGANISM: Homo sapiens

<400> SEQUENCE: 215
cuccuauaug augccuuucu uc                                          22

<210> SEQ ID NO 216
<211> LENGTH: 24
<212> TYPE: RNA
<213> ORGANISM: Homo sapiens

<400> SEQUENCE: 216
caaagugaug aguaauacug gcug                                        24

<210> SEQ ID NO 217
<211> LENGTH: 22
<212> TYPE: RNA
<213> ORGANISM: Homo sapiens

<400> SEQUENCE: 217
cuccugacuc cagguccugu gu                                          22

<210> SEQ ID NO 218
<211> LENGTH: 23
<212> TYPE: RNA
<213> ORGANISM: Homo sapiens

<400> SEQUENCE: 218
gaggcugaug ugaguagacc acu                                         23

<210> SEQ ID NO 219
<211> LENGTH: 23
<212> TYPE: RNA
<213> ORGANISM: Homo sapiens

<400> SEQUENCE: 219 ugagugggc ucccgggacg gcg                                          23

<210> SEQ ID NO 220

```
<211> LENGTH: 21
<212> TYPE: RNA
<213> ORGANISM: Homo sapiens

<400> SEQUENCE: 220
guuucaccau guuggucagg c                                              21

<210> SEQ ID NO 221
<211> LENGTH: 21
<212> TYPE: RNA
<213> ORGANISM: Homo sapiens

<400> SEQUENCE: 221
aauauuauac agucaaccuc u                                              21

<210> SEQ ID NO 222
<211> LENGTH: 21
<212> TYPE: RNA
<213> ORGANISM: Homo sapiens

<400> SEQUENCE: 222
cuauacaauc uacugucuuu c                                              21

<210> SEQ ID NO 223
<211> LENGTH: 22
<212> TYPE: RNA
<213> ORGANISM: Homo sapiens

<400> SEQUENCE: 223
uagcagcaca uaaugguuug ug                                             22

<210> SEQ ID NO 224
<211> LENGTH: 22
<212> TYPE: RNA
<213> ORGANISM: Homo sapiens

<400> SEQUENCE: 224
uggagagaaa ggcaguuccu ga                                             22

<210> SEQ ID NO 225
<211> LENGTH: 21
<212> TYPE: RNA
<213> ORGANISM: Homo sapiens

<400> SEQUENCE: 225
aggcggagac uugggcaauu g                                              21

<210> SEQ ID NO 226
<211> LENGTH: 23
<212> TYPE: RNA
<213> ORGANISM: Homo sapiens

<400> SEQUENCE: 226
ucaacaaaau cacugaugcu gga                                            23

<210> SEQ ID NO 227
<211> LENGTH: 19
<212> TYPE: RNA
<213> ORGANISM: Homo sapiens

<400> SEQUENCE: 227
acuggccugg gacuaccgg                                                 19
```

```
<210> SEQ ID NO 228
<211> LENGTH: 23
<212> TYPE: RNA
<213> ORGANISM: Homo sapiens

<400> SEQUENCE: 228
ugagcgccuc gacgacagag ccg                                           23

<210> SEQ ID NO 229
<211> LENGTH: 22
<212> TYPE: RNA
<213> ORGANISM: Homo sapiens

<400> SEQUENCE: 229
cuuagcaggu uguauuauca uu                                            22

<210> SEQ ID NO 230
<211> LENGTH: 22
<212> TYPE: RNA
<213> ORGANISM: Homo sapiens

<400> SEQUENCE: 230
auggccagag cucacacaga gg                                            22

<210> SEQ ID NO 231
<211> LENGTH: 20
<212> TYPE: RNA
<213> ORGANISM: Homo sapiens

<400> SEQUENCE: 231
ggcuccuugg ucuaggggua                                               20

<210> SEQ ID NO 232
<211> LENGTH: 17
<212> TYPE: RNA
<213> ORGANISM: Homo sapiens

<400> SEQUENCE: 232
cuccgggacg gcugggc                                                  17

<210> SEQ ID NO 233
<211> LENGTH: 22
<212> TYPE: RNA
<213> ORGANISM: Homo sapiens

<400> SEQUENCE: 233
gcuaaggaag uccugugcuc ag                                            22

<210> SEQ ID NO 234
<211> LENGTH: 22
<212> TYPE: RNA
<213> ORGANISM: Homo sapiens

<400> SEQUENCE: 234
ggagaaauua uccuuggugu gu                                            22

<210> SEQ ID NO 235
<211> LENGTH: 20
<212> TYPE: RNA
<213> ORGANISM: Homo sapiens

<400> SEQUENCE: 235
aaaagugauu gcaguguuug                                               20
```

```
<210> SEQ ID NO 236
<211> LENGTH: 21
<212> TYPE: RNA
<213> ORGANISM: Homo sapiens

<400> SEQUENCE: 236
ccaguccugu gccugccgcc u                                              21

<210> SEQ ID NO 237
<211> LENGTH: 21
<212> TYPE: RNA
<213> ORGANISM: Homo sapiens

<400> SEQUENCE: 237
aucauagagg aaaauccacg u                                              21

<210> SEQ ID NO 238
<211> LENGTH: 22
<212> TYPE: RNA
<213> ORGANISM: Homo sapiens

<400> SEQUENCE: 238
gaaguuguuc gugguggauu cg                                             22

<210> SEQ ID NO 239
<211> LENGTH: 22
<212> TYPE: RNA
<213> ORGANISM: Homo sapiens

<400> SEQUENCE: 239
cagcccggau cccagcccac uu                                             22

<210> SEQ ID NO 240
<211> LENGTH: 22
<212> TYPE: RNA
<213> ORGANISM: Homo sapiens

<400> SEQUENCE: 240
ugaaacauac acgggaaacc uc                                             22

<210> SEQ ID NO 241
<211> LENGTH: 22
<212> TYPE: RNA
<213> ORGANISM: Homo sapiens

<400> SEQUENCE: 241
aaacaaacau ggugcacuuc uu                                             22

<210> SEQ ID NO 242
<211> LENGTH: 22
<212> TYPE: RNA
<213> ORGANISM: Homo sapiens

<400> SEQUENCE: 242
ucagcaaaca uuuauugugu gc                                             22

<210> SEQ ID NO 243
<211> LENGTH: 22
<212> TYPE: RNA
<213> ORGANISM: Homo sapiens

<400> SEQUENCE: 243
caagcucgug ucuguggguc cg                                             22
```

<210> SEQ ID NO 244
<211> LENGTH: 21
<212> TYPE: RNA
<213> ORGANISM: Homo sapiens

<400> SEQUENCE: 244
uaggacacau ggucuacuuc u                                     21

<210> SEQ ID NO 245
<211> LENGTH: 21
<212> TYPE: RNA
<213> ORGANISM: Homo sapiens

<400> SEQUENCE: 245
cucacugaac aaugaaugca a                                     21

<210> SEQ ID NO 246
<211> LENGTH: 23
<212> TYPE: RNA
<213> ORGANISM: Homo sapiens

<400> SEQUENCE: 246
accuuggcuc uagacugcuu acu                                   23

<210> SEQ ID NO 247
<211> LENGTH: 22
<212> TYPE: RNA
<213> ORGANISM: Homo sapiens

<400> SEQUENCE: 247
caccuugcgc uacucagguc ug                                    22

<210> SEQ ID NO 248
<211> LENGTH: 22
<212> TYPE: RNA
<213> ORGANISM: Homo sapiens

<400> SEQUENCE: 248
uccgucucag uuacuuuaua gc                                    22

<210> SEQ ID NO 249
<211> LENGTH: 22
<212> TYPE: RNA
<213> ORGANISM: Homo sapiens

<400> SEQUENCE: 249
gcaugugaug aagcaaauca gu                                    22

<210> SEQ ID NO 250
<211> LENGTH: 23
<212> TYPE: RNA
<213> ORGANISM: Homo sapiens

<400> SEQUENCE: 250 uccccccaggu gugauucuga uuu                                  23

<210> SEQ ID NO 251
<211> LENGTH: 17
<212> TYPE: RNA
<213> ORGANISM: Homo sapiens

<400> SEQUENCE: 251
ggcgggugcg ggggugg                                                      17

<210> SEQ ID NO 252
<211> LENGTH: 22
<212> TYPE: RNA
<213> ORGANISM: Homo sapiens

<400> SEQUENCE: 252
ccucccacac ccaaggcuug ca                                                22

<210> SEQ ID NO 253
<211> LENGTH: 22
<212> TYPE: RNA
<213> ORGANISM: Homo sapiens

<400> SEQUENCE: 253
cacgcucaug cacacaccca ca                                                22

<210> SEQ ID NO 254
<211> LENGTH: 23
<212> TYPE: RNA
<213> ORGANISM: Homo sapiens

<400> SEQUENCE: 254
agcagcauug uacagggcua uca                                               23

<210> SEQ ID NO 255
<211> LENGTH: 22
<212> TYPE: RNA
<213> ORGANISM: Homo sapiens

<400> SEQUENCE: 255
cugaagcuca gagggcucug au                                                22

<210> SEQ ID NO 256
<211> LENGTH: 23
<212> TYPE: RNA
<213> ORGANISM: Homo sapiens

<400> SEQUENCE: 256
uaaggugcau cuagugcaga uag                                               23

<210> SEQ ID NO 257
<211> LENGTH: 22
<212> TYPE: RNA
<213> ORGANISM: Homo sapiens

<400> SEQUENCE: 257
ccuauucuug auuacuuguu uc                                                22

<210> SEQ ID NO 258
<211> LENGTH: 21
<212> TYPE: RNA
<213> ORGANISM: Homo sapiens

<400> SEQUENCE: 258 agggccccccc cucaauccug u                                                21

<210> SEQ ID NO 259
<211> LENGTH: 21
<212> TYPE: RNA
<213> ORGANISM: Homo sapiens

<400> SEQUENCE: 259

-continued agccgcgggg aucgccgagg g                                    21

<210> SEQ ID NO 260
<211> LENGTH: 21
<212> TYPE: RNA
<213> ORGANISM: Homo sapiens

<400> SEQUENCE: 260
aaucauucac ggacaacacu u                                    21

<210> SEQ ID NO 261
<211> LENGTH: 22
<212> TYPE: RNA
<213> ORGANISM: Homo sapiens

<400> SEQUENCE: 261
uacgcgcaga ccacaggaug uc                                   22

<210> SEQ ID NO 262
<211> LENGTH: 21
<212> TYPE: RNA
<213> ORGANISM: Homo sapiens

<400> SEQUENCE: 262
cuggauggcu ccuccauguc u                                    21

<210> SEQ ID NO 263
<211> LENGTH: 22
<212> TYPE: RNA
<213> ORGANISM: Homo sapiens

<400> SEQUENCE: 263
aguugccuuu uuguucccau gc                                   22

<210> SEQ ID NO 264
<211> LENGTH: 18
<212> TYPE: RNA
<213> ORGANISM: Homo sapiens

<400> SEQUENCE: 264
gggugcgggc cggcgggg                                        18

<210> SEQ ID NO 265
<211> LENGTH: 22
<212> TYPE: RNA
<213> ORGANISM: Homo sapiens

<400> SEQUENCE: 265
acccuaucaa uauugucucu gc                                   22

<210> SEQ ID NO 266
<211> LENGTH: 23
<212> TYPE: RNA
<213> ORGANISM: Homo sapiens

<400> SEQUENCE: 266
ccggucccag gagaaccugc aga                                  23

<210> SEQ ID NO 267
<211> LENGTH: 22
<212> TYPE: RNA
<213> ORGANISM: Homo sapiens

```
<400> SEQUENCE: 267
ugaguauuac auggccaauc uc                                       22

<210> SEQ ID NO 268
<211> LENGTH: 22
<212> TYPE: RNA
<213> ORGANISM: Homo sapiens

<400> SEQUENCE: 268
ccaaaacugc aguuacuuuu gc                                       22

<210> SEQ ID NO 269
<211> LENGTH: 27
<212> TYPE: RNA
<213> ORGANISM: Homo sapiens

<400> SEQUENCE: 269
accuucuugu auaagcacug ugcuaaa                                  27

<210> SEQ ID NO 270
<211> LENGTH: 24
<212> TYPE: RNA
<213> ORGANISM: Homo sapiens

<400> SEQUENCE: 270
agccuggaag cuggagccug cagu                                     24

<210> SEQ ID NO 271
<211> LENGTH: 22
<212> TYPE: RNA
<213> ORGANISM: Homo sapiens

<400> SEQUENCE: 271
uuagggcccu ggcuccaucu cc                                       22

<210> SEQ ID NO 272
<211> LENGTH: 23
<212> TYPE: RNA
<213> ORGANISM: Homo sapiens

<400> SEQUENCE: 272
acuccauuug uuuugaugau gga                                      23

<210> SEQ ID NO 273
<211> LENGTH: 23
<212> TYPE: RNA
<213> ORGANISM: Homo sapiens

<400> SEQUENCE: 273
cccaguguuc agacuaccug uuc                                      23

<210> SEQ ID NO 274
<211> LENGTH: 22
<212> TYPE: RNA
<213> ORGANISM: Homo sapiens

<400> SEQUENCE: 274
gaggguuggg uggaggcucu cc                                       22

<210> SEQ ID NO 275
<211> LENGTH: 21
<212> TYPE: RNA
<213> ORGANISM: Homo sapiens
```

```
<400> SEQUENCE: 275
ugcacggcac ugggacacg u                                              21

<210> SEQ ID NO 276
<211> LENGTH: 20
<212> TYPE: RNA
<213> ORGANISM: Homo sapiens

<400> SEQUENCE: 276
acugccccag gugcugcugg                                               20

<210> SEQ ID NO 277
<211> LENGTH: 21
<212> TYPE: RNA
<213> ORGANISM: Homo sapiens

<400> SEQUENCE: 277
gaacggcuuc auacaggagu u                                             21

<210> SEQ ID NO 278
<211> LENGTH: 21
<212> TYPE: RNA
<213> ORGANISM: Homo sapiens

<400> SEQUENCE: 278
aggggugcua ucugugauug a                                             21

<210> SEQ ID NO 279
<211> LENGTH: 22
<212> TYPE: RNA
<213> ORGANISM: Homo sapiens

<400> SEQUENCE: 279
uaaugccccu aaaaauccuu au                                            22

<210> SEQ ID NO 280
<211> LENGTH: 15
<212> TYPE: RNA
<213> ORGANISM: Homo sapiens

<400> SEQUENCE: 280
aggagauccu ggguu                                                    15

<210> SEQ ID NO 281
<211> LENGTH: 22
<212> TYPE: RNA
<213> ORGANISM: Homo sapiens

<400> SEQUENCE: 281
aaugcaccug ggcaaggauu ca                                            22

<210> SEQ ID NO 282
<211> LENGTH: 22
<212> TYPE: RNA
<213> ORGANISM: Homo sapiens

<400> SEQUENCE: 282
cgucaacacu ugcugguuuc cu                                            22

<210> SEQ ID NO 283
<211> LENGTH: 22
<212> TYPE: RNA
```

```
<213> ORGANISM: Homo sapiens

<400> SEQUENCE: 283
ugucuuacuc ccucaggcac au                                            22

<210> SEQ ID NO 284
<211> LENGTH: 21
<212> TYPE: RNA
<213> ORGANISM: Homo sapiens

<400> SEQUENCE: 284
gccccgggca gugugaucau c                                             21

<210> SEQ ID NO 285
<211> LENGTH: 24
<212> TYPE: RNA
<213> ORGANISM: Homo sapiens

<400> SEQUENCE: 285
aaagacauag gauagaguca ccuc                                          24

<210> SEQ ID NO 286
<211> LENGTH: 22
<212> TYPE: RNA
<213> ORGANISM: Homo sapiens

<400> SEQUENCE: 286
auaauacaug guuaaccucu uu                                            22

<210> SEQ ID NO 287
<211> LENGTH: 23
<212> TYPE: RNA
<213> ORGANISM: Homo sapiens

<400> SEQUENCE: 287
uauucauuua uccccagccu aca                                           23

<210> SEQ ID NO 288
<211> LENGTH: 23
<212> TYPE: RNA
<213> ORGANISM: Homo sapiens

<400> SEQUENCE: 288
aggaagcccu ggaggggcug gag                                           23

<210> SEQ ID NO 289
<211> LENGTH: 20
<212> TYPE: RNA
<213> ORGANISM: Homo sapiens

<400> SEQUENCE: 289
cggcucuggg ucugugggga                                               20

<210> SEQ ID NO 290
<211> LENGTH: 22
<212> TYPE: RNA
<213> ORGANISM: Homo sapiens

<400> SEQUENCE: 290
cuauacggcc uccuagcuuu cc                                            22

<210> SEQ ID NO 291
<211> LENGTH: 18
```

```
<212> TYPE: RNA
<213> ORGANISM: Homo sapiens

<400> SEQUENCE: 291
cgggcguggu ggugggg                                                  18

<210> SEQ ID NO 292
<211> LENGTH: 19
<212> TYPE: RNA
<213> ORGANISM: Homo sapiens

<400> SEQUENCE: 292
ggagauggag guugcagug                                                19

<210> SEQ ID NO 293
<211> LENGTH: 21
<212> TYPE: RNA
<213> ORGANISM: Homo sapiens

<400> SEQUENCE: 293
ugcaggacca agaugagccc u                                             21

<210> SEQ ID NO 294
<211> LENGTH: 24
<212> TYPE: RNA
<213> ORGANISM: Homo sapiens

<400> SEQUENCE: 294
uggcccugac ugaagaccag cagu                                          24

<210> SEQ ID NO 295
<211> LENGTH: 22
<212> TYPE: RNA
<213> ORGANISM: Homo sapiens

<400> SEQUENCE: 295
uaacacuguc ugguaaagau gg                                            22

<210> SEQ ID NO 296
<211> LENGTH: 21
<212> TYPE: RNA
<213> ORGANISM: Homo sapiens

<400> SEQUENCE: 296
cuccguuugc cuguuucgcu g                                             21

<210> SEQ ID NO 297
<211> LENGTH: 22
<212> TYPE: RNA
<213> ORGANISM: Homo sapiens

<400> SEQUENCE: 297
cuggcccucu cugcccuucc gu                                            22

<210> SEQ ID NO 298
<211> LENGTH: 21
<212> TYPE: RNA
<213> ORGANISM: Homo sapiens

<400> SEQUENCE: 298
caaaacguga ggcgcugcua u                                             21

<210> SEQ ID NO 299
```

```
<211> LENGTH: 20
<212> TYPE: RNA
<213> ORGANISM: Homo sapiens

<400> SEQUENCE: 299
ggauccgagu cacggcacca                                                    20

<210> SEQ ID NO 300
<211> LENGTH: 17
<212> TYPE: RNA
<213> ORGANISM: Homo sapiens

<400> SEQUENCE: 300
gagacugggg uggggcc                                                       17

<210> SEQ ID NO 301
<211> LENGTH: 21
<212> TYPE: RNA
<213> ORGANISM: Homo sapiens

<400> SEQUENCE: 301
uuagugcaua gucuuugguc u                                                  21

<210> SEQ ID NO 302
<211> LENGTH: 22
<212> TYPE: RNA
<213> ORGANISM: Homo sapiens

<400> SEQUENCE: 302
uuaauuuuuu guuucgguca cu                                                 22

<210> SEQ ID NO 303
<211> LENGTH: 23
<212> TYPE: RNA
<213> ORGANISM: Homo sapiens

<400> SEQUENCE: 303
uaauccuugc uaccugggug aga                                                23

<210> SEQ ID NO 304
<211> LENGTH: 22
<212> TYPE: RNA
<213> ORGANISM: Homo sapiens

<400> SEQUENCE: 304
aaaaguaauu gugguuuugg cc                                                 22

<210> SEQ ID NO 305
<211> LENGTH: 24
<212> TYPE: RNA
<213> ORGANISM: Homo sapiens

<400> SEQUENCE: 305
cugaagugau guguaacuga ucag                                               24

<210> SEQ ID NO 306
<211> LENGTH: 22
<212> TYPE: RNA
<213> ORGANISM: Homo sapiens

<400> SEQUENCE: 306
auucuaauuu cuccacgucu uu                                                 22
```

```
<210> SEQ ID NO 307
<211> LENGTH: 22
<212> TYPE: RNA
<213> ORGANISM: Homo sapiens

<400> SEQUENCE: 307
gacuauagaa cuuccccccu ca                                          22

<210> SEQ ID NO 308
<211> LENGTH: 21
<212> TYPE: RNA
<213> ORGANISM: Homo sapiens

<400> SEQUENCE: 308
aauggcgcca cuaggguugu g                                           21

<210> SEQ ID NO 309
<211> LENGTH: 20
<212> TYPE: RNA
<213> ORGANISM: Homo sapiens

<400> SEQUENCE: 309
accaggaggc ugaggcccu                                              20

<210> SEQ ID NO 310
<211> LENGTH: 22
<212> TYPE: RNA
<213> ORGANISM: Homo sapiens

<400> SEQUENCE: 310
acuccagccc cacagccuca gc                                          22

<210> SEQ ID NO 311
<211> LENGTH: 23
<212> TYPE: RNA
<213> ORGANISM: Homo sapiens

<400> SEQUENCE: 311
ccaguuaccg cuuccgcuac cgc                                         23

<210> SEQ ID NO 312
<211> LENGTH: 22
<212> TYPE: RNA
<213> ORGANISM: Homo sapiens

<400> SEQUENCE: 312
auccgcgcuc ugacucucug cc                                          22

<210> SEQ ID NO 313
<211> LENGTH: 22
<212> TYPE: RNA
<213> ORGANISM: Homo sapiens

<400> SEQUENCE: 313
uuuccggcuc gcguggugu gu                                           22

<210> SEQ ID NO 314
<211> LENGTH: 22
<212> TYPE: RNA
<213> ORGANISM: Homo sapiens

<400> SEQUENCE: 314
auauacaggg ggagacucuc au                                          22
```

```
<210> SEQ ID NO 315
<211> LENGTH: 22
<212> TYPE: RNA
<213> ORGANISM: Homo sapiens

<400> SEQUENCE: 315
accguggcuu ucgauuguua cu                                              22

<210> SEQ ID NO 316
<211> LENGTH: 22
<212> TYPE: RNA
<213> ORGANISM: Homo sapiens

<400> SEQUENCE: 316
ccaauauuac ugugcugcuu ua                                              22

<210> SEQ ID NO 317
<211> LENGTH: 23
<212> TYPE: RNA
<213> ORGANISM: Homo sapiens

<400> SEQUENCE: 317
caaagugcuc auagugcagg uag                                             23

<210> SEQ ID NO 318
<211> LENGTH: 21
<212> TYPE: RNA
<213> ORGANISM: Homo sapiens

<400> SEQUENCE: 318
ccucccaugc caagaacucc c                                               21

<210> SEQ ID NO 319
<211> LENGTH: 22
<212> TYPE: RNA
<213> ORGANISM: Homo sapiens

<400> SEQUENCE: 319
ugguuuaccg ucccacauac au                                              22

<210> SEQ ID NO 320
<211> LENGTH: 22
<212> TYPE: RNA
<213> ORGANISM: Homo sapiens

<400> SEQUENCE: 320
cugggaggug gauguuuacu uc                                              22

<210> SEQ ID NO 321
<211> LENGTH: 22
<212> TYPE: RNA
<213> ORGANISM: Homo sapiens

<400> SEQUENCE: 321
cugggagaag gcuguuuacu cu                                              22

<210> SEQ ID NO 322
<211> LENGTH: 20
<212> TYPE: RNA
<213> ORGANISM: Homo sapiens

<400> SEQUENCE: 322
uuggccaugg ggcugcgcgg                                                 20
```

```
<210> SEQ ID NO 323
<211> LENGTH: 21
<212> TYPE: RNA
<213> ORGANISM: Homo sapiens

<400> SEQUENCE: 323
ucucucggcu ccucgcggcu c                                              21

<210> SEQ ID NO 324
<211> LENGTH: 22
<212> TYPE: RNA
<213> ORGANISM: Homo sapiens

<400> SEQUENCE: 324
ucacccugca ucccgcaccc ag                                             22

<210> SEQ ID NO 325
<211> LENGTH: 19
<212> TYPE: RNA
<213> ORGANISM: Homo sapiens

<400> SEQUENCE: 325
gacuggacaa gcugaggaa                                                 19

<210> SEQ ID NO 326
<211> LENGTH: 24
<212> TYPE: RNA
<213> ORGANISM: Homo sapiens

<400> SEQUENCE: 326
gaaaaugaug aguagugacu gaug                                           24

<210> SEQ ID NO 327
<211> LENGTH: 22
<212> TYPE: RNA
<213> ORGANISM: Homo sapiens

<400> SEQUENCE: 327
uaguggauga ugcacucugu gc                                             22

<210> SEQ ID NO 328
<211> LENGTH: 17
<212> TYPE: RNA
<213> ORGANISM: Homo sapiens

<400> SEQUENCE: 328
accccacucc ugguacc                                                   17

<210> SEQ ID NO 329
<211> LENGTH: 22
<212> TYPE: RNA
<213> ORGANISM: Homo sapiens

<400> SEQUENCE: 329 caccccugu uuccuggccc ac                                              22

<210> SEQ ID NO 330
<211> LENGTH: 21
<212> TYPE: RNA
<213> ORGANISM: Homo sapiens

<400> SEQUENCE: 330
```

```
acacaugggu ggcuguggcc u                                          21

<210> SEQ ID NO 331
<211> LENGTH: 22
<212> TYPE: RNA
<213> ORGANISM: Homo sapiens

<400> SEQUENCE: 331
ugugacagau ugauaacuga aa                                         22

<210> SEQ ID NO 332
<211> LENGTH: 22
<212> TYPE: RNA
<213> ORGANISM: Homo sapiens

<400> SEQUENCE: 332
cagggaaaug ggaagaacua ga                                         22

<210> SEQ ID NO 333
<211> LENGTH: 22
<212> TYPE: RNA
<213> ORGANISM: Homo sapiens

<400> SEQUENCE: 333
cgaaaacagc aauuaccuuu gc                                         22

<210> SEQ ID NO 334
<211> LENGTH: 23
<212> TYPE: RNA
<213> ORGANISM: Homo sapiens

<400> SEQUENCE: 334
ugagugugug ugugagug ugu                                          23

<210> SEQ ID NO 335
<211> LENGTH: 21
<212> TYPE: RNA
<213> ORGANISM: Homo sapiens

<400> SEQUENCE: 335
ucuaguaaga guggcagucg a                                          21

<210> SEQ ID NO 336
<211> LENGTH: 22
<212> TYPE: RNA
<213> ORGANISM: Homo sapiens

<400> SEQUENCE: 336
uaugucugcu gaccaucacc uu                                         22

<210> SEQ ID NO 337
<211> LENGTH: 23
<212> TYPE: RNA
<213> ORGANISM: Homo sapiens

<400> SEQUENCE: 337
cugggaucuc cgggucuug guu                                         23

<210> SEQ ID NO 338
<211> LENGTH: 21
<212> TYPE: RNA
<213> ORGANISM: Homo sapiens

<400> SEQUENCE: 338
```
cugacuguug ccguccucca g                                             21

<210> SEQ ID NO 339
<211> LENGTH: 22
<212> TYPE: RNA
<213> ORGANISM: Homo sapiens

<400> SEQUENCE: 339
cuauacaacc uacugccuuc cc                                            22

<210> SEQ ID NO 340
<211> LENGTH: 26
<212> TYPE: RNA
<213> ORGANISM: Homo sapiens

<400> SEQUENCE: 340
aaguaguugg uuuguaugag augguu                                        26

<210> SEQ ID NO 341
<211> LENGTH: 23
<212> TYPE: RNA
<213> ORGANISM: Homo sapiens

<400> SEQUENCE: 341
aggaugagca aagaaaguag auu                                           23

<210> SEQ ID NO 342
<211> LENGTH: 22
<212> TYPE: RNA
<213> ORGANISM: Homo sapiens

<400> SEQUENCE: 342
uugcuugaac ccaggaagug ga                                            22

<210> SEQ ID NO 343
<211> LENGTH: 23
<212> TYPE: RNA
<213> ORGANISM: Homo sapiens

<400> SEQUENCE: 343
uggaguccag gaaucugcau uuu                                           23

<210> SEQ ID NO 344
<211> LENGTH: 21
<212> TYPE: RNA
<213> ORGANISM: Homo sapiens

<400> SEQUENCE: 344
ucagugcaug acagaacuug g                                             21

<210> SEQ ID NO 345
<211> LENGTH: 22
<212> TYPE: RNA
<213> ORGANISM: Homo sapiens

<400> SEQUENCE: 345
uguaacagca acuccaugug ga                                            22

<210> SEQ ID NO 346
<211> LENGTH: 21
<212> TYPE: RNA
<213> ORGANISM: Homo sapiens

```
<400> SEQUENCE: 346
uagcagcaca gaaauauugg c                                          21

<210> SEQ ID NO 347
<211> LENGTH: 23
<212> TYPE: RNA
<213> ORGANISM: Homo sapiens

<400> SEQUENCE: 347
uaauacugcc ggguaaugau gga                                        23

<210> SEQ ID NO 348
<211> LENGTH: 21
<212> TYPE: RNA
<213> ORGANISM: Homo sapiens

<400> SEQUENCE: 348
uaacagucuc cagucacggc c                                          21

<210> SEQ ID NO 349
<211> LENGTH: 22
<212> TYPE: RNA
<213> ORGANISM: Homo sapiens

<400> SEQUENCE: 349
cucaguagcc aguguagauc cu                                         22

<210> SEQ ID NO 350
<211> LENGTH: 23
<212> TYPE: RNA
<213> ORGANISM: Homo sapiens

<400> SEQUENCE: 350
ucagcaccag gauauuguug gag                                        23

<210> SEQ ID NO 351
<211> LENGTH: 20
<212> TYPE: RNA
<213> ORGANISM: Homo sapiens

<400> SEQUENCE: 351
auauggguuu acuaguuggu                                            20

<210> SEQ ID NO 352
<211> LENGTH: 22
<212> TYPE: RNA
<213> ORGANISM: Homo sapiens

<400> SEQUENCE: 352
ugagggacag augccagaag ca                                         22

<210> SEQ ID NO 353
<211> LENGTH: 23
<212> TYPE: RNA
<213> ORGANISM: Homo sapiens

<400> SEQUENCE: 353
uagugaguua gagaugcaga gcc                                        23

<210> SEQ ID NO 354
<211> LENGTH: 23
<212> TYPE: RNA
<213> ORGANISM: Homo sapiens
```

```
<400> SEQUENCE: 354
cgcauccccu agggcauugg ugu                                              23

<210> SEQ ID NO 355
<211> LENGTH: 21
<212> TYPE: RNA
<213> ORGANISM: Homo sapiens

<400> SEQUENCE: 355
gugcauugua guugcauugc a                                                21

<210> SEQ ID NO 356
<211> LENGTH: 22
<212> TYPE: RNA
<213> ORGANISM: Homo sapiens

<400> SEQUENCE: 356
cucgugggcu cuggccacgg cc                                               22

<210> SEQ ID NO 357
<211> LENGTH: 22
<212> TYPE: RNA
<213> ORGANISM: Homo sapiens

<400> SEQUENCE: 357
agaucgaccg uguuauauuc gc                                               22

<210> SEQ ID NO 358
<211> LENGTH: 22
<212> TYPE: RNA
<213> ORGANISM: Homo sapiens

<400> SEQUENCE: 358
aucgggaaug ucguguccgc cc                                               22

<210> SEQ ID NO 359
<211> LENGTH: 17
<212> TYPE: RNA
<213> ORGANISM: Homo sapiens

<400> SEQUENCE: 359
gaagauggac guacuuu                                                     17

<210> SEQ ID NO 360
<211> LENGTH: 22
<212> TYPE: RNA
<213> ORGANISM: Homo sapiens

<400> SEQUENCE: 360
uggcggcggu aguuaugggc uu                                               22

<210> SEQ ID NO 361
<211> LENGTH: 22
<212> TYPE: RNA
<213> ORGANISM: Homo sapiens

<400> SEQUENCE: 361
uuucuauuuc ucagugggc uc                                                22

<210> SEQ ID NO 362
<211> LENGTH: 22
<212> TYPE: RNA
```

<213> ORGANISM: Homo sapiens

<400> SEQUENCE: 362
aggacuggac ucccggcagc cc                                           22

<210> SEQ ID NO 363
<211> LENGTH: 18
<212> TYPE: RNA
<213> ORGANISM: Homo sapiens

<400> SEQUENCE: 363
cggugagcgc ucgcuggc                                                18

<210> SEQ ID NO 364
<211> LENGTH: 22
<212> TYPE: RNA
<213> ORGANISM: Homo sapiens

<400> SEQUENCE: 364
aggaccuucc cugaaccaag ga                                           22

<210> SEQ ID NO 365
<211> LENGTH: 22
<212> TYPE: RNA
<213> ORGANISM: Homo sapiens

<400> SEQUENCE: 365
aggcggggcg ccgcgggacc gc                                           22

<210> SEQ ID NO 366
<211> LENGTH: 21
<212> TYPE: RNA
<213> ORGANISM: Homo sapiens

<400> SEQUENCE: 366
aaggcagggc ccccgcuccc c                                            21

<210> SEQ ID NO 367
<211> LENGTH: 22
<212> TYPE: RNA
<213> ORGANISM: Homo sapiens

<400> SEQUENCE: 367
caagcucgcu ucuauggguc ug                                           22

<210> SEQ ID NO 368
<211> LENGTH: 21
<212> TYPE: RNA
<213> ORGANISM: Homo sapiens

<400> SEQUENCE: 368
agaggauacc cuuuguaugu u                                            21

<210> SEQ ID NO 369
<211> LENGTH: 22
<212> TYPE: RNA
<213> ORGANISM: Homo sapiens

<400> SEQUENCE: 369
ugagccccug ugccgccccc ag                                           22

<210> SEQ ID NO 370
<211> LENGTH: 21

```
<212> TYPE: RNA
<213> ORGANISM: Homo sapiens

<400> SEQUENCE: 370
uccuucugcu ccguccccca g                                              21

<210> SEQ ID NO 371
<211> LENGTH: 22
<212> TYPE: RNA
<213> ORGANISM: Homo sapiens

<400> SEQUENCE: 371
agaaggaaau ugaauucauu ua                                             22

<210> SEQ ID NO 372
<211> LENGTH: 21
<212> TYPE: RNA
<213> ORGANISM: Homo sapiens

<400> SEQUENCE: 372
agugaaugau ggguucugac c                                              21

<210> SEQ ID NO 373
<211> LENGTH: 19
<212> TYPE: RNA
<213> ORGANISM: Homo sapiens

<400> SEQUENCE: 373
aucccaccac ugccaccau                                                 19

<210> SEQ ID NO 374
<211> LENGTH: 25
<212> TYPE: RNA
<213> ORGANISM: Homo sapiens

<400> SEQUENCE: 374
gaacccauga gguugaggcu gcagu                                          25

<210> SEQ ID NO 375
<211> LENGTH: 19
<212> TYPE: RNA
<213> ORGANISM: Homo sapiens

<400> SEQUENCE: 375
uggauuuuug gaucaggga                                                 19

<210> SEQ ID NO 376
<211> LENGTH: 18
<212> TYPE: RNA
<213> ORGANISM: Homo sapiens

<400> SEQUENCE: 376
acguuggcuc ugguggug                                                  18

<210> SEQ ID NO 377
<211> LENGTH: 18
<212> TYPE: RNA
<213> ORGANISM: Homo sapiens

<400> SEQUENCE: 377
cagggaggug aaugugau                                                  18

<210> SEQ ID NO 378
```

```
<211> LENGTH: 22
<212> TYPE: RNA
<213> ORGANISM: Homo sapiens

<400> SEQUENCE: 378
cuccuggggc ccgcacucuc gc                                              22

<210> SEQ ID NO 379
<211> LENGTH: 23
<212> TYPE: RNA
<213> ORGANISM: Homo sapiens

<400> SEQUENCE: 379
agcugguguu gugaaucagg ccg                                             23

<210> SEQ ID NO 380
<211> LENGTH: 22
<212> TYPE: RNA
<213> ORGANISM: Homo sapiens

<400> SEQUENCE: 380
cagugguuuu acccuauggu ag                                              22

<210> SEQ ID NO 381
<211> LENGTH: 22
<212> TYPE: RNA
<213> ORGANISM: Homo sapiens

<400> SEQUENCE: 381
ugcccugugg acucaguucu gg                                              22

<210> SEQ ID NO 382
<211> LENGTH: 22
<212> TYPE: RNA
<213> ORGANISM: Homo sapiens

<400> SEQUENCE: 382
gcccaaaggu gaauuuuuug gg                                              22

<210> SEQ ID NO 383
<211> LENGTH: 21
<212> TYPE: RNA
<213> ORGANISM: Homo sapiens

<400> SEQUENCE: 383
cggcggggac ggcgauuggu c                                               21

<210> SEQ ID NO 384
<211> LENGTH: 20
<212> TYPE: RNA
<213> ORGANISM: Homo sapiens

<400> SEQUENCE: 384
ccccagggcg acgcggcggg                                                 20

<210> SEQ ID NO 385
<211> LENGTH: 22
<212> TYPE: RNA
<213> ORGANISM: Homo sapiens

<400> SEQUENCE: 385
accuugccuu gcugcccggg cc                                              22
```

-continued

```
<210> SEQ ID NO 386
<211> LENGTH: 22
<212> TYPE: RNA
<213> ORGANISM: Homo sapiens

<400> SEQUENCE: 386
aacuggccua caaagucccag gu                                              22

<210> SEQ ID NO 387
<211> LENGTH: 23
<212> TYPE: RNA
<213> ORGANISM: Homo sapiens

<400> SEQUENCE: 387
aguuuugcag guuugcaucc agc                                              23

<210> SEQ ID NO 388
<211> LENGTH: 22
<212> TYPE: RNA
<213> ORGANISM: Homo sapiens

<400> SEQUENCE: 388
auaagacgaa caaaagguuu gu                                               22

<210> SEQ ID NO 389
<211> LENGTH: 22
<212> TYPE: RNA
<213> ORGANISM: Homo sapiens

<400> SEQUENCE: 389
uuggggaaac ggccgcugag ug                                               22

<210> SEQ ID NO 390
<211> LENGTH: 22
<212> TYPE: RNA
<213> ORGANISM: Homo sapiens

<400> SEQUENCE: 390
agaguugagu cuggacgucc cg                                               22

<210> SEQ ID NO 391
<211> LENGTH: 22
<212> TYPE: RNA
<213> ORGANISM: Homo sapiens

<400> SEQUENCE: 391
ccuguucucc auuacuuggc uc                                               22

<210> SEQ ID NO 392
<211> LENGTH: 23
<212> TYPE: RNA
<213> ORGANISM: Homo sapiens

<400> SEQUENCE: 392
agaauugcgu uuggacaauc agu                                              23

<210> SEQ ID NO 393
<211> LENGTH: 22
<212> TYPE: RNA
<213> ORGANISM: Homo sapiens

<400> SEQUENCE: 393
acugauuucu uuugguguuc ag                                               22
```

```
<210> SEQ ID NO 394
<211> LENGTH: 22
<212> TYPE: RNA
<213> ORGANISM: Homo sapiens

<400> SEQUENCE: 394
caucuggcau ccgucacaca ga                                              22

<210> SEQ ID NO 395
<211> LENGTH: 21
<212> TYPE: RNA
<213> ORGANISM: Homo sapiens

<400> SEQUENCE: 395
gcugcaccgg agacugggua a                                               21

<210> SEQ ID NO 396
<211> LENGTH: 21
<212> TYPE: RNA
<213> ORGANISM: Homo sapiens

<400> SEQUENCE: 396
uacccagucu ccggugcagc c                                               21

<210> SEQ ID NO 397
<211> LENGTH: 21
<212> TYPE: RNA
<213> ORGANISM: Homo sapiens

<400> SEQUENCE: 397
accugaauua ccaaaagcuu u                                               21

<210> SEQ ID NO 398
<211> LENGTH: 21
<212> TYPE: RNA
<213> ORGANISM: Homo sapiens

<400> SEQUENCE: 398
ccaggcucug cagugggaac u                                               21

<210> SEQ ID NO 399
<211> LENGTH: 22
<212> TYPE: RNA
<213> ORGANISM: Homo sapiens

<400> SEQUENCE: 399
cugcccuagu cuagcugaag cu                                              22

<210> SEQ ID NO 400
<211> LENGTH: 22
<212> TYPE: RNA
<213> ORGANISM: Homo sapiens

<400> SEQUENCE: 400
uggggcggag cuuccggagg cc                                              22

<210> SEQ ID NO 401
<211> LENGTH: 23
<212> TYPE: RNA
<213> ORGANISM: Homo sapiens

<400> SEQUENCE: 401
agguuguccg uggugaguuc gca                                             23
```

```
<210> SEQ ID NO 402
<211> LENGTH: 23
<212> TYPE: RNA
<213> ORGANISM: Homo sapiens

<400> SEQUENCE: 402
ucccuguccu ccaggagcuc acg                                           23

<210> SEQ ID NO 403
<211> LENGTH: 22
<212> TYPE: RNA
<213> ORGANISM: Homo sapiens

<400> SEQUENCE: 403
caaucagcaa guauacugcc cu                                            22

<210> SEQ ID NO 404
<211> LENGTH: 22
<212> TYPE: RNA
<213> ORGANISM: Homo sapiens

<400> SEQUENCE: 404
caaucacuaa cuccacugcc au                                            22

<210> SEQ ID NO 405
<211> LENGTH: 22
<212> TYPE: RNA
<213> ORGANISM: Homo sapiens

<400> SEQUENCE: 405
aaucacuaac cacacggcca gg                                            22

<210> SEQ ID NO 406
<211> LENGTH: 22
<212> TYPE: RNA
<213> ORGANISM: Homo sapiens

<400> SEQUENCE: 406
uuuaagaaaa caccauggag au                                            22

<210> SEQ ID NO 407
<211> LENGTH: 23
<212> TYPE: RNA
<213> ORGANISM: Homo sapiens

<400> SEQUENCE: 407
agggacuuuu gggggcagau gug                                           23

<210> SEQ ID NO 408
<211> LENGTH: 20
<212> TYPE: RNA
<213> ORGANISM: Homo sapiens

<400> SEQUENCE: 408
ccguguuucc cccacgcuuu                                               20

<210> SEQ ID NO 409
<211> LENGTH: 23
<212> TYPE: RNA
<213> ORGANISM: Homo sapiens

<400> SEQUENCE: 409
```

```
aguggaugau ggagacucgg uac                                              23

<210> SEQ ID NO 410
<211> LENGTH: 22
<212> TYPE: RNA
<213> ORGANISM: Homo sapiens

<400> SEQUENCE: 410
guagauucuc cuucuaugag ua                                               22

<210> SEQ ID NO 411
<211> LENGTH: 20
<212> TYPE: RNA
<213> ORGANISM: Homo sapiens

<400> SEQUENCE: 411
acugggcuug gagucagaag                                                  20

<210> SEQ ID NO 412
<211> LENGTH: 22
<212> TYPE: RNA
<213> ORGANISM: Homo sapiens

<400> SEQUENCE: 412
uguccucuag ggccugcagu cu                                               22

<210> SEQ ID NO 413
<211> LENGTH: 22
<212> TYPE: RNA
<213> ORGANISM: Homo sapiens

<400> SEQUENCE: 413
ggaggaaccu uggagcuucg gc                                               22

<210> SEQ ID NO 414
<211> LENGTH: 21
<212> TYPE: RNA
<213> ORGANISM: Homo sapiens

<400> SEQUENCE: 414
uuucagauaa caguauuaca u                                                21

<210> SEQ ID NO 415
<211> LENGTH: 21
<212> TYPE: RNA
<213> ORGANISM: Homo sapiens

<400> SEQUENCE: 415
ugugcagcag gccaaccgag a                                                21

<210> SEQ ID NO 416
<211> LENGTH: 20
<212> TYPE: RNA
<213> ORGANISM: Homo sapiens

<400> SEQUENCE: 416
ggcggcggcg gaggcggggg                                                  20

<210> SEQ ID NO 417
<211> LENGTH: 20
<212> TYPE: RNA
<213> ORGANISM: Homo sapiens

<400> SEQUENCE: 417
```
uguuccucug ucucccagac                                           20

<210> SEQ ID NO 418
<211> LENGTH: 18
<212> TYPE: RNA
<213> ORGANISM: Homo sapiens

<400> SEQUENCE: 418
cucgaguugg aagaggcg                                             18

<210> SEQ ID NO 419
<211> LENGTH: 22
<212> TYPE: RNA
<213> ORGANISM: Homo sapiens

<400> SEQUENCE: 419
uggggauuug gagaaguggu ga                                        22

<210> SEQ ID NO 420
<211> LENGTH: 22
<212> TYPE: RNA
<213> ORGANISM: Homo sapiens

<400> SEQUENCE: 420
auggcaucgu ccccuggugg cu                                        22

<210> SEQ ID NO 421
<211> LENGTH: 23
<212> TYPE: RNA
<213> ORGANISM: Homo sapiens

<400> SEQUENCE: 421
agggaaaaaa aaaaggauuu guc                                       23

<210> SEQ ID NO 422
<211> LENGTH: 22
<212> TYPE: RNA
<213> ORGANISM: Homo sapiens

<400> SEQUENCE: 422
uccaggcagg agccggacug ga                                        22

<210> SEQ ID NO 423
<211> LENGTH: 22
<212> TYPE: RNA
<213> ORGANISM: Homo sapiens

<400> SEQUENCE: 423
uaggggcagc agaggaccug gg                                        22

<210> SEQ ID NO 424
<211> LENGTH: 26
<212> TYPE: RNA
<213> ORGANISM: Homo sapiens

<400> SEQUENCE: 424
cacaggacug acuccucacc ccagug                                    26

<210> SEQ ID NO 425
<211> LENGTH: 22
<212> TYPE: RNA
<213> ORGANISM: Homo sapiens -continued

```
<400> SEQUENCE: 425
cacacaagug gcccccaaca cu                                           22

<210> SEQ ID NO 426
<211> LENGTH: 20
<212> TYPE: RNA
<213> ORGANISM: Homo sapiens

<400> SEQUENCE: 426
cgccccuccu gccccacag                                               20

<210> SEQ ID NO 427
<211> LENGTH: 24
<212> TYPE: RNA
<213> ORGANISM: Homo sapiens

<400> SEQUENCE: 427
ggugggaugg agagaaggua ugag                                         24

<210> SEQ ID NO 428
<211> LENGTH: 21
<212> TYPE: RNA
<213> ORGANISM: Homo sapiens

<400> SEQUENCE: 428
aguggaccga ggaaggaagg a                                            21

<210> SEQ ID NO 429
<211> LENGTH: 22
<212> TYPE: RNA
<213> ORGANISM: Homo sapiens

<400> SEQUENCE: 429 agugggaac ccuuccauga gg                                            22

<210> SEQ ID NO 430
<211> LENGTH: 22
<212> TYPE: RNA
<213> ORGANISM: Homo sapiens

<400> SEQUENCE: 430
aauccuuugu cccuggguga ga                                           22

<210> SEQ ID NO 431
<211> LENGTH: 22
<212> TYPE: RNA
<213> ORGANISM: Homo sapiens

<400> SEQUENCE: 431
aauccacgcu gagcuuggca uc                                           22

<210> SEQ ID NO 432
<211> LENGTH: 25
<212> TYPE: RNA
<213> ORGANISM: Homo sapiens

<400> SEQUENCE: 432
aaaggauucu gcugucgguc ccacu                                        25

<210> SEQ ID NO 433
<211> LENGTH: 23
<212> TYPE: RNA
<213> ORGANISM: Homo sapiens
```

```
<400> SEQUENCE: 433
ucggggauca ucaugucacg aga                                              23

<210> SEQ ID NO 434
<211> LENGTH: 21
<212> TYPE: RNA
<213> ORGANISM: Homo sapiens

<400> SEQUENCE: 434
gcgacccaua cuugguuuca g                                                21

<210> SEQ ID NO 435
<211> LENGTH: 21
<212> TYPE: RNA
<213> ORGANISM: Homo sapiens

<400> SEQUENCE: 435
ucagcuacua ccucuauuag g                                                21

<210> SEQ ID NO 436
<211> LENGTH: 21
<212> TYPE: RNA
<213> ORGANISM: Homo sapiens

<400> SEQUENCE: 436
uagauaaaau auugguaccu g                                                21

<210> SEQ ID NO 437
<211> LENGTH: 22
<212> TYPE: RNA
<213> ORGANISM: Homo sapiens

<400> SEQUENCE: 437
ucaguuccag gccaaccagg cu                                               22

<210> SEQ ID NO 438
<211> LENGTH: 24
<212> TYPE: RNA
<213> ORGANISM: Homo sapiens

<400> SEQUENCE: 438
ucagaacaaa ugccgguucc caga                                             24

<210> SEQ ID NO 439
<211> LENGTH: 22
<212> TYPE: RNA
<213> ORGANISM: Homo sapiens

<400> SEQUENCE: 439
acucaaaacc cuucagugac uu                                               22

<210> SEQ ID NO 440
<211> LENGTH: 22
<212> TYPE: RNA
<213> ORGANISM: Homo sapiens

<400> SEQUENCE: 440
augcugacau auuuacuaga gg                                               22

<210> SEQ ID NO 441
<211> LENGTH: 21
<212> TYPE: RNA
```

```
<213> ORGANISM: Homo sapiens

<400> SEQUENCE: 441 ugggguuuacg uugggagaaac u                                          21

<210> SEQ ID NO 442
<211> LENGTH: 22
<212> TYPE: RNA
<213> ORGANISM: Homo sapiens

<400> SEQUENCE: 442
uucauuugcc ucccagccua ca                                           22

<210> SEQ ID NO 443
<211> LENGTH: 24
<212> TYPE: RNA
<213> ORGANISM: Homo sapiens

<400> SEQUENCE: 443
acuggcuagg gaaaaugauu ggau                                         24

<210> SEQ ID NO 444
<211> LENGTH: 23
<212> TYPE: RNA
<213> ORGANISM: Homo sapiens

<400> SEQUENCE: 444
gcagcagaga auaggacuac guc                                          23

<210> SEQ ID NO 445
<211> LENGTH: 22
<212> TYPE: RNA
<213> ORGANISM: Homo sapiens

<400> SEQUENCE: 445
uauguaauau gguccacauc uu                                           22

<210> SEQ ID NO 446
<211> LENGTH: 22
<212> TYPE: RNA
<213> ORGANISM: Homo sapiens

<400> SEQUENCE: 446
uauguaacau gguccacuaa cu                                           22

<210> SEQ ID NO 447
<211> LENGTH: 22
<212> TYPE: RNA
<213> ORGANISM: Homo sapiens

<400> SEQUENCE: 447
cgaaucauua uuugcugcuc ua                                           22

<210> SEQ ID NO 448
<211> LENGTH: 23
<212> TYPE: RNA
<213> ORGANISM: Homo sapiens

<400> SEQUENCE: 448
uuaaugcuaa ucgugauagg ggu                                          23

<210> SEQ ID NO 449
<211> LENGTH: 22
```

```
<212> TYPE: RNA
<213> ORGANISM: Homo sapiens

<400> SEQUENCE: 449
aucacacaaa ggcaacuuuu gu                                           22

<210> SEQ ID NO 450
<211> LENGTH: 21
<212> TYPE: RNA
<213> ORGANISM: Homo sapiens

<400> SEQUENCE: 450
gccccugggc cuauccuaga a                                            21

<210> SEQ ID NO 451
<211> LENGTH: 21
<212> TYPE: RNA
<213> ORGANISM: Homo sapiens

<400> SEQUENCE: 451
augaccuaug aauugacaga c                                            21

<210> SEQ ID NO 452
<211> LENGTH: 22
<212> TYPE: RNA
<213> ORGANISM: Homo sapiens

<400> SEQUENCE: 452
aucauagagg aaaauccaug uu                                           22

<210> SEQ ID NO 453
<211> LENGTH: 21
<212> TYPE: RNA
<213> ORGANISM: Homo sapiens

<400> SEQUENCE: 453
cggggcagcu caguacagga u                                            21

<210> SEQ ID NO 454
<211> LENGTH: 22
<212> TYPE: RNA
<213> ORGANISM: Homo sapiens

<400> SEQUENCE: 454
acugcugagc uagcacuucc cg                                           22

<210> SEQ ID NO 455
<211> LENGTH: 18
<212> TYPE: RNA
<213> ORGANISM: Homo sapiens

<400> SEQUENCE: 455
ucgaggagcu cacagucu                                                18

<210> SEQ ID NO 456
<211> LENGTH: 22
<212> TYPE: RNA
<213> ORGANISM: Homo sapiens

<400> SEQUENCE: 456
gugaacgggc gccaucccga gg                                           22

<210> SEQ ID NO 457
```

```
<211> LENGTH: 23
<212> TYPE: RNA
<213> ORGANISM: Homo sapiens

<400> SEQUENCE: 457
ccucagggcu guagaacagg gcu                                              23

<210> SEQ ID NO 458
<211> LENGTH: 23
<212> TYPE: RNA
<213> ORGANISM: Homo sapiens

<400> SEQUENCE: 458
uaagugcuuc cauguuuuag uag                                              23

<210> SEQ ID NO 459
<211> LENGTH: 22
<212> TYPE: RNA
<213> ORGANISM: Homo sapiens

<400> SEQUENCE: 459
aaaaacugag acuacuuuug ca                                               22

<210> SEQ ID NO 460
<211> LENGTH: 23
<212> TYPE: RNA
<213> ORGANISM: Homo sapiens

<400> SEQUENCE: 460
uaagugcuuc cauguuugag ugu                                              23

<210> SEQ ID NO 461
<211> LENGTH: 22
<212> TYPE: RNA
<213> ORGANISM: Homo sapiens

<400> SEQUENCE: 461
uacgucaucg uugucaucgu ca                                               22

<210> SEQ ID NO 462
<211> LENGTH: 21
<212> TYPE: RNA
<213> ORGANISM: Homo sapiens

<400> SEQUENCE: 462
cauuauuacu uuugguacgc g                                                21

<210> SEQ ID NO 463
<211> LENGTH: 21
<212> TYPE: RNA
<213> ORGANISM: Homo sapiens

<400> SEQUENCE: 463
uaauuuuaug uauaagcuag u                                                21

<210> SEQ ID NO 464
<211> LENGTH: 22
<212> TYPE: RNA
<213> ORGANISM: Homo sapiens

<400> SEQUENCE: 464
ucugggcaac aaagugagac cu                                               22
```

```
<210> SEQ ID NO 465
<211> LENGTH: 23
<212> TYPE: RNA
<213> ORGANISM: Homo sapiens

<400> SEQUENCE: 465
uacccuguag aaccgaauuu gug                                              23

<210> SEQ ID NO 466
<211> LENGTH: 23
<212> TYPE: RNA
<213> ORGANISM: Homo sapiens

<400> SEQUENCE: 466
cugauaagaa cagaggccca gau                                              23

<210> SEQ ID NO 467
<211> LENGTH: 22
<212> TYPE: RNA
<213> ORGANISM: Homo sapiens

<400> SEQUENCE: 467
agaauugugg cuggacaucu gu                                               22

<210> SEQ ID NO 468
<211> LENGTH: 24
<212> TYPE: RNA
<213> ORGANISM: Homo sapiens

<400> SEQUENCE: 468
agcgcgggcu gagcgcugcc aguc                                             24

<210> SEQ ID NO 469
<211> LENGTH: 22
<212> TYPE: RNA
<213> ORGANISM: Homo sapiens

<400> SEQUENCE: 469
uguuguacuu uuuuuuugu uc                                                22

<210> SEQ ID NO 470
<211> LENGTH: 22
<212> TYPE: RNA
<213> ORGANISM: Homo sapiens

<400> SEQUENCE: 470
uaacugguug aacaacugaa cc                                               22

<210> SEQ ID NO 471
<211> LENGTH: 23
<212> TYPE: RNA
<213> ORGANISM: Homo sapiens

<400> SEQUENCE: 471
aaaagugcuu acagugcagg uag                                              23

<210> SEQ ID NO 472
<211> LENGTH: 22
<212> TYPE: RNA
<213> ORGANISM: Homo sapiens

<400> SEQUENCE: 472
aaucauacac gguugaccua uu                                               22
```

-continued

```
<210> SEQ ID NO 473
<211> LENGTH: 22
<212> TYPE: RNA
<213> ORGANISM: Homo sapiens

<400> SEQUENCE: 473
uagcaccauu ugaaaucggu ua                                        22

<210> SEQ ID NO 474
<211> LENGTH: 22
<212> TYPE: RNA
<213> ORGANISM: Homo sapiens

<400> SEQUENCE: 474
gcugcgcuug gauuucgucc cc                                        22

<210> SEQ ID NO 475
<211> LENGTH: 22
<212> TYPE: RNA
<213> ORGANISM: Homo sapiens

<400> SEQUENCE: 475
uaauacugcc ugguaaugau ga                                        22

<210> SEQ ID NO 476
<211> LENGTH: 23
<212> TYPE: RNA
<213> ORGANISM: Homo sapiens

<400> SEQUENCE: 476
ugucacucgg cucggcccac uac                                       23

<210> SEQ ID NO 477
<211> LENGTH: 22
<212> TYPE: RNA
<213> ORGANISM: Homo sapiens

<400> SEQUENCE: 477
ugagaacuga auuccauggg uu                                        22

<210> SEQ ID NO 478
<211> LENGTH: 22
<212> TYPE: RNA
<213> ORGANISM: Homo sapiens

<400> SEQUENCE: 478
cugugcgugu gacagcggcu ga                                        22

<210> SEQ ID NO 479
<211> LENGTH: 21
<212> TYPE: RNA
<213> ORGANISM: Homo sapiens

<400> SEQUENCE: 479
cagcagcaca cugugguuug u                                         21

<210> SEQ ID NO 480
<211> LENGTH: 22
<212> TYPE: RNA
<213> ORGANISM: Homo sapiens

<400> SEQUENCE: 480
caacaaauca cagucugcca ua                                        22
```

```
<210> SEQ ID NO 481
<211> LENGTH: 22
<212> TYPE: RNA
<213> ORGANISM: Homo sapiens

<400> SEQUENCE: 481
ugaccuggga cucggacagc ug                                              22

<210> SEQ ID NO 482
<211> LENGTH: 22
<212> TYPE: RNA
<213> ORGANISM: Homo sapiens

<400> SEQUENCE: 482
uauguaacac gguccacuaa cc                                              22

<210> SEQ ID NO 483
<211> LENGTH: 22
<212> TYPE: RNA
<213> ORGANISM: Homo sapiens

<400> SEQUENCE: 483
cugcgcaagc uacugccuug cu                                              22

<210> SEQ ID NO 484
<211> LENGTH: 22
<212> TYPE: RNA
<213> ORGANISM: Homo sapiens

<400> SEQUENCE: 484
aacuagcucu guggauccug ac                                              22

<210> SEQ ID NO 485
<211> LENGTH: 22
<212> TYPE: RNA
<213> ORGANISM: Homo sapiens

<400> SEQUENCE: 485
uuaugguuug ccugggacug ag                                              22

<210> SEQ ID NO 486
<211> LENGTH: 22
<212> TYPE: RNA
<213> ORGANISM: Homo sapiens

<400> SEQUENCE: 486
cuguugccac uaaccucaac cu                                              22

<210> SEQ ID NO 487
<211> LENGTH: 23
<212> TYPE: RNA
<213> ORGANISM: Homo sapiens

<400> SEQUENCE: 487
uccaguacca cgugucaggg cca                                             23

<210> SEQ ID NO 488
<211> LENGTH: 22
<212> TYPE: RNA
<213> ORGANISM: Homo sapiens

<400> SEQUENCE: 488
```
uccugucuuu ccuuguugga gc                                          22

<210> SEQ ID NO 489
<211> LENGTH: 23
<212> TYPE: RNA
<213> ORGANISM: Homo sapiens

<400> SEQUENCE: 489
uuacaguugu ucaaccaguu acu                                         23

<210> SEQ ID NO 490
<211> LENGTH: 22
<212> TYPE: RNA
<213> ORGANISM: Homo sapiens

<400> SEQUENCE: 490
acgcccuucc cccccuucuu ca                                          22

<210> SEQ ID NO 491
<211> LENGTH: 22
<212> TYPE: RNA
<213> ORGANISM: Homo sapiens

<400> SEQUENCE: 491
gcucugacuu uauugcacua cu                                          22

<210> SEQ ID NO 492
<211> LENGTH: 22
<212> TYPE: RNA
<213> ORGANISM: Homo sapiens

<400> SEQUENCE: 492
uucugccucu guccaggucc uu                                          22

<210> SEQ ID NO 493
<211> LENGTH: 22
<212> TYPE: RNA
<213> ORGANISM: Homo sapiens

<400> SEQUENCE: 493
aaucagugaa ugccuugaac cu                                          22

<210> SEQ ID NO 494
<211> LENGTH: 22
<212> TYPE: RNA
<213> ORGANISM: Homo sapiens

<400> SEQUENCE: 494
acaguagucu gcacauuggu ua                                          22

<210> SEQ ID NO 495
<211> LENGTH: 22
<212> TYPE: RNA
<213> ORGANISM: Homo sapiens

<400> SEQUENCE: 495
aguucuucag uggcaagcuu ua                                          22

<210> SEQ ID NO 496
<211> LENGTH: 23
<212> TYPE: RNA
<213> ORGANISM: Homo sapiens

<400> SEQUENCE: 496
ccuccguguu accugccuc uag                                    23

<210> SEQ ID NO 497
<211> LENGTH: 22
<212> TYPE: RNA
<213> ORGANISM: Homo sapiens

<400> SEQUENCE: 497
agacccuggu cugcacucua uc                                    22

<210> SEQ ID NO 498
<211> LENGTH: 22
<212> TYPE: RNA
<213> ORGANISM: Homo sapiens

<400> SEQUENCE: 498
uucuggaauu cugugugagg ga                                    22

<210> SEQ ID NO 499
<211> LENGTH: 21
<212> TYPE: RNA
<213> ORGANISM: Homo sapiens

<400> SEQUENCE: 499
caucccuugc augguggagg g                                     21

<210> SEQ ID NO 500
<211> LENGTH: 22
<212> TYPE: RNA
<213> ORGANISM: Homo sapiens

<400> SEQUENCE: 500
cuagguaugg ucccagggau cc                                    22

<210> SEQ ID NO 501
<211> LENGTH: 22
<212> TYPE: RNA
<213> ORGANISM: Homo sapiens

<400> SEQUENCE: 501
uagguuaucc guguugccuu cg                                    22

<210> SEQ ID NO 502
<211> LENGTH: 23
<212> TYPE: RNA
<213> ORGANISM: Homo sapiens

<400> SEQUENCE: 502
acugcccuaa gugcuccuuc ugg                                   23

<210> SEQ ID NO 503
<211> LENGTH: 23
<212> TYPE: RNA
<213> ORGANISM: Homo sapiens

<400> SEQUENCE: 503
uaagugcuuc cauguuuugg uga                                   23

<210> SEQ ID NO 504
<211> LENGTH: 20
<212> TYPE: RNA
<213> ORGANISM: Homo sapiens

<400> SEQUENCE: 504
ccucugggcc cuuccuccag                                                   20

<210> SEQ ID NO 505
<211> LENGTH: 21
<212> TYPE: RNA
<213> ORGANISM: Homo sapiens

<400> SEQUENCE: 505
cuguacaggc cacugccuug c                                                 21

<210> SEQ ID NO 506
<211> LENGTH: 22
<212> TYPE: RNA
<213> ORGANISM: Homo sapiens

<400> SEQUENCE: 506
ugccuacuga gcugauauca gu                                                22

<210> SEQ ID NO 507
<211> LENGTH: 25
<212> TYPE: RNA
<213> ORGANISM: Homo sapiens

<400> SEQUENCE: 507
aaauaugaug aaacucacag cugag                                             25

<210> SEQ ID NO 508
<211> LENGTH: 22
<212> TYPE: RNA
<213> ORGANISM: Homo sapiens

<400> SEQUENCE: 508
aagaugugga aaaauuggaa uc                                                22

<210> SEQ ID NO 509
<211> LENGTH: 23
<212> TYPE: RNA
<213> ORGANISM: Homo sapiens

<400> SEQUENCE: 509
cucucaccac ugcccuccca cag                                               23

<210> SEQ ID NO 510
<211> LENGTH: 22
<212> TYPE: RNA
<213> ORGANISM: Homo sapiens

<400> SEQUENCE: 510
uggguuccug gcaugcugau uu                                                22

<210> SEQ ID NO 511
<211> LENGTH: 23
<212> TYPE: RNA
<213> ORGANISM: Homo sapiens

<400> SEQUENCE: 511
acuuaaacgu ggauguacuu gcu                                               23

<210> SEQ ID NO 512
<211> LENGTH: 22
<212> TYPE: RNA
<213> ORGANISM: Homo sapiens -continued
<210> SEQ ID NO 512
<211> LENGTH: 22
<212> TYPE: RNA
<213> ORGANISM: Homo sapiens

<400> SEQUENCE: 512
aauucccuug uagauaaccc gg                                              22

<210> SEQ ID NO 513
<211> LENGTH: 22
<212> TYPE: RNA
<213> ORGANISM: Homo sapiens

<400> SEQUENCE: 513
cuguacagcc uccuagcuuu cc                                              22

<210> SEQ ID NO 514
<211> LENGTH: 22
<212> TYPE: RNA
<213> ORGANISM: Homo sapiens

<400> SEQUENCE: 514
caaauucgua ucuaggggaa ua                                              22

<210> SEQ ID NO 515
<211> LENGTH: 22
<212> TYPE: RNA
<213> ORGANISM: Homo sapiens

<400> SEQUENCE: 515
ugcuggauca gugguucgag uc                                              22

<210> SEQ ID NO 516
<211> LENGTH: 23
<212> TYPE: RNA
<213> ORGANISM: Homo sapiens

<400> SEQUENCE: 516
guccaguuuu cccaggaauc ccu                                             23

<210> SEQ ID NO 517
<211> LENGTH: 24
<212> TYPE: RNA
<213> ORGANISM: Homo sapiens

<400> SEQUENCE: 517
gcugguuuca uauggugguu uaga                                            24

<210> SEQ ID NO 518
<211> LENGTH: 23
<212> TYPE: RNA
<213> ORGANISM: Homo sapiens

<400> SEQUENCE: 518
ucuggcaagu aaaaaacucu cau                                             23

<210> SEQ ID NO 519
<211> LENGTH: 20
<212> TYPE: RNA
<213> ORGANISM: Homo sapiens

<400> SEQUENCE: 519
gugcauugcu guugcauugc                                                 20

<210> SEQ ID NO 520
<211> LENGTH: 22
<212> TYPE: RNA

```
<213> ORGANISM: Homo sapiens

<400> SEQUENCE: 520
uuuccuaccc uaccugaaga cu                                              22

<210> SEQ ID NO 521
<211> LENGTH: 21
<212> TYPE: RNA
<213> ORGANISM: Homo sapiens

<400> SEQUENCE: 521
acagggccgc agauggagac u                                               21

<210> SEQ ID NO 522
<211> LENGTH: 22
<212> TYPE: RNA
<213> ORGANISM: Homo sapiens

<400> SEQUENCE: 522
gaaaucaagc gugggugaga cc                                              22

<210> SEQ ID NO 523
<211> LENGTH: 22
<212> TYPE: RNA
<213> ORGANISM: Homo sapiens

<400> SEQUENCE: 523
uuugaggcua cagugagaug ug                                              22

<210> SEQ ID NO 524
<211> LENGTH: 23
<212> TYPE: RNA
<213> ORGANISM: Homo sapiens

<400> SEQUENCE: 524
cggcccgggc ugcugcuguu ccu                                             23

<210> SEQ ID NO 525
<211> LENGTH: 22
<212> TYPE: RNA
<213> ORGANISM: Homo sapiens

<400> SEQUENCE: 525
aaccaucgac cguugagugg ac                                              22

<210> SEQ ID NO 526
<211> LENGTH: 22
<212> TYPE: RNA
<213> ORGANISM: Homo sapiens

<400> SEQUENCE: 526
ugggucuuug cgggcgagau ga                                              22

<210> SEQ ID NO 527
<211> LENGTH: 21
<212> TYPE: RNA
<213> ORGANISM: Homo sapiens

<400> SEQUENCE: 527
ugauugucca aacgcaauuc u                                               21

<210> SEQ ID NO 528
<211> LENGTH: 22
```

```
<212> TYPE: RNA
<213> ORGANISM: Homo sapiens

<400> SEQUENCE: 528
uaggauuaca agugucggcc ac                                    22

<210> SEQ ID NO 529
<211> LENGTH: 22
<212> TYPE: RNA
<213> ORGANISM: Homo sapiens

<400> SEQUENCE: 529
ugcccugccu guuucuccu uu                                     22

<210> SEQ ID NO 530
<211> LENGTH: 22
<212> TYPE: RNA
<213> ORGANISM: Homo sapiens

<400> SEQUENCE: 530
cggggagaga acgcagugac gu                                    22

<210> SEQ ID NO 531
<211> LENGTH: 22
<212> TYPE: RNA
<213> ORGANISM: Homo sapiens

<400> SEQUENCE: 531
aaucugagaa ggcgcacaag gu                                    22

<210> SEQ ID NO 532
<211> LENGTH: 23
<212> TYPE: RNA
<213> ORGANISM: Homo sapiens

<400> SEQUENCE: 532
uugaagagga ggugcucugu agc                                   23

<210> SEQ ID NO 533
<211> LENGTH: 24
<212> TYPE: RNA
<213> ORGANISM: Homo sapiens

<400> SEQUENCE: 533
gaugcgccgc ccacugcccc gcgc                                  24

<210> SEQ ID NO 534
<211> LENGTH: 21
<212> TYPE: RNA
<213> ORGANISM: Homo sapiens

<400> SEQUENCE: 534
uuaagacuug cagugauguu u                                     21

<210> SEQ ID NO 535
<211> LENGTH: 23
<212> TYPE: RNA
<213> ORGANISM: Homo sapiens

<400> SEQUENCE: 535
caaagacugc aauuacuuuu gcg                                   23

<210> SEQ ID NO 536
```

```
<211> LENGTH: 25
<212> TYPE: RNA
<213> ORGANISM: Homo sapiens

<400> SEQUENCE: 536
ugggaacggg uuccggcaga cgcug                                           25

<210> SEQ ID NO 537
<211> LENGTH: 22
<212> TYPE: RNA
<213> ORGANISM: Homo sapiens

<400> SEQUENCE: 537
cccugugccc ggcccacuuc ug                                              22

<210> SEQ ID NO 538
<211> LENGTH: 22
<212> TYPE: RNA
<213> ORGANISM: Homo sapiens

<400> SEQUENCE: 538
ccaauauugg cugugcugcu cc                                              22

<210> SEQ ID NO 539
<211> LENGTH: 22
<212> TYPE: RNA
<213> ORGANISM: Homo sapiens

<400> SEQUENCE: 539
uuuaacaugg ggguaccugc ug                                              22

<210> SEQ ID NO 540
<211> LENGTH: 22
<212> TYPE: RNA
<213> ORGANISM: Homo sapiens

<400> SEQUENCE: 540
caaccucgac gaucuccuca gc                                              22

<210> SEQ ID NO 541
<211> LENGTH: 22
<212> TYPE: RNA
<213> ORGANISM: Homo sapiens

<400> SEQUENCE: 541
cccaauacac ggucgaccuc uu                                              22

<210> SEQ ID NO 542
<211> LENGTH: 22
<212> TYPE: RNA
<213> ORGANISM: Homo sapiens

<400> SEQUENCE: 542
uuuuucauua uugcuccuga cc                                              22

<210> SEQ ID NO 543
<211> LENGTH: 20
<212> TYPE: RNA
<213> ORGANISM: Homo sapiens

<400> SEQUENCE: 543
acuguaaacg cuuucugaug                                                 20
```

```
<210> SEQ ID NO 544
<211> LENGTH: 18
<212> TYPE: RNA
<213> ORGANISM: Homo sapiens

<400> SEQUENCE: 544
cuaagaaguu gacugaag                                                    18

<210> SEQ ID NO 545
<211> LENGTH: 23
<212> TYPE: RNA
<213> ORGANISM: Homo sapiens

<400> SEQUENCE: 545
ugagcaccac acaggccggg cgc                                              23

<210> SEQ ID NO 546
<211> LENGTH: 21
<212> TYPE: RNA
<213> ORGANISM: Homo sapiens

<400> SEQUENCE: 546
auaggcacca aaaagcaaca a                                                21

<210> SEQ ID NO 547
<211> LENGTH: 22
<212> TYPE: RNA
<213> ORGANISM: Homo sapiens

<400> SEQUENCE: 547
uggcagugua uuguuagcug gu                                               22

<210> SEQ ID NO 548
<211> LENGTH: 22
<212> TYPE: RNA
<213> ORGANISM: Homo sapiens

<400> SEQUENCE: 548
gaagaacugu ugcauuugcc cu                                               22

<210> SEQ ID NO 549
<211> LENGTH: 19
<212> TYPE: RNA
<213> ORGANISM: Homo sapiens

<400> SEQUENCE: 549
cauccguccg ucuguccac                                                   19

<210> SEQ ID NO 550
<211> LENGTH: 22
<212> TYPE: RNA
<213> ORGANISM: Homo sapiens

<400> SEQUENCE: 550
gggagccagg aaguauugau gu                                               22

<210> SEQ ID NO 551
<211> LENGTH: 22
<212> TYPE: RNA
<213> ORGANISM: Homo sapiens

<400> SEQUENCE: 551
caaaacuggc aauuacuuuu gc                                               22
```

```
<210> SEQ ID NO 552
<211> LENGTH: 21
<212> TYPE: RNA
<213> ORGANISM: Homo sapiens

<400> SEQUENCE: 552
uccucuucuc ccuccuccca g                                              21

<210> SEQ ID NO 553
<211> LENGTH: 23
<212> TYPE: RNA
<213> ORGANISM: Homo sapiens

<400> SEQUENCE: 553
agcuucuuua cagugcugcc uug                                            23

<210> SEQ ID NO 554
<211> LENGTH: 20
<212> TYPE: RNA
<213> ORGANISM: Homo sapiens

<400> SEQUENCE: 554
cgggcguggu gguggggguq                                                20

<210> SEQ ID NO 555
<211> LENGTH: 23
<212> TYPE: RNA
<213> ORGANISM: Homo sapiens

<400> SEQUENCE: 555
cuggagauau ggaagagcug ugu                                            23

<210> SEQ ID NO 556
<211> LENGTH: 22
<212> TYPE: RNA
<213> ORGANISM: Homo sapiens

<400> SEQUENCE: 556 ugggguggucu ggagauuugu gc                                            22

<210> SEQ ID NO 557
<211> LENGTH: 19
<212> TYPE: RNA
<213> ORGANISM: Homo sapiens

<400> SEQUENCE: 557
gaugaugcug cugaugcug                                                 19

<210> SEQ ID NO 558
<211> LENGTH: 22
<212> TYPE: RNA
<213> ORGANISM: Homo sapiens

<400> SEQUENCE: 558
ucucccaacc cuuguaccag ug                                             22

<210> SEQ ID NO 559
<211> LENGTH: 21
<212> TYPE: RNA
<213> ORGANISM: Homo sapiens

<400> SEQUENCE: 559
ugauauguuu gauauuggqu u                                              21
```

```
<210> SEQ ID NO 560
<211> LENGTH: 22
<212> TYPE: RNA
<213> ORGANISM: Homo sapiens

<400> SEQUENCE: 560
cgggguuuug agggcgagau ga                                              22

<210> SEQ ID NO 561
<211> LENGTH: 22
<212> TYPE: RNA
<213> ORGANISM: Homo sapiens

<400> SEQUENCE: 561
acugcauuau gagcacuuaa ag                                              22

<210> SEQ ID NO 562
<211> LENGTH: 22
<212> TYPE: RNA
<213> ORGANISM: Homo sapiens

<400> SEQUENCE: 562
uaaucucagc uggcaacugu ga                                              22

<210> SEQ ID NO 563
<211> LENGTH: 23
<212> TYPE: RNA
<213> ORGANISM: Homo sapiens

<400> SEQUENCE: 563
caggcaguga cuguucagac guc                                             23

<210> SEQ ID NO 564
<211> LENGTH: 22
<212> TYPE: RNA
<213> ORGANISM: Homo sapiens

<400> SEQUENCE: 564
agauguccag ccacaauucu cg                                              22

<210> SEQ ID NO 565
<211> LENGTH: 23
<212> TYPE: RNA
<213> ORGANISM: Homo sapiens

<400> SEQUENCE: 565
uguguacaca cgugccaggc gcu                                             23

<210> SEQ ID NO 566
<211> LENGTH: 20
<212> TYPE: RNA
<213> ORGANISM: Homo sapiens

<400> SEQUENCE: 566
aaaagcuggg uugagagggu                                                 20

<210> SEQ ID NO 567
<211> LENGTH: 22
<212> TYPE: RNA
<213> ORGANISM: Homo sapiens

<400> SEQUENCE: 567
```

```
aggugguccg uggcgcguuc gc                                              22

<210> SEQ ID NO 568
<211> LENGTH: 22
<212> TYPE: RNA
<213> ORGANISM: Homo sapiens

<400> SEQUENCE: 568
caggcacggg agcucaggug ag                                              22

<210> SEQ ID NO 569
<211> LENGTH: 21
<212> TYPE: RNA
<213> ORGANISM: Homo sapiens

<400> SEQUENCE: 569
uaacgcauaa uauggacaug u                                               21

<210> SEQ ID NO 570
<211> LENGTH: 22
<212> TYPE: RNA
<213> ORGANISM: Homo sapiens

<400> SEQUENCE: 570
ucaggugugg aaacugaggc ag                                              22

<210> SEQ ID NO 571
<211> LENGTH: 22
<212> TYPE: RNA
<213> ORGANISM: Homo sapiens

<400> SEQUENCE: 571
aagcaauacu guuaccugaa au                                              22

<210> SEQ ID NO 572
<211> LENGTH: 21
<212> TYPE: RNA
<213> ORGANISM: Homo sapiens

<400> SEQUENCE: 572
gaccgagagg gccucggcug u                                               21

<210> SEQ ID NO 573
<211> LENGTH: 23
<212> TYPE: RNA
<213> ORGANISM: Homo sapiens

<400> SEQUENCE: 573
ugggccaggg agcagcuggu ggg                                             23

<210> SEQ ID NO 574
<211> LENGTH: 22
<212> TYPE: RNA
<213> ORGANISM: Homo sapiens

<400> SEQUENCE: 574
accgaagacu gugcgcuaau cu                                              22

<210> SEQ ID NO 575
<211> LENGTH: 22
<212> TYPE: RNA
<213> ORGANISM: Homo sapiens

<400> SEQUENCE: 575
```
acaacaguga cuugcucucc aa 22

<210> SEQ ID NO 576
<211> LENGTH: 22
<212> TYPE: RNA
<213> ORGANISM: Homo sapiens

<400> SEQUENCE: 576 ugcuggggc cacaugagug ug 22

<210> SEQ ID NO 577
<211> LENGTH: 21
<212> TYPE: RNA
<213> ORGANISM: Homo sapiens

<400> SEQUENCE: 577
ccaaaucuug aucagaagcc u 21

<210> SEQ ID NO 578
<211> LENGTH: 22
<212> TYPE: RNA
<213> ORGANISM: Homo sapiens

<400> SEQUENCE: 578 aggggaugg cagagcaaaa uu 22

<210> SEQ ID NO 579
<211> LENGTH: 21
<212> TYPE: RNA
<213> ORGANISM: Homo sapiens

<400> SEQUENCE: 579
auccuugcua ucugggugcu a 21

<210> SEQ ID NO 580
<211> LENGTH: 22
<212> TYPE: RNA
<213> ORGANISM: Homo sapiens

<400> SEQUENCE: 580
aaaaguaauu gugguuuuug cc 22

<210> SEQ ID NO 581
<211> LENGTH: 22
<212> TYPE: RNA
<213> ORGANISM: Homo sapiens

<400> SEQUENCE: 581
aaaaguaauu gcggauuuug cc 22

<210> SEQ ID NO 582
<211> LENGTH: 22
<212> TYPE: RNA
<213> ORGANISM: Homo sapiens

<400> SEQUENCE: 582
aaaaguaauu gcggucuuug gu 22

<210> SEQ ID NO 583
<211> LENGTH: 20
<212> TYPE: RNA
<213> ORGANISM: Homo sapiens

<400> SEQUENCE: 583
cgugccaccc uuucccccag          20

<210> SEQ ID NO 584
<211> LENGTH: 17
<212> TYPE: RNA
<213> ORGANISM: Homo sapiens

<400> SEQUENCE: 584
ucccaccgcu gccaccc             17

<210> SEQ ID NO 585
<211> LENGTH: 21
<212> TYPE: RNA
<213> ORGANISM: Homo sapiens

<400> SEQUENCE: 585
uggacugccc ugaucuggag a        21

<210> SEQ ID NO 586
<211> LENGTH: 22
<212> TYPE: RNA
<213> ORGANISM: Homo sapiens

<400> SEQUENCE: 586
uuuagagacg gggucuugcu cu       22

<210> SEQ ID NO 587
<211> LENGTH: 22
<212> TYPE: RNA
<213> ORGANISM: Homo sapiens

<400> SEQUENCE: 587
ucuacagugc acgugucucc ag       22

<210> SEQ ID NO 588
<211> LENGTH: 21
<212> TYPE: RNA
<213> ORGANISM: Homo sapiens

<400> SEQUENCE: 588
agggagggac gggggcugug c        21

<210> SEQ ID NO 589
<211> LENGTH: 22
<212> TYPE: RNA
<213> ORGANISM: Homo sapiens

<400> SEQUENCE: 589
ccaguauuaa cugugcugcu ga       22

<210> SEQ ID NO 590
<211> LENGTH: 21
<212> TYPE: RNA
<213> ORGANISM: Homo sapiens

<400> SEQUENCE: 590
ugagugccgg ugccugcccu g        21

<210> SEQ ID NO 591
<211> LENGTH: 21
<212> TYPE: RNA
<213> ORGANISM: Homo sapiens -continued

```
<400> SEQUENCE: 591
caagucacua gugguuccgu u                                              21

<210> SEQ ID NO 592
<211> LENGTH: 22
<212> TYPE: RNA
<213> ORGANISM: Homo sapiens

<400> SEQUENCE: 592
ucugcaagug ucagaggcga gg                                             22

<210> SEQ ID NO 593
<211> LENGTH: 22
<212> TYPE: RNA
<213> ORGANISM: Homo sapiens

<400> SEQUENCE: 593
auuguccuug cuguuggag au                                              22

<210> SEQ ID NO 594
<211> LENGTH: 22
<212> TYPE: RNA
<213> ORGANISM: Homo sapiens

<400> SEQUENCE: 594
ugaccgauuu cuccuggugu uc                                             22

<210> SEQ ID NO 595
<211> LENGTH: 22
<212> TYPE: RNA
<213> ORGANISM: Homo sapiens

<400> SEQUENCE: 595
gauaucagcu caguaggcac cg                                             22

<210> SEQ ID NO 596
<211> LENGTH: 21
<212> TYPE: RNA
<213> ORGANISM: Homo sapiens

<400> SEQUENCE: 596
cacagcaagu guagacaggc a                                              21

<210> SEQ ID NO 597
<211> LENGTH: 22
<212> TYPE: RNA
<213> ORGANISM: Homo sapiens

<400> SEQUENCE: 597
agcuuuuggg aauucaggua gu                                             22

<210> SEQ ID NO 598
<211> LENGTH: 22
<212> TYPE: RNA
<213> ORGANISM: Homo sapiens

<400> SEQUENCE: 598
uauaaaauga gggcaguaag ac                                             22

<210> SEQ ID NO 599
<211> LENGTH: 22
<212> TYPE: RNA
```

```
<213> ORGANISM: Homo sapiens

<400> SEQUENCE: 599
aggauuucag aaauacuggu gu                                    22

<210> SEQ ID NO 600
<211> LENGTH: 22
<212> TYPE: RNA
<213> ORGANISM: Homo sapiens

<400> SEQUENCE: 600
cggguggauc acgaugcaau uu                                    22

<210> SEQ ID NO 601
<211> LENGTH: 22
<212> TYPE: RNA
<213> ORGANISM: Homo sapiens

<400> SEQUENCE: 601
ugggcuggca gggcaagugc ug                                    22

<210> SEQ ID NO 602
<211> LENGTH: 22
<212> TYPE: RNA
<213> ORGANISM: Homo sapiens

<400> SEQUENCE: 602
ugugggaucu ggaggcaucu gg                                    22

<210> SEQ ID NO 603
<211> LENGTH: 22
<212> TYPE: RNA
<213> ORGANISM: Homo sapiens

<400> SEQUENCE: 603
uuucuucuua gacauggcaa cg                                    22

<210> SEQ ID NO 604
<211> LENGTH: 22
<212> TYPE: RNA
<213> ORGANISM: Homo sapiens

<400> SEQUENCE: 604
uuagccaauu guccaucuuu ag                                    22

<210> SEQ ID NO 605
<211> LENGTH: 23
<212> TYPE: RNA
<213> ORGANISM: Homo sapiens

<400> SEQUENCE: 605
uggagaucca gugcucgccc gau                                   23

<210> SEQ ID NO 606
<211> LENGTH: 22
<212> TYPE: RNA
<213> ORGANISM: Homo sapiens

<400> SEQUENCE: 606
ugaaacugga gcgccuggag ga                                    22

<210> SEQ ID NO 607
<211> LENGTH: 21
```

<212> TYPE: RNA
<213> ORGANISM: Homo sapiens

<400> SEQUENCE: 607
agcggugcuc cugcgggccg a                                              21

<210> SEQ ID NO 608
<211> LENGTH: 21
<212> TYPE: RNA
<213> ORGANISM: Homo sapiens

<400> SEQUENCE: 608
gagguugggg gaggauuugc u                                              21

<210> SEQ ID NO 609
<211> LENGTH: 22
<212> TYPE: RNA
<213> ORGANISM: Homo sapiens

<400> SEQUENCE: 609
ucaggacacu cugaacuug ga                                              22

<210> SEQ ID NO 610
<211> LENGTH: 23
<212> TYPE: RNA
<213> ORGANISM: Homo sapiens

<400> SEQUENCE: 610
uagcagcggg aacaguucug cag                                            23

<210> SEQ ID NO 611
<211> LENGTH: 24
<212> TYPE: RNA
<213> ORGANISM: Homo sapiens

<400> SEQUENCE: 611
ucugggcaca ggcggaugga cagg                                           24

<210> SEQ ID NO 612
<211> LENGTH: 22
<212> TYPE: RNA
<213> ORGANISM: Homo sapiens

<400> SEQUENCE: 612
caaaaacugc aauuacuuuu gc                                             22

<210> SEQ ID NO 613
<211> LENGTH: 20
<212> TYPE: RNA
<213> ORGANISM: Homo sapiens

<400> SEQUENCE: 613
aaaacugcag uuacuuuugc                                                20

<210> SEQ ID NO 614
<211> LENGTH: 22
<212> TYPE: RNA
<213> ORGANISM: Homo sapiens

<400> SEQUENCE: 614
ugugucacuc gaugaccacu gu                                             22

<210> SEQ ID NO 615

```
<211> LENGTH: 21
<212> TYPE: RNA
<213> ORGANISM: Homo sapiens

<400> SEQUENCE: 615
acagucugcu gagguuggag c                                              21

<210> SEQ ID NO 616
<211> LENGTH: 23
<212> TYPE: RNA
<213> ORGANISM: Homo sapiens

<400> SEQUENCE: 616
ugugcuugcu cgucccgccc gca                                            23

<210> SEQ ID NO 617
<211> LENGTH: 23
<212> TYPE: RNA
<213> ORGANISM: Homo sapiens

<400> SEQUENCE: 617
gggaugguag accggugacg ugc                                            23

<210> SEQ ID NO 618
<211> LENGTH: 21
<212> TYPE: RNA
<213> ORGANISM: Homo sapiens

<400> SEQUENCE: 618
ccccaccucc ucucuccuca g                                              21

<210> SEQ ID NO 619
<211> LENGTH: 22
<212> TYPE: RNA
<213> ORGANISM: Homo sapiens

<400> SEQUENCE: 619
uggaguguga caauggucuu ug                                             22

<210> SEQ ID NO 620
<211> LENGTH: 21
<212> TYPE: RNA
<213> ORGANISM: Homo sapiens

<400> SEQUENCE: 620
gugggcgggg gcaggugugu g                                              21

<210> SEQ ID NO 621
<211> LENGTH: 22
<212> TYPE: RNA
<213> ORGANISM: Homo sapiens

<400> SEQUENCE: 621
acccgucccg uucgucccg ga                                              22

<210> SEQ ID NO 622
<211> LENGTH: 22
<212> TYPE: RNA
<213> ORGANISM: Homo sapiens

<400> SEQUENCE: 622
cggaugagca aagaaagugg uu                                             22
```

```
<210> SEQ ID NO 623
<211> LENGTH: 22
<212> TYPE: RNA
<213> ORGANISM: Homo sapiens

<400> SEQUENCE: 623
cuggacugag ccaugcuacu gg                                              22

<210> SEQ ID NO 624
<211> LENGTH: 26
<212> TYPE: RNA
<213> ORGANISM: Homo sapiens

<400> SEQUENCE: 624
gaugaugaug gcagcaaauu cugaaa                                          26

<210> SEQ ID NO 625
<211> LENGTH: 22
<212> TYPE: RNA
<213> ORGANISM: Homo sapiens

<400> SEQUENCE: 625
ggcgacaaaa cgagacccug uc                                              22

<210> SEQ ID NO 626
<211> LENGTH: 20
<212> TYPE: RNA
<213> ORGANISM: Homo sapiens

<400> SEQUENCE: 626
ucguuugccu uuucugcuu                                                  20

<210> SEQ ID NO 627
<211> LENGTH: 22
<212> TYPE: RNA
<213> ORGANISM: Homo sapiens

<400> SEQUENCE: 627
ugugagguug gcauuguugu cu                                              22

<210> SEQ ID NO 628
<211> LENGTH: 22
<212> TYPE: RNA
<213> ORGANISM: Homo sapiens

<400> SEQUENCE: 628
ccaccucccc ugcaaacguc ca                                              22

<210> SEQ ID NO 629
<211> LENGTH: 23
<212> TYPE: RNA
<213> ORGANISM: Homo sapiens

<400> SEQUENCE: 629
uauggcuuuu uauuccuaug uga                                             23

<210> SEQ ID NO 630
<211> LENGTH: 23
<212> TYPE: RNA
<213> ORGANISM: Homo sapiens

<400> SEQUENCE: 630
uuauugcuua agaauacgcg uag                                             23
```

<210> SEQ ID NO 631
<211> LENGTH: 21
<212> TYPE: RNA
<213> ORGANISM: Homo sapiens

<400> SEQUENCE: 631
cauaaaguag aaagcacuac u                                              21

<210> SEQ ID NO 632
<211> LENGTH: 22
<212> TYPE: RNA
<213> ORGANISM: Homo sapiens

<400> SEQUENCE: 632
ggugcagugc ugcaucucug gu                                             22

<210> SEQ ID NO 633
<211> LENGTH: 22
<212> TYPE: RNA
<213> ORGANISM: Homo sapiens

<400> SEQUENCE: 633
caggccauau ugugcugccu ca                                             22

<210> SEQ ID NO 634
<211> LENGTH: 22
<212> TYPE: RNA
<213> ORGANISM: Homo sapiens

<400> SEQUENCE: 634
cugccaauuc cauaggucac ag                                             22

<210> SEQ ID NO 635
<211> LENGTH: 22
<212> TYPE: RNA
<213> ORGANISM: Homo sapiens

<400> SEQUENCE: 635
uaacacuguc ugguaacgau gu                                             22

<210> SEQ ID NO 636
<211> LENGTH: 21
<212> TYPE: RNA
<213> ORGANISM: Homo sapiens

<400> SEQUENCE: 636
gcugggaagg caaagggacg u                                              21

<210> SEQ ID NO 637
<211> LENGTH: 22
<212> TYPE: RNA
<213> ORGANISM: Homo sapiens

<400> SEQUENCE: 637
acagcaggca cagacaggca gu                                             22

<210> SEQ ID NO 638
<211> LENGTH: 21
<212> TYPE: RNA
<213> ORGANISM: Homo sapiens

<400> SEQUENCE: 638
ucuggcuguu guggugugca a                                              21

```
<210> SEQ ID NO 639
<211> LENGTH: 22
<212> TYPE: RNA
<213> ORGANISM: Homo sapiens

<400> SEQUENCE: 639
ugccuggaac auaguaggga cu                                              22

<210> SEQ ID NO 640
<211> LENGTH: 20
<212> TYPE: RNA
<213> ORGANISM: Homo sapiens

<400> SEQUENCE: 640
uagaggaagc uguggagaga                                                 20

<210> SEQ ID NO 641
<211> LENGTH: 22
<212> TYPE: RNA
<213> ORGANISM: Homo sapiens

<400> SEQUENCE: 641
uccccuucug caggccugcu gg                                              22

<210> SEQ ID NO 642
<211> LENGTH: 22
<212> TYPE: RNA
<213> ORGANISM: Homo sapiens

<400> SEQUENCE: 642
uucagccagg cuagugcagu cu                                              22

<210> SEQ ID NO 643
<211> LENGTH: 22
<212> TYPE: RNA
<213> ORGANISM: Homo sapiens

<400> SEQUENCE: 643 agaagggggug aaauuuaaac gu                                             22

<210> SEQ ID NO 644
<211> LENGTH: 19
<212> TYPE: RNA
<213> ORGANISM: Homo sapiens

<400> SEQUENCE: 644
aucgggcccu cggcgccgg                                                  19

<210> SEQ ID NO 645
<211> LENGTH: 23
<212> TYPE: RNA
<213> ORGANISM: Homo sapiens

<400> SEQUENCE: 645
ccugggcagc guguggcuga agg                                             23

<210> SEQ ID NO 646
<211> LENGTH: 20
<212> TYPE: RNA
<213> ORGANISM: Homo sapiens

<400> SEQUENCE: 646
```

```
ucuggccagc uacgucccca                                              20

<210> SEQ ID NO 647
<211> LENGTH: 22
<212> TYPE: RNA
<213> ORGANISM: Homo sapiens

<400> SEQUENCE: 647
guggaguccu ggggaaugga ga                                           22

<210> SEQ ID NO 648
<211> LENGTH: 22
<212> TYPE: RNA
<213> ORGANISM: Homo sapiens

<400> SEQUENCE: 648
aaaagcuggg uugagagggc aa                                           22

<210> SEQ ID NO 649
<211> LENGTH: 23
<212> TYPE: RNA
<213> ORGANISM: Homo sapiens

<400> SEQUENCE: 649
uuuaguguga uaauggcguu uga                                          23

<210> SEQ ID NO 650
<211> LENGTH: 22
<212> TYPE: RNA
<213> ORGANISM: Homo sapiens

<400> SEQUENCE: 650
ucagcaggca ggcuggugca gc                                           22

<210> SEQ ID NO 651
<211> LENGTH: 21
<212> TYPE: RNA
<213> ORGANISM: Homo sapiens

<400> SEQUENCE: 651
ugaguguugu cuacgagggc a                                            21

<210> SEQ ID NO 652
<211> LENGTH: 22
<212> TYPE: RNA
<213> ORGANISM: Homo sapiens

<400> SEQUENCE: 652
auuguagaac cuaagauugg cc                                           22

<210> SEQ ID NO 653
<211> LENGTH: 22
<212> TYPE: RNA
<213> ORGANISM: Homo sapiens

<400> SEQUENCE: 653
cuucccccca guaaucuuca uc                                           22

<210> SEQ ID NO 654
<211> LENGTH: 22
<212> TYPE: RNA
<213> ORGANISM: Homo sapiens

<400> SEQUENCE: 654
```

| | |
|---|---|
| uuuguucguu cggcucgcgu ga | 22 |

<210> SEQ ID NO 655
<211> LENGTH: 19
<212> TYPE: RNA
<213> ORGANISM: Homo sapiens

<400> SEQUENCE: 655

| | |
|---|---|
| acuggacuug gaggcagaa | 19 |

<210> SEQ ID NO 656
<211> LENGTH: 22
<212> TYPE: RNA
<213> ORGANISM: Homo sapiens

<400> SEQUENCE: 656

| | |
|---|---|
| gagcaaugua gguagacugu uu | 22 |

<210> SEQ ID NO 657
<211> LENGTH: 22
<212> TYPE: RNA
<213> ORGANISM: Homo sapiens

<400> SEQUENCE: 657

| | |
|---|---|
| uguguggauc cuggaggagg ca | 22 |

<210> SEQ ID NO 658
<211> LENGTH: 22
<212> TYPE: RNA
<213> ORGANISM: Homo sapiens

<400> SEQUENCE: 658

| | |
|---|---|
| uuugggacug aucuugaugu cu | 22 |

<210> SEQ ID NO 659
<211> LENGTH: 20
<212> TYPE: RNA
<213> ORGANISM: Homo sapiens

<400> SEQUENCE: 659

| | |
|---|---|
| gcucggacug agcagguggg | 20 |

<210> SEQ ID NO 660
<211> LENGTH: 23
<212> TYPE: RNA
<213> ORGANISM: Homo sapiens

<400> SEQUENCE: 660

| | |
|---|---|
| uucgggcugg ccugcugcuc cgg | 23 |

<210> SEQ ID NO 661
<211> LENGTH: 22
<212> TYPE: RNA
<213> ORGANISM: Homo sapiens

<400> SEQUENCE: 661

| | |
|---|---|
| uaauacuguc ugguaaaacc gu | 22 |

<210> SEQ ID NO 662
<211> LENGTH: 22
<212> TYPE: RNA
<213> ORGANISM: Homo sapiens

```
<400> SEQUENCE: 662
accugucugu ggaaaggagc ua                                              22

<210> SEQ ID NO 663
<211> LENGTH: 17
<212> TYPE: RNA
<213> ORGANISM: Homo sapiens

<400> SEQUENCE: 663
uuggaggcgu ggguuuu                                                    17

<210> SEQ ID NO 664
<211> LENGTH: 22
<212> TYPE: RNA
<213> ORGANISM: Homo sapiens

<400> SEQUENCE: 664
ccaggaggcg gaggaggugg ag                                              22

<210> SEQ ID NO 665
<211> LENGTH: 22
<212> TYPE: RNA
<213> ORGANISM: Homo sapiens

<400> SEQUENCE: 665
cuagugcucu ccguuacaag ua                                              22

<210> SEQ ID NO 666
<211> LENGTH: 22
<212> TYPE: RNA
<213> ORGANISM: Homo sapiens

<400> SEQUENCE: 666
cgcgcggccg ugcucggagc ag                                              22

<210> SEQ ID NO 667
<211> LENGTH: 22
<212> TYPE: RNA
<213> ORGANISM: Homo sapiens

<400> SEQUENCE: 667
ugugacaaua gagaugaaca ug                                              22

<210> SEQ ID NO 668
<211> LENGTH: 22
<212> TYPE: RNA
<213> ORGANISM: Homo sapiens

<400> SEQUENCE: 668
uuuggacaga aaacacgcag gu                                              22

<210> SEQ ID NO 669
<211> LENGTH: 22
<212> TYPE: RNA
<213> ORGANISM: Homo sapiens

<400> SEQUENCE: 669
aacuguuugc agaggaaacu ga                                              22

<210> SEQ ID NO 670
<211> LENGTH: 22
<212> TYPE: RNA
<213> ORGANISM: Homo sapiens
```

-continued

<400> SEQUENCE: 670
aacucguguu caaagccuuu ag                                               22

<210> SEQ ID NO 671
<211> LENGTH: 22
<212> TYPE: RNA
<213> ORGANISM: Homo sapiens

<400> SEQUENCE: 671
uuucuucuua gacauggcag cu                                               22

<210> SEQ ID NO 672
<211> LENGTH: 22
<212> TYPE: RNA
<213> ORGANISM: Homo sapiens

<400> SEQUENCE: 672
cuuccggucu gugagccccg uc                                               22

<210> SEQ ID NO 673
<211> LENGTH: 23
<212> TYPE: RNA
<213> ORGANISM: Homo sapiens

<400> SEQUENCE: 673 cuggggacg cgugagcgcg agc                                               23

<210> SEQ ID NO 674
<211> LENGTH: 21
<212> TYPE: RNA
<213> ORGANISM: Homo sapiens

<400> SEQUENCE: 674
auacauguca gauuguaugc c                                                21

<210> SEQ ID NO 675
<211> LENGTH: 22
<212> TYPE: RNA
<213> ORGANISM: Homo sapiens

<400> SEQUENCE: 675
aacgggaaug caggcuguau cu                                               22

<210> SEQ ID NO 676
<211> LENGTH: 23
<212> TYPE: RNA
<213> ORGANISM: Homo sapiens

<400> SEQUENCE: 676
ucugaguucc uggagccugg ucu                                              23

<210> SEQ ID NO 677
<211> LENGTH: 22
<212> TYPE: RNA
<213> ORGANISM: Homo sapiens

<400> SEQUENCE: 677
gagcaggcga ggcugggcug aa                                               22

<210> SEQ ID NO 678
<211> LENGTH: 22
<212> TYPE: RNA

```
<213> ORGANISM: Homo sapiens

<400> SEQUENCE: 678
agaagauugc agaguaaguu cc                                              22

<210> SEQ ID NO 679
<211> LENGTH: 25
<212> TYPE: RNA
<213> ORGANISM: Homo sapiens

<400> SEQUENCE: 679
agcggggagg aagugggcgc ugcuu                                           25

<210> SEQ ID NO 680
<211> LENGTH: 22
<212> TYPE: RNA
<213> ORGANISM: Homo sapiens

<400> SEQUENCE: 680
ugagggcucc aggugacggu gg                                              22

<210> SEQ ID NO 681
<211> LENGTH: 25
<212> TYPE: RNA
<213> ORGANISM: Homo sapiens

<400> SEQUENCE: 681
caugcugacc ucccuccugc cccag                                           25

<210> SEQ ID NO 682
<211> LENGTH: 23
<212> TYPE: RNA
<213> ORGANISM: Homo sapiens

<400> SEQUENCE: 682
ucaggcaaag ggauauuuac aga                                             23

<210> SEQ ID NO 683
<211> LENGTH: 22
<212> TYPE: RNA
<213> ORGANISM: Homo sapiens

<400> SEQUENCE: 683
aaggcccggg cuuuccuccc ag                                              22

<210> SEQ ID NO 684
<211> LENGTH: 22
<212> TYPE: RNA
<213> ORGANISM: Homo sapiens

<400> SEQUENCE: 684
ugcggggaca ggccagggca uc                                              22

<210> SEQ ID NO 685
<211> LENGTH: 22
<212> TYPE: RNA
<213> ORGANISM: Homo sapiens

<400> SEQUENCE: 685
agccaggcuc ugaagggaaa gu                                              22

<210> SEQ ID NO 686
<211> LENGTH: 21
```

```
<212> TYPE: RNA
<213> ORGANISM: Homo sapiens

<400> SEQUENCE: 686
cgccugccca gcccuccugc u                                         21

<210> SEQ ID NO 687
<211> LENGTH: 21
<212> TYPE: RNA
<213> ORGANISM: Homo sapiens

<400> SEQUENCE: 687
auagcaauug cucuuuugga a                                         21

<210> SEQ ID NO 688
<211> LENGTH: 22
<212> TYPE: RNA
<213> ORGANISM: Homo sapiens

<400> SEQUENCE: 688
aauguuggaa uccucgcuag ag                                        22

<210> SEQ ID NO 689
<211> LENGTH: 23
<212> TYPE: RNA
<213> ORGANISM: Homo sapiens

<400> SEQUENCE: 689
ucugcacugu gaguuggcug gcu                                       23

<210> SEQ ID NO 690
<211> LENGTH: 21
<212> TYPE: RNA
<213> ORGANISM: Homo sapiens

<400> SEQUENCE: 690
uugaaaggcu auuucuuggu c                                         21

<210> SEQ ID NO 691
<211> LENGTH: 21
<212> TYPE: RNA
<213> ORGANISM: Homo sapiens

<400> SEQUENCE: 691
ugcuguauug ucagguagug a                                         21

<210> SEQ ID NO 692
<211> LENGTH: 24
<212> TYPE: RNA
<213> ORGANISM: Homo sapiens

<400> SEQUENCE: 692
agggcuggac ucagcggcgg agcu                                      24

<210> SEQ ID NO 693
<211> LENGTH: 24
<212> TYPE: RNA
<213> ORGANISM: Homo sapiens

<400> SEQUENCE: 693
aauuugguuu cugaggcacu uagu                                      24

<210> SEQ ID NO 694
```

```
<211> LENGTH: 22
<212> TYPE: RNA
<213> ORGANISM: Homo sapiens

<400> SEQUENCE: 694
ugaggacagg gcaaauucac ga                                              22

<210> SEQ ID NO 695
<211> LENGTH: 21
<212> TYPE: RNA
<213> ORGANISM: Homo sapiens

<400> SEQUENCE: 695
uuucccuuuc cauccuggca g                                               21

<210> SEQ ID NO 696
<211> LENGTH: 23
<212> TYPE: RNA
<213> ORGANISM: Homo sapiens

<400> SEQUENCE: 696
cagggcucag ggauuggaug gag                                             23

<210> SEQ ID NO 697
<211> LENGTH: 22
<212> TYPE: RNA
<213> ORGANISM: Homo sapiens

<400> SEQUENCE: 697
auucugcauu uuuagcaagu uc                                              22

<210> SEQ ID NO 698
<211> LENGTH: 22
<212> TYPE: RNA
<213> ORGANISM: Homo sapiens

<400> SEQUENCE: 698
aacggcaaug acuuuuguac ca                                              22

<210> SEQ ID NO 699
<211> LENGTH: 22
<212> TYPE: RNA
<213> ORGANISM: Homo sapiens

<400> SEQUENCE: 699
gaaaguaauu gcuguuuug cc                                               22

<210> SEQ ID NO 700
<211> LENGTH: 22
<212> TYPE: RNA
<213> ORGANISM: Homo sapiens

<400> SEQUENCE: 700
aaaaguuauu gcgguuuugg cu                                              22

<210> SEQ ID NO 701
<211> LENGTH: 21
<212> TYPE: RNA
<213> ORGANISM: Homo sapiens

<400> SEQUENCE: 701
aaaaguaauu gcgguuuug c                                                21
```

```
<210> SEQ ID NO 702
<211> LENGTH: 22
<212> TYPE: RNA
<213> ORGANISM: Homo sapiens

<400> SEQUENCE: 702
caagaaccuc aguugcuuuu gu                                              22

<210> SEQ ID NO 703
<211> LENGTH: 22
<212> TYPE: RNA
<213> ORGANISM: Homo sapiens

<400> SEQUENCE: 703
auauuaccau uagcucaucu uu                                              22

<210> SEQ ID NO 704
<211> LENGTH: 22
<212> TYPE: RNA
<213> ORGANISM: Homo sapiens

<400> SEQUENCE: 704
uaaaacuuua agugugccua gg                                              22

<210> SEQ ID NO 705
<211> LENGTH: 22
<212> TYPE: RNA
<213> ORGANISM: Homo sapiens

<400> SEQUENCE: 705
cagagugaca agcugguuaa ag                                              22

<210> SEQ ID NO 706
<211> LENGTH: 21
<212> TYPE: RNA
<213> ORGANISM: Homo sapiens

<400> SEQUENCE: 706
acuggcauua gugggacuuu u                                               21

<210> SEQ ID NO 707
<211> LENGTH: 24
<212> TYPE: RNA
<213> ORGANISM: Homo sapiens

<400> SEQUENCE: 707
uacagaugca gauucucuga cuuc                                            24

<210> SEQ ID NO 708
<211> LENGTH: 22
<212> TYPE: RNA
<213> ORGANISM: Homo sapiens

<400> SEQUENCE: 708
cucauuuaag uagucugaug cc                                              22

<210> SEQ ID NO 709
<211> LENGTH: 19
<212> TYPE: RNA
<213> ORGANISM: Homo sapiens

<400> SEQUENCE: 709
uuauugucac guucugauu                                                  19
```

```
<210> SEQ ID NO 710
<211> LENGTH: 22
<212> TYPE: RNA
<213> ORGANISM: Homo sapiens

<400> SEQUENCE: 710
uucuggauaa caugcugaag cu                                               22

<210> SEQ ID NO 711
<211> LENGTH: 22
<212> TYPE: RNA
<213> ORGANISM: Homo sapiens

<400> SEQUENCE: 711
uugugucaau augcgaugau gu                                               22

<210> SEQ ID NO 712
<211> LENGTH: 22
<212> TYPE: RNA
<213> ORGANISM: Homo sapiens

<400> SEQUENCE: 712
cacacacugc aauuacuuuu gc                                               22

<210> SEQ ID NO 713
<211> LENGTH: 21
<212> TYPE: RNA
<213> ORGANISM: Homo sapiens

<400> SEQUENCE: 713
cacaagguau ugguauuacc u                                                21

<210> SEQ ID NO 714
<211> LENGTH: 22
<212> TYPE: RNA
<213> ORGANISM: Homo sapiens

<400> SEQUENCE: 714
uccauuacac uacccugccu cu                                               22

<210> SEQ ID NO 715
<211> LENGTH: 22
<212> TYPE: RNA
<213> ORGANISM: Homo sapiens

<400> SEQUENCE: 715
ugugcgcagg gagaccucuc cc                                               22

<210> SEQ ID NO 716
<211> LENGTH: 17
<212> TYPE: RNA
<213> ORGANISM: Homo sapiens

<400> SEQUENCE: 716
cgcgccgggc ccggguu                                                     17

<210> SEQ ID NO 717
<211> LENGTH: 18
<212> TYPE: RNA
<213> ORGANISM: Homo sapiens

<400> SEQUENCE: 717
cggggcggca ggggccuc                                                    18
```

```
<210> SEQ ID NO 718
<211> LENGTH: 18
<212> TYPE: RNA
<213> ORGANISM: Homo sapiens

<400> SEQUENCE: 718
gaggcugaag gaagaugg                                                 18

<210> SEQ ID NO 719
<211> LENGTH: 17
<212> TYPE: RNA
<213> ORGANISM: Homo sapiens

<400> SEQUENCE: 719
gcugggcgag gcuggca                                                  17

<210> SEQ ID NO 720
<211> LENGTH: 22
<212> TYPE: RNA
<213> ORGANISM: Homo sapiens

<400> SEQUENCE: 720
guggguacgg cccagugggg gg                                            22

<210> SEQ ID NO 721
<211> LENGTH: 17
<212> TYPE: RNA
<213> ORGANISM: Homo sapiens

<400> SEQUENCE: 721
gcuucuguag uguaguc                                                  17

<210> SEQ ID NO 722
<211> LENGTH: 18
<212> TYPE: RNA
<213> ORGANISM: Homo sapiens

<400> SEQUENCE: 722
cggcuggagg ugugagga                                                 18

<210> SEQ ID NO 723
<211> LENGTH: 21
<212> TYPE: RNA
<213> ORGANISM: Homo sapiens

<400> SEQUENCE: 723
uuacaggcgu gaaccaccgc g                                             21

<210> SEQ ID NO 724
<211> LENGTH: 24
<212> TYPE: RNA
<213> ORGANISM: Homo sapiens

<400> SEQUENCE: 724
ugggcuaagg gagaugauug ggua                                          24

<210> SEQ ID NO 725
<211> LENGTH: 21
<212> TYPE: RNA
<213> ORGANISM: Homo sapiens

<400> SEQUENCE: 725
```

-continued ccgucgccgc cacccgagcc g            21

<210> SEQ ID NO 726
<211> LENGTH: 22
<212> TYPE: RNA
<213> ORGANISM: Homo sapiens

<400> SEQUENCE: 726
gguccagagg ggagauaggu uc           22

<210> SEQ ID NO 727
<211> LENGTH: 24
<212> TYPE: RNA
<213> ORGANISM: Homo sapiens

<400> SEQUENCE: 727
cauagcccgg ucgcugguac auga         24

<210> SEQ ID NO 728
<211> LENGTH: 17
<212> TYPE: RNA
<213> ORGANISM: Homo sapiens

<400> SEQUENCE: 728
ccccgccacc gccuugg                 17

<210> SEQ ID NO 729
<211> LENGTH: 24
<212> TYPE: RNA
<213> ORGANISM: Homo sapiens

<400> SEQUENCE: 729
ugucagugac uccugcccu uggu          24

<210> SEQ ID NO 730
<211> LENGTH: 22
<212> TYPE: RNA
<213> ORGANISM: Homo sapiens

<400> SEQUENCE: 730
ucuggggaug aggacagugu gu           22

<210> SEQ ID NO 731
<211> LENGTH: 21
<212> TYPE: RNA
<213> ORGANISM: Homo sapiens

<400> SEQUENCE: 731
ucucaguaag uggcacucug u            21

<210> SEQ ID NO 732
<211> LENGTH: 18
<212> TYPE: RNA
<213> ORGANISM: Homo sapiens

<400> SEQUENCE: 732
agagcagaag gaugagau                18

<210> SEQ ID NO 733
<211> LENGTH: 22
<212> TYPE: RNA
<213> ORGANISM: Homo sapiens

<400> SEQUENCE: 733

```
ucaggccagg cacaguggcu ca                                          22

<210> SEQ ID NO 734
<211> LENGTH: 22
<212> TYPE: RNA
<213> ORGANISM: Homo sapiens

<400> SEQUENCE: 734 acuuccuca cucccgugaa gu                                           22

<210> SEQ ID NO 735
<211> LENGTH: 21
<212> TYPE: RNA
<213> ORGANISM: Homo sapiens

<400> SEQUENCE: 735
ugacagcgcc cugccuggcu c                                           21

<210> SEQ ID NO 736
<211> LENGTH: 17
<212> TYPE: RNA
<213> ORGANISM: Homo sapiens

<400> SEQUENCE: 736
aagacugaga ggaggga                                                17

<210> SEQ ID NO 737
<211> LENGTH: 23
<212> TYPE: RNA
<213> ORGANISM: Homo sapiens

<400> SEQUENCE: 737
agaacucuug cagucuuaga ugu                                         23

<210> SEQ ID NO 738
<211> LENGTH: 57
<212> TYPE: DNA
<213> ORGANISM: Homo sapiens
<220> FEATURE:
<223> OTHER INFORMATION: genomic sequence of miRNA precursor

<400> SEQUENCE: 738
ggccgcgccc cgtttcccag gacaaagggc actccgcacc ggaccctggt cccagcg    57

<210> SEQ ID NO 739
<211> LENGTH: 64
<212> TYPE: DNA
<213> ORGANISM: Homo sapiens
<220> FEATURE:
<223> OTHER INFORMATION: genomic sequence of miRNA precursor

<400> SEQUENCE: 739
cccactccct ggcgccgctt gtggagggcc caagtccttc tgattgaggc ccaacccgtg 60
gaag                                                              64

<210> SEQ ID NO 740
<211> LENGTH: 56
<212> TYPE: DNA
<213> ORGANISM: Homo sapiens
<220> FEATURE:
<223> OTHER INFORMATION: genomic sequence of miRNA precursor

<400> SEQUENCE: 740
```

```
cgccgggacc ggggtccggg gcggagtgcc cttcctcctg ggaaacgggg tgcggc          56
```

<210> SEQ ID NO 741
<211> LENGTH: 81
<212> TYPE: DNA
<213> ORGANISM: Homo sapiens
<220> FEATURE:
<223> OTHER INFORMATION: genomic sequence of miRNA precursor

<400> SEQUENCE: 741

```
gcttcacgtc cccaccggcg gcggcggcgg tggcagtggc ggcggcggcg gcggtggcgg     60
cggcggcggc ggcggcggct c                                              81
```

<210> SEQ ID NO 742
<211> LENGTH: 89
<212> TYPE: DNA
<213> ORGANISM: Homo sapiens
<220> FEATURE:
<223> OTHER INFORMATION: genomic sequence of miRNA precursor

<400> SEQUENCE: 742

```
gccgccccg ccgccgccgc cgccgccgcc gccgccgccg ccgcccgctt tcggctcggg      60
cctcaggtga gtcggagggg ccgggcgcc                                      89
```

<210> SEQ ID NO 743
<211> LENGTH: 22
<212> TYPE: RNA
<213> ORGANISM: Homo sapiens

<400> SEQUENCE: 743

```
ggcggagugc ccuucuuccu gg                                             22
```

<210> SEQ ID NO 744
<211> LENGTH: 22
<212> TYPE: RNA
<213> ORGANISM: Homo sapiens

<400> SEQUENCE: 744

```
ggagggccca aguccuucug au                                             22
```

<210> SEQ ID NO 745
<211> LENGTH: 22
<212> TYPE: RNA
<213> ORGANISM: Homo sapiens

<400> SEQUENCE: 745

```
gaccaggguc cggugcggag ug                                             22
```

<210> SEQ ID NO 746
<211> LENGTH: 17
<212> TYPE: DNA
<213> ORGANISM: Homo sapiens
<220> FEATURE:
<223> OTHER INFORMATION: genomic primer sequence

<400> SEQUENCE: 746

```
agggtccggt gcggagt                                                   17
```

<210> SEQ ID NO 747
<211> LENGTH: 12
<212> TYPE: RNA
<213> ORGANISM: Bos taurus

<400> SEQUENCE: 747

```
ggguccggug cg                                                          12

<210> SEQ ID NO 748
<211> LENGTH: 20
<212> TYPE: DNA
<213> ORGANISM: Homo sapiens
<220> FEATURE:
<223> OTHER INFORMATION: genomic primer sequence

<400> SEQUENCE: 748
tgcggagtgc cctttgtcct                                                  20

<210> SEQ ID NO 749
<211> LENGTH: 22
<212> TYPE: DNA
<213> ORGANISM: Homo sapiens
<220> FEATURE:
<223> OTHER INFORMATION: genomic primer sequence

<400> SEQUENCE: 749
ggagggccca agtccttctg at                                               22

<210> SEQ ID NO 750
<211> LENGTH: 14
<212> TYPE: RNA
<213> ORGANISM: Caenorhabditis remanei

<400> SEQUENCE: 750
cccaagugcu ucug                                                        14

<210> SEQ ID NO 751
<211> LENGTH: 18
<212> TYPE: DNA
<213> ORGANISM: Homo sapiens
<220> FEATURE:
<223> OTHER INFORMATION: genomic primer sequence

<400> SEQUENCE: 751
cggagtgccc ttcttcct                                                    18

<210> SEQ ID NO 752
<211> LENGTH: 12
<212> TYPE: RNA
<213> ORGANISM: Zea mays

<400> SEQUENCE: 752
gugcccuucu uc                                                          12
```